US006248755B1

(12) United States Patent
Chapman et al.

(10) Patent No.: US 6,248,755 B1
(45) Date of Patent: *Jun. 19, 2001

(54) PYRROLIDINE MODULATORS OF CHEMOKINE RECEPTOR ACTIVITY

(75) Inventors: Kevin Chapman, Scotch Plains; Jeffrey Hale; Dooseop Kim, both of Westfield; Christopher Lynch, Scotch Plains; Shrenik Shah, Metuchen; Kothandaraman Shankaran, Kendall Park; Dong-Ming Shen, Edison; Christopher Willoughby, Clark; Malcolm MacCoss, Freehold; Sander G. Mills, Scotch Plains; Jennifer L. Loebach, Westfield; Ravindra N. Guthikonda, Edison, all of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/542,617

(22) Filed: Apr. 4, 2000

Related U.S. Application Data

(60) Provisional application No. 60/128,033, filed on Apr. 6, 1999.

(51) Int. Cl.$^7$ .......................... A61K 31/50; A61K 31/44; C07D 411/00; C07D 221/02; C07D 211/68

(52) U.S. Cl. ............... 514/320; 514/252.13; 514/253.04; 514/253.09; 514/253.01; 514/254.04; 514/254.05; 514/254.01; 514/299; 514/321; 514/326; 514/333; 514/337; 514/362; 514/364; 514/366; 514/372; 514/373; 514/374; 546/256; 546/268.4; 546/276.4; 546/193; 546/198; 546/200; 546/201; 546/208; 546/209; 546/112

(58) Field of Search .................. 514/252.13, 253.04, 514/253.09, 253.01, 299, 321, 318, 320, 326, 333, 337, 343; 544/362, 364, 366, 372, 373, 374; 546/112, 193, 198, 200, 201, 209, 208, 256, 268.4, 276.4

(56) References Cited

U.S. PATENT DOCUMENTS

| 4,120,969 | * | 10/1978 | Welstead . |
| 4,324,791 | * | 4/1982 | Welstead . |
| 5,468,469 | | 11/1995 | Aszalos et al. . |
| 5,684,032 | | 11/1997 | Elliott et al. . |
| 5,776,954 | | 7/1998 | de Laszlo et al. . |

FOREIGN PATENT DOCUMENTS

| WO 99/09984 | 3/1999 | (WO) . |
| 1 013 276 | 6/2000 | (WO) . |
| WO 00/38680 | 7/2000 | (WO) . |
| WO 00/39125 | 7/2000 | (WO) . |

OTHER PUBLICATIONS

C. Dorn et al, "Discovery of Potent Human CCR5 Antagonists for the Treatment of HIV–I Infection", Abstract 117, 219th National Meeting of the American Chemical Society, San Francisco, CA, Mar. 2000.

L. Meurer et al, "Discovery of Potent Human CCR5 Antagonists for the Treatment of HIV–II Infection", Abstract 118, 219th National Meeting of the American Chemical Society, San Francisco, CA, Mar. 2000.

P. Finke et al, "Discovery of Potent Human CCR5 Antagonists for the Treatment of HIV–III Infection", Abstract 119, 219th National Meeting of the American Chemical Society, San Francisco, CA, Mar. 2000.

C. Caldwell et al, "Discovery of Potent Human CCR5 Antagonists for the Treatment of HIV–IV Infection", Abstract 120, 219th National Meeting of the American Chemical Society, San Francisco, CA, Mar. 2000.

J. J. Gomez–Reino et al., "Association of Rheumatoid Arthritis with a Functional Chemokine Receptor, CCR5", Arthritis & Rheumatism, vol. 42, No. 5, May 1999, pp. 989–992.

H. Hotoda, "Small–molecule inhibitors of HIV–1 entry via chemokine receptors", Drugs of the Future, vol. 24, No. 12, 1999, pp. 1355–1362.

T. J. Schall, "Biology of the Rantes/sis Cytokine Family", Cytokine, vol. 3, No. 3, May 1991, pp. 165–183.

P. M. Murphy, "The Molecular Biology of Leukocyte Chenoattractant Receptors", Annual Review of Immunology, vol. 12, 1994, pp. 593–633.

H. Deng et al., "Identification of a mojor co–receptor for primary isolates of HIV–1", Nature, vol. 381, Jun. 1996, pp. 661–666.

R. Horuk, "Molecular properties of the chemokine receptor family", Trends Pharm. Science, vol. 15, 1994, pp. 159–165.

(List continued on next page.)

Primary Examiner—D. Margaret Seaman
(74) Attorney, Agent, or Firm—Kenneth R. Walton; Melvin Winokur

(57) ABSTRACT

The present invention is directed to pyrrolidine compounds of the formula I:

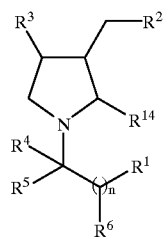

(wherein $R^1$, $R^2$, $R^3$, $R^4$, $R^5$, $R^6$, $R^{14}$ and n are defined herein) which are useful as modulators of chemokine receptor activity. In particular, these compounds are useful as modulators of the chemokine receptors CCR-5 and/or CCR-3.

39 Claims, No Drawings

OTHER PUBLICATIONS

A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.

K. Neote et al., "Molecular Cloning, Functional Expression, and Signaling Characteristics of C–C Chemokine Receptor", Cell, vol. 72, Feb. 1993, pp. 415–425.

C. Combadiere et al., "Cloning and Functional Expression of a Human Eosinophil CC Chemokine Receptor", J. Biol. Chem., vol. 270, No. 27, Jul. 1995, pp. 16491–16494.

C. A. Power et al., "Molecular Cloning and Functional Expression of a Novel Cc Chemokine Receptor cDNA from a Human Basophilic Line", J. Biol. Chem., vol. 270, No. 33, Aug. 1995, pp. 19495–19500.

M. Samson et al., "Molecular Cloning and Functional Expression of a New Human CC–Chemokine Receptor Gene", Biochemistry, vol. 35, 1996, pp. 3362–3367.

A. Chaudhuri et al., "Expression of the Duffy Antigen in K562 Cells," J. Biol. Chem., vol. 269, No. 11, Mar. 1994, pp. 7835–7838.

H. Kita et al., "Chemokines Active on Eosinophils: Potential Roles in Allergic Inflammation", J. Exp. Med., vol. 183, Jun. 1996, pp. 2421–2426.

D. Smith et al. "Blocking of HIV–1 Infectivity by a Soluable, Secreted Form of the CD4 Antigen", Science, vol. 238, 1987, pp. 1704–1707.

J. A. Levy, "Infection by Human Immunodeficiency Virus—DC4 is not Enough", N. Eng. J. Med., vol. 335, No. 20, Nov. 1996), pp. 1528–1530.

T. Dragic et al., "HIV–1 entry into CD4+ cells is mediated by the chemokine receptor CC–CKR5", Nature, vol. 381, Jun. 1996, pp. 667–673.

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistance to HIV–1 infection in caucasian individuals bearing mutant alleles of the CCR–5 cehmokine receptor gene", Nature, vol. 382, Aug. 1996, pp. 722–725.

C. M. Hill et al., "Natural resistence to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol. 383, Oct. 1996, p. 768.

W. S. Blair et al., "HIV–1 entry—an expanding portal for drug discovery", DDT, vol. 5, May 2000, pp. 183–194.

M. Baba et al., "A small–molecule, nonpeptide CCR5 antagonist with highly potent and selective anti HIV–1 activity", Proc. Natl. Acad. Sci., vol. 96, May 1999, pp. 5698–5703.

R. Horuk et al., "Chemokine Receptor Antagonists", Med. Res. Rev., vol. 20, No. 2, 2000, pp. 158–168.

M. Shiraishi et al., "Discovery of Novel, Potent, and Selective Small–Molecule CCR5 Antagonists as Anti–HIV–1 Agents: Synthesis and Biological Evaluation of Anilide Derivatives with a Quanternary Ammonium Moiety", J. Med. Chem., vol. 43, 2000, pp. 2049–2063.

* cited by examiner

PYRROLIDINE MODULATORS OF CHEMOKINE RECEPTOR ACTIVITY

This application claims the benefit of U.S. Provisional Application No. 60/128,033, filed Apr. 6, 1999, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C—X—C (α) and C—C (i), depending on whether the first two cysteines are separated by a single amino acid (C—X—C) or are adjacent (C—C). The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/ "CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR-4 (or "CKR-4" or "CC-CKR-4") [MIP-1α, RANTES, MCP-1] (Power, et al., *J. Biol. Chem.*, 270, 19495–19500 (1995)); CCR-5 (or "CKR-5" or "CC-CKR-5") [MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR-4, as well as the primary receptor CD4 (Levy, *N. Engl. J. Med.*, 335(20), 1528–1530 (Nov. 14 1996). The principal cofactor for entry mediated by the envelope glycoproteins of primary macrophage-trophic strains of HIV-1 is CCR5, a receptor for the β-chemokines RANTES, MIP-1α and MIP-1β (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that β-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1α and MIP-1β (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Absence of CCR-5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1α, MIP-1β, and MCP-3 are known to bind to chemokine receptors. As noted above, the inhibitors of HIV-1 replication present in supernatants of CD8+T cells have been characterized as the β-chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I:

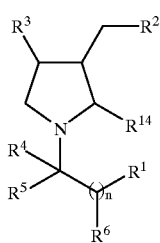

I wherein:
$R^1$ is selected from:
  (1) —$CO_2H$,
  (2) —$NO_2$,
  (3) -tetrazolyl,
  (4) -hydroxyisoxazole,
  (5) —$SO_2NH$—($CO_{0-3}$ alkyl)-$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
  (6) —$SO_2NHCO$—($C_{0-3}$ alkyl)-$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
  (7) —$P(O)(OH)_2$;
$R^2$ is selected from the group consisting of:

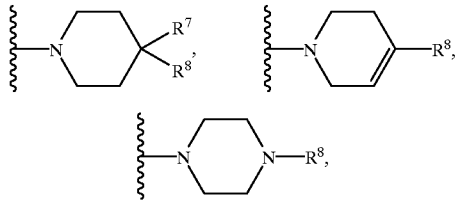

wherein $R^7$ is selected from:
  (1) hydrogen,
  (2) $C_{1-6}$ alkyl, which is unsubstituted or substituted with 1–4 substituents where the substituents are independently selected from: hydroxy, cyano, and halo,
  (3) cyano,
  (4) hydroxy, and
  (5) halo,
and wherein $R^8$ is selected from:
  phenyl, naphthyl, biphenyl, and heterocycle, which is unsubstituted or substituted with 1–7 of $R^{11}$ where $R^{11}$ is independently selected from:
    (a) halo,
    (b) cyano,
    (c) hydroxy,
    (d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_2(C_{1-6}$ alkyl), trifluoromethyl, —$NR^9R^{10}$ (where $R^9$ is defined above and $R^{10}$ is independently selected from the definitions of $R^9$), phenyl, naphthyl, biphenyl, and heterocycle, wherein phenyl, naphthyl, biphenyl, or heterocycle is unsubstituted or substituted with 1–7 of $R^{13}$ where $R^{13}$ is independently selected from: halo, cyano, hydroxy, $C_{1-6}$ alkyl, $C_{1-6}$ alkoxy, —$CO_2H$, —$CO_2(C_{1-6}$ alkyl), trifluoromethyl, —$NR^9R^{10}$, -($C_{1-6}$ alkyl)-$NR^9R^{10}$, —$SO_2R^9$, $C_{1-6}$ fluoroalkoxy, -($C_{1-6}$ alkyl)hydroxy, $C_{3-6}$ cycloalkyloxy, benzyloxy, phenoxy, and —$NO_2$,
    (e) —O—$C_{1-6}$ alkyl, which is unsubstituted or substituted with 1–5 of $R^{12}$,
    (f) -O-phenyl, which is unsubstituted or substituted with 1–5 of $R^{13}$,
    (g) -O-heterocycle, which is unsubstituted or substituted with 1–5 of $R^{13}$,
    (h) —$CF_3$,
    (i) —$CHF_2$,
    (j) —$CH_2F$,
    (k) —$NO_2$,
    (j) phenyl,
    (m) —$CO_2R^9$,
    (n) tetrazolyl,
    (o) —$NR^9R^{10}$,
    (p) —$NR^9$—$COR^{10}$,
    (q) —$NR^9$—$CO_2R^{10}$,
    (r) —CO—$NR^9R^{10}$,
    (s) —OCO—$NR^9R^{10}$,
    (t) —$NR^9CO$—$NR^9R^{10}$,
    (u) —$S(O)_m$-$R^9$, wherein m is an integer selected from 0, 1 and 2, (v) —S(O)₂—NR⁹R¹⁰,
(w) —NR⁹S(O)₂—R¹⁰,
(x) —NR⁹S(O)₂—NR⁹R¹⁰,
(y) $C_{2-6}$ alkenyl,
(z) furanyl, which is unsubstituted or substituted with benzyl which is unsubstituted or substituted with 1–7 of R¹³ wherein R¹³ is independently as defined above,
(aa) —CO—R⁹, and
(bb) —O—$C_{3-6}$ cycloalkyl;

R³ is selected from the group consisting of: phenyl, naphthyl, and heterocycle, which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —CO₂R⁹,
(g) —NR⁹R¹⁰, and
(h) —CONR⁹R¹⁰;

R⁴ is selected from:
$C_{1-10}$ alkyl, $C_{3-8}$ cycloalkyl, -($C_{1-3}$ alkyl)-$C_{3-8}$ cycloalkyl, -($C_{0-2}$ alkyl)-($C_{3-8}$ cycloalkylidenyl)-($C_{1-2}$ alkyl), $C_{2-10}$ alkenyl, $C_{2-10}$ alkynyl, phenyl, -($C_{1-6}$ alkyl)-phenyl, naphthyl, biphenyl, heterocycle, hydrogen, cyclohexenyl, dihydronaphthyl, tetrahydronaphthyl, and octahydronaphthyl, which is unsubstituted or substituted with 1–7 of R¹¹ where R¹¹ is independently as defined above;

R⁵ is selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —CO₂R⁹,
(g) —NR⁹R¹⁰, and
(h) —CONR⁹R¹⁰, or where R⁴ and R⁵ may be joined together to form a $C_{3-8}$ cycloalkyl ring which may be unsubstituted or substituted with 1–7 of R¹¹;

R⁶ is independently selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —CO₂R⁹,
(g) —NR⁹R¹⁰, and
(h) —CONR⁹R¹⁰;

R¹⁴ is hydrogen or $C_{1-6}$ alkyl;

n is an integer selected from 0, 1, 2 and 3;
and pharmaceutically acceptable salts thereof and individual diastereomers thereof.

In one embodiment, the present invention is directed to compounds of formula I':

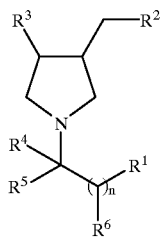

I' wherein:
R¹ is selected from:
(1) —CO₂H,
(2) —NO₂,
(3) -tetrazolyl,
(4) -hydroxyisoxazole,
(5) —SO₂NH—($C_{0-3}$ alkyl)-R⁹, wherein R⁹ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
(6) —P(O)(OH)₂;

R² is selected from the group consisting of:

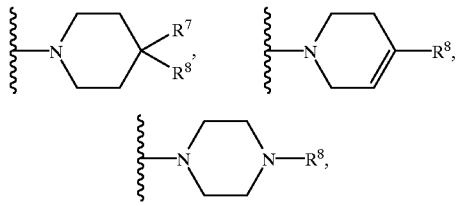

wherein R⁷ is selected from:
(1) hydrogen,
(2) $C_{1-6}$alkyl, which is unsubstituted or substituted with 1–4 substituents where the substituents are independently selected from: hydroxy, cyano, and halo,
(3) cyano,
(4) hydroxy, and
(5) halo,
and wherein R⁸ is selected from:
phenyl, naphthyl, biphenyl, and heterocycle, which is unsubstituted or substituted with 1–7 of R¹¹ where R¹¹ is independently selected from:
(a) halo,
(b) cyano,
(c) hydroxy,
(d) $C_{1-6}$alkyl, which is unsubstituted or substituted with 1–5 of R¹² where R¹² is independently selected from: halo, cyano, hydroxy, $C_{1-6}$alkoxy, —CO₂H, —CO₂($C_{1-6}$ alkyl), trifluoromethyl, —NR⁹R¹⁰ (where R⁹ is defined above and R¹⁰ is independently selected from the definitions of R⁹), phenyl, naphthyl, biphenyl, and heterocycle, wherein phenyl, naphthyl, biphenyl, or heterocycle is unsubstituted or substituted with 1–7 of R¹³ where R¹³ is independently selected from: halo, cyano, hydroxy, $C_{1-6}$alkyl, $C_{1-6}$alkoxy, —CO₂H, —CO₂($C_{1-6}$ alkyl), trifluoromethyl, and —NR⁹R¹⁰,
(e) —O—$C_{1-6}$alkyl, which is unsubstituted or substituted with 1–5 of R¹², (f) —O-phenyl, which is unsubstituted or substituted with 1–5 of $R^{13}$,
(g) —O-heterocycle, which is unsubstituted or substituted with 1–5 of $R^{13}$,
(h) —$CF_3$,
(i) —$CHF_2$,
(j) —$CH_2F$,
(k) —$NO_2$,
(l) phenyl,
(m) —$CO_2R^9$,
(n) tetrazolyl,
(o) —$NR^9R^{10}$,
(p) —$NR^9$—$COR^{10}$,
(q) —$NR^9$—$CO_2R^{10}$,
(r) —CO—$NR^9R^{10}$,
(s) —OCO—$NR^9R^{10}$,
(t) —$NR^9CO$—$NR^9R^{10}$,
(u) —$S(O)_m$—$R^9$, wherein m is an integer selected from 0, 1 and 2,
(v) —$S(O)_2$—$NR^9R^{10}$,
(w) —$NR^9S(O)_2$—$R^{10}$, and
(x) —$NR^9S(O)_2$—$NR^9R^{10}$;

$R^3$ is selected from the group consisting of:
phenyl, naphthyl, and heterocycle, which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^4$ is selected from:
$C_{1-10}$ alkyl, $C_{3-8}$ cycloalkyl, —($C_{1-3}$ alkyl)-$C_{3-8}$ cycloalkyl, $C_{2-10}$ alkenyl, $C_{2-10}$ alkynyl, phenyl, —($C_{1-6}$ alkyl)-phenyl, naphthyl, biphenyl, heterocycle, hydrogen, cyclohexenyl, dihydronaphthyl, tetrahydronaphthyl, and octahydronaphthyl, which is unsubstituted or substituted with 1–7 of $R^{11}$ where $R^{11}$ is independently as defined above;

$R^5$ is selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$, or where $R^4$ and $R^5$ may be joined together to form a $C_{3-8}$ cycloalkyl ring which may be unsubstituted or substituted with 1–7 of $R^{11}$;

$R^6$ is independently selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl, (e) —O—$C_{1-3}$ alkyl,
(f) —$CO_2R^9$,
(g) —$NR^9R^{10}$, and
(h) —$CONR^9R^{10}$;

n is an integer selected from 0, 1, 2 and 3;

and pharmaceutically acceptable salts thereof and individual diastereomers thereof.

Preferred compounds of the present invention include those of formula Ia:

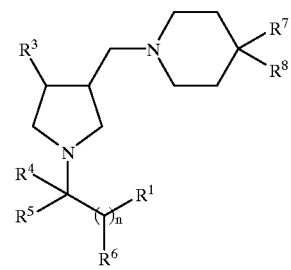

Ia wherein $R^1$, $R^3$, $R^4$, $R^5$, $R^6$, $R^7$, $R^8$ and n are defined herein;

and pharmaceutically acceptable salts and individual diastereomers thereof.

More preferred compounds of the present invention include those of formula Ic:

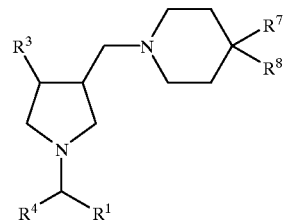

Ic wherein $R^1$, $R^3$, $R^4$, $R^7$ and $R^8$ are defined herein;

and pharmaceutically acceptable salts and individual diastereomers thereof.

Highly preferred compounds of the present invention include those of formula Id:

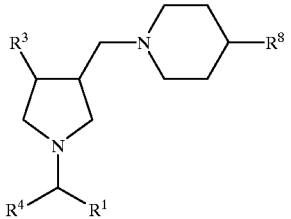

Id wherein $R^1$, $R^3$, $R^4$ and $R^8$ are defined herein;

and pharmaceutically acceptable salts and individual diastereomers thereof.

More highly preferred compounds of the present invention include those of formula Ie:

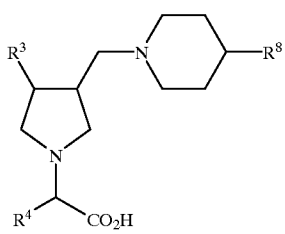

Ie wherein $R^3$, $R^4$ and $R^8$ are defined herein;
and pharmaceutically acceptable salts and individual diastereomers thereof.

In the present invention it is preferred that $R^1$ is selected from:
(1) —$CO_2H$,
(2) —$P(O)(OH)_2$, and
(3) -tetrazolyl.

In the present invention it is more preferred that $R^1$ is selected from:
(1) —$CO_2H$, and
(2) -tetrazolyl.

In the present invention it is even more preferred that $R^1$ is —$CO_2H$.

In the present invention it is preferred that $R^2$ is

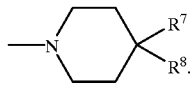

In the present invention it is preferred that $R^3$ is selected from the group consisting of:
phenyl and thienyl, which may be unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl.

In the present invention it is more preferred that $R^3$ is selected from the group consisting of:
phenyl and thienyl, which may be unsubstituted or substituted with 1–5 substituents where the substituents are independently selected from:
(a) halo,
(b) trifluoromethyl,
(c) hydroxy, and
(d) $C_{1-3}$ alkyl.

In the present invention it is even more preferred that $R^3$ is selected from the group consisting of:
phenyl, which may be unsubstituted or substituted with 1–5 substituents where the substituents are independently selected from:
(a) fluoro, and
(b) chloro; and
unsubstituted thienyl.

In the present invention it is most preferred that $R^3$ is unsubstituted phenyl, (3-fluoro)phenyl or 3-thienyl.

In the present invention it is preferred that $R^4$ is $C_{1-10}$ alkyl, $C_{3-8}$ cycloalkyl, or —($C_{1-3}$ alkyl)-$C_{3-8}$ cycloalkyl, which is unsubstituted or substituted with 1–5 substituents where the substituents are independently selected from:
(a) halo,
(b) hydroxy,
(c) -$C_{1-6}$alkyl, which is unsubstituted or substituted with halo, cyano, —$CO_2H$, hydroxy or trifluoromethyl,
(d) —O—$C_{1-6}$alkyl, which is unsubstituted or substituted halo, cyano, —$CO_2H$, hydroxy or trifluoromethyl,
(e) —$CF_3$,
(f) —$CHF_2$,
(g) —$CH_2F$, and
(h) —$CO_2H$.

In the present invention it is more preferred that $R^4$ is selected from: isopropyl, isobutyl, sec-butyl, t-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl. In an aspect of this embodiment, in the present invention it is more preferred that $R^4$ is selected from: isopropyl, isobutyl, secbutyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl.

In the present invention it is even more preferred that $R^4$ is selected from: isopropyl, sec-butyl, t-butyl, cyclohexyl, cyclopentyl, cyclobutyl, cyclopropyl, —$CH_2$-cyclobutyl, and —$CH_2$-cyclopropyl. In an aspect of this embodiment, in the present invention it is even more preferred that $R^4$ is selected from: isopropyl, cyclohexyl, cyclopentyl, cyclobutyl, cyclopropyl, —$CH_2$-cyclobutyl, and —$CH_2$-cyclopropyl.

In the present invention it is most preferred that $R^4$ is selected from: cyclohexyl, isopropyl, sec-butyl, t-butyl, —$CH_2$-cyclobutyl and —$CH_2$-cyclopropyl. In an aspect of this embodiment, in the present invention it is most preferred that $R^4$ is selected from: cyclohexyl, isopropyl, —$CH_2$-cyclobutyl and —$CH_2$-cyclopropyl.

In the present invention it is preferred that $R^5$ is hydrogen.
In the present invention it is preferred that $R^6$ is hydrogen or unsubstituted $C_{1-6}$ alkyl.
In the present invention it is more preferred that $R^6$ is hydrogen.
In the present invention it is preferred that $R^7$ is hydrogen, fluoro, hydroxy or $C_{1-6}$ alkyl.
In the present invention it is more preferred that $R^7$ is hydrogen or fluoro.
In the present invention it is even more preferred that $R^7$ is hydrogen.

In a preferred embodiment of the present invention, $R^8$ is selected from unsubstituted or substituted: pyrazolyl, thiazolyl, oxazolyl, pyridyl, imidazolyl, isoxazolyl, imidazopyridyl, imidazothiophenyl, indazolyl, tetrahydroimidazopyridyl, and tetrahydroindazolyl. In a preferred aspect of this embodiment, $R^8$ is selected from unsubstituted or substituted: pyrazolyl, thiazolyl, oxazolyl, imidazolyl, imidazopyridyl, tetrahydroimidazopyridyl, and tetrahydroindazolyl. In a further, more preferred aspect of this embodiment, $R^8$ is selected from substituted or unsubstituted: pyrazolyl, thiazolyl, imidazopyridyl, and tetrahydroindazolyl.

In the present invention it is preferred that $R^8$ is selected from: phenyl, benzoimidazolyl, imidazolyl, imidazopyridyl, isoxazolyl, oxazolyl, pyrazolyl, pyridyl, thiazolyl, imidazothiophenyl, indazolyl, tetrahydroimidazopyridyl, and tetrahydroindazolyl, which is unsubstituted or substituted with 1–7 substituents where the substituents are independently selected from:
(a) halo,
(b) cyano,
(c) hydroxy,
(d) $C_{1-6}$alkyl, which is unsubstituted or substituted with 1–5 of $R^{12}$ where $R^{12}$ is independently selected from: halo, cyano, hydroxy, $C_{1-6}$alkoxy, —$CO_2H$, —$CO_2(C_{1-6}$ alkyl), trifluoromethyl, —$NR^9R^{10}$ where $R^9$ and $R^{10}$ are independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
and phenyl, naphthyl, biphenyl, or heterocycle, which is unsubstituted or substituted with 1–7 of $R^{13}$ where $R^{13}$ is independently selected from: halo, cyano, hydroxy, $C_{1-6}$alkoxy, —$CO_2H$, —$CO_2(C_{1-6}$ alkyl), trifluoromethyl, and —$NR^9R^{10}$,
(e) —O—$C_{1-6}$alkyl, which is unsubstituted or substituted with 1–5 of $R^{12}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$.

In an aspect of the preceding embodiment, in the present invention it is preferred that $R^8$ is selected from: phenyl, benzoimidazolyl, imidazolyl, imidazopyridyl, isoxazolyl, oxazolyl, pyrazolyl, pyridyl, and thiazolyl; which is unsubstituted or substituted with 1–7 substituents as set forth in the preceding paragraph.

In the present invention it is more preferred that $R^8$ is selected from: phenyl, pyrazolyl, imidazolyl, benzoimidazolyl, isoxazolyl, oxazolyl, pyridyl, thiazolyl, imidazopyridyl, tetrahydroimidazopyridyl, and tetrahydroindazolyl;
which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) phenyl,
(h) $C_{1-6}$alkyl, which is unsubstituted or substituted with phenyl, which is unsubstituted or substituted with 1–4 of $R^{13}$ where $R^{13}$ is independently selected from: halo, cyano, hydroxy, $C_{1-6}$alkoxy, —$CO_2H$, —$CO_2(C_{1-6}$ alkyl), and trifluoromethyl, and
(i) —O—$C_{1-6}$alkyl.

In an aspect of the preceding embodiment, in the present invention it is preferred that $R^8$ is selected from: phenyl, pyrazolyl, imidazolyl, benzoimidazolyl, isoxazolyl, oxazolyl, pyridyl, and thiazolyl; which is unsubstituted or substituted with 1–5 substituents as set forth in the preceding paragraph.

In the present invention it is even more preferred that $R^8$ is selected from: pyrazolyl, imidazolyl, benzoimidazolyl, isoxazolyl, pyridyl, and thiazolyl, imidazopyridyl, and tetrahydroindazolyl;
which is unsubstituted or substituted with 1–3 substituents where the substituents are independently selected from:
(a) fluoro,
(b) chloro,
(c) $C_{1-6}$alkyl,
(d) —$CH_2$-phenyl,
(e) —$CH_2CH_2$-phenyl, and
(f) phenyl.

In an aspect of the preceding embodiment, in the present invention it is even more preferred that $R^8$ is selected from: pyrazolyl, imidazolyl, benzoimidazolyl, isoxazolyl, and pyridyl; which is unsubstituted or substituted with 1–3 substituents as set forth in the preceding paragraph.

In the present invention it is still more preferred that $R^8$ is selected from: pyrazolyl, benzoimidazolyl, isoxazolyl, and imidazolyl,
which is substituted with 1–3 substituents where the substituents are independently selected from:
(a) fluoro,
(b) methyl,
(c) ethyl,
(d) —$CH_2$-phenyl,
(e) —$CH_2CH_2$-phenyl, and In the present invention it is most preferred that $R^8$ is selected from: benzoimidazol-1-yl, (2-methyl)benzoimidazol-1-yl, (2-methyl-5-fluoro)benzoimidazol-1-yl, (2-methyl-5,6-difluoro)benzo-imidazol-1-yl, isoxazolo-5-yl, 5-benzyl-isoxazolo-5-yl, pyrazol-5-yl, 1-ethyl-3-benzyl-pyrazol-5-yl, 3-benzyl-pyrazol-5-yl, and 1-ethyl-4-phenethyl-pyrazol-5-yl.

In the present invention it is preferred that $R^{14}$ is hydrogen.

In the present invention it is preferred that n is an integer selected from 0 and 1.

In the present invention it is more preferred that n is an integer which is 0.

It is to be understood that embodiments of the present invention include, but are not limited to, compounds of formula I or of formula I' wherein $R^1, R^2, R^3, R^4, R^5, R^6, R^7, R^8$ and n are defined in accordance with one of the embodiments or aspects thereof as set forth above. Any and all possible combinations of preferred, more preferred, even more preferred, highly preferred, more highly preferred, and most preferred definitions of these variables in formulas I and I' are within the scope of the present invention.

The compounds of the instant invention have at least two asymmetric centers at the ring junction of the substituents bearing $R^2$ and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention.

The relative configurations of more preferred compounds of this invention are of the trans orientation, depicted as:

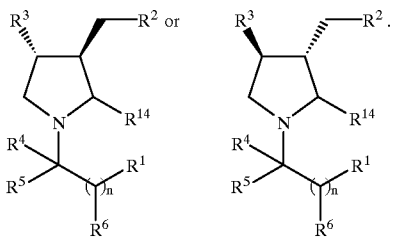

In one aspect, the relative configurations of the more preferred compounds of this invention are of the trans orientation, i.e. as depicted:

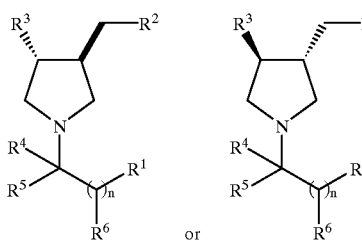

The relative configurations of the most preferred compounds of this invention with respect to the configuration of the substituent on the pyrrolidine nitrogen are of the orientation as depicted:

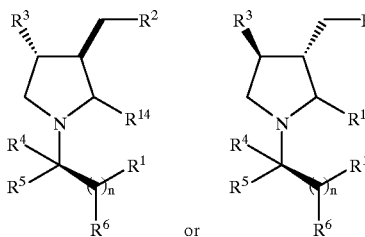

In one aspect, the relative configurations of the most preferred compounds of this invention with respect to the configuration of the substituent on the pyrrolidine nitrogen are of the orientation as depicted:

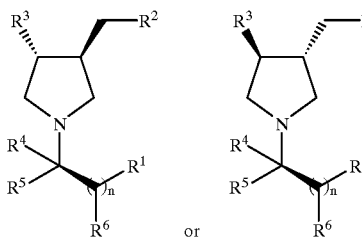

In a preferred aspect the present invention is a compound of formula (II):

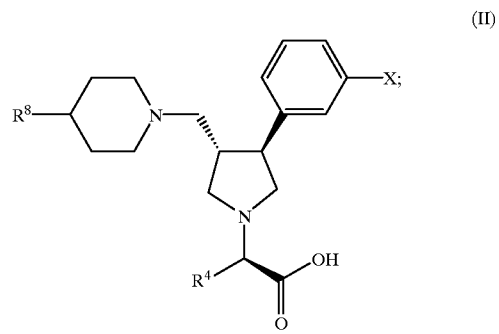

wherein $R^4$ is selected from the group consisting of

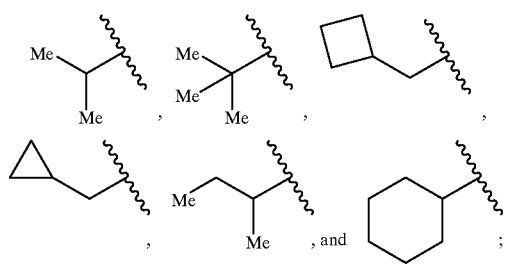

$R^8$ is selected from the group consisting of

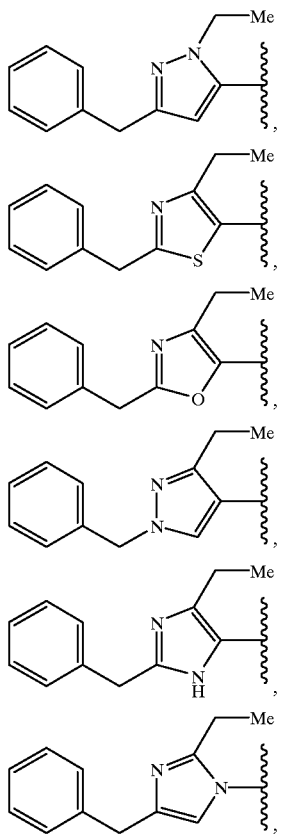

-continued

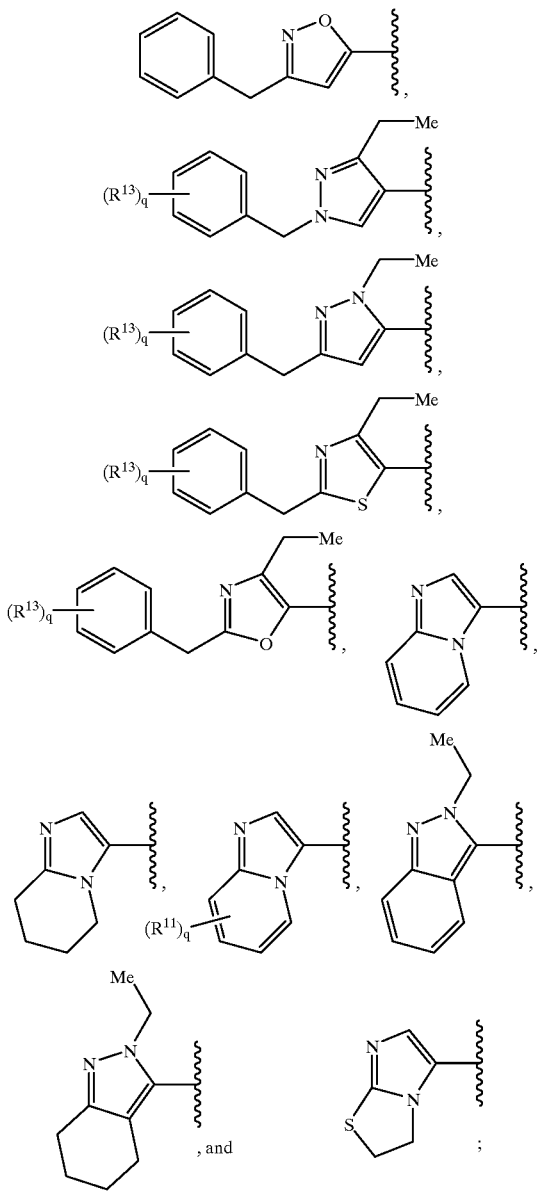

, and $R^{11}$ and $R^{13}$ are each independently selected from the group consisting of F, Cl, $CF_3$, $OCH_3$, $OCH_2CH_3$, $OCF_3$, O -cyclobutyl, CN, O-cyclopropyl, $CH_3$, $CH_2CH_3$, $CH(CH_3)_2$, $C(CH_3)_3$, and $SO_2CH_3$;

X is hydrogen or fluoro; and q is an integer equal to 1 or 2;

and pharmaceutically acceptable salts thereof and individual diastereomers thereof.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, propyl, butyl, pentyl, hexyl, heptyl and octyl. Likewise, $C_0$, as in $C_0$ alkyl is defined to identify the presence of a direct covalent bond.

As with "$C_{1-8}$ alkyl", the term "$C_{1-6}$ alkyl" means linear or branched chain alkyl groups having from 1 to 6 carbon atoms and includes all of the hexyl alkyl, pentyl alkyl, etc. isomers.

The term "$C_3-C_8$ cycloalkyl" refers to a cyclic ring selected from cyclopropyl, cyclobutyl, cyclopentyl, cyclohexyl, cycloheptyl, and cyclooctyl. The term "$C_3-C_6$ cycloalkyl" refers to a cyclic ring selected from cyclopropyl, cyclobutyl, cyclopentyl, and cyclohexyl. Similar terms (e.g., "$C_4-C_6$ cycloalkyl") have analogous meanings.

The term "$C_{1-6}$ alkoxy" means an —O-alkyl group wherein alkyl is $C_{1-6}$ alkyl as defined above. Suitable alkoxy groups include, but are not limited to, methoxy, ethoxy, n-propoxy, isopropoxy, n-butoxy, isobutoxy, tert-butoxy, and sec-butoxy.

The term "$C_{1-6}$ fluoroalkoxy" means a $C_{1-6}$ alkoxy group as defined above in which the alkyl group is substituted with one or more fluorine atoms. Exemplary fluoroalkoxy groups include, but are not limited to, trifluoromethoxy, 2,2,2-trifluoroethoxy, fluoromethoxy, and difluoromethoxy.

The term "$C_3-C_8$ cycloalkyloxy" means an —O-cycloalkyl group wherein the cycloalkyl group is $C_3-C_8$ cycloalkyl as defined above. The term refers to cyclopropyloxy, cyclobutyloxy, cyclohexyloxy, and so forth.

The term "-($C_{1-6}$ alkyl)hydroxy" refers to a $C_{1-6}$ alkyl group as defined above which is substituted on one its carbons by a hydroxy group. Exemplary groups include hydroxymethyl, hydroxyethyl, 3-hydroxy-n-propyl, 2-hydroxy-n-propyl, and so forth.

The term "$C_{3-8}$ cycloalkylidenyl" refers to a $C_{3-8}$ cycloalkyl group as defined above in which one of the ring carbons is attached to each of two carbon atoms not in the ring such that the three carbon atoms form a carbon chain or part of a carbon chain. Thus, "-($C_{1-2}$ alkyl)-($C_{3-8}$ cycloalkylidenyl)-($C_{1-2}$ alkyl)" refers to and encompasses such groups as:

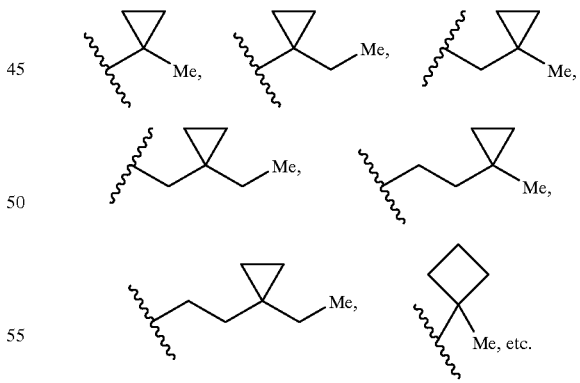

The term "heterocycle" (which may alternatively be referred to as "heterocyclic") refers to a 4- to 8-membered monocyclic ring, a 7- to 11-membered bicyclic system, or a 10 to 15-membered tricyclic ring system, any ring of which is saturated or unsaturated (partially or totally), and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure. A preferred heterocycle is a 4- to 8-membered monocyclic ring or a 7- to 11-membered bicyclic system, as defined and described above.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothiopheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms are used interchangeably: "indazolyl" and "benzopyrazolyl"; "pyridinyl" and "pyridyl".

In the expression " . . . which is unsubstituted or substituted with . . . ", "which" is intended to refer back to all preceding chemical groups in the particular definition in which the expression appears, unless a contrary meaning is expressed or is implied by the context. Furthermore, the term "substituted" in the expression includes mono- and poly-substitution by a named substituent to the extent such single and multiple substitution is chemically allowed in any of the named chemical groups. Thus, for example, the expression "is independently selected from: hydrogen, $C_{1-6}$ alkyl, $C_{5-6}$ cycloalkyl, benzyl or phenyl, which is unsubstituted or substituted with 1-3 substituents . . . ", encompasses hydrogen, $C_{1-6}$ alkyl, $C_{5-6}$ cycloalkyl, benzyl, phenyl, mono- and di- and tri-substituted $C_{1-6}$ alkyl, mono- and di- and tri-substituted $C_{5-6}$ cycloalkyl, mono- and di- and tri-substituted benzyl and mono- and di- and tri-substituted phenyl.

Exemplifying the invention is the use of the compounds disclosed in the Examples and herein.

Specific compounds within the present invention include a compound which is selected from the group consisting of:

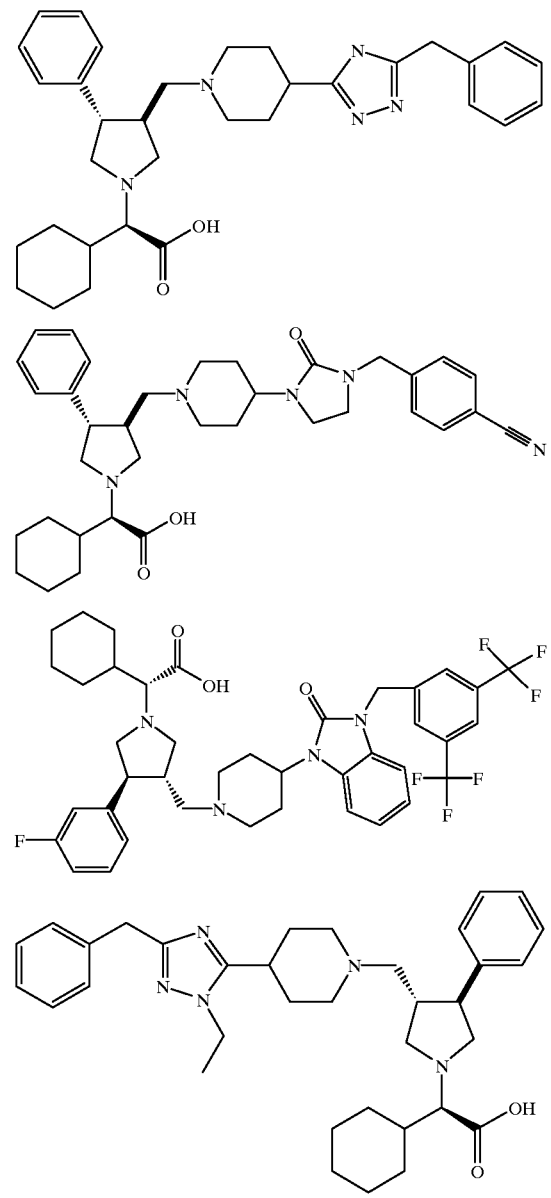

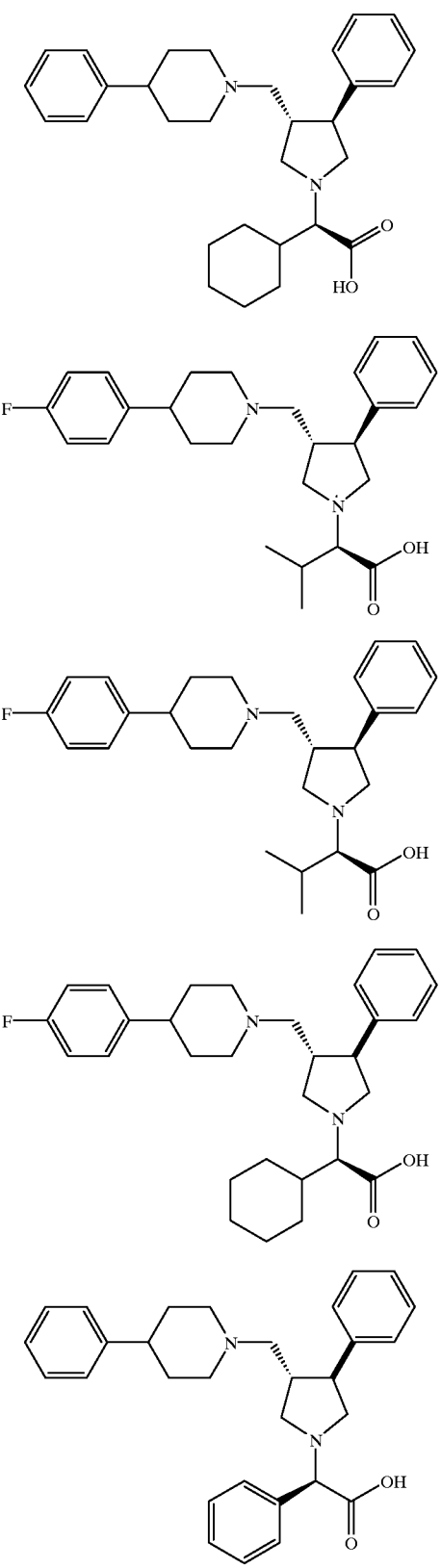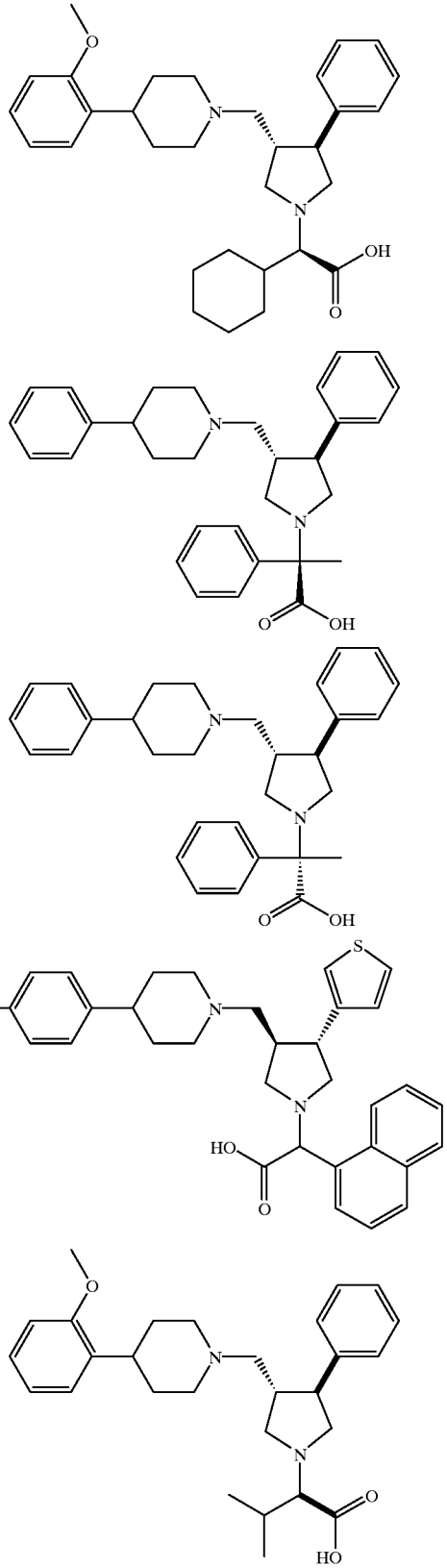

21
-continued
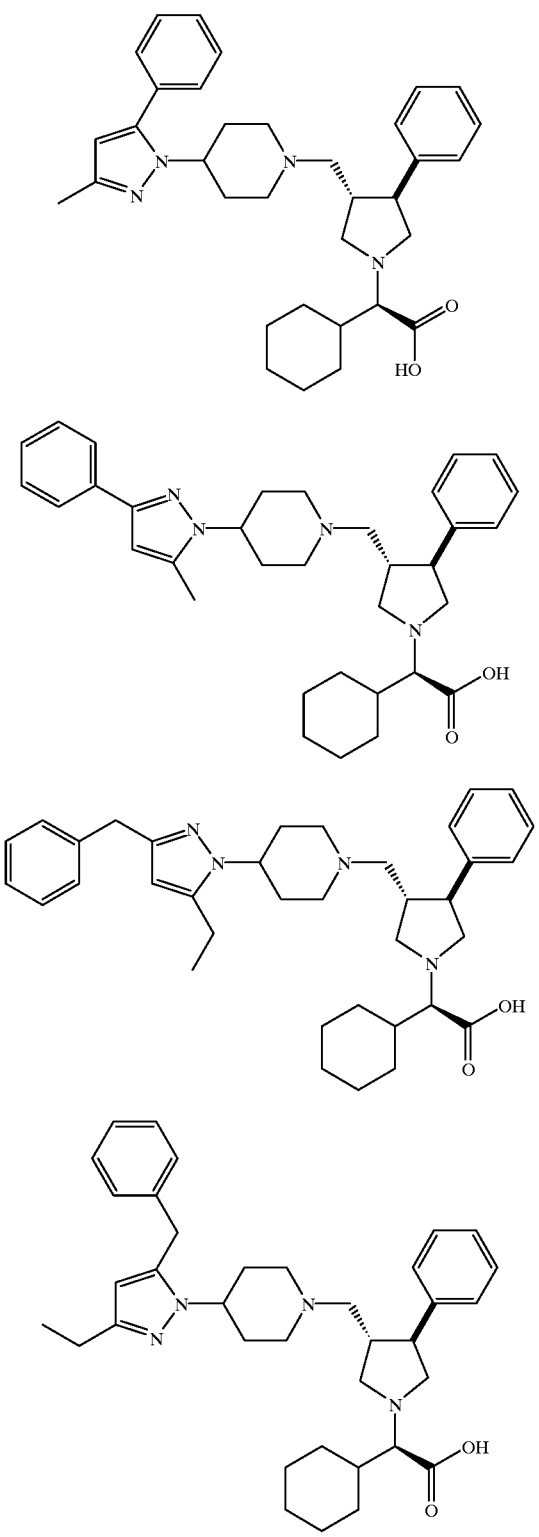
22
-continued
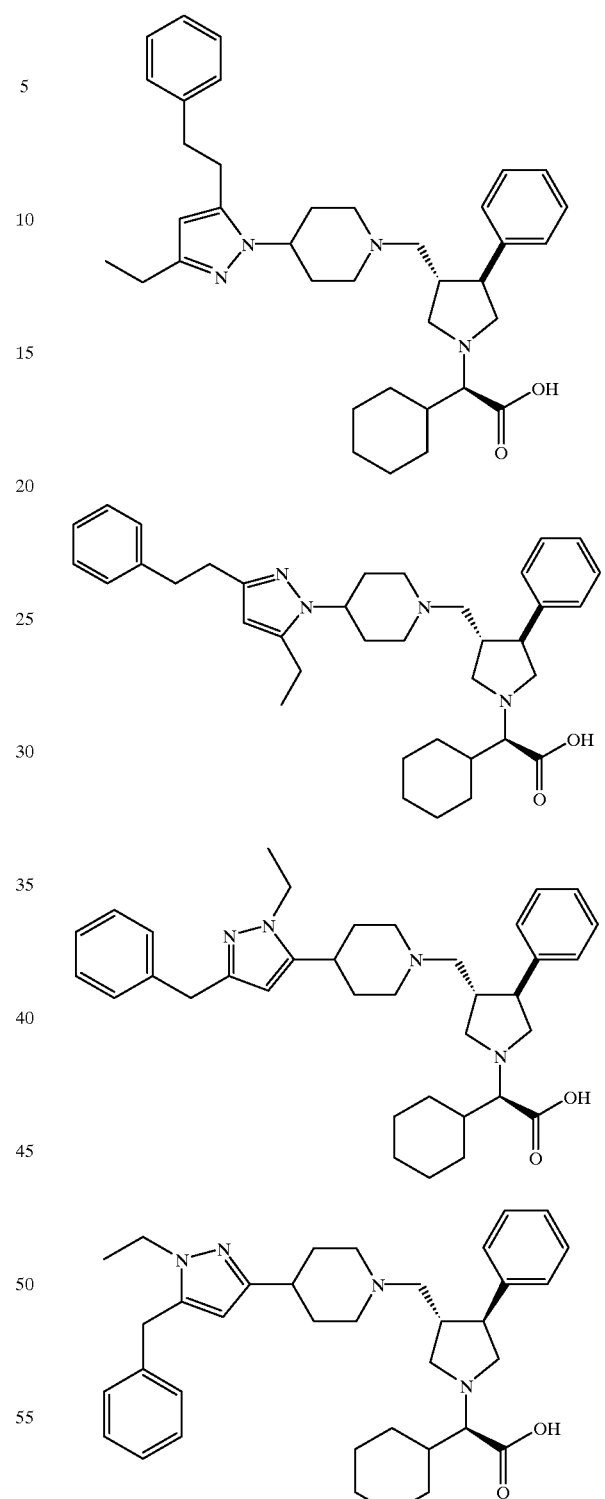

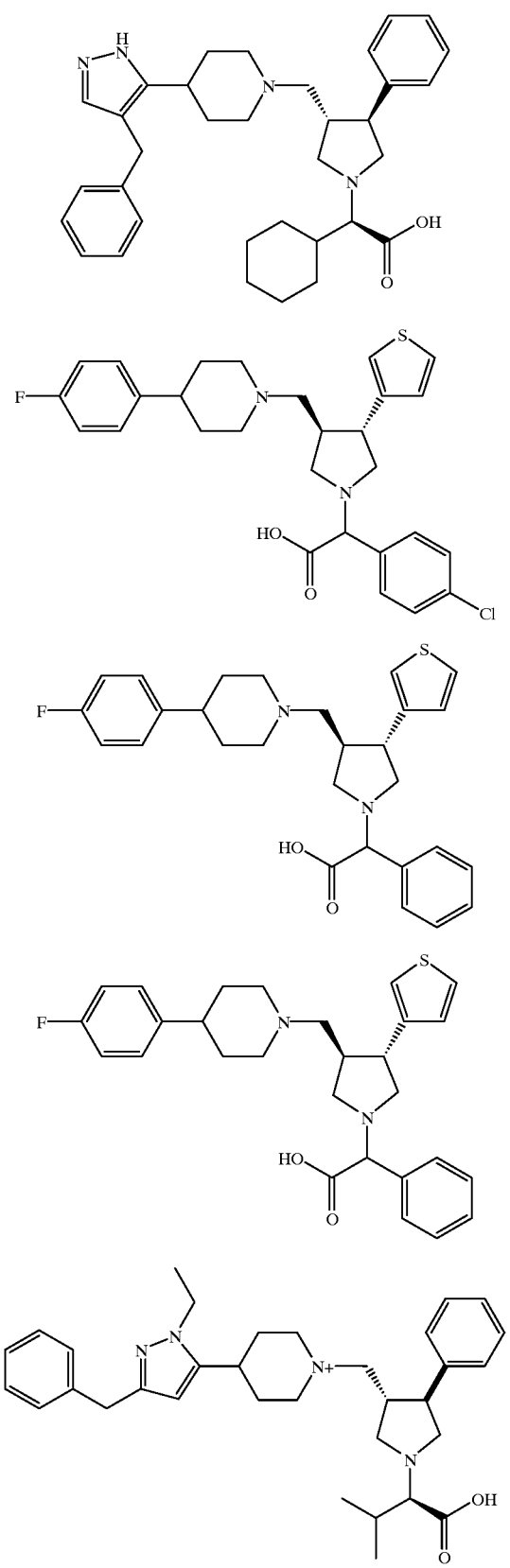
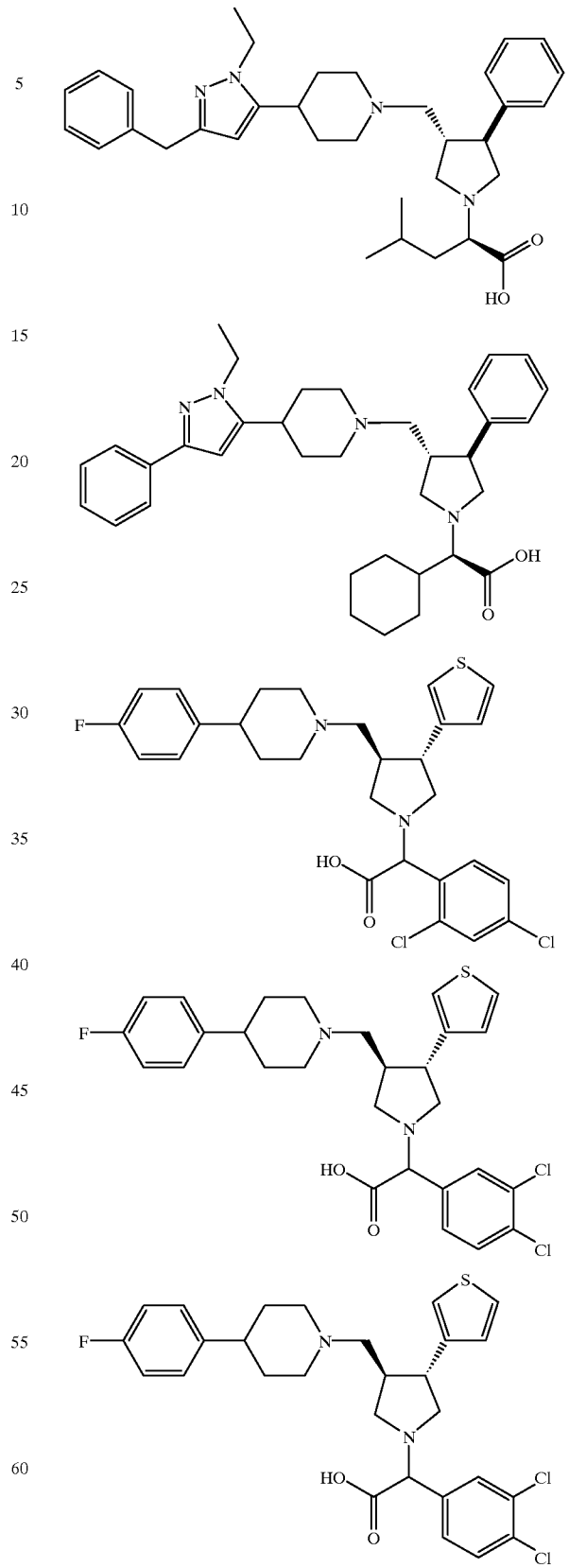

-continued
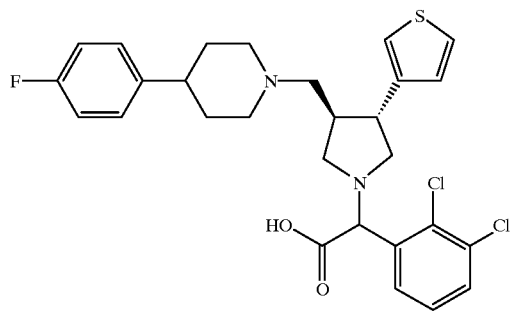
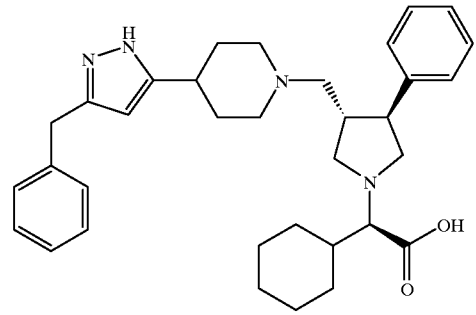
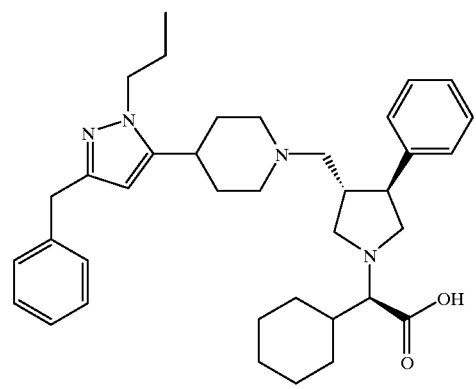
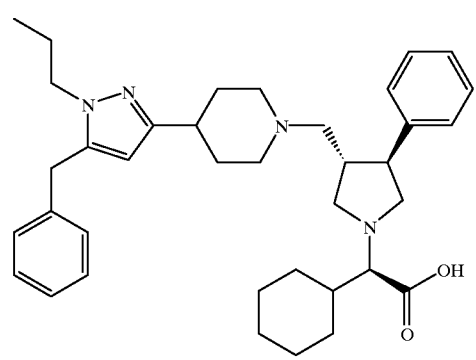
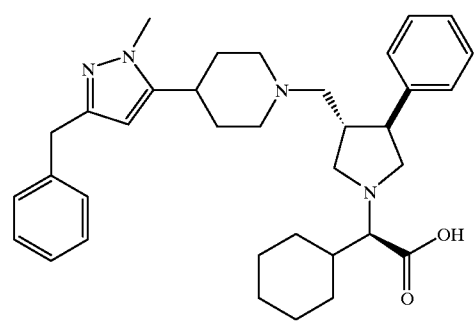
-continued
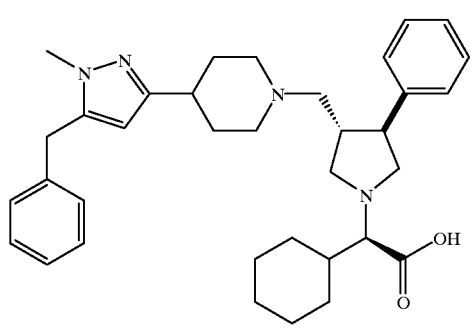
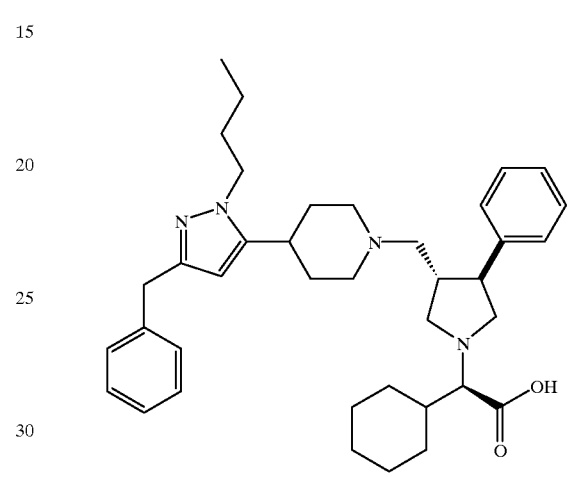
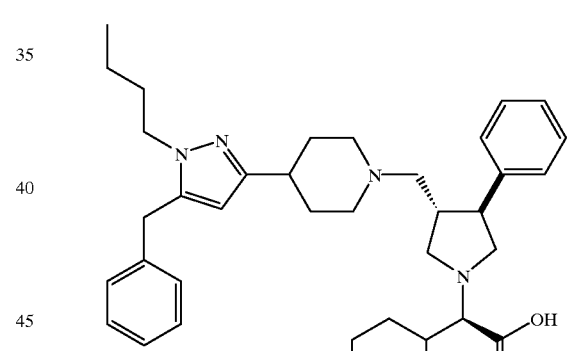
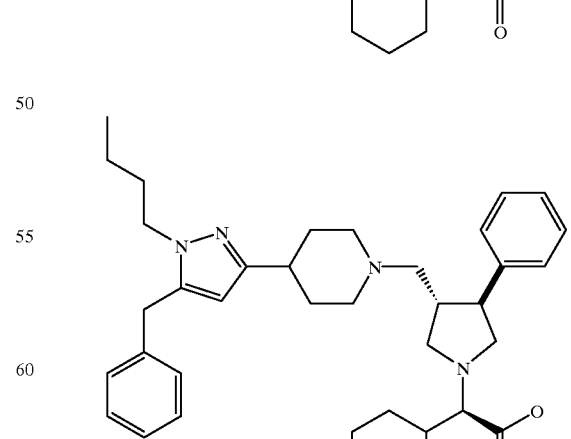

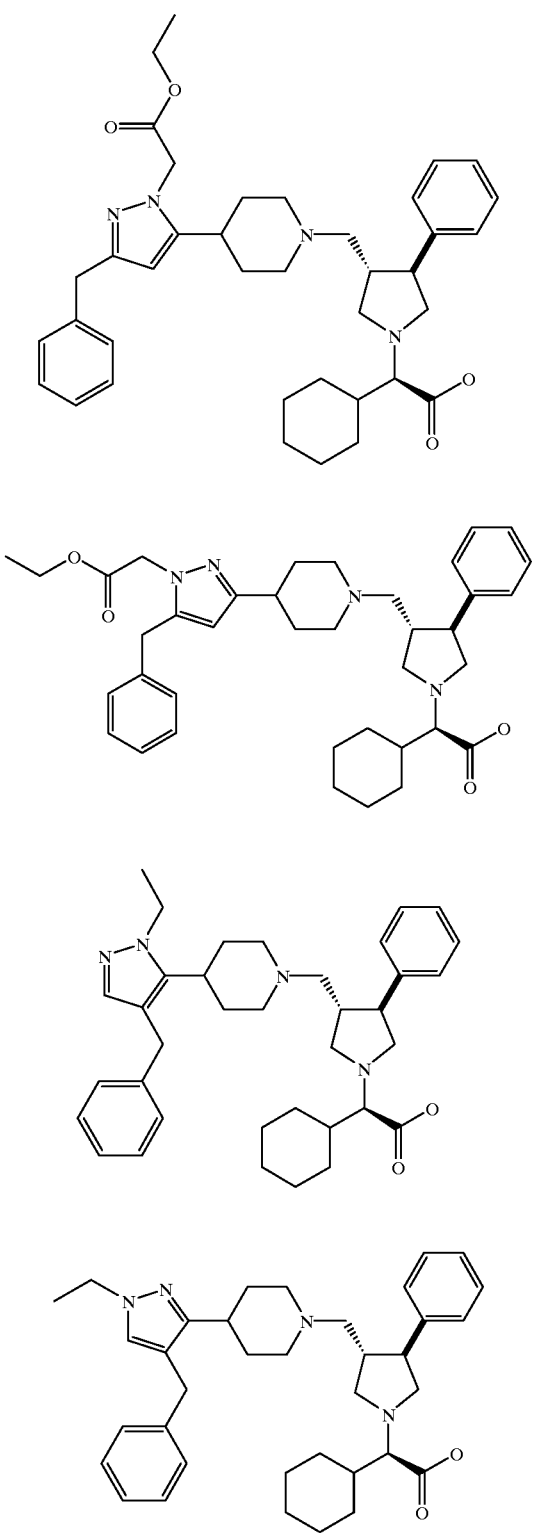
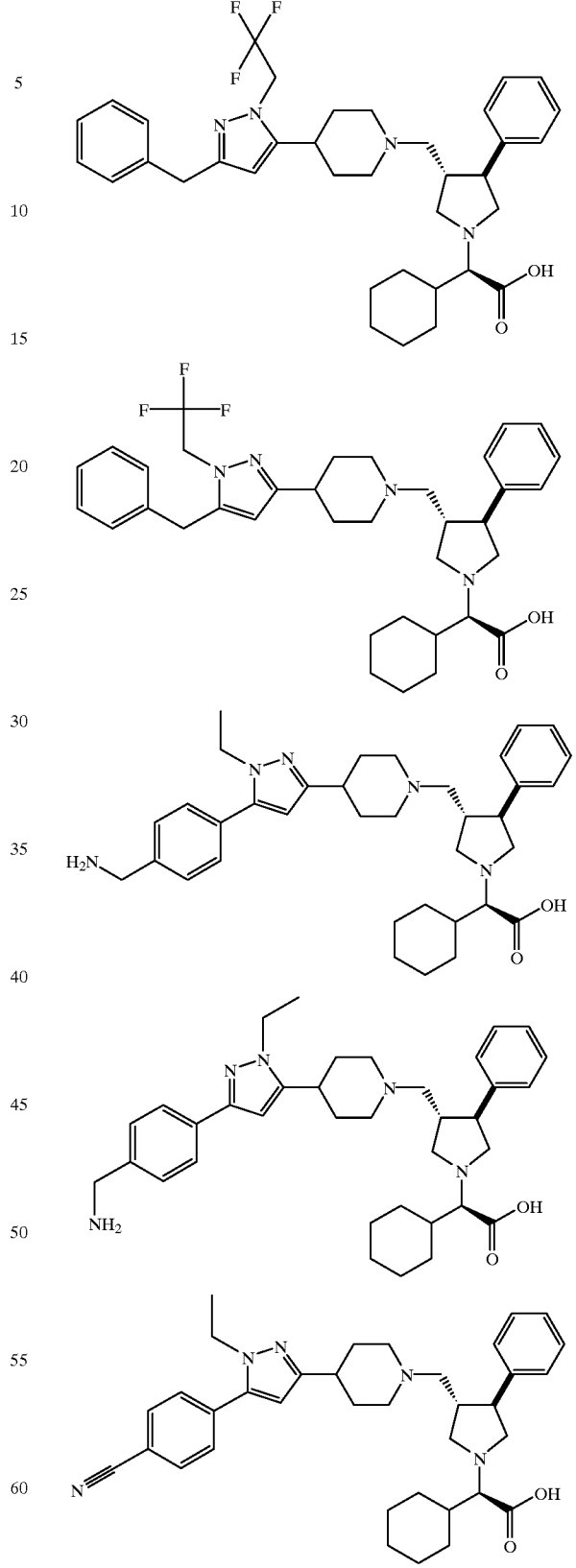

29
-continued
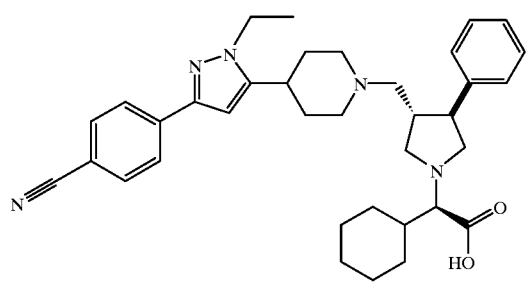
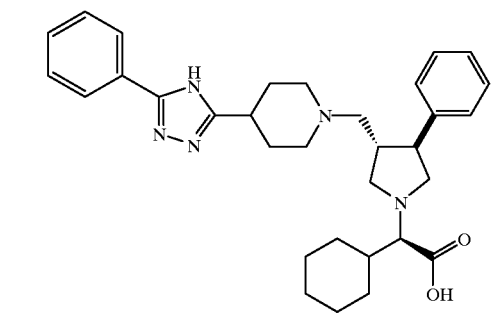
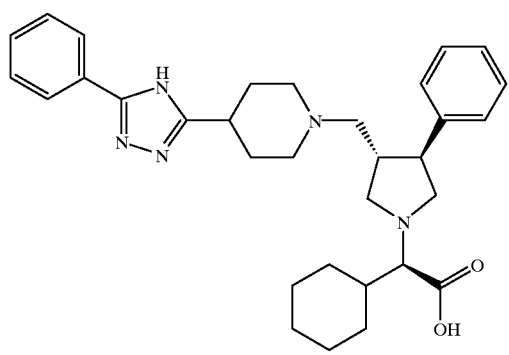
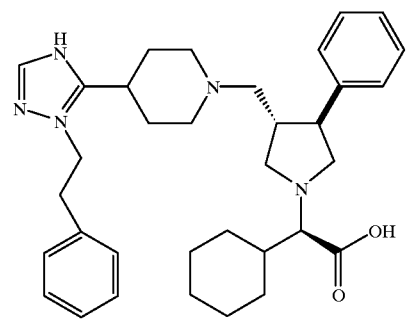
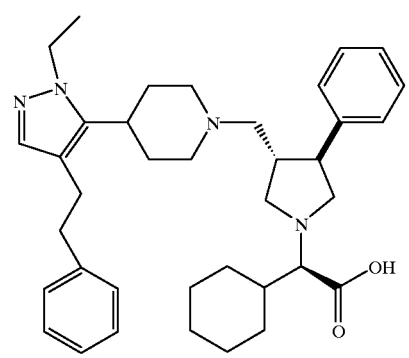
30
-continued
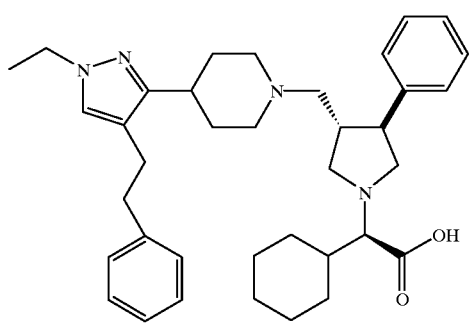
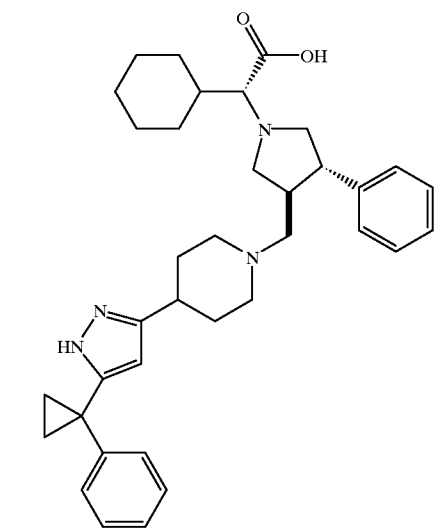
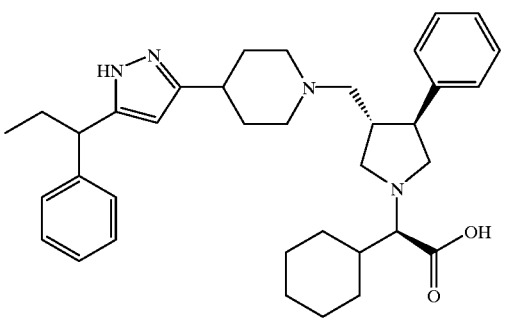
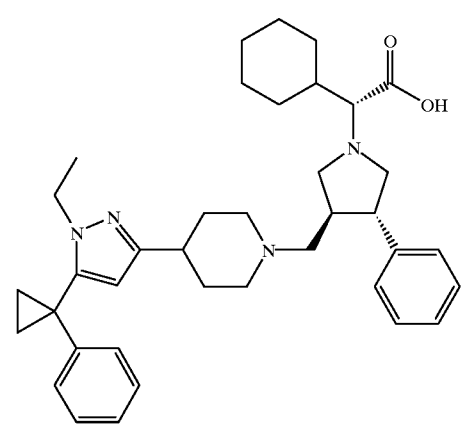

31
-continued
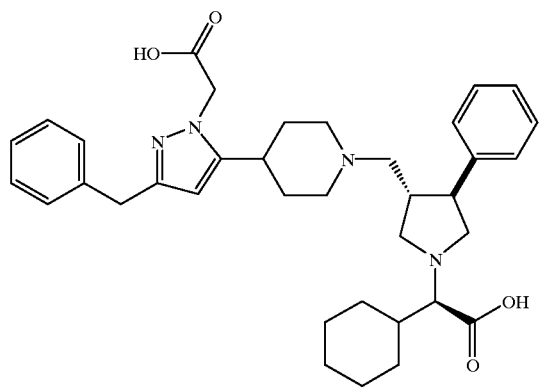
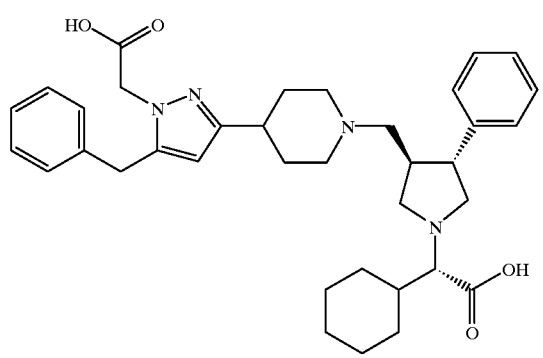
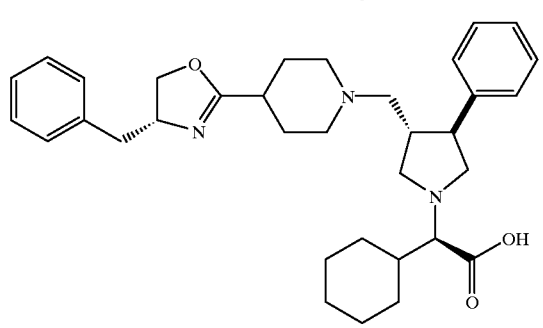
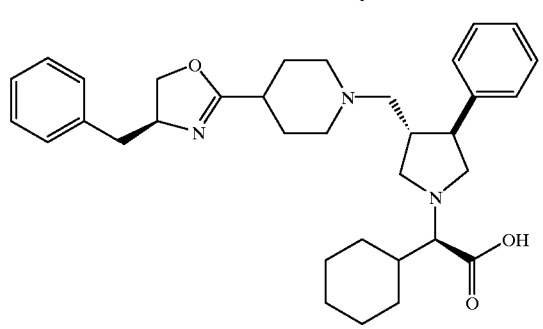
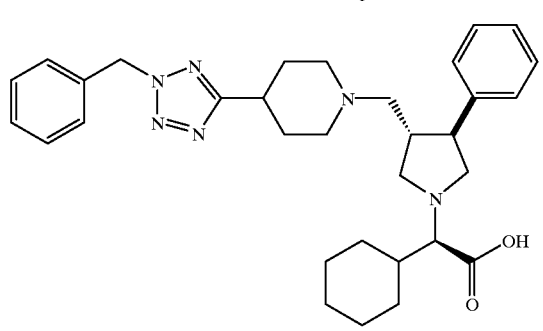
32
-continued
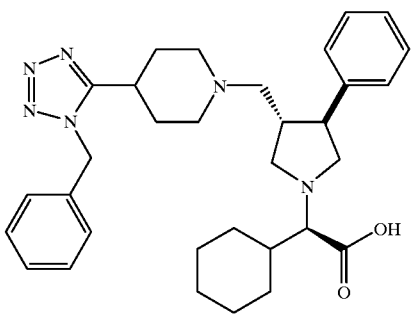
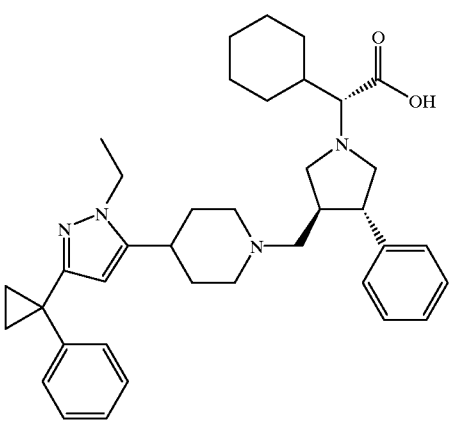
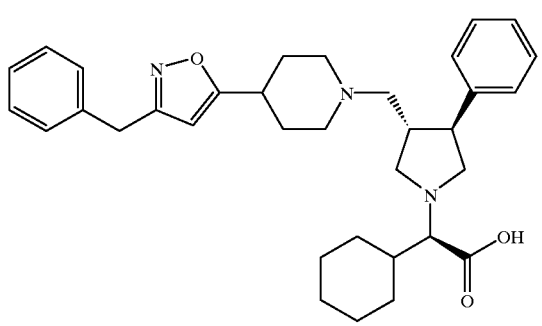
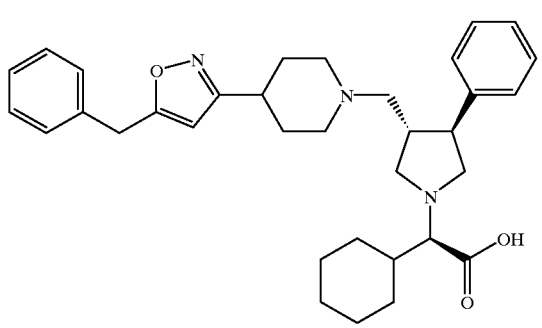
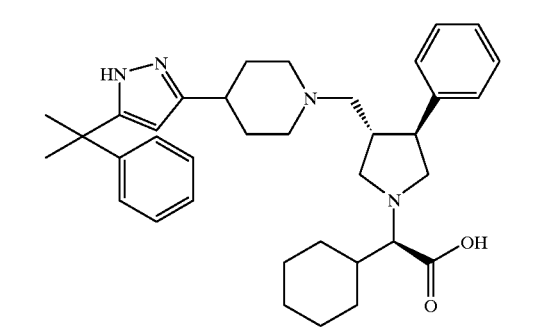

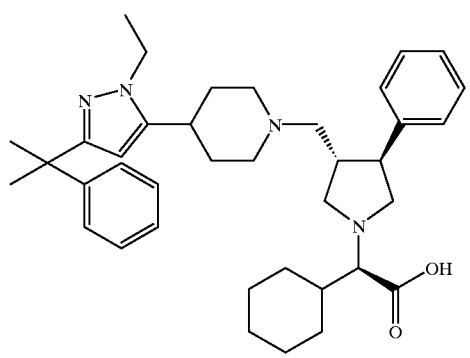
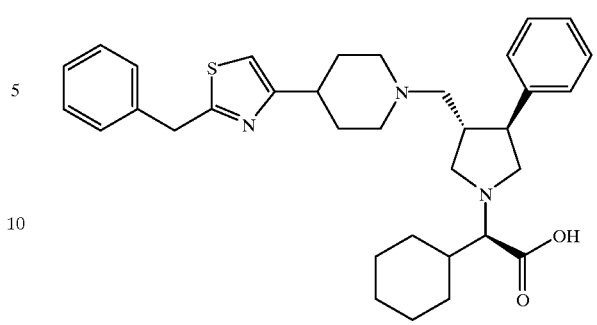
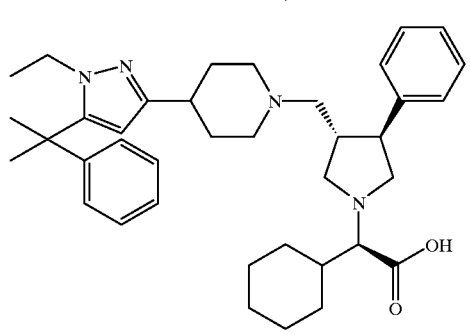
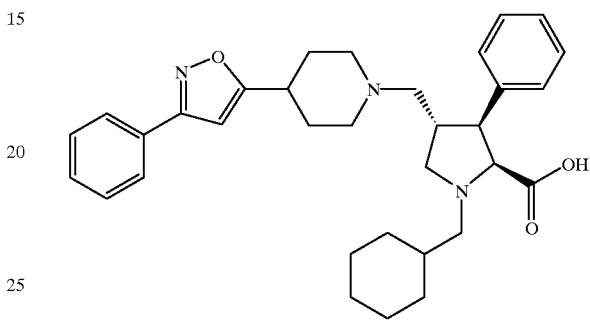
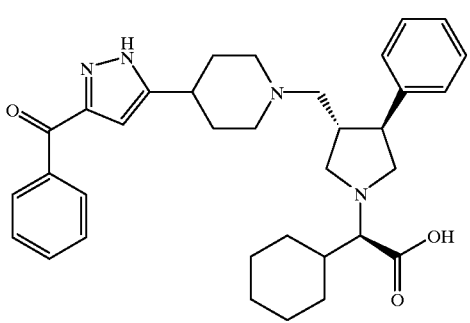
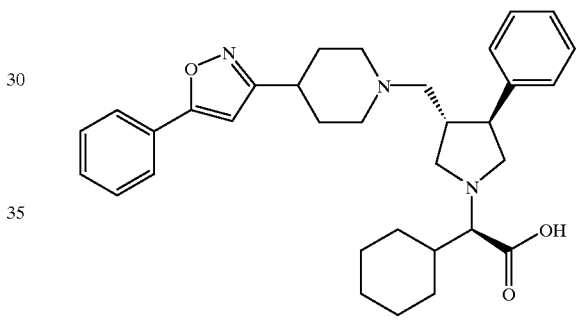
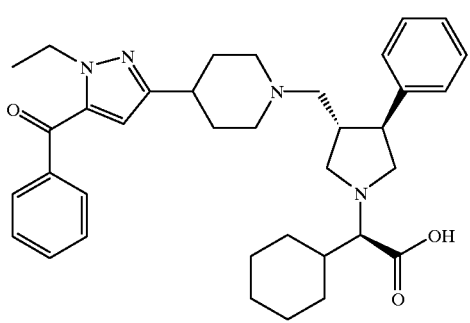
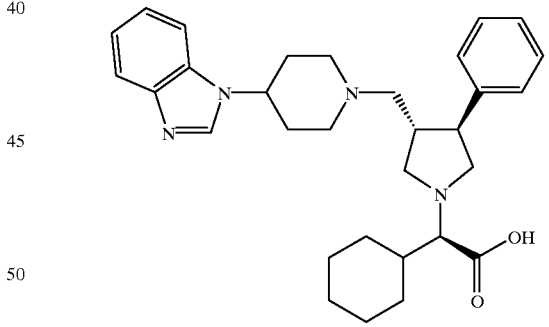
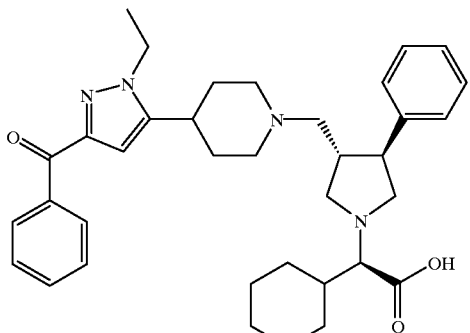
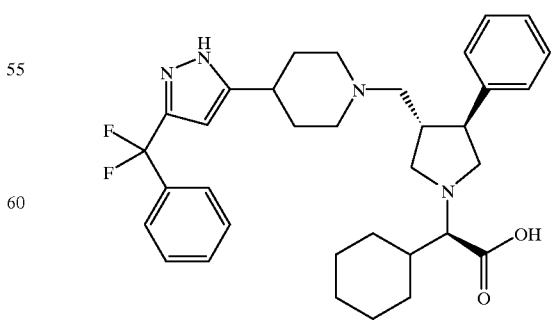

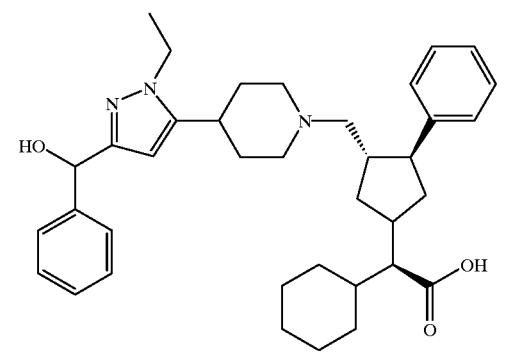
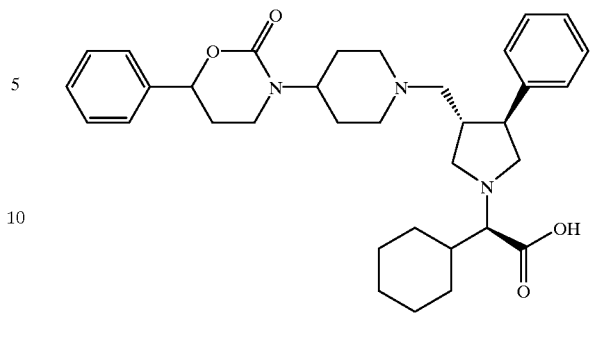
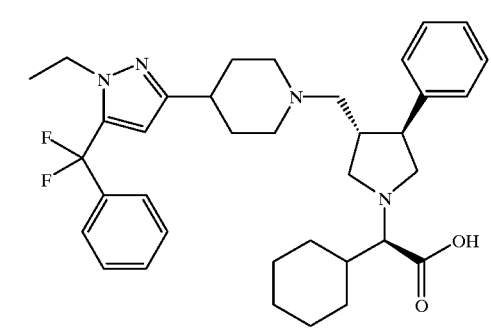
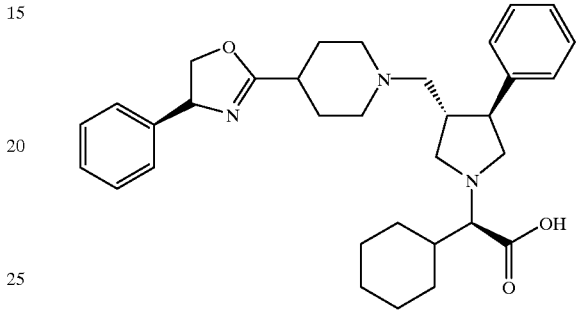
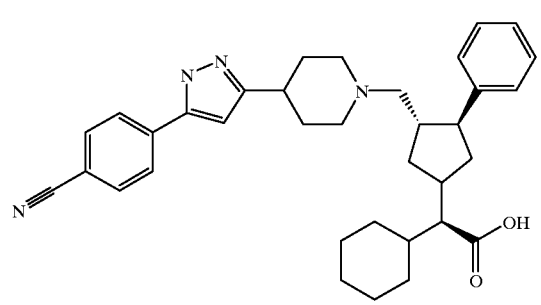
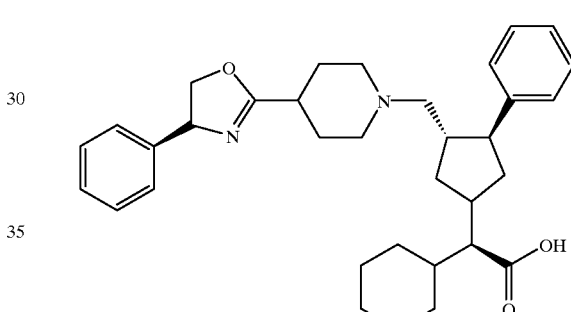
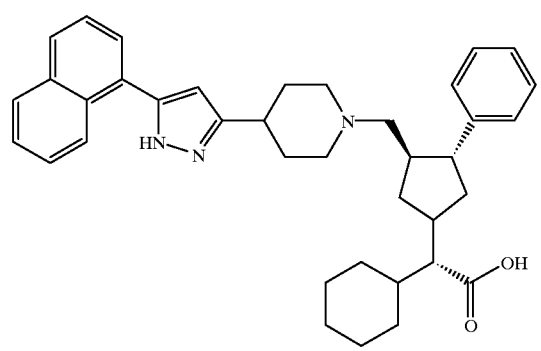
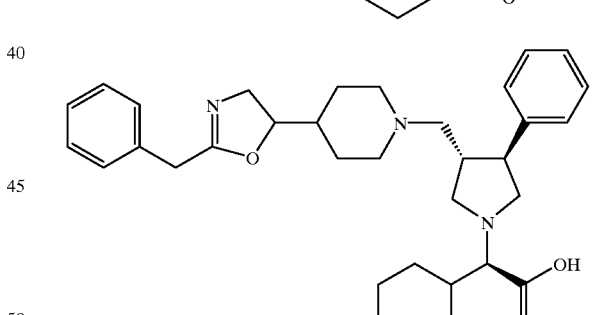
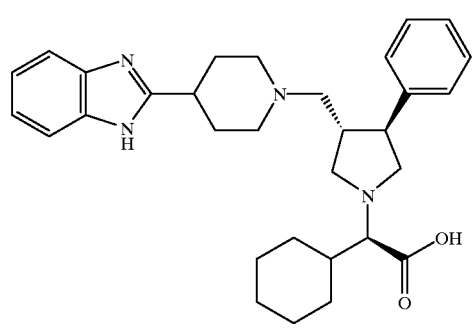
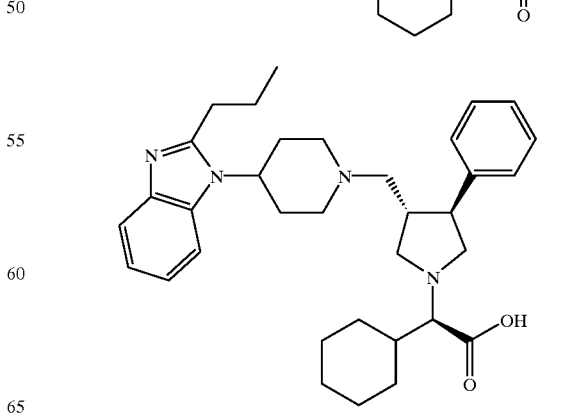

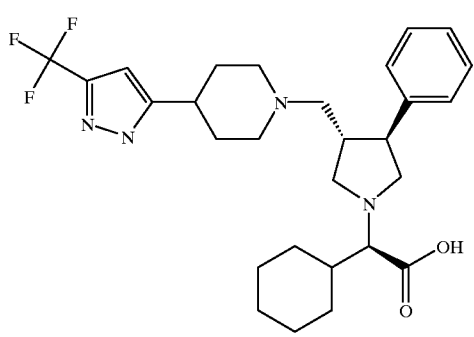
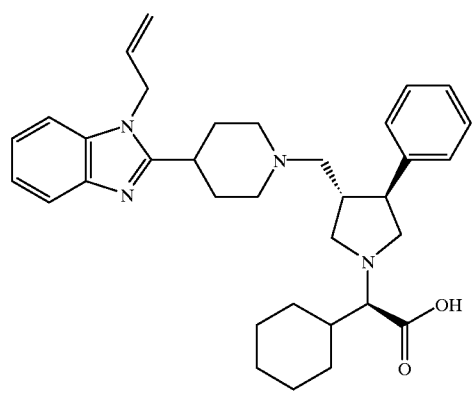
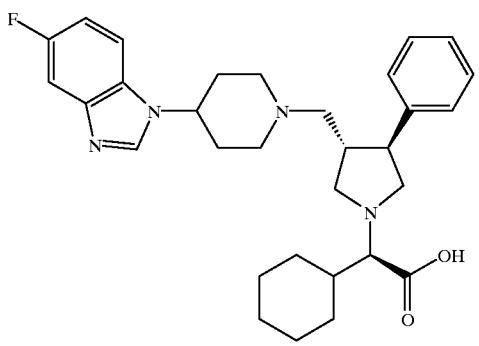
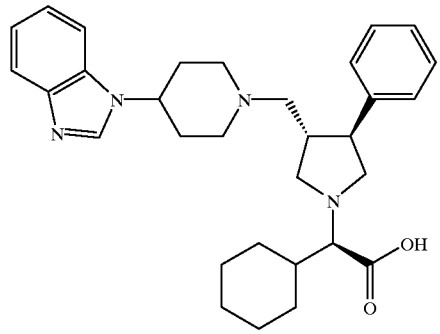
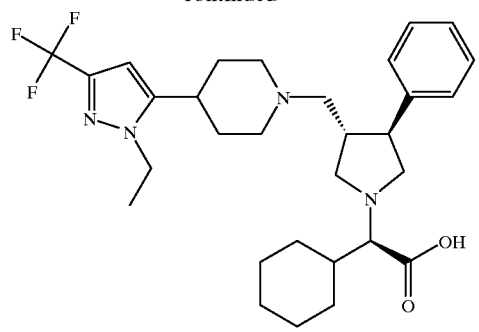
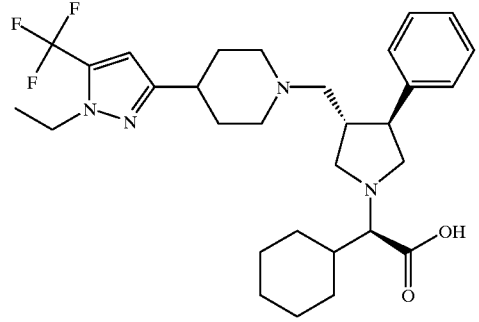
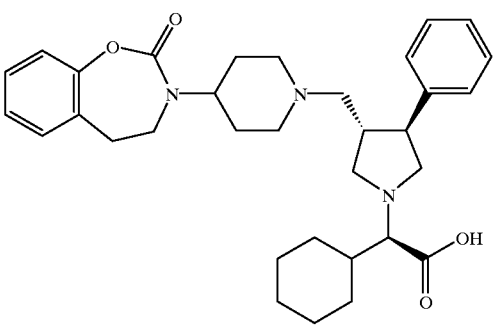
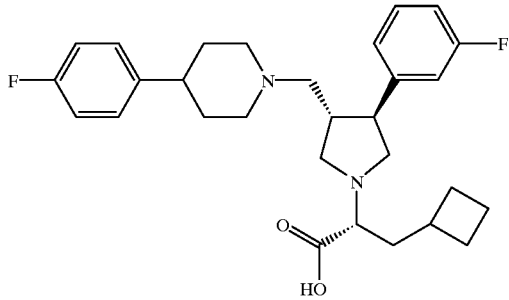
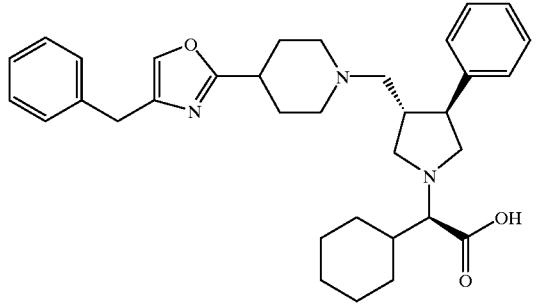

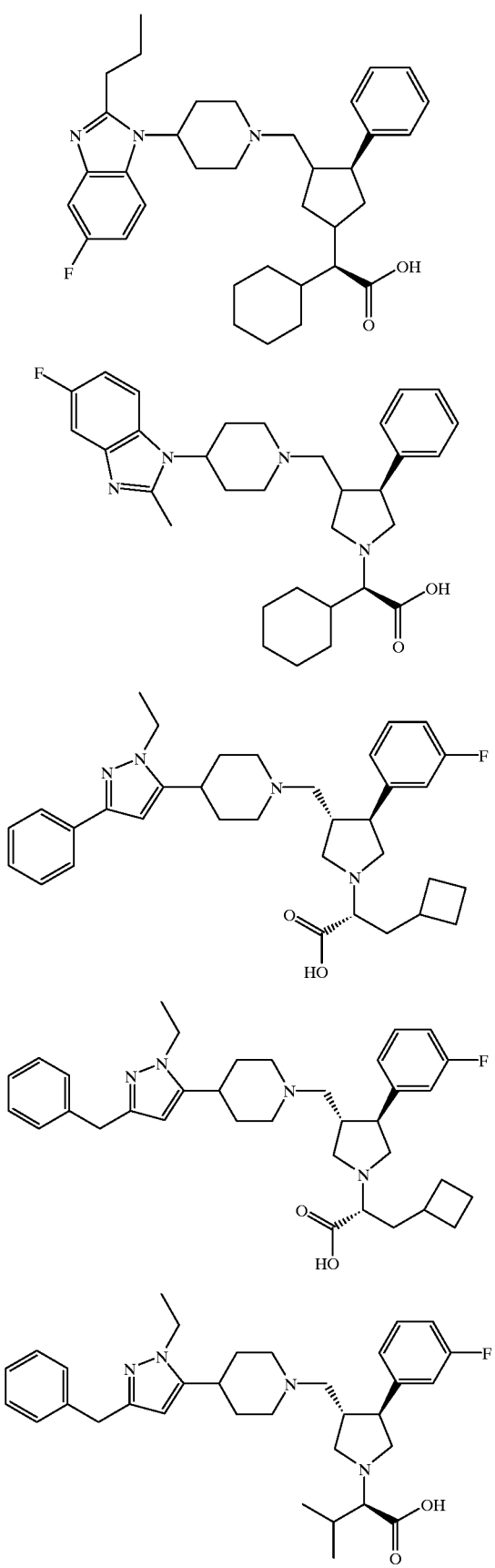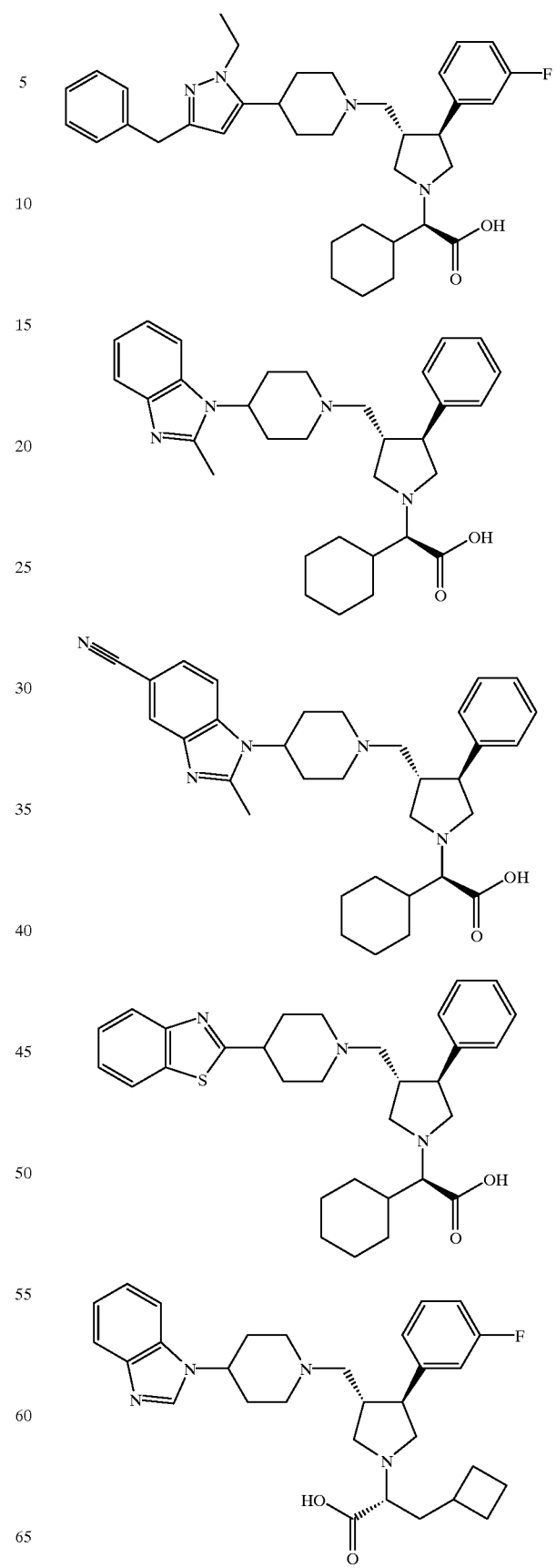

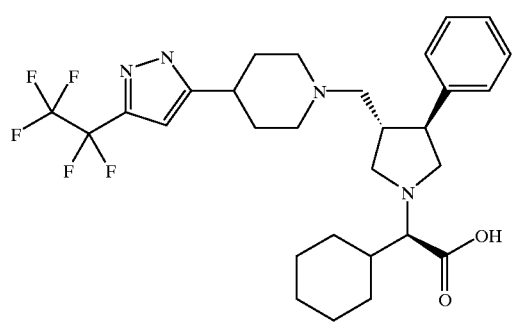
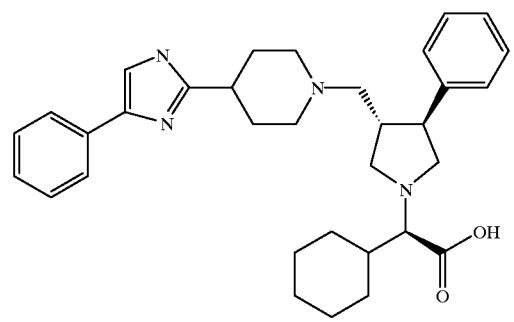
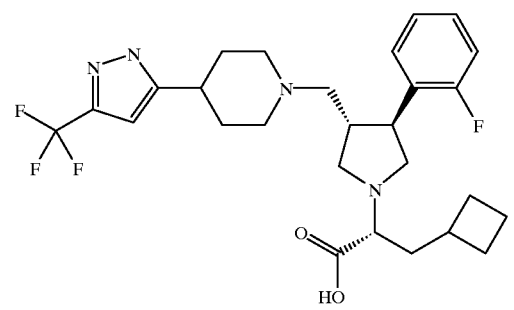
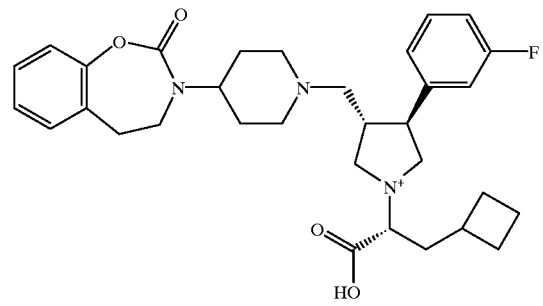
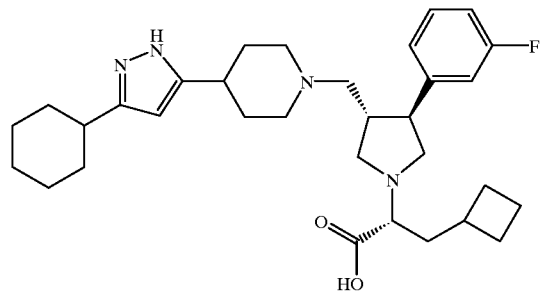
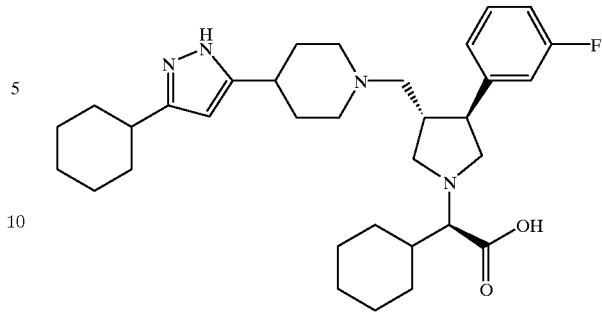
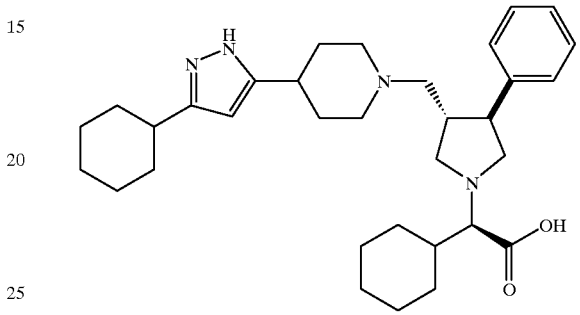
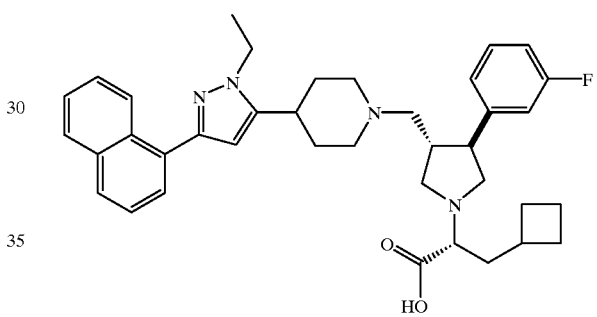
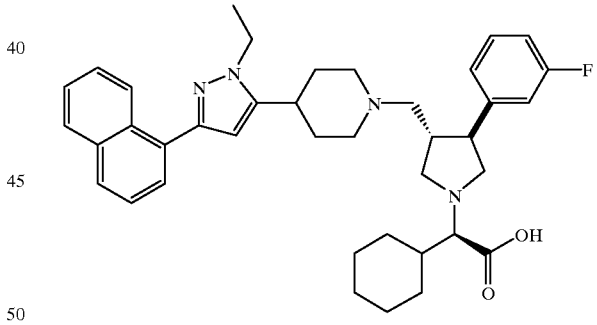
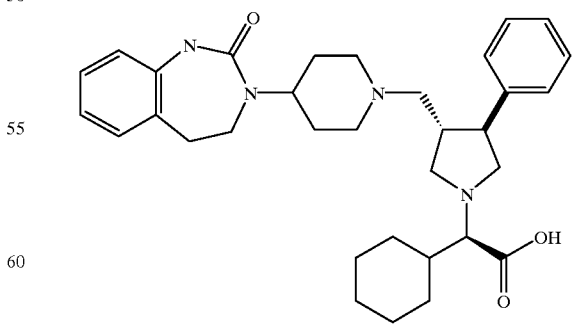

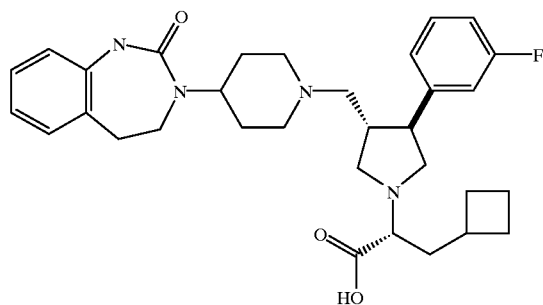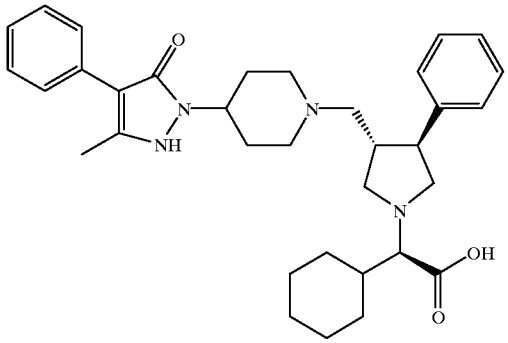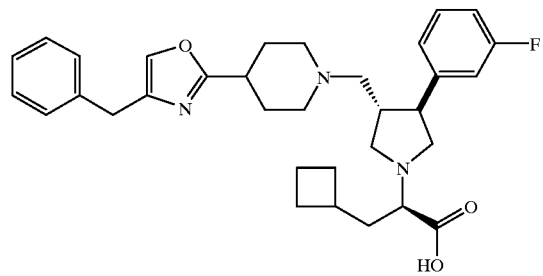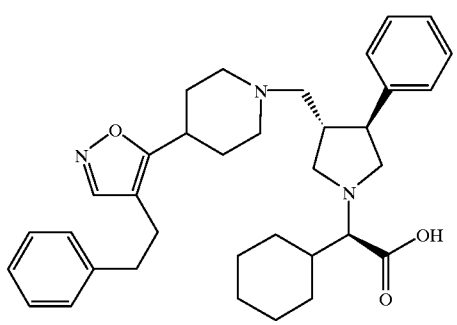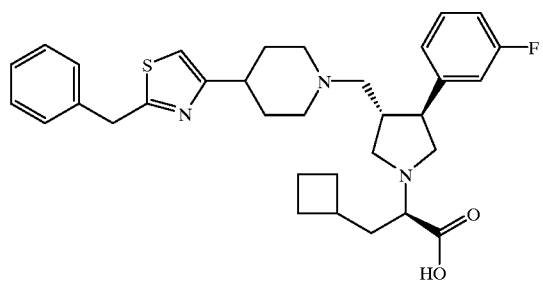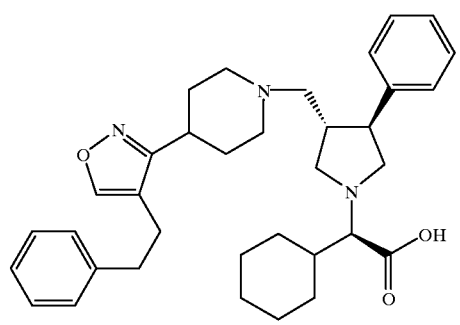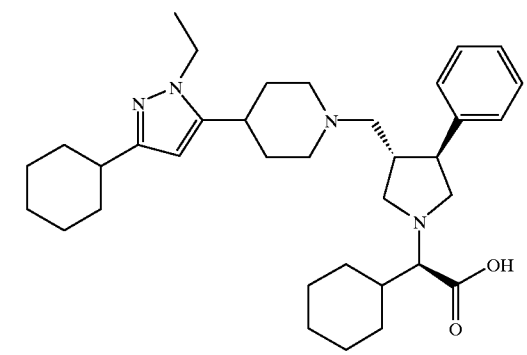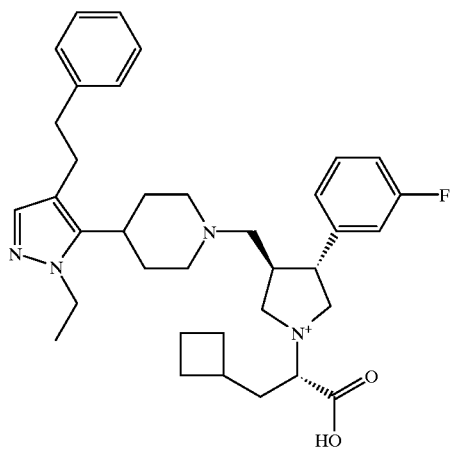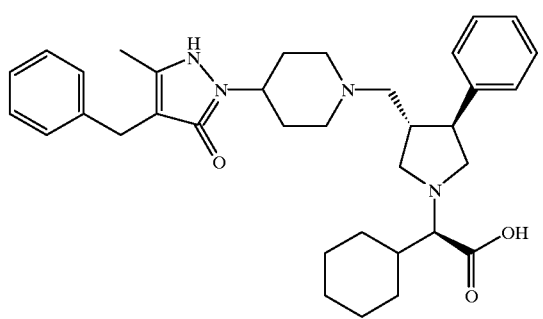

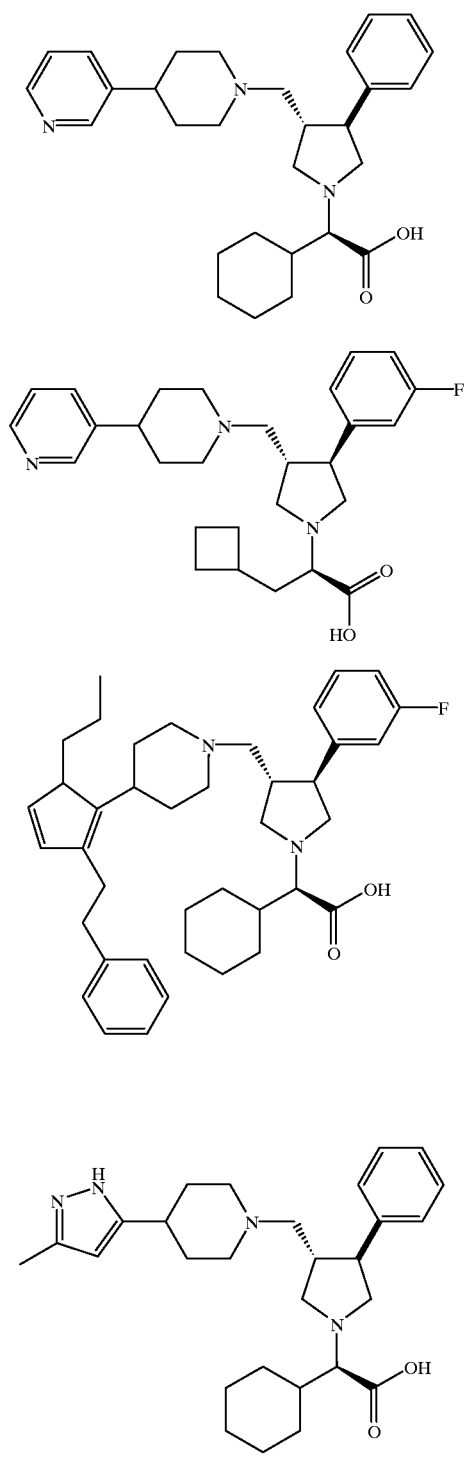
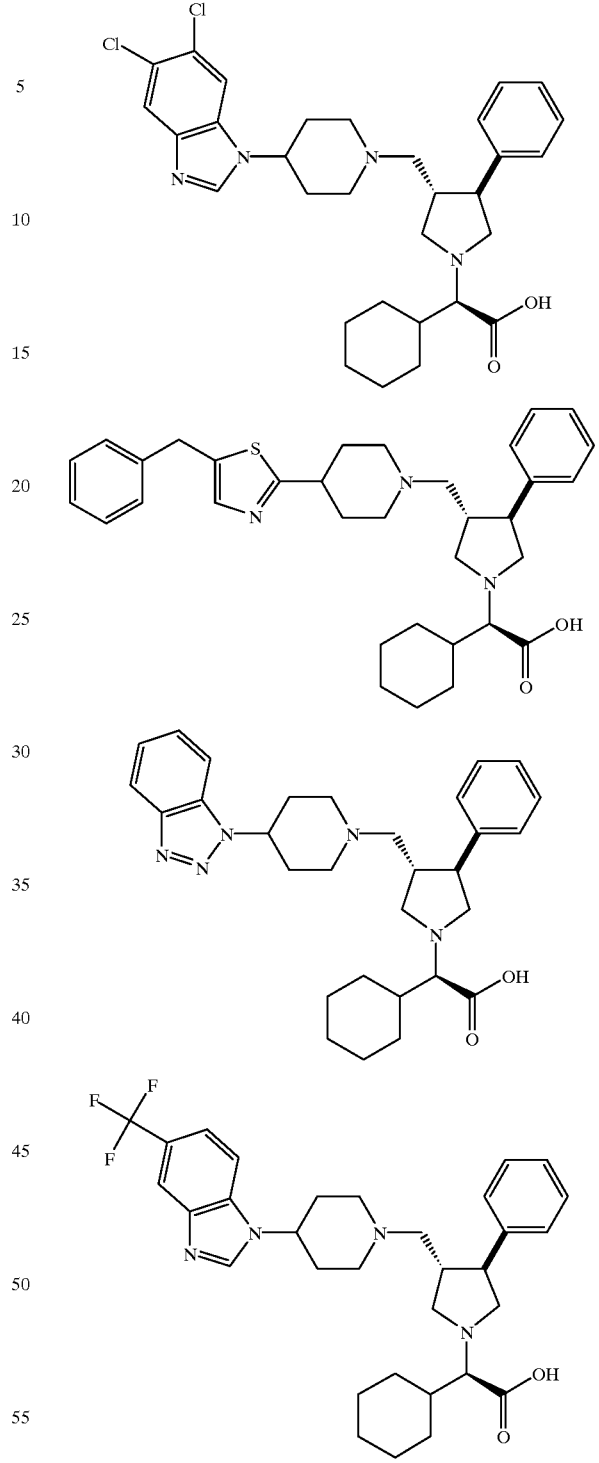

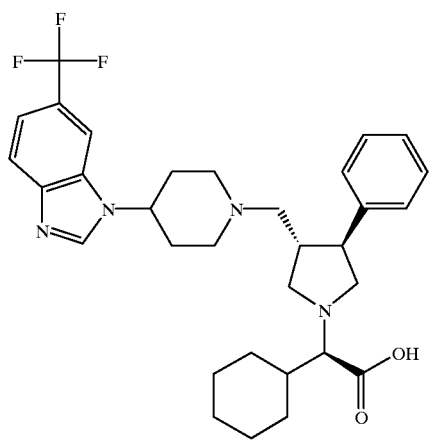
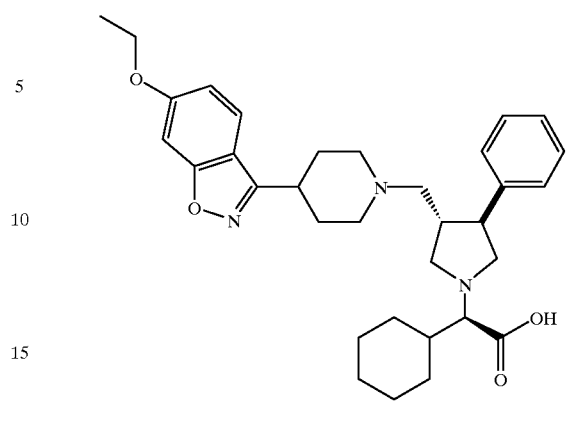
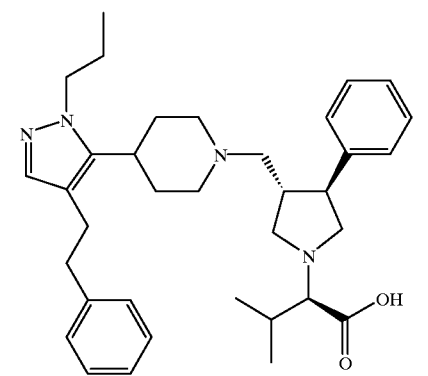
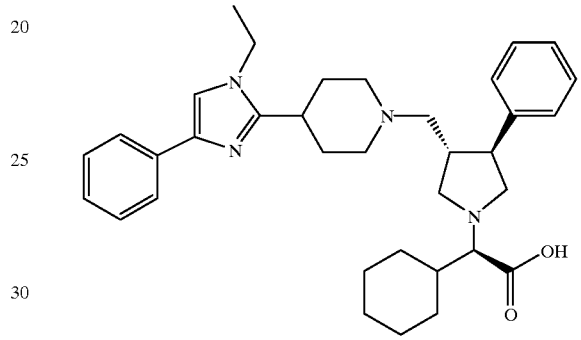
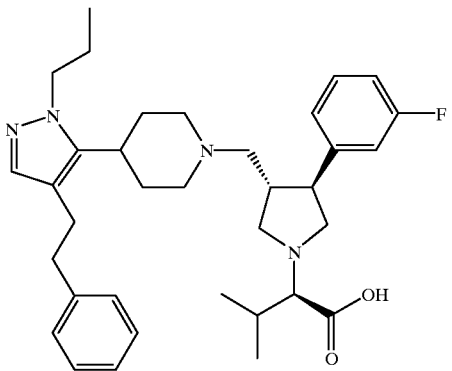
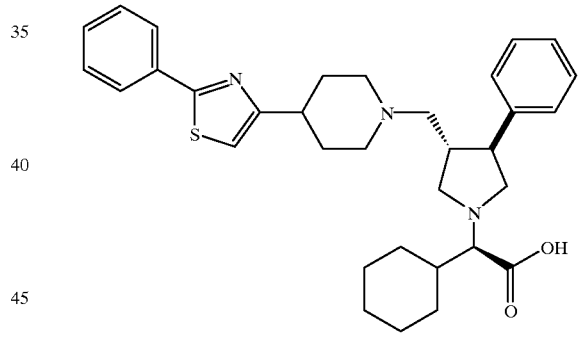
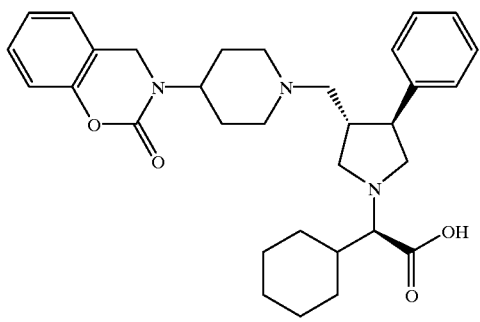
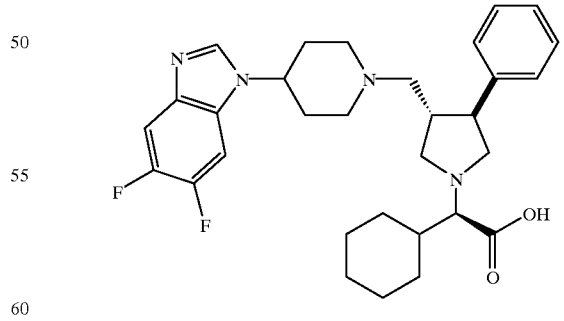

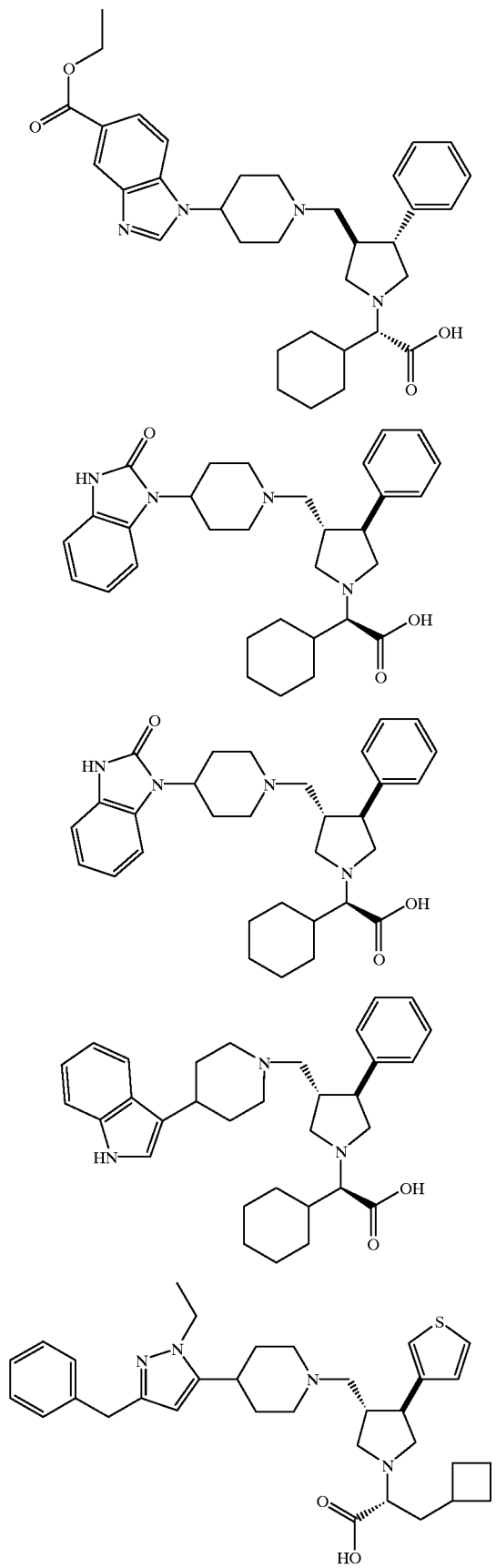
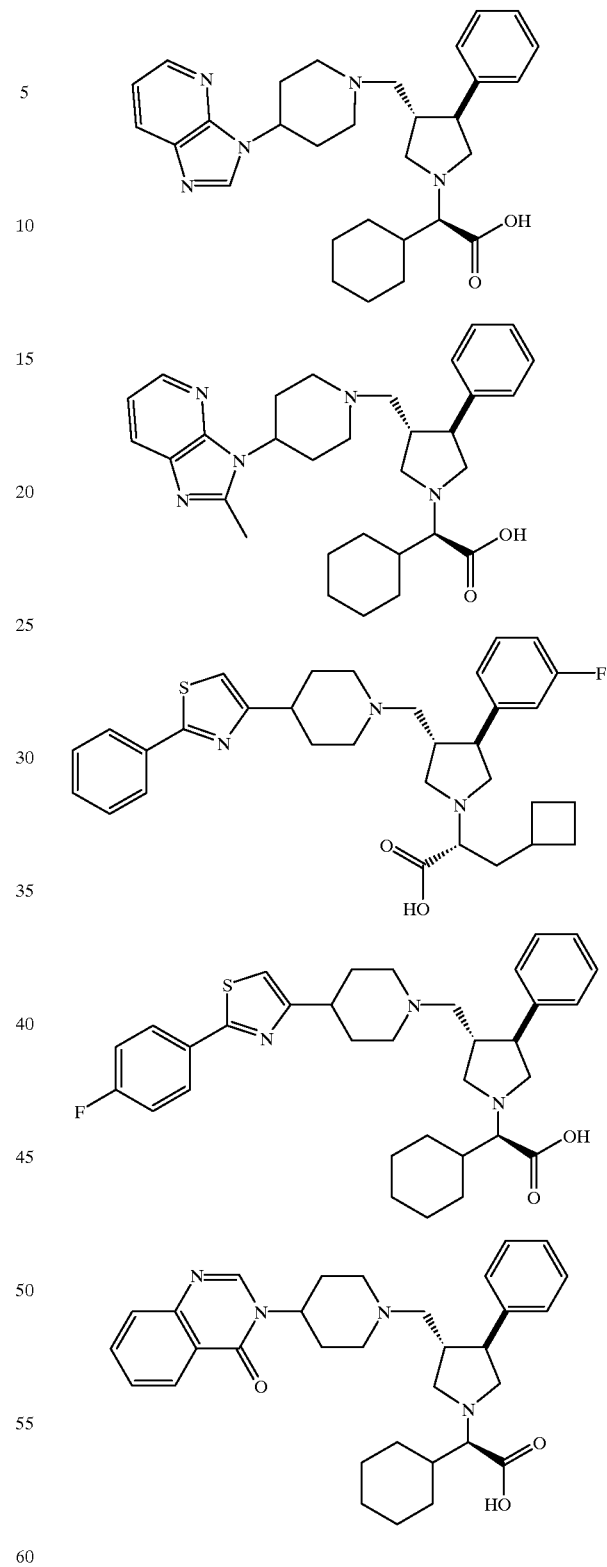
and pharmaceutically acceptable salts thereof and individual diastereomers thereof.
Specific compounds within the present invention also include compounds selected from the group consisting of:

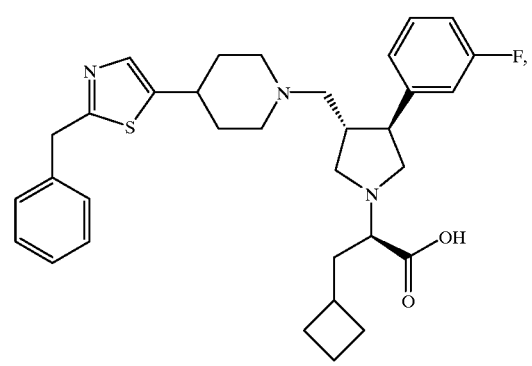
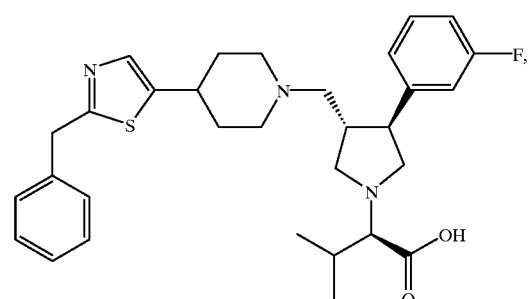
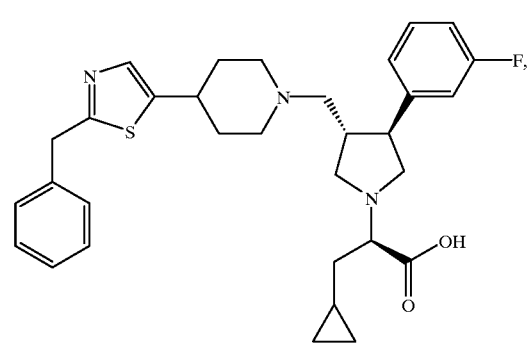
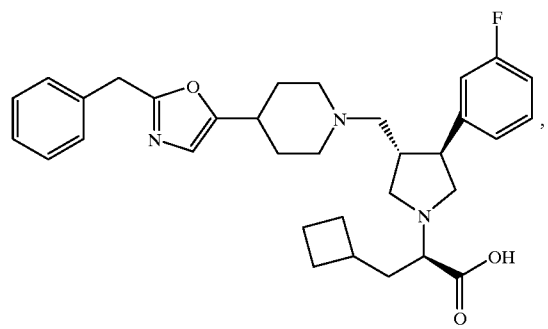
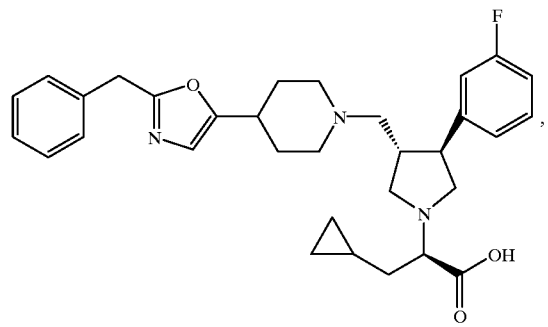
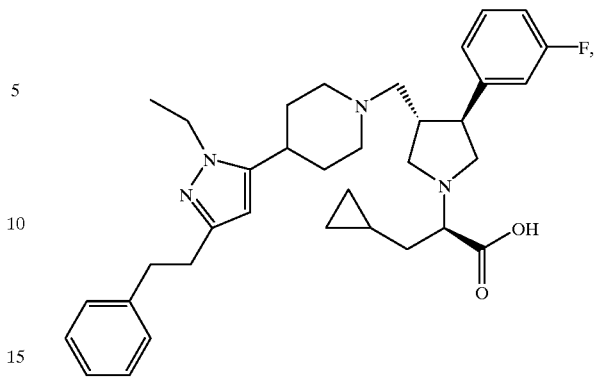
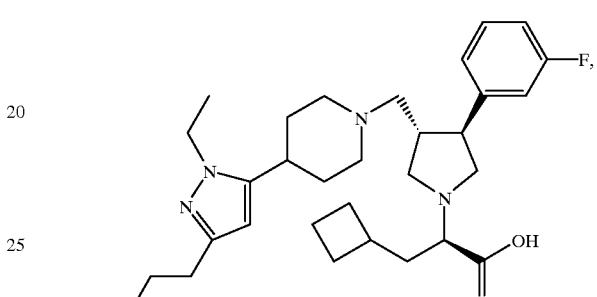
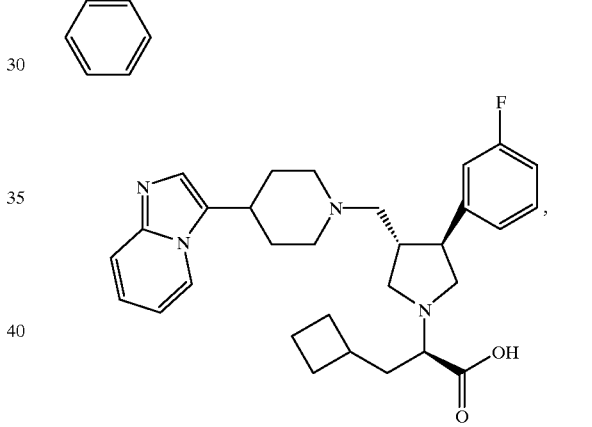
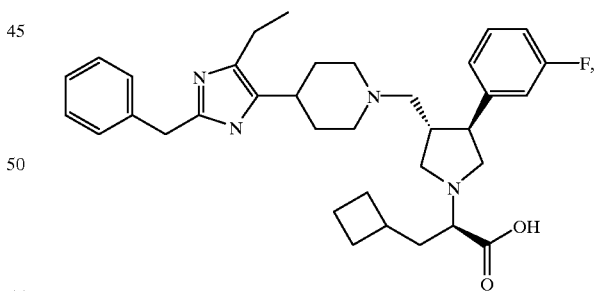
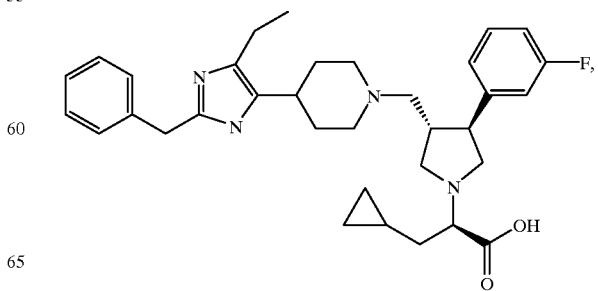

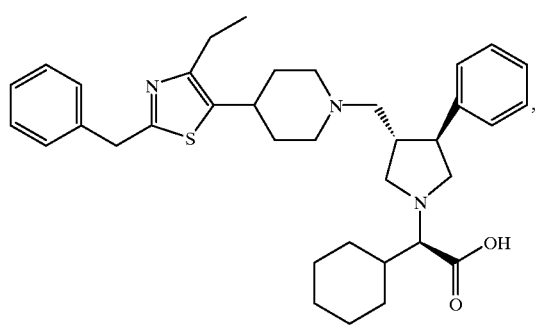
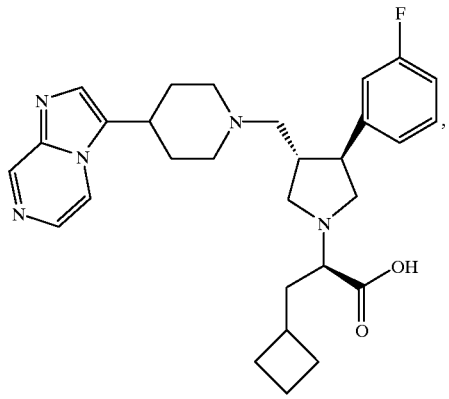
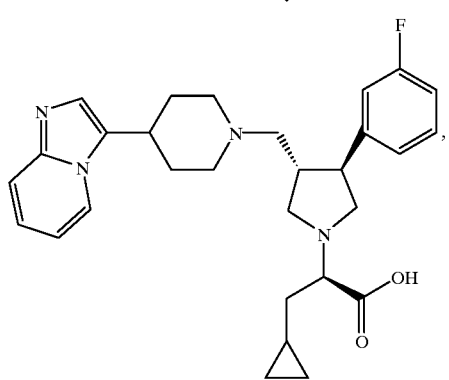
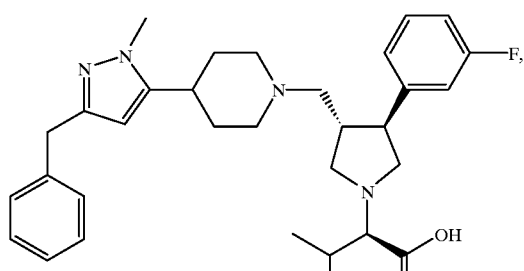
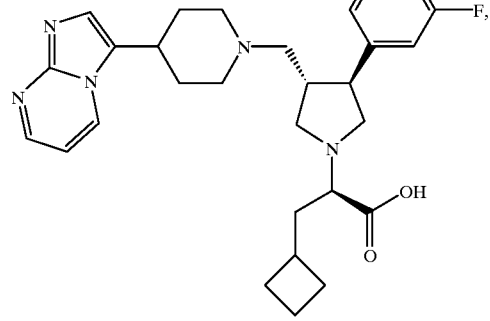

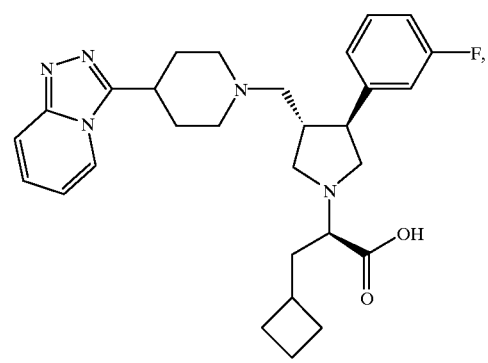
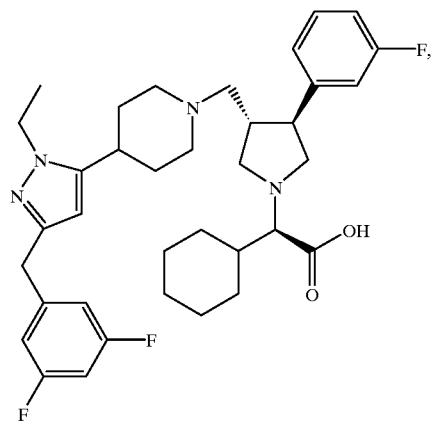
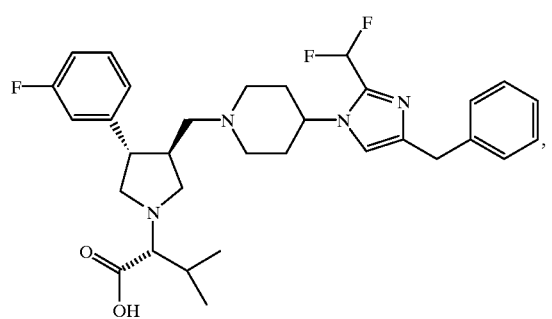
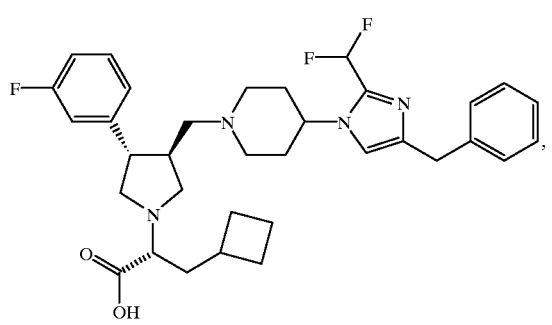
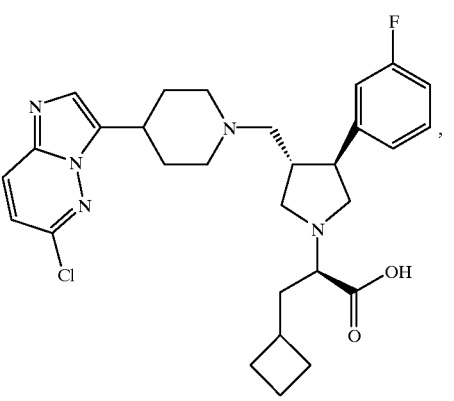
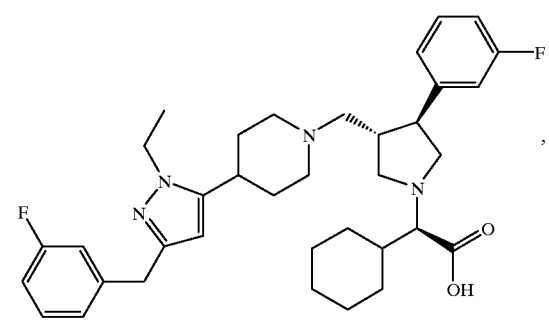
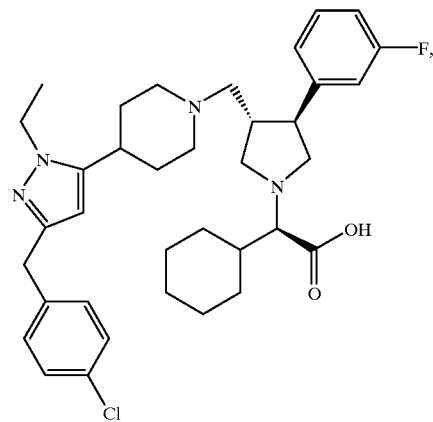
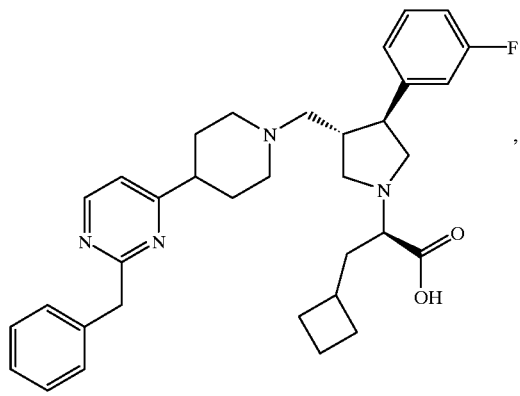

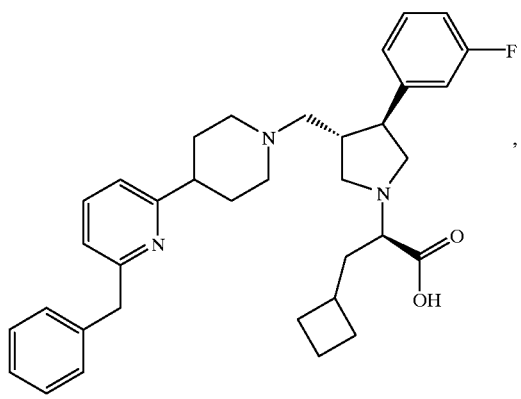
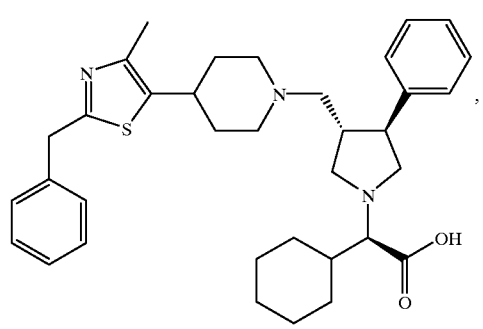
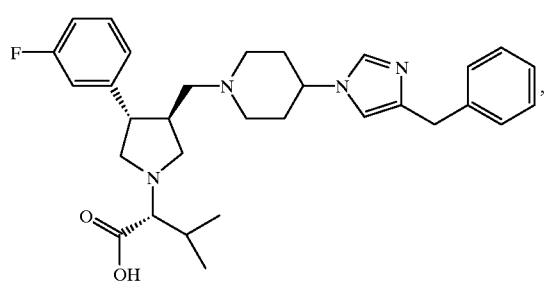
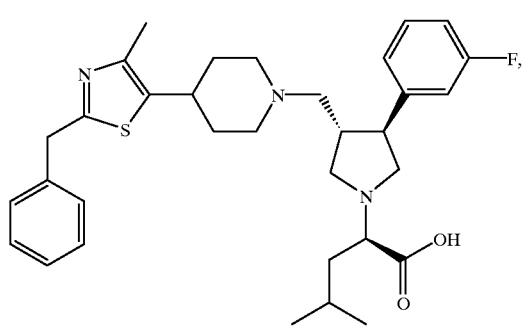
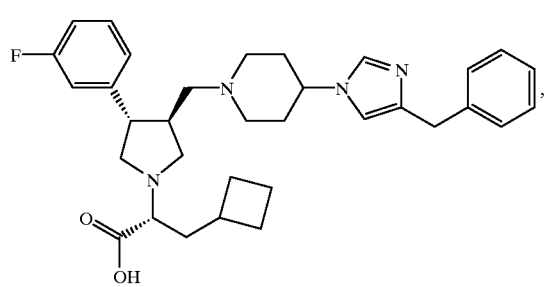
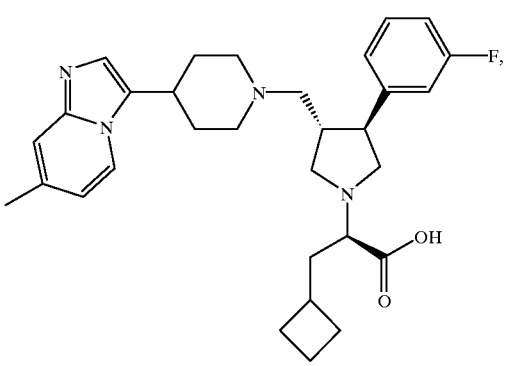
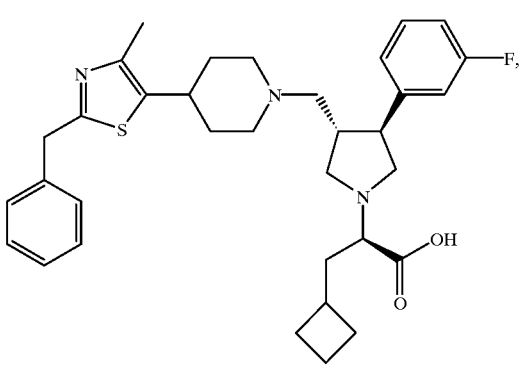
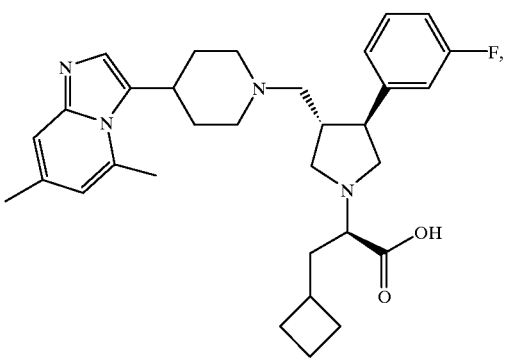

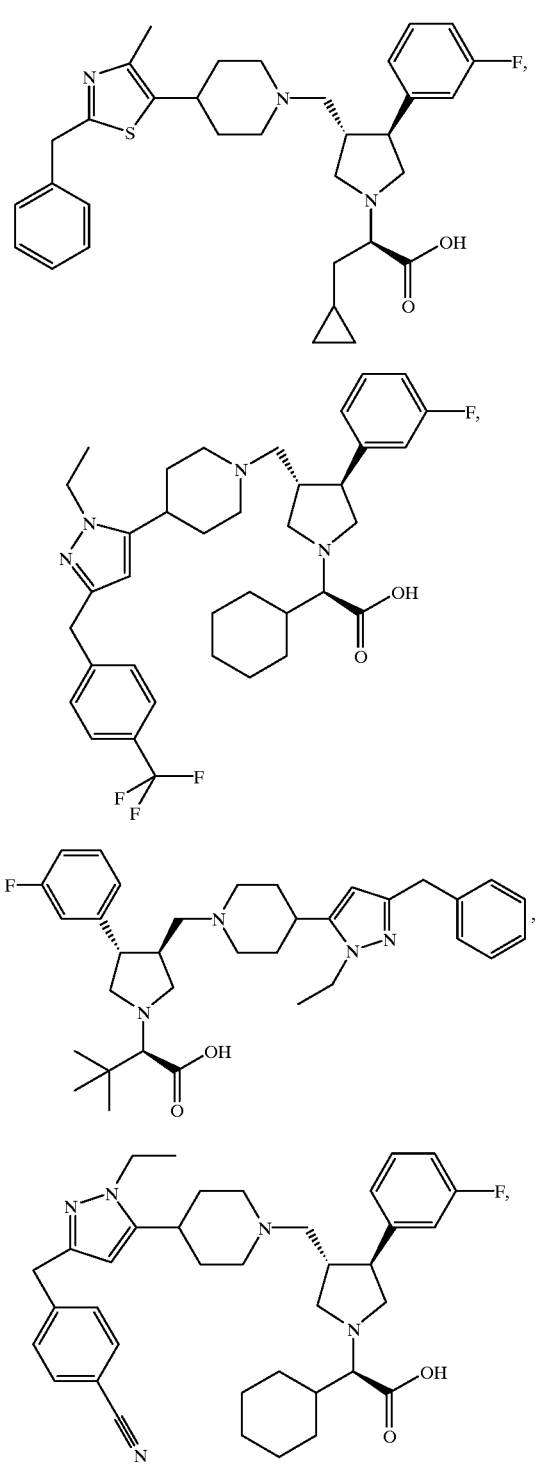
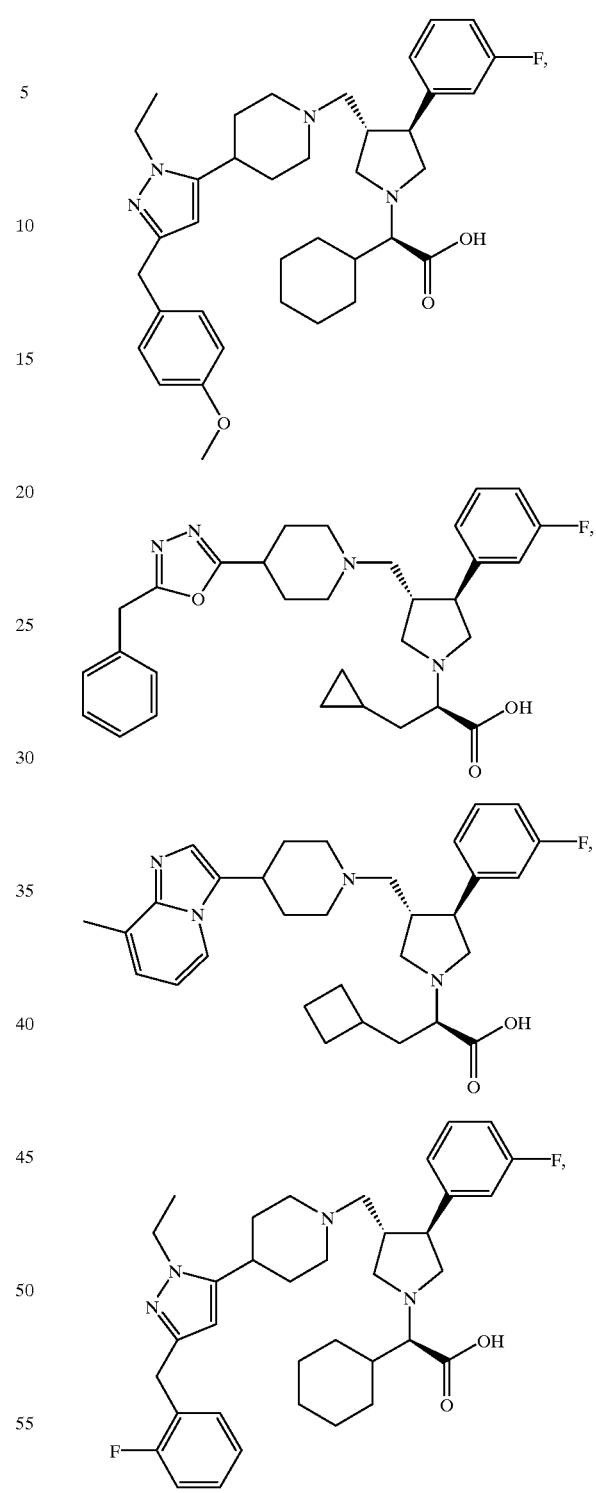

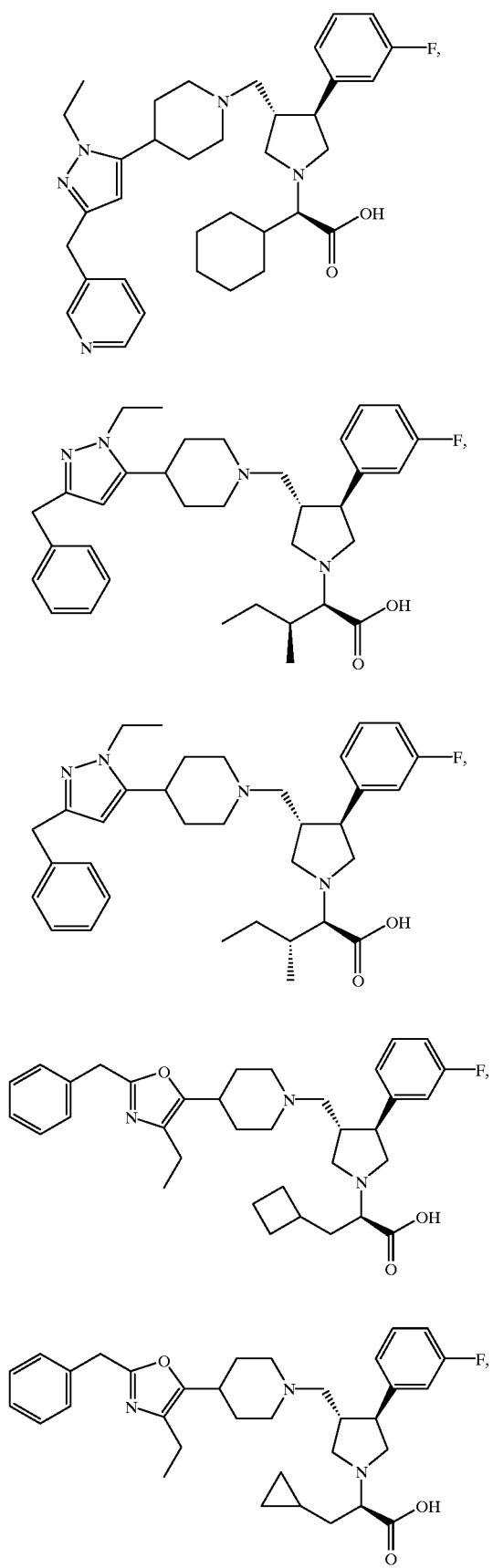
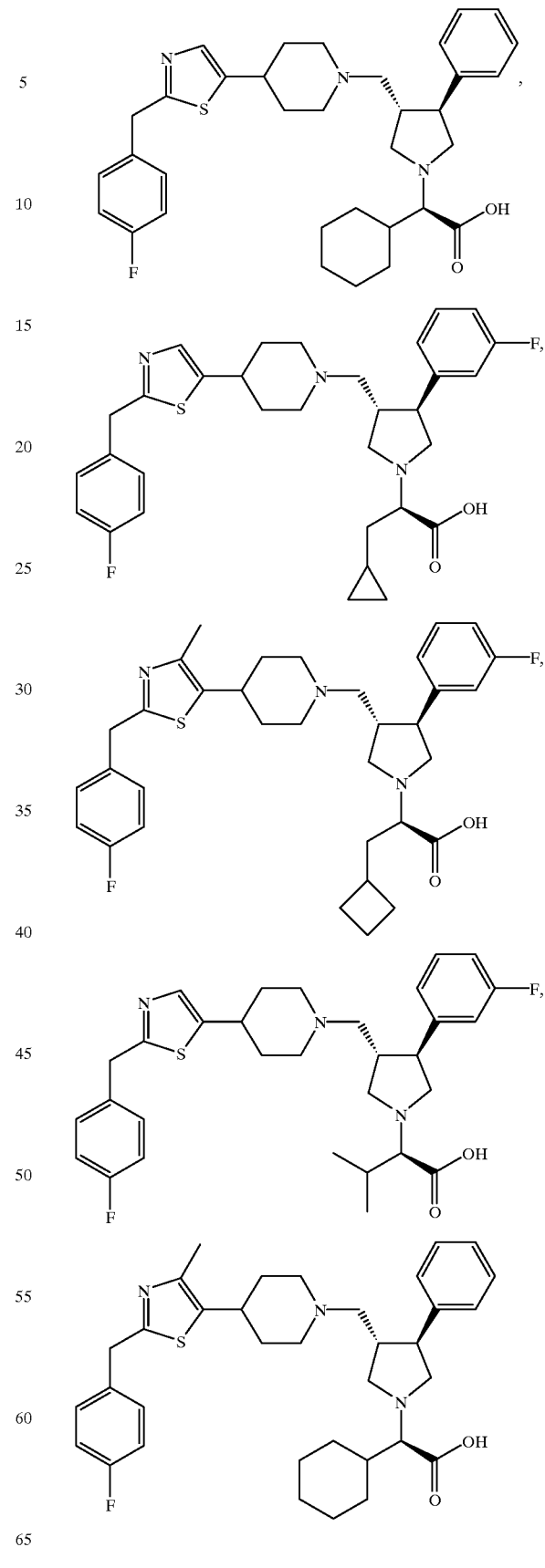

-continued
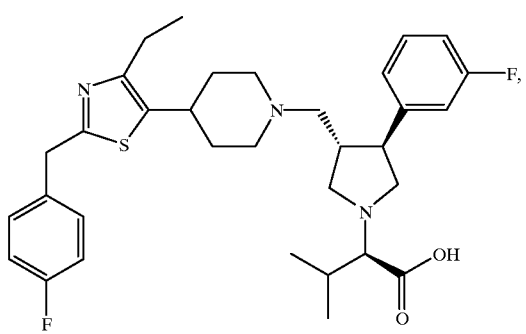
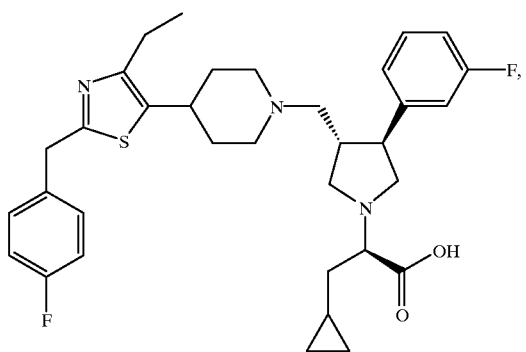
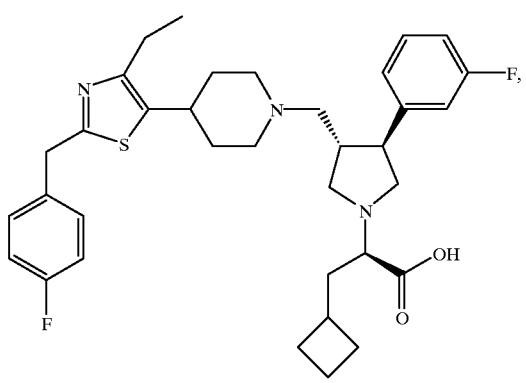
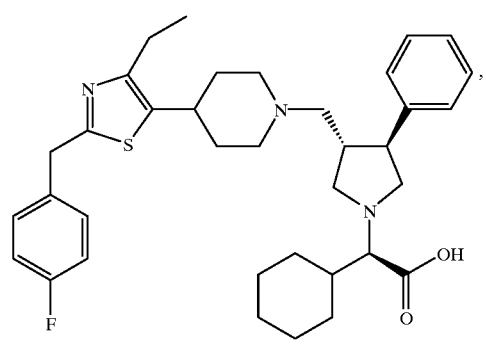
-continued
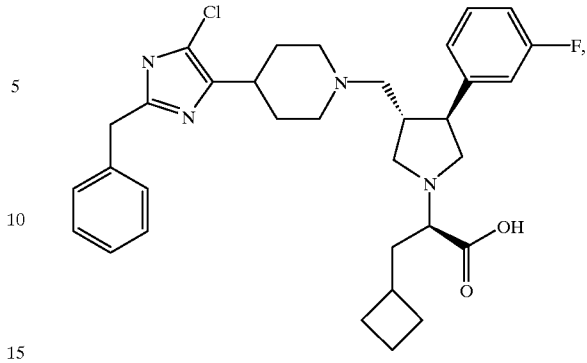
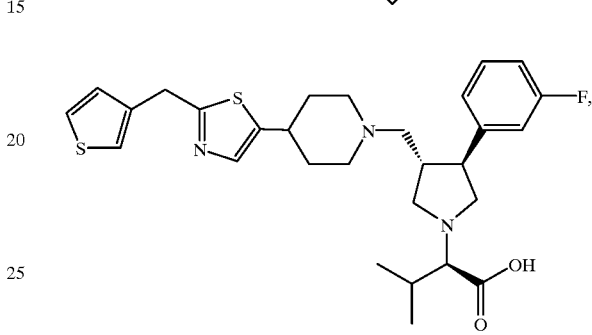
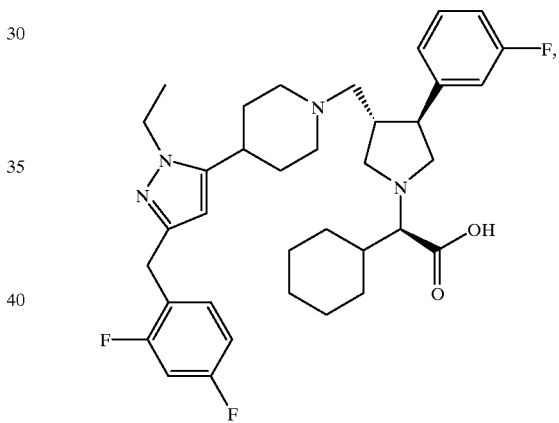
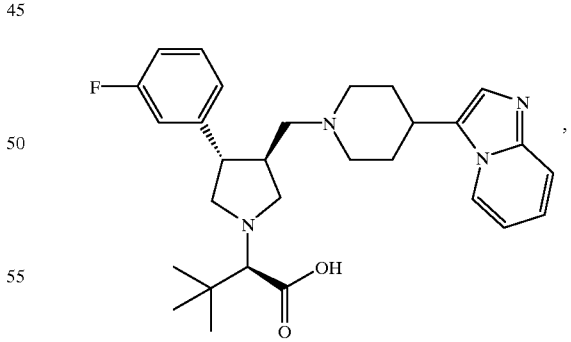

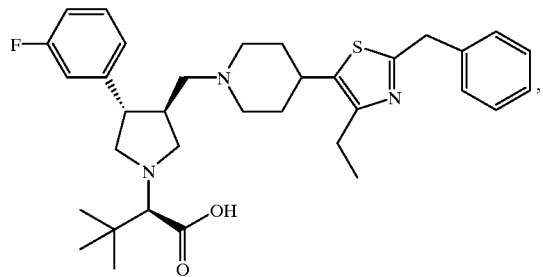
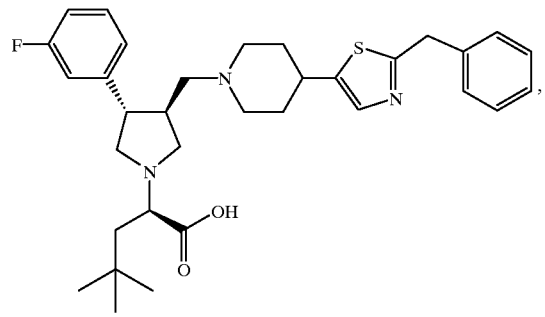
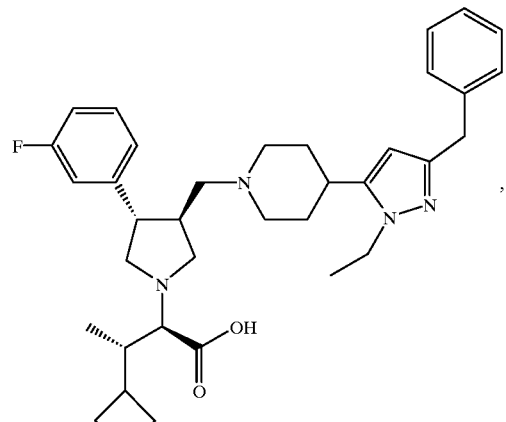
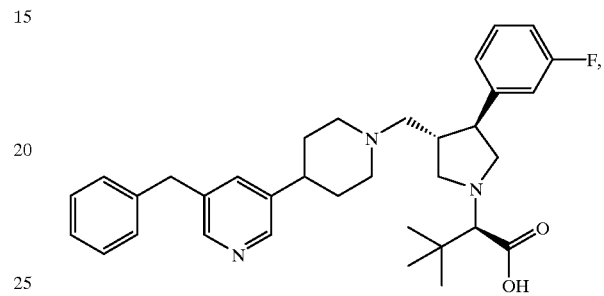
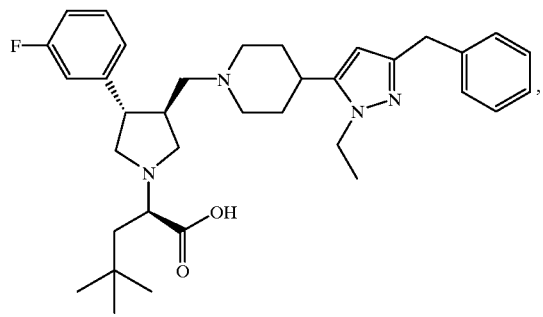
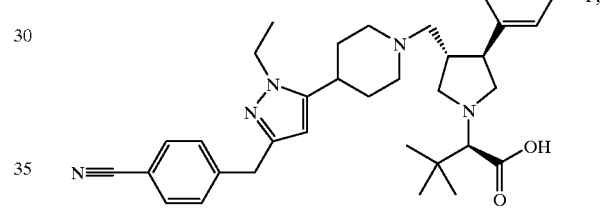
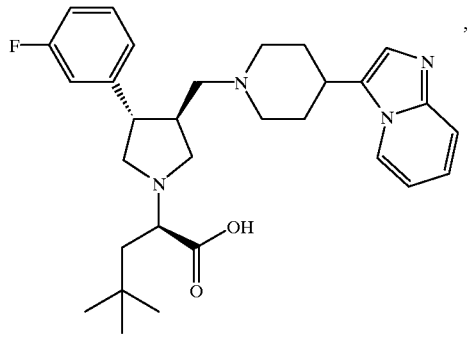
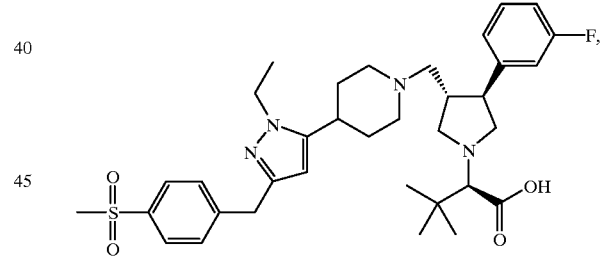
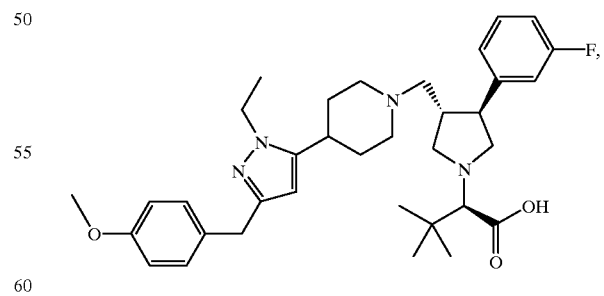

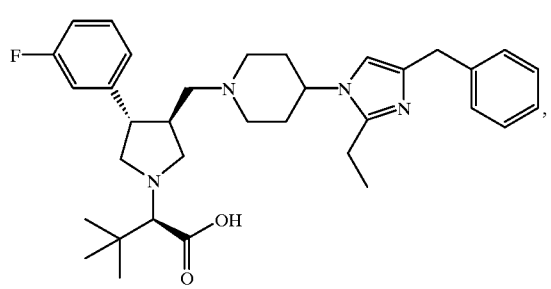
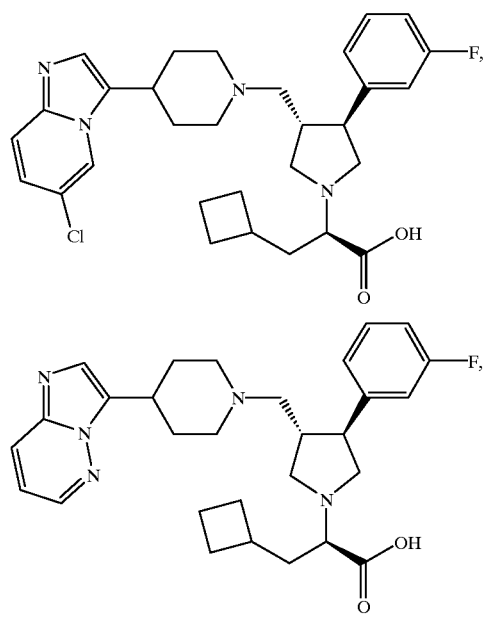
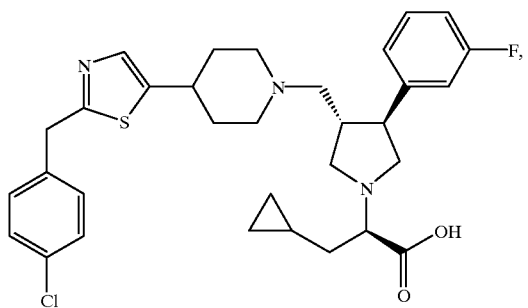
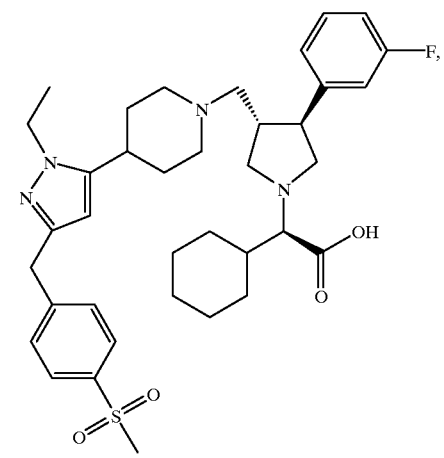
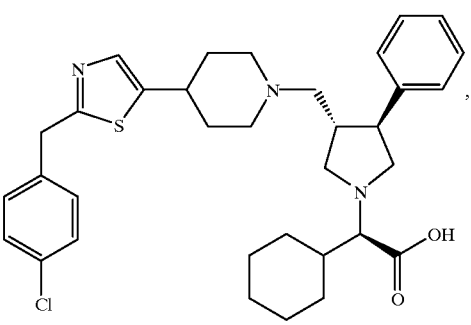
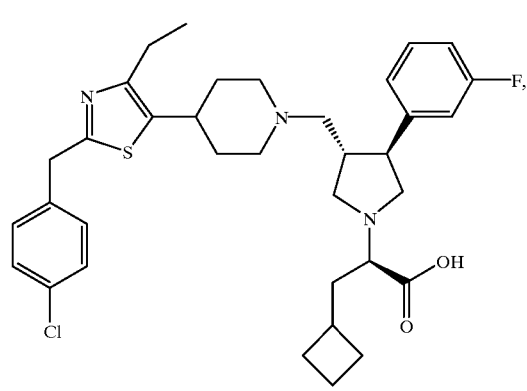
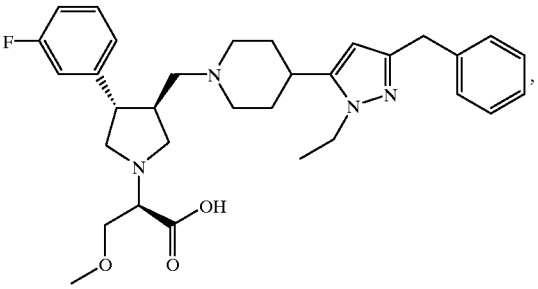
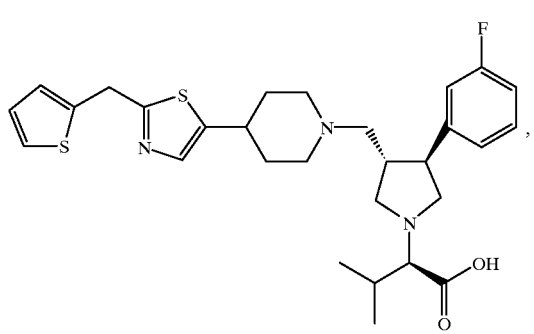
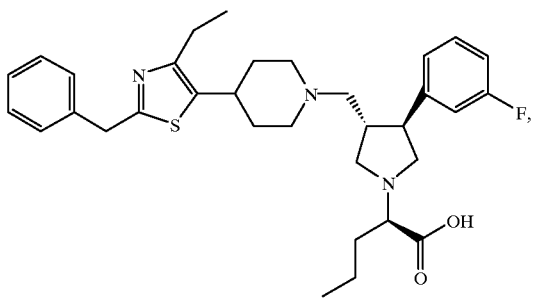

-continued
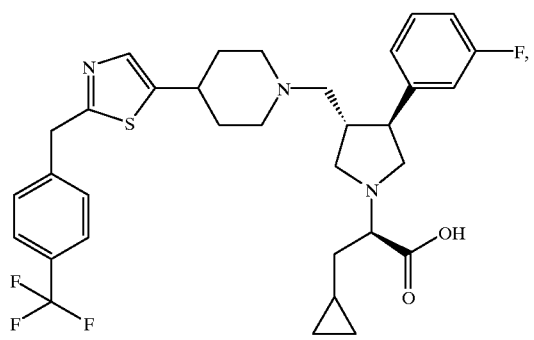
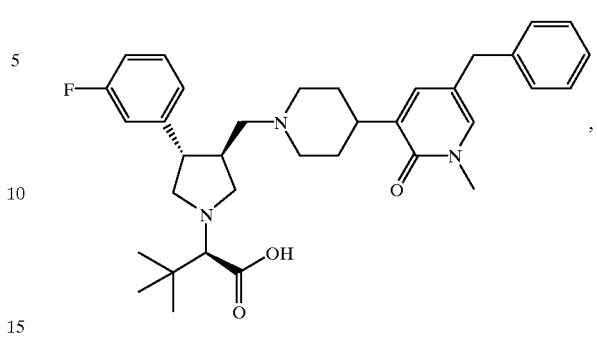
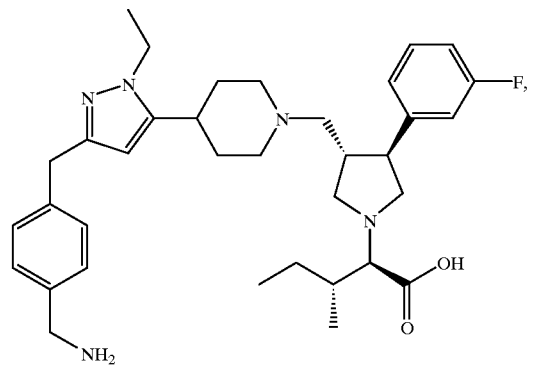
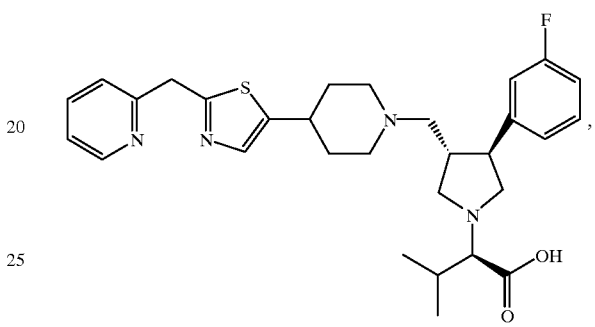
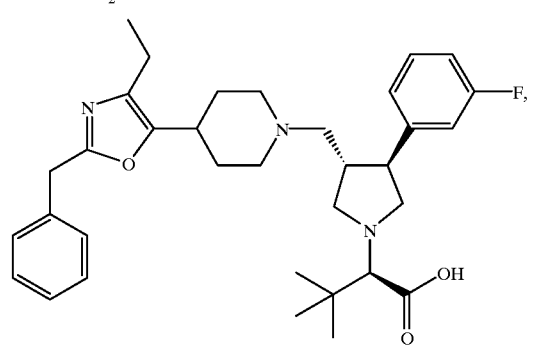
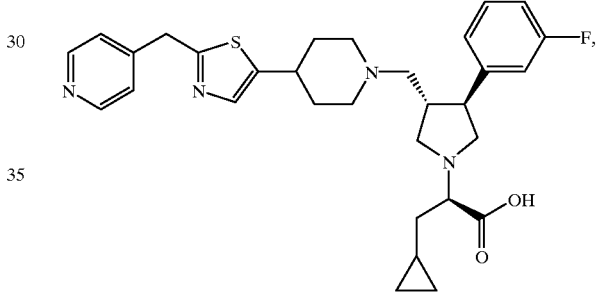
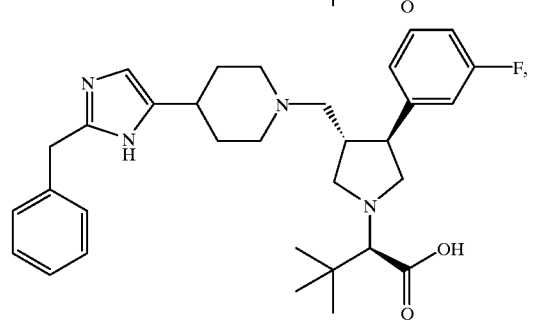
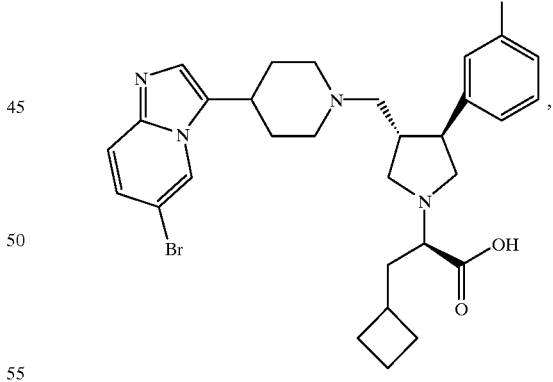

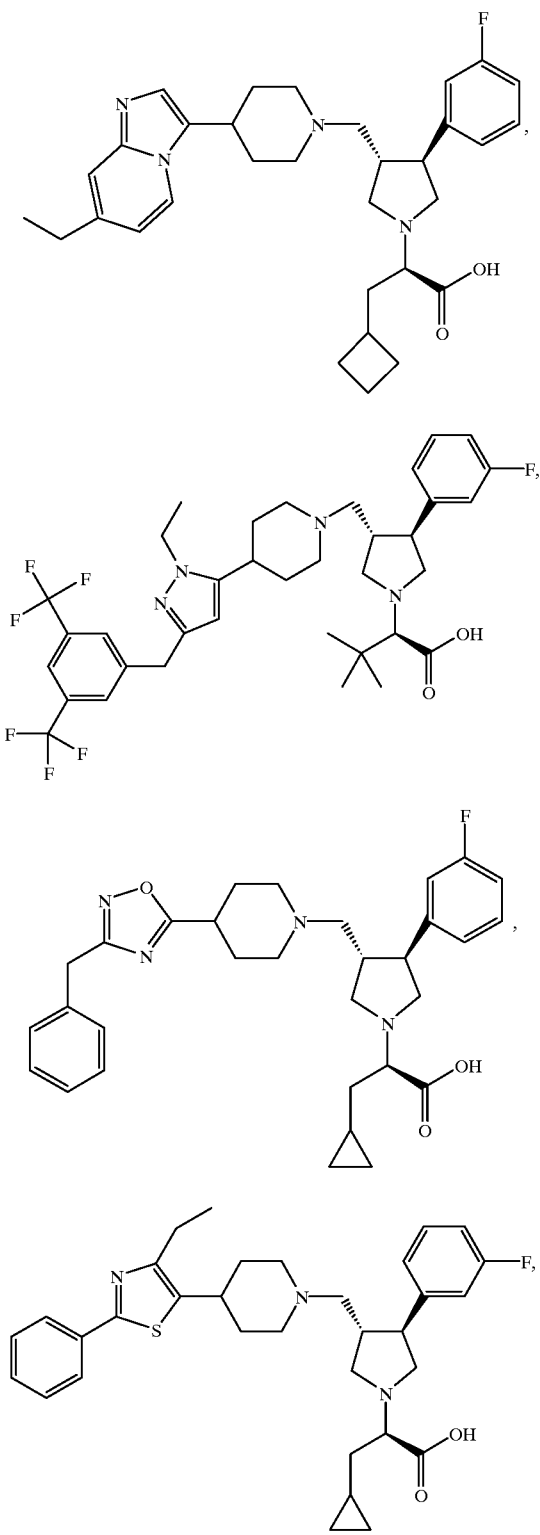
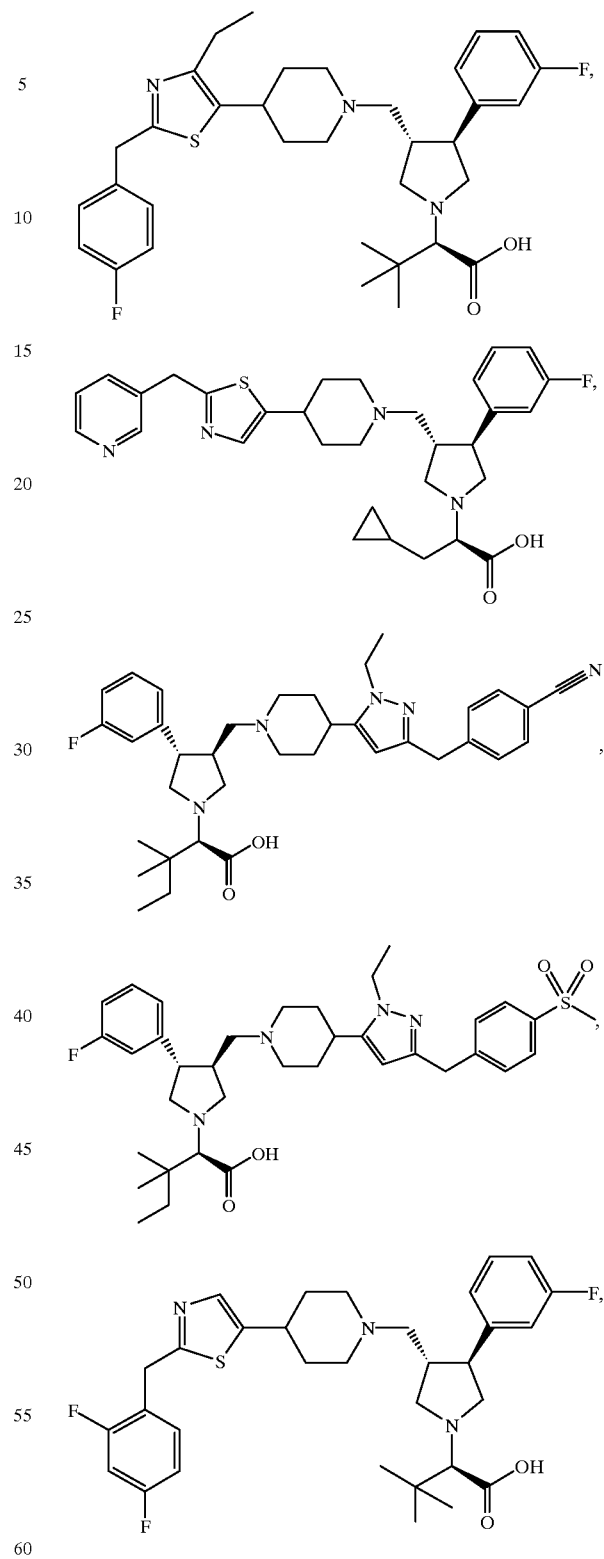

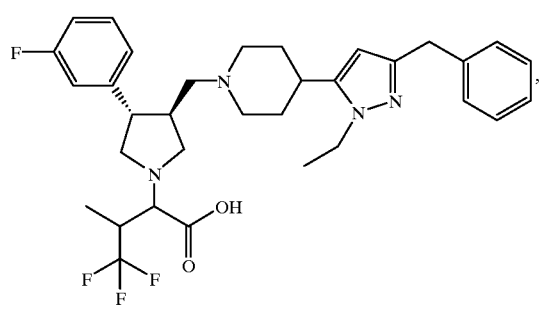
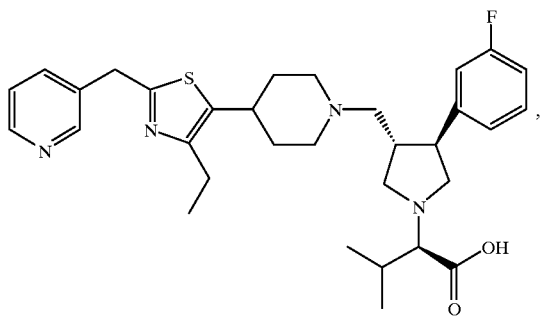
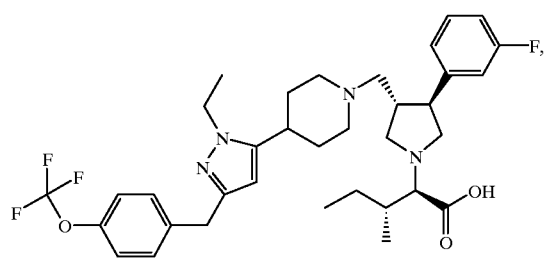
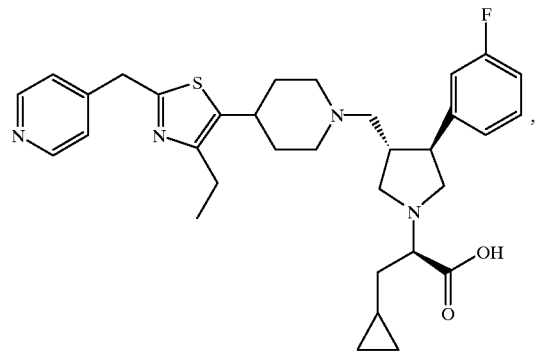
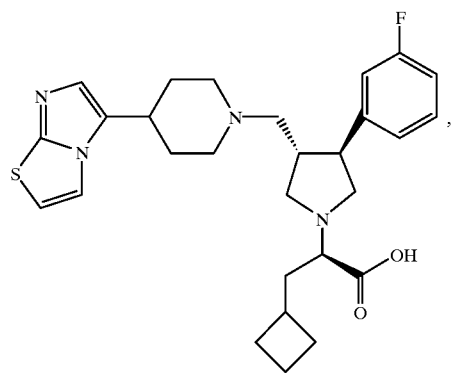
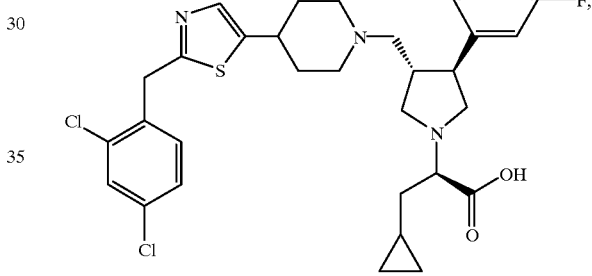
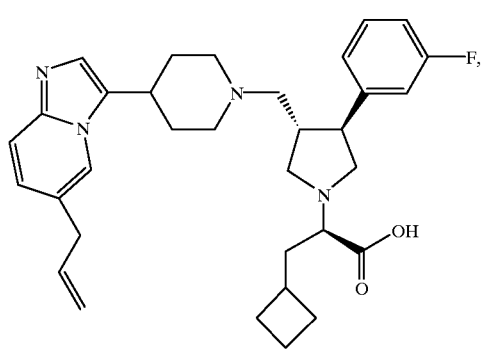
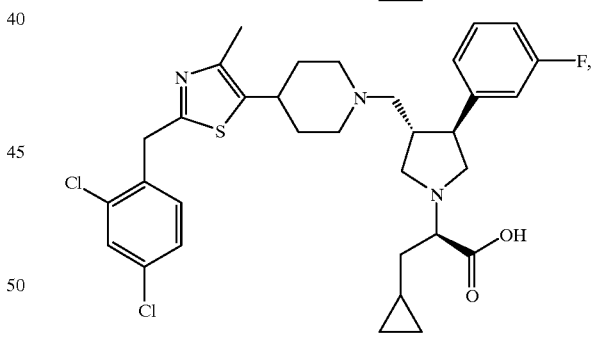
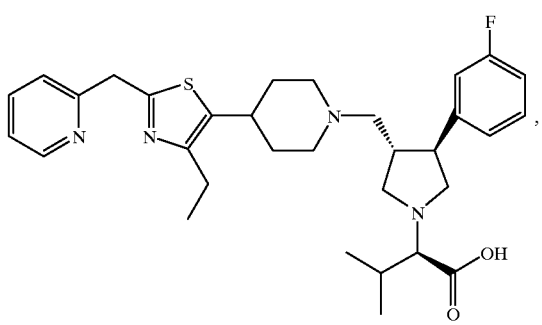
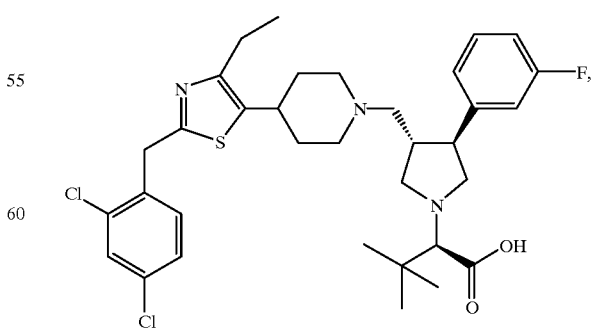

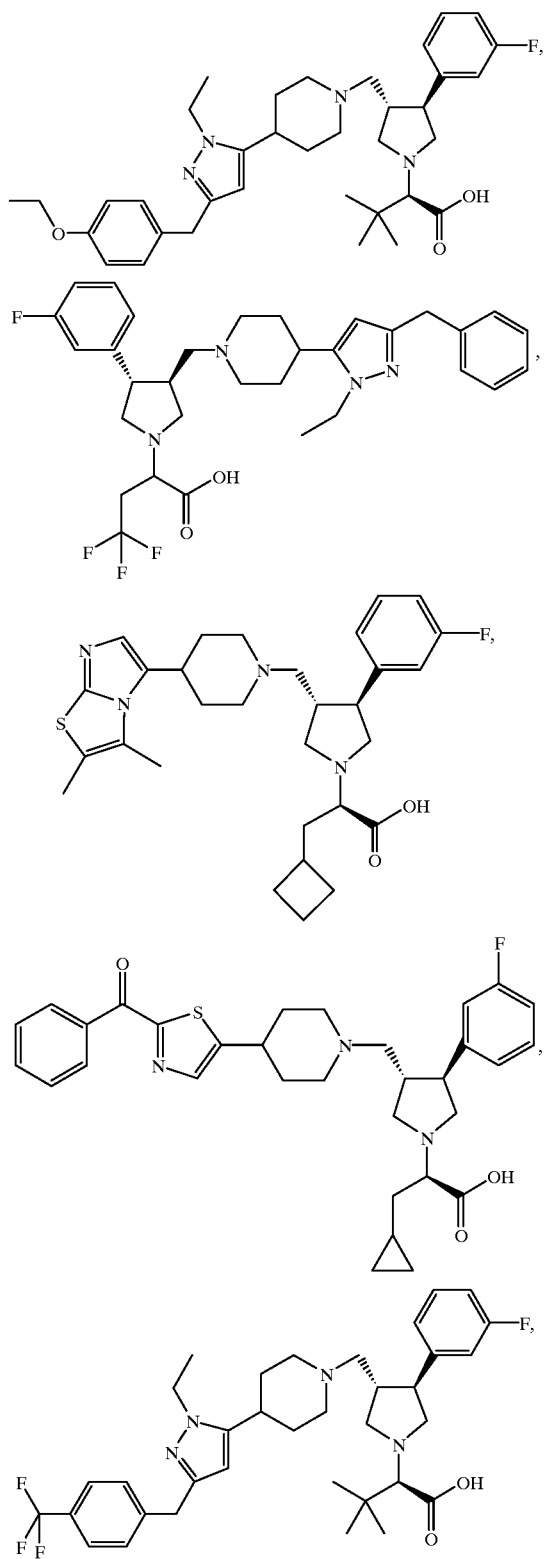
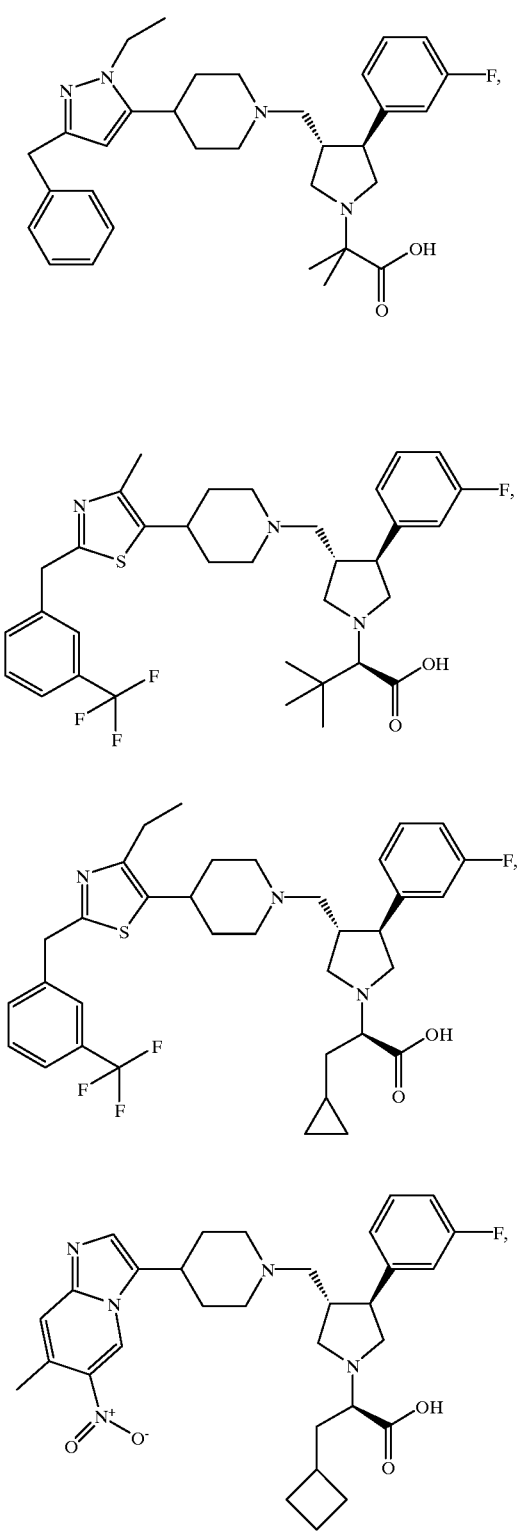

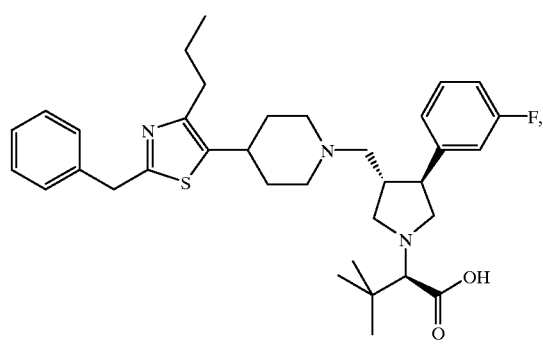
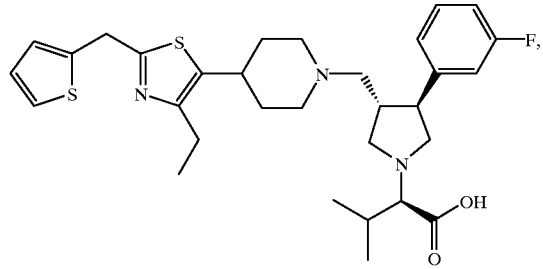
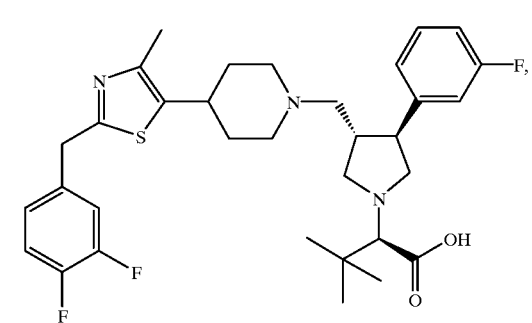
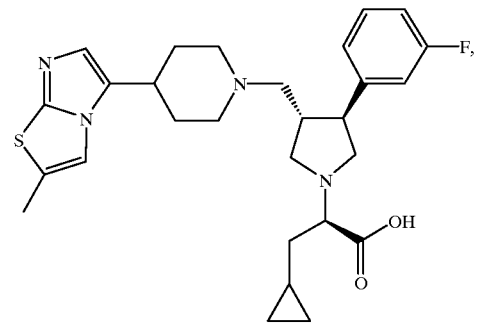
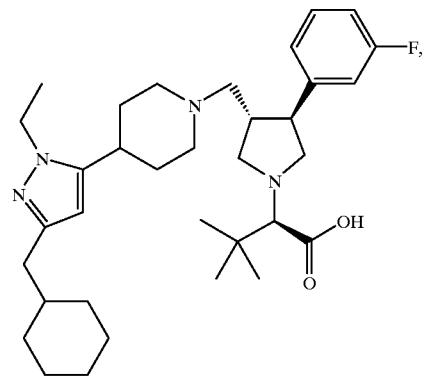
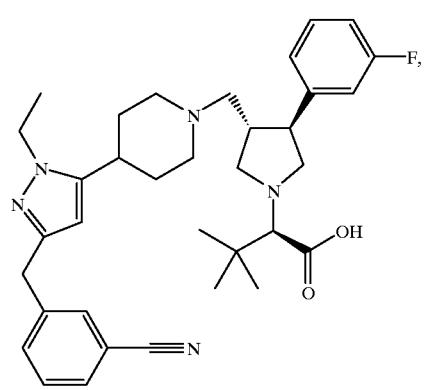
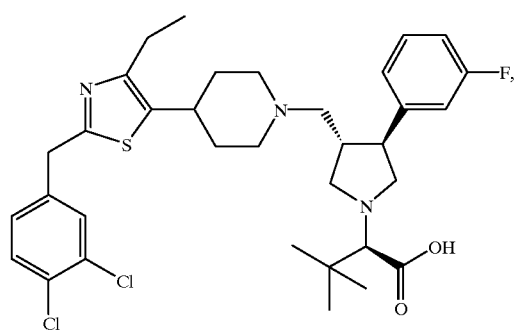
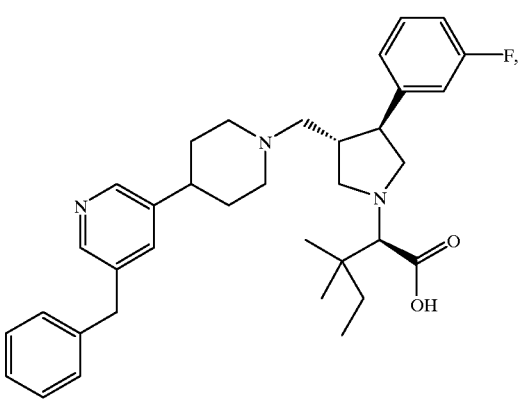
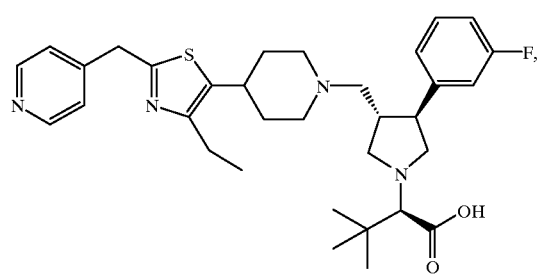
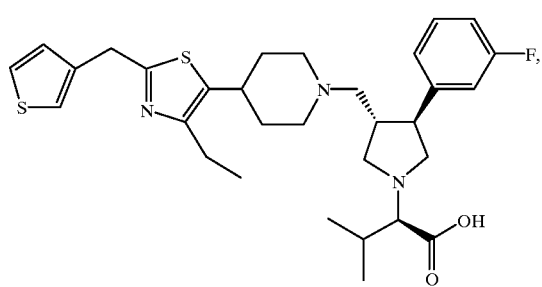

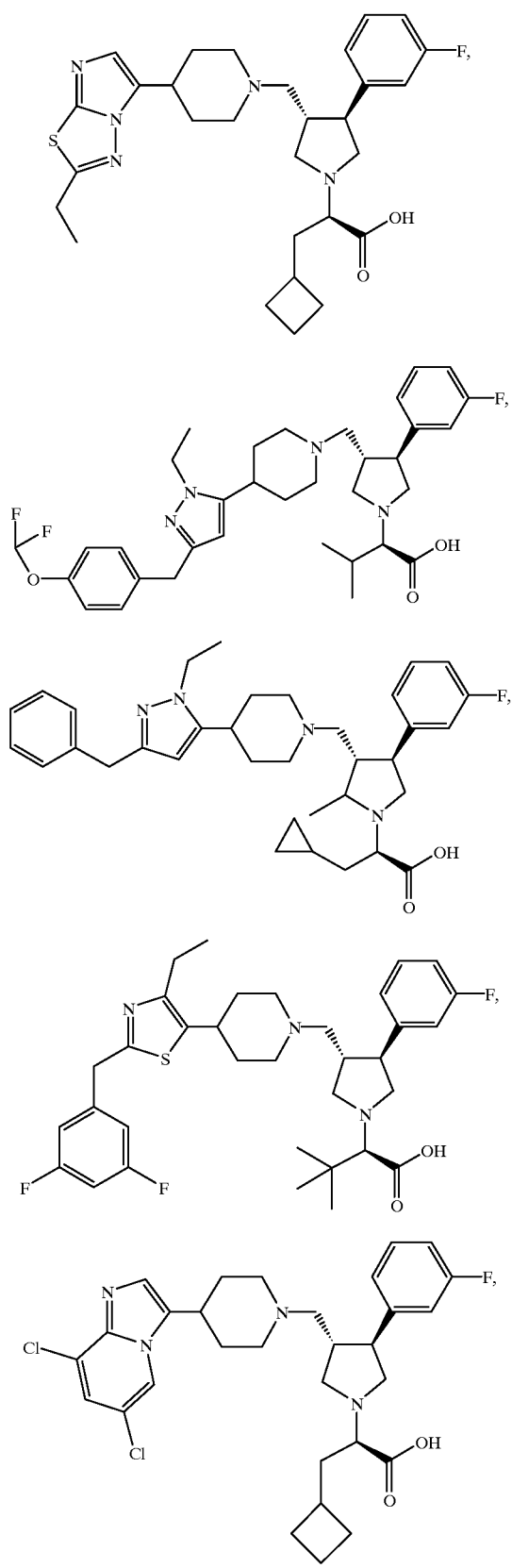
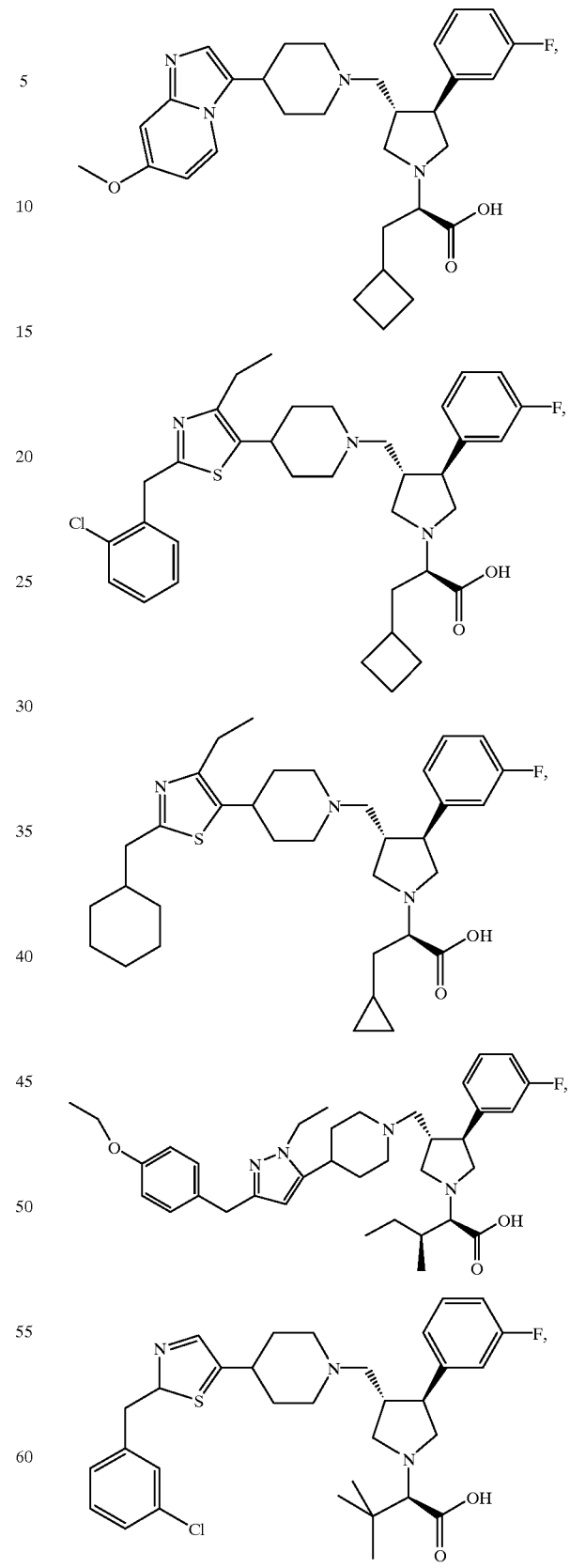

81
-continued
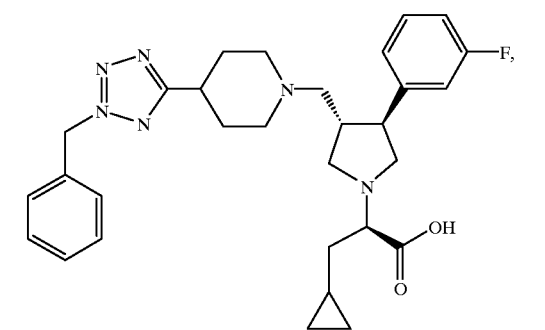
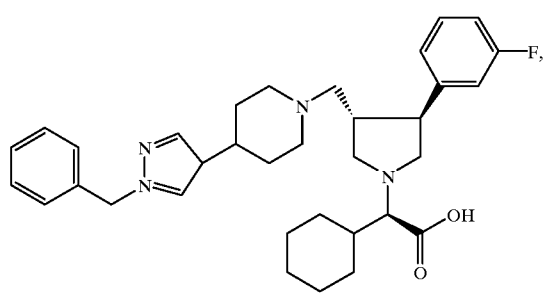
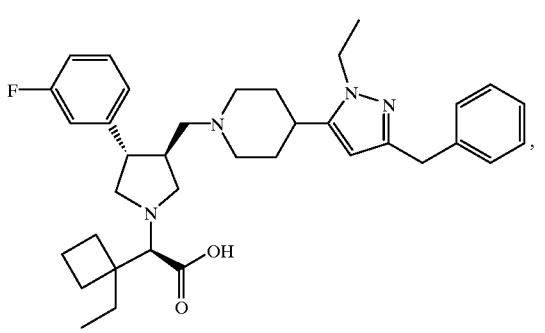
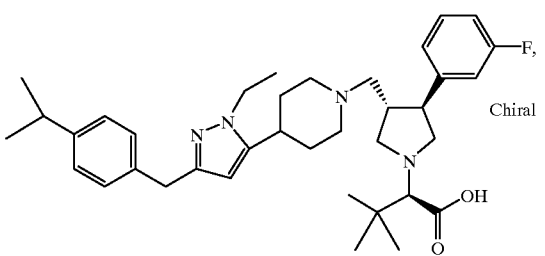
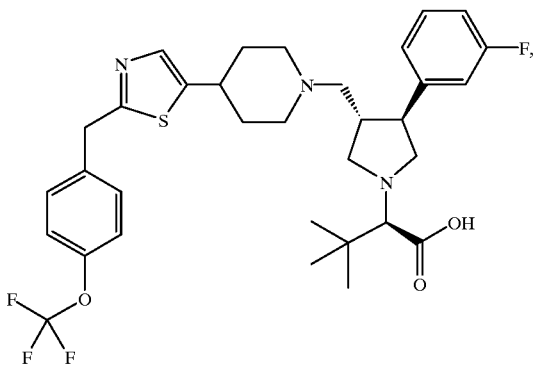
82
-continued
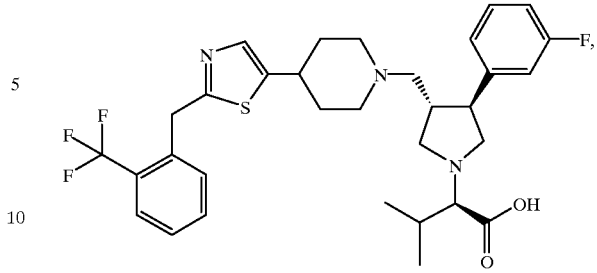
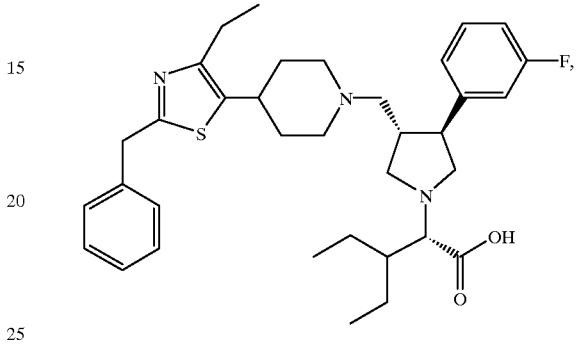
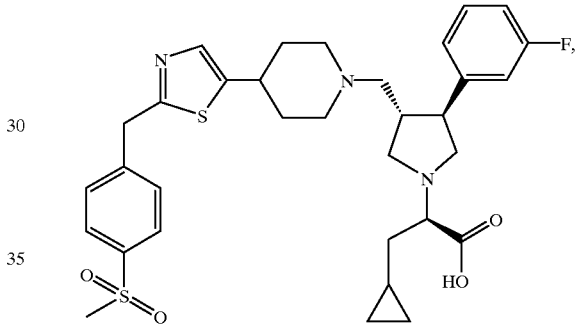
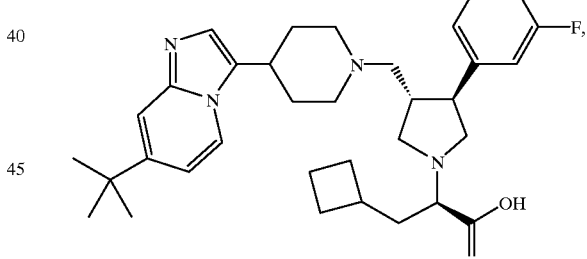
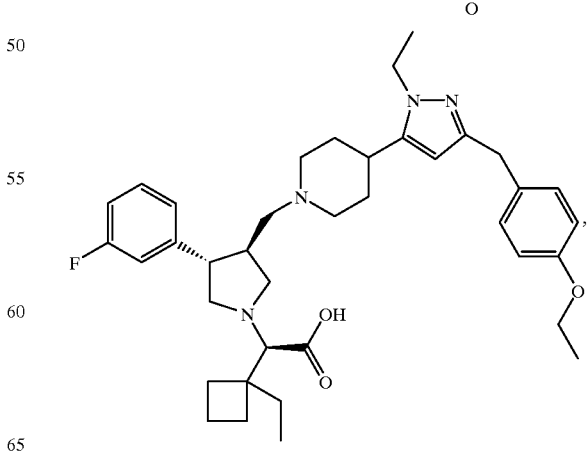

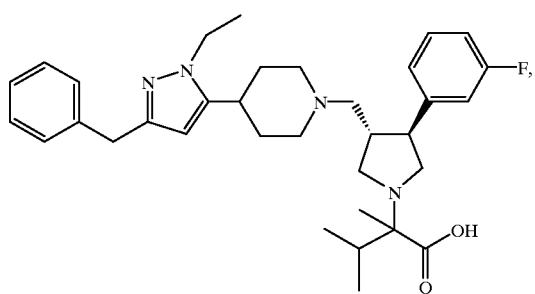
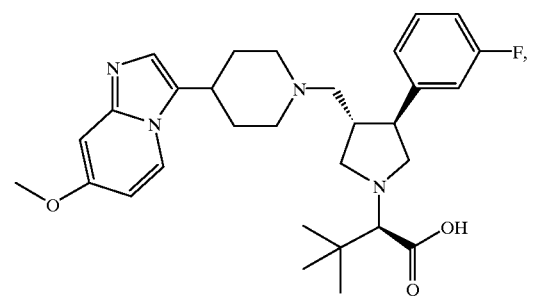
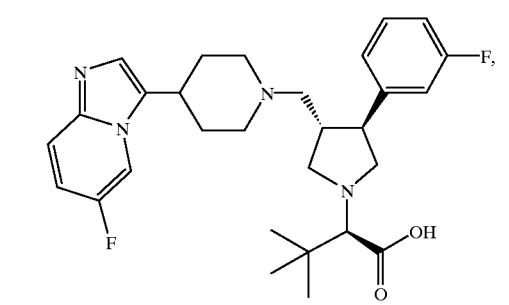
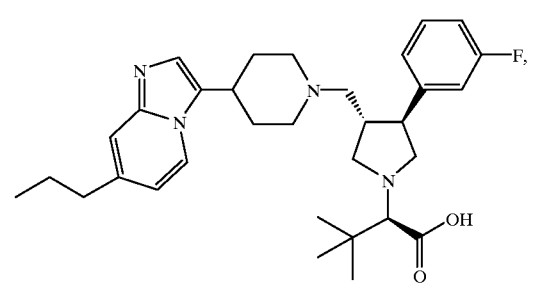
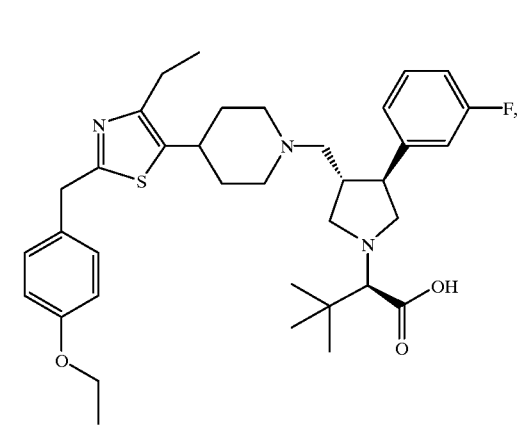
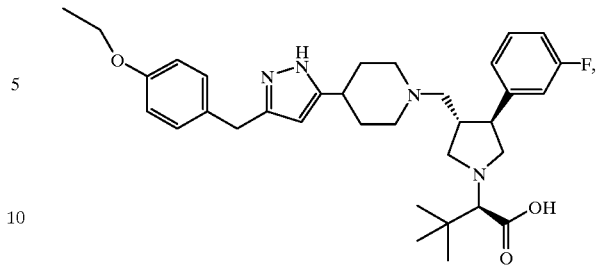
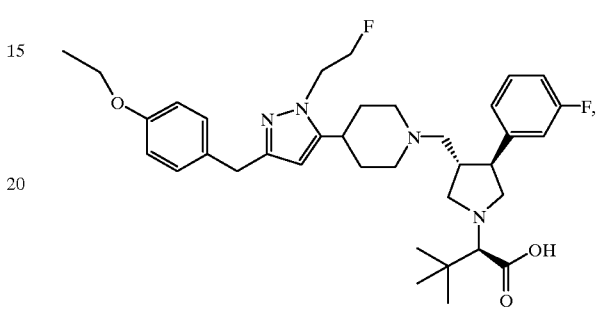
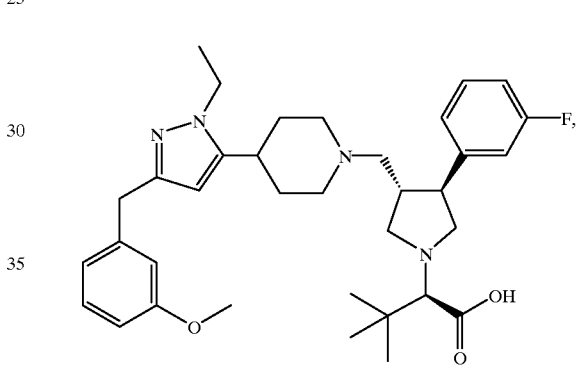
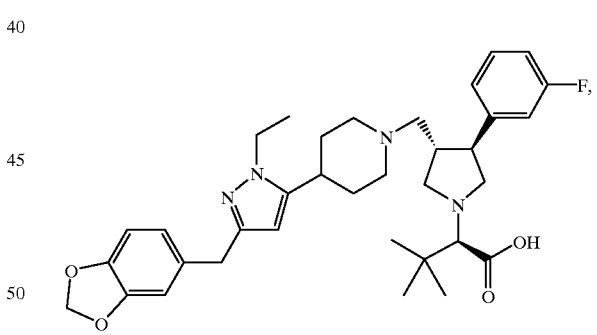
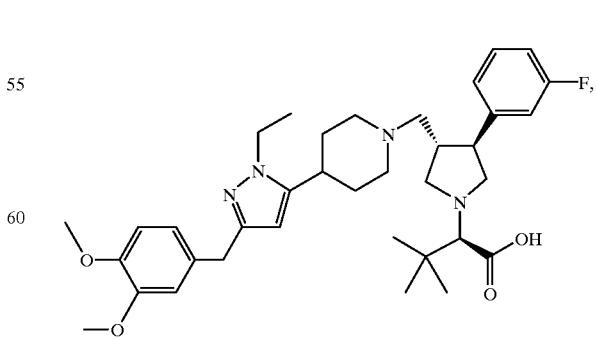

85
-continued
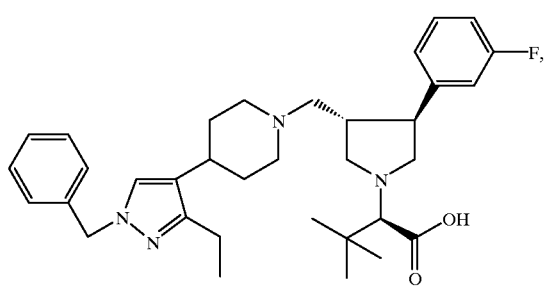
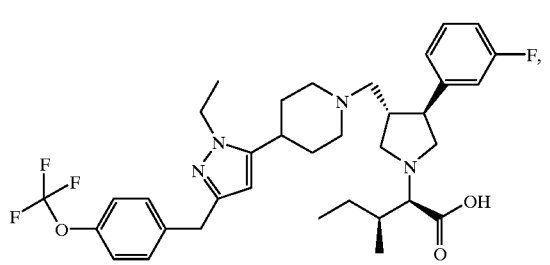
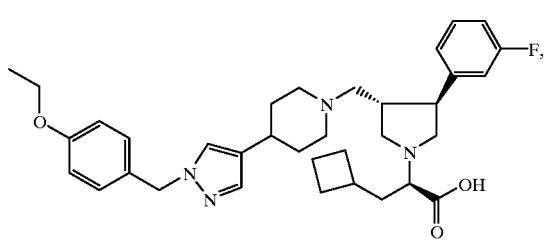
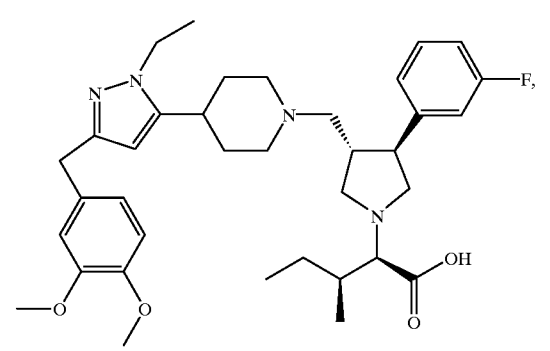
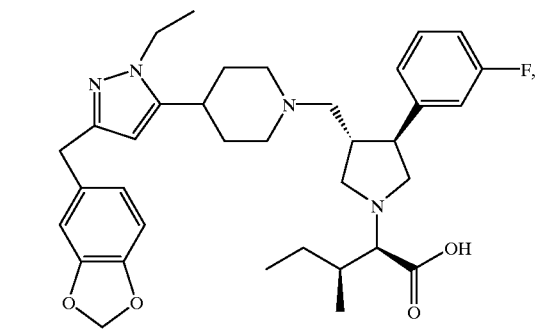
86
-continued
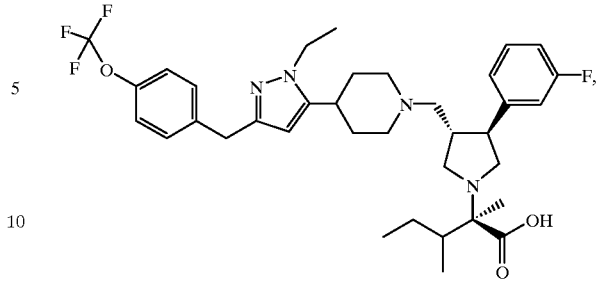
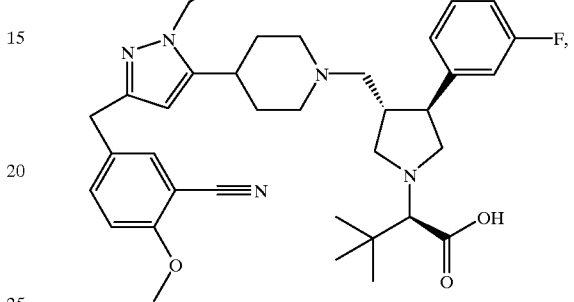
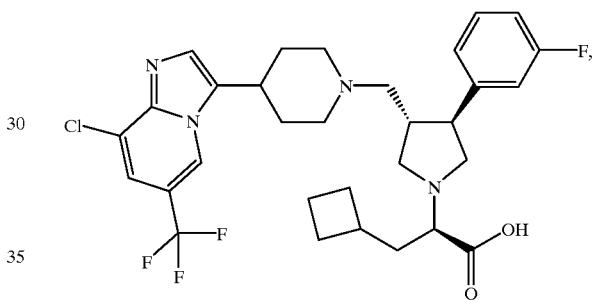
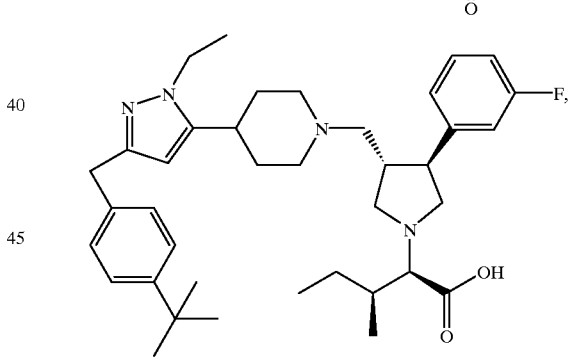
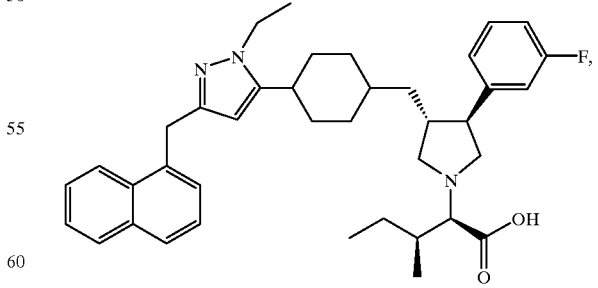

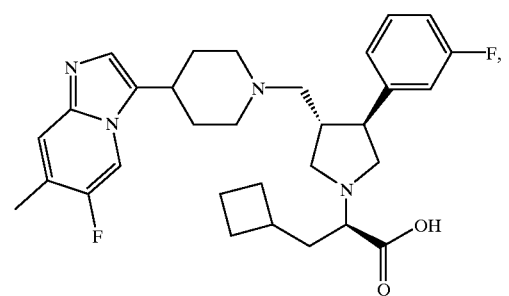
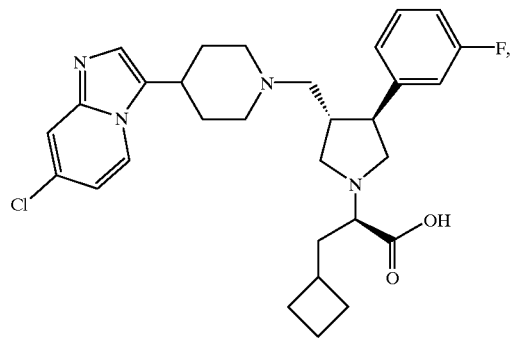
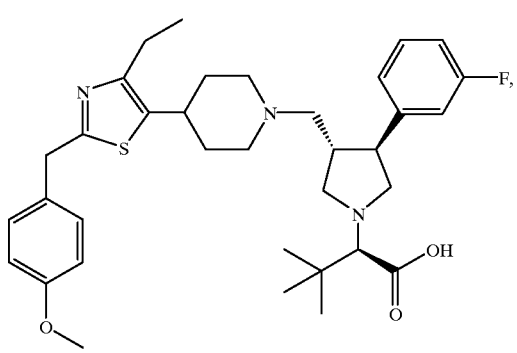
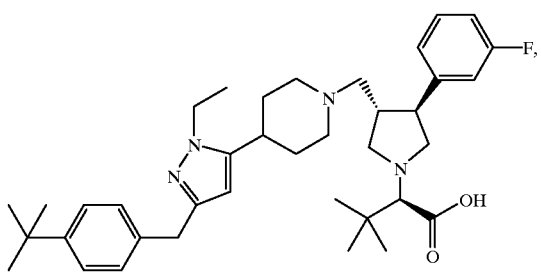
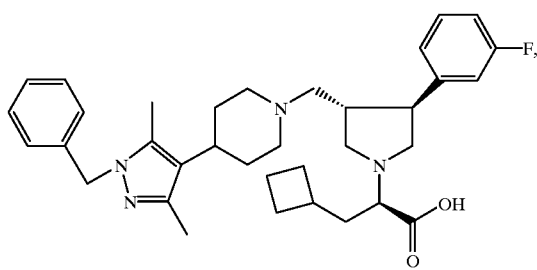
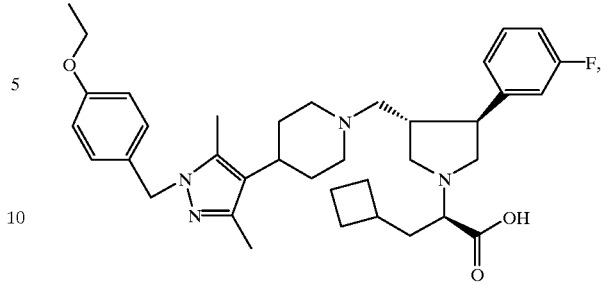
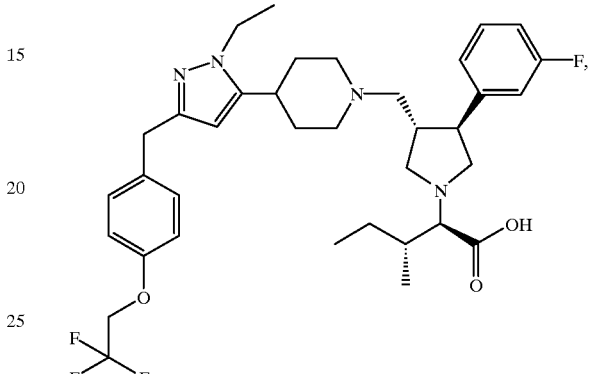
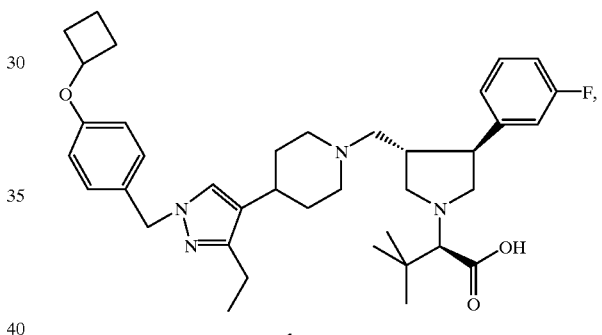
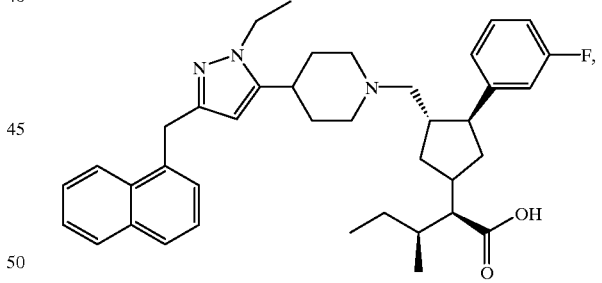
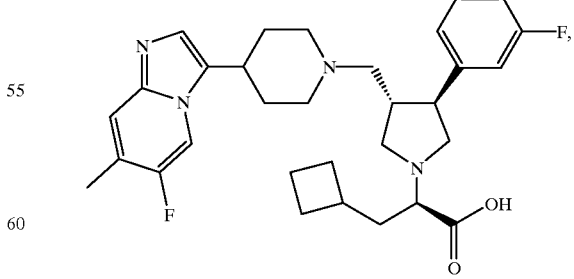

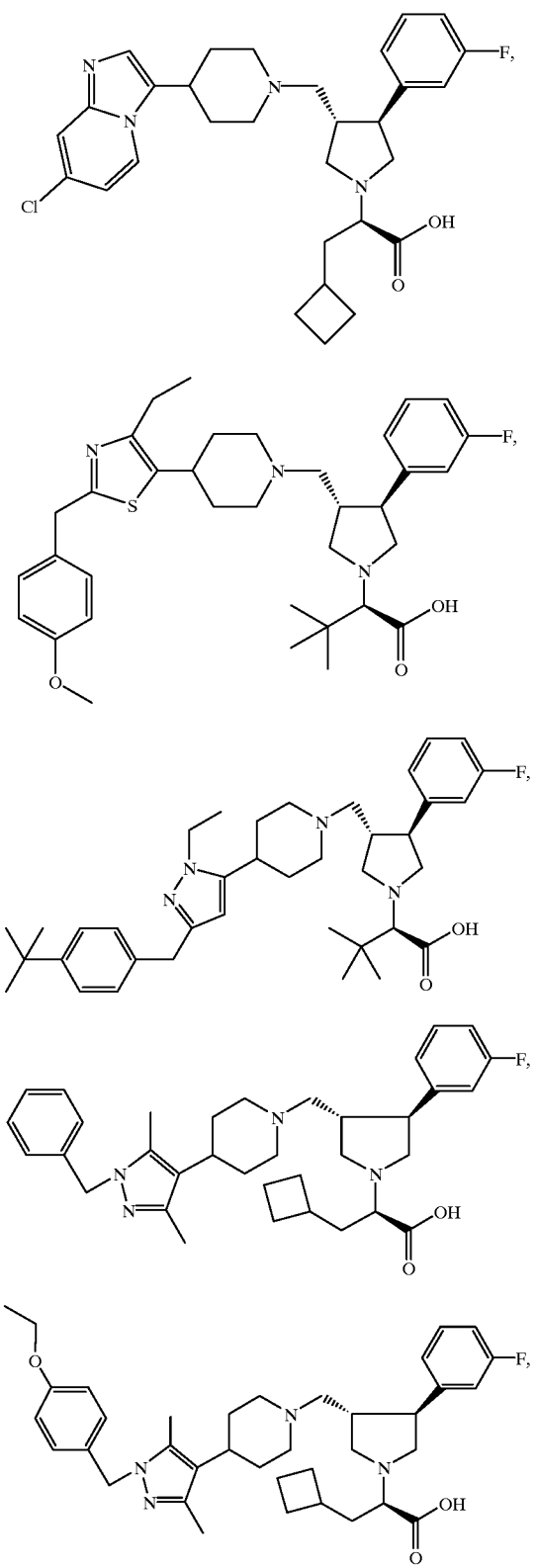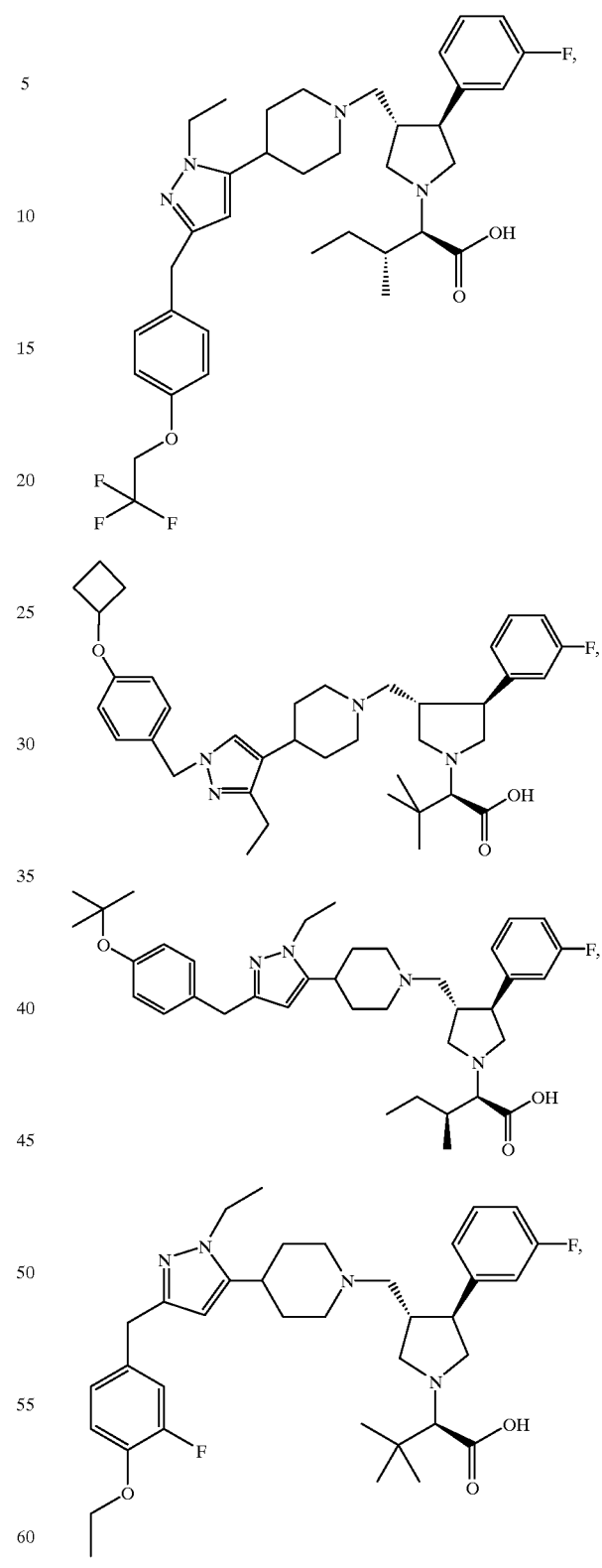

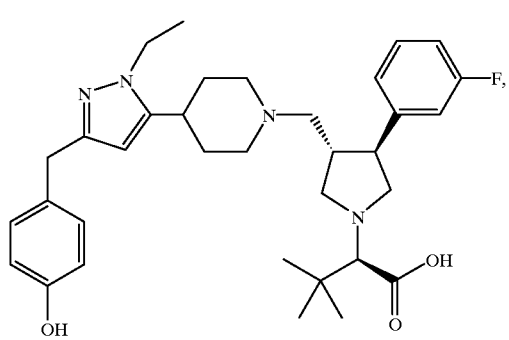
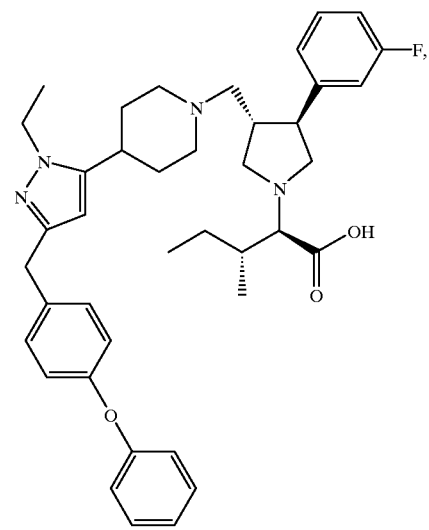
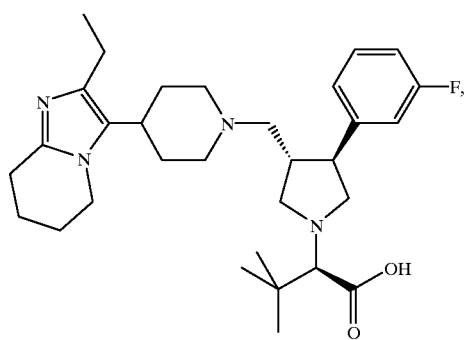
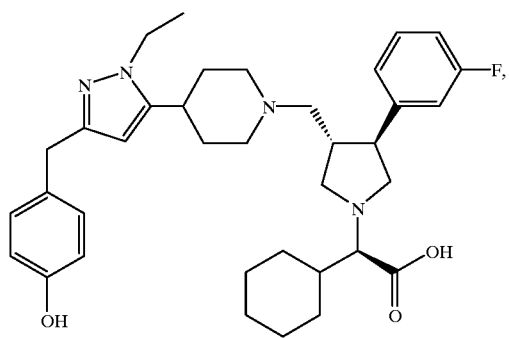
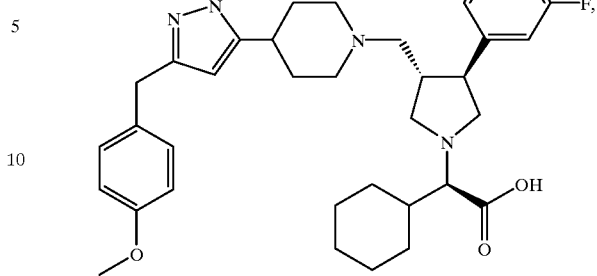
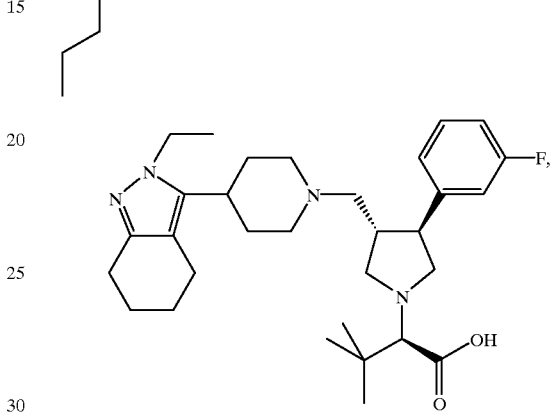
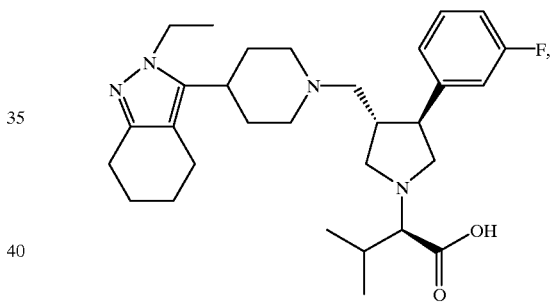
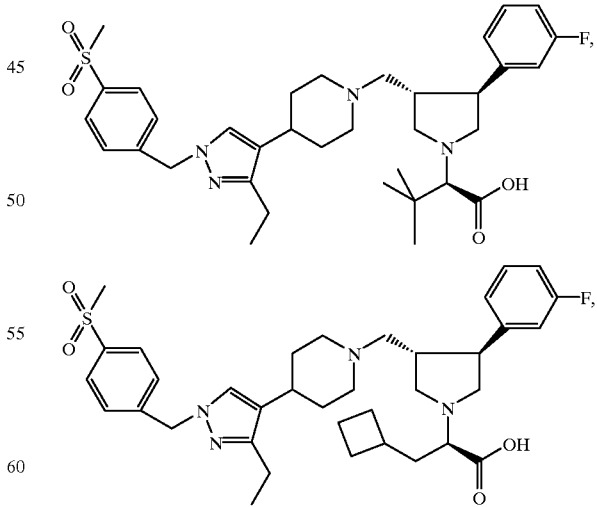

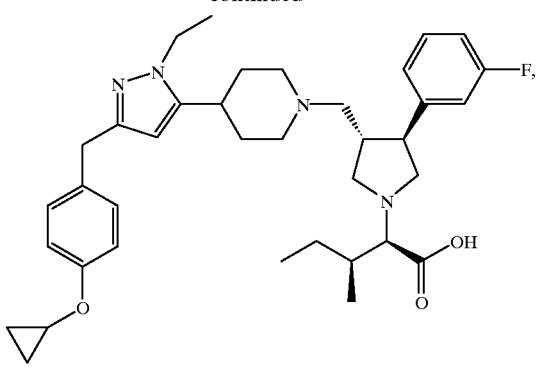

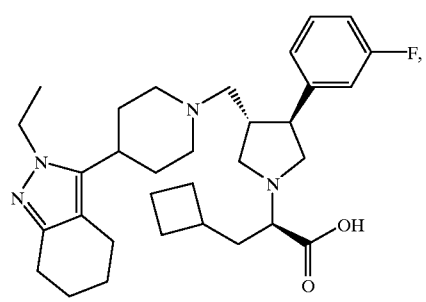

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, including CCR-5 and/or CCR-3.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-5 binding, and the assay for CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR-5 or the CCR-3 receptor in the aforementioned assays, generally with an $IC_{50}$ of less than about 1 $\mu$M. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata*, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-5 and/or CCR-3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-5 and/or CCR-3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-5 or CCR-3, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxyephedrine; an antiitussive such as codeine, hydrocodone, caramiphen, carbetapentane, or dextramethorphan; a diuretic; and a sedating or nonsedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as 2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| ANTIVIRALS | | |
|---|---|---|
| Drug Name | Manufacturer | Indication |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (−) 6-Chloro-4(S)-cyclopropylethynyl- | Merck | HIV infection, AIDS, ARC |

ANTIVIRALS

| Drug Name | Manufacturer | Indication |
|---|---|---|
| 4(S)-trifluoro-methyl-1,4-dihydro-2H-3,1-benzoxazin-2-one | | (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (−) 6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| T-20 | Trimeris | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| Amprenivir VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Squibb | HIV infection, AIDS, ARC (protease inhibitor) |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |

| IMMUNO-MODULATORS | | |
|---|---|---|
| Drug Name | Manufacturer | Indication |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |

| ANTI-INFECTIVES | | |
|---|---|---|
| Drug Name | Manufacturer | Indication |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

| OTHER | | |
|---|---|---|
| Drug Name | Manufacturer | Indication |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2 (R)-phenylmethyl-4-(S)-hydroxy-5-(1 -(4-(2-benzo[b] furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−)6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy- propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.) The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

SCHEME 1

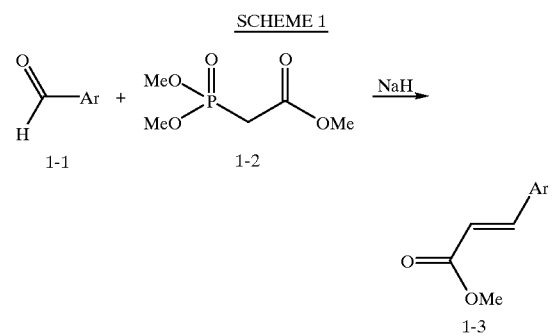

The preparation of cinnamate esters such as 1–3 as intermediates that can be used for the synthesis of compounds within the scope of the instant invention is detailed in Scheme 1. Cinnamate esters of structure 1–3 can be obtained commercially or can be synthesized by reacting a suitable aromatic aldehyde 1-1 with a phosphonoacetate such as 1-2 or a stabilized Wittig reagent in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

SCHEME 2

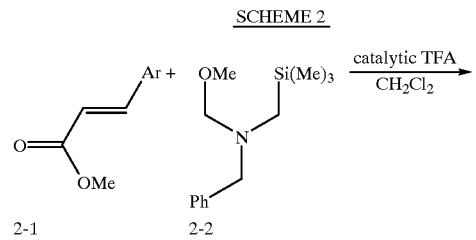

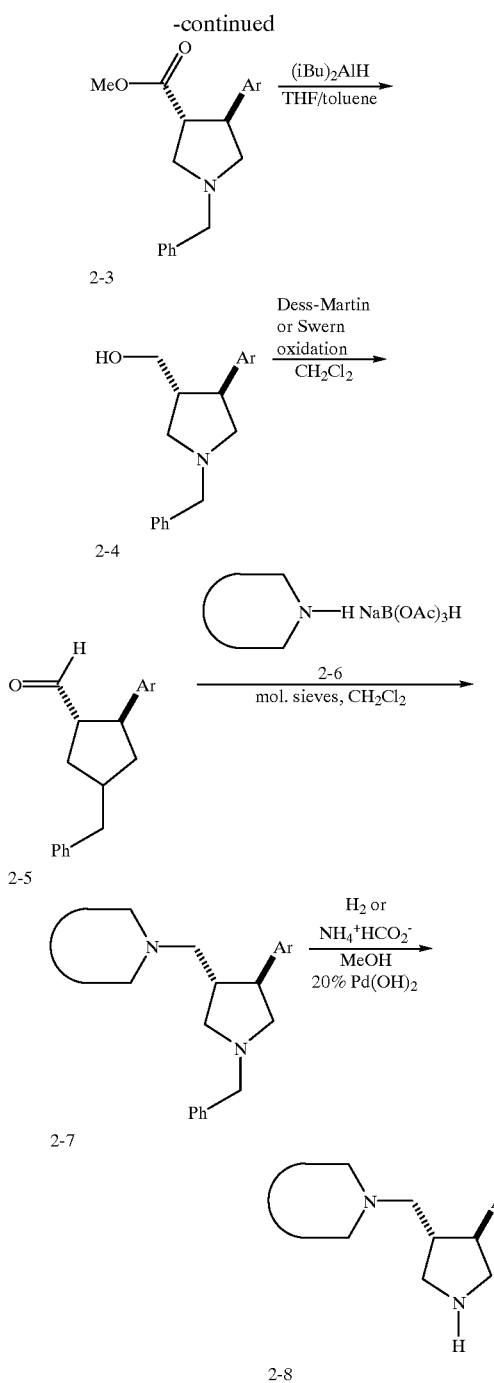

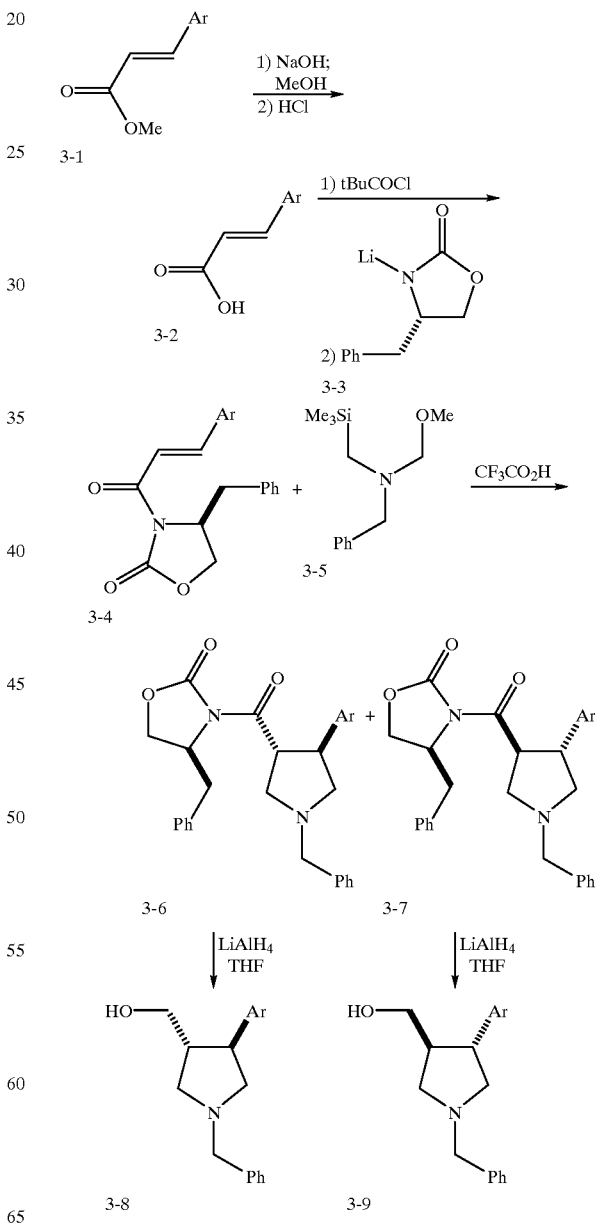

methoxyethoxy)aluminum hydride, provides the primary alcohol 2-4. Oxidation to the aldehyde 2-5 can be carried out under numerous conditions, such as with the Dess-Martin periodinane, with DMSO and oxalyl chloride at low temperature, followed by triethylamine (Swern oxidation), or with various chromium trioxide-based reagents (see March J. "Advanced Organic Chemistry", 4th ed., John Wiley & Sons, New York, pp. 1167–1171 (1992)). Reductive amination with cyclic amine 2-6 then provides diamine 2-7, which can itself be a chemokine receptor modulator. Alternatively, the N-benzyl group is cleaved in a hydrogen atmosphere or with ammonium formate in the presence of 20% palladium hydroxide to provide the secondary amine 2-8.

SCHEME 3

The preparation of compounds within the scope of the instant invention which bear a 1,3,4-trisubstituted pyrrolidine framework is detailed in Scheme 2. Treatment of a trans-cinnamic ester such as 2-1 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride, according to the procedure of Padwa et al (J. Org. Chem. 1987, 52, 235) preferentially affords the 3,4-trans pyrrolidine 2-3. Executing this sequence starting from the cis-cinnamic ester results in preferential formation of the 3,4-cis pyrrolidine. Reduction of ester 2-3, for example, with diisobutylaluminum hydride, lithium aluminium hydride, or sodium bis(2-

Scheme 3 shows the preparation of optically pure pyrrolidine intermediates. Hydrolysis of unsaturated ester 3-1 provided acid 3-2, which is converted to diacyl derivative 3-4 by activation of the acid group, for example by formation of a mixed anhydride with pivaloyl chloride, followed by reaction with the lithium salt of 4-(S)-benzyloxazolidin-2-one (3-3). Treatment of 3-4 with commercially available N-benzyl-N-methoxymethyl-N-(trimethylsilyl)-methylamine (2-2) in the presence of a substoichiometric amount of an acid such as TFA, titanium tetrafluoride, lithium fluoride or cesium fluoride according to the procedure of Padwa et al (J. Org. Chem. 1987, 52, 235) affords the diastereomeric pyrrolidines 3-6 and 3-7, which can be separated by flash chromatography, preparative thin layer chromatography, medium pressure liquid chromatography, high pressure liquid chromatography, fractional crystallization, or similar methods known in the art. The separated products are then individually reduced, for example with lithium alumium hydride (LAH) or other strong hydride reducing agents, to provide pyrrolidines 3-8 and 3-9 in optically enriched form.

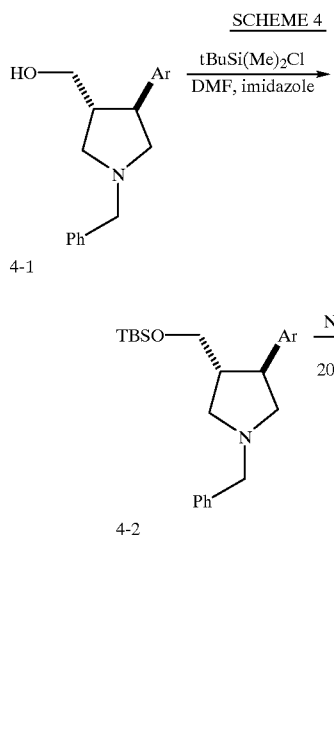

Preparation of a protected pyrrolidine for use as an intermediate in the synthesis of compounds in the instant invention is shown in Scheme 4. The pyrrolidine 4-1 (prepared as shown in Schemes 2 and 3) is protected with a suitable protecting group such as t-butyl-dimethylsilyl to provide silyl ether 4-2. Other silyl groups can also be used in this role, as can other protecting groups for a hydroxy residue (see Greene, T. W.; Wuts, P. G. M. "Protective Groups in Organic Synthesis", 2nd edition, Wiley-Interscience, New York, pp. 10–143 (1991)), subject to the group being stable to conditions used to remove the benzyl group and being removable under conditions that would not adversely affect the remainder of the molecule. Removal of the benzyl group on nitrogen is then carried out by hydrogenolysis, for example by transfer hydrogenation with ammonium formate in the presence of 20% palladium hydroxide or with catalytic hydrogenation with 10% palladium on carbon under one or more atmospheres of hydrogen. Alternatively, compound 4-1 can be debenzylated first under the conditions noted above and then silylated on the hydroxy group, to provide 4-3.

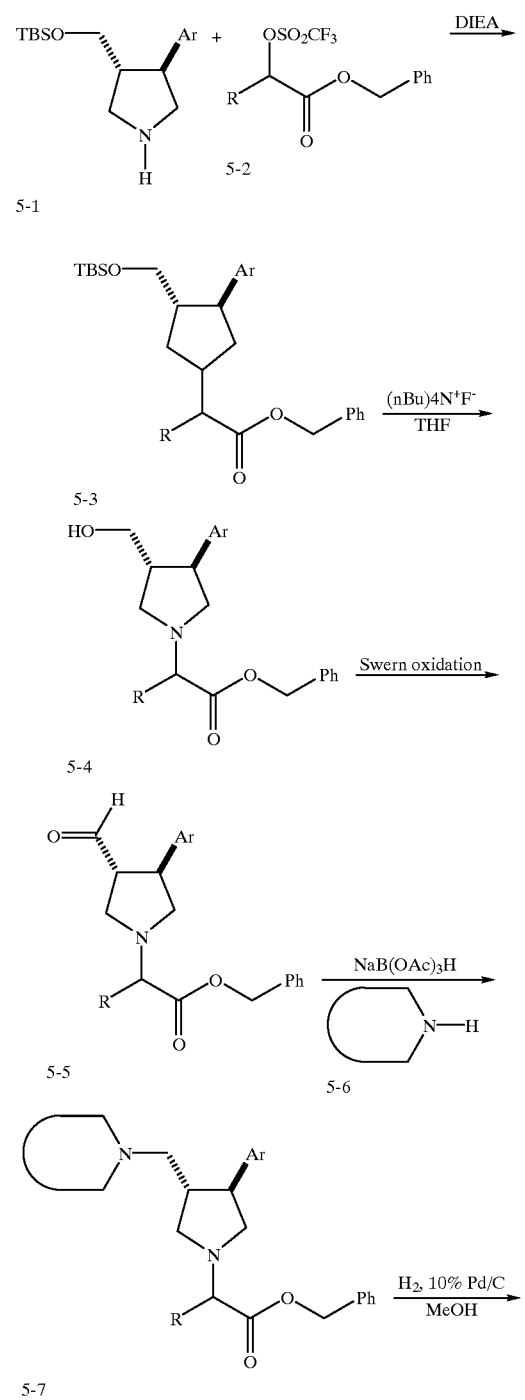

-continued

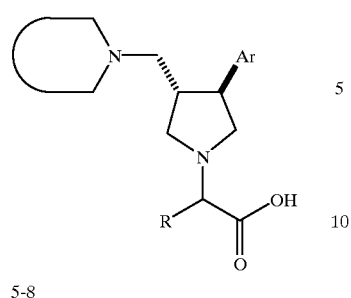

5-8

Preparation of some 1,3,4-trisubstituted pyrrolidines within the scope of the instant invention is given in Scheme 5. Alkylation of pyrrolidine 5-1 with the trifluoromethane-sulfonate (triflate) ester of a suitable alpha-hydroxy ester derivative 5-2 in the presence of a hindered base such as DIEA ((N,N-(diisopropyl)ethylamine) or a sparingly soluble base such as potassium carbonate provides the N-substituted product 5-3. Triflate ester 5-2 is prepared by treating the parent alpha-hydroxy ester with triflic anhydride in the presence of a suitable hindered tertiary amine, such as DIEA, 2,6-lutidine or 2,6-di-t-butyl-4-methylpyridine at or below room temperature in a suitable inert solvent such as dichloromethane or 1,2-dichloroethane. Alternatively, other leaving groups can be employed to activate the alpha-position on ester 5-2 instead of a triflate, such as chloride, bromide, iodide, methanesulfonate, p-toluenesulfonate, etc. Deprotection of silyl ether 5-3 is carried out with tetrabutylammonium fluoride in THF, to afford alcohol 5-4. Alternatively, acidic conditions can be used to remove the silyl group, for example aqueous trifluoroacetic acid, hydrogen fluoride in pyridine, hydrochloric acid, etc. Oxidation of 5-4 to the aldehyde 5-5 is accomplished using the Swern oxidation conditions. Other methods 10 for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 5-6 then provides diamine 5-7, which can itself be a chemokine receptor antagonist. Cleavage of the benzyl group with catalytic hydrogenation, for example under an atmosphere of hydrogen in the presence of 10% palladium on carbon as catalyst in methanol or ethanol as solvent, provides acid 5-8. Alternatively, the benzyl ester can be cleaved by treatment with strong aqueous base if the remainder of the molecule is stable to those conditions.

SCHEME 6

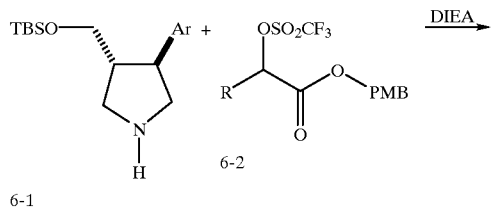

-continued

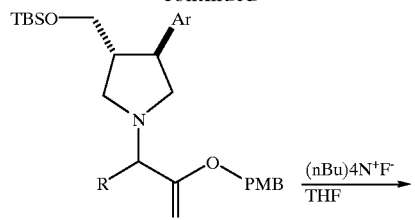

6-3

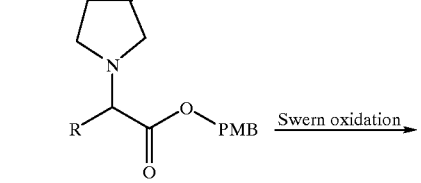

6-4

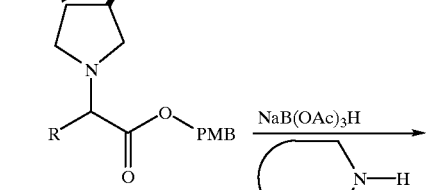

6-5

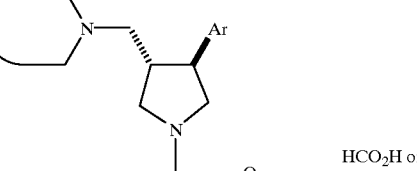

6-6

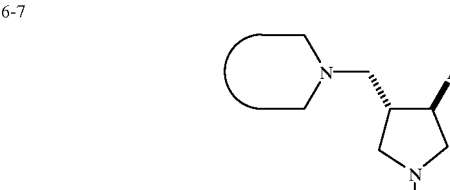

6-7

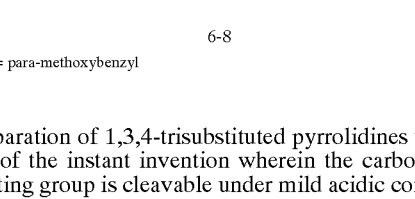

6-8

PMB = para-methoxybenzyl

Preparation of 1,3,4-trisubstituted pyrrolidines within the scope of the instant invention wherein the carboxylic acid protecting group is cleavable under mild acidic conditions is given in Scheme 6. Alkylation of pyrrolidine 6-1 with the triflate ester of a suitable alpha-hydroxy ester derivative 6-2 in the presence of a hindered base such as DIEA or a sparingly soluble base such as potassium carbonate provides the N-substituted product 6-3 (PMB=para-methoxybenzyl). Triflate ester 6-2 is prepared by treating the parent alpha-hydroxy ester with triflic anhydride in the presence of a suitable hindered tertiary amine, such as DIEA, 2,6-lutidine or 2,6-di-t-butyl-4-methylpyridine at or below room temperature in a suitable inert solvent such as dichloromethane or 1,2-dichloroethane. Alternatively, other leaving groups can be employed to activate the alpha-position on ester 6-2 instead of a triflate, such as chloride, bromide, iodide, methanesulfonate, p-toluenesulfonate, etc. Deprotection of silyl ether 6-3 is carried out with tetrabutylammonium fluoride in THF, to afford alcohol 6-4. Alternatively, mildly acidic conditions in some cases can be used to selectively remove the silyl group, for example aqueous trifluoroacetic acid, hydrogen fluoride in pyridine, hydrochloric acid, etc. Oxidation of 6-4 to the aldehyde 6-5 is accomplished using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 6-6 then provides diamine 6-7, which can itself be a chemokine receptor antagonist. Cleavage of the PMB group with acid, for example with formic acid or trifluoroacetic acid plus anisole, provides acid 6-8. Alternatively, the ester can be cleaved by treatment with strong aqueous base or by catalytic hydrogenation if the remainder of the molecule is stable to those conditions.

SCHEME 7

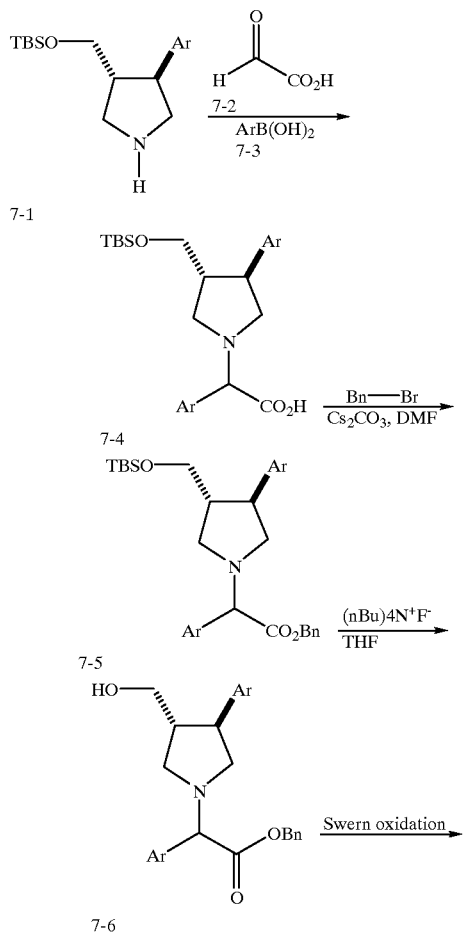

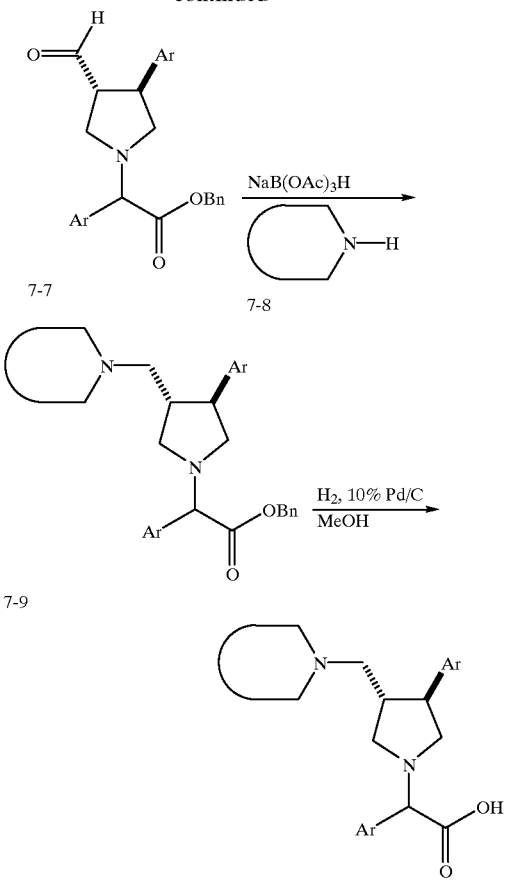

An alternative route for the synthesis of pyrrolidines with a 1-(α-arylacetic acid) substituent is given in Scheme 7. Reaction of the protected pyrrolidine 7-1 with glyoxylic acid in the presence of an aryl boronic acid 7-3 provides the N-aralkylated product 74 (see Petasis, N. A.; Goodman, A.; Zavialov, I. A. Tetrahedron 1997, 53, 16463–16470; and PCT Int. Appl. WO 9800398). Protection of the acid by alkylation with benzyl bromide in DMF in the presence of cesium carbonate provides ester 7-5. Deprotection of the silyl group with tetrabutylammonium fluoride in THF, or with mild acid such as aqueous trifluoroacetic acid, then provides alcohol 7-6. Alternatively, simultaneous removal of the silyl group of 7-4 and formation of the ester can be carried out by heating 7-4 in an anhydrous solution of the esterifying alcohol in the presence of acid, such as toluenesulfonic acid, triflic acid, hydrochloric acid, and the like. The alcohol 7-6 is oxidized to aldehyde 7-7 using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 7-8 then provides diamine 7-9, which can itself be a chemokine receptor antagonist. Deprotection of the benzyl ester is carried out with catalytic hydrogenation, for example under an atmosphere of hydrogen in the presence of 10% palladium on carbon as catalyst in methanol or ethanol as solvent, provides acid 7-10. Alternatively, the benzyl ester can be cleaved by treatment with strong aqueous base if the remainder of the molecule is stable to those conditions.

SCHEME 8

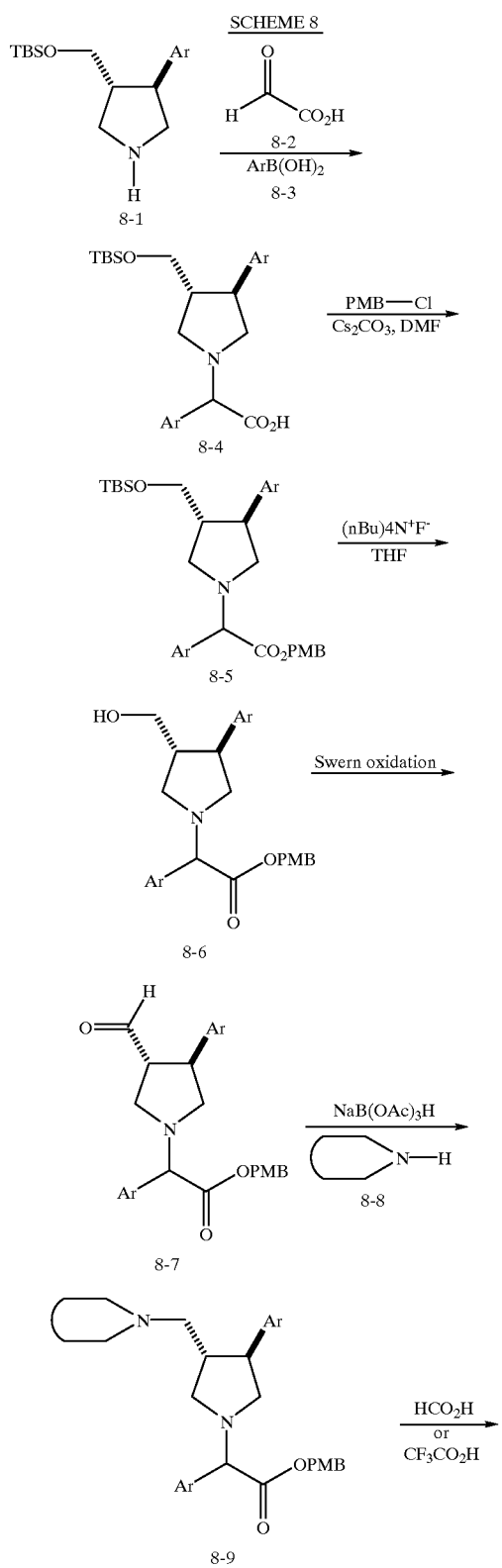

An alternative route for the synthesis of pyrrolidines with a 1-(α-arylacetic acid) substituent, wherein the carboxylic acid protecting group can be cleaved in mild acid, is given in Scheme 8. Reaction of the protected pyrrolidine 8-1 with glyoxylic acid in the presence of an arylboronic acid 8-3 provides the N-aralkylated product 8-4, according to the procedure of Petasis, N. A.; Goodman, A.; Zavialov, I. A. *Tetrahedron* 1997, 53, 16463–16470 (see also PCT Int. Appl. WO 9800398). Protection of the acid by alkylation with para-methoxybenzyl chloride in DMF in the presence of cesium carbonate provides ester 8-5. Deprotection of the silyl group with tetrabutylammonium fluoride in THF, provides alcohol 8-6. The alcohol 8-6 is oxidized to aldehyde 8-7 using the Swern oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 8-8 then provides diamine 8-9, which can itself be a chemokine receptor antagonist. Deprotection of the p-methoxybenzyl ester is carried out by treatment with formic acid, trifluroacetic acid plus anisole, or other moderate acids, at temperatures from 0 degrees C. to 120 degrees C., to provide the chemokine receptor antagonist 8-10.

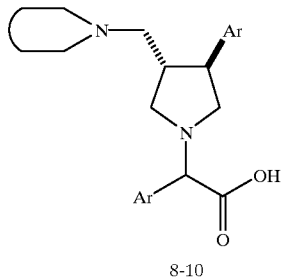

8-10

SCHEME 9

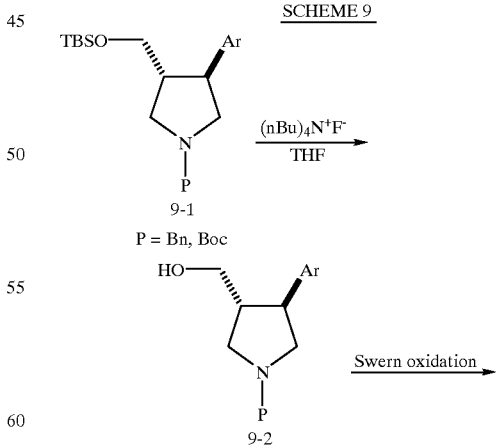

P = Bn, Boc

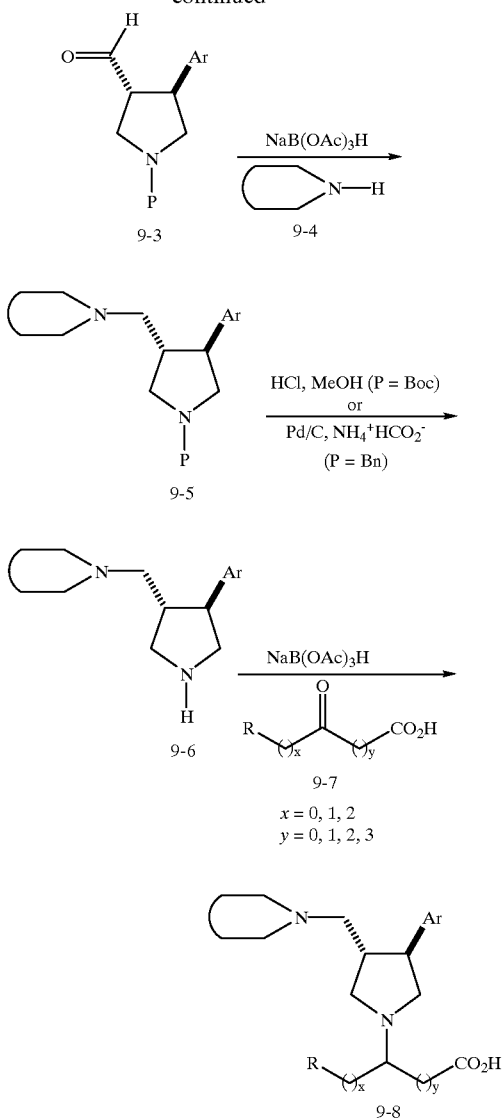

effect transfer hydrogenation. Reductive amination with keto-acid 9-7 then provides pyrrolidine 9-8.

SCHEME 10

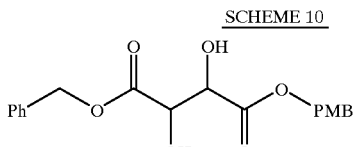

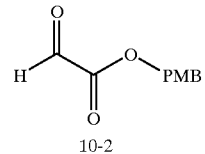

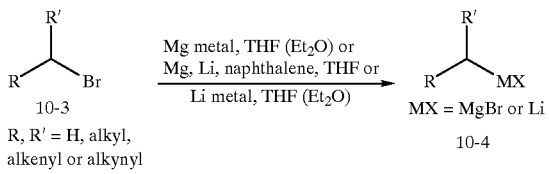

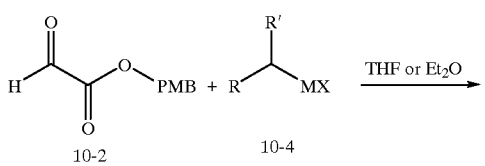

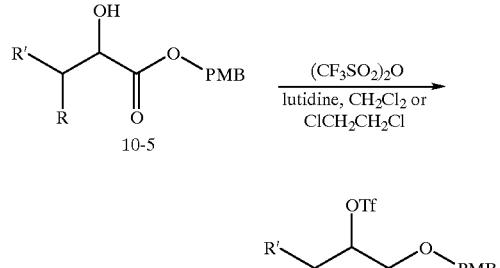

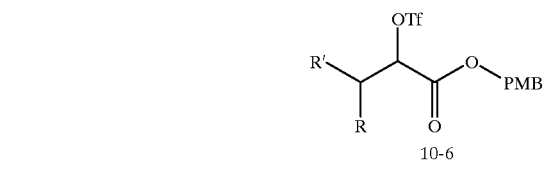

Another method of preparing compounds within the scope of the instant invention is given in Scheme 9. Doubly protected pyrrolidine 9-1 (obtained either as shown in Scheme 4 for 4-2 when P=benzyl or by protection of 4-3 with Boc anhydride in THF/water in the presence of triethylamine when P=Boc) is desilylated with tetrabutylammonium fluoride in THF to provide alcohol 9-2. Oxidation of 9-2 to 9-3 is carried out using Swern's oxidation conditions. Other methods for oxidizing a primary hydroxy group to an aldehyde can also be used, for example the Dess-Martin periodinane, or with various chromium trioxide-based reagents (see March J. "Advanced Organic Chemistry", 4th ed., John Wiley & Sons, New York, pp. 1167–1171 (1992)). Reductive amination with cyclic amine 9-4 then provides diamine 9-5, which can itself be a chemokine receptor antagonist. Deprotection of the pyrrolidine nitrogen, when P=Boc, can be carried out with HCl in methanol or with trifluoroacetic acid and anisole in dichloromethane, to give secondary amine 9-6. When P=benzyl, debenzylation is carried out in the presence of palladium on carbon as a catalyst, using either hydrogen gas or ammonium formate to Scheme 10 illustrates preparation of intermediate 2-alkyl-2-trifluoromethanesulfonoxyacetic acid derivatives when the 1-alkyl-1-hydroxyacetic acid is not commerically available. Treatment of the para-methoxybenzyl ester of 5 tartaric acid with lead tetraacetate in benzene provides the glyoxylic ester 10-2. Separately, a commercially available alkyl bromide (such as cyclobutylmethyl bromide) is treated with magnesium metal (in the absence or presence of lithium/naphthalene) or with lithium metal to provide the organometallic intermediate 10-4. Adding 10-4 to the aldehyde 10-2 provides the 2-hydroxy-ester 10-5. Formation of the trifluoromethanesulfonate ester is carried out under standard conditions (for example, with trifluoromethansulfonic anhydride in the presence of a hindered base such as 2,6-lutidine or DIEA in a halogenated solvent at between −78 degrees C.

to room temperature, preferably near 0 degrees C., to give 10-6, which is then employed as described above.

SCHEME 11

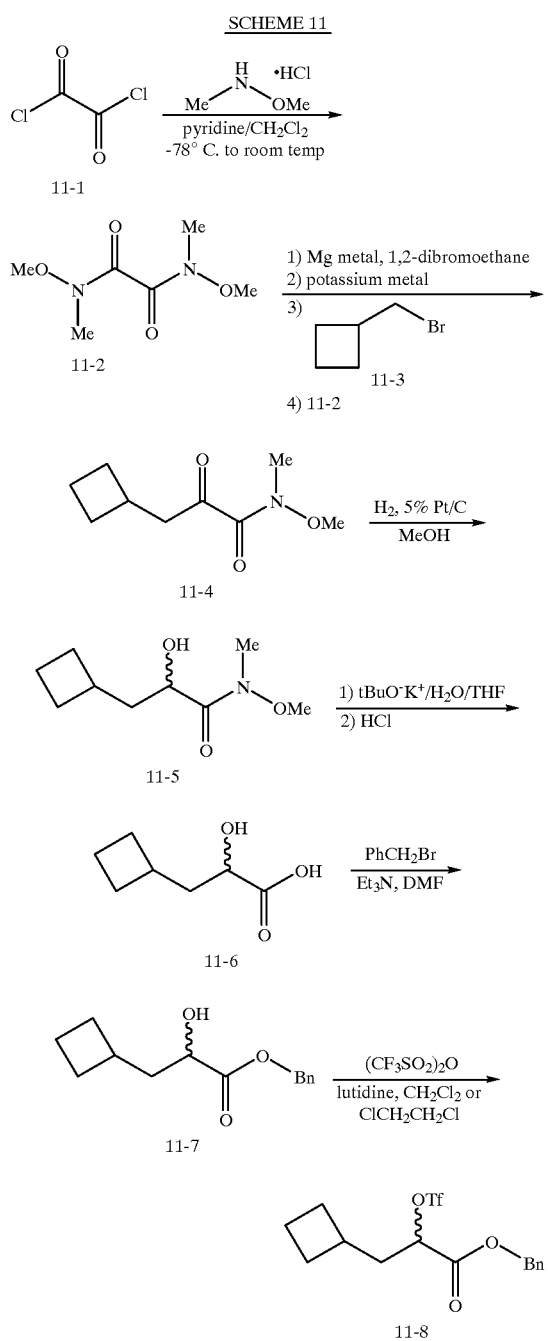

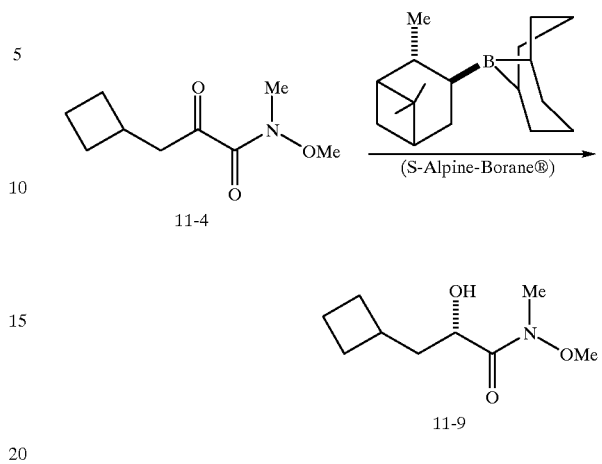

Scheme 11 illustrates an alternate preparation of intermediate 2-alkyl-2-trifluoromethanesulfonoxyacetic acid derivatives; in this example, the side chain is exemplified by a cyclobutylmethyl subunit. Treatment of oxalyl chloride (11-1) with N-methyl-N-methoxyamine hydrochloride in the presence of pyridine yields the bis amide 11-2 (also called the bis-Weinreb amide). In a separate vessel, formation of magnesium dibromide in THF, followed by addition of potassium metal, forms a very reactive grade of magnesium metal. Addition of a suitable aliphatic bromide or iodide, for example cyclobutylmethyl bromide (11-3), provides the desired organomagnesium reagent in situ. Addition of bis-amide 11-2, followed by suitable workup, affords the keto-ester 11-4. This compound is reduced by hydrogenation in the presence of 5% platinum on carbon and triethylamine to the racemic alcohol 11-5. Hydrolysis with potassium t-butoxide in THF/water followed by acidification yields the hydroxy acid 11-6. Acid 11-6 is then protected, for example as the benzyl ester, by treatment with benzyl bromide and triethylamine in DMF, to provide 11-7. This ester is then activated with triflic anhydride (or other triflating agents) under the usual conditions. Alternatively, keto-ester 11-4 can be reduced enantioselectively, for example with B-isopinocampheyl-9-borabicyclo[3.3.1]nonane (also known as S-Alpine-borane®) to provide S-hydroxy derivative 11-9, which can be carried through the rest of the sequence as for 11-5.

SCHEME 12

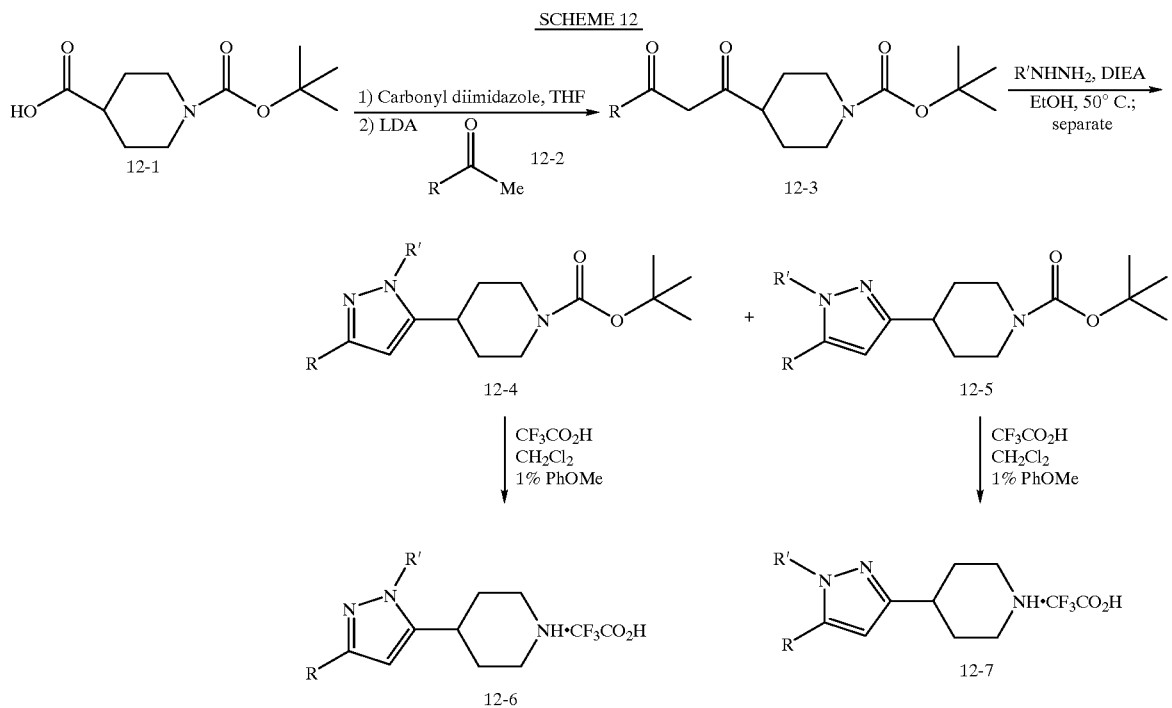

One preparation of piperidine subunits containing functionalized pyrazoles at C4 of the piperidine is given in Scheme 12. Treatment of piperidine 12-1 with carbonyldiimidazole to form the acyl imidazole, followed by addition of a dialkyl or alkyl-aryl ketone 12-3. (12-2) in the presence of lithium diisopropylamide (LDA) gives the diketone 12-3. Treatment with a monoalkyhydrazine in an alcohol solvent at temperatures between 0 to 100 degrees C. (preferably about 50 degrees C.) optionally in the presence of a hindered base such as DIEA then provides a mixture of the isomeric pyrazoles 12-4 and 12-5. After separation of these compounds by chromatography or crystallization, the individual products are deblocked under acidic conditions (for example trifluoroacetic acid and anisole with or without methylene chloride as a cosolvent) to provide the piperidine salts 10-6 and 10-7, which are then used as the cyclic secondary amine component as shown above in Scheme 2 and in Schemes 5 through 9.

SCHEME 13

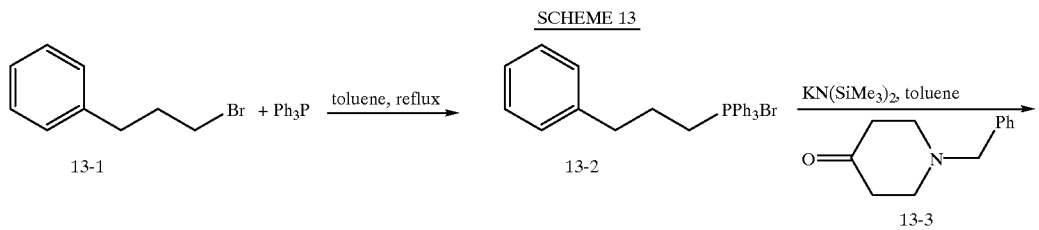

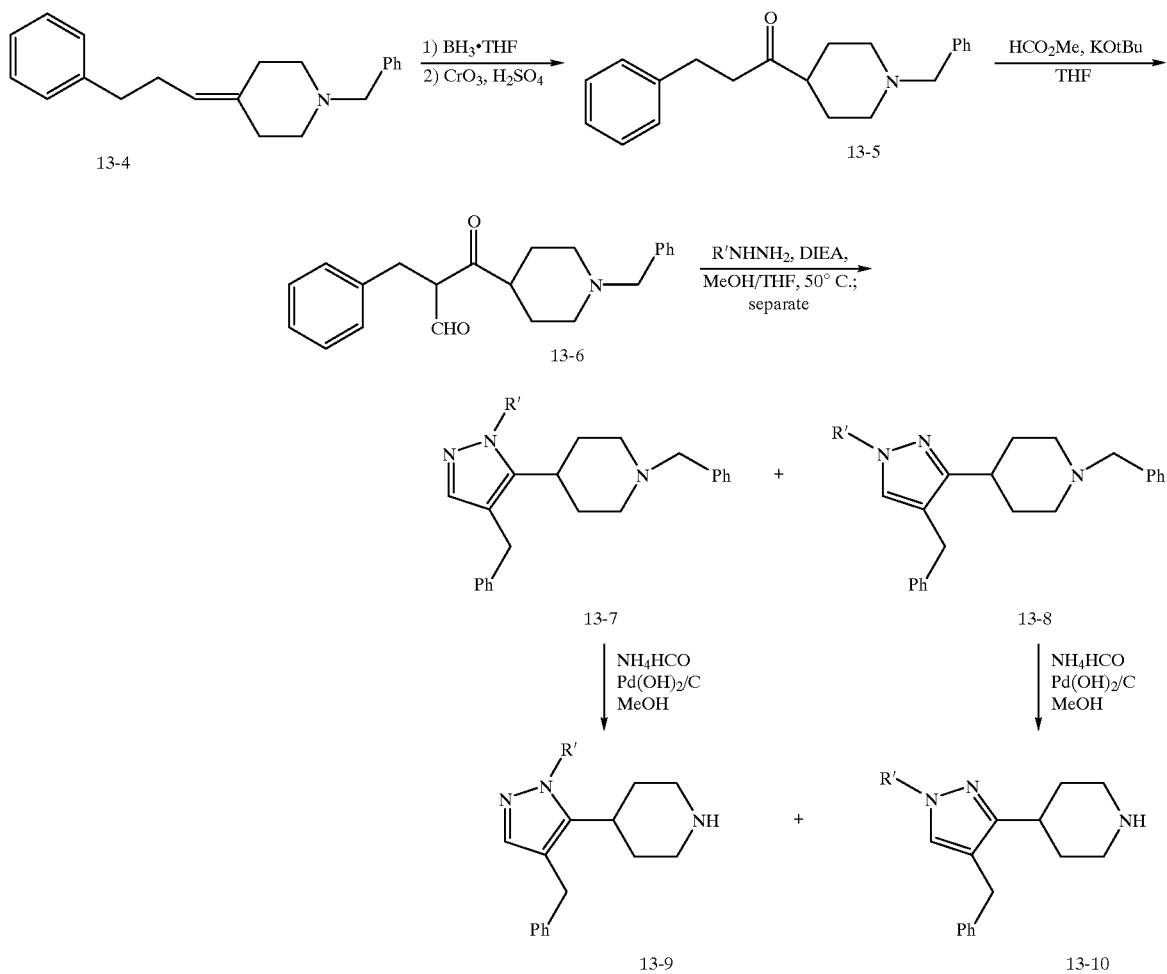

Another preparation of piperidine subunits containing functionalized pyrazoles at C4 of the piperidine is given in Scheme 13. Treatment of commercially available bromide 13-1 with triphenylphosphine in refluxing toluene provides phosphonium salt 13-2, which after treatment with a strong anhydrous base such as potassium hexamethyldisilazide in toluene and the piperidine ketone 13-3 provides the olefin 13-4. Hydroboration followed by an oxidative workup with chromic acid then affords ketone 13-5. Selective formylation of 13-5 with methyl formate in the presence of potassium t-butoxide affords ketoaldehyde 13-6. Heating of 13-6 with a monoalkylhydrazine in methanol optionally in the presence of a hindered (or insoluble) base such as DIEA then provides a mixture of the 1,5-disubstituted pyrazoles 13-7 and 13-8. After separation by chromatography, crystallization or fractional distillation, the purified isomers are deprotected under transfer hydrogenation conditions to provide the piperidines 13-9 and 13-10, which are then utilized as the cyclic secondary amine component as shown above in Scheme 2 and in Schemes 5-9.

SCHEME 13A

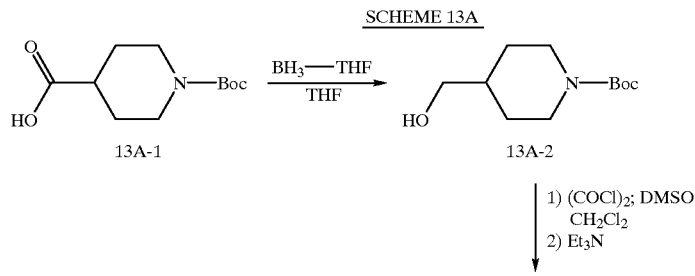

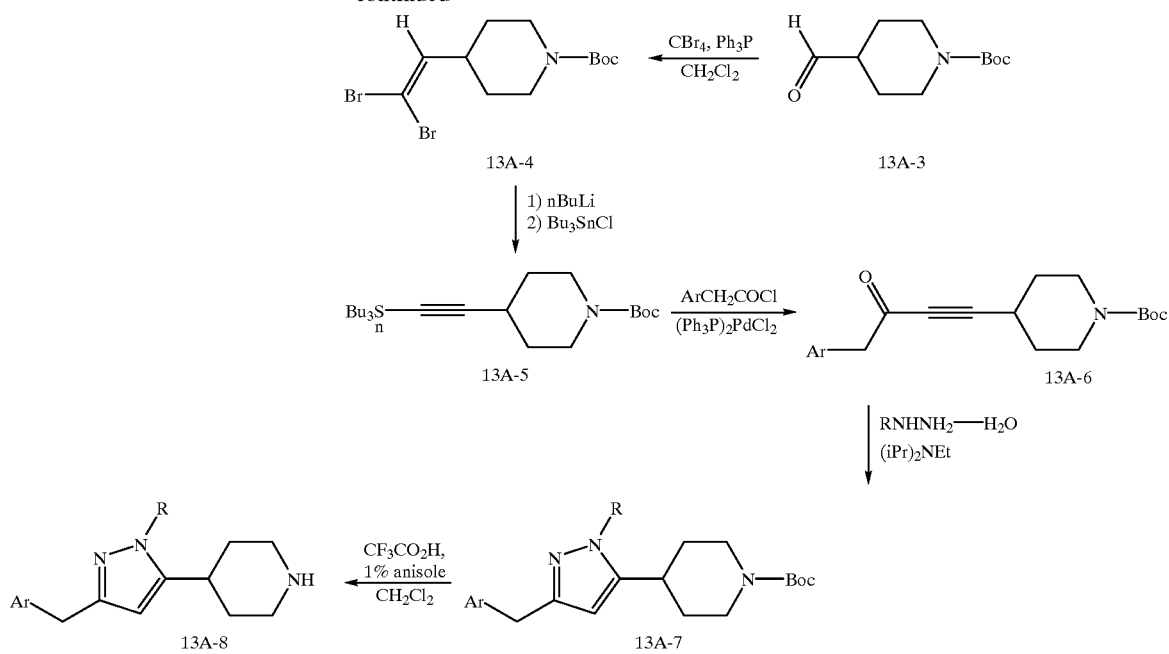

An alternate preparation of piperidine subunits containing functionalized pyrazoles at C4 of the piperidine is given in Scheme 13A. Treatment of commercially available isonipecotic acid under reducing conditions with borane-THF complex provides primary alcohol 13A-2. Oxidation under standard conditions, for example using Swern's conditions, yields aldehyde 13A-3. Treatment of 13A-3 with carbon tetrabromide in the presence of triphenylphosphine affords dibromo-olefin 13A-4, which upon treatment with n-butyllithium followed by tributyl tin chloride provides stannyl acetylene 13A-5. Coupling of 13A-5 with an acid chloride ArCH$_2$COCl in the presence of a suitable palladium catalyst, such as dichlorobis(triphenylphosphine)palladium, in refluxing dichloromethane provided unsaturated ketone 13A-6. Treatment of acetylenic ketone 13A-6 with a monoalkylhydrazine in a suitable solvent, such as ethanol, affords pyrazole 13A-7. Deprotection of this compound under acidic conditions, for example with HCl in methanol or with trifluoroacetic acid in dichloromethane in the presence of anisole, provides the desired pyrazole derivative 13A-8, which is then utilized as the cyclic secondary amine component as shown above in Scheme 2 and in Schemes 5-9.

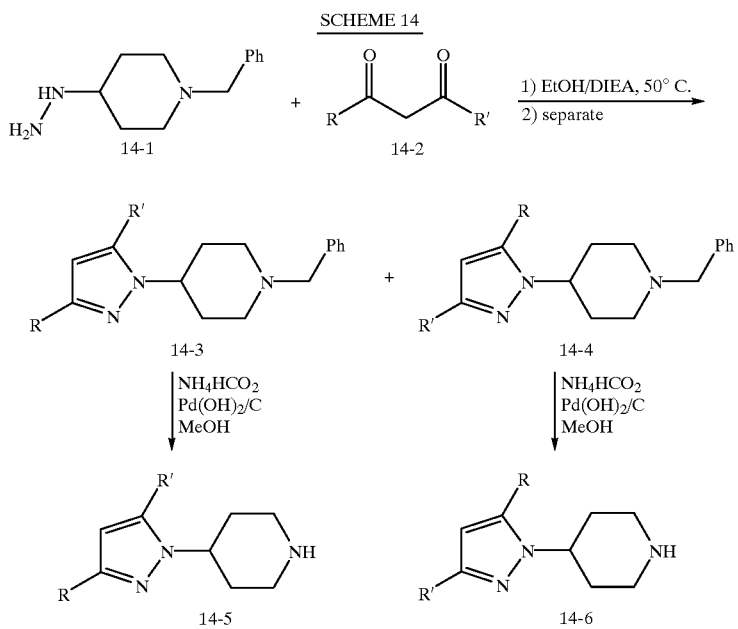

A preparation of piperidine subunits containing 3,5-difunctionalized pyrazoles linked through N1 to C4 of the piperidine is given in Scheme 14. Treatment of commercially available hydrazine 14-1 with diketone 14-2 in ethanol at 0 to 90 degrees C. (prefereably 50 degrees C.) in the presence of DIEA provides a mixture of pyrazoles 14-3 and 14-4, which are separated under standard conditions, for example HPLC. Removal of the benzyl groups by transfer hydrogenation provides the secondary piperidines 14-5 and 14-6, which are then utilized as the cyclic secondary amine component as shown above in Scheme 2 and in Schemes 5-9.

SCHEME 15

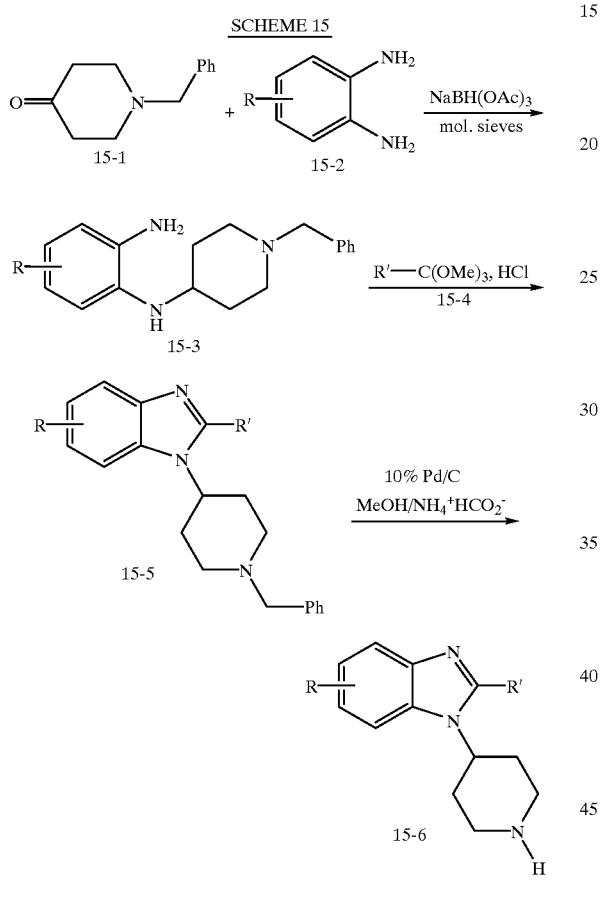

SCHEME 16

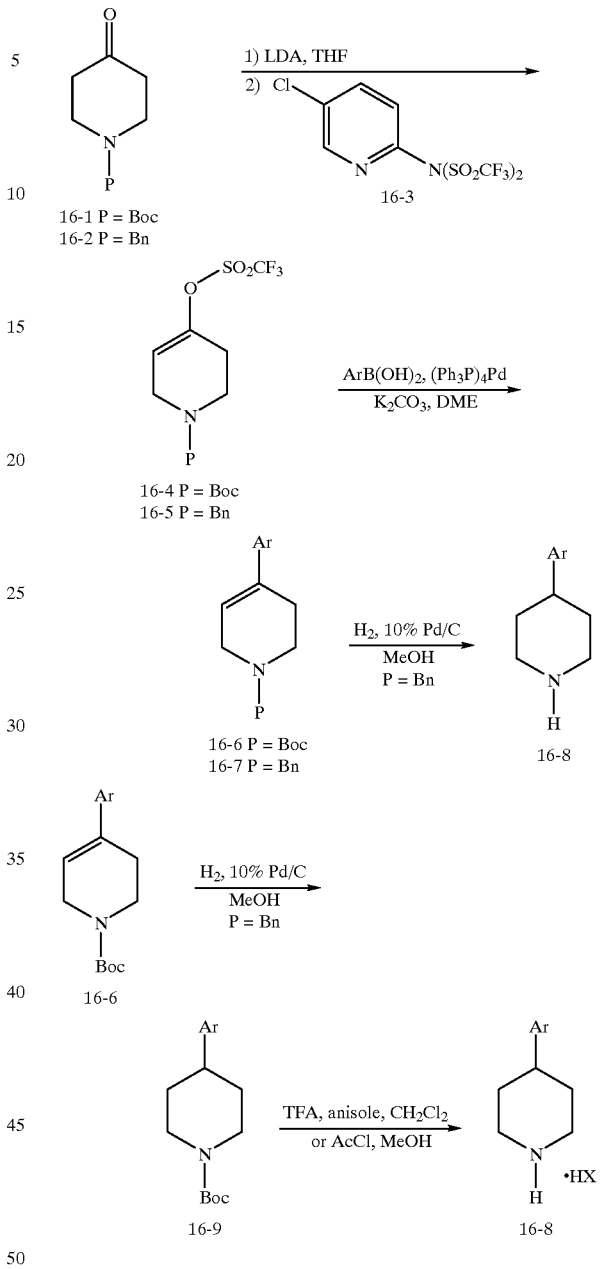

A preparation of 4-(benzimidazol-1-yl)piperidine subunits is given in Scheme 15. Combining piperidone 15-1 and diamine 15-2 in the presence of sodium triacetoxy borohydride under dehydrating conditions provides reductive amination product 15-3. Addition of a suitably substituted ortho ester 15-4 in the presence of a acid catalyst, for example concentrated hydrochloric acid, provides benzimidazole intermediate 15-5. Deprotection under reductive conditions, for example with palladium on carbon under transfer hydrogenation conditions, then provides secondary amine 15-6, , which is then utilized as the cyclic secondary amine component as shown above in Scheme 2 and in Schemes 5-9.

One method of generating 4-aryl piperidines as intermediates is given in Scheme 16. Reaction of commercially available 16-1 or 16-2 with a strong base, such as LDA, LiHDMS, NaHMDS, KHMDS, or NaH followed by treating with a suitable triflating agent, such as 5-chloropyrid-2-yl triflimide (16-3), N-phenyl triflimide or triflic anhydride, provides enol triflates 16-4 or 16-5. Heating with commercially available aryl boronic acids in the presence of a suitable palladium(0) catalyst such as tetrakis triphenylphosphine palladium, a base (such as potasssium carbonate or sodium carbonate), in a solvent such as DME, THF, dioxane or toluene/ethanol, effects coupling to provide the unsaturated products 16-6 or 16-7. In the case of 16-7, treatment with a heterogeneous palladium catalyst in methanol or ethanol in an atmosphere of hydrogen provides the desired intermediate 16-8. Alternatively, the Boc protected derivative 16-6 is hydrogenated under standard conditions to provided the saturated piperidine 16-9, which is then deprotected under acidic conditions (such as trifluoroacetic acid and anisole in methylene chloride), to provide 16-8 as a salt, which is then utilized as the cyclic secondary amine component as shown above in Scheme 2 and in Schemes 5 through 9.

SCHEME 17

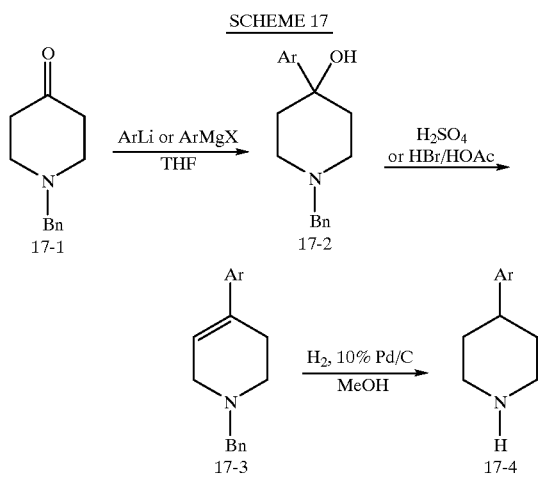

An alternative method of generating 4-aryl piperidines as intermediates is given in Scheme 17. Reaction of commercially available 17-1 with an aryl magnesium halide or with an aryllithium (in the presence or absence of anhydrous cerium trichloride) provides tertiary alcohol 17-2, which upon treatment under acidic conditions (such as sulfuric acid, HBr in acetic acid, HCl in acetic acid) or under dehydrating conditions (such as with thionyl chloride in pyridine or with phosphorus oxychloride) provides olefin 17-3. Hydrogenation under standard conditions using either hydrogen gas or a hydrogen donor (such as ammonium formate or cyclohexene) effects reduction of the double bond and cleavage of the N-benzyl group to provide the desired intermediate 17-4. Under some circumstances it may be preferable to reduce the double bond under non-hydrogenolytic conditions, for example with triethylsilane and trifluoroacetic acid or under dissolving metal conditions (for example, sodium or lithium metal in ammonia or a lower alkyl amine). If the N-benzyl group is not removed under these conditions, it may be cleaved by treatment with either vinyl chloroformate and then hydrogen chloride or by treatment with 2-chloroethyl chloroformate followed by heating in methanol. The product 17-4 is then utilized as the cyclic secondary amine component as shown above in Scheme 2 and in Schemes 5 through 9.

GENERAL

Concentration of solutions was carried out on a rotary evaporator under reduced pressure. Flash chromatography (FC) was carried out on silica gel (230–400 mesh). NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

HPLC CONDITIONS

HPLC A. Retention time using the following conditions: Column: YMC ODS A, 5µ4.6×50 mm; Gradient Eluant: 10:90 to 90:10 v/v $CH_3CN/H_2O+0.5\%$ TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5 µ4.6×100 mm column; Gradient Eluant: 10:90 to 90:10 v/v $CH_3CN/H_2O+0.5\%$ TFA over 10 min, hold 2 min; Detection: PDA, 200–400 nm; Flow Rate: 2.25 mL/min.

Pyrrolidine 1

3-(R)-(t-Butyldimethylsilyloxymethyl)-4-(S)-phenyl pyrrolidine

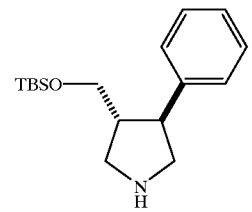

Step A: 3-((E)-Cinnamoyl)-4-(S)-benzyl oxazolidin-2-one

A solution of 222 g (1.5 mol) of trans-cinnamic acid and 250 mL (1.77 mol) of TEA in 3 L of THF at −78° C. was treated with 200 mL of trimethylacetyl chloride maintaining the internal temperature at less than −65° C. The resulting mixture was warmed to 0° C, then cooled to −78° C.

In a separate flask, a solution of 4-(S)-benzyl-oxazolidin-2-one in 2.05 L of THF at −20° C. was treated with 660 mL of 2.5 M n-butyllithium in hexanes over 45 min. The resulting turbid mixture was cooled to −78° C. and then transferred via cannula to the flask containing the mixed anhydride. The resulting mixture was allowed to warm to rt and was stirred for 20 h. The reaction was quenched with 300 mL of sat'd $NH_4Cl$; the resulting mixture was partitioned between EtOAc and $H_2O$ and the layers were separated. The organic layer was dried over $MgSO_4$. The aqueous layer was extracted with 2×EtOAc; the extracts were dried and all of the organic extracts were combined. Partial concentration in vacuo caused precipitation of a solid; the mixture was diluted with hexanes and allowed to stand at rt for 1.5 h. The precipitate was filtered and dried to afford 402.2 g (87%) of the title compound: $^1$H NMR (500 MHz) δ 2.86 (dd, J=13.5, 9.5, 1H), (3.38, J=13.5, 3.5, 1H), 4.20–4.27 (m, 2H), 4.78–4.83 (m, 1H), 7.24–7.42 (5H), 7.63–7.65 (m, 1H), 7.92 (app d, J=2.5, 1H).

Step B: 3-(1-Benzyl-4-(S)-phenylpyrrolidine-3-(R)-carbonyl)-4-(S)-benzyl oxazolidin-2-one and 3-(1-benzyl-4-(R)-phenyl-pyrrolidine-3-(S)-carbonyl)-4-(S)-benzyl oxazolidin-2-one A solution of 402 g (1.3 mol) of 3-((E)-cinnamoyl)-4-(S)-benzyl oxazolidin-2-one (from Step A) and 474 g (2.0 mol) of N-methoxymethyl-N-trimethylsilylmethyl benzyl amine in 4 L of $CH_2Cl_2$ at −10° C. was treated with 6 mL of trifluoroacetic acid. The resulting mixture was stirred cold for 4 h and then was treated with an additional 4 mL of trifluoroacetic acid. The reaction mixture was warmed to rt and stirred for 20 h. The reaction was quenched with 2 L of sat'd $NaHCO_3$ and the layers were separated. The organic layer was washed with 1 L of sat'd NaCl and concentrated. Chromatography on 10 kg of silica gel using 4:1 v/v hexanes/EtOAc (24 L), then 7:3 v/v hexanes/EtOAc (36 L), then 3:2 v/v hexanes/EtOAc (32 L) afforded 260.9 g (45%) of 3-(1-benzyl-4-(S)-phenylpyrrolidine-3-(R)-carbonyl)-4-

(S)-benzyl oxazolidin-2-one and 247.5 g (43%) of 3-(1-benzyl-4-(R)-phenylpyrrolidine-3-(S)-carbonyl)-4-(S)-benzyl oxazolidin-2-one. For 3-(1-benzyl-4-(S)-phenylpyrrolidine-3-(R)-carbonyl)-4-(S)-benzyl oxazolidin-2-one: $^1$H NMR (500 MHz) δ 2.66 (t, J=8.0, 1H), 2.78 (dd, J=13.0, 9.0, 1H), 2.87 (dd, J=9.0, 4.5, 1H), 3.21–3.27 (m, 2H), 3.64 (d, J=11.5, 1H), 3.77 (d, J=11.5, 1H), 4.10–4.15 (m, 2H), 4.61–4.65 (m, 1H), 7.16–7.38 (15H). For 3-(1-benzyl-4-(R)-phenylpyrrolidine-3-(S)-carbonyl)-4-(S)-benzyl oxazolidin-2-one: $^1$H NMR (500 MHz) δ 2.69–2.76 (m, 2H), 2.82 (dd, J=9.5, 5.5, 1H), 3.14–3.22 (3H), 3.64 (d, J=13.0, 1H), 3.74 (d, J=13.0, 1H), 4.07–4.12 (m, 2H), 4.16 (t, J=9.0, 1H), 4.26–4.30 (m, 1H), 4.65–4.69 (m, 1H), 7.03–7.40 (15H).

Step C: 1-Benzyl-3-(R)-hydroxymethyl-4-(S)-phenylpyrrolidine

A solution of 3-(1-benzyl-4-(S)-phenylpyrrolidine-3-(R)-carbonyl)-4-(S)-benzyl oxazolidin-2-one (from Step B) in 2.5 L of THF at 10° C. was treated with 1.18 L of 1.0 M lithium aluminum hydride solution in THF over a period of 2 h. The resulting mixture was warmed to rt and stirred for 20 h. The reaction was quenched by adding 40 mL of H$_2$O, then 40 mL of 2.0 N NaOH, then 115 mL of H$_2$O and then was stirred at rt for 1.5 h. The mixture was filtered and the filtrate was concentrated. Chromatography on 4 kg of silica using 4:1 hexanes/acetone (14 L), then 7:3 hexanes/acetone as the eluant to afford 108.4 g (69%) of the title compound: $^1$H NMR (400 MHz) δ 2.38–2.46 (m, 2H), 2.78–2.88 (3H), 3.20–3.26 (2H), 3.65 (dd, J=12.0, 4.0, 1H), 3.66 (app s, 2H), 3.74 (dd, J=12.0, 4.0, 1H), 7.18–7.34 (10H); ESI-MS 268 (M+H); HPLC A: 2.35 min.

Step D: 1-Benzyl-3-(R)-(t-butyldimethylsilyloxymethyl)-4-(S)-phenyl pyrrolidine

A solution of 82.0 g (0.31 mol) of 1-benzyl-3-(R)-hydroxymethyl-4-(S)-phenyl pyrrolidine (from Step C) and 46.5 g (0.36 mol) of N,N-diisopropylethylamine in 1 L of CH$_2$Cl$_2$ was treated with 54.2 g (0.36 mol) of t-butyldimethylsilyl chloride and the resulting mixture was stirred at rt for 20 h. The reaction was quenched with 750 mL of sat'd NaHCO3 and the layers were separated. The organic layer was combined with 150 g of silica gel and aged for 45 min. The mixture was filtered and the filtrate was concentrated to afford 117 g (100%) of the title compound.

Step E: 3-(R)-(t-Butyldimethylsilyloxymethyl)-4-(S)-phenylpyrrolidine

A mixture of 117 g (0.31 mol) of 1-benzyl-3-(R)-(t-butyldimethylsilyloxymethyl)4-(S)-phenyl pyrrolidine (from Step D), 31.5 g (0.50 mol) ammonium formate, 20.0 g of 20% palladium hydroxide on carbon in 1.5 L of MeOH was heated at 55° C. for 2.5 h. The mixture was cooled and filtered through a pad of Celite. The filtrate was concentrated. The residue was dissolved in 1 L of CH$_2$Cl$_2$, washed with 300 mL of 10% NH4OH solution, 200 mL of sat'd NaCl, dried over MgSO4 and concentrated to afford 89.2 g (99%) of the title compound: $^1$H NMR (400 MHz) δ-0.09 (s, 3H), -0.08 (s, 3H), 0.77 (s, 9H), 2.25–2.30 (m, 1H), 2.84–2.96 (4H), 3.18 (dd, J=11.2, 3.2, 1H), 3.29–3.36 (m, 1H), 3.44 (dd, J=10.0, 6.0), 3.56 (dd, J=10.0, 4.4, 1H); ESI-MS 292 (M+H); HPLC A: 3.44 min.

Pyrrolidine 2

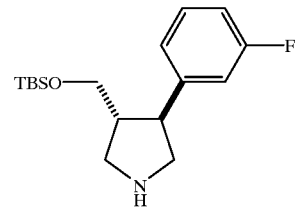

3-(R)-(t-Butyldimethylsilyloxymethyl)-4-(S)-(3-fluoro)phenylpyrrolidine

The title compound was prepared using procedures analogous to those described to prepare Pyrrolidine 1, except that trans-(3-fluoro)cinnamic acid was substituted for trans-cinnamic acid in Step A. For the title compound: $^1$H NMR (400 MHz): δ 0.013 (s, 3H), 0.016 (s, 3H), 0.87 (s, 9H), 2.09 (br s, 1H), 2.30–2.37 (m, 1H), 2.88–2.90 (3H), 2.23 (dd, J=8.0, 11.2, 1H), 3.39 (dd, J=6.8, 10.0. 1H), 3.56 (dd, J=6.0, 10.0, 1H), 3.64 (dd, J=5.2, 10.0), 6.86–6.91 (m, 1H), 6.95 (dt, J=12.0, 2.4, 1H), 7.01 (d, J=7.6, 1H), 7.22–7.27 (m, 1H); ESI-MS 310 (M+H); HPLC A: 3.05 min.

Pyrrolidine 3

(3-(R)-((t-Butyldimethylsilyloxy)methyl)-4-(S)-(3-thienyl)pyrrolidine

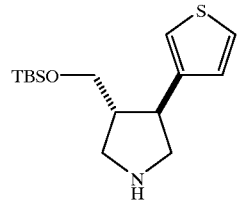

Step A: 1-(Prop-2-enyl)-3-(R)-(hydroxymethyl)-4-(S)-(3-thienyl) pyrrolidine

The title compound was prepared using procedures analogous to those used to prepare 1-benzyl-3-(R)-(hydroxymethyl)-4-(S)-phenylpyrroldine (Pyrrolidine 1, Step C), except that trans-3-(3-thienyl)acrylic was substituted for trans-cinnamic acid in Step A and N-methoxymethyl-N-trimethylsilylmethyl(prop-2-enyl)amine was substituted for N-methoxymethyl-N-trimethylsilylmethyl benzyl amine in Step B. For the title compound: $^1$H NMR (500 MHz) δ 2.30–2.34 (m, 1H), 2.44 (t, J=8.5, 1H), 2.67 (t, J=9.0, 1H), 2.77 (dd, J=5.0, 9.0, 1H), 3.02–3.15 (4H), 3.53 (dd, J=7.5, 10.0, 1H), 3.64 (dd, J=5.0, 10.0, 1H), 5.07 (d, J=10.0, 1H), 5.17 (d, J=17.5, 1H), 5.83–5.91 (m, 1H), 6.97–6.99 (2H), 7.20–7.22 (m, 1H); ESI-MS 224 (M+H).

Step B: 1-(Prop-2-enyl)-3-(R)-(t-butyldimethylsilyloxymethyl)-4-(S)-(3-thienyl)pyrrolidine A solution of 1.06 g (4.75 mmol) of 1-(prop-2-enyl)-(3-(R)-(hydroxymethyl))-4-(S)-(3-thienyl)pyrrolidine (from Step A) in 12.0 mL of CH$_2$Cl$_2$ at 0° C. was treated with 0.99 mL (5.7 mmol) of N,N-diisopropylethylamine and 855 mg (5.6 mmol) of t-butyldimethylsilyl chloride. After warming to rt and stirring for 20 h, the solution was partitioned between 100 mL of ether and 100 mL of H$_2$O. After separating the phases, the aqueous layer was extracted with 100 mL of ether. The combined organic phases were dried over MgSO$_4$ and concentrated. The residue was purified by flash chromatography eluting with 3:1 v/v hexanes/EtOAc to yield 1.24 g (77%) of the title compound: $R_F$: 0.54 (3:2 v/v hexanes/EtOAc); $^1$HNMR (300 Mhz) δ 0.0 (s, 6H), 0.86 (s, 9H), 2.35 (m, 1H), 2.52–2.71 (m, 3H), 2.97–3.20 (m, 4H), 3.54–3.66 (m, 2H), 5.06–5.21 (m, 2H), 5.89 (m, 1H). 6.98–7.02 (m, 2H), 7.22 (m, 1H).

Step C: 3-(R)-(t-Butyldimethylsilyloxymethyl)-4-(S)-(3-thienyl)pyrrolidine

A solution of 3.7 g (11.0 mmol) of 1-(prop-2-enyl)-3-(R)-(t-butyldimethylsilyloxymethyl)-4-(S)-(3-thienyl)pyrrolidine (from Step B) in 16% aqueous acetonitrile (degassed with nitrogen) was treated with 540 mg (0.58 mmol) of chlorotris(triphenylphosphine)rhodium. The reaction was warmed to reflux and the propanal that formed was removed via azeotropic distillation with the solvents. Additional solvent was added periodically to maintain a constant reaction volume. After 6 h, TLC indicated the absence of starting material. The reaction was cooled to rt and concentrated. The residue was purified by flash chromatography eluting with a gradient of 97:2:1 v/v/v $CH_2Cl_2$/MeOH/ $NH_4OH$, then 94:5:1 v/v/v $CH_2Cl_2$/MeOH/$NH_4OH$, then 89:10:1 v/v/v $CH_2Cl_2$/MeOH/$NH_4OH$ to yield 2.76 g (84%) of the title compound: $R_F$: 0.26 (97:2:1 v/v/v $CH_2Cl_2$/MeOH/$NH_4OH$); $^1$HNMR (300 MHz) δ 0.0 (s, 6H), 0.86 (s, 9H), 2.36 (m, 1H), 2.93–3.70 (m, 7H), 6.99–7.06 (m, 2H), 7.28 (m, 1H).

Hydroxy Ester 1

2-(S)-Hydroxy-3-(cyclopropyl)propanoic acid, (4-methoxy)benzyl ester

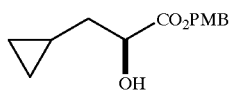

Step A: 2-(S)-Hydroxy-3-cyclopropyl propanoic acid

A 1 L, 3-neck flask was equipped with two dropping funnels, one containing 21.3 mL of 2.0 N $H_2SO_4$ and the other containing 21.3 mL of 2.0 N $NaNO_2$. A mixture of 5.00 g (38.7 mmol) of 2-(S)-amino-3-cyclopropyl propanoic acid in 28 mL of $H_2O$ at 0° C. was treated with a sufficient amount of the acid solution to dissolve the solids. The remaining $H_2SO_4$ solution and the $NaNO_2$ solution were added maintaing the internal temperature at less than 5° C. The resulting mixture was stirred cold for 3 h, then warmed to rt and stirred for 20 h. The reaction mixture was saturated with NaCl and extracted with 4×100 mL of EtOAc. The extracts were dried over $MgSO_4$ and concentrated to afford 4.30 g (85%) of the title compound: $^1$H NMR (300 MHz): δ 0.13–0.18 (m, 2H), 0.48–0.54 (m, 2H), 0.89 (m, 1H), 1.67–1.76 (m, 2H), 4.37 (dd, J=6.4, 4.7 Hz, 1H).

Step B: 2-(S)-Hydroxy-3-(cyclopropyl)propanoic acid, 4-(methoxy)benzyl ester

A solution of 4.30 g (33 mmol) of 2-(S)-hydroxy-3-(cyclopropyl)propanoic acid (from Step A), 6.40 mL (46 mmol) of TEA and 5.90 mL (44 mmol) of 4-(methoxy)benzyl chloride in 40 mL of DMF was stirred at rt for 2 h. The mixture was partitioned between 500 mL of ether and 300 mL of $H_2O$ and the layers were separated. The organic layer was washed with 300 mL of 2.0 N HCl, 300 mL of sat'd $NaHCO_3$, 2×300 mL of $H_2O$, 300 mL of sat'd NaCl, dried over $MgSO_4$ and concentrated. Flash chromatography on 500 g of silica gel using 5:1 v/v hexanes/EtOAc as the eluant afforded 4.30 g (52%, 97.5% ee) of the title compound: $R_F$: 0.20 (4:1 v/v hexanes/EtOAc); $^1$H NMR (300 MHz): δ-0.01–0.09 (m, 2H), 0.40–0.45 (m, 2H), 0.84 (m, 1H), 1.55–1.67 (m, 2H), 2.82 (br m, 1H), 3.81 (s, 3H), 4.25 (br m, 1H), 5.14 (ABq, J=11.8, 2H), 6.90 (d, J=8.7, 2H), 7.29 (d, J=8.7, 2H). HPLC: Chiracel OB 4.6×250 mm column, 65:35 v/v hexanes/EtOH, 0.5 mL/min, 220 nm. Retention times: (S)-enantiomer, 20.4 min; (R)-enantiomer, 17.3 min.

Hydroxy Ester 2

2-(S)-Hydroxy-3-(cyclobutyl)propanoic acid, benzyl ester

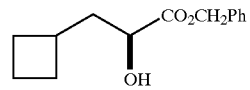

Step A: N,N'-Dimethyl-N,N'-dimethoxy oxamide

A mixture of 48.0 g (0.49 mol) of N,O-dimethylhydroxylamine.HCl in 250 mL of 3:2 v/v $CH_2Cl_2$/pyridine was cooled to −78° C. and was treated with 17.4 mL (0.2 mol) of oxalyl chloride maintaining the internal temperature at less than −70° C. The resulting mixture was allowed to warm to rt and stirred for 20 h. The reaction was quenched with 250 mL of sat'd NaCl and the quenched mixture was extracted with 3×400 mL of $CH_2Cl_2$. The extracts were combined, dried over $MgSO_4$ and concentrated. Recrystallization from 250 mL of MTBE afforded 24.28 g (69%) of the title compound: $^1$H NMR (500 MHz) δ 3.25 (s, 6H), 3.75 (s, 6H).

Step B: N-Methyl-N-methoxy 2-oxo-3-cyclobutyl propanamide

A suspension of 4.86 g (0.20 mol) of magnesium turnings in 250 mL of THF was treated with 2.0 mL (0.022 mol) of 1,2-dibromoethane and then was warmed until gas evolution from the surface of the Mg was visible. 15.2 mL (0.178 mol) of 1,2-dibromoethane was added at rate to maintain a gentle reflux. After the addition, the resulting mixture was heated at reflux for 30 min, then cooled to rt. Potassium (15.6 g, 0.40 mol) was added in ~1 g portions; the mixture was warmed until the potassium started to react and a fine black precipitate formed. This was repeated until all of the potassium was added to the reaction mixture. The resulting suspension of Mg was cooled to 0° C.

The finely divided Mg was treated with 22.5 mL (0.20 mol) of bromomethylcyclobutane maintaining the internal temperature at <5° C. The resulting mixture was stirred cold for 1 h, then was treated with 26.40 g (0.15 mol) of N,N'-dimethyl-N,N'-dimethoxy oxamide (from Step A) in portions as a solid. The resulting mixture was stirred at 0° C. for 16 h. The reaction was poured onto a mixture of 100 mL conc. HCl and 500 g of ice under $N_2$ atmosphere. The quenched mixture was extracted with 1.5 L of EtOAc. The extract was washed with 500 mL of sat'd NaCl, dried over $MgSO_4$ and concentrated. Flash chromatography on 500 g of silica gel using 3:1 v/v hexanes/EtOAc as the eluant afforded 22.3 g (80%) of the title compound: $^1$H NMR (500 MHz) δ 1.66–1.76 (m, 2H), 1.82–1.98 (m, 2H), 2.12–2.22 (m, 2H), 2.74–2.84 (3H), 3.20 (s, 3H), 3.66 (s, 3H).

Step C: N-Methyl-N-methoxy 2-(S)-hydroxy-3-cyclobutyl propanamide

A mixture of 11.40 g (61.5 mmol) of N-methyl-N-methoxy 2-oxo-3-cyclobutyl propanamide (from Step B) and 250 mL 0.5 N (R)-Alpine Borane® solution in THF was concentrated and stirred at rt for 5 days. The mixture was cooled to 0° C. and quenched with 6.8 mL (75.0 mmol) of isobutyraldehyde. The resulting mixture was diluted with 200 mL of ether and treated with 7.5 mL (125 mmol) of ethanolamine. The precipitate that formed was filtered and the filtrate was concentrated. Flash chromatography on 500 g of silica gel using 9:1 v/v $CH_2Cl_2$ as the eluant afforded 11.48 g (99%, 91% ee) of the title compound: $^1$H NMR (500 MHz) δ 1.59–1.70 (m, 2H), 1.67 (s, 1H), 1.77–1.83 (m, 2H), 1.82–1.92 (m, 1H), 2.03–2.13 (m, 2H), 2.53–2.60 (m, 1H), 3.23 (s, 3H), 3.72 (s, 3H), 4.31 (app d, J=5.5, 1H); HPLC: Chiralpak AS 4.6×250 mm column, 75/25 hexanes/iPrOH, 0.5 mL/min, 210 nm. Retention Times: (S)-Enantiomer, 13.3 min; (R)-enantiomer, 17.2 min.

Step D: 2-(S)-Hydroxy-3-(cyclobutyl)propanoic acid

A suspension of 33.66 g (0.3 mol) of potassium t-butoxide in 50 mL of THF was treated with 5.40 mL (0.3 mol) of $H_2O$. The resulting mixture was treated with a solution of 11.48 g (0.061 mol) of N-methyl-N-methoxy 2-(S)-hydroxy-3-cyclobutyl propanamide (from Step C) in 20 mL of THF and stirred at rt for 20 h. The mixture was concentrated and the residue was partitioned between 300 mL of ether and 200 mL of $H_2O$ and the layers were separated. The pH of the aqueous layer was adjusted to 2 with concentrated HCl and extracted with 300 mL of EtOAc. The extract was washed with 100 mL of sat'd NaCl, dried over $MgSO_4$ and concentrated to afford 7.50 g (85%) of the title compound: $^1$H NMR (500 MHz) δ 1.66–1.76 (m, 2H), 1.78–1.98 (4H), 2.06–2.16 (m, 2H), 2.51–2.61 (m, 1H), 4.20 (dd, J=8.0, 4.0, 1H).

Step E: 2-(S)-Hydroxy-3-(cyclobutyl)propanoic acid, benzyl ester

A mixture of 1.05 g (7.3 mmol) of 2-(S)-hydroxy-3-(cyclobutyl)propanoic acid (from Step D), 40 mL (10.0 mmol) of TEA and 1.20 mL (10.0 mmol) of benzyl bromide in 8 mL of DMF was stirred at rt for 2 h. The mixture was partitioned between 200 mL of ether and 100 mL of $H_2O$ and the layers were separated. The organic layer was washed with 100 mL of 2.0 N HCl, 100 mL of sat'd $NaHCO_3$, 2×100 mL of $H_2O$, 100 mL of sat'd NaCl, dried over $MgSO_4$ and concentrated. Flash chromatography on 60 g of silica gel using 4:1 v/v hexanes/ether as the eluant afforded 1.20 g (70%) of the title compound: $^1$H NMR (500 MHz) δ 1.58–1.70 (m, 2H), 1.72–1.82 (m, 2H), 1.84–1.92 (m, 2H), 1.98–2.10 (m, 2H), 2.46–2.58 (m, 1H), 2.63 (br s, 1H), 4.15 (dd, J=7.5, 3.0), 7.33–7.40 (m, 5H).

Hydroxy Ester 3

2-(S)-Hydroxy-3-(cyclopentyl)propanoic acid, benzyl ester

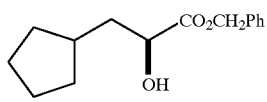

Step A: N-Methoxy-N-methyl-cyclopentylacetamide

A solution of 2.0 mL (15.9 mmol) of cyclopentylacetic acid in 80 mL of $CH_2Cl_2$ at 0° C. was treated with 3.7 mL (33.6 mmol) of N-methyl-morpholine and 2.2 mL (16.9 mmol) of isobutyl chloroformate. After stirring for 20 min, 1.61 g (16.5 mmol) of N,O-dimethyl-hydroxylamine.HCl was added. The reaction was warmed to rt and stirred for 3 h. The reaction was partitioned between 200 mL of EtOAc and 200 mL 2.0 N HCl. After separating the phases, the organic layer was washed with 200 mL of 1.0 N $NaHCO_3$, dried over $Na_2SO_4$ and concentrated. Flash chromatography on silica gel using 4:1 v/v hexanes/EtOAc afforded 2.28 g (83%) of the title compound as a colorless oil. $R_F$: 0.27 (4:1 v/v hexanes/ EtOAc). $^1$H NMR (300 MHz): δ 1.12–1.23 (m, 2H), 1.51–1.89 (m, 6H), 2.28 (m, 1H), 2.44 (d, J=7.5, 2H), 3.18 (s, 3H), 3.67 (s, 3H).

Step B: Cyclopentylmethylene phenyl ketone

A solution of 1.98 g (11.5 mmol) of N-methoxy-N-methyl-cyclopentylacetamide (from Step A) in 115 mL of THF at 0° C. was treated with 13.0 mL of 1.8 M phenyl-lithium in cyclohexane/diethylether over 40 min. After stirring for 1 h, the reaction was quenched with 2.0 N HCl and warmed to rt. The quenched reaction was partitioned between 200 mL of ether and 200 mL 2.0 N HCl and the layers were separated. The organic layer was washed with 200 mL of 1.0 N $NaHCO_3$, dried over $Na_2SO_4$ and concentrated. Flash chromatography on silica gel using 9:1 v/v hexanes/EtOAc afforded 1.57 g (72%) of the title compound: $R_F$: 0.66 (4:1 v/v hexanes/EtOAc); $^1$H NMR (300 MHz): δ 1.14–1.22 (m, 2H), 1.52–1.67 (m, 4H), 1.82–1.92 (m, 2H), 2.37 (m, 1H), 2.98 (d, J=7.1, 2H), 7.26–7.61 (m, 5H).

Step C: (S)-2-Cyclopentyl-1-phenylethanol

A solution of 2.7 mL of 1.0 M (R)-2-methyl-CBS-oxazaborolidine solution in toluene in 4 mL of $CH_2Cl_2$ at −25° C. was treated with 1.4 mL of 2.0 M borane methyl sulfide complex in THF and stirred cold for 10 min. A solution of 501 mg (2.66 mmol) of cyclopentylmethylene phenyl ketone (from Step B) in 2 mL of $CH_2Cl_2$ was added over 25 min and the resulting mixture was stirred cold for an additional 45 min. The reaction was quenched by pouring it into cold (−25° C.) MeOH. The quenched reaction was warmed to rt and stirred for 45 min until gas evolution ceased. The mixture was concentrated and the residue dissolved in 20 mL of MeOH and concentrated again. Flash chromatography on silica gel using 17:3 v/v hexanes/EtOAc afforded 413 mg (81%) of the title compound: $R_F$: 0.53 (4:1 v/v hexanes/ EtOAc); $^1$H NMR (300 MHz): δ 1.10–1.17 (m, 2H), 1.47–1.89 (m, 9H), 4.69 (m, 1H), 7.25–7.35 (m, 5H).

Step D: Acetic acid, (S)-2-cyclopentyl-1-phenylethyl ester

A solution of 406 mg (2.13 mmol) of (S)-2-cyclopentyl-1-phenylethanol (from Step C) in 9 mL of pyridine was treated with 1 mL of acetic anhydride. After stirring for 6 h, the reaction was concentrated. Flash chromatography on silica gel using 93:7 v/v hexanes/EtOAc afforded 495 mg (100%) of the title compound: $R_F$: 0.75 (4:1 v/v hexanes/EtOAc); $^1$H NMR (300 MHz): δ 1.10–1.21 (m, 2H), 1.44–2.04 (m, 9H), 2.05 (s, 3H), 5.75 (dd, J=8.0, 6.1, I H), 7.25–7.34 (m, 5H).

Step E: (S)-2-Acetoxy-3-(cyclopentyl)propanoic acid

A solution of 479 mg, (2.0 mmol) of acetic acid, (S)-2-cyclopentyl-1-phenylethyl ester (from Step D) in 14 mL of 2:2:3 v/v/v $CCl_4$/$CH_3CN$/$H_2O$ was treated with 6.59 g (28.9 mmol) of periodic acid and 7.8 mg (0.037 mmol) of $RuCl_3 \cdot H_2O$. The reaction was warmed to 33° C. and stirred for 4 h. After cooling to 0° C., 100 mL of ether was added. After stirring, for 10 min and separating the phases, the aqueous layer was extracted with 2×100 mL of ether. The combined organic layers were dried over $Na_2SO_4$ and concentrated to give 395 mg (95%) of the title compound: $R_F$: 0.62 (90:10:1 v/v/v $CH_2Cl_2$/MeOH/HOAc); $^1$H NMR (300 MHz): δ 1.09–1.98 (m, 11H), 2.14 (s, 3H), 5.03 (dd, J=8.8, 4.3, 1H), 8.9 (br, 1H).

Step F: 2-(S)-Hydroxy-3-(cyclopentyl)propanoic acid

A solution of 395 mg (1.97 mmol) of 2-(S)-acetoxy-3-(cyclopentyl)propanoic acid (from Step E) in 10 mL MeOH and 1 mL of $H_2O$ was treated with 1.29 g (9.33 mmol) of $K_2CO_3$ and stirred at rt for 30 h. The volatiles were removed under reduced pressure. The crude product was partitioned between 100 mL of ether and 100 mL of $H_2O$ and the layers were separated. The aqueous layer was acidified to pH 1–2 using 2.0 N HCl and extracted with 3×150 mL of EtOAc.

The combined organic layers were dried over Na$_2$SO$_4$ and concentrated to give 287 mg (92%) of the title compound: 1HNMR (300 MHz) δ 1.11–2.15 (m, 11H), 4.27 (dd, J=8.1, 4.7, 11H), 6.5 (br, 11H).

Step G: 2-(S)-Hydroxy-3-(cyclopentyl)propanoic acid, benzyl ester

A solution of 287 mg (1.81 mmol) of 2-(S)-hydroxy-3-(cyclopentyl)propanoic acid (from Step F) in 8 mL of DMF was treated with 0.38 mL (2.72 mmol) of TEA and 0.33 mL (2.77 mmol) of benzyl bromide and stirred at rt for 22 h. The reaction was diluted with 200 ml of ether and washed with 200 mL of H$_2$O, 200 mL of 2.0 N HCl, 200 mL of 1.0 N NaHCO3, 200 mL of H$_2$O and 200 mL of sat'd NaCl. The organic layer was dried over MgSO$_4$ and concentrated. Flash chromatography on silica gel using 17:3 v/v hexanes/EtOAc afforded 102 mg (22%, 95.5% ee) of the title compound: R$_F$: 0.40 (4:1 v/v hexanes/EtOAc); $^1$H NMR (300 MHz): δ 1.04–1.17 (m, 2H), 1.46–1.87 (m, 8H), 1.99 (m, 1H), 2.65 (m, 1H), 4.22 (dd, J=7.8, 4.8, 11H), 5.23 (ABq, J=12.3, 2H), 7.32–7.41 (m, 5H). HPLC: Chirapak AS 4.6×250 mm column, 17:3 v/v hexanes/iPrOH, 0.5 mL/min, 220 nm. Retention times: (S)-Enantiomer, 12.2 min; (R)-enantiomer, 15.3 min.

The following α-hydroxy benzyl and (4-methoxy)benzyl esters were prepared from the corresponding α-hydroxy acids (obtained from commercial sources or prepared as above) using esterification conditions analogous to those described above:

Hydroxy Ester 4

2-(S)-Hydroxy-3-(cyclobutyl)propanoic acid, (4-methoxy) benzyl ester

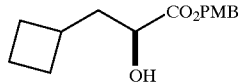

$^1$H NMR (500 MHz) δ 1.56–1.94 (6H), 1.98–2.12 (m, 2H), 2.44–2.56 (m, 1H),2.64 (br s, 1H), 3.82 (s, 3H), 4.11–4.13 (m, 1H), 5.19 (ABq, J=25.0, 2H), 6.90 (d, J=9.0, 2H), 7.30 (d, J=9.0, 2H).

Hydroxy Ester 5

2-(S)-Hydroxy-2-(cyclohexyl)acetic acid, benzyl ester

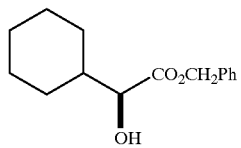

R$_F$: 0.37(4:1 v/v hexanes/EtOAc); $^1$H NMR (300 MHz) 1.11–1.38 (m, 11H), 2.65 (d, J=6.3 Hz, 1H), 4.06 (dd, J=6.3, 3.5 Hz, 1H), 5.22 (s, 2H), 7.30–7.39 (m, 5H).

Hydroxy Ester 6

2-(S)-Hydroxy-2-(cyclohexyl)acetic acid, (4-methoxy) benzyl ester

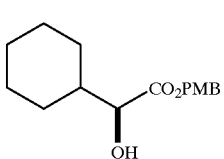

$^1$H NMR (500 MHz) δ 1.10–1.80 (11H), 2.68 (t, J=5.7 Hz, 1H), 3.83 (s, 3H), 4.06 (dd, J=6.1, 3.6 Hz, 1H), 5.17 (s, 2H), 6.91 (d, J=8.6 Hz, 1H), 7.31 (d, J=8.6 Hz, 1H).

Hydroxy Ester 7

2-(S)-Hydroxy-3-methylbutanoic acid, benzyl ester

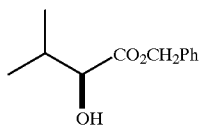

R$_F$: 0.39 (4:1 v/v hexanes/EtOAc); $^1$H NMR (300 MHz) δ 0.83 (d, J=7.0, 3H), 1.01 (d, J=7.0, 3H), 2.08 (m, 1H), 2.67 (d, J=6.3, 1H), 4.08 (dd, J=6.0, 3.6, 1H), 5.22 (ABq, J=12.1, 2H), 7.34–7.39 (m, 5H).

Hydroxy Ester 8

2-(S)-Hydroxy-3-methylbutanoic acid, (4-methoxy) benzyl ester

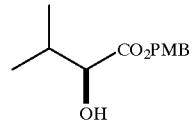

$^1$H NMR (500 M, CDCl$_3$): δ 7.30~7.33 (m, 2H), 6.90~6.93 (m, 2H), 5.20 (AB d, 11.9 Hz, 1H), 5.15 (AB d, 11 .9 Hz, 1H), 4.07 (d, 3.4 Hz, 1H), 3.83 (s, 3H), 2.68 (br s, 1H), 2.04~2.13 (m, 1H), 1.01 (d, 7.0 Hz, 3H), 0.83 (d, 6.9 Hz, 3H).

Hydroxy Ester 9

2-(S)-Hydroxy-3-(S)-methylpentanoic acid, benzyl ester

R$_F$: 0.67 (2:1 v/v hexanes/EtOAc); $^1$H NMR (500 MHz) δ 7.35~7.42 (m, 5H), 5.26 (AB d, 3=12.1 Hz, 1H), 5.22 (AB d, J=12.2 Hz, 1H), 4.14 (br s, 1H), 2.71 (br s, 1H), 1.81~1.89 (m, 1H), 1.30~1.38 (m, 1H), 1.20~1.29 (m, 1H), 0.99 (d, J=7.1 Hz, 3H), 0.88 (t, J=7.5 Hz, 3H).

Hydroxy Ester 10

2-(S)-Hydroxy-3-(R)-methylpentanoic acid, benzyl ester

R$_F$: 0.64 (2:1 v/v hexanes/EtOAc); $^1$H NMR (500 MHz) δ 7.35~7.42 (m, 5H), 5.26 (AB d, J=12.2 Hz, 1H), 5.23 (AB d, J=12.2 Hz, 1H), 4.25 (dd, J=2.8 & 5.6 Hz, 1H), 2.70 (br d, J=~3.8 Hz, 1H), 1.82~1.89 (m, 1H), 1.51~1.60 (m, 1H), 1.29~1.38 (m, 1H), 0.96 (t, J=7.5 Hz, 3H), 0.80 (d, J=6.9 Hz, 3H).

Hydroxy Ester 11

2-(S)-Hydroxy-3-(S)-methylpentanoic acid, (4-methoxy) benzyl ester

R$_F$: 0.38 (4:1 v/v hexanes/EtOAc); $^1$H NMR (500 MHz) δ 7.30–7.33 (m, 2H), 6.89~6.92 (m, 2H), 5.19 (AB d, J=11.9 Hz, 1H), 5.15 (AB d, J=11.9 Hz, 1H), 4.10 (dd, J=3.7 & 6.0 Hz, 1H), 3.83 (s, 3H), 2.71 (d, J=5.9 Hz, 1H), 1.78~1.86 (m, 1H), 1.18~1.36 (m, 2H), 0.97 (d, J=7.1 Hz, 3H), 0.87 (t, J=7.3 Hz, 3H).

Hydroxy Ester 12

2-(S)-Hydroxy-3-(cyclopropyl)propanoic acid, benzyl ester

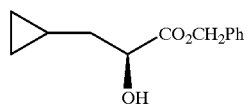

¹H NMR (300 MHz, CDCl₃): δ 7.33~7.47 (m, 5H), 5.21 (s, 2H), 4.28~4.37 (m, 1H), 2.80~2.90 (m, 1H), 1.60~1.72 (m, 2H), 0.79~0.0.91 (m, 1H), 0.40~0.53 (m, 2H), 0.00~0.14 (m, 2H),

Aldehyde 1

2-(R)-(3-(R)-Formyl-4-(S)-phenylpyrrolidin-1-yl)-3-(cyclobutyl)propionic acid, benzyl ester

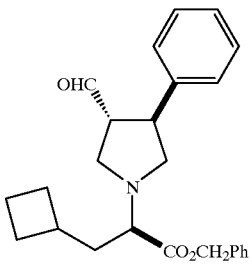

Step A: 2-(R)-(3-(R)-(t-Butyldimethylsilyloxymethyl)-4-(S)-phenylpyrrolidin-1-yl)-3-(cyclobutyl)propionic acid, benzyl ester A solution of 1.84 g (7.8 mmol) of 2-(S)-hydroxy-3-(cyclobutyl)propionic acid, benzyl ester (Hydroxy Ester 2) in 30 mL of CH₂Cl₂ at −5° C. was treated with 1.40 mL (8.4 mmol) of trifluoromethanesulfonic anhydride maintaining the internal temperature at less than 0° C. The resulting mixture was stirred cold for 2 min, then treated with 1.10 mL (9.6 mmol) of 2,6-lutidene, maintaining the internal temperature at less than 0° C. The resulting mixture was stirred cold for 30 min, then treated with a solution of 2.65 g (9.5 mmol) of 3-(R)-(t-butyldimethylsilyloxymethyl)-4-(S)-phenylpyrrolidine (Pyrroldine 1) in 10 mL of CH₂Cl₂ and 3.00 mL (31.2 mmol) of DIEA. The resulting mixture was warmed to rt and stirred for 20 h. The reaction was quenched with 50 mL of sat'd NaHCO₃ and the quenched mixture was extracted with 200 mL of ether. The ether extract was dried over MgSO₄ and concentrated. Flash chromtography on 150 g of silica gel using 20:1 v/v hexanes/ether as the eluant afforded 3.23 g (81 % based on Hydroxy Ester 2) of the title compound: ¹H NMR (300 MHz) δ-0.25 (s, 3H), −0.21 (s, 3H), 0.84 (s, 9H), 1.57–2.07 (8H), 2.29–2.39 (2H), 2.66–2.77 (m, 2H), 2.93 (q, J=7.8, 1H), 3.06 (t, J=8.4, 1H), 3.19 (t, J=8.4, 1H), 3.26 (dd, J=2.1, 6.3, 1H), 3.45–3.60 (m, 2H), 5.15 (s, 2H), 7.17–7.38 (1OH).

Step B: 2-(R)-(3-(R)-Hydroxymethyl-4-(S)-phenylpyrrolidin-1-yl)-3-(cyclobutyl)propionic acid, benzyl ester A solution of 3.20 g (6.3 mmol) of 2-(R)-(3-(R)-(t-butyldimethylsilyloxymethyl)-4-(S)-phenylpyrrolidin-1-yl)-3-(cyclobutyl) propionic acid, benzyl ester (from Step A) in 40 mL of THF at 0° C. was treated with 10 mL of 1.0 M tetrabutylammonium fluoride solution in THF. The resulting mixture was warmed to rt and stirred for 2.5 h. The reaction mixture was partitioned between 200 mL of ether and 100 mL of 50% sat'd NaHCO₃ and the layers were separated. The organic layer was dried over MgSO4 and concentrated. Flash chromatography on 100 g of silica gel using 2:1 v/v hexanes/ether as the eluant afforded 2.34 g (94%) of the title compound: ¹H NMR (500 MHz) δ 1.56–2.07 (8H), 2.15 (br s, 1H), 2.27–2.37 (2H), 2.64 (t, J=11.0, 1H), 2.80 (dd, J=6.5, 11.0), 3.04–3.11 (2H), 3.23–3.30 (2H), 3.56 (dd, J=7.5, 13.0, 1H), 3.68 (dd, J=5.5, 13.0, 1H), 5.15 (ABq, J=20.0, 2H), 7.17–7.40 (1OH).

Step C: 2-(R)-(3-(R)-Formyl-4-(S)-phenylpyrrolidin-1-yl)-3-(cyclobutyl)propionic acid, benzyl ester A solution of 1.29 mL (14.8 mmol) of oxalyl chloride in 15 mL of CH₂Cl₂ at −78° C. was treated with 2.10 mL (29.7 mmol) of DMSO maintaining the temperature at less than −60° C. The resulting mixture was stirred cold for 5 min. A solution of 2.33 g (5.9 mmol) of 2-(R)-(3-(R)-(hydroxymethyl)-4-(S)-phenylpyrrolidin-1-yl)-3-(cyclobutyl)propionic acid, benzyl ester (from Step B) in 10 mL of CH₂Cl₂ was added maintaining the temperature at less than −60° C. The resulting mixture was stirred cold for 30 min. The mixture was treated with 10.3 mL (59.3 mmol) of DIEA maintaining the temperature at less than −60° C. The reaction was warmed to 0° C., stirred for 20 min and quenched with H₂O. The mixture was partitioned between 250 mL of CH₂Cl₂ and 100 mL of H₂O and the layers were separated. The aqueous layer was extracted with 250 mL of CH₂Cl₂. The combined organic phases were dried over Na₂SO₄ and concentrated. Flash chromatography on 100 g of silica gel using 4:1 v/v hexanes/ether as the eluant afforded 2.30 g (97%) of the title compound: ¹H NMR (300 MHz) δ 1.54–2.08 (m, 8H), 2.31 (m, 1H), 2.75 (t, J=8.6 Hz, 1H), 2.96 (m, 1H), 3.11–3.35 (m, 4H), 3.56 (q, J=7.9 Hz, 1H), 5.16 (s, 2H), 7.19–7.39 (m, 1OH), 9.63 (d, J=2.2 Hz, 1H).

The following 1,3,4-trisubstituted pyrrolidine aldehydes were prepared from the appropriate α-hydroxy ester and 3,4-disubstituted pyrroldine using procedures analogous to those described for the preparation of Aldehyde 1.

Aldehyde 2

2-(R)-(3-(R)-Formyl-4-(S)-(3-fluorophenyl)pyrrolidin-1-yl)-3-(cyclobutyl)propionic acid, benzyl ester

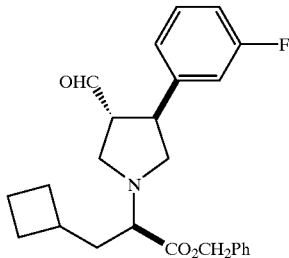

The title compound was prepared from ax-Hydroxy Ester 2 and 4Pyrrolidine 2: R$_F$: 0.60 (7:3 v/v hexane/EtOAc); ¹H NMR (300 MHz) δ 1.57–2.08 (m, 8H), 2.29 (m, 1H), 2.73 (br t, 1H), 2.92 (m, 1H), 3.14–3.34 (m, 4H), 3.56 (br q, 1H), 5.16 (s, 2H), 6.88–6.99 (m, 3H), 7.20–7.39 (m, 6H), 9.62 (d, J=2.0, 1H).

Aldehyde 3

2-(R)-(3-(R)-Formyl-4-(S)-phenylpyrrolidin-1-yl)-3-(cyclobutyl)propionic acid, (4-methoxy)benzyl ester

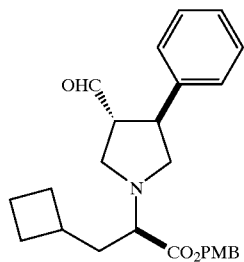

The title compound was prepared from α-Hydroxy Ester 4 and Pyrrolidine 1.

Aldehyde 4

2-(R)-(3-(R)-Formyl-4-(S)-phenylpyrrolidin-1-yl)-2-(cyclohexyl) acetic acid, benzyl ester

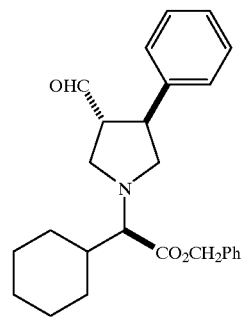

The title compound was prepared from α-Hydroxy Ester 5 and Pyrrolidine 1: $R_F$: 0.50 (4:1 v/v hexanes/EtOAc); $^1$H NMR (500 MHz) δ 0.94–1.03 (m, 2H), 1.05–1.29 (4H), 1.59 (app d, J=12.5, 1H), 1.67–1.84 (3H), 1.96 (app d, J=12.5, 1H), 2,71 (t, J=8.5, 1H), 2.93–2.96 (m, 1H), 3.17–3.22 (3H), 3.32 (t, J=8.5, 1H), 3.55 (q, J=8.0, 1H), 5.19 (app s, 2H), 7.19–7.41 (10H), 9.64 (d, J=2.0, 1H).

Aldehyde 5

2-(R)-(3-(R)-Formyl-4-(S)-phenylpyrrolidin-1-yl)-2-(cyclohexyl) acetic acid, (4-methoxy)benzyl ester

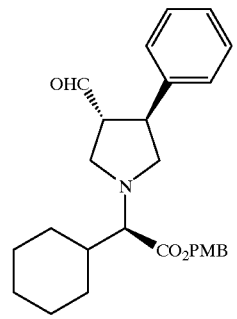

The title compound was prepared from α-Hydroxy Ester 6 and Pyrrolidine 1: $^1$H NMR (500 MHz) δ 0.95–1.98 (10H), 2.68 (t, J=8.6, 1H), 2.91–2.95 (m, 1H), 3.16–3.23 (3H), 3.29 (t, J=8.3, 1H), 3.48–3.56 (2H), 3.83 (s, 3H), 5.12 (s, 2H), 6.88–6.91 (2H), 7.17–7.35 (7H), 9.63 (d, J=2.3, 1H).

Aldehyde 6

2-(R)-(3-(R)-Formyl-4-(S)-(3-fluorophenyl)pyrrolidin-1-yl)-2-(cyclohexyl) acetic acid, benzyl ester

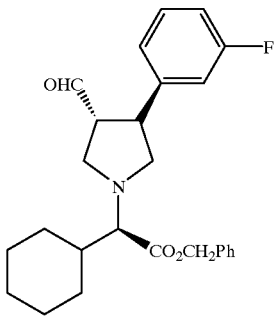

The title compound was prepared from x-Hydroxy Ester 5 and Pyrrolidine 2.

Aldehyde 7

2-(R)-(3-(R)-Formyl-4-(S)-(3-fluorophenyl)pyrrolidin-1-yl)-2-(cyclohexyl) acetic acid, (4-methoxy)benzyl ester

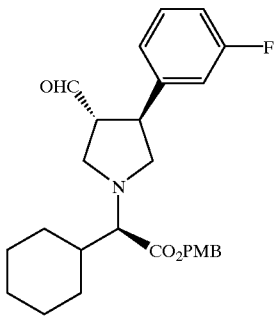

The title compound was prepared from α-Hydroxy Ester 6 and Pyrrolidine 2.

Aldehyde 8

2-(R)-(3-(R)-Formyl-4-(S)-phenylpyrrolidin-1-yl)-3-methyl butanonic acid, benzyl ester

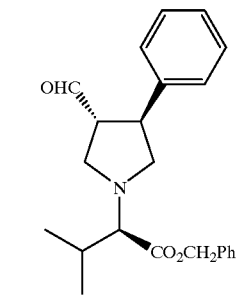

The title compound was prepared from α-Hydroxy Ester 7 and Pyrrolidine 1: $R_F$: 0.77 (3:2 v/v hexanes/EtOAc); $^1$H NMR (300 MHz) δ 0.89 (d, J=6.8, 3H), 1.00 (d, J=6.8, 3H), 2.08 (m, 1H), 2.66 (dd, J=8.9, 8.0, 1H), 2.92 (m, 1H), 3.08 (d, J=10.0, 1H), 3.17 (d, J=6.6, 1H), 3.28 (t, J=8.4, 1H), 3.53 (m, 1H), 5.17 (s, 2H), 7.16–7.38 (m, 10H), 9.63 (d, J=2.1, 1H).

Aldehyde 9

2-(R)-(3-(R)-Formyl-4-(S)-phenylpyrrolidin-1-yl)-3-methyl butanonic acid, (4-methoxy)benzyl ester

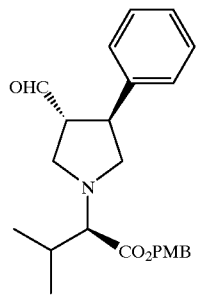

The title compound was prepared from α-Hydroxy Ester 8 and Pyrrolidine 1.

Aldehyde 10

2-(R)-(3-(R)-Formyl-4-(S)-(3-fluorophenyl)pyrrolidin-1-yl)-3-methyl butanonic acid, benzyl ester

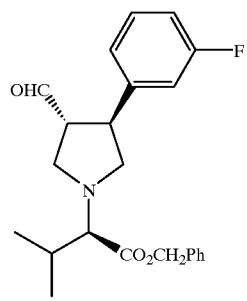

The title compound was prepared from α-Hydroxy Ester 7 and Pyrrolidine 2.

Aldehyde 11

2-(R)-(3-(R)-Formyl-4-(S)-(3-fluorophenyl)pyrrolidin-1-yl)-3-methyl butanonic acid, (4-methoxy)benzyl ester

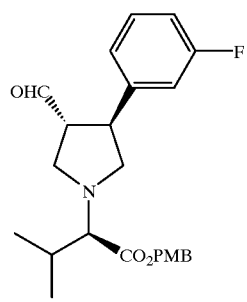

The title compound was prepared from α-Hydroxy Ester 8 and Pyrrolidine 2: $^1$H NMR (500 MHz) δ 0.91 (d, J=6.5, 3H), 1.00 (d, J=6.5, 3H), 2.04–2.09 (m, 1H), 2.68 (t, J=8.5, 1H), 2.88–2.92 (m, 1H), 3.06 (d, J=10.0, 1H), 3.14–3.19 (2H), 3.26 (t, J=8.5, 1H), 3.55 (q, J=7.5, 1H), 3.82 (s, 3H), 5.13 (app s, 2H), 6.88–6.97 (4H), 7.18–7.34 (5H), 9.64 (d, J=1.5, 1H).

Aldehyde 12

2-(R)-(3-(R)-Formyl-4-(S)-(3-fluorophenyl)pyrrolidin-1-yl)-3-(cyclopropyl)propionic acid, (4-methoxy)benzyl ester

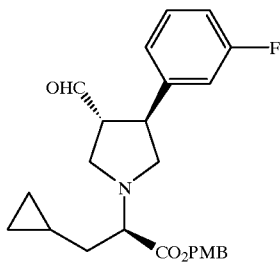

The title compound was prepared from α-Hydroxy Ester 1 and Pyrrolidine 2: $R_F$: 0.40 (7:3 v/v hexanes/EtOAc); $^1$H NMR (300 MHz) δ 0.01–0.10 (m, 2H), 0.36–0.49 (m, 2H), 0.69 (m, 1H), 1.54–1.76 (m, 2H), 2.64–3.61 (m, 7H), 3.80 (s, 3H), 5.12 (s, 2H), 6.84–7.04 (m, 5H), 7.21–7.34 (m, 3H), 9.63 (d, J=1.9, 1H).

Aldehyde 13

2-(R)-(3-(R)-Formyl-4-(S)-(3-thienyl)pyrrolidin-1-yl)-3-(cyclobutyl)propionic acid, (4-methoxy)benzyl ester

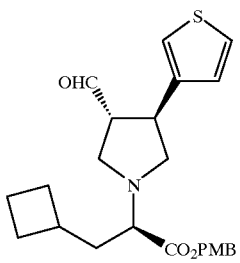

The title compound was prepared from (α-Hydroxy Ester 2 and Pyrrolidine 3: $R_F$: 0.56 (4:1 v/v hexanes/EtOAc); $^1$H NMR (300 Mhz) δ 1.56–2.05 (m, 8H), 2.27 (m, 1H), 2.69 (br t, 1H), 2.89 (m, 1H), 3.06–3.31 (m, 4H), 3.63 (br q, 1H), 3.81 (s, 3H), 5.09 (s, 2H), 6.86–6.96 (m, 4H), 7.25–7.33 (m, 3H), 9.63 (d, J=2.2, 1H).

Aldehyde 14

2-(R)-(3-(R)-Formyl-4-(S)-(3-fluorophenyl)pyrrolidin-1-yl)-3-(S)-methylpentanoic acid, benzyl ester Step A: 2-(S)-Trifluoromethanesulfonyl-3-(S)-methylpentanoic acid, benzyl ester A solution of 1.887 g triflic anhydride (6.69 mmole) in 5 mL DCM was cooled in a ice acetone bath at about –13° C. To this was added a solution of 1.416 g (6.37 mmole) 2-(S)-hydroxy-3-(S)-methylpentanoic acid, benzyl ester (Hydroxy acid 9 ), 0.751 g 2,6-lutidine in 10 mL DCM dropwise with stirring under nitrogen over 10 minutes. After stirring in the cold bath for one hour, the reaction mixture was transferred into a separatory funnel with 150 mL ether. It was washed with 60 mL water (3×) and brine (1×), dried over sodium sulfate, and concentrated to give the crude product (2.248 g). FC (0~35% ethyl acetate in hexanes) gave the title compound (1.764 g) as a colorless oil. $R_f$: 0.77 (30% ethyl acetate in hexanes). $^1$H NMR (500 MHz) δ 7.36–7.42 (m, 5H), 5.30 (AB d, J=11.9 Hz, 11H), 5.26 (AB d, J=12.1 Hz, 1H), 5.06 (d, 3.9 Hz, 1H), 2.12~2.19 (m, 1H), 1.41–1.49 (m, 1H), 1.26~1.35 (m, 1H), 1.05 (d, J=6.8 Hz, 3H), 0.90 (t, J=7.6 Hz, 3H).

Step B: 2-(R)-(3-(R)-(t-Butyldimethylsilyloxymethyl)-4-(S)-(3-fluorophenyl)pyrrolidin-1-yl)-3-(S)-methylpentanoic acid, benzyl ester A solution of 1.02 g DIEA (7.891 mmole) and 1.437 g (4.642 mmole) 3-(R)-(t-butyldimethylsilyloxymethyl)-4-(S)-(3-fluorophenyl)pyrrolidine (Pyrrolidine 2) in 5 mL DCM. was treated with a solution of 1.645 g (4.642 mmole) 2-(S)-trifluoromethane-sulfonyl-3-(S)-methylpentanoic acid, benzyl ester (from Step A above) in 10 mL DCM. After stirring over night at room temperature, the reaction mixture was transferred into a separatory funnel with 125 mL ether. It was washed with 75 mL 2% sodium bicarbonate, water (2×) and brine, dried over sodium sulfate, and concentrated to give the crude product (2.59 g). FC (5~105% ethyl acetate in hexanes with 1% triethylamine) gave the title compound (2.378 g) as a colorless oil. $R_f$: 0.70 (5% ethyl acetate in hexanes with 1% triethylamine). $^1$H NMR (500 MHz) δ 7.33–7.41 (m, 5H), 7.20–7.24 (m, 1H), 6.98 (d, J=7.5 Hz, 1H), 6.94 (d, J=10.3 Hz, 1H), 6.87–6.90 (m, 1H), 5.18 (s, 2H), 3.55 (dd, J=5.5 & 9.8 Hz, 1H), 3.50 (dd, J=7.1 & -~9.9 Hz, 1H), 3.14–3.20 (m, 2H), 3.08~3.12 (m, 1H), 2.91~2.96 (m, 1H), 2.70~2.73 (m, 1H), 2.62–2.65 (m, 1H), 2.28~2.34 (m, 1H), 1.83~1.90 (m, 1H), 1.41~1.48 (m, 1H), 1.06~1.12 (m, 1H), 1.01 (d, J=6.7 Hz, 3H), 0.90 (t, J=7.4 Hz, 3H), 0.87 (s, 9H), 0.01 (s, 6H).

Step C: 2-(R)-(3-(R)-(Hydroxymethyl)-4-(S)-(3-fluorophenyl)pyrrolidin-1-yl)-3-(S)-methylpentanoic acid, benzyl ester The product from Step B above in 20 mL THF was treated with 10 mL 1 N tetrabutylammonium fluoride in THF overnight. The reaction mixture was partitioned between 300 mL of ether and 150 mL icy water. The organic layer was washed with 75 mL 5% NaHCO$_3$ (3×) and saturated brine. The organic layer was dried over Na$_2$SO$_4$ and concentrated. Flash chromatography on 100 g of silica gel using 15~50% ethyl acetate in hexanes with 1% triethylamine afforded 1.587 g of the title compound as a colorless oil: $^1$H NMR (500 MHz) δ 7.33–7.42 (m, 5H), 7.22~7.26 (m, 1H), 6.98 (d, J=7.8 Hz, 1H), 6.88~6.94 (m, 2H), 5.19 (s, 2H), 3.67 (dd, J=4.8 & 10.5 Hz, 1H), 3.55–3.58 (m, 1H), 3.06~3.30 (m, 4H), 2.75~2.79 (m, 1H), 2.63~2.67 (m, 1H), 2.31~2.36 (m, 1H), 1.97 (br s, ~1H, OH?), 1.87~1.91 (m, 1H), 1.43–1.51 (m, 1H), 1.05~1.14 (m, 1H), 1.02 (d, J=6.6 Hz, 3H), 0.90 (t, J=7.3 Hz, 3H).

Step D: 2-(R)-(3-(R)-Formyl-4-(S)-(3-fluorophenyl)pyrrolidin-1-yl)-3-(S)-methylpentanoic acid, benzyl ester After cooling 0.605 g (4.767 mmole) oxalyl chloride in 30 m L DCM in a dry ice acetone bath under nitrogen, 0.748 g (9.569 mmole) DMSO in 5 mL DCM was added over 5 minutes. After stirring for 15 minutes, a solution of the alcohol (1.587 g, 3.987 mmole) from Step C above in 30 mL DCM was added over 20 minutes. After an additional 20 minutes, a solution of 2.017 g (19.935 mmole) triethylamine in 5 mL DCM was added over 5 minutes. The cooling bath was allowed to warm up overnight. The reaction mixture was transferred into a separatory funnel with ether and was washed with 1 N NaOH, water, and saturated brine. The organic layer was dried over sodium sulfate and concentrated to give 1.63 g crude product. FC on silica gel (5~40% ethyl acetate in hexanes) gave 1.257 g title compound as a colorless oil. $R_f$: 0.44 (20% ethyl acetate in hexanes). $^1$H NMR (500 MHz) δ 9.64 (d, J=2.1 Hz, 1H), 7.33~7.41 (m, 5H), 7.24~7.27 (m, 1H), 6.90~6.98 (m, 3H), 5.21 (AB d, J=12.2 Hz, 1H), 5.18 (AB d, J=12.2 Hz, 1H), 3.54~3.58 (m, 1H), 3.26~3.29 (m, 1H), 3.14~3.22 (m, 3H), 2.89~2.93 (m, 1H), 2.68~2.71 (m, 1H), 1.86~1.93 (m, 1H), 1.39–1.47 (m, 1H), 1.04~1.15 (m, 1H), 0.99 (d, J=6.7 Hz, 3H), 0.91 (t, J=7.5 Hz, 3H). Some starting material was also recovered (0.298 g). $R_f$: 0.13 (20% ethyl acetate in hexanes).

Aldehyde 15

2-(R)-(3-(R)-Formyl-4-(S)-(3-fluorophenyl)pyrrolidin-1-yl)-3-(R)-methylpentanoic acid, benzyl ester Step A: 2-(S)-Trifluoromethanesulfonyl-3-(R)-methylpentanoic acid, benzyl ester A solution of 1.334 g triflic anhydride (6.00 mmole) in 5 mL DCM was cooled in a ice acetone bath at about -13° C. A solution of 1.777 g (6.3 mmole) 2-(S)-hydroxy-3-(R)-methylpentanoic acid, benzyl ester (Hydroxy acid 10 ), 0.707 g 2,6-lutidine in 50 mL DCM was added dropwise with stirring under nitrogen over 15 minutes. After stirring in the cold bath for half an hour and without cooling for another half an hour, the reaction mixture was transferred into a separatory funnel with 150 mL ether. It was washed with 60 mL water (3×) and brine (1×), dried over sodium sulfate, and concentrated to give the crude product (2.187 g). FC (0~25% ethyl acetate in hexanes) gave the title compound (1.29 g) as a colorless oil. $R_f$: 0.83 (30% ethyl acetate in hexanes). $^1$H NMR (500 MHz) δ 7.35~7.43 (m, 5H), 5.30 (AB d, J=11.9 Hz, 1H), 5.28 (AB d, J=11.9 Hz, 1H), 5.14 (d, J=3.0 Hz, 1H), 2.09~2.17 (m, 1H), 1.48~1.57 (m, 1H), 1.32~1.41 (m, 1H), 0.98 (t, J=7.4 Hz, 3H), 0.945 (d, J=6.8 Hz, 3H).

Step B: 2-(R)-(3-(R)-(t-Butyldimethylsilyloxymethyl)-4-(S)-(3-fluorophenyl)pyrrolidin-1-yl)-3-(R)-methylpentanoic acid, benzyl ester A solution of 0.708 g DIEA (5.476 mmole) and 0.997 g (3.221 mmole) 3-(R)-(t-butyldimethylsilyloxymethyl)-4-(S)-(3-fluorophenyl)pyrrolidine (Pyrrolidine 2) in 5 mL DCM. was treated with a solution of 1.141 g (3.221 mmole) 2-(S)-trifluoromethane-sulfonyl-3-(R)-methylpentanoic acid, benzyl ester (from Step A above) in 5 mL DCM. After stirring over night at room temperature, the reaction mixture was transferred into a separatory funnel with 125 mL ether. It was washed with 75 mL 2% sodium bicarbonate, water (2×) and brine, dried over sodium sulfate, and concentrated to give the crude product (1.813 g). FC (5~105% ethyl acetate in hexanes with 1% triethylamine) gave the title compound (1.666 g) as a colorless oil. $R_f$: 0.70 (5% ethyl acetate in hexanes with 1% triethylamine). $^1$H NMR (500 MHz) δ 7.33~7.42 (m, 5H), 7.20–7.24 (m, 1H), 6.98 (d, J=7.5 Hz, 1H), 6.95 (d, J=10.0 Hz, 1H), 6.87–6.90 (m, 1H), 5.19 (s, 2H), 3.56 (dd, J=5.5 & 9.8 Hz, 1H), 3.50 (dd, J=7.1 & ~10.8 Hz, 1H), 3.14–3.20 (m, 2H), 3.08~3.11 (m, 1H), 2.91~2.96 (m, 1H), 2.68~2.72 (m, 1H), 2.61~2.65 (m, 1H), 2.29~2.33 (m, 1H), 1.84~1.90 (m, 1H), 1.68~1.76 (m, 1H), 1.16~1.23 (m, 1H), 0.89~0.94 (t & d, 6H), 0.87 (s, 9H), 0.01 (s, 6H).

Step C: 2-(R)-(3-(R)-(Hydroxymethyl)-4-(S)-(3-fluorophenyl)pyrrolidin- 1-yl)-3-(R)-methylpentanoic acid, benzyl ester The product from Step B above in 15 mL TBF was treated with 7 mL I N tetrabutylammonium fluoride in THF overnight. The reaction mixture was partitioned between 300 mL of ether and 150 mL icy water. The organic layer was washed with 75 mL 5% NaHCO$_3$ (3×) and saturated brine. The organic layer was dried over Na$_2$SO$_4$ and concentrated. Flash chromatography on 100 g of silica gel using 20~40% ethyl acetate in hexanes with 1% triethylamine afforded 1.24 g of the title compound as a colorless oil: $^1$H NMR (500 MHz) δ 7.33~7.42 (m, 5H), 7.21~7.26 (m, 1H), 6.98 (d, J=7.6 Hz, 1H), 6.88~6.95 (m, 2H), 5.19 (s, 2H), 3.66~3.69 (m, 1H), 3.55~3.60 (m, 1H), 3.24~3.28 (m, 1H), 3.18 (d, J=9.2 Hz, 1H), 3.05~3.12 (m, 2H), 2.72 (dd, J=5.0 & 9.1 Hz, 1H), 2.60 (dd, J=7.7 & 9.0 Hz, 1H), 2.28~2.34 (m, 1H), 1.99~2.02 (m, 1H, OH?), 1.84~1.91 (m, 1H), 1.61~1.69 (m, ~1H), 1.16~1.25 (m, 1H), 0.92 (t, J=7.6 Hz, 3H), 0.91 (d, J=7.6 Hz, 3H).

Step D: 2-(R)-(3-(R)-Formyl-4-(S)-(3-fluorophenyl)pyrrolidin-1-yl)-3-(R)-methylpentanoic acid, benzyl ester The title compound (1.031 g) was obtained from the alcohol in Step C above using the same procedure as described in Aldehyde 14 Step D. $R_f$: 0.47 (20% ethyl acetate in hexanes). $^1$H NMR (500 MHz) δ 9.64 (s, 1H), 7.34~7.42 (m, 5H), 7.24~7.28 (m, 1H), 6.91~6.99 (m, 3H), 5.20 (s, 2H), 3.53~3.58 (m, 1H), 3.12~3.29 (m, 4H), 2.89~2.94 (m, 1H), 2.66~2.71 (m, 1H), 1.88~1.93 (m, 1I), 1.63~1.70 (m, 1H), 1.15~1.21 (m, 1H), 0.89~0.93 (m, 6H).

Aldehyde 16

2-(R)-(3-(R)-Formyl-4-(S)-(3-fluorophenyl)pyrrolidin-1-yl)-3-(S)-methylpentanoic acid, (4-methoxy)benzyl ester Step A: 2-(S)-Trifluoromethanesulfonyl-3-(S)-methylpentanoic acid, (4-methoxy)benzyl ester The title compound was obtained from Hydroxyester 11 using the same procedure as described in Aldehyde 14 Step A for its benzyl analog. $^1$H NMR (500 MHz) δ 7.31~7.34 (m, 2H), 6.89~6.93 (m, 2H), 5.24 (AB d, J=11.7 Hz, 1H), 5.19 (AB d, J=11.9 Hz, 1H), 5.03 (d, 4.2 Hz, 1H), 3.83 (s, 3H), 2.09~2.17 (m, 1H), 1.41~1.49 (m, 1H), 1.39~1.47 (m, 1H), 1.24~1.33 (m, 1H), 1.03 (d, J=6.9 Hz, 3H), 0.89 (t, J=7.5 Hz, 3H).

Step B: 2-(R)-(3-(R)-(t-Butyldimethylsilyloxymethyl)-4-(S)-(3-fluorophenyl)pyrrolidin-1-yl)-3-(S)-methylpentanoic acid, (4-methoxy)benzyl ester The title compound was obtained from triflate (Step A above) using the same procedure as described in Aldehyde 14 Step B for its benzyl analogue. $R_f$: 0.26 (1:15 ethyl acetate and hexanes). $^1$H NMR (500 MHz) δ 7.31~7.34 (m, 2H), 7.19~7.24 (m, 1H), 6.86~6.97 (m, 5H), 5.11 (s, 2H), 3.83 (s, 3H), 3.55 (dd, J=5.6 & 10.0 Hz, 1H), 3.495 (dd, J=7.0 & 9.9 Hz, 1H), 3.12~3.16 (m, 2H), 3.06~3.10 (m, 1H), 2.90~2.94 (m, 1H), 2.695 (dd, J=7.2 & 9.0 Hz, 1H), 2.62~2.65 (dd, J=6.6 & 9.0 Hz, 1H), 2.27~2.33 (m, 1H), 1.82~1.88 (m, 1H), 1.41~1.46 (m, 1H), 1.04~1.10 (m, 1H1), 1.00 (d, J=6.7 Hz, 3H), 0.89 (t, J=7.3 Hz, 3H), 0.86 (s, 9H), 0.00 (s, 6H).

Step C: 2-(R)-(3-(R)-(Hydroxymethyl)-4-(S)-(3-fluorophenyl)pyrrolidin-1-yl)-3-(S)-methylpentanoic acid, (4-methoxy)benzyl ester The title compound was obtained from triflate from Step B above using the same procedure as described in Aldehyde 14 Step C for its benzyl analogue. $^1$H NMR (500 MHz) δ 7.32~7.35 (m, 2H), 7.21~7.26 (m, 1H), 6.88~6.97 (m, 5H), 5.13 (s, 2H), 3.82 (s, 3H), 3.67 (dd, J=4.8 & 10.3 Hz, 1H), 3.57 (dd, J=6.2 & 10.3 Hz, 1H), 3.22~3.26 (m, 1H), 3.15 (d, J=9.3 Hz, 1H), 3.09~3.12 (m, 1H), 3.03~3.08 (m, 1H), 2.73 (dd, J=4.9 & 9.3 Hz, 1H), 2.61 (dd, J=7.7 & 9.1 Hz, 1H), 2.27~2.33 (m, 1H), 1.84~1.89 (m, 1H), 1.41~1.49 (m, 1H), 1.03~1.10 (m, 1H), 1.00 (d, J=6.6 Hz, 3H), 0.89 (t, J=7.3 Hz, 3H).

Step D: 2-(R)-(3-(R)-Formyl-4-(S)-(3-fluorophenyl)pyrrolidin-1-yl)-3-(S)-methylpentanoic acid, (4-methoxy)benzyl ester The title compound was obtained from the alcohol (Step C above) using the same procedure as described in Aldehyde 14 Step D for its benzyl analogue. $^1$H NMR (500 MHz) δ 9.64 (d, J=2.1 Hz, 1H), 7.32~7.35 (m, 2H), 7.23~7.27 (m, 1H), 6.88~6.96 (m, 5H), 5.14 (AB d, J=11.9 Hz, 1H), 5.11 (AB d, J=11.9 Hz, 1H), 3.82 (s, 3H), 3.52~3.57 (m, 1H), 3.24~3.27 (m, 1H), 3.12~3.20 (m, 3H), 2.88~2.92 (m, 1H), 2.68 (dd, J=7.8 & 8.9 Hz, 1H), 1.84~1.91 (m, 1H), 1.38~1.45 (m, 1H), 1.05~1.13 (m, 1H), 0.98 (d, J=6.7 Hz, 3H), 0.90 (t, J=7.3 Hz, 3H).

Aldehyde 17

α-(R)-(3-(R)-Formyl-4-(S)-(3-fluorophenyl)pyrrolidin-1-yl)-tert-butylacetic acid, benzyl ester

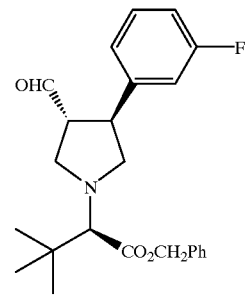

Step A: 3,3-dimethyl-2-(S)-hydroxybutyric acid benzyl ester (S)-3,3-dimethyl-2-hydroxybutyric acid (2.1 grams, 15.9 mmol) and triethylamine (3.3 mL, 23.8 mmoL) were dissolved in 15 mL DMF. Benzylbromide (2.8 mL, 23.8 mmol) was added and the mixture was stirred overnight. Ethyl acetate was added and the mixture was washed with water (3x) and sat'd NaCl then dried over sodium sulfate and concentrated. Flash chromatography (150 g silica, 7/1 Hexane / EtOAc) afforded 3.4 grams (96%) of the title compound. $^1$H NMR (300 MHz, CDCl$_3$). δ 0.98 (s, 9H), 2.75 (d, 1H), 3.85 (d, 1H), 5.23, (s, 2H), 7.27–7.3 (m, 5H).

Step B: 3,3-dimethyl-2-(S)-trifluoromethanesulfonylbutyric acid benzyl ester A solution of 3,3-dimethyl-2-(S)-hydroxybutyric acid benzyl ester (3.4 grams, 15.3 mmol, from Step A) in 60 mL dichloromethane was cooled to −78° C. under nitrogen. 2,6-lutidine (2.3 mL, 19.9 mmol) then trifluoromethanesulfonic anhydride (3.1 mL, 18.4 mmol) were added dropwise via syringe. The mixture was warmed to room temperature and stirred for 1 h. Water was added and the mixture was extracted with ethyl acetate. The organic layer was dried over sodium sulfate and concentrated. Flash chromatography (150 g silica, 20/1 Hexane / EtOAc) afforded 3.3 grams (61%) of the desired triflate. $^1$H NMR (400 MHz, CDCl$_3$). δ 1.05 (s, 9H), 4.8, (s, 1H), 5.25 (dd, 2H), 7.3~7.4 (m, 5H).

Step C: α-(R)-((3-(R)-(tert butyldimethylsilyloxy)methyl)-4-(S)-(3-fluorophenyl)pyrrolidin-1-yl)-tert-butylacetic acid A dry flask was charged 10 mL DMF and 3,3-dimethyl-2-(S)-trifluoromethanesulfonylbutyric acid benzyl ester, (2.2 grams, 6.4 mmol). The vessel was purged with nitrogen and 3-(R)-(t-butyldimethylsilyloxymethyl)-4-(S)-(3-fluoro)phenyl pyrrolidine (2.7 grams, 8.9 mmol, Pyrrolidine 2) then diisopropylethyl amine (1.8 mL, 10.2 mmol) were added. The mixture was heated to 50 C overnight. Water (200 mL) was added and the mixture was extracted with ether (2×150 mL). The combined organics were dried over sodium sulfate and concentrated. Flash chromatography (150 g silica, 30/1 Hexane/EtOAc) afforded 2.0 grams (61%) of product. $^1$H NMR (400 MHz, CDCl$_3$) δ 0 (s, 6H), 0.84 (s, 9H), 1.05 (s, 9H), 2.25–2.35 (m, 1H), 2.8~2.94 (m, 3H), 3.1–3.22 (m, 3H), 3.45–3.58 (m, 2H), 5.1–5.25 (dd, 2H), 6.83–6.99 (m, 3H), 7.19–7.24 (m, 1H), 7.3–7.42 (m, 5H).

Step D: α-(R)-(3-(R)-Formyl-4-(S)-(3-fluorophenyl) pyrrolidin-1-yl)-tert-butylacetic acid, benzyl ester The title compound was prepared in two steps from α-(R)-(3-(S)-tert butyldimethylsilyloxy)methyl)-4-(S)-(3-fluorophenyl)pyrrolidin-1-yl)-tert-butylacetic acid (Step C) using procedures analogous to those in for Aldehyde 1 Steps B and C. $^1$H NMR (400 MHz, CDCl$_3$). δ 1.05 (s, 9H), 2.88–2.96 (m, 2H), 3.2–3.35 (m, 4H), 3.48–4.53 (q, 1H), 5.11–5.25 (dd, 2H), 6.89–6.99 (m, 3H), 7.21–7.26 (m, 1H). 7.35–7.45 (m, 5H), 9.61 (s, 1H).

Aldehyde 18

α-(R)-(3-(R)-Formyl-4-(S)-(3-fluorophenyl)pyrrolidin-1-yl)-tert-butylacetic acid, 4-methoxybenzyl ester

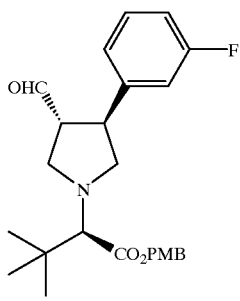

The title compound was prepared in an analagous fashion to aldehyde 17 except that in Step A 4-methyoxybenzyl chloride was used rather than benzyl bromide. $^1$H NMR (400 MHz, CDCl$_3$). δ 1.05 (s, 9H), 2.85–2.96 (m, 2H), 3.18–3.36 (m, 4H), 3.45–4.53 (q, 1H), 3.82, (s, 3H), 5.05–5.22 (dd, 2H), 6.89–6.99 (m, 5H), 7.21–7.26 (m, 1H). 7.35–7.45 (m, 2H), 9.61 (s, 1H).

EXAMPLE 1

α-(R)-(3-(S)-((4-(3-Benzyl-1-ethyl-(1H-pyrazol-5-yl)) piperidin-1-yl)methyl)-4-(S)-phenylpyrrolidin-1-yl)-cyclohexaneacetic acid, trifluoroacetic acid salt Step A: 1-(1-(tert-Butoxycarbonyl)piperidin-4-yl)-4-phenyl-butane-1,3-dione Method A:

n-Butyl lithium (100 mL, 0.16 mole) was added to a stirred solution of diisopropylamine (16.16 g, 22.4 mL, 0.16 mole, distilled) in THF (450 mL) at 0° C. over 45 min under nitrogen. Stirring was continued for 10 min at 0° C. after the addition was complete. After cooling to −78° C., phenylacetone (21.45 g, 21.13 mL, 0.16 mole) in THF (100 mL) was added dropwise over 15 min with stirring. This solution was stirred at −78° C. for 1 h. Meanwhile, a solution of N-Boc isonipecotic acid (18.32 g, 0.080 mole) and carbonyl diimidazole (12.98 g, 0.080 mole) in THF (150 mL) was prepared. After stirring for 15 min, this solution was cannulated into the enolate solution dropwise over 15 min. The reaction was stirred at <−70° C. for 1 h and then allowed to warm to rt over 3 h. The reaction was quenched with 1M citric acid (250 mL) and stirred for 16 h. The organic layer was separated and washed with 250 mL each of saturated sodium bicarbonate solution, water and brine. After drying over sodium sulfate, the organic layer was concentrated to give an oil. The residue was purified by FC on silica gel (10% ethyl acetate in 60–80° C. petroleum ether) to give separation of the two isomers. The first higher R$_f$ fractions afforded pure title compound as the minor product (3.5 g) as an oil.

$^1$H NMR (500 MHz, CDCl$_3$): δ 7.34–7.37 (m, 2 H), 7.25–7.31 (m, 3 H), 5.46 (s, 1 H), 4.11–4.17 (m, 2 H), 3.63 (s, 2H), 2.70–2.76 (m, 2 H), 2.29 (tt, J=11.7 and 3.7 Hz, 1 H), 1.75–1.80 (m, 2 H), 1.47–1.61 (m, 2 H), 1.47 (s, 9 H). MS (ESI): m/z 346 (M+1).

The lower R$_f$ fractions contained phenylacetone and major product 1-(1-(t-butoxycarbonyl)piperidin-4-yl)-2-phenylbutane-1,3-dione from which the latter crystallized on standing to give 7 g white solid (m.p. 105–106° C.). $^1$H NMR (360 MHz, CDCl$_3$): δ 15.23 (s, 1 H), 7.3–7.45 (m, 3 H), 7.15–7.2 (m, 2 H), 4–4.1 (m, 2 H), 2.35–2.50 (m, 2 H), 2.2–2.3 (m, 1 H), 1.87 (s, 3 H), 1.5–1.75 (m, 4 H), 1.43 (s, 9 H).

MS (ESI): m/z 346 (M+1).

Method B:

Step 1: 1 -(t-Butoxycarbonyl)piperidine4-N-methyl-N-methoxycarboxamide

N-Boc isonipecotic acid (13.566 g, 59.2 mmol), N,O-dimethyl hydroxylamine hydrochloride (8.657 g, 88.7 mmol), and 1-hydroxybenzotriazole hydrate (15.99 g, 118.3 mmol) were dissolved in DMF (225 mL) in a 500 mL round-bottom flask and diisopropylethylamine (15.29 g, 20.6 mL, 118.3 mmol) was then added with stirring at rt. 1-Ethyl-3-(3-dimethylamino-propyl)carbodiimide (17.01 g, 88.74 mmol) was added in several portions over 10 min with stirring. After 22 h, the reaction mixture was poured into a water and ice mixture (600 mL) and was extracted with ethyl acetate (5×125 mL). The combined organic layers were washed with 1N HCl (2×200 mL), 5% sodium bicarbonate (2×200 mL), water and brine, dried over sodium sulfate and concentrated to give the title compound (15.58 g) as a yellowish oil.

$^1$H NMR (500 MHz, CDCl$_3$): δ 4.11–4.20 (m, 2 H), 3.72 (br s, 3 H), 3.20 (br s, 3 H), 2.75–2.86 (m, 3 H), 1.63–1.76 (m, 4 H), 1.47 (s, 9 H).

Step 2: 4-Acetyl-1-(t-butoxycarbonyl)piperidine

After dissolving the above Weinreb amide in anhydrous ether (400 mL) under nitrogen and cooling the solution in an ice bath, 1.4M methyl magnesium bromide (55 mL) in 3:1 toluene and THF was added with stirring and cooling over 30 min. After stirring at 0° C. for 1 h, the reaction was poured into a mixture of ice water (400 mL) and acetic acid (0.8 mL, 150 mmol). The layers were separated and the aqueous layer was extracted twice with ether. The combined organic layers were washed with 0.1N HCl (200 mL), 3% sodium bicarbonate (200 mL), water (200 mL) and brine (200 mL), dried over sodium sulfate, and concentrated to give the crude product (14.322 g). FC (20–80% ethyl acetate in hexanes) gave the title comopound (9.440 g) as a yellowish oil. R$_f$: 0.27 (25% ethyl acetate in hexanes). Some starting Weinreb amide was also recovered (3.212 g). R$_f$: 0.10 (25% ethyl acetate in hexanes).

$^1$H NMR (500 MHz, CDCl$_3$): δ 4.07–4.14 (m, 2 H), 2.75–2.83 (m, 2 H), 2.46 (tt, J=11.3 and 3.8 Hz, 1 H), 2.17 (s, 3 H), 1.82–1.87 (m, 2 H), 1.48–1.57 (m, 2 H), 1.46 (s, 9 H).

Step 3: 1-(1 -(t-Butoxycarbonyl)piperidin-4-yl)-4-phenyl-butane- 1,3-dione

To a suspension of 60% sodium hydride (1.07 g) in THF (15 mL) at 0° C. was added a solution of 4-acetyl-1-(t-butoxycarbonyl)-piperidine from Step B2 (3.03 g, 13.3 mmol) and methyl phenylacetate (6.01 g, 39.9 mmol) in THF (6 mL) over 20 min. The reaction was stirred for another 4 h as it was allowed to warm to rt. The mixture was diluted with ether (30 mL) and poured into 1N HCl. The layers were separated and the aqueous layer was extracted three times with ether. The combined organic layers were washed with brine (150 ML), dried over sodium sulfate and concentrated. The crude product was purified by FC (20% ethyl acetate in hexanes) to give the title compound (3.02 g). $R_f$: 0.30 (20% ethyl acetate in hexane). Its NMR was the same as that obtained from the product of Method A above.

Step B: 4-(3-Benzyl-1-ethyl-(1H-pyrazol-5-yl))-1-(tert-butoxy-carbonyl)piperidine Method A:

1-(1-(t-Butoxycarbonyl)piperidin-4-yl)-4-phenyl-butane-1,3-dione (from Step A, either Method A or Method B), (0.851 g, 2.46 mmol) in methanol (25 mL) was added over 10 min to a suspension of ethylhydrazine oxalate (0.444 g, 2.96 mmol) in methanol (5 mL) in a 60° C. oil bath. After 15 h, the reaction was concentrated in vacuo and the residue was purified by repeated FC using a gradient of 50–100% ethyl acetate in hexanes to give first 4-(5-benzyl-1-ethyl-(1H-pyrazol-3-yl))-1-(t-butoxycarbonyl)piperidine (0.148 g total) as the higher $R_f$ product isomer and then the title compound (0.373 g total) as the lower $R_f$. $^1$H NMR (500 MHz): δ 7.26–7.31 (m, 4H), 7.19–7.23 (m, 1H), 5.72 (s, 1H), 4.16–4.24 (m, 2H), 4.08 (q, J=7.3 Hz, 2H), 3.94 (s, 2H), 2.76–2.82 (m, 2H), 2.66 (tt, J=3.6 & 11.9 Hz, 1H), 1.80–1.85 (m, 2H), 1.49–1.58 (m, 2H), 1.48 (s, 9H), 1.45 (t, J=7.3 Hz, 3H); ESI-MS 370.2 (M+H), HPLC A: 3.70 min. The other isomer's ESI-MS 370.2 (M+H), HPLC A: 3.77 min.

Method B:

Step 1: 1-(t-Butoxycarbonyl)-4-hydroxymethyl-piperidine

A solution of 25.03 g (109.2 mmole) N-Boc isonipecotic acid was dissolved in 200 mL TBF and treated with 200 mL 1 M borane-tetrahydrofuran complex in THF, and the mixture was stirred overnight. The mixture was concentrated under vacuum, diluted with 750 mL ethyl acetate, and washed with 150 mL 1 N HCl (6×) and then saturated brine. The organic layer was dried over sodium sulfate and concentrated to give 24.327 g of crude product as a white solid. H NMR (500 MHz) δ 4.15 (br d, J=13.7 Hz, 2H), 3.52 (d, J=6.2 Hz, 2H), 2.69–2.75 (m, 2H), 1.71–1.75 (m, 2H), 1.62–1.70 (m, 1H), 1.47 (s, 9H), 1.12–1.21 (m, 2H). This was used as is in the next step.

Step 2: 1-(t-Butoxycarbonyl)-4-formyl-piperidine

A mixture of 17.62 g (135.6 mmole) oxalyl chloride and 250 mL DCM in a dry ice acetone bath was treated with a solution of 21.19 g (271.2 mmole) DMSO in 150 mL DCM over 20 minutes. After stirring for 20 minutes, a solution of 24.327 g 1-(t-butoxycarbonyl)-4-hydroxymethyl-piperidine (from Step 1 above) in 150 mL DCM was added over one hour. After an additional 15 minutes, 57.17 (565 mmole) triethylamine in 150 mL DCM was added over half an hour. The reaction mixture was allowed to warm up over night in the cooling bath. The reaction mixture was concentraed under vacuum to remove about 400 mL DCM, and the residue was partitioned between 1 L ether and 300 mL water. To this was added 200 mL 1 N NaOH, the layers were separated, and the organic layer was washed with 150 mL 1 N NaOH (2×), water (3×), and saturated brine, dried over sodium sulfate, and concentrated to give 22.562 g crude product. FC (10–60% ethyl acetate in hexanes) gave 20.58 g title compound as slightly yellowish oil. $R_f$: 0.29 (3:1 v/v hexanes/EtOAc); $^1$H NMR (500 MHz) δ 9.68 (d, J=0.7 Hz, 1H), 3.96–4.02 (m, 2H), 2.92–2.97 (m, 2H), 2.40–2.45 (m, 1H), 1.88–1.94 (m, 2H), 1.53–1.64 (m, 2H), 1.47 (s, 9H).

Step 3: 1-(t-Butoxycarbonyl)-4-(2,2-dibromoethen-1-yl)-piperidine

A solution of 48.615 g (146.6 mmole) carbon tetrabromide in 150 mL DCM was added dropwise with stirring to a solution of 76.895 g (293.2 mmole) triphenylphosphine in 150 mL DCM in a 1-L rb flask with ice bath cooling over 1.75 hours. After 40 minutes, a solution of 15.631 g (73.29 mmole) 1-(t-butoxycarbonyl)-4-formyl-piperidine (from Step 2 above) in 100 mL DCM was added to the resulting brown suspension with stirring and cooling over 40 minutes. After one hour, 200 mL ether and 400 mL hexanes was added. The top suspension was filtered through Celite, and the residue was resuspended in 150 mL DCM and treated with 300 mL ether. The mixture was filtered, and the solid was washed with hexanes till total filtrate was 2 L. The filtrate was filtered again through Celite and washed with hexanes. The filtrate was washed with 100 mL 5% $NaHCO_3$, 300 mL water (2×), and 150 mL brine. The organic layer was dried over $Na_2SO_4$ and concentrated under vacuum to give 53.458 g crude product as a yellowish solid. Flash chromatography (PC) on 250 g silica gel (0–15% EtOAc in hexanes) gave 21.595 g title compound as a white solid. $R_F$: 0.57 (15% EtOAc in hexanes); $^1$H NMR (500 MHz) δ 6.25 (d, J=8.9 Hz, 1H), 4.04–4.12 (m, 2H), 2.75–2.83 (m, 2H), 2.42–2.50 (m, 1H), 1.69–1.75 (m, 2H), 1.47 (s, 9H), 1.29–1.37 (m, 2H).

Step 4: 1-(t-Butoxycarbonyl)-4-(2-tributylstannylethyn-1-yl)-piperidine

A mixture of 23.199 g (62.85 mmole) 1-(t-butoxycarbonyl)-4-(2,2-dibromoethen-1-yl)-piperidine (prepared as in Step 3 above) and 600 mL anhydrous THF was cooled with dry ice acetone bath under nitrogen. To this mixture was added 88 mL of a 1.6 M BuLi solution in hexanes dropwise with stirring and cooling over 50 minutes. After one hour, the flask was transferred into an ice bath. After another hour, a solution of 28.64 g (87.99 mmole) tributyltin chloride in 100 mL THF was added with stirring and cooling over 35 minutes. After three hours, the mixture was concentrated under vacuum to remove some THF, and the residue was partitioned between 600 mL ice water and 800 mL ether. The organic layer was washed with 200 mL of water (1×), 2% $NaHCO_3$ (1×), water (2×), and saturated brine (1×), dried over $Na_2SO_4$ and concentrated under vacuum to give 30.104 g crude product as a green-yellowish liquid. FC on 275 g silica gel using cold 2.5–15% EtOAc in hexanes as quickly as possible to give 27.115 g title compound as a colorless liquid. $R_F$: 0.45 (10% EtOAc in hexanes); H NMR (500 MHz) δ 3.63–3.67 (m, 2H), 3.25–3.30 (m, 2H), 2.64–2.69 (m, 1H), 1.74–1.79 (m, 2H), 1.54–1.64 (m, 8H), 1.47 (s, 9H), 1.32–1.39 (m, 6H), 0.96–0.99 (m, 6H), 0.92 (t, J=7.3 Hz, 9H).

Step 5: 4-(1 -(t-Butoxycarbonyl)piperidin-4-yl)- 1 -phenyl-2-butanon-3-yne

To a mixture of 1.727 g (3.466 mmole) 1-(t-butoxycarbonyl)-4-(2-tributyl-stannylethyn-1-yl)-piperidine (prepared in Step 4 above) in 18 mL 1,2-dichloroethane was added 0.536 g (3.466 mmole) phenylacetyl chloride and 50 mg dichlorobis-(triphenylphosphine)palladium (II). The mixture was refluxed under nitrogen for 2 hours, then concentrated under vacuum. Purifying the residue on silica gel (5–35% ethyl acetate in hexanes) gave 0.784 g title compound as a yellow oil. $R_F$: 0.27 (20% EtOAc in hexanes); $^1$H NMR (500 MHz) δ 7.34–7.38 (m, 2H), 7.28–7.32 (m, 1H), 7.24–7.27 (m, 2H), 3.82 (s, 2H), 3.49–3.54 (m, 2H), 3.17–3.23 (m, 2H), 2.68–2.73 (m, 1H), 1.72–1.77 (m, 2H), 1.51–1.57 (m, 2H), 1.47 (s, 9H). Tetrakis (triphenylphosphine)palladium gave a similar result.

Step 6: 4-(3-Benzyl-1-ethyl-(1H-pyrazol-5-yl))-1-(tert-butoxycarbonyl)-piperidine Heating 1.204 g (3.677 mmole) 4-(1-(t-butoxycarbonyl) piperidin-4-yl)-1-phenyl-2-butanon-3-yne (prepared in Step 5 above) with 0.662 g (4.413 mmole) ethylhydrazine oxalate and 1.252 g (9.687 mmole) DIEA in 20 mL ethanol overnight gave 8:1 ratio of the title compound and its isomer 4-(5-benzyl-1-ethyl-(1H-pyrazol-3-yl))-1-(tert-butoxycarbonyl)piperidine. Use of ethyhydrazine free base gave even more favorable ratios of the desired title compound. The desired isomer can be isolated by recrystallization using hexanes or by silica gel chromatography using 5–10% MeCN in DCM in addition to the procedure described in Method A above.

Step C: 4-(3-Benzyl-1-ethyl-(1H-pyrazol-5-yl)) piperidine, trifluoro-acetic acid salt To a solution of 4-(3-benzyl-1-ethyl-(1H-pyrazol-5-yl)-1-(t-butoxycarbonyl)-piperidine (from Step B, lower $R_f$ isomer) (0.373 g, 1.01 mmol) and anisole (0.219 mL, 2.02 mmol) in dichloromethane (15 mL) was added trifluoroacetic acid (1.555 mL, 20.2 mmol). The reaction was stirred at rt for 2.5 h and then concentrated. The residue was purified on preparative reverse-phase HPLC using 9.4×250 mm semi-preparative Zorbax SB-C18 column with 17.5–35% acetonitrile gradient in water having 0.5% (v/v) TFA over 15 min at 6.05 mL per minute to give the title di-TFA salt compound as an oil. When a mixture of isomers from Step B is used, separation is also possible at this step with the above Prep HPLC conditions in which the title isomer elutes prior to 4-(5-benzyl-1-ethyl-(1H-pyrazol-3-yl))piperidine. $^1$H NMR (500 MHz, CD$_3$OD): δ 7.15–7.27 (m, 5H), 5.88 (s, 1H), 4.13 (q, 7.1 Hz, 2H), 3.89 (s, 2H), 3.42–3.47 (m, 2H), 3.10–3.16 (m, 2H), 3.07 (tt, 11.9 & 3.6 Hz, 1H), 2.09 (br d, 14.3 Hz, 2H), 1.73-1.82 (m, 2H), 1.50 (t, 7.1 Hz, 3H); ESI-MS 270.0 (M+H), HPLC A: 1.68 min. 4-(5-Benzyl-1-ethyl-(1H-pyrazol-3-yl))piperidine's $^1$H NMR (500 MHz, CD$_3$OD): 7.28–7.31 (m, 2H), 7.20–7.24 (m, 1H), 7.18–7.20 (m, 2H), 5.92 (s, 1H), 4.02 (q, 7.3 Hz, 2H), 4.01 (s, 2H), 3.43 (ddd, 13.1, 3.5, 3.2 Hz, 2H), 3.07–3.13 (m, 2H), 2.93 (tt, 11.3 and 3.8 Hz, 1H), 2.12–2.17 (m, 2H), 1.81–1.90 (m, 2H), 1.19 (t, 7.3 Hz, 3H); ESI-MS 270.0 (M+H), HPLC A: 1.97 min.

Step D: α-(R)-(3-(S)-((4-(3-Benzyl-1-ethyl-(1H-pyrazol-5-yl))piperidin-1-yl)methyl)-4-(S)-phenylpyrrolidin-1-yl)-cyclohexaneacetic acid, benzyl ester, trifluoroacetic acid salt 4-(3-Benzyl-1-ethyl-(1H-pyrazol-5-yl))piperidine trifluoro-acetic acid salt prepared Step C (70.1 mg) was dissolved in 2 mL 1,2-dichloroethane. To this solution was added 57 mg x-(R)-(3-(R)-formyl-4-(S)-phenylpyrrolidin-1-yl)-cyclohexaneacetic acid, benzyl ester (prepared above as Aldehyde 4), 98.2 uL of diisopropylethylamine, and 89.7 mg sodium triacetoxyborohydride in that order. After stirring the reaction mixture overnight, solvent was removed and the residue was purified on RP-HPLC using the same column as in Step C above with 45–75% acetonitrile gradient at 7.5 mL per minute in three batches to give 88 mg of the title compound as a gel. ESI-MS 659.4 (M+H), HPLC A: 3.00 min.

Step E: α-(R)-(3-(S)-((4-(3-Benzyl-1-ethyl-(1H-pyrazol-5-yl))piperidin-1-yl)methyl)-4-(S)-phenylpyrrolidin-1-yl)-cyclohexaneacetic acid, trifluoroacetic acid salt The product from Step D above was dissolved in 2 mL MeOH and to it was added 8.9 mg 10% Pd/C, and the mixture was stirred under a baloon of hydrogen for 1 hr. After filtering the reaction mixture, the filtrate was concentrated under reduced pressure, and the residue was lyophilized from 7:3 water and acetonitrile mixture to give 76.3 mg of the title compound as a white solid. ESI-MS 569.4 (M+H), HPLC A: 2.34 min.

EXAMPLE 2

α-(R)-(3-(S)-((4-(3-Benzyl-(1H-pyrazol-5-yl))piperidin-1-yl)methyl)-4-(S)-phenylpyrrolidin-1-yl)-cyclohexaneacetic acid, trifluoroacetic acid salt Step A: 4-(3-Benzyl-(1H-pyrazol-5-yl))-1-(tert-Butoxycarbonyl)-piperidine, trifluoroacetic acid salt A solution of 1-(1-(t-butoxycarbonyl)piperidin-4-yl)-4-phenyl-butane-1,3-dione (prepared as in Step A of Example 1) (30 mg, 0.087 mmol), hydrazine dihydrochloride (10.9 mg, 0.1 mmol) and DIPEA (0.045 mL, 0.25 mmol) in methanol (1 mL) was heated at 50° C. for 16 h. The volatiles were then removed under reduced pressure. Purification of the residue was done on preparative reverse-phase HPLC using a 9.4×250 mm Semi-preparative Zorbax SB-C18 column with 35–50% MeCN gradient in water having 0.5% (v/v) TFA over 15 min to give the title compound (45.2 mg) as a gel. ESI-MS 342.1 (M+H), 286.0 (base peak, M+H-C4H8), HPLC A: 3.02 min.

Step B: 4-(3-Benzyl-(1H-pyrazol-5-yl))piperidine, trifluoroacetic acid salt

To a solution of 4-(3-benzyl-(1H-pyrazol-5-yl))-1-(t-butoxycarbonyl)piperidine TFA salt (from Step A) in dichloromethane (1.5 mL) was added anisole (0.017 mL) and TFA (0.230 mL). After several h at rt, volatiles were removed under reduced pressure. Purification of the residue was done by preparative reverse-phase HPLC using a 9.4×250 mm Semi-preparative Zorbax SB-C18 column with a 15–25% acetonitrile gradient in water having 0.5% (v/v) TFA over 15 min at 6.0 mL per minute to give the title compound (40.7 mg) as a gel. $^1$H NMR (500 MHz, CD$_3$OD): δ 7.26–7.30 (m, 2H), 7.19–7.23 (m, 3H), 6.05 (s, 1H), 3.98 (s, 2H), 3.41–3.45 (m, 2h), 3.07–3.13 (m, 2H), 2.97–3.04 (m, 1H), 2.15–2.19 (m, 2H), 1.82–1.91 (m, 2H); ESI-MS 241.9 (M+H), HPLC A: 1.52 min.

Step C: α-(R)-(3-(S)-((4-(3-Benzyl-(1H-pyrazol-5-yl)) piperidin-1-yl)-methyl)-4-(S)-phenylpyrrolidin-1-yl)-cyclohexaneacetic acid, benzyl ester, trifluoroacetic acid salt 4-(3-Benzyl-(1H-pyrazol-5-yl))piperidine trifluoroacetic acid salt prepared in last step (20.8 mg) was dissolved in 1 mL 1,2-dichloroethane. To this solution was added 14.2 mg α-(R)-(3-(R)-formyl-4-(S)-phenylpyrrolidin-1-yl)-cyclohexaneacetic acid, benzyl ester (prepared above as Aldehyde 4), 31 uL of diisopropylethylamine, and 28 mg sodium triacetoxyborohydride in that order.The reaction mixture was stirred at room temperature for 21 hours, after which the solvent was removed under reduced pressure. The residue was purified on preparative reverse-phase HPLC using a 9.4×250 mm Zorbax SB-C18 column with 45~70% MeCN gradient in water having 0.5% (v/v) TFA over 15 minutes at 7.5 mL per minute. The fractions containing pure product were concentrated under reduced pressure to give 29.4 mg of the title compound as a gel. Retention time of 4.60 minute on Zorbax SB-C18 column (4.6×75 mm) eluting with 20~100% gradient of MeCN in water with 0.1 % TFA over 5 minutes at 2 mL per minute.

Step D: α-(R)-(3-(S)-((4-(3-Benzyl-( lH-pyrazol-5-yl)) piperidin-1-yl)-methyl)-4-(S)-phenylpyrrolidin-1-yl)-cyclohexaneacetic acid, trifluoroacetic acid salt The product from Step C above was dissolved in 1 mL MeOH, 8.9 mg 10% Pd/C was added, and the mixture was stirred under a balloon of hydrogen for 30 minutes. After filtering the mixture, the filtrate was concentrated under reduced pressure, and the residue was lyophilized from 7:3 water and acetonitrile mixture to give 22.7 mg of the title compound as a white solid. ESI-MS 541.5 (M+H), HPLC A: 2.22 min.

EXAMPLE 3

α-(R)-(3-(S)-((4-(3-Benzyl-1 -ethyl-( 1H-pyrazol-5-yl)) piperidin- 1 -yl)methyl)-4-(S)-phenylpyrrolidin-1-yl)-isopropylacetic acid, trifluoroacetic acid salt Step A: a-(R)-(3-(S)-((4-(3-Benzyl-1-ethyl-(1H-pyrazol-5-yl))piperidin-1-yl)methyl)-4-(S)-phenylpyrrolidin-1-yl)-isopropylacetic acid, benzyl ester, trifluoroacetic acid salt 4-(3-Benzyl-1-ethyl-(1H-pyrazol-5-yl))piperidine trifluoro-acetic acid salt prepared in Example 1, Step C (23 mg) was dissolved in 0.1 mL 1,2-dichloroethane. To this solution was added 11 mg α-(R)-(3-(R)-formyl-4-(S)-phenylpyrrolidin-1-yl)-isopropylacetic acid, benzyl ester (prepared above as Aldehyde 8), 21 uL of diisopropylethylamine, and 480 uL of 0.25 M sodium tri-acetoxyborohydride in 1,2-dichloroethane in that order. The reaction mixture was stirred for 72 hr, after which solvent was removed and the residue was purified on preparative reverse-phase HPLC using a 9.4×250 mm Zorbax SB-C18 column with 40~75% MeCN gradient in water having 0.5% (v/v) TFA over 15 minutes at 7.5 mL per minute. The combined product-containing fractions were concentrated and the residue again purified by preparative HPLC using a 30~75% gradient at 7.0 mL per minute. The combined fractions containing product were concentrated under reduced pressure to give 22.6 mg title compound as a gel. ESI-MS 619.5 (M+H), HPLC A: 2.90 min.

Step B: α-(R)-(3-(S)-((4-(3-Benzyl-1-ethyl-(1H-pyrazol-5-yl))piperidin-1-yl)methyl)-4-(S)-phenylpyrrolidin-1-yl)-isopropylacetic acid, trifluoroacetic acid salt The product from Step A above was dissolved in 1 mL MeOH. To this solution was added 7 mg 10% Pd/C and the mixture was stirred under an atmosphere of hydrogen. The mixture was filtered and the filtrate concentrated under reduced pressure. The residue was lyophilized from 7:3 water and acetonitrile mixture to give 15.9 mg of the title compound as a white solid. ESI-MS 529.4 (M+H), HPLC A: 2.06 min.

EXAMPLE 4

α-(R)-(3-(S)-((4-(3-Benzyl- 1-ethyl-(1H-pyrazol-5-yl)) piperidin- 1 -yl)methyl)-4-(S)-phenylpyrrolidin-1-yl)-isobutylacetic acid, trifluoroacetic acid salt Step A: α-(R)-(3-(S)-((4-(3-Benzyl-1-ethyl-(1H-pyrazol-5-yl))piperidin-1-yl)methyl)-4-(S)-phenylpyrrolidin-1-yl)-isobutylacetic acid, benzyl ester, trifluoroacetic acid salt 4-(3-Benzyl- 1-ethyl-(1H-pyrazol-5-yl))piperidine trifluoroacetic acid salt prepared in Example 1, Step C (23 mg) was dissolved in 0.1 mL 1,2-dichloroethane. To this solutionh was added 11.4 mg α-(R)-(3-(R)-formyl-4-(S)-phenylpyrrolidin-1-yl)-isobutylacetic acid, benzyl ester (prepared by a procedure similar to that for Aldehyde 1, starting from (S)-2-hydroxy-4-methylvaleric acid), 21 uL of diisopropylethylamine, and 480 uL of 0.25 M sodium tri-acetoxyborohydride in 1,2-dichloroethane in that order. After stirring the reaction for 72 hr, the mixture was concentrated under reduced pressure and the residue was purified on preparative reverse-phase HPLC using a 9.4x250 mm Zorbax SB-C18 column with 35~75% MeCN gradient in water having 0.5% (v/v) TFA over 15 minutes at 7.5 mL per minute. Fractions containing product were pooled and solvent was removed under reduced pressure to give 15 mg of the title compound as a gel. ESI-MS 633.5 (M+H), HPLC A: 3.05 min.

Step B: α-(R)-(3-(S)-((4-(3-Benzyl-1-ethyl-(1H-pyrazol-5-yl))piperidin-1-yl)methyl)-4-(S)-phenylpyrrolidin-1-yl)-isobutylacetic acid, trifluoroacetic acid salt The product from Step A above was dissolved in 1 mL MeOH and then treated with 5.2 mg 10% Pd/C. The mixture was stirred under one atmosphere of hydrogen for 2 hours, then filtered and the filtrate was concentrated under reduced pressure. The residue was lyophilized from 7:3 water and acetonitrile mixture to give 11.0 mg of the title compound as a white solid. ESI-MS 543.5 (M+H), TALC A: 2.22 min.

EXAMPLE 5

α-(R)-(3-(S)-((4-(5-Benzyl-isoxazol-3-yl)piperidin-1-yl) methyl)-4-(S)-phenyl-pyrrolidin-1-yl)-cyclohexaneacetic acid, trifluoroacetic acid salt Step A: 4-(5-Benzyl-isoxazol-3-yl)-1-(tert-butoxycarbonyl)piperidine and 4-(3-benzyl-isoxazol-5-yl)-1 -(tert-butoxy-carbonyl)-piperidine, trifluoroacetic acid salts To a solution of 80.2 mg of 1-(1-(tert-butoxycarbonyl)-piperidin-4-yl)-4-phenyl-butane-1,3-dione (from Example 1, Step A) in 1 mL ethanol was added 61 uL diisopropyl-ethylamine and 19.3 mg hydroxylamine hydrochloride and the mixture was heated at 50° C. over night. The reaction mixture was purified on preparative reverse-phase HPLC using a 9.4×250 mm Zorbax SB-C18 column with 45~65% MeCN gradient in water having 0.5% (v/v) TFA over 15 minutes at 7.5 mL per minute. Fractions containing product were pooled and concentrated under reduced pressure to give about 41 mg title compounds as a gel. The two isomers were not separated under these conditions. The two isomers showed one peak at 8.97 minute on Zorbax SB-C18 column (4.6×75 mm) eluting with 20~100% gradient of MeCN in water with 0.1% TFA over 10 minutes at 1 mL per minute.

Step B: 4-(5-Benzyl-isoxazol-3-yl)piperidine and 4-(3-benzyl-isoxazol-5-yl)piperidine, trifluoroacetic acid salts The product from Step A was treated with 33 uL anisole and 277 uL trifluoroacetic acid in 3 mL dichloromethane for a few hours until HPLC showed consumption of starting material. The isomers were separated on preparative reverse-phase HPLC using a 9.4×250 mm Zorbax SB-C18 column with 20~35% MeCN gradient in water having 0.5% (v/v) TFA over 15 minutes at 6.25 mL per minute. Fractions containing the fast-eluting isomer were combined to give 13.9 mg 4-(5-benzyl-isoxazol-3-yl)piperidine trifluoroacetic acid salt as a gel. $^1$H NMR (500 MHz, CD$_3$OD): δ7.21~7.31 (m, 5H), 6.06 (s, 1H), 3.95 (s, 2H), 3.41~3.44 (m, 2H), 3.09~3.19 (m, 3H), 2.22 (br d, 14.0 Hz, 2H), 1.83~1.91 (m, 2H); ESI-MS 242.9 (M+H), HPLC A: 1.86 min. Combination of fractions for slow-eluting isomer gave 5.6 mg of 4-(3-Benzyl-isoxazol-5-yl)-piperidine trifluoroacetic acid salt. $^1$H NMR (500 MHz, CD$_3$OD): δ7.23~7.33 (m, 5H), 6.07 (s, 1H), 4.09 (s, 2H), 3.41~3.45 (m, 2H), 3.09~3.14 (m, 2H), 3.07 (tt, 11.2 & 3.8 Hz, 1H), 2.16~2.21 (m, 2H), 1.85~1.93 (m, 2H); ESI-MS 242.9 (M+H), HPLC A: 1.95 min. The isomers were assigned based on comparison of chemical shifts of benzylic and 4-piperidine protons with similar compounds in the literature (Rowley, et al. *J. Med. Chem.* 1997, 40, 2374–2385).

Step C: α-(R)-(3-(S)-((4-(5-Benzyl-isoxazol-3-yl)piperidin-1-yl)methyl)-4-(S)-phenyl-pyrrolidin-1-yl)-cyclohexaneacetic acid, benzyl ester, trifluoroacetic acid salt A solution of 13 mg of 4-(5-benzyl-isoxazol-3-yl) piperidine trifluoroacetic acid salt from Step B in 0.6 mL 1,2-dichloroethane was combined with 11 mg α-(R)-(3-(R)-formyl-4-(S)-phenylpyrrolidin-1-yl)-cyclohexaneacetic acid, benzyl ester (prepared above as Aldehyde 4), 19 uL diisopropylethyl amine and 23 mg sodium triacetoxyboro-hydride overnight. The solvent was removed under reduced pressure and the residue was purified on preparative reverse-phase HPLC using a 9.4×250 mm Zorbax SB-C18 column with 45~65% MeCN gradient in water having 0.5% (v/v)

TFA over 15 minutes at 7.5 mL per minute. Fractions containing product were pooled and concentrated under reduced pressure to give 26.3 mg of the title compound as a gel. ESI-MS 632.4 (M+H), HPLC A: 2.99 min.

Step D: α-(R)-(3-(S)-((4-(5-Benzyl-isoxazol-3-yl)piperidin-1-yl)methyl)-4-(S)-phenyl-pyrrolidin-1-yl)-cyclohexaneacetic acid, trifluoroacetic acid salt The product from Step C above was dissolved in 1 mL MeOH, treated with 2.1 mg 10% Pd/C, and stirred under one atmosphere of hydrogen for 35 minutes. The mixture was then filtered and the filtrate concentrated under reduced pressure. The residue was purified on preparative reverse-phase HPLC using a 9.4×250 mm Zorbax SB-C18 column with 35~55% MeCN gradient in water having 0.5% (v/v) TFA over 15 minutes at 7.5 mL per minute. Fractions containing product were pooled and concentrated under reduced pressure. The residue was lyophilized from 7:3 water and acetonitrile mixture to give 14.3 mg of the title compound as a white solid. ESI-MS 542.5 (M+H), HPLC A: 2.28 min.

EXAMPLE 6

α-(R)-(3-(S)-((4-(3-Benzyl-1-ethyl-(1H-pyrazol-5-yl))piperidin-1-yl)methyl)-4-(S)-(3-fluorophenyl) pyrrolidin-1-yl)-isopropylacetic Acid, Trifluoroacetic Acid Salt Step A: (S)-2-Hydroxy-3-methylbutyric acid, para-methoxybenzyl ester The title compound was prepared by reacting 14.652 g of (S)-2-hydroxy-3-methylbutyric acid with 21.21 g cesium carbonate and 20.396 of para-methoxybenzyl chloride in 300 mL of DMF at room temperature for 40 hours. The reaction mixture was poured into 400 mL of ice water, extracted with 5×150 mL ether, and the combined ether solution was washed with 5×100 mL water and 100 mL saturated brine. After drying over $Na_2SO_4$ and filtration, the filtrate was concentrated under reduced pressure to give 30.62 g of crude product, which was purified by flash chromatography on silica gel with 10~30% ethyl acetate in hexanes to afford 29.12 g title compound as a colorless oil (99%). RF: 0.58 (30% EtOAc in hexane). $^1$H NMR (500 MHz, $CDCl_3$): δ7.30~7.33 (m, 2H), 6.90~6.93 (m, 2H), 5.20 (AB d, 11.9 Hz, 1H), 5.15 (AB d, 11.9 Hz, 1H), 4.07 (d, 3.4 Hz, 1H), 3.83 (s, 3H), 2.68 (br s, 1H), 2.04~2.13 (m, 1H), 1.01 (d, 7.0 Hz, 3H), 0.83 (d, 6.9 Hz, 3H).

Step B: α-(R)-(3-(R)-((tert-Butyldimethylsilyloxy)methyl)-4-(S)-(3-fluorophenyl)pyrrolidin-1-yl)-isopropylacetic acid, para-methoxybenzyl ester A solution of 7.506 g of (S)-2-hydroxy-3-methylbutyric acid, para-methoxybenzyl ester from Step A in 100 mL dichloromethane was cooled with a dry ice acetone bath under nitrogen. To this mixture was added 4.19 mL 2,6-lutidine followed by a solution of 5.30 mL of trifluoromethanesulfonic anhydride in 15 mL dichloromethane over 10 minutes with stirring. After 20 minutes, a solution of 10.45 mL diisopropylethylamine in 15 mL dichloromethane was added over 10 minutes with stirring and cooling. Following 20 minutes of stirring, a solution of 9.284 g 3-(R)-((tert-butyldimethylsilyloxy)methyl)-4-(S)-(3-fluorophenyl)pyrrolidine(prepared above as Pyrrolidine 2) in 15 mL dichloromethane was added over 35 minutes. After an additional 45 minutes at −78° C., the reaction flask was transferred to an ice bath and allowed to warm up. After 5 hours, the reaction mixture was diluted with 300 mL ether, washed with 5% sodium bicarbonate (1×), water (3×), and saturated brine (1×), dried over $Na_2SO_4$, and concentrated under reduced pressure to give 24.31 g of crude product. Flash chromatography on silica gel with 5~10% ethyl acetate in hexanes gave 14.84 g of the title compound as a colorless oil (93%). $R_F$: 0.31 (5% EtOAc in hexane). $^1$H NMR (500 MHz, $CDCl_3$): δ7.32~7.35 (m, 2H), 7.19~7.24 (m, 1H), 6.93~6.98 (m, 2H), 6.86~6.92 (m, 3H), 5.12 (s, 3H), 3.83 (s, 3H), 3.55 (dd, 9.8 & 5.7 Hz, 1H), 3.50 (dd, 7.1 & 9.9 Hz, 1H), 3.13~3.17 (m, 1H), 3.07~3.11 (m, 1H), 3.05 (d, 9.8 Hz, 1H), 2.90~2.95 (m, 1H), 2.70 (dd, 7.4 & 9.0 Hz, 1H), 2.62 (dd, 6.6 & 9.0 Hz, 1H), 2.27~2.34 (m, 1H), 2.00~2.07 (m, 1H), 1.02 (d, 6.6 Hz, 3H), 0.90 (d, 6.6 Hz, 3H), 0.86 (s, 9H), 0.005 (s, 3H), 0.003 (s, 3H).

Step C: α-(R)-(3-(R)-(Hydroxymethyl)-4-(S)-(3-fluorophenyl)-pyrrolidin-1-yl)-isopropylacetic Acid, Para-methoxybenzyl Ester The title compound was prepared from 14.84 g of α-(R)-(3-(S)-((tert-butyldimethylsilyloxy)methyl)-4-(S)-(3-fluorophenyl)-pyrrolidin-1-yl)-isopropylacetic acid, para-methoxybenzyl ester (from Step B above) and 125 mL of 1M solution of tetrabutylammonium fluoride in 125 mL of THF using a procedure analogous to that described in Example 1, Step B, Aldehyde 1. After purification with flash chromatography on silica gel, 10.75 g of the title compound was obtained as a colorless oil. $R_F$: 0.23 (30% EtOAc in hexanes with 1% (v/v) $Et_3N$). $^1$H NMR (500 MHz, $CDCl_3$): δ7.33~7.36 (m, 2H), 7.22~7.26 (m, 1H), 6.88~6.98 (m, 5H), 5.14 (AB d, 12.3 Hz, 1H), 5.13 (AB d, 12.3 Hz, 1H), 3.82 (s, 3H), 3.68 (dd, 4.6 & 10.6 Hz, 1H), 3.57 (dd, 6.1 & 10.5 Hz, 1H), 3.25~3.29 (m, 1H), 3.05~3.16 (m, 3H), 2.73~2.77 (m, 1H), 2.60~2.64 (m, 1H), 2.29~2.35 (m, 1H), 2.02~2.10 (m, 1H), 1.03 (d, 6.6 Hz, 3H), 0.91 (d, 6.7 Hz, 3H).

Step D: α-(R)-(3-(R)-Formyl-4-(S)-(3-fluorophenyl)-pyrrolidin-1-yl)-isopropylacetic acid, para-methoxybenzyl ester The title compound was prepared from 3.53 g of α-(R)-(3-(S)-(hydroxymethyl)-4-(S)-(3-fluorophenyl)pyrrolidin-1-yl)-isopropylacetic acid, para-methoxybenzyl ester (from Step C), 0.89 mL of oxalyl chloride, 1.448 mL DMSO, and 5.924 mL of diisopropylethylamine in 150 mL of $CH_2Cl_2$ using a procedure analogous to that described for Aldehyde 1, Step C to provide 3.32 g of the title compound as a yellowish viscous oil (94%) after flash chromatography on silica gel eluting with 15~35% ethyl acetate in hexanes. $R_F$: 0.38 (20% EtOAc in hexanes). $^1$H NMR (500 MHz, $CDCl_3$): δ9.64 (d,1.8 Hz, 1H), 7.32~7.34 (m, 2H), 7.23~7.28 (m, 1H), 6.87~6.97 (m, 5H), 5.13 (s, 2H), 3.82 (s, 3H), 3.55 (dd, 7.1 & 14.4 Hz, 1H), 3.25~3.28 (m, 1H), 3.13~3.20 (m, 2H), 3.07 (d, 9.6 Hz, 1H), 2.88~2.93 (m, 1H), 2.66~2.70 (m, 1H), 2.03~2.10 (m, 1H), 1.00 (d, 6.4 Hz, 3H), 0.91 (d, 6.6 Hz, 3H).

Step E: α-(R)-(3-(S)-((4-(3-Benzyl-1-ethyl-(1H-pyrazol-5-yl))piperidin-1-yl)methyl)-4-(S)-(3-fluorophenyl) pyrrolidin-1-yl)-isopropylacetic acid, para-methoxybenzyl ester, trifluoroacetic acid salt The title compound was obtained by reacting 298.3 mg 4-(3-Benzyl-1-ethyl-(1H-pyrazol-5-yl)-piperidine trifluoroacetic acid salt from Example 1, Step C with 272.8 mg of the aldehyde from the last step, 0.209 mL diisopropylethylamine, and 254.3 mg sodium triacetoxyborohydride in 20 mL 1,2-dichloroethane using a procedure similar to that described in Example 1, Step D. The product was purified on preparative reverse-phase HPLC using a 9.4×250 mm Zorbax SB-C18 column with 37.5~57.5% MeCN gradient in water having 0.5% (v/v) TFA over 15 minutes at 8.0 mL per minute. Fractions containing pure product were pooled and concentrated under reduced pressure to give 0.585 g of the title compound as a gel. ESI-MS 667.3 (M+H), BPLC A: 2.84 min.

159

Step F: α-(R)-(3-(S)-((4-(3-Benzyl-1-ethyl-(1H-pyrazol-5-yl))piperidin-1-yl)methyl)-4-(S)-(3-fluorophenyl) pyrrolidin-1-yl)-isopropylacetic acid, hydrochloride salt The product from Step E was treated with 60 mL 96% formic acid at room temperature overnight. After removing the formic acid under reduced pressure. the residue was dissolved in 20 mL methanol and loaded on three 15×15 mm Varian Bond Elut®. They were washed with methanol and then eluted with 2M ammonium in methanol. Removal of solvent under reduced pressure gave a colorless gel. The product was purified further on preparative using a 9.4×250 mm Zorbax SB-C18 column with 30~45% MeCN gradient in water having 0.5% (v/v) TFA over 15 minutes at 7.1 mL per minute. Fractions containing product were pooled and concentrated under reduced pressure to give 333 mg gel as a trifluoroacetic acid salt, which was exchanged to the hydrochloride salt using 16 g Amberlite® IRA-400(Cl) ion exchange resin with methanol. The final product was lyophilized from 7:3 water and acetonitrile mixture to give 247 mg of the title compound as a white solid. $^1$H NMR (400 MHz, CD$_3$OD): δ7.44~7.49 (m, 1H), 7.30~7.34 (m, 2H), 7.22~7.26 (m, 2H), 7.09~7.19 (m, 4H), 5.81 (s, 1H), 4.16 (br s, 1H), 4.08 (q, 7.2 Hz, 2H), 3.96~4.02 (m, 1H), 3.82~3.86 (m, 2H), 3.86 (s, 2H), 3.53~3.67 (m, 3H), 3.37~3.49 (m, 2H), 3.20~3.25 (m, 1H), 3.10~3.17 (m, 1H), 2.93~3.02 (m, 3H), 2.81~2.87 (m, 1H), 2.36~2.43 (m, 1H), 1.87~2.05 (m, 4H), 1.36 (t, 7.2 Hz, 3H), 1.18 (d, 6.9 Hz, 3H), 1.00 (d, 6.6 Hz, 3H). $^{19}$F NMR showed no signal for trifluoroacetic acid. ESI-MS 547.3 (M+H), HPLC A: 2.18 min.

EXAMPLE 7

α-(R)-(3-(S)-((4-(Pyridin-3-yl)piperidin-1-yl) methyl)-4-(S)-(3-fluorophenyl)pyrrolidin-1-yl)-β-cyclobutylpropionic Acid, Trifluoroacetic Acid Salt Step A: α-(R)-(3-(S)-((4-(Pyridin-3-yl)piperidin-1-yl) methyl)-4-(S)-(3-fluorophenyl)pyrrolidin-1-yl)-β-cyclobutylpropionic acid, benzyl ester, trifluoroacetic acid salt The title compound was prepared using 20.4 mg of α-(R)-(3-(R)-formyl-4-(S)-(3-fluorophenyl)pyrrolidin-1-yl)-β-cyclobutylpropionic acid, benzyl ester (prepared above as Aldehyde 2), 11.7 mg 4-(pyridin-3-yl)piperidine dihydrochloride, 26 uL diisopropylethylamine, and 21.1 mg sodium triacetoxyborohydride in 2 mL 1,2-dichloroethane using a procedure similar to that described in Example 1, Step D. The product was purified on preparative reverse-phase HPLC using a 9.4×250 mm Zorbax SB-C18 column with 30~45% MeCN gradient in water having 0.5% (v/v) TFA over 15 minutes at 7.1 mL per minute. Fractions containing product were pooled and then concentrated under reduced pressure to give 48.8 mg of the title compound as a gel. ESI-MS 556.3 (M+H), HPLC A: 2.59 min.

Step B: α-(R)-(3-(S)-((4-(Pyridin-3-yl)piperidin-1-yl) methyl)-4-(S)-(3-fluorophenyl)pyrrolidin-1-yl)-β-cyclobutylpropionic acid, trifluoroacetic acid salt The benzyl ester from the last step was debenzylated using 6.7 mg 10% Pd/C in 1.5 mL MeOH under hydrogen for 1 hour using a procedure described in Example 1, Step E. The crude product was purified on preparative reverse-phase HPLC using a 9.4×250 mm Zorbax SB-C 18 column with 25~40% MeCN gradient in water having 0.5% (v/v) TFA over 15 minutes at 6.65 mL per minute. Fractions containing product were pooled and concentrated under reduced pressure to give 29.5 mg of a gel. Lyophilization from 7:3 water and acetonitrile mixture gave 23.9 mg of the title compound as a white solid. ESI-MS 466.2 (M+H), HPLC A: 1.58 min.

EXAMPLE 8

α-(R)-(3-(S)-((4-(4-Benzyl-1-ethyl-(1H-pyrazol-5-yl))piperidin-1-yl)methyl)-4-(S)-phenylpyrrolidin-1-yl)-cyclohexaneacetic acid, Trifluoroacetic Acid Salt Step A: (3-Phenylpropyl)triphenylphosphonium bromide The title compound was obtained by heating 43.80 g 1-bromo-3-phenylpropane and 52.458 g triphenylphosphine in 200 mL toluene in 120~130° C. oil bath for 3 days, at which point the mixture was cooled and the solid was collected by filtration, washed with toluene, and then dried to give 83.37 g of a colorless solid (90%). $^1$H NMR (500 MHz, CD$_3$OD): δ7.86~7.93 (m, 3H), 7.69~7.75 (m, 12H), 7.26~7.30 (m, 2H), 7.19~7.23 (m, 1H), 7.15~7.18 (m, 2H), 3.33~3.39 (m, 2H), 2.85 (t, 7.4 Hz, 2H), 1.92~2.00 (m, 2H).

Step B: 1-Benzyl-4-(3-phenylpropylidene)piperidine

A solution of 100 mL of 0.5M potassium bis(trimethylsilyl)amide in toluene was added to a mixture of 23.07 g (3-phenylpropyl)triphenylphosphonium bromide from Step A in 150 mL toluene in an ice bath over 15 minute with stirring under nitrogen. After stirring for 15 more minutes, a solution of 8.515 g of 1-benzyl-4-piperidone in 50 mL toluene was added over 30 minutes with stirring. The reaction mixture was stirred as it was allowed to warm to room temperature overnight. After 15 hours, the reaction mixture was poured into 200 mL cold 1N HCl. The layers were separated and the toluene layer was washed with 2×200 mL 1N HCl. The combined HCl solution and an oily interfacial layer was washed with 100 mL toluene. After adding 30 g KOH, the aqueous layer was extraced with 3×150 mL of ether. The combined ether solution was washed with 100 mL each of water and saturated brine, dried over Na$_2$SO$_4$, filtered, and concentrated under reduced pressure. The residue was purified by silica gel flash chromatography using 10~15% ethyl acetate in hexanes having 3% (v/v) Et$_3$N to give 8.2 g of the title compound as a colorless oil. R$_F$: 0.38 (10% EtOAc in hexanes having 3% (v/v) Et$_3$N). $^1$H NMR (500 MHz, CDCl$_3$): δ7.34 (d, 4.3 Hz, 4H), 7.25~7.30 (m, 2H), 7.17~7.21 (m, 4H), 5.19 (t, 7.2 Hz, 1H), 3.51 (s, 3H), 2.64~2.67 (m, 2H), 2.41~2.44 (m, 2H), 2.29~2.35 (m, 4H), 2.18~2.22 (m, 4H).

Step C: 1-(1-Benzylpiperidin-4-yl)-3-phenyl-1-propanone

To a solution of 1.115 g 4-(3-phenylpropylidene)-1-benzylpiperidine from Step B in 40 mL anhydrous ether under nitrogen was added 11.5 mL 1M borane solution in THF with stirring. After stirring for three hours, 2 mL of water was added dropwise, and the mixture was stirred for 30 min. After cooling with ice, a solution prepared from 0.287 g chromic anhydride, 0.624 mL concentrated sulfuric acid and 15 mL water was added dropwise with vigorous magnetic stirring over 5 minutes. After stirring for an additional 5 minutes, the cooling bath was removed. After 1.5 hours more, 100 mL each of 0.5N NaOH & ether was added, and the mixture was stirred to disolve a solid residue. After separating the layers, the aqueous layer was extracted with 2×100 mL ether. The combined ether layer was washed with 100 mL each of EDTA, water, and saturated brine, dried over Na$_2$SO$_4$, and concentrated under reduced pressure to give a colorless gel. The oxidation step were then repeated with half of the reagent used above. Flash chromatography on silica gel with 30~50% EtOAc in hexanes with 3% (v/v) Et$_3$N gave 0.293 g of the title compound as a colorless gel. R$_F$: 0.41 (30% EtOAc in hexanes having 3% (v/v) Et$_3$N). $^1$H NMR (500 MHz, CDCl$_3$): δ7.17~7.33 (m, ~10H), 3.51 (s, 2H), 2.88~2.92 (m, 2H), 2.75~2.80 (m, 2H), 2.26~2.32 (m, 1H), 1.98~2.04 (m, 2H), 1.76~1.82 (m, 2H), 1.63~1.72 (m, 4H). ESI-MS 308.1 (M+H), HPLC A: 2.45 min.

Step D: 1-(1-Benzylpiperidin-4-yl)-2-formyl-3-phenyl-1-propanone

Into a 100 mL 3-neck round-bottom flask was weighed 0.336 g KO-t-Bu and 4 mL anhydrous THF was added. The mixture was cooled with an ice bath under nitrogen, and to it was added a solution of 0.29 g 1-(1-benzylpiperidin-4-yl)-3-phenyl-1-propanone from the last step and 1.80 g methyl formate in 12 mL THF over 5 minute with stirring. After stirring for an additional 15 min, the cooling bath was removed, and the yellowish cloudy mixture was stirred for 2 hours. The mixture was then poured into water, extracted with 4×50 mL ether, 40 mL dichloromethane, and 3×40 mL THF and the combined organic layers were washed with 50 mL each of water and saturated brine, dried over $Na_2SO_4$, and concentrated under reduced pressure to give 0.414 g of the title compound as a sticky yellowish solid. This crude product was used without further purification in the next step. $R_F$: 0.59 (EtOAc with 3% (v/v) $Et_3N$ and 5% (v/v) MeOH). $^1$H NMR (500 MHz, DMSO-$d_6$): δ7.97 (s, 1H), 7.20~7.30 (m, 5H), 7.14~7.17 (m, 2H), 7.04~7.09 (m, 3H), 6.85 (s, 1H), 3.45 (s, ~2H), 2.81~2.89 (m, 1H), 2.76~2.80 (m, 2H), 1.97~2.03 (m, 2H), 1.46~1.56 (m, 4H). The Ph—$CH_2$—C= signal was not observed, possibly overlapping with the large water signal. ESI-MS 336.1 (M+H), HPLC A: 2.32 min.

Step E: 4-(4-Benzyl-1-ethyl-(1H-pyrazol-5-yl))-1-benzylpiperidine, trifluoroacetic acid salt and 4-(4-Benzyl-1-ethyl-(1H-pyrazol-3-yl))-1-benzylpiperidine, trifluoroacetic acid salt A mixture of 0.10 g of crude 1-(1-benzylpiperidin-4-yl)-2-formyl-3-phenyl-1-propanone from the last step, 60.5 mg ethylhydrazine oxalate and 0.139 mL diisopropylethylamine in 3.5 mL MeOH and 0.5 mL THF were heated at 50° C. for 8 hours. HPLC and LC/MS showed two isomeric products in a ratio of about 1:5. After removing solvent under reduced pressure, the mixture was purified on preparative reverse-phase BPLC using a 9.4×250 mm Zorbax SB-C18 column with 40~60% and 35~55% MeCN gradient in water having 0.5% (v/v) TFA over 15 minutes. Combining the fractions containing the fast-eluting, minor isomer gave 17.6 mg 4-(4-benzyl-1-ethyl-(1H-pyrazol-5-yl))-1-benzylpiperidine, trifluoroacetic acid salt as a solid after lyophilization. $^1$H NMR (500 MHz, $CD_3OD$): δ7.46~7.52 (m, ~6H), 7.24~7.27 (m, 2H), 7.12~7.19 (m, 3H), 4.32 (s, 2H), 4.21 (q, 7.2 Hz, 2H), 3.89 (s, 2H), 3.53~3.57 (m, 2H), 3.19~3.27 (m, 1H), 3.09~3.15 (m, 2H), 21.8~2.28 (m, 2H), 1.92~1.97 (m, 2H), 1.38 (t, 7.2 Hz, 3H); ESI-MS 360.2 (M+H), HPLC A: 2.34 min. The slow-eluting, major isomer gave 87.9 mg of a gel. It is the isomeric 4-(4-benzyl-1-ethyl-(1H-pyrazol-3-yl))-1-benzylpiperidine, trifluoroacetic acid salt. $^1$H NMR (500 MHz, $CD_3OD$): δ7.47~7.52 (m, 5H), 7.33 (s, 1H), 7.23~7.27 (m, 2H), 7.14~7.18 (m, 3H), 4.29 (s, 2H), 4.07 (q, 7.3 Hz, 2H), 3.80 (s, 2H), 3.46~3.50 (m, 2H), 2.98~3.05 (m, 2H), 2.84~2.91 (m, 1H), 1.84~1.99 (m, 4H), 1.38 (t, 7.3 Hz, 3H); ESI-MS 360.2 (M+H), HPLC A: 2.65 min.

Step F: 4-(4-Benzyl-1-ethyl-(1H-pyrazol-5-yl))-piperidine, trifluoroacetic acid salt and 4-(4-benzyl-1-ethyl-(1H-pyrazol-3-yl))-piperidine, trifluoroacetic acid salt A mixture of 47.3 mg of ammonium formate, 5 mg 20% Pd(OH)$_2$/C and 17.6 mg 4-(4-benzyl-1-ethyl-(1H-pyrazol-5-yl))-1-benzylpiperidine, trifluoroacetic acid salt (obtained from the last step) was treated with 2 mL MeOH, and the mixture was heated in a 60° C. oil bath with stirring for 1.5 hours. After removing the solvent under reduced pressure, the residue was purified on preparative reverse-phase HPLC using a 9.4×250 mm Zorbax SB-C18 column with 20~35% MeCN gradient in water having 0.5% (v/v) TFA over 15 minutes at 6.25 mL per minute. Fractions containing product were pooled and concentrated under reduced pressure to give 13.3 mg 4-(4-benzyl-1-ethyl-(1H-pyrazol-5-yl))-piperidine, trifluoroacetic acid salt as a gel. It had a retention time of 5.37 minute on Zorbax SB-C18 column (4.6×75 mm) eluting with 20~100% gradient of MeCN in water with 0.1% TFA over 10 minutes at 1 mL per minute. Similar treatment of the major product 4-(4-benzyl-1-ethyl-(1H-pyrazol-3-yl))-1-benzylpiperidine, trifluoroacetic acid salt from the last step gave 54.1 mg 4-(4-benzyl-1-ethyl-(1H-pyrazol-3-yl))-piperidine, trifluoroacetic acid salt. It had a retention time of 6.30 minute on Zorbax SB-C 18 column (4.6×75 mm) eluting with 20~100% gradient of MeCN in water with 0.1% TFA over 10 minutes at 1 mL per minute. $^1$H NMR (500 MHz, $CD_3OD$): δ7.45 (s, 1H), 7.24~7.28 (m, 2H), 7.15~7.20 (m, 3H), 5.48 (s, <1H, N-H?), 3.87 (s, 2H), 3.38~3.43 (m, 2H), 2.92~3.04 (m, 3H), 1.84~1.94 (m, 4H). Its identity was established by NOESY and NOE difference spectra.

Step G: α-(R)-(3-(S)-((4-(4-Benzyl-1-ethyl-(1H-pyrazol-5-yl))piperidin-1-yl)methyl)-4-(S)-phenylpyrrolidin-1-yl)-cyclohexaneacetic acid, benzyl ester, trifluoroacetic acid salt The title compound was prepared from 13.3 mg 4-(4-benzyl-1-ethyl-(1H-pyrazol-5-yl))-piperidine, trifluoroacetic acid salt from the last step, 8.9 mg of α-(R)-(3-(R)-formyl-4-(S)-phenylpyrrolidin-1-yl)-cyclohexaneacetic acid, benzyl ester (prepared above as Aldehyde 4), 6 uL of diisopropylethyl amine, and 7 mg sodium triacetoxyborohydride in 0.75 mL 1,2-dichloroethane using a very similar procedure as described in Example 1, Step D. Purification on preparative reverse-phase HPLC using a 9.4×250 mm Zorbax SB-C18 column with 45~70% MeCN gradient in water having 0.5% (v/v) TFA over 15 minutes at 8 mL per minute afforded 19.8 mg of the title compound as a gel. It had a retention time of 9.47 minute on Zorbax SB-C18 column (4.6×75 mm) eluting with 20~100% gradient of MeCN in water with 0.1% TFA over 10 minutes at 1 mL per minute.

Step H: α-(R)-(3-(S)-((4-(4-Benzyl-1-ethyl-(1H-pyrazol-5-yl))piperidin-1-yl)methyl)-4-(S)-phenylpyrrolidin-1-yl)-cyclohexaneacetic acid, trifluoroacetic acid salt Treating 19.8 mg α-(R)-(3-(S)-((4-(4-benzyl-1-ethyl-(1H-pyrazol-5-yl))piperidin-1-yl)methyl)-4-(S)-phenylpyrrolidin-1-yl)-cyclohexaneacetic acid, benzyl ester, trifluoroacetic acid salt from the last step with 5.4 mg Pd/C in 1 mL MeOH under hydrogen for 1.5 hour gave the title compound. After filtering the mixture and removng solvent under reduced pressure, the product was lyophilized from 7:3 mixture of water and acetonitrile to give 12.9 mg as a white solid. $^1$H NMR (500 MHz, $CD_3OD$): δ7.41~7.45 (m, 4H, phenyl on pyrrolidine), 7.35~7.38 (m, 1H, phenyl on pyrrolidine), 7.22~7.25 (m, 2H, m-), 7.13~7.17 (m, 1H, p-), 7.10~7.12 (m, 3H, o- and pyrazole), 4.13 (quartet, 7.2 Hz, 2H), 4.05 (br s, 1H, a-H of acid), 3.94~3.99 (m, 1H, pyrr), 3.83 (s, 2H), 3.78~3.84 (m, 1H, pyrr), 3.57~3.67 (m, 3H, 2 pip & 1 pyrr), 3.52 (br d, 12.1 Hz, 1H, pyrr), 3.37 (dd, 13.5 & 10.3 Hz, 1H, pyrr), 3.26~3.33 (m, 1H, pyrr), 2.99~3.14 (m, 4H, 2 pip & 2 pyrr), 2.77~2.83 (m, 1H, CH of pip), 2.18~2.27 (m, 2H, pip), 2.00~2.05 (m, 1H, CH of cyclohex), 1.78~1.88 (m, 4H, 2 each from cyclohex and pip), 1.70 (br d, 12.6 Hz, 1H, cyclohex), 1.44~1.51 (m, 1H, cyclohex), 1.34 (t, 7.1 Hz, 3H), 1.28~1.40 (m, 2H, cyclohex), 1.04~1.20 (m, 2H, cyclohex); ESI-MS 569.5 (M+H), HPLC A: 2.32 min. NOE difference spectra showed it had the correct isomer of pyrazole

EXAMPLE 9

α-(R)-(3-(S)-((4-(4-(2-phenylethyl)-1-ethyl-(1H-pyrazol-5-yl))piperidin-1-yl)methyl)-4-(S)-phenylpyrrolidin-1-yl)-cyclohexaneacetic Acid, Trifluoroacetic Acid Salt Step A: 4-Phenylbutyl bromide To a solution of 4-phenyl-1-butanol (21.75 g) in acetonitrile (300 mL) was added triphenylphosphine dibromide (67.23 g) in portions with stirring over 10 min. After stirring over night under nitrogen, methanol (4 mL) was added and after 1.5 h, the solvent was removed under reduced pressure. Hexanes (200 mL) and ~75 g silica gel were added to the residue and the mixture was filtered and the filter cake was eluted with hexanes. The clear filtrate was concentrated to give 32.8 g of clear colorless liquid. This product was again eluted through silica gel using 1.5 L hexanes to give the title compound (24.7 g) as a colorless liquid. $^1$H NMR (500 MHz, CDCl3): δ7.28–7.32 (m, 2 H), 7.20–7.23 (m, 3 H), 3.44 (t, J=6.8 Hz, 2 H), 2.67 (t, J =7.6 Hz, 2 H), 1.93–1.89 (m, 2 H), 1.77–1.84 (m, 2 H).

Step B: (4-Phenylbutyl)triphenylphosphonium bromide

A solution of 4-phenylbutyl bromide (from the Step A) and triphenylphosphine (19.00 g) in toluene (100 mL) was heated at 120–130° C. for 3 days. The reaction was cooled to rt and the solid precipitate was collected by filtration, washed with toluene and air dried. The solid was disslved in a 2:1 mixture of water and acetonitrile and gave the title compound (30.6 g) as a white solid after lyophilization. $^1$H NMR (500 MHz, CD3OD): δ7.84–7.89 (m, 2 H), 7.71–7.81 (m, 15 H), 7.20–7.23 (m, 1H), 7.11–7.15 (m, 2 H), 3.37–3.43 (m, 2 H), 2.66 (t, J=7.5 Hz, 2 H), 1.87 (tt, J=7.5 and 7.3 Hz, 2 H), 1.63–1.70 (m, 2 H).

Step C: 1-Benzyl-4-(4-phenylbutylidene)piperidine

A 0.62M solution of potassium bis(trimethylsilyl)amide in THF (180 mL, 112 mmol) in toluene (250 mL) was added to a mixture of (4-phenylbut-1-yl)triphenylphosphonium bromide (from the Step B) (53 g) in toluene (250 mL) in an ice bath over 15 min with stirring under nitrogen. After stirring for a further 15 min, a solution of 1-benzyl-4-piperidone (16.9 g) in toluene (100 mL) was added over 30 min with stirring. The reaction mixture was allowed to warm to rt over 15 h. The reaction mixture was then poured into cold 1N HCl (400 mL) and the layers were separated. The organic layer was extracted with two more portions of 1N HCl. The combined cloudy HCl solution and an oil layer in between were washed with toluene (200 mL) before the aqueous layer was basified by the addition of potassium hyroxide (30 g). The aqueous layer was extracted with ether (3×150 mL) and the combined organic layers were washed with water and brine, dried over sodium sulfate and concentrated. The crude product was purified by FC (10~15% ethyl acetate in hexanes having 4% (v/v) TEA) to give the title compound (16 g) as a colorless oil. R$_f$: 0.47 (20% ethyl acetate in hexanes having 4% (v/v) TEA). $^1$H NMR (500 MHz, CDCl$_3$): δ7.26–7.38 (m, 7 H), 7.18–7.21 (m, 3 H), 5.18 (t, J=7.4 Hz, 1 H), 3.54 (s, 2 H), 2.61–2.64 (m, 2 H), 2.42–2.49 (m, 4 H), 2.22–2.27 (m, 4 H), 2.02–2.07 (m, 2 H), 1.65–1.71 (m, 2 H).

Step D: 1-(1-Benzylpiperidin-4-yl)-4-phenyl-1-butanone

To a solution of 4-(4-phenylbutylidene)-1-benzylpiperidine (from the Step C) (4.37 g) in anhydrous ether (150 mL) under nitrogen with stirring was add 1M borane solution in TEF (45 mL). The reaction was stirred for 3 h when water (2 mL) was added dropwise. The mixture was stirred a further 30 min and was then cooled in an ice bath. A solution of chromic anhydride (2.5 g), concentrated sulfuric acid (5.44 mL) and water (125 mL) was added dropwise with vigorous magnetic stirring over 5 min. After another 5 min, the ice bath was removed. After 1.5 h at rt, 0.5N sodium hydroxide and ether (400 mL each) were added and the mixture was stirred until the residue dissolved. The layers were separated and the aqueous layer was extracted twice with ether. The combined ether layers were washed with an aqueous EDTA solution, water and brine (100 mL each), dried over sodium sulfate and concentrated under reduced pressure to give a colorless gel. Flash chromatography on silica gel with 30–50% ethyl acetate in hexanes with 3% (v/v) TEA gave the title compound (1 g) as a colorless gel. R$_f$: 0.43 (30% ethyl acetate in hexanes with 3% (v/v) TEA). $^1$H NMR (500 MHz, CDCl$_3$): δ7.25–7.33 (m, 7 H), 7.16–7.22 (m, 3 H), 3.51 (s, 2 H), 2.89–2.93 (m, 2 H), 2.63 (t, J=7.6 Hz, 2 H), 2.46 (t, J=7.2 Hz, 2 H), 2.38 (tt, J=11.5 and 3.9 Hz, 1 H), 1.99–2.03 (m, 2 H), 1.92 (tt, J=7.2 and 7.6 Hz, 2 H), 1.76–1.81 (m, 2 H), 1.65–1.72 (m, 2 H).

Step E: 1-(1-Benzylpiperidin-4-yl)-2-formyl-4-phenyl-1-butanone

To a solution of potassium t-butoxide (0.673 g) in THF (20 mL) under nitrogen and cooled in an ice bath was added a solution of 1-(1-benzylpiperidin-4-yl)-4-phenylbutan-1-one (from Step D) (0.71 g) and methyl formate (3.76 mL) in THF (12 mL) over 5 minute. The reaction was stirred for 15 min before being allowed to warm to rt for 2 h. The reaction was poured into water and extracted with ether (4×100 mL), dichloromethane (100 mL), and TFA (100 mL). The combined organic layers were washed with water and brine, dried over sodium sulfate and concentrate under reduced pressure. The crude product was purified by FC on silica gel eluting with 5 and 20% methanol in ethyl acetate with 4% TEA to afford the title compound (0.8 g). $^1$H NMR (500 MHz, CDCl$_3$) showed a 3:1 ratio of enol (δ8.54 ppm) and aldehyde (δ9.54 ppm) forms. Other signals from the two forms were only partially resolved. The title compound had a retention time of 9.47 min on a Zorbax SB-C18 column (4.6×75 mm) eluting with 20–100% gradient of acetonitrile in water with 0.1% TFA over 10 min at 1 mL per min.

Step F: 4-(4-(2-phenylethyl)-1-ethyl-(1H-pyrazol-5-yl))-1-benzylpiperidine, trifluoroacetic acid salt A solution of 1-(1-benzylpiperidin-4-yl)-2-formyl-4-phenyl-1-butanone (from the Step E) (76.5 mg) and ethylhydrazine oxalate (45 mg) in methanol (4 mL) was heated at 45° C. for 15.5 h. The solvent was removed under reduced pressure. The residue was purified by preparative reverse-phase HPLC using a 9.4×250 mm Semi-preparative Zorbax SB-C18 column with 30–50% acetonitrile gradient in water having 0.5% (v/v) TFA over 15 min at 7.1 mL per min to give the title compound (45 mg) as the faster-eluting, minor isomer.
$^1$H NMR (500 MHz, CD$_3$OD): δ7.46–7.52 (m, 5 H), 7.37 (s, 1 H), 7.21–7.24 (m, 2 H), 7.12–7.15 (m, 3 H), 4.32 (s, 2 H), 4.17 (q, J=7.2 Hz, 2 H), 3.53 (br d, J=12.4 Hz, 2 H), 3.06–3.12 (m, 3 H), 2.79–2.88 (m, 4 H), 2.10–2.20 (m, 2 H), 1.78 (br d, J=14.2 Hz, 2 H), 1.34 (t, J=7.2 Hz, 3 H). The isomeric assignment was confirmed by a NOESY spectrum. HPLC/MS (ESI): m/z 374.3 (M+H), 2.51 min.

Step G: 4-(4-(2-phenylethyl)-1-ethyl-(1H-pyrazol-5-yl))-piperidine, trifluoroacetic acid salt A mixture of ammonium formate (119 mg), 20% Pd(OH)$_2$/C (5 mg) and 4-(4-(2-phenylethyl)-1-ethyl-(1H-pyrazol-5-yl))-1-benzylpiperidine di-TFA salt (from the Step F) in methanol (2 mL) was heated at 60° C. for 1.5 h. The solvent was removed under reduced pressure and the residue was purified by preparative reverse-phase HPLC using a 9.4×250 mm Semi-preparative Zorbax SB-C18 column with 20–35% acetonitrile gradient in water having 0.5% (v/v) TFA over 15 min at 6.25 mL per min to give 4-(4-(2-phenylethyl)-1-ethyl-(1H-pyrazol-5-yl))piperidine di-TFA salt (25 mg) as a gel. $^1$H NMR (500 MHz, CD$_3$OD): δ7.40 (s, 1 H), 7.22–7.25 (m, 2 H), 7.13–7.17 (m, 3 H), 4.20 (q, J=7.3 Hz, 2 H), 3.42–3.46 (m, 2 H), 3.05–3.15 (m, 3 H), 2.83–2.90 (m, 4 H), 2.04–2.14 (m, 2 H), 1.74–1.79 (m, 2 H), 1.36 (t, J=7.4 Hz, 3 H). The isomer assignment was confirmed by an NOE difference spectrum.

Step H: α-(R)-(3-(S)-((4-(2-phenylethyl)-1-ethyl-(1H-pyrazol-5-yl))piperidin-1-yl)methyl)-4-(S)-phenylpyrrolidin-1-yl)-cyclohexaneacetic acid, benzyl ester, trifluoroacetic acid salt The title compound was prepared from 15.4 mg of 4-(4-(2-phenylethyl)-1-ethyl-(1H-pyrazol-5-yl))-piperidine, trifluoroacetic acid salt from the last step, 10.1 mg α-(R)-(3-(R)-formyl-4-(S)-phenylpyrrolidin-1-yl)-cyclohexaneacetic acid, benzyl ester (prepared above as Aldehyde 4), 7.8 uL of diisopropylethyl amine, and 11 mg sodium triacetoxyborohydride in 1 mL 1,2-dichloroethane using a very similar procedure as described in Example 1, Step D. Purification on preparative reverse-phase HPLC using a 9.4×250 mm Zorbax SB-C18 column with 45~70% MeCN gradient in water having 0.5% (v/v) TFA over 15 minutes at 7.75 mL per minute afforded 24.0 mg of the title compound as a gel. It had a retention time of 4.97 minute on Zorbax SB-C18 column (4.6×75 mm) eluting with 20~100% gradient of MeCN in water with 0.1% TFA over 5 minutes at 2 mL per minute.

Step I: α-(R)-(3-(S)-((4-(2-phenylethyl)-1-ethyl-(1H-pyrazol-5-yl))piperidin-1-yl)methyl)-4-(S)-phenylpyrrolidin-1-yl)-cyclohexaneacetic acid, trifluoroacetic acid salt The product from the last step was treated with 10 mg 10% Pd/C in 1.5 mL MeOH under hydrogen for 1 hour. Similar work-up and purification as described in Example 8, Step H gave 17.8 mg of the title compound as a white solid. ESI-MS 583.6 (M+H), HPLC A: 2.46 min.

EXAMPLE 10

α-(R)-(3-(S)-((4-(4-(2-(phenylethyl)-isoxazol-3-yl))piperidin-1-yl)methyl)-4-(S)-phenylpyrrolidin-1-yl)-cyclohexaneacetic acid, trifluoroacetic acid salt Step A: 4-(4-(2-Phenylethyl)-isoxazol-3-yl)-1-benzyl-piperidine, trifluoroacetic acid salts The title compound was prepared from 76.5 mg 1-(1-benzylpiperidin-4-yl)-2-formyl-4-phenyl-1-butanone from Example 9, Step E and 17.4 mg hydroxylamine hydrochloride in 3.5 mL MeOH using a procedure similar to that described in Example 5, Step A. The product contained the title compound and its isomer 4-(4-(2-phenylethyl)-isoxazol-5-yl)-1-benzyl-piperidine, trifluoroacetic acid salts. The two isomers have retention times of 7.60 and 8.40 minutes on Zorbax SB-C18 column (4.6×75 mm) eluting with 20~100% gradient of MeCN in water with 0.1% TFA over 10 minutes at 1 mL per minute. ESI-MS 347.2 (M+H).

Step B: 4-(4-(2-Phenylethyl)-isoxazol-3-yl)-piperidine, trifluoroacetic acid salts Debenzylation of 96.7 mg of a mixture of products from the last step using a procedure similar to that described in Example 8, Step D gave a mixture of two isomeric isoxazoles by BPLC and LC/MS. ESI-MS 257.1 (M+H), HPLC A: 1.71 and 2.07 min. They were separated on preparative reverse-phase HPLC using a 9.4×250 mm Zorbax SB-C18 column with 20~40% MeCN gradient in water having 0.5% (v/v) TFA over 15 minutes at 6.25 mL per minute, to give 9.2 mg of the title compound as a solid. $^1$H NMR (500 MHz, CD$_3$OD): δ8.20 (s, 1H), 7.23~7.26 (m, 2H), 7.15~7.18 (m, 1H), 7.11~7.13 (m, 2H), 3.35~3.38 (m, 2H), 2.94~3.00 (m, 2H), 2.90 (tt, 3.7 & 11.7 Hz, 1H), 2.84~2.87 (m, 2H), 2.76~2.79 (m, 2H), 1.81~1.90 (m, 2H), 1.55~1.60 (m, 2H). It has almost identical NMR as the other isomer. They were assigned tentatively according the elution order compared with products from Example 5, Step B.

Step C: α-(R)-(3-(S)-((4-(4-(2-(phenylethyl)-isoxazol-3-yl))piperidin-1-yl)methyl)-4-(S)-phenylpyrrolidin-1-yl)-cyclohexaneacetic acid, para-methoxybenzyl ester, trifluoroacetic acid salt The title compound was prepared from the product in the last step, 7.4 mg α-(R)-(3-(R)-formyl-4-(S)-phenylpyrrolidin-1-yl)-cyclohexaneacetic acid, para-methoxybenzyl ester (prepared above as Aldehyde 5), 6.6 uL diisopropylethyl amine and 8.3 mg sodium triacetoxyborohydride using a procedure similar to that in Example 5, Step C. Purification on preparative reverse-phase HPLC using a 9.4×250 mm Zorbax SB-C18 column with 45~70% MeCN gradient in water having 0.5% (v/v) TFA over 15 minutes at 8 mL per minute afforded 15.7 mg of the title compound as a gel. It had a retention time of 9.33 minute on Zorbax SB-C18 column (4.6×75 mm) eluting with 20~100% gradient of MeCN in water with 0.1% TFA over 10 minutes at 1 mL per minute.

Step D: α-(R)-(3-(S)-((4-(4-(2-(phenylethyl)-isoxazol-3-yl))piperidin-1-yl)methyl)-4-(S)-phenylpyrrolidin-1-yl)-cyclohexaneacetic acid, trifluoroacetic acid salt The product from the last step was treated with 2 mL 96% formic acid overnight. The formic acid was removed under reduced pressure and the residue was dissolved in 1 mL methanol. This solution was loaded onto a Varian Bond Elut, washed with methanol, and eluted with 2M ammonium in methanol. Removal of solvent under reduced pressure gave a colorless gel. Purification on preparative reverse-phase HPLC using a 9.4×250 mm Zorbax SB-C18 column with 35~55% MeCN gradient in water having 0.5% (v/v) TFA over 15 minutes at 7.65 mL per minute afforded a gel, which was lyophilized from 7:3 mixture of water and acetonitrile to give 9.5 mg of the title compound as a white solid. ESI-MS 556.3 (M+H), HPLC A: 2.81 min.

EXAMPLE 11

α-(R)-(3-(S)-((4-(4-(2-phenylethyl)-1-n-propyl-(1H-pyrazol-5-yl))piperidin-1-yl)methyl)-4-(S)-(3-fluorophenyl)pyrrolidin-1-yl)-cyclohexaneacetic acid, trifluoroacetic acid salt Step A: 4-(4-(2-phenylethyl)-1-n-propyl-(1H-pyrazol-5-yl))-1-benzyl-piperidine, trifluoroacetic acid salt The title compound (58.4 mg) was isolated as the minor product from the reaction of 76.5 mg of 1-(1-benzylpiperidin-4-yl)-2-formnyl-4-phenyl-1-butanone from Example 9, Step E and 41 mg n-propyl hydrazine oxalate in 3.5 mL MeOH in a similar procedure described in Example 9, Step E.ESI-MS 388.4 (M+H), HPLC A: 2.69 min. The major product, 89.8 mg 4-(4-(2-phenylethyl)-1-n-propyl-(1H-pyrazol-3-yl))-1-benzyl-piperidine, trifluoroacetic acid salt had ESI-MS 388.4 (M+H), HPLC A: 3.01 min.

Step B: 4-(4-(2-Phenylethyl)-1-n-propyl-(1H-pyrazol-5-yl))-piperidine, trifluoroacetic acid salt The title compound (50.3 mg) was prepared from 58.4 mg of the minor product from the last step using a procedure very similar to that described in Example 9, Step F. It had a retention time of 7.57 minute on Zorbax SB-C18 column (4.6×75 mm) eluting with 20~100% gradient of MeCN in water with 0.1% TFA over 10 minutes at 1 mL per minute.

Step C: α-(R)-(3-(S)-((4-(4-(2-phenylethyl)-1-n-propyl-(1H-pyrazol-5-yl))piperidin-1-yl)methyl)-4-(S)-(3-fluorophenyl)pyrrolidin-1-yl)-cyclohexaneacetic acid, benzyl ester, trifluoroacetic acid salt The title compound was prepared from 11.4 mg 4-(4-(2-phenylethyl)-1-n-propyl-(1H-pyrazol-5-yl))-piperidine, trifluoroacetic acid salt from the last step, 9.0 mg α-(R)-(3-(R)-formyl-4-(S)-(3-fluorophenyl)-pyrrolidin-1-yl)-cyclohexaneacetic acid, benzyl ester (prepared above as Aldehyde 6), 7.4 uL of diisopropylethylamine, and 9.9 mg sodium triacetoxyborohydride in 1.5 mL 1,2-dichloroethane using a procedure similar to that described in Example 9, Step G. Purification on preparative reverse-phase HPLC using a 9.4×250 mm Zorbax SB-C18 column with 45~65% MeCN gradient in water having 0.5% (v/v) TFA over 15 minutes at 8 mL per minute afforded 19.0 mg of the title compound as a gel. It had a retention time of 5.03 minutes on Zorbax SB-C18 column (4.6×75 mm) eluting with 20~100% gradient of MeCN in water with 0.1% TFA over 5 minutes at 2 mL per minute.

Step D: α-(R)-(3-(S)-((4-(4-(2-phenylethyl)-1-n-propyl-(1H-pyrazol-5-yl))piperidin-1-yl)methyl)-4-(S)-(3-fluorophenyl)pyrrolidin-1-yl)-cyclohexaneacetic acid, trifluoroacetic acid salt The title compound (15.3 mg) was prepared from the product of the last step using a procedure very similar to that in Example 9, Step I. ESI-MS 615.3 (M+H), HPLC A: 2.70 min.

EXAMPLE 12

α-(R)-(3-(S)-((4-(3-Phenyl-1-ethyl-(1H-pyrazol-5-yl))piperidin-1-yl)methyl)-4-(S)-phenylpyrrolidin-1-yl)-cyclohexaneacetic acid, trifluoroacetic acid salt Step A: 4-(3-Phenyl-1-ethyl-(1H-pyrazol-5-yl))piperidine, trifluoro-acetic acid salt The title compound was isolated as the minor product from the reaction of 58.4 mg of 1-phenyl-3-(piperidin-4-yl)-propane-1,3-dione hydrochloride, 39.3 mg ethylhydrazine oxalate, 95 uL diisopropylethyl amine in 1 mL ethanol at 50° C. over night. The two isomeric products were separated on preparative reverse-phase HPLC using a 9.4×250 mm Zorbax SB-C18 column with 18~35% MeCN gradient in water having 0.5% (v/v) TFA over 15 minutes at 6 mL per minute. Fractions containing the fast-eluting minor product were combined and concentrated under reduced pressure to give 17.8 mg of the title compound as a gel. $^1$H NMR (500 MHz, CD$_3$OD): δ7.72~7.75 (m, 2H), 7.36~7.39 (m, 2H), 7.27~7.31 (m, 1H), 6.49 (s, 1H), 4.21 (q, 7.1 Hz, 2H), 3.51 (br d, 12.6 Hz, 2H), 3.12~3.22 (m, 3H), 2.18 (br d, 12.7 Hz, 2H), 1.87~1.95 (m, 2H), 1.45 (t, 7.1 Hz, 3H). NOE difference spectrum confirmed the identity of the isomers. ESI-MS 255.9 (M+H), HPLC A: 1.77 min., compared with 1.91 min. for its isomer.

Step B: α-(R)-(3-(S)-((4-(3-Phenyl-1-ethyl-(1H-pyrazol-5-yl))piperidin-1-yl)methyl)-4-(S)-phenylpyrrolidin-1-yl)-cyclohexaneacetic acid, benzyl ester, trifluoroacetic acid salt The title compound was prepared from the product in the last step, 19 mg α-(R)-(3-(R)-formyl-4-(S)-phenylpyrrolidin-1-yl)cyclo-hexaneacetic acid, benzyl ester (prepared above as Aldehyde 4), 16 uL of diisopropylethylamine, and 39 mg sodium triacetoxyborohydride in 1 mL 1,2-dichloroethane using a procedure similar to that described in Example 1, D. Purification on preparative reverse-phase HPLC using a 9.4×250 mm Zorbax SB-C18 column with 40~75% MeCN gradient in water having 0.5% (v/v) TFA over 15 minutes at 7.5 mL per minute afforded 23.2 mg of the title compound as a gel. ESI-MS 645.5 (M+H), HPLC A: 3.19 min.

Step C: α-(R)-(3-(S)-((4-(3-Phenyl-1-ethyl-(1H-pyrazol-5-yl))piperidin-1-yl)methyl)-4-(S)-phenylpyrrolidin-1-yl)-cyclohexaneacetic acid, trifluoroacetic acid salt The title compound (18.8 mg) was prepared from the product of the last step using a procedure similar to that described in Examples 1, Step E. ESI-MS 555.5 (M+H), HPLC A: 2.38 min.

EXAMPLE 13

α-(R)-(3-(S)-((4-(3-(3,4-Difluorobenzyl)-1-ethyl-(1H-pyrazol-5-yl))piperidin-1-yl)methyl)-4-(S)-phenylpyrrolidin-1-yl)-isopropylacetic Acid, Ammonium Salt Step A: 1-Benzyl-N-methoxy-N-methyl-piperidine-4-carboxamide A 2-L round-bottom flask was charged with 25.832 g isonipecotic acid, 30.5 mL benzaldehyde, 41.8 mL triethylamine, and 500 mL 1,2-dichloroethane to which was added 63.6 g sodium triacetoxyborohydride in portions over 20 minutes with stirring. After 24 hours, 4 mL benzaldehyde was added along with 21.2 g sodium triacetoxyborohydride in portions with 400 mL 1,2-dichloroethane. After an additional 8 hours, 4 mL of benzaldehyde was added along with 8.8 g sodium triacetoxyborohydride in portions. After stirring for additional 20 hours, the reaction mixture was poured into a separatory funnel, 300 mL each of ice water and concentrated HCl was added, the layers were separated, and the organic layer was washed with 4×75 mL 0.5M HCl. The combined aqueous layer was washed with 2×200 mL ether and was then concentrated under reduced pressure to constant weight to give 142 g of crude 1-benzyl-piperidine-4-carboxylic acid. To this material was added 39.02 g of N,O-dimethyl hydroxylamine hydrochloride, 81.08 g 1-hydroxybenzotriazole hydrate and 750 mL DMF with stirring. Next was added 174 mL diisopropylethylamine with stirring followed by 76.68 g 1-ethyl-3-(3-dimethylamino-propyl)carbodiimide in several portions over 5 minutes with stirring. After stirring for 72 hr, the cloudy reaction mixture was poured into 2 L ice water containing 100 mL 5N NaOH. The mixture was extracted with 500 and 4×250 mL ether, and the combined ether was washed with water (3×300 mL) and saturated brine (300 mL), dried over Na$_2$SO$_4$, filtered, and concentrated under reduced pressure to give 51.13 g of a yellow liquid. Flash chromatography on silica gel eluting with 40~100% ethyl acetate in hexanes with 1% (v/v) Et$_3$N gave 47.32 g title compound as a yellowish oil. R$_F$: 0.16 (25% EtOAc in hexanes with 1% (v/v) Et$_3$N). $^1$H NMR (500 MHz, CDCl$_3$): δ7.31~7.36 (m, 4H), 7.24~7.28 (m, 1H), 3.71 (s, 3H), 3.53 (s, 2H), 3.20 (s, 3H), 2.94~2.98 (m, 2H), 2.63~2.70 (m, 1H), 2.01~2.07 (m, 2H), 1.82~1.90 (m, 2H), 1.70~1.74 (m, 2H).

Step B: 1-Benzyl-4-acetylpiperidine

A solution of 47.32 g 1-benzyl-N-methyl-N-methoxy-piperidine-4-carboxamide in 1.5 L anhydrous ether in a 2-L 3-neck round-bottom flask fitted with a nitrogen bubbler, an overhead stirrer, and an addition funnel was cooled with an ice-acetone bath, and was treated with 270 mL of a 1.53M solution of methylmagnesium bromide in 1:3 THF:toluene with stirring over 70 minutes. After stirring in an ice bath for additional two hours, the mixture was quenched with 15 mL EtOAc, stirred for 10 minutes, and then poured into 2 L of ice water. After adjusting the pH to 8~9, the layers were separated. The mixture was extracted with 4×250 mL ether, the combined ether solution was washed with 300 mL each of water and saturated brine, and then dried over $Na_2SO_4$. Removal of solvent under reduced pressure gave 40.68 g of crude product. This material was purified by flash chromatography on silica gel eluting with 25%~40% EtOAc in hexanes with 1% $Et_3N$ to give 39.533 g of the title compound as a yellowish liquid. $R_F$: 0.20 (20% EtOAc in hexanes with 1% (v/v) $Et_3N$). 1H NMR (500 MHz, $CDCl_3$): δ7.32~7.35 (m, 4H), 7.25~7.30 (m, 1H), 3.53 (s, 2H), 2.91~2.95 (m, 2H), 2.28~2.34 (m, 1H), 2.16 (s, 3H), 2.01~2.07 (m, 2H), 1.83~1.88 (m, 2H), 1.66~1.74 (m, 2H).

Step C: 1-(1-Benzylpiperidin-4-yl)-4-(3,4-difluorophenyl) butane-1,3-dione

The title compound was prepared in 67% yield from 2.18 g 1-benzyl-4-acetylpiperidine from the last step, 5.58 g methyl 3,4-difluorophenylacetate from Fisher esterification, and 0.8 g 60% NaH in 15 mL anhydrous THF using a procedure similar to that described in Example 1, Step A Method B. $R_F$: 0.28 (15% EtOAc in hexanes). $^1$H NMR (500 MHz, $CDCl_3$): δ7.32~7.35 (m, 4H), 7.26~7.30 (m, 1H), 7.06~7.15 (m, 3H), 6.95~6.98 (m, 1H), 5.47 (s, 1H), 3.57 (s, 2H), 3.54 (br s, 2H), 2.96 (br d, 11.5 Hz, 2H), 2.17~2.21 (m, 1H), 2.02~2.10 (m, 2H), 1.70~1.83 (m, 4H).

Step D: 4-(3-(3,4-Difluorobenzyl)-1-ethyl-(1H-pyrazol-5-yl))-1-benzyl-piperidine The title compound was prepared from 1-(1-benzylpiperidin-4-yl)-4-(3,4-difluorophenyl)butane-1,3-dione and ethylhydrazine oxalate using a procedure similar to that described in Example 1, Step B. $R_F$: 0.29 (2:1 EtOAc to hexanes with 1% (v/v) $Et_3N$). It was the fast-eluting isomer on silica gel. $^1$H NMR (500 MHz, $CDCl_3$): δ7.29~7.33 (m, 4H), 7.23~7.28 (m, 1H), 7.05~7.14 (m, 2H), 6.97~7.01 (m, 1H), 5.86 (s, 1H), 4.06 (q, 7.2 Hz, 2H), 3.84 (s, 2H), 3.55 (s, 2H), 2.97 (br d, 11.9 Hz, H), 2.64 (tt, 12.1 & 3.7 Hz, 1H), 2.12~2.16 (m, 2H), 1.83 (br d, 13.1 Hz, 2H), 1.62~1.71 (m, 2H), 1.35 (t, 7.2 Hz, 3H); ESI-MS 396.2 (M+H), HPLC A: 3.43 min., compared with 3.54 min. for its isomer.

Step E: 4-(3-(3,4-Difluorobenzyl)-1-ethyl-(1H-pyrazol-5-yl))piperidine, trifluoroacetic acid salt The title compound was prepared from the product of the last step using a procedure similar to that described in Example 8, Step F. $^1$H NMR (500 MHz, $CDCl_3$): δ7.06~7.18 (m, 2H), 6.99~7.03 (m, 1H), 5.92 (s, 1H), 4.13 (q, 7.2 Hz, 2H), 3.87 (s, 2H), 3.43~3.48 (m, 2H), 3.10~3.18 (m, 2H), 3.07 (tt, 11.9 & 3.7 Hz, 1H), 2.10 (br d, 14.1 Hz, 2H), 1.73~1.84 (m, 2H), 1.40 (t, 7.2 Hz, 3H); ESI-MS 306.0 (M+H), HPLC A: 3.25 min., compared with 3.50 min. for its isomer.

Step F: α-(R)-(3-(S)-((4-(3-(3,4-Difluorobenzyl)-1-ethyl-(1H-pyrazol-5-yl))piperidin-1-yl)methyl)-4-(S)-phenylpyrrolidin-1-yl)-isopropylacetic acid, para-methoxybenzyl ester, trifluoroacetic acid salt The title compound was prepared from 29 mg 4-(3-(3,4-difluorobenzyl)-1-ethyl-(1H-pyrazol-5-yl))piperidine, trifluoroacetic acid salt from the last step, 20.4 mg α-(R)-(3-(R)-formyl-4-(S)-phenyl-pyrrolidin-1-yl)-isopropylacetic acid, para-methoxybenzyl ester (prepared above as Aldehyde 9), Steps B~D, 37.9 uL diisopropylethylamine, and 34.6 mg sodium triacetoxyborohydride in 1.5 mL 1,2-dichloroethane. After HPLC purification, 58.3 mg title compound was isolated as a gel. ESI-MS 685.3 (M+H), HPLC A: 4.13 min.

Step G: α-(R)-(3-(S)-((4-(3-(3,4-Difluorobenzyl)-1-ethyl-(1H-pyrazol-5-yl))piperidin-1-yl)methyl)-4-(S)-phenylpyrrolidin-1-yl)-isopropyl acetic acid, ammonium salt The title compound was prepared from the product of the last step using a procedure similar to that described in Example 10, Step D. After lyophilization, 32.7 mg of the title compound was obtained as a white solid. ESI-MS 565.4 (M+H), HPLC A: 3.75 min.

EXAMPLE 14

α-(R)-(3-(S)-((4-(3-(3,4-Difluorobenzyl)-1-ethyl-(1H-pyrazol-5-yl))piperidin-1-yl)methyl)-4-(S)-(3-fluorophenyl)pyrrolidin-1-yl)-isopropylacetic Acid, Ammonium Salt Step A: α-(R)-(3-(S)-((4-(3-(3,4-Difluorobenzyl)-1-ethyl-(1H-pyrazol-5-yl))piperidin-1-yl)methyl)-4-(S)-(3-fluorophenyl)pyrrolidin-1-yl)-isopropylacetic acid, para-methoxybenzyl ester, trifluoroacetic acid salt The title compound was prepared from 29 mg 4-(3-(3,4-difluorobenzyl)-1-ethyl-(1H-pyrazol-5-yl))piperidine, trifluoroacetic acid salt prepared in Example 13, Step E, 21.4 mg α-(R)-(3-(R)-Formyl-4-(S)-(3-fluorophenyl)-pyrrolidin-1-yl)-isopropylacetic acid, para-methoxybenzyl ester (prepared above as Aldehyde 11), 37.9 uL diisopropylethylamine, and 34.6 mg sodium triacetoxyborohydride in 1.5 mL 1,2-dichloroethane. After HPLC purification, 52.5 mg title compound was isolated as a gel. 703.3 (M+H), HPLC A: 4.20 min.

Step B: α-(R)-(3-(S)-((4-(3-(3,4-Difluorobenzyl)-1-ethyl-(1H-pyrazol-5-yl))piperidin-1-yl)methyl)-4-(S)-(3-fluorophenyl)pyrrolidin-1-yl)-isopropylacetic acid, ammonium salt The title compound was prepared from the product of the last step using a procedure similar to that described in Example 10, Step D. After lyophilization, 29.2 mg of the title compound was obtained as a white solid. ESI-MS 583.4 (M+H), HPLC A: 3.84 min.

EXAMPLE 15

α-(R)-(3-(S)-((4-(3-(4-Fluorobenzyl)-1-ethyl-(1H-pyrazol-5-yl))piperidin-1-yl)methyl)-4-(S)-(3-fluorophenyl)pyrrolidin-1-yl)-isopropylacetic Acid, Ammonium Salt Step A: 4-(3-(4-Fluorobenzyl)-1-ethyl-(1H-pyrazol-5-yl)) piperidine, trifluoroacetic acid salt The title compound was prepared using a procedure similar to that described in Example 13, Steps C~E starting with methyl 4-fluorophenylacetate. $^1$H NMR (500 MHz, $CDCl_3$): δ7.20~7.23 (m, 2H), 6.96~7.00 (m, 2H), 5.89 (s, 1H), 4.12 (q, 7.2 Hz, 2H), 3.87 (s, 2H), 3.43~3.47 (m, 2H), 3.11~3.17 (m, 2H), 3.06 (tt, 11.9 & 3.6 Hz, 1H), 2.06~2.11 (m, 2H), 1.73~1.82 (m, 2H), 1.39 (t, 7.2 Hz, 3H); ESI-MS 288.0 (M+H), HPLC A: 2.86 min., compared with 3.30 min. for its isomer.

Step B: α-(R)-(3-(S)-((4-(3-(4-Fluorobenzyl)-1-ethyl-(1H-pyrazol-5-yl))piperidin-1-yl)methyl)-4-(S)-(3-fluorophenyl)pyrrolidin-1-yl)-isopropylacetic acid, para-methoxybenzyl ester, trifluoroacetic acid salt The title compound was prepared from 28 mg 4-(3-(4-fluorobenzyl)-1-ethyl-(1H-pyrazol-5-yl))piperidine, trifluoroacetic acid salt prepared in the last step, 21.3 mg α-(R)-(3-(R)-formyl-4-(S)-(3-fluorophenyl)-pyrrolidin-1-yl)-isopropylacetic acid, para-methoxybenzyl ester (prepared above as Aldehyde 11), 37.9 uL diisopropylethylamine, and 34.5 mg sodium triacetoxyborohydride in 1.5 mL 1,2-dichloroethane. After HPLC purification, 39.9 mg title compound was isolated as a gel. ESI-MS 685.4 (M+H), HPLC A: 4.54 min.

Step C: α-(R)-(3-(S)-((4-(3-(4-Fluorobenzyl)-1-ethyl-(1H-pyrazol-5-yl))piperidin-1-yl)methyl)-4-(S)-(3-fluorophenyl)pyrrolidin-1-yl)-isopropylacetic acid, ammonium salt The title compound was prepared from the product of the last step using a procedure similar to that described in Example 10, Step D. After lyophilization, 22.9 mg of the title compound was obtained as a white solid. ESI-MS 565.4(M+H), HPLC A: 3.60 min.

EXAMPLE 16

α-(R)-(3-(S)-((4-(3-Benzyl-1-ethyl-(1H-pyrazol-5-yl))piperidin-1-yl)methyl)-4-(S)-3-phenylpyrrolidin-1-yl)-cyclobutylacetic Acid, Ammonium Salt Step A: α-(R)-(3-(S)-((4-(3-Benzyl-1-ethyl-(1H-pyrazol-5-yl))piperidin-1-yl)methyl)-4-(S)-phenylpyrrolidin-1-yl)-cyclobutylacetic acid, para-methoxybenzyl ester, trifluoroacetic acid salt The title compound was prepared from 28 mg 4-(3-benzyl)-1-ethyl-(1H-pyrazol-5-yl))piperidine, trifluoroacetic acid salt prepared in Example 1, Step C, 20.6 mg α-(R)-(3-(R)-formyl-4-(S)-phenyl-pyrrolidin-1-yl)-cyclobutylacetic acid, para-methoxybenzyl ester, 39.2 uL diisopropylethylamine, and 35.8 mg sodium triacetoxyborohydride in 1.5 mL 1,2-dichloroethane. After HPLC purification, 16.2 mg title compound was isolated as a gel. ESI-MS 661.4 (M+H), HPLC A: 4.04 min.

Step F: α-(R)-(3-(S)-((4-(3-Benzyl-1-ethyl-(1H-pyrazol-5-yl))piperidin-1-yl)methyl)-4-(S)-phenylpyrrolidin-1-yl)-cyclobutylacetic acid, ammonium salt The title compound was prepared from the product of the last step using a procedure similar to that described in Example 10, Step D. After lyophilization, 13 mg title compound was obtained as a white solid. ESI-MS 541.4 (M+H), HPLC A: 3.58 min.

EXAMPLES 17 TO 21

Examples 17 to 21 in Table 1 were prepared by reductive amination of α-(R)-(3-(R)-formyl-4-(S)-phenylpyrrolidin-1-yl)-cyclohexaneacetic acid, benzyl ester (prepared above as Aldehyde 4) and appropriate 4-pyrazolylpiperidine followed by hydrogenolysis using a procedure similar to the one detailed in Steps D and E of Example 1. The 4-(pyrazol-1-yl)piperidines were in turn prepared by reaction of commercially available 1-benzyl-4-hydrazinopiperidine dihydrochloride with 1,3-diketones followed by debenzylation. The isomeric 4-pyrazolylpiperidines were separated or enriched by reverse phase HPLC on a Zorbax SB-C18 column. Their structures were determined by NOESY or NOE difference spectra. The diketones are either commercially available (1-phenylbutane-1,3-dione) or prepared using procedures similar to those in the literature (Gotterill, A. and Gill, M. *Aust. J. Chem.* 1994, 47, 1363–74).

TABLE 1

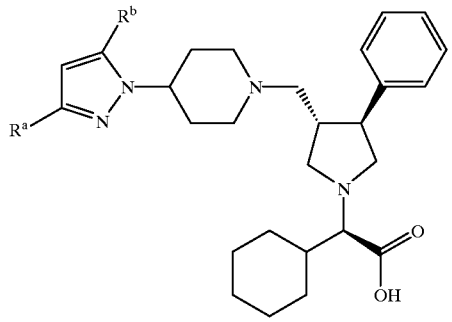

| EXAMPLE # | $R^a$ | $R^b$ | ESI-MS (M + H); HPLC A (min.) |
|---|---|---|---|
| 17 | Me | phenyl | 541.4 m/Z; 2.44 |
| 18 | phenyl | Me | 541.4 m/Z; 2.50 |

TABLE 1-continued

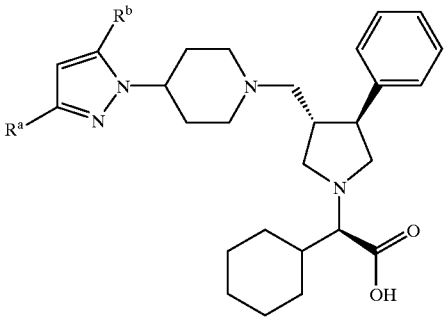

| EXAMPLE # | $R^a$ | $R^b$ | ESI-MS (M + H); HPLC A (min.) |
|---|---|---|---|
| 19 | benzyl & ethyl (Me) 2:3 ratio | Me & benzyl 2:3 ratio | 569.4 m/Z; 2.65 |
| 20 | ethyl (Me) | phenethyl | 583.4 m/Z; 2.78 |
| 21 | phenethyl & ethyl (Me) 1:1 ratio | Me & phenethyl 1:1 ratio | 583.4 m/Z; 2.78 |

EXAMPLE 22 TO 35

Examples 22 to 35 in Table 2 were prepared by reductive amination of α-(R)-(3-(R)-formyl-4-(S)-phenylpyrrolidin-1-yl)-cyclohexaneacetic acid, benzyl ester (prepared above as Aldehyde 4) and appropriate 4-pyrazolylpiperidine followed by hydrogenolysis using a procedure similar to the one detailed in Steps D and E of Example 1. The first example in this table used the 4-(pyrazolyl)-piperidine derived from deprotection of the minor product in Example 1, Step B. The second example used the minor isoxazole in Example 5 Step B. The other 4-(pyrazolyl)piperidines were prepared by a procedure similar to that in Steps B and C of of Example 1 using appropriate commercially available hydrazines instead of ethyl hydrazine. The isomeric 4-pyrazolylpiperidines were separated on reverse phase HPLC either before or after removal of the tert-butoxycarbonyl group. Their structures were determined by NOESY or NOE difference spectra. The last two examples in this table were prepared by saponification of the corresponding pyrazolylpiperidine ethyl esters before reductive amination. The unusual retention times of Examples 24 and 25 were because they were analyzed months after the others in the Table.

TABLE 2

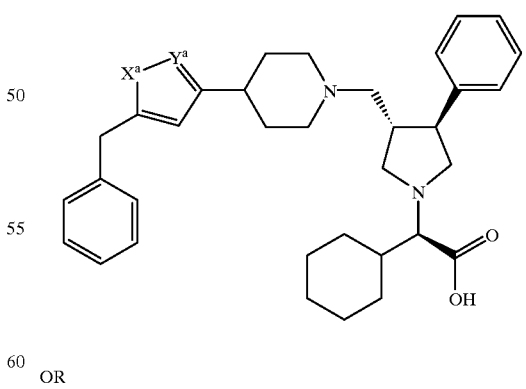

OR

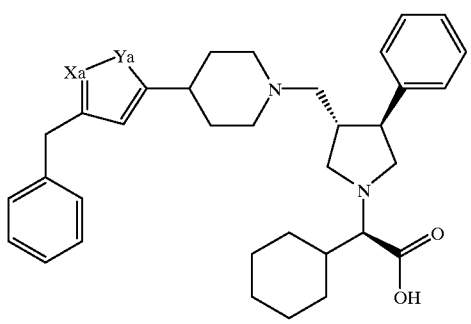

| EXAMPLE # | $X^a$ | $Y^a$ | ESI-MS (M + H); HPLC A (min.) |
|---|---|---|---|
| 22 | N—CH$_2$CH$_3$ | N | 569.5 m/Z; 2.48 |
| 23 | O | N | 542.4 m/Z; 2.32 |
| 24 | N | N—CH$_2$CH$_2$CH$_3$ | 583.4 m/Z; 2.93 |
| 25 | N—CH$_2$CH$_2$CH$_3$ | N | 583.4 m/Z; 3.09 |
| 26 | N | N—CH$_3$ | 555.5 m/Z; 2.25 |
| 27 | N—CH$_3$ | N | 569.5 m/Z; 2.39 |
| 28 | N | N—(CH$_2$)$_3$CH$_3$ | 597.5 m/Z; 2.62 |
| 29 | N—(CH$_2$)$_3$CH$_3$ | N | 597.5 m/Z; 2.81 |
| 30 | N | N—CH$_2$CF$_3$ | 623.5 m/Z; 2.57 |
| 31 | N—CH$_2$CF$_3$ | N | 623.5 m/Z; 2.66 |
| 32 | N | N—CH$_2$CO$_2$Et | 627.5 m/Z; 2.46 |
| 33 | N—CH$_2$CO$_2$Et | N | 627.5 m/Z; 2.54 |
| 34 | N | N—CH$_2$CO$_2$H | 599.5 m/Z; 2.22 |
| 35 | N—CH$_2$CO$_2$H | N | 599.4 m/Z; 2.26 |

EXAMPLE 36 TO 51

Examples 36 to 51 in Table 3 were prepared by reductive amination of α-(R)-(3-(R)-formyl-4-(S)-phenylpyrrolidin-1-yl)-cyclohexaneacetic acid, benzyl ester (prepared above as Aldehyde 4) or other appropriate aldehydes prepared similarly with appropriate 4-pyrazolylpiperidine followed by hydrogenolysis using a procedure similar to the one detailed in Steps D and E of Example 1. Some of the aldehydes used have para-methoxybenzyl protecting group. The last step for those compounds used a procedure similar to that in Example 10, Step D. The first example in this table used the major isomer of 4-(pyrazolyl)-piperidine from Example 12, Step A. The other 4-(pyrazolyl)-piperidines were prepared by Claisen condensation of appropriate esters with 4-acetyl-1-(tert-butoxycarbonyl)piperidine prepared in Example 1, Step 1 Method B using procedures similar to that described therein. The resulting 1,3-diketones were cyclized with appropriate hydrazines to give isomeric 4-(pyrazolyl) piperidines. The isomers were separated on preparative reverse-phase HPLC at this stage or after removal of Boc protecting group. The last two examples in this table were side-products from hydrogenolysis of the benzyl esters under hydrogen during the preparation of the two previous examples.

TABLE 3

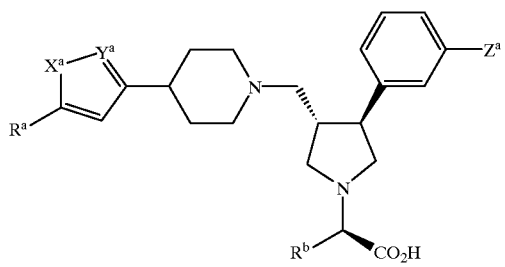

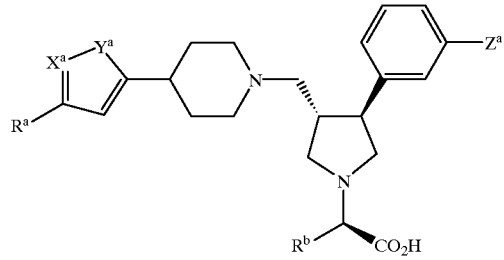

| EXAMPLE # | $R^a$ | $R^b$ | $X^a$ | $Y^a$ | $Z^a$ | ESI-MS (M + H); HPLC A (min.) |
|---|---|---|---|---|---|---|
| 36 | phenyl | cyclohexyl | N-Et | N | H | 555.5 m/Z; 2.46 |
| 37 | 4-CN-phenyl | cyclohexyl | N—H | N | H | 552.5 m/Z; 2.20 |

TABLE 3-continued
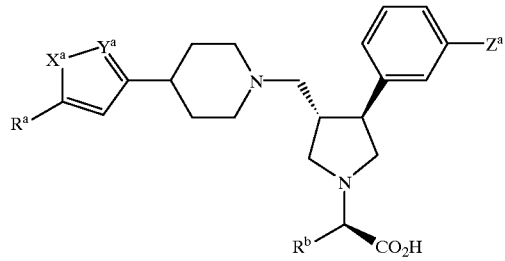
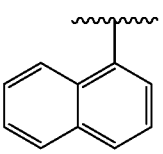
| EXAMPLE # | Rᵃ | Rᵇ | Xᵃ | Yᵃ | Zᵃ | ESI-MS (M + H); HPLC A (min.) |
|---|---|---|---|---|---|---|
| 38 | 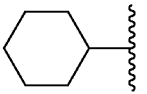 | 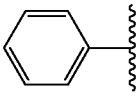 | N—H | N | H | 577.7 m/Z; 2.42 |
| 39 | 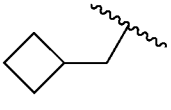 | 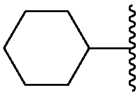 | N | N-Et | F | 559.4 m/Z; 2.44 |
| 40 | 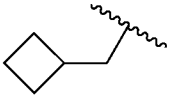 | 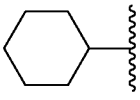 | N—H | N | F | 537.3 m/Z; 2.70 |
| 41 | 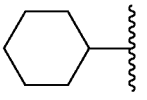 | 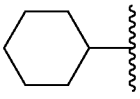 | N—H | N | F | 551.4 m/Z; 2.76 |
| 42 | 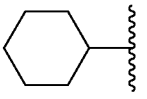 | 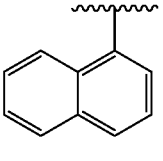 | N—H | N | H | 533.4 m/Z; 2.70 |
| 43 | 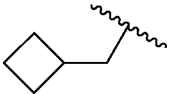 | 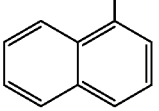 | N | N-Et | F | 609.2 m/Z; 3.03 |
| 44 | 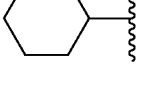 | | N | N-Et | F | 623.3 m/Z; 3.08 |

TABLE 3-continued
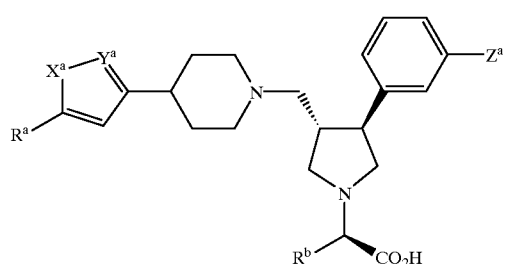
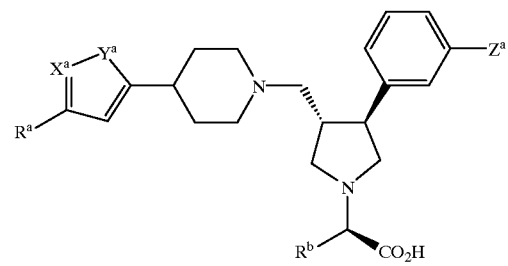
| EXAMPLE # | R$^a$ | R$^b$ | X$^a$ | Y$^a$ | Z$^a$ | ESI-MS (M + H); HPLC A (min.) |
|---|---|---|---|---|---|---|
| 45 | 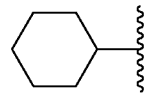 | 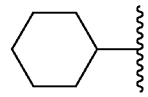 | N | N-Et | H | 561.5 m/Z; 2.35 |
| 46 | 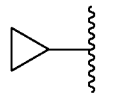 | 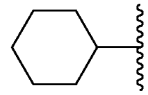 | N | N—H | F | 509.3 m/Z; 2.35 |
| 47 | 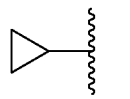 | 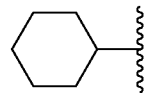 | N | N—H | H | 491.3 m/Z; 2.35 |
| 48 | 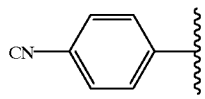 | 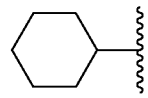 | N-Et | N | H | 580.5 m/Z; 2.40 |
| 49 | 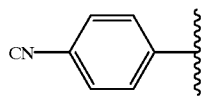 | 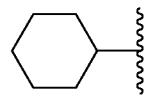 | N | N-Et | H | 580.5 m/Z; 2.42 |
| 50 | 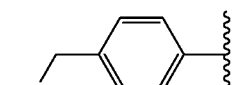 | 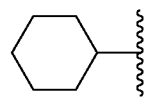 | N-Et | N | H | 584.5 m/Z; 1.76 |
| 51 | 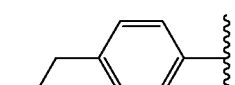 | 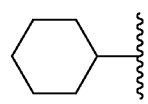 | N | N-Et | H | 584.6 m/Z; 1.79 |
EXAMPLE 52 TO 63
Examples 52 to 63 in Table 4 were prepared using procedures similar to those described for Examples 6, and 8 to 11.

TABLE 4

| EXAMPLE # | Rª | Rᵇ | Xª | Yª | Zª | ESI-MS (M + H); HPLC A (min.) |
|---|---|---|---|---|---|---|
| 52 | phenyl | cyclohexyl | N—H | N | H | 541.4 m/Z; 2.32 |
| 53 | phenyl | cyclohexyl | N-Et | N | H | 569.5 m/Z; 2.53 |
| 54 | benzyl | cyclohexyl | N—H | N | H | 555.5 m/Z; 2.45 |
| 55 | benzyl | cyclohexyl | N-Et | N | H | 583.6 m/Z; 2.69 |
| 56 | benzyl | cyclohexyl | O | N | H | 556.3 m/Z; 2.81 |
| 57 | benzyl | cyclobutylmethyl | N | N-Et | F | 587.3 m/Z; 2.51 |
| 58 | benzyl | isopropyl | N | N-n-Pr | H | 557.4 m/Z; 2.43 |

TABLE 4-continued

| EXAMPLE # | R$^a$ | R$^b$ | X$^a$ | Y$^a$ | Z$^a$ | ESI-MS (M + H); HPLC A (min.) |
|---|---|---|---|---|---|---|
| 59 | benzyl | isopropyl | N | N-n-Pr | F | 575.4 m/Z; 2.49 |
| 60 | benzyl | cyclohexyl | N | N-Me | H | 569.4 m/Z; 2.94 |
| 61 | benzyl | cyclohexyl | N-Me | N | H | 569.4 m/Z; 3.06 |
| 62 | benzyl | cyclohexyl | N | N-n-Pr | H | 597.4 m/Z; 3.04 |
| 63 | benzyl | cyclohexyl | N-n-Pr | N | H | 597.4 m/Z; 3.23 |

EXAMPLE 64 TO 76

Examples 64 to 76 in Table 5 were prepared using procedures similar to those described for Examples 1 and 2. Example 65 was isolated as the by-product during the final debenzylation for Example 64. The pyrazole formation step for Example 72 only gave one isomer. Its isomer, Example 73, was obtained by hydrolysis of its gem-difluoro analogue during the deprotection of Boc group after formation of the pyrazolylpiperidine. Example 75 was isolated as a by-product of Example 73 as the result of over reduction during the final debenzylation step.

TABLE 5
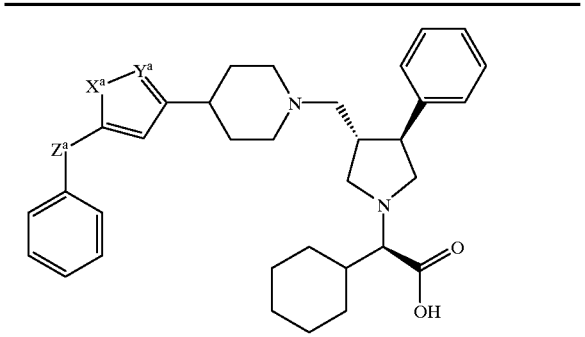
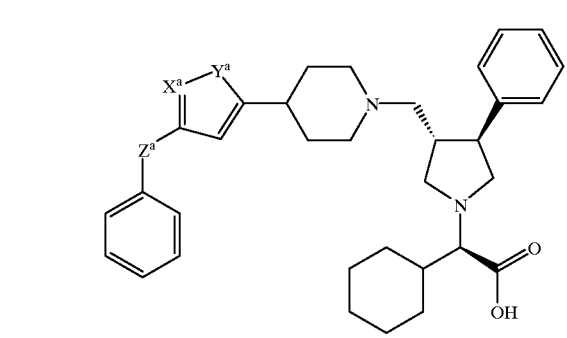
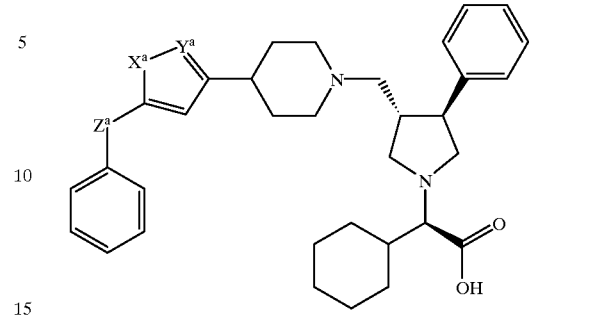
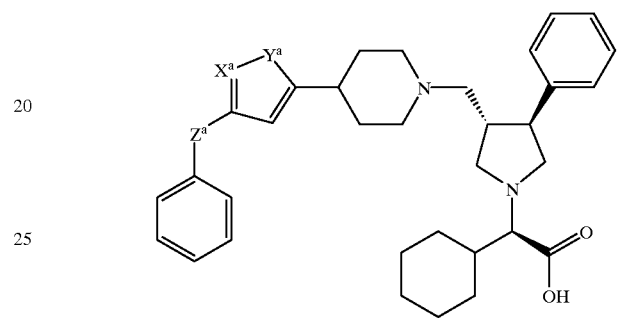
| EXAMPLE # | X$^a$ | Y$^a$ | Z$^a$ | ESI-MS (M + H); HPLC A (min.) |
|---|---|---|---|---|
| 64 | N—H | N | 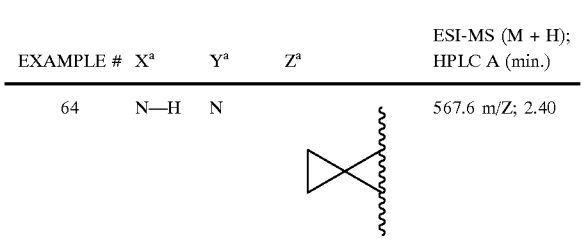 | 567.6 m/Z; 2.40 |
| 65 | N—H | N | 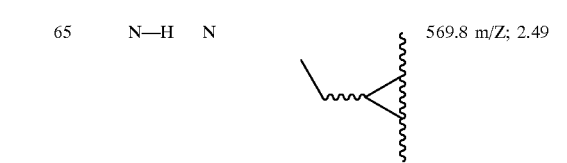 | 569.8 m/Z; 2.49 |
| 66 | N-Et | N | 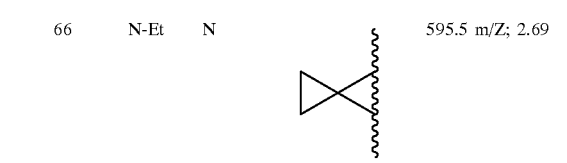 | 595.5 m/Z; 2.69 |
| 67 | N | N-Et | 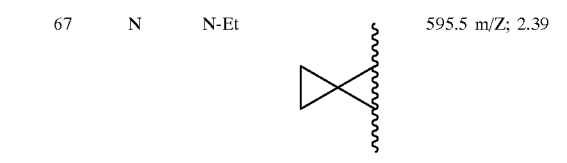 | 595.5 m/Z; 2.39 |
| 68 | N—H | N | 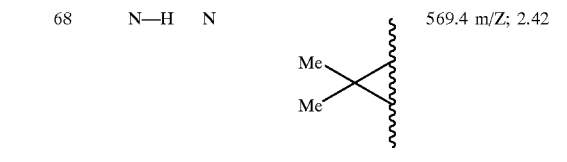 | 569.4 m/Z; 2.42 |
| 69 | N | N-Et | 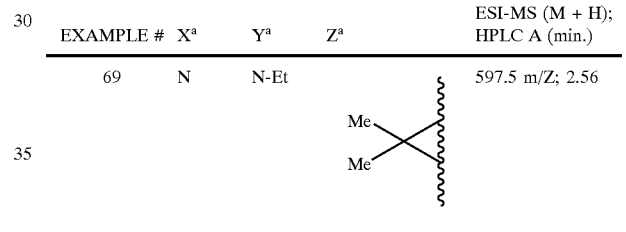 | 597.5 m/Z; 2.56 |
| 70 | N-Et | N | 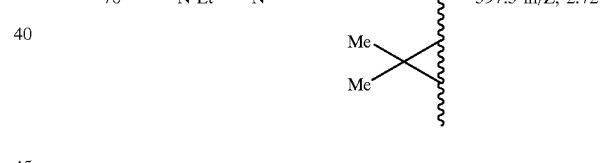 | 597.5 m/Z; 2.72 |
| 71 | N | N—H | 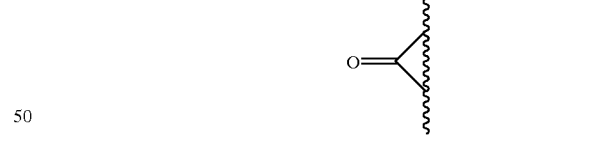 | 555.5 m/Z; 2.06 |
| 72 | N-Et | N | 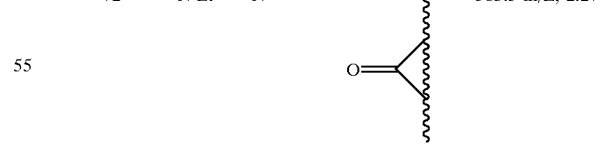 | 583.5 m/Z; 2.27 |
| 73 | N | N-Et | 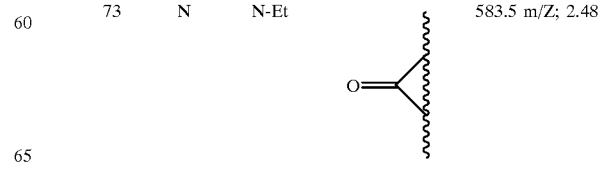 | 583.5 m/Z; 2.48 |

TABLE 5-continued
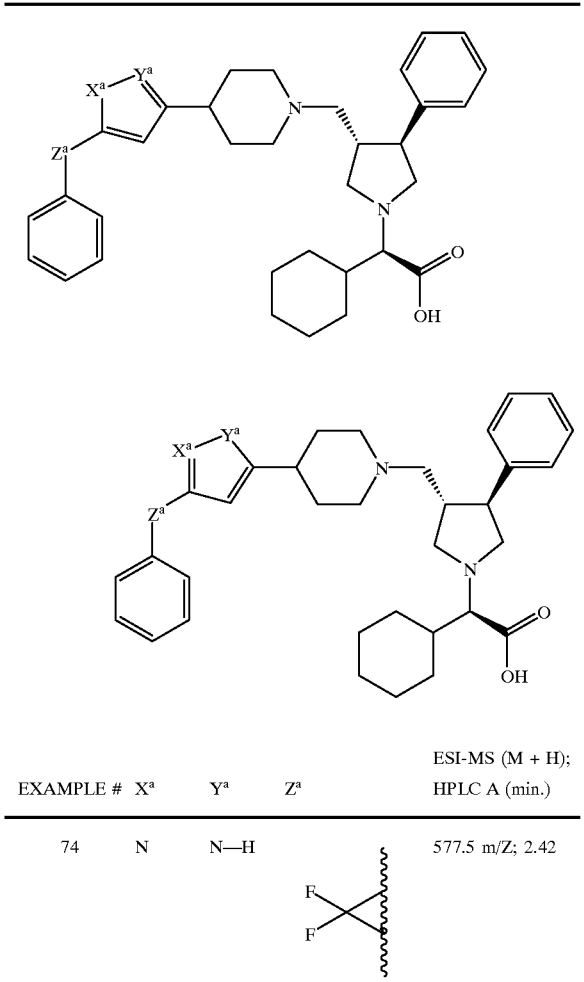
| EXAMPLE # | $X^a$ | $Y^a$ | $Z^a$ | ESI-MS (M + H); HPLC A (min.) |
|---|---|---|---|---|
| 74 | N | N—H | (CF2) | 577.5 m/Z; 2.42 |
| 75 | N | N-Et | (HO-) | 585.5 m/Z; 2.08 |
TABLE 5-continued
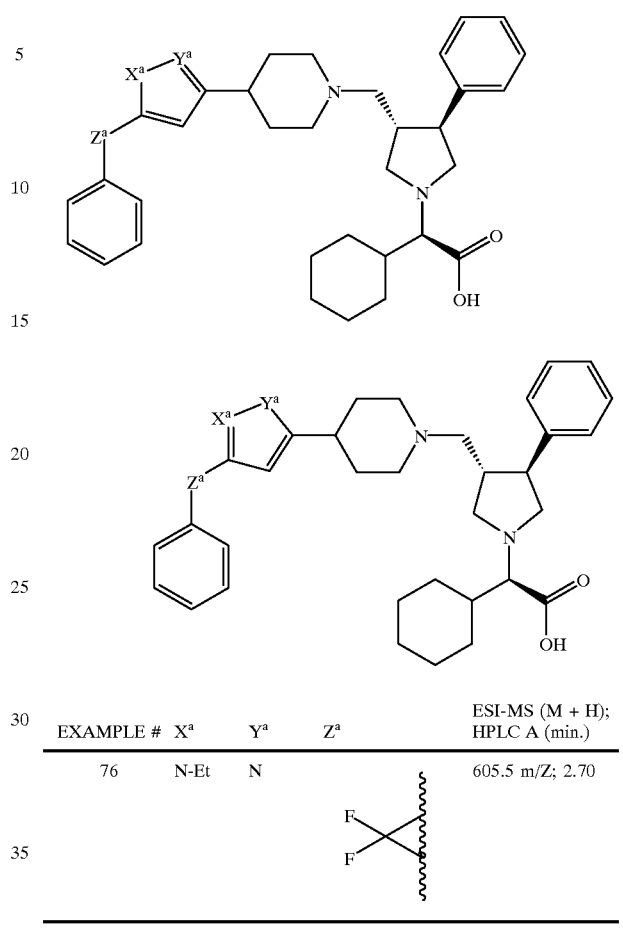
| EXAMPLE # | $X^a$ | $Y^a$ | $Z^a$ | ESI-MS (M + H); HPLC A (min.) |
|---|---|---|---|---|
| 76 | N-Et | N | (CF2) | 605.5 m/Z; 2.70 |
EXAMPLE 77 TO 85
Examples 77 to 85 in Table 6 were prepared using procedures similar to those described for Examples 1 to 3, 6 and 13 to 15.
TABLE 6
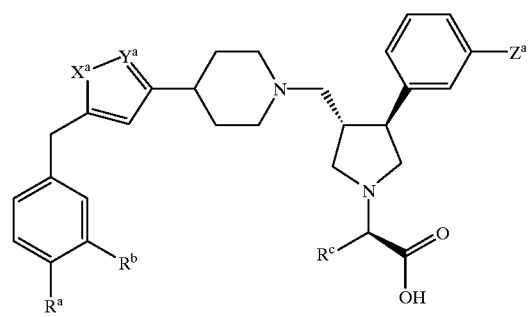

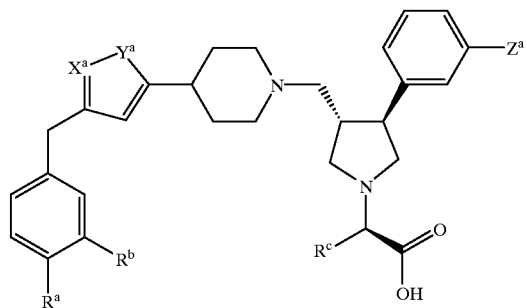

| EXAMPLE # | R$^a$ | R$^b$ | R$^c$ | X$^a$ | Y$^a$ | Z$^a$ | ESI-MS (M + H); HPLC A (min.) |
|---|---|---|---|---|---|---|---|
| 77 | H | H | cyclobutylmethyl | N | N-Et | F | 573.3 m/Z; 2.40 |
| 78 | H | H | cyclohexyl | N | N-Et | F | 587.4 m/Z; 2.45 |
| 79 | F | F | iPr | N | N—H | F | 555.5 m/Z; 2.44 |
| 80 | F | H | iPr | N | N—H | F | 537.3 m/Z; 2.32 |
| 81 | F | H | iPr | N | N-Et | H | 547.4 m/Z; 3.59 |
| 82 | F | H | cyclohexyl | N-Et | N | F | 605.3 m/Z; 3.90 |
| 83 | F | H | cyclohexyl | N | N-Et | F | 605.3 m/Z; 3.98 |
| 84 | H | H | iPr | N | N-n-Pr | F | 561.4 m/Z; 2.89 |
| 85 | F | F | cyclohexyl | N-Et | N | F | 623.4 m/Z; 4.06 |

EXAMPLES 86 to 88

Examples 86 to 88 in Table 7 were prepared using procedures similar to that described for Examples 7 using aldehydes prepared above as Aldehydes 4, 10 and 12. The pyridyl piperidine was prepared by the method of Scheme 16.

TABLE 7

| EXAMPLE # | R | Z | ESI-MS (M + H); HPLC A (min.) |
|---|---|---|---|
| 86 | cyclohexyl | H | 462.3 m/Z; 1.62 |
| 87 | cyclopropylmethyl | F | 452.3 m/Z; 1.97 |
| 88 | isopropyl | F | 440.2 m/Z; 1.86 |

EXAMPLE 89

α-(R)-(3-(S)-((4-(Benzothiazol-2-yl)piperidin-1-yl)
methyl)-4-(S)-phenylpyrrolidin-1-yl)-
cyclohexaneacetic Acid Step A: 1-(4-(Benzothiazol-2-yl)piperidin-1-yl)ethanone To a mixture of 1.43 g of 1-acetylpiperidine-4-carboxylic acid and 1.05 g of 2-aminothiophenol was added 5 mL of polyphosphoric acid. After stirring at 110° C. for 18 hours, the reaction was cooled to 40° C. The syrup was poured onto ice and water was added to keep the solution temperature below 10° C. The resulting dark brown solution was basified with ammonium hydroxide. Aqueous phase was extracted with EtOAC (3x). The combined organic phases were washed with brine and dried over anhydrous MgSO₄. Concentration under reduced pressure afforded 1.41 g of the title compound as a solid.

Step B: 2-(Piperidin-4-yl)benzothiazole

To a solution of 1.4 g of 1-(4-(benzothiazol-2-yl)piperidin-1-yl)ethanone in 10 mL of MeOH was added 7.5 mL of KOH (45 wt. % solution). After refluxing for 18 hours, the reaction was cooled to room temperature. The mixture was partitioned between EtOAc and water. The organic phase was washed with brine and dried over MgSO₄. Concentration under reduced pressure gave 540 mg of the title compound as a solid.

Step C: α-(R)-(3-(S)-((4-(Benzothiazol-2-yl)piperidin-1-yl)methyl)-4-(S)-phenylpyrrolidin-1-yl)-cyclohexaneacetic acid, 4-methoxybenzyl ester To a solution of 52 mg of α-(R)-(3-(R)-formyl-4-(S)-phenylpyrrolidin-1-yl)-cyclohexaneacetic acid, 4-methoxybenzyl ester (prepared above as Aldehyde 5) and 50 mg of 2-(piperidin-4-yl)benzothiazole (from Step B) in 2.5 mL of THF was added two spatula tips of 3 Å molecular sieves. After stirring at room temperature for 20 mim., 50 mg of sodium triacetoxyborohydride was added and the reaction was stirred at room temperature for 18 hours. The reaction was quenched with MeOH and diluted with EtOAc. After filtering molecular sieves, the filtrate was concentrated under reduced pressure. The residue was partitioned between EtOAc and water. The organic layer was washed with brine and dried over anhydrous MgSO₄. Concentration under reduced pressure followed by flash chromatography eluting with 20% EtOAc in hexane followed by 50% EtOAc in hexane afforded 56 mg of the title compound as a white solid.

Step D: α-(R)-(3-(S)-((4-(Benzothiazol-2-yl)piperidin-1-yl)methyl)-4-(S)-phenylpyrrolidin-1-yl)-cyclohexaneacetic acid A solution of 50 mg of α-(R)-(3-(S)-((4-(benzothiazol-2-yl)piperidin-1-yl)methyl)-4-(S)-phenylpyrrolidin-1-yl)-cyclohexaneacetic acid, 4-methoxybenzyl ester (from Step C) in 2 mL of formic acid (96%) was stirred at room temperature for 18 hours. After concentration under reduced pressure, the residue was purified by flash chromatography eluting with 10% MeOH in CH₂Cl₂, and then CHCl₃: MeOH: NH₄OH=80:15:1 to give 34 mg of the title compound as a white solid. $^1$H NMR (400 MHz, CD₃OD): δ1.10–2.35 (m, 9H), 2.41 (br d, 2H), 2.56 (br t, 2H), 2.8–3.25 (m, 10 H), 3.4–3.75 (m, 6H), 7.25–7.45 (m, 6H), 7.48 (t, J=7.3 Hz, 1H), 7.89 (d, J=7.8 Hz, 1H), 7.93 (d, J=8.2 Hz, 1H); ESI-MS 518 (M+1); HPLC A: 2.88 min.

EXAMPLE 90

α-(R)-(3-(S)-((4-(1-Allyl-1-H-benzoimidazol-2-yl)
piperidin-1-yl)methyl)-4-(S)-phenylpyrrolidin-1-yl)-
cyclohexaneacetic Acid Step A: 1-(4-(1-H-Benzoimidazol-2-yl)-piperidin-1-yl)ethanone The title compound was prepared using a procedure analogous to that described in Example 89 Step A.

Step B: 1-(4-(1-Allyl-1-H-benzoimidazol-2-yl)piperidin-1-yl)ethanone

The title compound was prepared from 1-(4-(1-H-benzoimidazol-2-yl)-piperidin-1-yl)ethanone (from Step A), sodium hydride, allyl bromide and DMF.

Step C: α-(R)-(3-(S)-((4-(1-Allyl-1-H-benzoimidazol-2-yl)piperidin-1-yl)methyl)-4-(S)-phenylpyrrolidin-1-yl)-cyclohexaneacetic acid The title compound was prepared using procedures analogous to those described in Example 89 Steps C and D except TFA and anisole were used in place of formic acid in Example 89 Step D. ESI-MS 541 (M+1); EPLC A: 1.87 min.

EXAMPLE 91

α-(R)-(3-(S)-((4-Benzotriazol-1-yl-piperidin-1-yl)
methyl)-4-(S)-phenylpyrrolidin-1-yl)-
cyclohexaneacetic Acid The title compound was prepared from 4-benzotriazol-1-yl-piperidine HCl salt and of α-(R)-(3-(R)-formyl-4-(S)-phenylpyrrolidin-1-yl)-cyclohexaneacetic acid, 4-methoxybenzyl ester (prepared above as Aldehyde 5) using procedures analogous to those described in Example 89 Steps C and D except TFA and anisole were used in place of formic acid in Example 89, Step D. ESI-MS 502 (M+1); HPLC A: 2.02 min.

EXAMPLE 92

α-(R)-(3-(S)-((4-(1-H-Indol-3-yl)piperidin-1-yl)
methyl)-4-(S)-phenylpyrrolidin-1-yl)-
cyclohexaneacetic Acid The title compound was prepared from 4-(1-H-indol-3-yl)piperidine HCl salt (prepared as described by D. Beck et al, Helv. Chim. Acta. 1968, 51 (2), 260) and of α-(R)-(3-(R)-formyl-4-(S)-phenylpyrrolidin-1-yl)-cyclohexaneacetic acid, 4-methoxybenzyl ester (prepared above as Aldehyde 5) using procedures analogous to those described in Example 89 Steps C and D except TFA and anisole were used in place of formic acid in Example 89 Step D. ESI-MS 500 (M+1); HPLC A: 3.57 min.

EXAMPLE 93

α-(R)-(3-(S)-((4-(6-Ethoxy-benzo[d]isoxazol-3-yl)piperidin-1-yl)methyl)-4-(S)-phenylpyrrolidin-1-yl)-cyclohexaneacetic Acid and α-(R)-(3-(S)-((4-(6-fluorobenzo[d]isoxazol-3-yl)piperidin-1-yl)methyl)-4-(S)-phenylpyrrolidin-1-yl)-cyclohexaneacetic Acid Step A: 1-(4-((2,4-Difluorophenyl)-hydroxyimino-methyl)piperidin-1-yl)ethanone The title compound was prepared from 1-(4-(2,4-difluoro-benzoyl)piperidin-1-yl)ethanone, hydroxylamine hydrochloride and sodium acetate in refluxing EtOH.

Step B: α-(R)-(3-(S)-((4-(6-Ethoxy-benzo[d]isoxazol-3-yl)piperidin-1-yl)methyl)-4-(S)-phenylpyrrolidin-1-yl)-cyclohexaneacetic acid and α-(R)-(3-(S)-((4-(6-fluoro-benzo [d]isoxazol-3-yl)piperidin-1-yl)methyl)-4-(S)-phenylpyrrolidin-1-yl)-cyclohexaneacetic acid A solution of 1-(4-((2,4-difluorophenyl)-hydroxyimino-methyl)piperidin-1-yl)ethanone (from Step A) and KOH (45 wt. % solution) in EtOH was refluxed for 24 hours. The products were coupled with of α-(R)-(3-(R)-formyl-4-(S)-phenylpyrrolidin-1-yl)-cyclohexaneacetic acid, 4-methoxybenzyl ester (prepared above as Aldehyde 5) using a procedure analogous to that described in Example 89, Step C. The products were treated with TFA and anisole for 18 hours and concentrated under reduced pressure. The residue was purified by prep HPLC (Zorbax-RX C8 column, 30% $CH_3CN$ 15 min. and 100% $CH_3CN$, 20 mL/min., 254 nm) to provide α-(R)-(3-(S)-((4-(6-ethoxy-benzo[d]isoxazol-3-yl)piperidin-1-yl)methyl)-4-(S)-phenylpyrrolidin-1-yl)-cyclohexaneacetic acid: ESI-MS 546 (M+1); HPLC A: 3.01 min.; and α-(R)-(3-(S)-((4-(6-fluoro-benzo[d]isoxazol-3-yl)piperidin-1-yl)methyl)-4-(S)-phenylpyrrolidin-1-yl)-cyclohexaneacetic acid: ESI-MS 520 (M+1); HPLC A: 2.88 min.

EXAMPLE 94

α-(R)-(3-(S)-((4-(4-Oxo-4-H-quinazolin-3-yl)piperidin-1-yl)methyl)-4-(S)-phenylpyrrolidin-1-yl)-cyclohexaneacetic Acid Step A: 2-Amino-N-(1-benzyl-piperidin-4-yl)benzamide To a solution of 1.0 g 2-aminobenzoic acid and 1.39 g of 4-amino-1-benzylpiperidine in 10 mL of methylene chloride was added 1.18 g of HOBT followed by 2.10 g of EDC. After stirring at rt for 6 hours, the reaction mixture was diluted with methylene chloride. The organic phase was washed with brine and dried over anhydrous $MgSO_4$. Concentration under reduced pressure followed by flash chromatography eluting with 9% EtOAc in hexane, 50% EtOAc in hexane and 10% MeOH in EtOAc afforded 309 mg of the title compound as a viscous oil.

Step B: 3-(1-Benzyl-piperidin-4-yl)-3-H-quinazolin-4-one

To a solution of 200 mg 2-amino-N-(1-benzyl-piperidin-4-yl)benzamide (from Step A) in 5 mL of trimethyl orthoformate was added 0.2 mL of concentrated HCl. After stirring at 85° C. for 14 hours, the reaction was cooled to room temperature. The reaction mixture was partitioned betweem EtOAc and aqueous sodium bicarbonate. Aqueous phase was extracted with EtOAc (3×). The combined organic phases were washed with brine and dried over anhydrous $MgSO_4$. Concentration under reduced pressure afforded 120 mg of the title compound as a viscous oil.

Step C: 3-(Piperidin-4-yl)-3-H-quinazolin-4-one

To a solution of 100 mg of 3-(1-benzyl-piperidin-4-yl)-3-H-quinazolin-4-one (from Step B) in 6 mL of MeOH was added 100 mg of ammonium formate followed by 100 mg of 10% palladium on carbon. After refluxing for 5 hours, the mixture was filtered through celite. Concentration under reduced pressure afforded 59 mg of the title compound as a foamy solid.

Step D: α-(R)-(3-(S)-((4-(4-Oxo-4-H-quinazolin-3-yl)piperidin-1-yl)methyl)-4-(S)-phenylpyrrolidin-1-yl)-cyclohexaneacetic acid The title compound was prepared using procedures analogous to those described in Example 89, Steps C and D except TFA and anisole were used in place of formic acid. ESI-MS 529 (M+1); HPLC A: 3.44 min.

EXAMPLE 95

α-(R)-(3 -(S)-((4-Benzoimidazol-1-yl-piperidin-1-yl)methyl)-4-(S)-phenylpyrrolidin-1-yl)-cyclohexaneacetic Acid Step A: 1-N-(1-Benzyl-piperidin-4-yl)-benzene-1,2-diamine To a solution of 1.0 g 1-benzyl4-piperidone and 1.14 g of 1,2-phenylenediamine in 15 mL of THF was added two spatula tips of molecular sieves 4Å. After stirring at room temperature for 10 minutes, 1.34 g of sodium triacetoxyborohydride was added and the reaction was stirred at room temperature for 18 hours. The reaction was quenched with 50 mL of $CH_3OH$ and diluted with EtOAc. After filtering molecular sieves, the filtrate was concentrated under reduced pressure. The residue was partitioned between 50 mL of EtOAc and 30 ml saturated $NaHCO_3$ aqueous solution. After separating layers, the aqueous phase was extracted with 2×50 mL EtOAc. The combined organic phases were washed with 15 mL of brine, dried over $MgSO_4$ and concentrated under reduced pressure. The residue was purified by flash chromatography eluting with 100% EtOAc, then 90% EtOAc in $CH_3OH$ to give 666 mg of the title compound as a solid. $^1$H NMR (400 MHz, $CDCl_3$): δ1.56 (m, 2H), 2.07 (m, 2H), 2.18(m, 2H), 2.87 (d, J=11.6 Hz, 2H), 3.29(m, 1H), 3.56(s, 2H), 6.69 (m, 3H), 6.72(m, 1H), 7.25–7.61(m, 5H). ESI-MS 282 (M+H); HPLC A: 1.92 min.

Step B: 1-(1-Benzyl-piperidin-4-yl)-1-H-benzoimidazole

To a solution of 200 mg of N-(1-benzyl-piperidin-4-yl)-benzene-1,2-diamine (from Step A) in 6 mL of trimethyl orthoformate was added 0.2 mL concentrated HCl. After stirring at 80° C. for 16 hours, the reaction mixture was diluted with 30 ml of EtOAc. The organic phase was washed with 15 mL saturated $NaHCO_3$ aqueous solution. After separating layers, the aqueous phase was extracted with 2×20 mL EtOAc. The combined organic phases were washed with 10 mL of brine, dried over $MgSO_4$ and concentrated under reduced pressure to give 198 mg yellow solid. $^1$H NMR (400 MHz, $CDCl_3$): δ2.11–2.22 (m, 6H), 3.06 (m, 2H), 3.58(s, 2H), 4.20 (s, 1H), 7.24–7.34(m, 7H),7.42(m, 1H), 7.81 (m, 1H), 8.04(s, 1H). ESI-MS 292 (M+H); HPLC A: 1.80 min.

Step C: 1-Piperidin-4-yl-1-H-benzoimidazole

To a solution of 196 mg of 1-(1-benzyl-piperidin-4-yl)-1-H-benzoimidazole (from Step B) in 10 mL of $CH_3OH$ was added 200 mg 10% palladium on carbon and 200 mg ammonium formate. After the reaction was refluxed for 4 hours, the mixture was cooled down to room temperature, filtered through Celite and washed with CH$_3$OH. The filtrate was concentrated under reduced pressure to give 160 mg of the title compound as oil. $^1$H NMR (400 MHz, CD$_3$OD): δ2.13(m, 4H), 2.92(m, 2H), 3.27(m, 2H), 4.56(m, 1H), 7.28(m, 2H), 7.66(t, J=5.9 Hz, 2H), 8.25(s, 1H). ESI-MS 201 (M+H); HPLC A: 0.61 min.

Step D: α-(R)-(3-(S)-((4-Benzoimidazol-1-yl-piperidin-1-yl)methyl)4-(S)-phenyl-pyrrolidin-1-yl)-cyclohexaneacetic acid, 4-methoxy-benzyl ester To a solution of 60 mg of α-(R)-(3-(R)-formyl-4-(S)-phenylpyrrolidin-1-yl)-cyclohexaneacetic acid, 4-methoxy-benzyl ester (prepared above as Aldehyde 5) and 70 mg of 1-piperidin-4-yl-1-H-benzoimidazole (from Step C) in 4 mL THF and 1 mL of DMF was added 1 spatula tip of 4Å molecular sieves. After stirring at room temperature for 10 minutes, 80 mg sodium triacetoxyborohydride was added. Continued to stir at room temperature for another 10 hours. The reaction was concentrated and diluted with 20 ml of EtOAc and washed with 10 mL saturated NaHCO$_3$ aqueous solution. After separating layers, the aqueous phas was extracted with 2×10 mL EtOAc. The combined organic phases were washed with 8 mL of brine, dried over MgSO$_4$ and concentrated under reduced pressure. The residue was purified by flash chromatography eluting with 100% EtOAc, then 90% EtOAc in CH$_3$OH to give 40 mg of the title compound as an oil. $^1$H NMR (400 MHz, CDCl$_3$): δ1.17–3.73 (m, 31H), 4.07 (m, 1H), 5.10(d, J=2.1 Hz, 2H), 6.86 (d, J=8.5, 2H), 7.16–7.36 (m, 10H), 7.78(m, 1H), 7.93(s. 1H). ESI-MS 621 (M+H); HPLC A: 2.96 min.

Step E: α-(R)-(3-(S)-((4-Benzoimidazol-1-yl-piperidin-1-yl)methyl)-4-(S)-phenylpyrrolidin-1-yl)-cyclopentaneacetic acid To 26.5 mg of α-(R)-(3-(S)-((4-benzoimidazol-1-yl-piperidin-1-yl)methyl)-4-(S)-phenyl-pyrrolidin-1-yl)-cyclohexaneacetic acid, 4-methoxy-benzyl ester (from Step D) was added 0.2 mL of anisole and 2 mL of TFA. After stirring at room temperature for 1.5 hours, concentrated under pressure. The residue was purified by flash chromatography eluting with 10% CH$_3$OH in CH$_2$Cl$_2$, then 15% CH$_3$OH/1% NH$_4$OH in CH$_2$Cl$_2$ to give 24 mg of the title compound as a solid. $^1$H NMR (400 MHz, CDCl$_3$): δ1.17–3.73 (m, 28H), 4.35 (m, 1H), 7.27 (m, 3H), 7.46(m, 4H), 7.55(s. 1H). 7.65(d, J=7.4 Hz, 1H), 8.17(d, J=5.0 Hz, 1H). ESI-MS 510 (M+H); HPLC A: 1.67 min.

EXAMPLE 96

α-(R)-(3-(S)-((4-Benzoimidazol-1-yl-piperidin-1-yl)methyl)-4-(S)-(3-fluorophenyl)pyrrolidin-1-yl)-3-cyclobutylpropionic Acid Step A: α-(R)-(3-(S)-((4-Benzoimidazol-1-yl-piperidin-1-yl)methyl)-4-(S)-(3-fluorophenyl)pyrrolidin-1-yl)-3-cyclobutylpropionic acid, benzyl ester The title compound was prepared from 22 mg of α-(R)-(3-(R)-formyl-4-(S)-(3-fluorophenyl)pyrrolidin-1-yl)-3-cyclobutylpropionic acid, benzyl ester (prepared above as Aldehyde 2), 27 mg of 1-piperidin-4-yl-1-H-benzoimidazole (from Example 95, Step C) and 40 mg of sodium triacetoxyborohydride in 4 mL of THF and 1 mL of DMF, using a procedure analogous to that described in Example 95, Step D to provide 23 mg of the title compound.

Step B α-(R)-(3-(S)-((4-Benzoimidazol-1-yl-piperidin-1-yl)methyl)-4-(S)-(3-fluorophenyl)pyrrolidin-1-yl)-3-cyclobutylpropionic acid The title compound was prepared from 20 mg of α-(R)-(3-(S)-((4-benzoimidazol-1-yl-piperidin-1-yl)methyl)-4-(S)-(3-fluorophenyl) pyrrolidin-1-yl)-3-cyclobutylpropionic acid, benzyl ester (from, step A) and 10 mg of 10% palladium on carbon in 4 mL of MeOH using a procedure analogous to that described in Example 1, Step E, except that the title compound was purified by flash chromatography eluting with 10% CH$_3$OH in CH$_2$Cl$_2$, then 15% CH$_3$OH and 1% NH$_4$OH in CH$_2$Cl$_2$ to give 12 mg of the title compound as solid. ESI-MS 505 (M+H); HPLC A: 1.68 min.

EXAMPLE 97

α-(R)-(3-(S)-((4-(2-Methyl-benzoimidazol-1-yl)piperidin-1-yl)methyl)-4-(S)-phenylpyrrolidin-1-yl)-cyclohexaneacetic Acid Step A: 1-(1-Benzyl-piperidin-4-yl)-2-methyl-1-H-benzoimidazole The title compound was prepared from 125 mg of N-(1-benzyl-piperidin-4-yl)-benzene-1,2-diamine (from Example 95, Step A) and 0.15 mL of concentrated HCl using a procedure analogous to that described in Example 95, Step B, except 14 ml of triethyl orthoacetate was used in place of trimethyl orthoformate to provide 123 mg of the title compound as a viscous oil Step B: 1-Piperidin-4-yl-2-methyl-1-H-benzoimidazole The title compound was prepared from 120 mg of 1-(1-benzyl-piperidin-4-yl)-1-H-benzoimidazole (from Step A), 100 mg of 10% palladium on carbon and 100 mg of ammonium formate in 5 mL of MeOH using a procedure analogous to that described in Example 95, Step C to provide 70 mg of the title compound as a solid.

Step C: α-(R)-(3-(S)-((4-(2-Methyl-benzoimidazol-1-yl)piperidin-1-yl)methyl)-4-(S)-phenylpyrrolidin-1-yl)-cyclohexaneacetic acid, 4-methoxy-benzyl ester The title compound was prepared from 60 mg of α-(R)-(3-(R)-formyl-4-(S)-phenylpyrrolidin-1-yl)-cyclohexaneacetic acid, 4-methoxy-benzyl ester (prepared above as Aldehyde 5), 50 mg of 1-1-piperidin-4-yl-2-methyl-1-H-benzoimidazole (from Step B) and 80 mg of sodium triacetoxyborohydride in 4 mL THF and 1 mL of DMF, using a procedure analogous to that described in Example 95, Step D to provide 61 mg of the title compound as an oil.

Step D: α-(R)-(3-(S)-((4-(2-Methyl-benzoimidazol-1-yl)piperidin-1-yl)methyl)-4-(S)-phenylpyrrolidin-1-yl)-cyclohexaneacetic acid The title compound was prepared from 57 mg of α-(R)-(3-(S)-((4-(2-methyl-benzoimidazol-1-yl)piperidin-1-yl)methyl)-4-(S)-phenyl-pyrrolidin-1-yl)-cyclohexaneacetic acid, 4-methoxy-benzyl ester (from Step C), 4 mL of TFA and 0.3 mL of anisole, using a procedure analogous to that described in Example 95, Step E to provide 48 mg of the title compound as a white solid. ESI-MS 515 (M+H); HPLC A: 1.81 min.

EXAMPLE 98

α-(R)-(3-(S)-((4-(5-Fluoro-benzoimidazol-1-yl)-piperidin-1-ylmethyl))-4-(S)-phenylpyrrolidin-1-yl)-cyclohexaneacetic Acid Step A: 1-N-(1-Benzyl-piperidin-4-yl)-4-fluoro-benzene-1,2-diamine The title compound was prepared from 750 mg 1-benzyl-4-piperidone, 1.0 g of 4-fluoro-benzene-1,2-diamine and 1.0 g sodium triacetoxyborohydride in 10 mL of THF, using a procedure analogous to that described in Example 95, Step A to provide 70 mg of the title compound as a brown solid.

Step B: 1-(1-Benzyl-piperidin-4-yl)-5-fluoro-1-H-benzoimidazole

The title compound was prepared from 170 mg of 1-N-(1-benzyl-piperidin-4-yl)-4-fluoro-benzene-1,2-diamine (from Step A), 7 mL of trimethyl orthoformate, and 0.2 mL of concentrated HCl, using a procedure analogous to that described in Example 95, Step B to provide 123 mg of the title compound as a viscous brown oil Step C: 1-Piperidin-4-yl-5-fluoro-1-H-benzoimidazole The title compound was prepared from 120 mg of 1-(1-benzyl-piperidin-4-yl)-5-fluoro-1-H-benzoimidazole (from Step B), 120 mg of 10% palladium on carbon and 120 mg ammonium formate in 5 mL of MeOH, using a procedure analogous to that described in Example 95, Step C to provide 93 mg of the title compound as a solid.

Step D: α-(R)-(3-(S)-((4-(5-Fluoro-benzoimidazol-1-yl)-piperidin-1-ylmethyl))-4-(S)-phenylpyrrolidin-1-yl)-cyclohexaneacetic acid, 4-methoxy-benzyl ester The title compound was prepared from 40 mg of α-(R)-(3-(R)-formyl-4-(S)-phenylpyrrolidin-1-yl)-cyclohexaneacetic acid, 4-methoxy-benzyl ester (prepared above as Aldehyde 5), 40 mg 1-piperidin-4-yl-5-fluoro-1-H-benzoimidazole (from Step C ) and 60 mg of sodium triacetoxyborohydride in 4 mL of THF and 1 mL of DMF, using a procedure analogous to that described in Example 95, Step D to provide 43 mg of the title compound as an oil.

Step E α-(R)-(3-(S)-((4-(5-Fluoro-benzoimidazol-1-yl)-piperidin-1-ylmethyl))-4-(S)-phenylpyrrolidin-1-yl)-cyclohexaneacetic acid The title compound was prepared from 41 mg of α-(R)-(3-(S)-((4-(5-fluoro-benzoimidazol-1-yl)-piperidin-1-ylmethyl))-4-(S)-phenyl-pyrrolidin-1-yl)-cyclohexaneacetic acid, 4-methoxy-benzyl ester (from Step D) and 4 mL of TFA, 0.3 mL of anisole, using a procedure analogous to that described in Example 95, Step E to provide 30 mg of the title compound as a solid. ESI-MS 519 (M+H); TPLC A: 1.65 min.

EXAMPLE 99

α-(R)-(3-(S)-((4-Imidazo[4,5-b]pyridin-3-yl-piperidin-1-yl)methyl)-4-(S)-phenylpyrrolidin-1-yl)-cyclohexaneacetic Acid Step A: (1-Benzyl-piperidin-4-yl)-(3-nitro-pyridin-2-yl)-amine To a solution of 1.64 g 2-chloro-3-nitropyridine and 1.37 g of 1-benzyl-piperidin-4-ylamine in 20 mL THF was added diisopropylethylamine. The reaction was refluxed for 6 hours. The reaction was cooled down, diluted with 50 mL of EtOAc and washed with 30 mL of saturated NaHCO$_3$ aqueous solution. After separating layers, the aqueous phase was extracted with 2×30 mL of EtOAc. The combined organic phases were washed with 15 mL of brine, dried over MgSO$_4$ and concentrated under reduced pressure. The residue was purified by flash chromatography eluting with 25% EtOAc in hexane, then 50% EtOAc in hexane and 100% EtOAc to give 823 mg of the title compound as a yellow solid.

Step B: 2-N-(1-Benzyl-piperidin-4-yl)-pyridine-2,3-diamine

To a solution of (1-Benzyl-piperidin-4-yl)-(3-nitro-pyridin-2-yl)-amine (from Step A) in 10 mL of THF was added 2.4 g of SnCl$_2$ and 1 mL of concentrated HCl at room temperature, stirred at room temperature for 2 hours. The reaction was diluted with 40 mL of EtOAc and washed with 30 mL of saturated NaHCO$_3$ aqueous solution. After separating layers, the aqueous phase was extracted with 2×15 mL of EtOAc. The combined organic phases were washed with 15 mL of brine, dried over MgSO$_4$ and concentrated under reduced pressure to give 603 mg of yellow soid.

Step C: 3-(1-Benzyl-piperidin-4-yl)-3-H-imidazo[4,5-b]pyridine

The title compound was prepared from 153 mg of 2-N-(1-benzyl-piperidin-4-yl)-pyridine-2,3-diamine (from Step B), 6 mL of trimethyl orthoformate, and) 0.2 mL of concentrated HCl, using a procedure analogous to that described in Example 95, Step B to provide 139 mg of the title compound as a yellow solid.

Step D: 3-(Piperidin-4-yl)-3-H-imidazo[4,5-b]pyridine

The title compound was prepared from 130 mg of 3-(1-benzyl-piperidin-4-yl)-3-H-imidazo[4,5-b]pyridine (from Step C), 130 mg of 10% palladium on carbon and 130 mg of ammonium formate in 6 mL of MeOH, using a procedure analogous to that described in Example 95, Step C to provide 86 mg of the title compound as a solid Step E: α-(R)-(3-(S)-((4-Imidazo[4,5-b]pyridin-3-yl-pipeiidin-1-yl)methyl))-4-(S)-phenylpyrrolidin-1-yl)-cyclohexaneacetic acid, 4-methoxy-benzyl ester The title compound was prepared from 60 mg of α-(R)-(3-(R)-formyl-4-(S)-phenylpyrrolidin-1-yl)-cyclohexaneacetic acid, 4-methoxy-benzyl ester (prepared above as Aldehyde 5), 60 mg 1-piperidin-4-yl-5-fluoro-1-H-benzoimidazole (from Step D ) and 75 mg of sodium triacetoxyborohydride in 4 mL of THF and 1 mL of DMF, using a procedure analogous to that described in Example 95, Step D to provide 48 mg of the title compound as an oil.

Step F α-(R)-(3-(S)-((4-Imidazo[4,5-b]pyridin-3-yl-piperidin-1-yl)methyl))-4-(S)-phenylpyrrolidin-1-yl)-cyclohexaneacetic acid The title compound was prepared from 46 mg of α-(R)-(3-(S)-((4-imidazo[4,5-b]pyridin-3-yl-piperidin-1-yl)methyl))-4-(S)-phenyl-pyrrolidin-1-yl)-cyclohexaneacetic acid, 4-methoxy-benzyl ester (from Step E), 4 mL of TFA and 0.3 mL of anisole, using a procedure analogous to that described in Example 95, Step E to provide 34 mg of the title compound as a solid. ESI-MS 502 (M+1); HPLC A: 2.93 min.

EXAMPLE 100

α-(R)-(3-(S)-((2-Methyl-4-imidazo[4,5-b]pyridin-3-yl-piperidin-1-yl)methyl)-4-(S)-phenylpyrrolidin-1-yl)-cyclohexaneacetic Acid The title compound was prepared using procedures analogous to those described in Example 99, except trimethyl orthoacetate was employed in place of trimethyl orthoformate in Step C to provide the title compound as a white solid. ESI-MS 516 (M+1).

EXAMPLE 101

α-(R)-(3-(S)-((4-(1-H-Benzoimidazol-2-yl)-piperidin-1-yl)methyl)-4-(S)-phenylpyrrolidin-1-yl)-cyclohexaneacetic Acid The title compound was prepared using procedures analogous to those described in Example 89, except phenylenediamine was employed in placed of 2-aminothiophenol in Step A to provide 9 mg of the title compound as a white solid. ESI-MS 501 (M+1); HPLC A: 1.71 min.

EXAMPLES 102~110

Examples 102 to 110 in Table 8 were prepared according to the general procedure given in Example 95, employing the appropriate commercially available substituted phenylene-1,2-diamines or 2,3-diaminopyridine in Step A, and the appropriate commercially available trimethyl orthoacetate or trimethyl orthobuyate in Step B in place of trimethyl orthoformate.

TABLE 8

| EX # | R$^a$ | MS m/Z (M + 1) |
|---|---|---|
| 102 | 2-propyl-benzimidazole | 543 |
| 103 | imidazo-pyridine | 502 |
| 104 | F-2-propyl-benzimidazole | 561 |
| 105 | F-2-methyl-benzimidazole | 532 |
| 106 | NC-2-methyl-benzimidazole | 526 |
| 107 | 5,6-diCl-benzimidazole | 569 |

TABLE 8-continued

| EX # | R$^a$ | MS m/Z (M + 1) |
|---|---|---|
| 108 | F$_3$C-benzimidazole (CF3 at 5 position: 6 position = 2:1) | 569 |
| 109 | 5,6-diF-benzimidazole | 537 |
| 110 | ethoxycarbonyl-benzimidazole | 573 |

EXAMPLE 111

α-(R)-(3-(S)-((4-(4-benzyltri azol-2-yl)piperidin-1-yl)methyl)-4-(S)-phenylpyrrolidin-1-yl)-cyclohexaneacetic Acid Step A: 4-Carboxy-1-benzylpiperidylhydrazide
A solution of 4-ethoxycarbonyl-1-benzyl piperidine (10.0 grams, 40 mmol) and hydrazine (2.5 mL, 80 mmol) in 250 mL n-butanol was refluxed for 16 h. At this time the tlc (2/1 hexane/EtOAc) showed a substantial amount of ester remaining. An additional 10 mL (320 mmol) hydrazine was added and refluxing was continued for 48 h at which point analysis showed no ester remaining. The solvent was removed to give a white solid which was used without further purification.

Step B: 4-(4-benzyltriazol-2-yl)-1-benzylpiperidine
A solution of (4-Carboxy-1-benzylpiperidyl)hydrazide (772 mg, 3.31 mmol, from Step A) and thiophenylacetamide (900 mg, 5.9 mmol) in 20 mL n-butanol was refluxed for 48 h. Analysis by tlc (19/1 CH$_2$Cl$_2$/MeOH) showed no thioamide remaining. The solvent was removed and the product was chromatographed (40 grams silica, 19/1 CH$_2$Cl$_2$/MeOH eluent), afforded 627 mg (57%) of the title compound.

Step C: 4-(4-benzyltriazol-2-yl)piperidine

A mixture of 4-(4-benzyltriazol-2-yl)-1-benzylpiperidine (627 mg, 1.9 mmol, from Step B), 10% palladium on carbon (400 mg, 0.38 mmol) and ammonium formate (770 mg, 11.3 mmol) in 20 mL MeOH was refluxed for 1 h. The mixture was filtered through celite and concentrated. The residue was dissolved in chloroform and the solution was washed with 1M aqueous NaOH. The organic layer was dried over $Na_2SO_4$ and concentrated to afford 41 mg (9%) of product was obtained which was used in the next step without purification.

Step D: α-(R)-(3-(S)-((4-(4-benzyltriazol-2-yl)piperidin-1-yl)methyl)-4-(S)-phenylpyrrolidin-1-yl)-cyclohexaneacetic acid A Solution of α-(R)-(3-(R)-Formyl-4-(S)-phenylpyrrolidin-1-yl)-cyclohexaneacetic acid, para-methoxybenzyl ester (52 mg, 0.12 mmol, (prepared above as Aldehyde 5)), 4-(4-benzyltriazol-2-yl)piperidine (41 mg, 0.17 mmol from Step C) and sodium triacetoxyborohydride, (51 mg 0.24 mmol) in 1 mL of 1,2-dichloroethane was stirred for 12 h. The solvent was removed and the product was purified by preprative HPLC (column: YMC Combi-prep ODS-A 20×50 mm, gradient: 5% acetonitrile/water w/0.1% TFA for 1 min then ramp to 100% acetonitrile w/0.1% TFA over 6 min, flow: 20 mL/min). The so isolated material was stirred in 3 mL formic acid for 16 h. After removal of solvent the residue was purified by ion exchange chromatography (3 grams SCX resin, 100% MeOH→2.0M $NH_3$/MeOH) to give 17 mg (42%) of the title compound. $^1$H NMR (500 MHz, $CD_3OD$). δ1.0–3.6 (m, 29H), 4.05 (s, 2H), 7.15–7.35 (m, 10H), ESI-MS. M/z; (M+H)=542.4 (obs), 542.34 (calc.).

EXAMPLE 112

2-(R)-(3-(S)-(4-(4-Fluorophenyl)piperidin-1-yl) methyl)-4(S)-phenylpyrrolidin-1-yl)-2-(cyclohexyl) acetic Acid Step A: 2-(R)-(3-(S)-(4-(4-Fluorophenyl)piperidin-1-yl) methyl)-4-(S)-phenylpyrrolidin-1-yl)-2-(cyclohexyl) acetic acid, benzyl ester A solution of 33 mg (0.08 mmol) of 2-(R)-(3-(R)-formyl-4-(S)-phenylpyrrolidin-1-yl)-2-(cyclohexyl)acetic acid, benzyl ester ((prepared above as Aldehyde 4) and 16 mg (0.09 mmol) of 4-(4-fluorophenyl)piperidine in 2 mL of $CH_2Cl_2$ was treated with 26 mg (0.12 mmol) of sodium triacetoxyborohydride and the resulting mixture was stirred at rt for 1 h. The reaction mixture was partitioned between 25 mL of $CH_2Cl_2$ and 25 mL of sat'd $NaHCO_3$ and the layers were separated. The aqueous layer was extracted with 25 mL of $CH_2Cl_2$. The combined organic extracts were washed with 50 mL of sat'd NaCl, dried over $MgSO_4$ and concentrated. Flash chromatography using 9:1 v/v hexanes/EtOAc as the eluant afforded 31 mg (68%) of the title compound: $^1$H NMR (500 MHz) δ0.97–3.31 (29H), 5.19 (ABq, J=12.1, 2H), 6.97–7.43 (14H).

Step B: 2-(R)-(3-(S)-(4-(4-Fluorophenyl)piperidin-1-yl) methyl)-4-(S)-phenylpyrrolidin-1-yl)-2-(cyclohexyl) acetic acid A mixture of 31 mg (0.05 mmol) of 2-(R)-(3-(S)-(4-(4-fluorophenyl)piperidin-1-yl)methyl)4-(S)-phenylpyrrolidin-1-yl)-2-(cyclohexyl)acetic acid, benzyl ester (from Step A) and 16 mg of 10% palladium on carbon in 4 mL of MeOH was hydrogenated at 40 psi on a Parr shaker for 1 h. The reaction mixture was filtered through a 0.45 g nylon filter and concentrated to give 25 mg (100%) of the title compound: $^1$H NMR (500 MHz) δ0.89–4.00 (29H), 6.94–7.40 (9H); ESI-MS 479 (M+H).

EXAMPLE 113

2-(R)-(3-(S)-(4-Phenylpiperidin-1-yl)methyl)-4-(S)-phenyl pyrrolidin-1-yl)-2-(cyclohexyl)acetic Acid The title compound was prepared using procedures analogous to those described in EXAMPLE 112, substituting 4-phenylpiperidine for 4-(4-fluorophenyl)piperidine in Step A. For the title compound: ESI-MS 461 (M+H); HPLC B: 5.73 min.

EXAMPLE 114

2-(R)-(3-(S)-(4-(2-Methoxyphenyl)piperidin-1-yl) methyl)-4-(S)-phenyl pyrrolidin-1-yl)-2-(cyclohexyl)acetic Acid The title compound was prepared using procedures analogous to those described in EXAMPLE 112, substituting 4-(2-methoxyphenyl)piperidine for 4-(4-fluorophenyl) piperidine in Step A. For the title compound: $^1$H NMR (500 MHz) δ0.86–3.92 (29H), 3.78 (s, 3H), 6.83 (d, 8.2, 1H), 6.89 (t, 7.3, 1H), 7.08 (d, 7.3, 1H), 7.16–7.35 (6H); ESI-MS 491 (M+H).

EXAMPLE 115

2-(R)-(3-(S)-(4-(4-Fluorophenyl)piperi din-1-yl) methyl)-4-(S)-phenyl pyrrolidin-1-yl)-3-methylbutanoic Acid The title compound was prepared using procedures analogous to those described in EXAMPLE 112, substituting 2-(R)-(3-(R)-formyl-4-(S)-phenylpyrrolidin-1-yl)-3-methylbutanoic acid, benzyl ester (prepared above as Aldehyde 8) for 2-(R)-(3-(R)-formyl-4-(S)-phenylpyrrolidin-1-yl)-2-(cyclohexyl)acetic acid, benzyl ester in Step A. For the title compound: ESI-MS 439 (M+H); HPLC B: 5.24 min.

EXAMPLE 116

2-(R)-(3-(S)-(4-(4-Fluorophenyl)piperidin-1-yl) methyl)-4-(S)-phenyl pyrrolidin-1-yl)-3-(cyclobutyl) propanoic Acid The title compound was prepared using procedures analogous to those described in EXAMPLE 112, substituting 2-(R)-(3-(R)-formyl-4-(S)-(3-fluorophenyl)pyrrolidin-1-yl)-3-(cyclobutyl)propanoic acid, benzyl ester (prepared above as Aldehyde 2) for 2-(R)-(3-(R)-formyl-4-(S)-phenylpyrrolidin-1-yl)-2-(cyclohexyl)acetic acid, benzyl ester in Step A. For the title compound: $R_F$: $^1$H NMR (300 MHz, $CD_3OD$) δ1.44–2.08 (m, 14H), 2.24–2.46 (m, 4H), 2.66–2.74 (m, 2H), 2.90 (m, 11), 3.07–3.36 (m, 4H), 3.48–3.58 (m, 2H), 6.81–7.08 (m, 7H), 7.24 (m, 1H); ESI-MS 483 (M+H); HPLC A: 2.61 min.

EXAMPLE 117

2-(R)-(3-(S)-(4-(2-Methoxyphenyl)piperidin-1-yl) methyl)-4-(S)-phenyl pyrrolidin-1-yl)-3-methylbutanoic Acid The title compound was prepared using procedures analogous to those described in EXAMPLE 112, substituting 2-(R)-(3-(R)-formyl-4-(S)-phenylpyrrolidin-1-yl)-3-methylbutanoic acid, benzyl ester(prepared above as Aldehyde 8) for 2-(R)-(3-(R)-formyl-4-(S)-phenylpyrrolidin-1-yl)-2-(cyclohexyl)acetic acid, benzyl ester and substituting 4-(2-methoxyphenyl)piperidine for 4-(4-fluorophenyl)

piperidine in Step A. For the title compound: $^1$H NMR (500 MHz) δ0.89–3.86 (19H), 1.06 (d, J=6.2, 3H), 1.13 (d, J=6.2, 3H), 3.78 (s, 3H), 6.83 (d, 8.0, 1H), 6.89 (t, 7.4, 1H), 7.08 (d, 7.4, 1H), 7.18 (t, 7.7, 1H), 7.23–7.34 (5H); ESI-MS 451 (M+H).

EXAMPLE 118

2-(R)-(3-(S)-(4-Phenylpiperidin-1-yl)methyl)-4-(S)-phenyl pyrrolidin-1-yl)-2-(phenyl)acetic Acid Step A: 2-(R/S)-(3-(S)-(t-Butyldimethylsilyloxymethyl)-4-(S)-phenylpyrrolidin-1-yl)-2-(phenyl)acetic acid, benzyl ester The title compound was prepared from 3-(R)-(t-butyldimethylsilyloxymethyl)-4-(S)-phenyl pyrrolidine (prepared above as Pyrrolidine 1) and (S)-mandelic acid, benzyl ester using a procedure analogous to that described in the preparation given above of Aldehyde 1. The title compound was obtained as a mixture of diastereomers: R$_F$: 0.68 (4:1 v/v hexanes/EtOAc).

Step B: 2-(R)-(3-(S)-Hydroxymethyl-4-(S)-phenylpyrrolidin-1-yl)-2-(phenyl)acetic acid, benzyl ester and 2-(S)-(3-(S)-Hydroxymethyl-4-(S)-phenylpyrrolidin-1-yl)-2-(phenyl)acetic acid, benzyl ester The title compounds were prepared from 2-(R/S)-(3-(S)-(t-butyldimethylsilyloxymethyl)-4-(S)-phenylpyrrolidin-1-yl)-2-(phenyl)acetic acid, benzyl ester (from Step A) using a procedure analogous to that described in the preparation given above of Aldehyde 1. The diastereomers were separated by preparative HPLC (Chiracel AD 2.0×25 cm column, 7:3 v/v hexanes/iPrOH, 9.0 mL/min, 220 nm) to provide the title compounds. For 2-(R)-(3-(R)-hydroxymethyl-4-(S)-phenylpyrrolidin-1-yl)-2-(phenyl) acetic acid, benzyl ester: Retention time, 15.3 min; $^1$H NMR (300 MHz) δ2.39–3.18 (m, 6H), 3.59–3.75 (m, 2H), 4.09 (s, 1H), 5.13 (s, 2H), 7.15–7.48 (m, 15H). For 2-(S)-(3-(R)-hydroxymethyl-4-(S)-phenylpyrrolidin-1-yl)-2-(phenyl) acetic acid, benzyl ester: Retention time, 21.5 min; $^1$H NMR (300 MHz) δ2.1–2.9 (m, 5H), 3.18–3.32 (m, 2H), 3.58–3.71 (m, 2H), 4.19 (s, 1H), 5.11 (ABq, J=12.3, 2H), 7.17–7.49 (m, 15H).

Step C: 2-(R)-(3-(R)-Formyl-4-(S)-phenylpyrrolidin-1-yl)-2-(phenyl)acetic acid, benzyl ester The title compound was prepared from of 2-(R)-(3-(R)-hydroxymethyl-4-(S)-phenylpyrrolidin-1-yl)-2-(phenyl) acetic acid, benzyl ester (from Step B) using a procedure analogous to that described in the preparation given above of Aldehyde 1: R$_F$: 0.69 (3:2 v/v hexanes/EtOAc); $^1$H NMR (300 MHz) δ2.70–3.32 (m, 5H), 3.61 (q, J=7.4, 1H), 4.15 (s, 1H), 5.12 (s, 2H), 7.13–7.48 (m, 15H), 9.68 (d, J=1.9, 1H).

Step D: 2-(R)-(3-(S)-(4-Phenylpiperidin-1-yl)methyl)-4-(S)-phenyl pyrrolidin-1-yl)-2-(phenyl)acetic acid The title compound was prepared from 2-(R)-(3-(R)-formyl-4-(S)-phenylpyrrolidin-1-yl)-2-(phenyl)acetic acid, benzyl ester (from Step C) and 4-phenylpiperidine using procedures analogous to those described in EXAMPLE 112. For the title compound: ESI-MS 455 (M+H).

EXAMPLE 119

2-(R)-(3-(S)-(4-Phenylpiperidin-1-yl)methyl)-4-(S)-phenyl pyrrolidin-1-yl)-2-(phenyl)propionic Acid Step A: 2-(R/S)-(3-(S)-(t-Butyldimethylsilyloxymethyl-4-(S)-phenylpyrrolidin-1-yl)-2-(phenyl)propionic acid, benzyl ester A solution of 113 mg (0.21 mmol) of 2-(R/S)-(3-(S)-(t-butyldimethylsilyloxymethyl)-4-(S)-phenylpyrrolidin-1-yl)-2-(phenyl)acetic acid, benzyl ester (from Example 118, Step A) in 1 mL of THF at −78° C. was treated with 0.66 mL (0.33 mmol) of 0.5N potassium bis(trimethylsilyl) amide solution in toluene. The resulting mixture was stirred cold for 15 minutes, then treated with 0.055 mL (0.88 umnol) of methyl iodide. The resulting mixture was stirred cold for 45 minutes, then quenched with 25 mL of 1N NaHCO$_3$. The quenched mixture was extracted with 25 mL of ether. The layers were separated and the aqueous layer was extracted with 25 mL of ether. The combined organic extracts were dried over MgSO$_4$ and concentrated. Flash chromatography using 9:1 v/v hexane/EtOAc as the eluant afforded 105 mg (90%) of the title compounds as a mixture of diastereomers: R$_F$: 0.64 (4:1 v/v hexane/EtOAc); $^1$H NMR (300 MHz) δ0.00 (2s, 6H), 0.85, 0.90 (2s, 9H), 1.70, 1.75 (2s, 3H), 2.30–3.70 (m, 8H), 5.30 (s, 2H), 7.10–7.45 (m, 15H).

Step B: 2-(R)-(3-(S)-Hydroxymethyl-4-(S)-phenylpyrrolidin-1-yl)-2-(phenyl)propionic acid, benzyl ester and 2-(S)-(3-(S)-Hydroxymethyl-4-(S)-phenylpyrrolidin-1-yl)-2-(phenyl) propionic acid, benzyl ester The title compounds were prepared from 2-(R/S)-(3-(S)-(t-butyldimethylsilyloxymethyl)-4-(S)-phenylpyrrolidin-1-yl)-2-(phenyl)propionic acid, benzyl ester (from Step A) using a procedure analogous to that described in the preparation given above of Aldehyde 1. The diastereomers were separated by preparative HPLC (Chiracel AD 2.0×25 cm column, 7:3 v/v hexanes/iPrOH, 9.0 mL/min, 220 nm) to provide the title compounds. For 2-(R)-(3-(S)-hydroxymethyl-4-(S)-phenylpyrrolidin-1-yl)-2-(phenyl) propionic acid, benzyl ester: Retention time, 14.3 min; $^1$H NMR (300 MHz) δ1.73 (s, 3H), 2.35 (m, 1H), 2.89–3.09 (m, 5H), 3.52–3.69 (m, 2H), 5.25 (s, 2H), 7.14–7.38 (m, 15H). For 2-(S)-(3-(S)-hydroxymethyl-4-(S)-phenylpyrrolidin-1-yl)-2-(phenyl)propionic acid, benzyl ester: Retention time, 25.7 min; $^1$H NMR (300 MHz) δ1.70 (m, 3H), 2.36 (m, 1H), 2.61 (t, J=8.7, 1H), 2.72 (dd, J=9.0, 5.7, 1H), 3.07 (q, J=7.9, 1H), 3.17–3.24 (m, 2H), 3.52 (dd, J=10.5, 5.8, 1H), 3.66 (dd, J=10.5, 4.3, 1H), 5.23 (ABq, J=12.3, 2H), 7.14–7.43 (m, 15H).

Step C: 2-(R)-(3-(S)-Formyl-4-(S)-phenylpyrrolidin-1-yl)-2-(phenyl) propionic acid, benzyl ester The title compound was prepared from 2-(R)-(3-(S)-hydroxymethyl-4-(S)-phenylpyrrolidin-1-yl)-2-(phenyl) propionic acid, benzyl ester (from Step B) using a procedure analogous to that described in preparation of Aldehyde 1. For the title compound: R$_F$: 0.46 (4:1 v/v hexane/EtOAc); $^1$H NMR (300 MHz, CDCl$_3$) δ1.73 (s, 3H), 2.95–3.10 (m, 3H), 3.33 (m, 1H), 3.50–3.63 (m, 2H), 5.25 (s, 2H), 7.12–7.38 (m, 15H), 9.62 (d, J=1.6 Hz).

Step D: 2-(R)-(3-(S)-(4-Phenylpiperidin-1-yl)methyl)-4-(S)-phenyl pyrrolidin-1-yl)-2-(phenyl)acetic acid The title compound was prepared from 2-(R)-(3-(S)-fonmyl-4-(S)-phenylpyrrolidin-1-yl)-2-(phenyl) propionic acid, benzyl ester (from Step C) and 4-phenylpiperidine using procedures analogous to those described in EXAMPLE 112. For the title compound: ESI-MS 469 (M+H).

EXAMPLE 120

2-(S)-(3-(S)-(4-Phenylpiperidin-1-yl)methyl)-4-(S)-phenyl pyrrolidin-1-yl)-2-(phenyl)propionic Acid The title compound was prepared from 2-(S)-(3-(S)-hydroxymethyl-4-(S)-phenylpyrrolidin-1-yl)-2-(phenyl) propionic acid, benzyl ester (from EXAMPLE 119, Step B) using procedures analogous to those described in EXAMPLE 119 Steps C and D. For the title compound: ESI-MS 469 (M+H).

EXAMPLE 121

2-(R)-(3-(S)-(4-((2-Benzyl)tetrazol-5-yl)piperidin-1-yl)methyl)-4-(S)-phenylpyrrolidin-1-yl)-2-(cyclohexyl)acetic Acid Step A: 1-(t-Butoxycarbonyl)-4-cyanopiperidine Isonipecotamide (10.0 g, 78.0 mmol) was added in portions to 25 mL of $POCl_3$ at 0° C. The cooling was removed and the mixture was allowed to reach rt. The mixture was heated at reflux for 2 h, then cooled to rt. The mixture was poured onto 100 g of ice. The pH of the aqueous mixture was adjusted to 11 with solid KOH and extracted with 4×200 mL of $CH_2Cl_2$. The extracts were combined, dried over $MgSO_4$ and concentrated to afford 8.0 g of crude (4-cyano) piperidine.

The crude (4-cyano)piperidine was dissolved in 50 mL of MeOH and treated with 17.0 g (78.0 mmol) of di-t-butyl dicarbonate and the resulting mixture was stirred at rt for 1 h. The mixture was concentrated. Flash chromatography on 250 g of silica gel using 1:1 v/v hexanes/ether afforded 13.4 g (80%) of the title compound: $^1$H NMR (300 MHz) δ1.46 (s, 9H), 1.76–1.96 (4H), 2.78–2.82 (m, 1H), 3.31–3.37 (m, 2H), 3.63–3.69 (m, 2H).

Step B: 1-(t-Butoxycarbonyl)-4-(1H-tetrazol-5-yl)piperidine

A mixture of 2.10 g (10.0 mmol) of 1-(t-butoxycarbonyl)-4-cyanopiperidine (from Step A), 1.95 g (30.0 mmol) of sodium azide and 1.60 g (30.0 mmol) of ammonium chloride in 20 mL of DMF was stirred at 100° C. for 20 h. The mixture was cooled and partitioned between 200 mL of $CH_2Cl_2$ and 200 mL of 1.0N HCl and the layers were separated. The organic layer was washed with 200 mL of $H_2O$, dried over $MgSO_4$ and concentrated. Flash chromatography on 50 g of silica gel using 4:1 v/v $CH_2Cl_2$/EtOAc+1% HOAc, then 2:1 v/v $CH_2Cl_2$/EtOAc+1% HOAc as the eluant afforded 1.51 g (60%) of the title compound: $^1$H NMR (500 MHz) δ1.49 (s, 9H), 1.83–1.89 (m, 2H), 2.13–2.15 (m, 2H), 2.96–3.04 (m, 2H), 3.13–3.36 (m, 1H), 4.14–4.22 (m, 2H).

Step C: 1-(t-Butoxycarbonyl)-4-((1-benzyl)tetrazol-5-yl)piperidine and 1-(t-Butoxycarbonyl)-4-((2-benzyl)tetrazol-5-yl)piperidine A solution of 438 mg (1.7 mmol) of 1-(t-butoxycarbonyl)-4-(1H-tetrazol-5-yl)piperidine (from Step B) in 2 mL of DMF at 0° C. was treated with 83 mg (0.50 mmol) of NaH (60% in mineral oil) and 0.41 mL (3.4 mmol) of benzyl bromide. The resulting mixture was warmed to rt and stirred for 2.5 h. The mixture was partitioned between 50 mL of ether and 50 mL of water and the layers were separated. The organic layer was washed with 50 mL sat'd NaCl, dried over $MgSO_4$ and concentrated. Flash chromatography using 2:1 v/v $CH_2Cl_2$/ether, then 1:2 v/v $CH_2Cl_2$/ether afforded 85 mg (15%) of 1-butoxycarbonyl)-4-((2-benzyl)tetrazol-5-yl)piperidine. Elution with 2:1 v/v EtOAc/$CH_2Cl_2$ afforded 95 mg (17%) of 1-(butoxycarbonyl)-4-((1-benzyl)tetrazol-5-yl)piperidine. For 1-(butoxycarbonyl)-4-((2-benzyl)tetrazol-5-yl)piperidine: $^1$H NMR (500 MHz) δ1.47 (s, 9H), 1.76–1.84 (2H), 2.02–2.05 (2H), 2.91–2.95 (2H), 3.07–3.12 (m, 1H), 4.00–4.20 (2H), 5.71 (s, 2H), 7.35–7.40 (5H). For 1-(butoxycarbonyl)-4-((1-benzyl)tetrazol-5-yl)piperidine: $^1$H NMR (500 MHz) δ1.45 (s, 9H), 1.59–1.61 (2H), 1.76–1.84 (2H), 2.70–2.80 (2H), 2.85–2.89 (m, 1H), 4.00–4.20 (2H), 5.55 (s, 2H), 7.17–7.19 (2H), 7.36–7.39 (3H).

Step D: 4-((2-Benzyl)tetrazol-5-yl)piperidine

A solution of 85 mg (0.25 mmol) of 1-(t-butoxycarbonyl)-4-((2-benzyl)tetrazol-5-yl)piperidine (from Step C) in 2 mL of 1:1 v/v $CH_2Cl_2$/TFA was stirred at rt for 2 h. The solution was concentrated. Flash chromatography on silica gel using 19:1:0.1 v/v/v $CH_2Cl_2$/MeOH/$NH_4OH$ as the eluant afforded 57 mg (94%) of the title compound.

Step E: 2-(R)-(3-(S)-(4-((2-Benzyl)tetrazol-5-yl)piperidin-1-yl)methyl)-4-(S)-phenylpyrrolidin-1-yl)-2-(cyclohexyl)acetic acid, (4-methoxy)benzyl ester The title compound was prepared from 2-(R)-(3-(R)-formyl-4-(S)-phenylpyrrolidin-1-yl)-2-(cyclohexyl)acetic acid, (4-methoxy)benzyl ester (Aldehyde 5) and 4-((2-benzyl)tetrazol-5-yl)piperidine (from Step D) using a procedure analogous to that described EXAMPLE 112, Step A. For the title compound: $^1$H NMR (500 MHz) δ0.89–3.25 (29H), 3.81 (s, 3H), 5.12 (ABq, J=11.9, 2H), 5.71 (s, 2H), 6.89–7.38 (14H).

Step F: 2-(R)-(3-(S)-(4-((2-Benzyl)tetrazol-5-yl)piperidin-1-yl)methyl)-4-(S)-phenylpyrrolidin-1-yl)-2-(cyclohexyl)acetic acid A solution of 53 mg (0.08 mmol) of 2-(R)-(3-(S)-(4-((2-benzyl)tetrazo-5-yl)piperidin-1-yl)methyl)4-(S)-phenylpyrrolidin-1-yl)-2-(cyclohexyl)acetic acid, (4-methoxy)benzyl ester (from Step E) in 1 mL of 96% formic acid was stirred at rt for 2 h. The solution was concentrated. Flash chromatography using 19:1:0.1 v/v/v $CH_2Cl_2$/MeOH/$NH_4OH$ as the eluant afforded 25 mg (57%) of the title compound: $^1$H NMR (500 MHz) δ0.82–3.79 (29H), 5.68 (s, 2H), 7.20–7.38 (10H); ESI-MS 543 (M+H); HPLC A: 1.87 min.

EXAMPLE 122

2-(R)-(3-(S)-(4-((1-Benzyl)tetrazo-5-yl)piperidin-1-yl)methyl)-4-(S)-phenylpyrrolidin-1-yl)-2-(cyclohexyl)acetic Acid The title compound was prepared from 1-(t-butoxycarbonyl)-4-((1-benzyl)tetrazol-5-yl)piperidine using procedures analogous to those described in EXAMPLE 121, Steps D–F. For the title compound: $^1$H NMR (500 MHz) δ0.85–3.64 (29H), 5.48 (s, 2H), 7.11–7.33 (10H); ESI-MS 543 (M+H); HPLC A: 1.79 min.

EXAMPLE 123

2-(R)-((3-(S)-(((1-Ethyl-3-benzyl)pyrazol-5-yl)piperidin-1-yl)methyl)-4-(S)-(3-thienyl)pyrrolidin-1-yl)-3-(cyclobutyl)propionic Acid The title compound was prepared from 2-(R)-(3-(R)-formyl-4-(S)-(3-thienyl)pyrrolidin-1-yl)-3-(cyclobutyl) propionic acid, (4-methoxy)benzyl ester (prepared above as Aldehyde 13) and ((1-ethyl-3-benzyl)pyrazol-5-yl) piperidine (prepared in Example 1, Step C) using procedures analogous to those described in EXAMPLE 112, Step A and EXAMPLE 121, Step F. For the title compound: $^1$H NMR (300 MHz, $CD_3OD$) δ1.10–3.96 (34H), 5.63 (br s, 1H), 6.99–7.36 (8H); ESI-MS 561 (M+H); HPLC A: 2.52 min.

EXAMPLE 124

α-(R)-(3-(S)-((4-(4-Benzyl-5-methyl- 1H-pyrazol-3 (2H)-on-2-yl)-piperidin-1-yl)methyl)-4-(S)-phenylpyrrolidin-1-yl)-cyclo-hexaneacetic Acid Step A: 1-Benzyl-4-(4-benzyl-5-methyl-1H-pyrazol-3(2H)-on-2-yl)-piperidine A mixture of 1.52 g 1-benzyl-4-hydrazinopiperidine and 2.0 g of ethyl 2-benzylacetoacetate in 20 mL of xylenes was refluxed for 1 hour. The solvent was removed under reduced pressure and the residue purified by silica gel chromatography (300 mL column). Elution with 0–5% MeOH in dichloromethane gave 1.61 g of product, 1-benzyl-4-(4-benzyl-5-methyl-1H-pyrazol-3(2H)-on-2-yl)-piperidine. ESI-MS 362.2 (M+H); HPLC A: 2.05 min.

Step B: 4-(4-Benzyl-5-methyl-1H-pyrazole-3(2H)-on-2-yl)-piperidine

To a solution of 0.52 g of 1-benzyl-4-(4-benzyl-5-methyl-1H-pyrazol-3(2H)-on-2-yl)-piperidine in 20 mL of EtOH under nitrogen was added 0.2 g of Pearlman's catalyst and 2.5 mL of 1,4-cyclohexadiene. This mixture was refluxed for 3 hours, filtered through Celite and concentrated under reduced pressure to give 0.43 g of 4-(4-benzyl-5-methyl-1H-pyrazole-3(2H)-on-2-yl)-piperidine. ESI-MS 271.9 (M+H); HPLC A: 1.68 min.

Step C: α-(R)-(3-(S)-((4-(4-Benzyl-5-methyl-1H-pyrazol-3 (2H)-on-2-yl)-piperidin-1-yl)methyl)-4-(S)-phenylpyrrolidin-1-yl)-cyclo-hexaneacetic acid 4-methoxybenzyl ester To a stirred solution of 0.44 g of α-(R)-(3-(R)-formyl-4-(S)-phenylpyrrolidin-1-yl)-cyclohexaneacetic acid 4-methoxybenzyl ester (prepared above as Aldehyde 5) and 0.55 g of 4-(4-benzyl-5-methyl-1H-pyrazole-3(2H)-on-2-yl)-piperidine in 3 mL 1,2-dichloroethane, 0.5 mL MeOH and 0.1 mL HOAc is added 0.3 g of powdered molecular sieves (4A). After 15 minutes, 0.1 g of sodium triacetoxyborohydride was added and stirring was continued overnight. The reaction mixture was poured into a rapidly stirred mixture of ethyl acetate and saturated sodium bicarbonate solution (~15 mL each). After 15 minutes the mixture was filtered through Celite, the aqueous layer separated and extracted with 25 mL ethyl acetate. The combined organic layers were washed with saturated sodium bicarbonate solution, water, then brine, dried with sodium sulfate and concentrated under reduced pressure to give 0.068 g of α-(R)-(3-(S)-((4-(4-benzyl-5-methyl-1H-pyrazol-3(2H)-on-2-yl)-piperidin-1-yl)methyl)-4-(S)-phenylpyrrolidin-1-yl)-cyclohexaneacetic acid 4-methoxybenzyl ester suitable for use in the next step. ESI-MS 691.3 (M+H); HPLC A: 3.20 min.

Step D: α-(R)-(3-(S)-((4-(4-Benzyl-5-methyl-1H-pyrazol-3 (2H)-on-2-yl)piperidin-1-yl)methyl)-4-(S)-phenylpyrrolidin-1-yl)-cyclo-hexaneacetic acid The material from Step C was dissolved in ~2 ml of 96% formic acid and stirred at room temperature for 3 hours. Toluene (10 mL) was then added and the mixture concentrated under reduced pressure. The residue was chromatographed on silica gel (10 mL column). Elution with 5% methanol in dichloromethane (100 mL) followed by 90:10:1 dichloromethane:methanol:ammonium hydroxide gave 0.028 g of α-(R)-(3-(S)-((4-(4-benzyl-5-methyl-1H-pyrazol-3(2H)-on-2-yl)- piperidin-1-yl)methyl)-4-(S)-phenylpyrrolidin-1-yl)-cyclohexaneacetic acid ESI-MS 571.4 (M+H); HPLC A: 2.61 min.

EXAMPLE 125

α-(R)-(3-(S)-((4-(5-Methyl4-phenyl-1 H-pyrazol-3 (2H)-on-2-yl)-piperidin-1-yl)methyl)-4-(S)-phenylpyrrolidin-1-yl)-cyclo-hexaneacetic Acid Step A: 1-Benzyl-4-(5-methyl-4-phenyl-1H-pyrazol-3(2H)-on-2-yl)-piperidine When 1.4 g of 1-benzyl-4-hydrazinopiperidine and 2.0 g of ethyl 2-phenylacetoacetate were used in the procedure of Example 124, Step A, there was obtained 1.84 g of 1-benzyl-4-(5-methyl-4-phenyl-1H-pyrazol-3(2H)-on-2-yl)-piperidine. ESI-MS 348.2 (M+H); HPLC A: 1.95 min.

Step B: 4-(5-Methyl4-phenyl-1H-pyrazol-3(2H)-on-2-yl)-piperidine

When 0.11 g of 1-benzyl-4-(5-methyl-4-phenyl-1H-pyrazol-3(2H)-on-2-yl)- piperidine was debenzylated according to the procedure of Example 124, Step B, there was obtained 0.078 g of 4-(5-methyl-4-phenyl-1H-pyrazol-3(2H)-on-2-yl)-piperidine. ESI-MS 257.9 (M+H); HPLC A: 1.52 min.

Step C: α-(R)-(3-(S)-((4-(5-Methyl-4-phenyl- 1H-pyrazol-3 (2H)-on-2-yl)piperidin-1-yl)methyl)-4-(S)-phenylpyrrolidin-1-yl)-cyclo-hexaneacetic acid 4-methoxybenzyl ester When 0.070 g of 4-(5-methyl-4-phenyl-1H-pyrazol-3 (2H)-on-2-yl)-piperidine and 0.043 g of α-(R)-(3-(R)-formyl-4-(S)-phenylpyrrolidin-1-yl)-cyclohexaneacetic acid 4-methoxybenzyl ester were used in the procedure of Example 124, Step C, there was obtained 0.061 g of α-(R)-(3-(S)-((4-(5-methyl-4-phenyl-1H-pyrazol-3(2H)-on-2-yl)-piperidin-1-yl)methyl)-4-(S)-phenylpyrrolidin-1-yl)-cyclohexaneacetic acid 4-methoxybenzyl ester after chromatography on silica gel (20 mL column—elution with 3% MeOH in dichlormethane). ESI-MS 677.3 (M+H); TPLC A: 2.85 min.

Step D: α-(R)-(3-(S)-((4-(5-Methyl-4-phenyl-1H-pyrazol-3 (2H)-on-2-yl)-piperidin-1-yl)methyl)-4-(S)-phenylpyrrolidin-1-yl)-cyclohexaneacetic acid When the material from Step C was deblocked according to the procedure of Example 124, Step D, there was obtained 0.041 g of α-(R)-(3-(S)-((4-(5-methyl-4-phenyl-1H-pyrazol-3(2H)-on-2-yl)-piperidin-1-yl)methyl)-4-(S)-phenylpyrrolidin-1-yl)-cyclohexaneacetic acid. ESI-MS 557.3 (M+H); HPLC A: 2.19 min.

EXAMPLE 126

α-(R)-(3-(S)-((4-(8,9-dihydro-7H-5-oxa-7-aza-benzocyclohepten-6-one-7-yl)-piperidine-1-yl) methyl)-4-(S)-phenylpyrrolidin-1-yl)-cyclohexaneacetic Acid Step A: 1-t-Butyloxycarbonyl-4-(8,9-dihydro-7H-5-oxa-7-aza-benzocyclohepten-6-one-7-yl)-piperidine To a solution of 0.15 g (1.1 mmol) of 2-(2-hydroxy)-phenylethylamine in 2 mL of methylene chloride, 0.11 g (0.55 mmol) of 1-t-butoxycarbonyl-4-piperidone, and 0.25 g (1.18 mmol) of Na(OAc)3BH were added. After stirring for 1 hr, the reaction was diluted with CH2Cl2, washed with water and brine. The organic layer was dried and concentrated in vacuo, leaving 0.2 g of the residue. This residue was dissolved in 2 mL of methylene chloride and 0.089 g (0.55 mmol) of 1,1'-carbonyldiimidazole and 10 mg (0.08 mmol) of 4-dimethylaminopyridine were added. After stirring the mixture overnight, it was diluted with methylene chloride and washed with water and brine. The methylene chloride layer was dried and concentrated in vacuo. The residue was purified by prep TLC using 50% EtOAc-hexane as an eluent to isolate 58 mg of the title compound. ¹H NMR (500 MHz, CDCl₃): δ1.49 (s, 9H), 1.62 (m, 2H), 1.80 (m, 2H), 2.78 (br s, 2H), 3.0 (t, 2H, J=6 Hz), 3.66 (t, 2H, J=6 Hz), 4.21 (m, 3H), 7.1–7.3 (m, 4H).

Step B: 4-(8,9-dihydro-7H-5-oxa-7-aza-benzocyclohepten-6-one-7-yl)-piperidine hydrochloride Acetyl chloride (0.2 mL, 2.8 mmol) was added to 2 mL of methanol and stirred for 10 min. This solution of HCl in MeOH was added to 58 mg of 1-t-butyloxycarbonyl-4-(8,9-dihydro-7H-5-oxa-7-aza-benzocyclohepten-6-one-7-yl)-piperidine (Step A) and stirred for 2 hr. The reaction was concentrated in vacuo, the residue was diluted with EtOAc and the solution was concentrated again in vacuo leaving 46 mg of the title compound which was sufficiently pure for use in the next step. ¹H NMR (500 MHz, CDCl₃): δ2.06 (m, 2H), 2.35 (m, 2H), 3.02 (m, 4H), 3.5–3.8 (m, 4H), 4.35 (br s, 1H), 7.1–7.3 (m, 4H), 9.6 (br, 2H).

Step C: α-(R)-(3-(S)-((4-(8,9-dihydro-7H-5-oxa-7-aza-benzocyclohepten-6-one-7-yl)-piperidine -1-yl)methyl)-4-(S)-phenylpyrrolidin-1-yl)-cyclohexaneacetic acid, 4-methoxybenzyl ester The title compound (36 mg) was prepared by reductive amination of 31 mg of α-(R)-(3-(R)-formyl-4-(S)-phenylpyrrolidin-1-yl)- cyclohexaneacetic acid, 4-methoxybenzyl ester (prepared above as Aldehyde 5) with 22 mg of 4-(8,9-dihydro-7H-5-oxa-7-aza-benzocyclohepten-6-one-7-yl)-piperidine hydrochloride according to the procedure of Example 1, step D. ¹H NMR (500MHz, CDCl₃): δ0.9–1.3 (m, 5H), 1.5–2.0 (m, 12H), 2.25–3.3 (m, 13H), 3.63 (m, 2H), 3.82 (s, 3H), 3.96 (m, 1H), 5.13 (ABq, 2H), 6.9–7.4 (m, 13H).

Step D: α-(R)-(3-(S)-((4-(8,9-dihydro-7H-5-oxa-7-aza-benzocyclohepten-6-one-7-yl)-pipreidine -1-yl)methyl)-4-(S)-phenylpyrrolidin-1-yl)-cyclohexaneacetic acid Removal of the 4-methoxybenzyl ester protecting group from 36 mg of α-(R)-(3-(S)-((4-(8,9-dihydro-7H-5-oxa-7-aza-benzocyclohepten-6-one-7-yl)-pipreidine-1-yl)methyl)-4-(S)-phenylpyrrolidin-1-yl)-cyclohexaneacetic acid, 4-methoxybenzyl ester as described in Example 1, step E, furnished 30 mg of the title compound as a dihydrochloride after purification on a Varian SCX ion-exchange column. LC-MS (Method A): Retention Time: 2.18 min. Mass Spectrum: 546 (M+1).

EXAMPLE 127

α-(R)-(3-(S)-((4-(5-Benzyl-thiazol-2-yl) -piperidine-1-yl)methyl)-4-(S)-phenylpyrrolidin-1-yl)-cyclohexaneacetic Acid Step A: 1-t-Butyloxycarbonyl-isonipecot-thioamide To a solution of 500 mg of 1-Boc-isonipecotamide in 5 ml of 1,4-dioxane was added 243 mg of phosphorous pentasulfide. The reaction was stirred at 100° C. for 1 hour. The solvent was then evaporated under reduced pressure. The residue was purified by flash chromatography with 30% EtOAc in hexane to give 74 mg of the title compound.

Step B: 4-(5-Benzyl-thiazol-2-yl)-1-t-butyloxycarbonyl-piperidine

To a solution of 65 mg of 1-bromo-3-phenyl-2-propanone (from reacting the acid chloride with diazomethane followed by hydrogen bromide) in 4 ml EtOH was added 74 mg of 1-boc-isonipecot-thioamide (from Step A). The reaction was stirred for 2 hours at 80° C. The solvent was then evaporated under reduced pressure. The residue was purified by flash chromatography with 10% EtOAc in hexane to give 37 mg of the title compound.

Step C: 4-(5-Benzyl-thiazol-2-yl) -piperidine hydrochloride

To 37 mg of 4-(5-benzyl-thiazol-2-yl)-1-t-butyloxycarbonyl-piperidine (from Step B) was added 4 ml of a saturated solution of hydrochloric acid in methanol. The reaction was stirred for 3.5 hours at room temperature. The methanol was evaporated under reduced pressure to give 24 mg of the title compound. ESI-MS 259 (M+H); HPLC A: 2.00 min.

Step D: α-(R)-(3-(S)-((4-(5-Benzyl-thiazol-2-yl) -piperidine-1-yl)methyl)-4-(S)-phenylpyrrolidin-1-yl)-cyclohexaneacetic acid, 4-methoxybenzyl ester To a solution of 24 mg of 4-(5-benzyl-thiazol-2-yl) -piperidine hydrochloride (from Step C) in 3 ml DCE was added 8 mg of triethylamine. After 20 minutes, 35 mg of α-(R)-(3-(R)-Formyl-4-(S)-phenylpyrrolidin-1-yl)-cyclohexaneacetic acid, 4-methoxybenzyl ester (prepared above as Aldehyde 5) was added, followed by 31 mg of sodium triacetoxyborohydride. The reaction was stirred overnight at room temperature. The solvent was evaporated under reduced pressure. The residue was purified by flash chromatography with 10% EtOAc in hexane followed by 50% EtOAc in hexane to give 44 mg of the title compound.

Step E: α-(R)-(3-(S)-((4-(5-Benzyl-thiazol-2-yl) -piperidine-1-yl)methyl)-4-(S)-phenylpyrrolidin-1-yl)-cyclohexaneacetic acid To 44 mg of α-(R)-(3-(S)-((4-(5-benzyl-thiazol-2-yl) -piperidine-1-yl)methyl)-4-(S)-phenylpyrrolidin-1-yl)-cyclohexaneacetic acid, 4-methoxybenzyl ester (from Step D) were added 125 mg of anisole and 3 ml of triflouroacetic acid. The reaction was stirred at room temperature for 1 hour. The trifluoroacetic acid was evaporated under reduced pressure. The residue was purified by flash chromatography with 20% MeOH in EtOAc followed by 20% MeOH+2% NH₄OH in EtOAc to give 36.7 mg of the title compound. ESI-MS 558 (M+H); HPLC A: 2.59 min.

EXAMPLE 128

α-(R)-(3-(S)-((4-(2-Phenyl-thiazol-5-yl)-pipendine-1-yl)methyl)-4-(S)-phenylpyrrolidin-1-yl)-cyclohexaneacetic Acid Step A: 1-Benzoyl-4-(2-phenyl-thiazol-5-yl)-piperidine To 150 mg of 2-bromo-1-(1-benzoyl-4-piperidyl)-1-ethanone in 6 ml of EtOH was added 66 mg of thiobenzamide. The reaction was stirred at 80° C. for 2 hours. The solvent was evaporated under reduced pressure. The residue was purified by flash chromatography with 50% EtOAc in hexane to give 55 mg of the title compound.

Step B: 4-(2-Phenyl-thiazol-5-yl)-piperidine

To 55 mg of 1-benzoyl-4-(2-phenyl-thiazol-5-yl)-piperidine in 4.5 ml of MeOH and 0.5 ml of H₂O was added 354 mg of potassium hydroxide. The reaction was stirred at 70° C. overnight. The reaction was then cooled to room temperature and 20 ml of H₂O was added. This aqueous layer was extracted with 4×25 ml EtOAc. The combined organic phases were dried over MgSO₄ and concentrated under reduced pressure to give 25 mg of the title compound.

Step C: α-(R)-(3-(S)-((4-(2-Phenyl-thiazol-5-yl)-piperidine-1-yl)methyl)-4-(S)-phenylpyrrolidin-1-yl)-cyclohexaneacetic acid, 4-methoxybenzyl ester To 12 mg of 4-(2-phenyl-thiazol-5-yl)-piperidine (from Step B) in 3 ml of DCE was added 35 mg of a-(R)-(3-(R)-formyl4-(S)-phenylpyrrolidin-1-yl)-cyclohexaneacetic acid, p-methoxybenzyl ester (prepared above as Aldehyde 5) followed by 19 mg of sodium triacetoxyborohydride. The reaction was stirred overnight at room temperature. The solvent was evaporated under reduced pressure. The residue was purified by flash chromatography with 10% EtOAc in hexane followed by 50% EtOAc in hexane to give 28 mg of the title compound.

Step D: α-(R)-(3-(S)-((4-(2-Phenyl-thiazol-5-yl)-piperidine-1-yl)methyl)-4-(S)-phenylpyrrolidin-1-yl)-cyclohexaneacetic acid To 28 mg of α-(R)-(3-(S)-((4-(2-phenyl-thiazol-5-yl)-piperidine -1-yl)methyl)-4-(S)-phenylpyrrolidin-1-yl)-cyclohexaneacetic acid, 4-methoxybenzyl ester (from Step C) were added 150 mg of anisole and 3 ml of triflouroacetic acid. The reaction was stirred at room temperature for 1 hr. The trifluoroacetic acid was evaporated under reduced pressure. The residue was purified by flash chromatography with 20% MeOH in EtOAc followed by 20% MeOH+2% NH$_4$OH in EtOAc to give 24 mg of the title compound. LC-MS (Method A): Retention Time: 2.72 min. Mass Spectrum: 544 (M+H).

EXAMPLE 129

α-(R)-(3-(S)-((4-(2-benzyl-thiazol-5-yl)-piperidine-1-yl)methyl)-4-(S)-phenylpyrrolidin-1-yl)-cyclohexaneacetic Acid This compound was synthesized in a manner similar to example 128 by substituting benzyl thioamide in Step A instead of thiobenzamide. LC-MS (Method A): Retention Time: 2.51 min. Mass Spectrum: 558.5 (M+H).

EXAMPLES 130–155

Examples 130–155 in Table 9 were prepared according to the procedure described in Example 126, employing the appropriate piperidine and aldehyde in Step C and removing the ester protecting group as in step D.

TABLE 9

| EX # | R$^a$ | R$^b$ | R$^c$ | HPLC RT (min) | MS m/Z (M + 1) |
|---|---|---|---|---|---|
| 130 | cyclohexyl | H | Ph-substituted 1,3-oxazinan-2-one | 2.13 | 560 |
| 131 | cyclobutyl | 3-F | benzo-fused oxazepinone | 2.50 | 550 |
| 132 | cyclohexyl | H | benzo-fused diazepinone (NH) | 2.13 | 545 |
| 133 | cyclobutyl | 3-F | benzo-fused diazepinone (NH) | 2.25 | 549 |
| 134 | cyclohexyl | H | benzo-fused 1,3-oxazin-2-one | 2.15 | 532 |

TABLE 9-continued
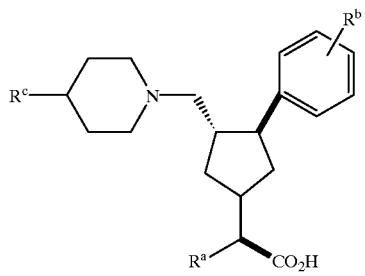
| EX # | R$^a$ | R$^b$ | R$^c$ | HPLC RT (min) | MS m/Z (M + 1) |
|---|---|---|---|---|---|
| 135 | cyclohexyl | H | 3-phenylisoxazol-5-yl | — | 528 |
| 136 | cyclohexyl | 3-F | 5-phenylisoxazol-3-yl | — | 528 |
| 137 | cyclohexyl | H | 4-phenyl-1H-imidazol-2-yl | 2.05 | 527 |
| 138 | cyclohexyl | H | 1-ethyl-4-phenyl-imidazol-2-yl | 2.37 | 555 |
| 139 | cyclohexyl | H | 3-(trifluoromethyl)-1H-pyrazol-5-yl | 2.29 | 519 |
| 140 | cyclobutylmethyl | 3-F | 3-(trifluoromethyl)-1H-pyrazol-5-yl | 2.35 | 523 |

TABLE 9-continued
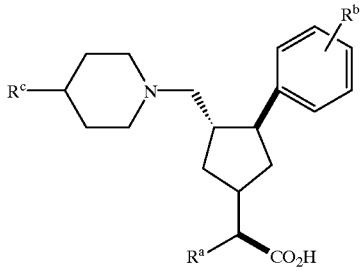
| EX # | R$^a$ | R$^b$ | R$^c$ | HPLC RT (min) | MS m/Z (M + 1) |
|---|---|---|---|---|---|
| 141 |  | H | 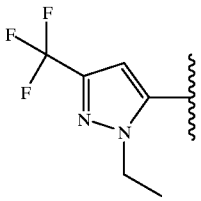 | 2.34 | 547 |
| 142 |  | H | 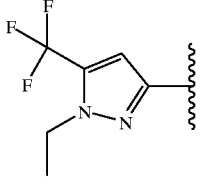 | 2.29 | 547 |
| 143 |  | H | 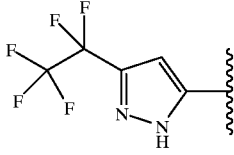 | — | 596 |
| 144 |  | H | 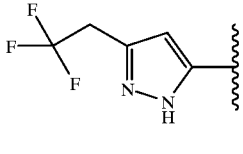 | 2.80 | 533 |
| 145 |  | H | 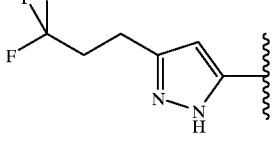 | 3.44 | 547 |
| 146 |  | H | 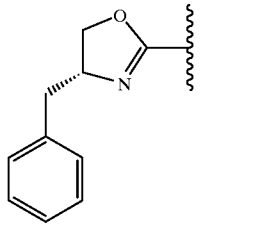 | — | 562 (M + NH4) |

TABLE 9-continued

| EX # | R$^a$ | R$^b$ | R$^c$ | HPLC RT (min) | MS m/Z (M + 1) |
|---|---|---|---|---|---|
| 147 | cyclohexyl | H | 4-benzyl-oxazoline | — | 544 |
| 148 | cyclohexyl | H | 4-phenyl-oxazoline | 2.00 | 548 (M + NH4) |
| 149 | cyclohexyl | H | 2-benzyl-oxazoline (5-yl) | 2.08 | 562 (M + NH4) |
| 150 | cyclohexyl | H | 4-benzyl-oxazole | 2.45 | 542 |
| 151 | cyclohexyl | H | 2-phenyl-thiazole | 3.79 | 548 |

TABLE 9-continued

| EX # | R$^a$ | R$^b$ | R$^c$ | HPLC RT (min) | MS m/Z (M + 1) |
|---|---|---|---|---|---|
| 152 | cyclohexyl | H | 2-(4-fluorophenyl)thiazol-4-yl | 3.89 | 562 |
| 153 | cyclohexyl | H | 3-methyl-1H-pyrazol-5-yl | 1.95 | 465 |
| 154 | cyclobutylmethyl | 3-F | 4-benzyloxazol-2-yl | 2.64 | 546 |
| 155 | cyclobutylmethyl | 3-F | 2-benzylthiazol-4-yl | 2.96 | 562 |

Note:
The " ⌇ " in R$^a$ represents a single bond; i.e., it does not denote stereoiomerism.

EXAMPLE 156

α-(R)-(3-(S)-((4-N-(5-Methyl-1,2,4-oxadiazol-3-yl)-N-(2-phenethyl)aminopiperidin-1-yl)methyl)-4-(S)-phenylpyrrolidin-1-yl)-cyclohexaneacetic Acid Step A: 4-N-(2-Phenethyl)-1-(tert-butoxycarbonyl) aminopiperidine To a solution of tert-butyl-4-oxo-1-piperidinecarboxylate in methylene chloride was added 2-phenethylamine, NaBH(OAc)$_3$ and HOAc. The mixture was stirred at ambient temperature for 16 hours and quenched by addition of H$_2$O. The aqueous layer was neutralized with NaHCO$_3$ and extracted with CH$_2$Cl$_2$. The combined organic layer was washed with saturated NaHCO$_3$ and brine and dried over MgSO$_4$. Evaporation of solvent gave an off-white solid. This material was used without further purification. ESI-MS 305 (M+H); HPLC A: 2.54 min.

Step B: 1-Acetyl-3-(1-tert-butoxycarbonylpiperidin-4-yl)-3-(2-phenethyl)thiourea To a suspension of NaSCN in acetone was added acetyl chloride at ambient temperature. The mixture was stirred for 2 hours and a solution 4-N-(2-phenethyl)-1-(tert-butoxycarbonyl)aminopiperidine was added. The reaction was stirred for 2 hours at ambient temperature, and then refluxed for 1.5 hours. After extractive work up, a yellow solid was afforded. This material was used without further purification. ESI-MS 350 (M-t-Bu+H); HPLC A: 3.39 min.

Step C: 1-Acetyl-3-(1-tert-butoxycarbonylpiperidin-4-yl)-3-(2-phenethyl)-2-methyl-2-thiopseudourea To a methanol solution of 1-acetyl-3-(1-tert-butoxycarbonylpiperidin-4-yl)-3-(2-phenethyl)thiourea was added methyl iodide and DIEA. After stirring for 3 hours, the solvent was removed in vacuo and the reaction mixture was purified by flash chromatography on silica. The product appeared as a clear oil. ESI-MS 420 (M+H); HPLC A: 3.19 min.

Step D: 1-tert-Butoxycarbonyl-4-N-(5-methyl-1,2,4-oxadiazole-3-yl)-4-N-(2-phenethyl)aminopiperidine To an ethanol solution of 1-acetyl-3-(1-tert-butoxycarbonylpiperidin-4-yl)-3-(2-phenethyl)-2-methyl-2-thiopseudourea was added $NH_2NH_2$. The reaction mixture was refluxed for 16 hours before ethanol was removed in vacuo. Purification by flash chromatography on silica afforded the product as a clear oil. ESI-MS 387 (M+H); HPLC A: 3.79 min.

Step E: 4-N-(5-Methyl-1,2,4-oxadiazole-3-yl)-N-(2-phenethyl)aminopiperidine 1-tert-Butoxycarbonyl-4-N-(5-methyl-1,2,4-oxadiazole-3-yl)-N-(2-phenethyl)aminopiperidine was dissolved in a mixture of 1:1 $TFA/CH_2Cl_2$. The mixture was allowed to stand for 30 minutes at ambient temperature before the solvents were removed in vacuo. The residue was washed with saturated $NaHCO_3$. The resulting suspension was extracted with ethyl acetate. The combined organic layer was dried over $MgSO_4$. Evaporation of solvent resulted in a clear oil. ESI-MS 287 (M+H); HPLC A: 2.04 min.

Step F: α-(R)-(3-(S)-((4-N-(5-Methyl-1,2,4-oxadiazole-3-yl)-N-(2-phenethyl)aminopiperidin-1-yl)methyl)-4-(S)-phenylpyrrolidin-1-yl)-cyclohexaneacetic acid, benzyl ester To a solution of 4-N-(5-methyl-1,2,4-oxadiazole-3-yl)-N-(2-phenethyl)aminopiperidine and α-(R)-(3-(R)-formyl-4-(S)-phenylpyrrolidin-1-yl)-cyclohexaneacetic acid, benzyl ester (prepared above as Aldehyde 5) in $CH_2Cl_2$ was added $NaHB(OAc)_3$ and HOAc. The reaction mixture was stirred for 16 hours. After extractive work up, the crude product was purified by flash chromatography on silica. ESI-MS 676 (M+H); HPLC A: 3.21 min.

Step G: α-(R)-(3-(S)-((4-N-(5-Methyl-1,2,4-oxadiazole-3-yl)-N-(2-phenethyl)aminopiperidin-1-yl)methyl)-4-(S)-phenylpyrrolidin-1-yl)-cyclohexaneacetic acid To a solution of α-(R)-(3-(S)-((4-N-(5-methyl-1,2,4-oxadiazole-3-yl)-N-(2-phenethyl)aminopiperidin-1-yl)methyl)-4-(S)-phenylpyrrolidin-1-yl)-cyclohexaneacetic acid, benzyl ester in methanol was added 10% Pd/C, the reaction mixture was vigorously stirred for 45 minutes under 1 atm of hydrogen. The mixture was filtered and methanol removed in vacuo. The crude product was purified by reverse phase HPLC. ESI-MS 586 (M+H); HPLC A: 2.54 min.

EXAMPLE 157

α-(R)-(3-(S)-((4-N-(5-Methyl-1,3,4-triazol-2-yl)-N-(2-phenethyl)aminopiperidin-1-yl)methyl)-4-(S)-phenylpyrrolidin-1-yl)-cyclohexaneacetic Acid Step A: 4-N-(5-Methyl-1,3,4-triazol-2-yl)-N-(2-phenethyl)aminopiperidine The title compound was prepared from 1-acetyl-3-(1-tert-butoxycarbonylpiperidin-4-yl)-3-(2-phenethyl)-2-methyl-2-thiopseudourea (From Example 156, Step C) using a procedure analogous to that described in Example 156, Steps D to E, employing $NH_2NH_2$ instead of $NH_2OH$. ESI-MS 286 (M+H); HPLC A: 1.28min.

Step B: α-(R)-(3-(S)-((4-N-(5-Methyl-1,3,4-triazol-2-yl)-N-(2-phenethyl)aminopiperidin-1-yl)methyl)-4-(S)-phenylpyrrolidin-1-yl)-cyclohexaneacetic acid The title compound was prepared by using procedures analogous to that described in Example 156, Step E to G. ESI-MS 585 (M+H); HPLC A: 2.00 mm.

EXAMPLE 158

α-(R)-(3-(S)-((4-N-(1,3,-Thiazol-2-yl)-N-(2-phenethyl)aminopiperidin-1-yl)methyl)-4-(S)-phenylpyrrolidin-1-yl)-cyclohexaneacetic Acid Step A: 1-(1-tert-Butoxycarbonylpiperidin-4-yl)-1-(2-phenethyl)thiourea To a solution of 1-acetyl-3-(1-tert-butoxycarbonylpiperidin-4-yl)-3-(2-phenethyl)thiourea (From Example 156, Step C) in methanol was added $NH_2NH_2$. The mixture was refluxed for 35 minutes. The solvent was removed and the crude product was purified by flash chromatography on silica. ESI-MS 364 (M+H); HPLC A: 3.31 min.

Step B: 1-tert-Butoxycarbonyl-4-N-(1,3-thiazol-2-yl)-N-(2-phenethyl)aminopiperidine To a solution of 1-(1-tert-butoxycarbonylpiperidin-4-yl)-1-(2-phenethyl)thiourea in ethanol was added DIEA and chloroacetaldehyde. The mixture was heated at 90° C. for 1.5 hours. After evaporating the solvent, the crude product was purified by flash chromatography on silica. ESI-MS 388 (M+H); HPLC A: 2.82 min.

Step C: 4-N-(1,3,-Thiazol-2-yl)-N-(2-phenethyl)aminopiperidine

The title compound was prepared using a procedure analogous to that described in Example 156, Step E. The compound was purified by reverse phase HPLC. ESI-MS 288 (M+H); HPLC A: 1.52 min.

Step D: α-(R)-(3-(S)-((4-N-(1,3,-Thiazol-2-yl)-N-(2-phenethyl)aminopiperidin-1-yl)methyl)-4-(S)-phenylpyrrolidin-1-yl)-cyclohexaneacetic acid, 4-methoxybenzyl ester The title compound was prepared from 4-N-(1,3,-thiazol-2-yl)-N-(2-phenethyl)aminopiperidine using a procedure analogous to that described in Example 156, Step F, α-(R)-(3-(R)-formnyl-4-(S)-phenylpyrrolidin-1-yl)-cyclohexaneacetic acid, 4-methoxybenzyl ester (prepared above as Aldehyde 5) was used instead of α-(R)-(3-(R)-formyl4-(S)-phenylpyrrolidin-1-yl)-cyclohexaneacetic acid, benzyl ester. ESI-MS 707 (M+H); HPLC A: 3.09 min.

Step E: α-(R)-(3-(S)-((4-N-(1,3,-Thiazol-2-yl)-N-(2-phenethyl)aminopiperidin-1-yl)methyl)-4-(S)-phenylpyrrolidin-1-yl)-cyclohexaneacetic acid The title compound was prepared by dissolving α-(R)-(3-(S)-((4-N-(1,3,-thiazol-2-yl)-N-(2-phenethyl)aminopiperidin-1-yl)methyl)-4-(S)-phenylpyrrolidin-1-yl)-cyclohexaneacetic acid, 4-methoxybenzyl ester in neat formic acid, the solution was allowed to stand for 16 hours before the formic acid was removed in vacuo. The crude product was purified by reverse phase HPLC and ESI-MS 587 (M+H); HPLC A: 2.23 min.

EXAMPLE 159

α-(R)-(3-(S)-((4-N-(4-Methyl-1,3,-Thiazol-2-yl)-N-(2-phenethyl)aminopiperidin-1-yl)methyl)-4-(S)-phenylpyrrolidin-1-yl)-cyclohexaneacetic Acid The title compound was prepared using a procedure analogous to that described in Example 158, Steps A to E, except in Step B bromoacetone was used instead of chloroacetaldehyde and the compound was purified by flash chromatography on silica. ESI-MS 601 (M+H); HPLC A: 2.22 min.

EXAMPLE 160

α-(R)-(3-(S)-((Piperidin-1-yl)methyl)-4-(S)-phenylpyrrolidin-1-yl)-cyclohexaneacetic Acid The title compound was prepared using a procedure analogous to that described in Example 156, Steps F to G, except piperidine was used in Step F instead of 4-N-(5-methyl-1,2,4-oxadiazole-3-yl)-N-(2-phenethyl) aminopiperidine, and the compound was purified by flash chromatography on silica. ESI-MS 385 (M+H); HPLC A: 2.14 min.

EXAMPLE 161

α-(R)-(3-(S)-((4-Propylpiperidin-1-yl)methyl)-4-(S)-phenylpyrrolidin-1-yl)-cyclohexaneacetic Acid The title compound was prepared using a procedure analogous to that described in Example 156, Steps F to G, except 4-propylpiperidine was used in Step F instead of 4-N-(5-methyl-1,2,4-oxadiazol-3-yl)-N-(2-phenethyl) aminopiperidine; and the compound was purified by flash chromatography on silica. ESI-MS 427 (M+H); HPLC A: 2.28 min.

EXAMPLE 162

Example 162 in Table 10 was prepared in a fashion analogous to that shown above for related compounds.

grams, 12 mmol) in 15 mL THF was added. The mixture was warmed to room temperature, quenched with sat'd ammonium chloride and extracted with EtOAc. The EtOAc layer was separated and washed with sat'd NaCl then dried over sodium sulfate and concentrated. Flash chromatography (100 g silica, 10/1 Hexane/EtOAc) afforded 1.9 grams (58%) of the title compound. $^1$H NMR (400 MHz, CDCl$_3$). δ1.5 (s, 9H), 2.4–2.48 (m, 2H), 3.62–3.68 (t, 2H), 4.05–4.07 (m, 2H), 5.77–5.8 (bs, 1H).

Step B: N-tert-butoxycarbonyl-4-trimethylstannyl-2,5,6-trihydropyridine

A dry flask under nitrogen was charged with 20 mL THF, LiCl (1.6 grams, 37.3 mmol), tetrakistriphenylphosphine palladium(0), (331 mg, 0.28 mmol) and hexamethyldistannane (1.2 mL, 5.7 mmol). N-tert-butoxycarbonyl-2,5,6-trihydropyridine-4-trifluoromethane sulfonate (1.9 grams, 5.7 mmol) was added and the mixture was stirred overnight at 60 C. The mixture was diluted with water and extracted with EtOAc (3×150 mL). The combined organics were dried over sodium sulfate and concentrated. Flash chromatography (100 g silica, 20/1 Hexane/EtOAc) afforded 1.56 grams (79%) of the title compound. $^1$H NMR (300 MHz, CDCl$_3$). δ0.5 (s, 9H), 1.5 (s, 9H), 2.25–2.35 (m, 2H), 3.62–3.68 (t, 2H), 3.95–3.97 (m, 2H), 5.77–5.8 (bs, 1H).

Step C: 3-bromo-5-benzylpyridine

A dry flask under nitrogen was charged with zinc chloride (16 mL, 0.5M in THF, 8 mmol), and a solution of phenylmagnesium chloride (4 mL, 2.0M in THF, 8 mmol). The

TABLE 10

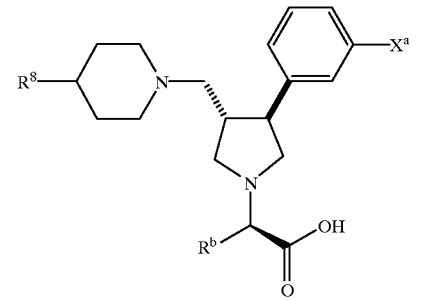

| EXAMPLE # | R$^a$ | R$^b$ | X$^a$ | ESI-MS M/z (M + 1) |
|---|---|---|---|---|
| 162 | 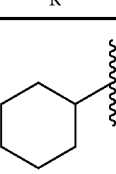 | | H | 584.3 |

EXAMPLE 163

2-(R)-(3-(S)-((4-(5-Benzylpyrid-3-yl)piperidin-1-yl)methyl)-4-(S)-(3-fluorophenyl)pyrrolidin-1-yl)-tert-butylacetic Acid Step A: N-tert-butoxycarbonyl-2,5,6-trihydropyridine-4-trifluoromethane sulfonate A dry flask under nitrogen was charged with a solution of sodium hexamethyldisilazide (11 mL, 1.0M in THF) and was cooled to −78 C. A solution of N-tert-butoxycarbonyl-4-piperidone (2.0 grams, 10 mmol) in 10 mL THF was added dropwise via cannula. After 30 min. a solution of 2-(N,N-bis(trifluoromethanesulfonyl) amino-5-chloropyridine (4.7 mixture was heated to 50 C for 3 h then cooled to room temperature and transferred via cannula to a solution of 3,5-dibromopyridine (1.26 grams, 5.3 mmol), copper iodide (61 mg, 0.32 mmol), and bis(diphenylphosphino)ferrocene palladium dichloride (218 mg, 0.27 mmol) in 15 mL THF. The resulting mixture was heated to 50 C overnight. Sat'd ammonium chloride was added and the mixture was extracted with EtOAc. The organic portion was dried over sodium sulfate and concentrated. Flash chromatography (8/1 hexane/EtOAc) afforded 433 mg (33%) of the title compound. $^1$H NMR (400 MHz, CDCl$_3$). δ4.02 (s, 2H), 7.18–7.4 (m, 8H), 7.65 (s, 1H).

Step D: 4-((5-benzyl)pyrid-3-yl)piperidine, trifluoroacetate salt

A flask was purged with nitrogen and charged with DMF, 3-bromo-5-benzylpyridine (618 mg, 2.5 mmol, from Step C), tetrakis triphenylphosphine palladium (58 mg, 0.05 mmol), and N-tert-butoxycarbonyl-4-trimethylstannyl-2,5,6-trihydropyridine (1.04 grams, 3 mmol). The mixture was heated to 100 C and stirred for 10 h. An additional portion of tetrakis triphenylphosphine palladium (40 mg, 0.03 mmol) was added and stirring was continued for 14 h. The solution was cooled and diluted with ethyl acetate then washed washed with water, dried over sodium sulfate and concentrated. Flash chromatography (2.5/1 hexane/ethyl acetate) afforded 590 mg (67%) of the coupling product. The product was dissolved in 4 mL methanol and 50 mg 10% Pd/C was added. The mixture was stirred under 1 atm of hydrogen for 3 h. The catalyst was filtered off and the residue was dissolved in 1/1 TFA/DCM. Removal of the solvent and drying under vacuum afforded the title compound as its TFA salt. $^1$H NMR (500 MHz, CDCl$_3$). δ1.55–1.64 (m, 2H), 1.75–1.8 (d, 2H), 2.57–2.62 (m, 1H), 2.68–2.73 (t, 2H), 3.15–3.2 (d, 2H), 7.14–7.15 (d, 2H), 7.19–7.21 (m, 1H), 7.26–7.32 (m, 3H), 8.30–8.31 (d, 2H).

Step E: 2-(R)-(3-(S)-((4-(5-Benzylpyrid-3-yl)piperidin-1-yl)methyl)-4-(S)-(3-fluorophenyl)pyrrolidin-1-yl)-tert-butylacetic acid A solution of Aldehyde 17 (0.065 mmol) was stirred with 15 mg 10% Pd/C in 1.5 mL methanol under 1 atm of hydrogen for 1 h. The catalyst was filtered off and the solvent was removed. The residue was dissolved in 1.5 ML DCE and 4-((5-benzyl)pyrid-3-yl)piperidine TFA (44 mg, 0.12 mmol, from Step D), triethylamine (0.02 mL, 0.12 mmol) and sodium triacetoxyborohydride (42 mg, 0.19 mmol) were added. The mixture was stirred overnight and then concentrated. The product was purified by preparative HPLC (C-18 stationary phase, 10%→90% acetonitrile/water/0.1% TFA) to provide 20 mg (47%) of the title compound as a TFA salt. $^1$H NMR (500 MHz, CDCl$_3$). δ1.22 (s, 9H), 2.05–2.13 (m, 4H), 2.87–2.93 (q, 1H), 3.01–3.18 (m, 4H), 3.3–3.45 (m, 2H), 3.52–3.62 (m, 3H), 3.65–3.71 (d, 1H), 3.97 (s, 1H), 4.01–4.08 (t, 1H), 4.18 (s, 2H), 4.23–4.28 (t, 1H), 7.07–7.13 (m, 1H), 7.2–7.26 (m, 4H), 7.30–7.35 (m, 2H), 7.43–7.48 (m, 2H), 8.19 (s, 1H), 858 (d, 2H). ESI-MS, M/z; (M+H)=544.5 (obs), 544.3 (calc.).

EXAMPLE 164

2-(R)-(3-(S)-((4-((1-(4-methylsulfonylbenzyl)-3-ethyl)pyrazol-4-yl)piperidine-1-yl)methyl)-4-(S)-(3-fluorophenyl)pyrrolidin-1-yl)-tert-butylacetic Acid Step A: N-tert-Butoxycarbonyl-4-piperidylacetaldehyde A solution of oxalyl chloride (2.4 mL, 27.5 mmol) in 125 mL DCM as cooled to −78 C and DMSO (3.3 mL, 47.1 mmol) was added slowly. After 10 in a solution of 2-(N-tert-butoxycarbonyl-4-piperidyl)ethanol (4.5 grams, 19.6 mol) in 10 mL DCM was added. The mixture was stirred for 20 min then triethylamine (13.6 mL, 98.1 mmol) was added and the mixture was warmed to room temperature. After 30 min the mixture was diluted with ethyl acetate and washed with water (3×). The organic portion was dried over sodium sulfate and concentrated. Flash chromatography (3/1 hexane/EtOAc) afforded 3.7 grams (83%) of the desired aldehyde. $^1$H NMR (400 MHz, CDCl$_3$). δ1.13–1.43 (m, 2H), 1.48 (s, 9H), 1.68–1.77 (m, 2H), 2.04–2.11 (m, 1H), 2.38–2.41 (d, 2H), 2.71–2.8 (m, 2H), 4.04–4.14 (m, 2H), 9.8 (s, 1H).

Step B: 3-Ethyl-4-(N-t-butoxycarbonylpiperid-4-yl)-1H-pyrazole

A solution of N-tert-Butoxycarbonyl-4-piperidylacetaldehyde (4.5 grams, 19.8 mmol, from Step A), and morpholine (1.7 mL, 19.8 mmol) in 100 mL benzene was refluxed using a dean-stark apparatus. After refluxing over night the mixture was concentrated to provide the enamine. The crude enamine was dissolved in 40 mL DCM and the solution was cooled to 10 C. Propionyl chloride (1.7 mL, 19.8 mmol) and then triethylamine (1.4 mL, 9.9 mmol) were added. The mixture was gradually warmed to room temperature and stirred for 40 h then concentrated. The residue was dissolved in 60 mL of ethanol and hydrazine (6.2 mL, 198 mmol) was added. The solution was refluxed for 5 h. The solvent was removed and ethyl acetate was added. The organic was washed with water and sat'd sodium chloride then dried over magnesium sulfate and concentrated. Flash chromatography (0.5% MeOH/DCM →2% MeOH/DCM) afforded 2.1 grams (38%) of the title compound. $^1$H NMR (400 MHz, CDCl$_3$). δ1.25–1.31 (t, 3H), 1.44–1.57 (m, 1H), 1.46 (s, 9H), 1.78–1.83 (s, 2H), 2.53–2.6 (m, 1H), 2.62–2.7 (q, 2H), 2.77–2.82 (m, 2H), 4.12–4.23 (m, 2H), 7.32 (s, 1H).

Step C: 4-((1-(4-methylsulfonylbenzyl)-3-ethyl)pyrazol-4-yl)-N-t-butoxylcarbonylpiperidine A dry flask was charged with 5 mL DMF and sodium hydride (224 mg, 60% dispersion in mineral oil, 5.6 mmol). A solution of 3-Ethyl-4-(N-t-butoxycarbonylpiperid-4-yl)-1H-pyrazole (1.3 grams, 4.7 mmol, from Step B) in 5 mL DMF was added. The mixture was stirred for 1 h at room temperature and a solution of (4-methylsulfonyl)benzyl chloride (1.05 grams, 5.2 mmol) in 5 mL DMF was added. After 3 h the solvent was removed and the product was purified by preparative HPLC (35% acetonitrile/water→85% acetonitrile/water, C-18 stationary phase) to give 0.5 grams of product as a mixture of isomeric N-alkylation products. The isomers were separated by preparative HPLC using a chiral stationary phase (Chiralcel-OJ, 1/1 hexane/ethanol) to provide 210 mg (10%) of the desired isomer along with 70 mg (3%) of the undesired isomer. The substitution pattern of both isomers was determined by NOE difference $^1$H NMR. $^1$H NMR (400 MHz, CDCl$_3$, desired isomer). δ1.25–1.31 (t, 3H), 1.38–1.47 (m, 1H), 1.46 (s, 9H), 1.8–1.85 (m, 2H), 2.5–2.6 (m, 1H), 2.6–2.66 (q, 2H), 2.75–2.82 (m, 2H), 3.03 (s, 3H), 4.13–4.22 (m, 2H), 5.32 (s, 2H), 7.13 (s, 1H), 7.28–7.31 (d, 2H), 7.89–7.91 (d, 2H).

Step D: 2-(R)-(3-(S)-((4-((1-(4-methylsulfonylbenzyl)-3-ethyl)pyrazol-4-yl)piperidine-1-yl)methyl)-4-(S)-(3-fluorophenyl)pyrrolidin-1-yl)-tert-butylacetic acid The title compound was prepared from Aldehyde 17 and 4-((1-(4-methylsulfonylbenzyl)-3-ethyl)pyrazol-4-yl)-N-t-butoxylcarbonyl piperidine (from Step C) using the procedure described in EXAMPLE Step E to provide the product as a TFA salt. $^1$H NMR (500 MHz, CDCl$_3$). δ1.18 (s, 9H), 1.15–1.21 (t, 3H), 1.44–1.61 (m, 2H), 1.74–1.83 (m, 2H), 1.99–2.06 (t, 1H), 2.18–2.23 (m, 1H), 2.39–2.44 (m, 2H), 2.52–2.62 (m, 3H), 7.72–2.8 (m, 1H), 2.84–2.9 (m, 1H), 3.02–3.08 (m, 1H), 3.09 (s, 3H), 3.15–3.21 (q, 1H), 3.32–3.4 (m, 3H), 3.81–3.92 (m, 2H), 5.35 (s, 2H), 6.98–7.02 (m, 1H), 7.15–7.2 9m, 2H), 7.35–7.37 (d, 2H), 7.43 (s, 1H), 7.898–7.91 (d, 2H). ESI-MS, M/z; (M+H)=639.4 (obs), 639.3 (calc.).

EXAMPLE 165

2-(R)-(3-(S)-((4-(4-Benzyl-1-ethyl-(1H-pyrazol-5-yl))piperidin-1-yl)methyl)-4-(S)-(3-fluorophenyl) pyrrolidin-1-yl)-3,(R)-cyclobutylbutyric Acid Step A: Cyclobutylacetic acid A solution of bromomethyl cyclobutane (26.5 grams, 178 mmol) and potassium cyanide (2.34 grams, 359 mmol) in 90 mL DMSO was heated to 50 C for 48 h. The mixture was diluted with ethyl acetate and washed with 1N NaOH. The organic layer was dried and concentrated. The crude material was suspended in 6N HCl and the mixture was refluxed overnight. The mixture was cooled and extracted with ether. The organic layer was dried over sodium sulfate and concentrated to afford 11.7 grams of product (25%) $^1$H NMR (400 MHz, CDCl$_3$). δ1.5–1.6 (m, 2H), 1.63–1.8 (m, 2H), 1.95–2.05 (m, 2H), 2.25 (d, 2H), 2.45–2.6 (m, 1H).

Step B: (R)-N-cyclobutylacetyl-4-benzyl oxazolidinone

A round bottom flask was charged with cyclobutyl acetic acid (6.8 grams, 59.8 mmol, from Step A) and 200 mL dry THF. The mixture was cooled to −78 C and triethylamine (10 mL, 71.8 mmol) was added. Pivaloyl chloride (8.1 mL, 65.8 mmol) was added and the mixture was warmed to 0 C and stirred for 1.5 h. A separate flask was charged with (R)-benzyl oxazolidinone and 100 mL THF. The solution was cooled to −78 C and a solution of n-butyllithium (44.9 mL, 1.6M in hexane, 71.8 mmol) was added dropwise via syringe. After warming to 0 C and stirring for 30 min this solution was added via cannula to the above flask containing the mixed anhydride. The resulting mixture was warmed to room temperature and stirred for 2.5 h. EtOAc was added and the mixture was washed with water and sat'd NaCl. The organic portion was dried over sodium sulfate and concentrated. Flash chromatography (15/1 hexane/EtOAc) afforded 11 grams (67%) of the desired acyl oxazolidinone. $^1$H NMR (400 MHz, CDCl$_3$). δ1.72–1.81 (m, 2H), 1.85–1.99 (m, 2H), 2.18–2.28 (m, 2H), 2.72–2.82 (m, 2H), 3.0–3.18 (m, 2H), 3.27–3.33 (dd, 1H), 4.15–4.23 (m, 2H), 4.63–4.7 (m, 1H), 7.18–7.38 (m, 5H).

Step C: N-((R)-2-cyclobutyl)propionyl-(R)-4-benzyl oxazolidinone (R)-N-cyclobutylacetyl-4-benzyl oxazolidinone (11 grams, 40.2 mmol, from Step B) was dissolved in 200 mL dry THF. The solution was cooled to −78 C under a nitrogen atmosphere. A solution of lithium hexamethyldisilazide (48.2 mL, 1.0M in THF, 48.2 mmol) was added and the mixture was stirred for 30 min. Iodomethane (3.75 mL, 60.3 mmol) was added and the mixture was gradually warmed to room temperature and quenched by adding water. The mixture was extracted with ethyl acetate and the organic portion was dried over sodium sulfate and concentrated. Flash chromatography (20/1 hexane/ethyl acetate) afforded 7.5 grams (65%) of the title compound. $^1$H NMR (400 MHz, CDCl$_3$). δ1.16 (d, 3H), 1.62–1.93 (m, 4H), 2.02–2.16 (m, 2H), 2.58–2.7 (m, 1H), 2.75–2.82 (dd, 1H), 3.22–3.3 (dd, 1H), 3.7–3.8 (m, 1H), 4.17–4.23 (m, 2H), 4.68–4.73 (m, 1H), 7.2–7.4 (m, 5H).

Step D: N-Methyl-N-methoxy-(R)-2-cyclobutylpropionamide

A flask was charged with 60 mL THF, N-((R)-2-cyclobutyl)propionyl-(R)-4-benzyl oxazolidinone (7.5 grams, 26.1 mmol, from Step C), and 32 mL water. The solution was cooled to 0 C and hydrogen peroxide (11.7 mL, 30%, 104 mmol) was added. Lithium hydroxide (1.25 grams, 52.2 mmol) was added and the mixture was stirred for 6 h at room temperature. The reaction was quenched with aqueous sodium sulfite and partitioned between water and methylene chloride. Sodium bicarbonate was added and the layers were separated. The aqueous layer was acidified with 2N HCl and extracted with ether. The ether layers were combined and dried over sodium sulfate then concentrated to give 2.9 grams (87%) of the desired acid. The acid (2.9 grams, 18.7 mmol) was dissolved in 25 mL NMP and BBTU (17.7 grams, 46.8 mmol), HOBt (9.5 grams, 70.1 mmol) and diisopropylethylamine (16.3 mL, 93.5 mmol) was added. N-O-dimethylhydroxylamine hydrochloride (3.65 grams, 37.4 mmol) was added and the mixture was stirred for 5 h. The mixture was then diluted with ether and washed with water and sat'd NaCl. The ether was removed to give a precipitate which was filtered off and washed with 1/1 ether/pentane. The ether/pentane washes were combined and concentrated. Flash chromatography (1/1 pentane/ether) afforded 2.62 grams (71%) of the desired amide. $^1$H NMR (400 MHz, CDCl$_3$). δ1.05 (d, 3H), 1.62–1.93 (m, 4H), 1.98–2.12 (m, 2H), 2.5–2.3 (m, 1H), 3.18 (s, 3H), 3.72 (s, 3H).

Step E: (R)-Cyclobutylpropiophenone

A dry flask was charged with N-Methyl-N-methoxy-(R)-2-cyclobutylpropionamide (2.62 grams, 15.4 mmol, from Step D). The vessel was purged with nitrogen and 40 mL THF was added. The mixture was cooled to −10 C and a solution of phenyllithium (30 mL, 1.8M, 53.9 mmol) was added. The solution was stirred for 1 h at −10 C then the reaction was quenched with sat'd ammonium chloride. The mixture was extracted with ethyl acetate and the organic portion was dried over sodium sulfate and concentrated. Flash chromatography (99/1 hexane/ethyl acetate) afforded 2.06 grams (70%) of the title compound. $^1$H NMR (400 MHz, CDCl$_3$). δ1.13 (d, 3H), 1.59–1.7 (m, 1H), 1.73–2.0 (m, 5H), 2.05–2.15 (m, 1H), 2.6–2.7 (m, 1H), 3.43–3.53 (m, 1H), 7.44–7.5 (t, 2H), 7.55–7.6 (m, 1H), 7.97–8.0 (d, 2H).

Step F: (R)-1-phenyl-(R)-2-cyclobutyl propanol

A dry flask was charged with 25 mL THF and a solution of L-selectride® (12.6 mL, 1M in THF, 12.6 mmol) was added. The solution was cooled to −78 C and a solution of (R)-Cyclobutylpropiophenone (2.38 grams, 12.6 mmol) in 5 mL THF was added. After stirring at −78 C for 1 h the was warmed to room temperature gradually overnight. Sat'd sodium bicarbonate was added and the mixture was extrated with ethyl acetate. The organic portion was washed with water and sat'd NaCl. The solvent was removed and the residue was dissolved in methanol (100 mL). Concentrated HCl (1 mL) was added and the mixture was stirred at 50 C for 15 hours. After removal of the solvent the product was purified by flash chromatography (100/1 hexane/ethyl acetate→20/1 hexane ethyl acetate) to afford 1.4 grams (58%) of product. $^1$H NMR (500 MHz, CDCl$_3$). δ0.68 (d, 3H), 1.64–1.98 (m, 6H), 2.02–2.09 (m, 1H), 2.11–2.19 (m, 1H), 4.58 (d, 1H), 7.23–7.38 (m, 5H).

Step G: (R)-1-phenyl-(S)-2-cyclobutyl propyl acetate

A solution of (R)-1-phenyl-(R)-2-cyclobutyl propanol (1.12 grams, 5.9 mmol, from Step F), triphenylphosphine (3.86 grams, 14.7 mmol), and acetic acid (0.84 mL, 14.7 mmol) in 20 mL dry THF was cooled to −78 C. Diisopropylazodicarboxylate (2.9 mL, 14.7 mmol) was added and the mixture was warmed to room temperature over 1 hour and stirred for 30 min. The solvent was removed and the residue was suspended in 95/5 hexane/ethyl acetate and filtered through a plug of silica eluting until all product had come through (to remove triphenylphosphine oxide). After removal of the solvent the product was purified by flash chromatography (99/1 hexane/ethyl acetate) to give 0.86 grams (67%) of the title compound. $^1$H NMR (500 MHz, CDCl$_3$). δ0.81 (d, 3H), 1.59–2.0 (m, 7H), 2.1 (s, 3H), 2.1–2.2 (m, 1H), 5.68 (d, 1H), 7.23–7.31 (m, 3H), 7.36–7.38 (m, 2H).

Step H: Benzyl-(2S)-hydroxy-(3R)-cyclobutyl butyrate

A solution of (R)-1-phenyl-(S)-2-cyclobutyl propyl acetate (0.98 grams, 4.49 mmol, from Step G), periodic acid (14.3 grams, 62.9 mmol) in 21 mL 1/1/1 CCl4/acetonitrile/water was heated to 32 C for Ruthenium trichloride (47 mg, 0.22 mmol) was added in three portions over 5 h. The mixture was cooled to 0 C, diluted with ethyl acetate and stirred for 20 min. The layers were separated and the organic portion was washed with water and sat'd sodium chloride then dried over sodium sulfate and concentrated. The residue was dissolved in 30 mL of methanol and 6 mL water. Potassium carbonate (2.5 grams, 18 mmol) was added and the mixture was stirred at 50 C overnight. The mixture was diluted with ether and the layers were separated. The aqueous layer was acidified with HCl and extracted with ethyl acetate (3×). The ethyl acetate portions were combined, dried over sodium sulfate and concentrated. The crude hydroxyacid was dissolved in 2 mL DMF and triethyl amine (1 mL, 7.2 mmol) was added. Benzyl bromide (0.86 mL, 7.2 mmol) was added and the mixture was stirred overnight. Ethyl acetate was added and the mixture was washed with water and sat'd sodium chloride. The organic portion was dried over sodium sulfate and concentrated. Flash chromatography (99/1→97/3 hexane/ethyl acetate) afforded 0.41 grams (37%) of the title compound. $^1$H NMR (500 MHz, CDCl$_3$). δ0.86 (d, 3H), 1.6–1.7 (m, 1H), 1.71–1.78 (m, 2H), 1.81–1.9 (m, 2H), 2.01–2.11 (m, 2H), 2.32–2.41 (m, 1I1), 2.62 (bs, 1H), 4.2 (s, 1H), 5.22 (dd, 2H), 7.33–7.41 (m, 5H).

Step I: 2-(R)-(3-(R)-Formyl-4-(S)-(3-fluorophenyl)pyrrolidin-1-yl)-3-(R)-cyclobutylbutyric acid, benzyl ester The title compound was prepared in a manner analogous to that described for Aldehyde 17 Steps B–D from Benzyl-(2S)-hydroxy-(3R)-cyclobutyl butyrate (from Step H) and Pyrrolidine 2 except that dichloromethane as used in place of DMF in the triflate displacement step (Aldehyde 17 Step C). $^1$H NMR (500 MHz, CDCl$_3$). δ0.86 (d, 3H), 1.6–2.05 (m, 9H), 2.16–2.23 (m, 1H), 2.61–2.7 (t, 1H), 2.92–2.98 (m, 1H), 3.08–3.17 (m, 2H), 3.2–3.23 (t, 1H), 3.52–3.6 (q, 1H), 5.19 (s, 2H), 6.88–7.02 (m, 3H), 7.21–7.26 (m, 1H), 7.31–7.41 (m, 5H) 9.65 (s, 1H).

Step J: 2-(R)-(3-(S)-((4-(4-Benzyl-1-ethyl-(1H-pyrazol-5-yl))piperidin-1-yl)methyl)-4-(S)-(3-fluorophenyl)pyrrolidin-1-yl)-3,(R)-cyclobutylbutyric acid The title compound was prepared from 2-(R)-(3-(R)-Formyl-4-(S)-(3-fluorophenyl)pyrrolidin-1-yl)-3-(R)-cyclobutylbutyric acid, benzyl ester (20 mg, 0.047 mmol) and Benzyl-1-ethyl-(1H-pyrazol-5-yl))-piperidine TFA (30 mg, 0.06 mmol, from EXAMPLE 8 Step F) using the procedure described in EXAMPLE Step G. $^1$H NMR (500 MHz, CDCl$_3$). δ0.83 (d, 3H), 1.38 (t, 3H), 1.5–3.6 (26H) 3.7 (s, 2H), 4.0 (q, 2H), 5.65 (s, 1H), 6.85–6.95 (m, 1H), 7.0–7.12 (m, 2H), 7.17–7.3 (m, 6H). ESI-MS, M/z; (M+H)=587.7 (obs), 587.4 (calc.).

EXAMPLE 166

2-(R)-(3-(S)-((4-(4-Benzyl-1-ethyl-(1H-pyrazol-5-yl))piperidin-1-yl)methyl)-4-(S)-(3-fluorophenyl)pyrrolidin-1-yl)-4,4-dimethylpentanoic acid Step A: (S)-2-Hydroxy,4,4-dimethylpentanoic acid benzyl ester A suspension of (S)-tert-butyl alanine (2.2 grams, 15.7 mmol) in 10 mL water and 10 mL dioxane was cooled to 0 C and a 2N sulfuric acid solution (8.3 mL, 16.7 mmol) was added. Next a solution of sodium nitrite (8.3 mL, 2N, 16.7 mmol) was added and the mixture was stirred overnight, gradually being allowed to reach room temperature. The mixture was saturated with sodium chloride and extracted with ethyl acetate (4×). The combined organics were dried and concentrated. The crude was taken up in 10 mL DMF and triethyl amine (23.5 mmol) and benzyl bromide (23.5 mmol) were added. After stirring overnight the mixture was diluted with ethyl acetate and washed 3× with water. The organic portion was a dried over sodium sulfate and concentrated. Flash chromatography (8/1 hexane/ethyl acetate) afforded 1.4 grams (40%) of the title compound $^1$H NMR (300 MHz, CDCl$_3$). δ1.0 (s, 9H), 1.48–1.6 (m, 1H), 1.77–1.83 (m, 1H), 4.15–4.19 (d, 1H).

Step B: 2-(R)-(3-(R)-Formyl-4-(S)-(3-fluorophenyl)pyrrolidin-1-yl)-4,4-dimethylpentanoic acid, benzyl ester The title compound was prepared in a manner identical to that described for Aldehyde 1 Steps A–C starting with pyrrolidine 2 and (S)-2-hydroxy-4,4-dimethylpentanoic acid benzyl ester (from Step A) $^1$H NMR (300 MHz, CDCl$_3$). δ0.97 (s, 9H), 1.5–1.6 (dd, 1H), 1.81–1.96 (dd, 1H), 2.68–2.76 (t, 1H), 2.9–2.97 (q, 1H), 3.13–3.32 (m, 3H), 3.5–3.6 (m, 2H), 5.1–5.23 (dd, 2H), 6.95–7.0 (m, 3H), 7.2–7.3 (m, 1H), 7.31–7.4 (m, 5H), 9.6 (s, 1H).

Step C: 2-(R)-(3-(S)-((4-(4-Benzyl-1-ethyl-(1H-pyrazol-5-yl))piperidin-1-yl)methyl)-4-(S)-(3-fluorophenyl)pyrrolidin-1-yl)-4,4-dimethylpentanoic acid A solution of 2-(R)-(3-(R)-Formyl-4-(S)-(3-fluorophenyl)pyrrolidin-1-yl)-4,4-dimethylpentanoic acid, benzyl ester (27 mg, 0.065 mmol, from Step B) in 2 mL methanol was stirred over 20 mg 10% Pd/C under 1 atm of hydrogen. After 1 h the mixture was filtered and concentrated. The crude material was dissolved in 2 mL DCE and 4-(4-Benzyl-1-ethyl-(1H-pyrazol-5-yl))-piperidine HCl (26 mg, 0.085 mmol, from EXAMPLE 8 Step F), triethylamine (21 μL, 0.15 mmol) and sodium triacetoxyborohydride (32 mg, 0.15 mmol) were added. The solution was stirred overnight then Boc anhydride (19 mg, 0.085 mmol) was added and stirring was continued for 3 h. The mixture was concentrated and the product was purified by flash chromatography (95/5 DCM/MeOH→95/5/0.5 DCM/MeOH/NH4OH) to afford 14 mg (37%) of the title compound. $^1$H NMR (500 MHz, CDCl$_3$). δ1.03 (s, 9H), 1.31–1.34 (t, 3H), 1.36–1.45 (m, 1H), 1.5–1.59 (m, 1H), 1.64–1.72 (m, 2H), 1.76–1.8 (d, 1H), 1.91–2.0 (m, 2H), 2.08–2.13 (t, 1H), 2.37–2.4 (dd, 1H), 2.46–2.6 (m, 2H), 2.77–2.8 (m, 2HO, 2.96–3.0 (d, 1H), 3.18–3.37 (m, 2H), 3.56–3.6 (d, 1H), 3.7–3.82 (m, 2H), 3.85 (s, 2H), 4.01–4.05 (q, 2H), 5.72 (s, 1H), 6.97–7.0 (t, 1H), 7.13–7.2 (m, 5H), 7.22–7.28 (m, 2H), 7.33–7.4 (m, 1H). ESI-MS, M/z; (M+H)=575.6 (obs), 575.37 (calc.).

EXAMPLE 167

2-(R)-(3-(S)-((4-(4-Benzyl-1-ethyl-(1 H-pyrazol-5-yl))piperidin-1-yl)methyl)-4-(S)-(3-fluorophenyl)pyrrolidin-1-yl)-3,3-trimethylenepentanioc Acid Step A: Ethyl 3,3-trimethylene acrylate A solution of triethylphosphonoacetate (17 mL, 85.6 mmol), in 150 mL dry THF was cooled to −78° C. A solution of sodium hexamethyldisilazide (86 mL, 1.0M in THF, 86 mmol) was added. The mixture was warmed to 0 C for 30 min and cyclobutanone (5 grams, 71.3 mmol) was added. The mixture was warmed to room temperature and stirred overnight. Sat'd ammonium chloride was added and the mixture was extracted with ethyl acetate. The organic was dried over sodium sulfate and concentrated. Flash chromatography (30/1 hexane/ether) afforded 8.0 grams (80%) of the desired compound. $^1$H NMR (300 MHz, CDCl$_3$). δ1.25 (t, 3H), 2.0–2.2 (p, 2H), 2.8–2.9 (t, 2H), 3.1–3.2 (t, 2H), 4.1–4.2 (q, 2H), 5.58 (s, 1H).

Step B: (R)-1-phenylethylcarboxymethyl ether

A two neck flask fitted with a reflux condenser and an addition funnel was flushed with nitrogen and charged with sodium hydride (16.2 grams, 60% dispersion in mineral oil, 405 mmol) and 300 mL dry THF. A solution of (R)-1-phenylethanol (15 mL, 135 mmol, in 100 mL THF) was added and the mixture was heated to reflux. A solution of bromoacetic acid (22.5 grams, 162 mmol in 100 mL THF) was added dropwise over 30 min. The resulting mixture was refluxed overnight. After cooling to room temperature the reaction mixture was carefully quenched with water and 500 mL of 1N NaOH. The solution was washed with ether (2×) and then acidified to pH1 with conc HCl. The resulting acid solution was extracted with ethyl acetate (3×200 mL) and the combined organic portions were dried over sodium sulfate and concentrated to afford 20.9 grams (85%) of the desired product. $^1$H NMR (400 MHz, CDCl$_3$). δ1.57 (d, 3H), 3.92–4.13, (dd, 2H), 4.6 (q, 1H), 7.3–7.42 (m, 5H).

Step C: 3,3-trimethyleneprop-2-enyl-(R)-1-phenylethoxyacetate

A solution of ethyl 3,3-trimethylene acrylate (7.8 grams, 55.6 mmol, from Step A) in 200 mL ether was cooled to −20 C and a solution of DIBAL (78 mL, 1.5M in toluene, 116.8 mmol) was added dropwise. The mixture was warmed to room temperature and carefully quenched with water then sodium hydroxide. The layers were separated and the organic phase was dried and concentrated (the product is somewhat volatile). In a separate flask (R)-1-phenylethylcarboxymethyl ether (4.7 grams, 26 mmol) was dissolved in 100 mL dry THF and N-methylmorpholine (3.4 mL, 31.3 mmol) was added. Pivaloyl chloride (3.5 mL, 28.6 mmol) was added and the mixture was warmed to room temperature and stirred for 30 min. A solution of ethyl 3,3-trimethylene acrylate (3.8 grams, 39 mmol) and DMAP (159 mg, 1.3 mmol) in 10 mL THF was added and the mixture was stirred overnight. Ethyl acetate was added and the mixture was washed with water, 2N HCl and sat'd NaCl. The organic portion was dried over sodium sulfate and concentrated. Flash chromatography (20/1 hexane/EtOAc) gave 4.5 grams (66%) of product.

Step D: (S)-2-((R)-1-phenylethoxy)-3,3-trimethylene pent-4-enoic acid benzyl ester A solution of 3,3-trimethyleneprop-2-enyl-(R)-1-phenylethoxyacetate (4.5 grams, 17.3 mmol) in 60 mL THF was cooled to −78° C. TMSCI (9.1 mL, 72 mmol) was added followed by potassium hexamethyldisilazide (77 mL, 0.5M in toluene, 38.5 mmol). The mixture was stirred for 30 min then warmed to room temperature and stirred for an additional hour. 1N NaOH was added and the mixture was washed with ether. The aqueous portion was acidified with conc. HCl and extracted with ethyl acetate. The EtOAc portion was dried and concentrated to give 4.5 grams (100%) of the desired product as a 2.5/1 ratio of diastereomers. The crude acid was dissolved in 15 mL DMF and diisopropylethyl amine (4.6 mL, 26.5 mmol) was added. Benzyl bromide (2.7 mL, 22.9 mmol) was added and the mixture was stirred overnight. Methyl-t-butyl ether was added and the mixture was washed with water, 2N HCl and sat'd NaCl. The organic layer was dried over sodium sulfate and concentrated. Flash chromatography (20/1 hexanelmethyl-t-butyl ether) gave 2.6 grams of the desired major diastereomer. $^1$H NMR (400 MHz, CDCl$_3$). δ1.5 (d, 3H), 1.8–2.0 (m, 4H), 2.28–2.4 (m, 2H), 3.93 (s, 1H), 4.55 (q, 1H), 4.82–4.95 (dd, 2H), 5.16–5.18 (m, 2H), 5.93–6.01 (dd, 1H), 7.2–7.4 (m, 10H).

Step E: (S)-2-hydroxy-3,3-trimethylene pent-4-enoic acid benzyl ester

A solution of (S)-2-((R)-1-phenylethoxy)-3,3-trimethylene pent-4-eneoic acid benzyl ester (2.6 grams, 7.4 mmol) in 50 mL 1/1 TFA/DCM was stirred for 30 min then concentrated. Flash chromatography (6/1 Hexane/EtOAc) afforded 1.6 grams 88% of (S)-2-hydroxy-3,3-trimethylene pent-4-enoic acid benzyl ester. $^1$H NMR (400 MHz, CDCl$_3$). δ1.6, (bs, 1H), 1.8–2.1 (m, 4H), 2.2–2.28 (m, 2H), 4.3 (s, 1H), 5.1–5.23 (m, 4H), 5.95–6.05 (dd, 1H), 7.29–7.32 (m, 5H).

Step F: 2-(R)-(3-(R)-Formyl-4-(S)-(3-fluorophenyl)pyrrolidin-1-yl)-3,3-trimethylenepent-4-eneoic acid, benzyl ester The title compound was prepared from (S)-2-hydroxy-3,3-trimethylene pent-4-eneoic acid benzyl ester (from Step E) and Pyrrolidine 2 according to the procedures described for Aldehyde 17 Steps B–D. $^1$H NMR (400 MHz, CDCl$_3$). δ1.7–1.8 (m, 1H), 1.82–1.96 (m, 2H), 2.1–2.2 (m, 2H), 2.25–2.38 (m, 1H), 2.7–2.8 (t, 1H), 2.83–2.97 (m, 1H), 3.07–3.22 (m, 3H), 3.46 (s, 1H), 3.5–3.6 (q, 1H), 5.15–5.25 (m, 4H), 6.14–6.2 (dd, 1H), 6.88–7.02 (m, 3H), 7.2–7.27 (m, 1H), 7.38–7.42 (m, 5H), 9.6 (s, 1H).

Step G: 2-(R)-(3-(S)-((4-(4-Benzyl-1-ethyl-(1H-pyrazol-5-yl))piperidin-1-yl)methyl)-4-(S)-(3-fluorophenyl)pyrrolidin-1-yl)-3,3-trimethylene pentanoic acid A solution of -(R)-(3-(R)-Formyl-4-(S)-(3-fluorophenyl)pyrrolidin-1-yl)-3,3-trimethylenepent-4-enoic acid, benzyl ester (52 mg, 0.12 mmol, from Step F), Benzyl-1-ethyl-(1H-pyrazol-5-yl))-piperidine HCl (55 mg, 0.161 mmol, from EXAMPLE 8 Step F), triethylamine (0.052 mL, 0.37 mmol) and sodium triacetoxyborohydride (52 mg, 0.24 mmol) was stirred overnight. The mixture was passed through a plug of silica eluting with 19/1 DCM/MeOH and concentrated. The residue was taken up in 3 mL MeOH and stirred over 50 mg 10% Pd/C for 3 h under a hydrogen atmosphere. The catalyst was filtered off and the product was isolated by flash chromatography (95/5 DCM/MeOH→95/5/0.5 DCM/MeOH/NH4OH) to afford 43 mg (60%) of the title compound. $^1$H NMR (500 MHz, CDCl$_3$). δ1.13–1.16 (t, H), 1.28–1.32 (t, 3H), 1.38–2.03 (m, 10H), 2.1–2.18 (t, 1H), 2.3–2.38 (q, 1H), 2.39–2.43 (m, 1H), 2.55–2.63 (m, 3H), 2.7–2.83 (m, 2H), 2.96–3.0 (d, 2H), 3.14–3.21 (q, 1H), 3.38–3.47 (m, 2H), 3.48–3.59 (m, 2H), 3.7 (s, 1H), 3.85 (s, 2H), 4.0–4.04 (q, 2), 5.7 (s, 1H), 6.97–7.0 (t, 1H), 7.13–7.2 (m, 5H), 7.22–7.28 (m, 2H), 7.33–7.4 (m, 1H). ESI-MS, M/z; (M+H)=587.56 (obs), 587.37 (calc.).

EXAMPLES 168–215

Examples 168–215 were prepared using procedures analogous to those described in Example 167.

TABLE 11

| EXAMPLE # | Rᵃ | Rᵇ | Z | ESI-MS M/z (M + H) |
|---|---|---|---|---|
| 168 | 2-ethylpyridin-3-yl | cyclobutylmethyl | F | 494.5 |
| 169 | 5-benzylpyridin-3-yl | cyclopropylmethyl | F | 542.5 |
| 170 | 5-benzylpyridin-3-yl | isobutyl | H | 512.5 |
| 171 | 5-benzylpyridin-3-yl | isobutyl | F | 530.5 |
| 172 | 2-benzylpyrimidin-4-yl | cyclobutylmethyl | F | 557.5 |
| 173 | thieno[3,2-d]pyrimidin-4-yl | cyclobutylmethyl | F | 523.4 |

TABLE 11-continued
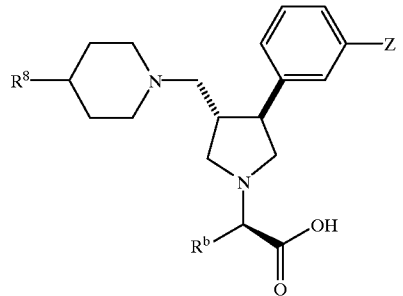
| EXAMPLE # | Rᵃ | Rᵇ | Z | ESI-MS M/z (M + H) |
|---|---|---|---|---|
| 174 | 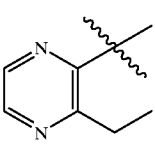 | 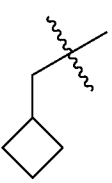 | F | 495.5 |
| 175 | 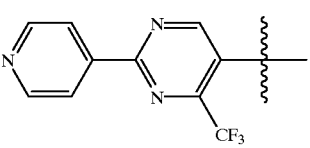 | 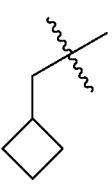 | F | 612.4 |
| 176 | 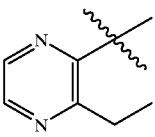 | 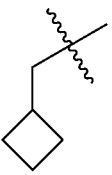 | F | 556.5 |
| 177 | 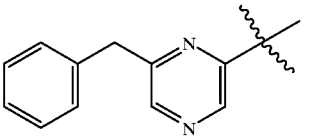 | 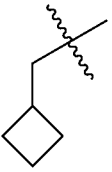 | F | 557.5 |
| 178 | 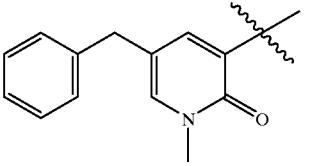 | 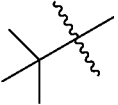 | F | 574.5 |
| 179 | 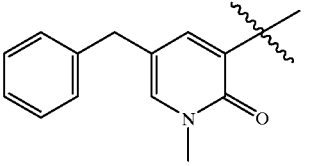 | 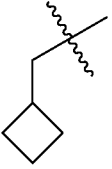 | F | 586.5 |

TABLE 11-continued
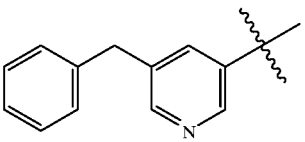
| EXAMPLE # | R^a | R^b | Z | ESI-MS M/z (M + H) |
|---|---|---|---|---|
| 180 | 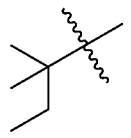 | 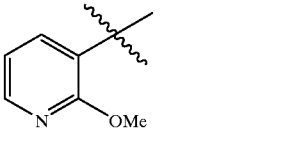 | F | 558.5 |
| 181 | 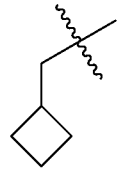 | 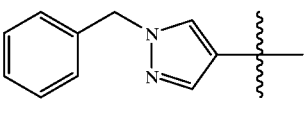 | F | 496.5 |
| 182 | 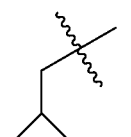 | 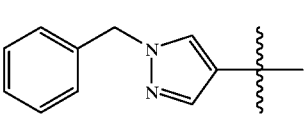 | F | 545.5 |
| 183 | 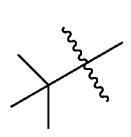 | 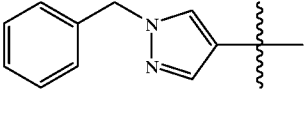 | F | 533.5 |
| 184 | 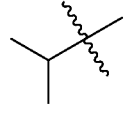 | 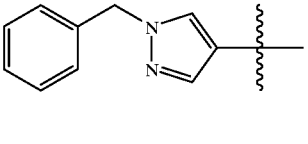 | F | 519.5 |
| 185 | 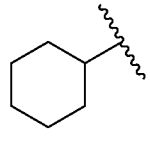 | 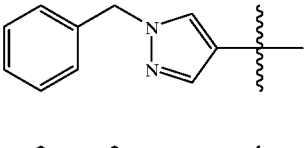 | F | 559.5 |
| 186 | 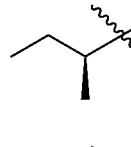 | 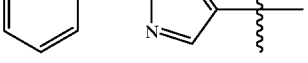 | F | 533.5 |
| 187 | 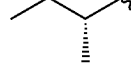 | | F | 533.5 |

TABLE 11-continued
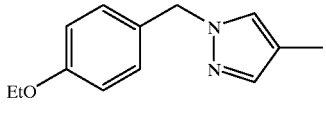
| EXAMPLE # | Rᵃ | Rᵇ | Z | ESI-MS M/z (M + H) |
|---|---|---|---|---|
| 188 | 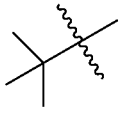 | 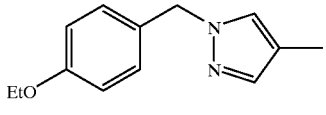 | F | 577.5 |
| 189 | 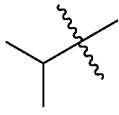 | 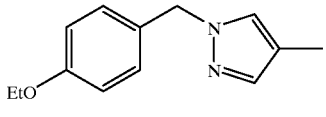 | F | 563.5 |
| 190 | 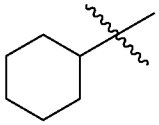 | 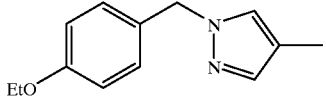 | F | 603.5 |
| 191 | 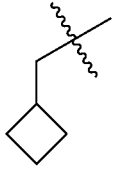 | 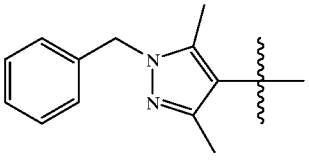 | F | 589.5 |
| 192 | 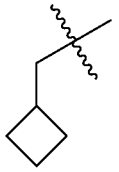 | 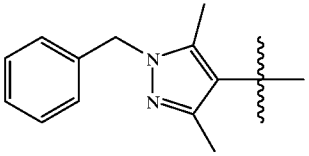 | F | 573.5 |
| 193 | 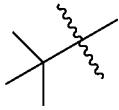 | 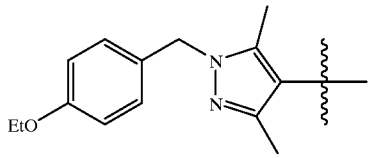 | F | 561.6 |
| 194 | 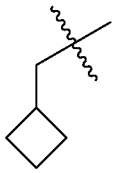 | | F | 617.5 |

TABLE 11-continued
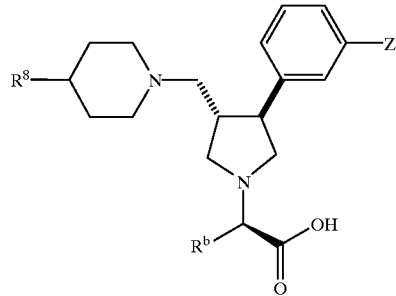
| EXAMPLE # | Rª | Rᵇ | Z | ESI-MS M/z (M + H) |
|---|---|---|---|---|
| 195 | 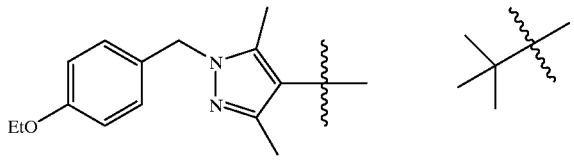 | 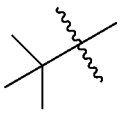 | F | 605.5 |
| 196 | 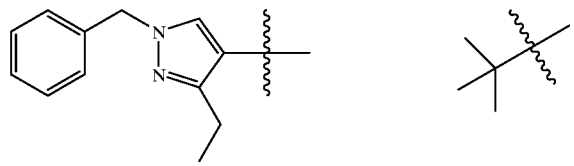 | 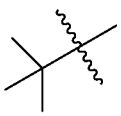 | F | 561.6 |
| 197 | 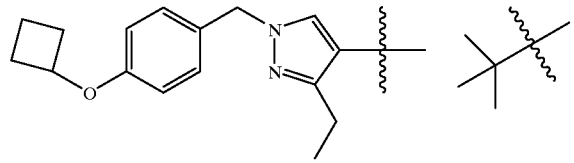 | 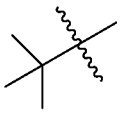 | F | 631.6 |
| 198 | 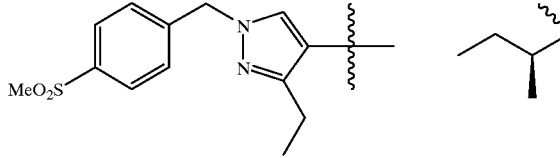 | 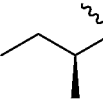 | F | 639.5 |
| 199 | 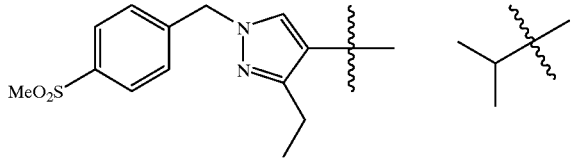 | 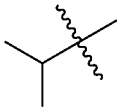 | F | 625.4 |
| 200 | 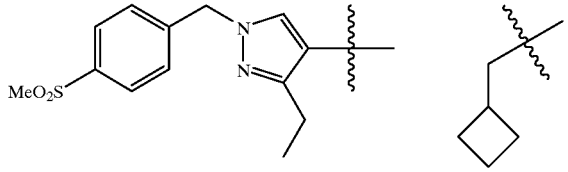 | 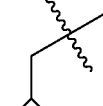 | F | 651.5 |

TABLE 11-continued

| EXAMPLE # | R$^a$ | R$^b$ | Z | ESI-MS M/z (M + H) |
|---|---|---|---|---|
| 201 | | | F | 665.5 |
| 202 | | | F | 600.4 |
| 203 | | | F | 653.5 |
| 204 | | | F | 619.4 |
| 205 | | | F | 631.5 |
| 206 | | | F | 487.7 |

TABLE 11-continued

| EXAMPLE # | Rª | Rᵇ | Z | ESI-MS M/z (M + H) |
|---|---|---|---|---|
| 207 | | | F | 561.5 |
| 208 | | | F | 493.3 |
| 209 | | | F | 578.4 |
| 210 | | | F | 507.4 |
| 211 | | | F | 564.3 |
| 212 | | | F | 561.5 |

TABLE 11-continued

| EXAMPLE # | R$^a$ | R$^b$ | Z | ESI-MS M/z (M + H) |
|---|---|---|---|---|
| 213 | 3-benzyl-1-ethyl-pyrazol-5-yl | CH$_2$CH(OMe)- | F | 549.3 |
| 214 | 3-benzyl-1-ethyl-pyrazol-5-yl | CH(CH$_3$)(CF$_3$)- | F | 601.4 |
| 215 | 3-benzyl-1-ethyl-pyrazol-5-yl | CH$_2$C(CF$_3$)- | F | 587.4 |

EXAMPLE 216

2-(R)-(2-Methyl-3-(S)-((4-(3-benzyl-1-ethyl-(1H-pyrazol-5-yl))piperidin-1-yl)methyl)-4-(S)-(3-fluorophenyl)pyrrolidin-1-yl)-3-(cyclopropyl) propionic Acid Step A: 3-(R)-((tert-Butyldimethylsilyloxy)methyl)-4-(S)-(3-fluorophenyl)-1-tert-butoxycarbonylpyrrolidine Di-tert-butyl dicarbonate (0.74 g, 3.4 mmol) was added to a solution of pyrrolidine 2 (1.0 g, 3.4 mmol) in 50 mL of 2:1 THF/water. The reaction mixture was stirred at room teperature overnight, then diluted with ethyl acetate and washed with 1N HCl, 1N NaOH, and brine. The solution was dried over MgSO$_4$, filtered, and concentrated to provide 1.4 g (98% yield) of the title compound. $^1$H NMR (300 MHz, CDCl$_3$) δ0.00 (s, 6H), 0.87 (s, 9H), 1.50 (s, 9H), 2.38–2.48 (m, 1H), 3.17–3.44 (m, 3H), 3.44–3.52 (m, 1H), 3.59–3.69 (m, 1H), 3.72–3.91 (m, 2H), 6.93–6.98 (m, 2H), 7.00–7.03 (m, 1H), 7.25–7.35 (m, 1H); ESI-MS (M+H): 410.1; HPLC A: 5.16 min.

Step B: 2-Methyl-3-(R)-((tert-butyldimethylsilyloxy) methyl)-4-(S)-(3-fluorophenyl)-1-tert-butoxycarbonylpyrrolidine N,N,N',N'-Tetramethylethylenediamine (0.268 mL, 2.4 mmol) was added to a solution of 3-(R)-((tert-butyldimethylsilyloxy)methyl)-4-(S)-(3-fluorophenyl)-1-tert-butoxycarbonylpyrrolidine (1.0 g, 2.4 mmol, from Step A) in 5 mL of diethyl ether at −78° C. under nitrogen. sec-Butyllithium (2.2 mL, 1.3M in cyclohexane, 2.8 mmol) was then added dropwise. After 45 min., (MeO)$_2$SO$_2$ (0.298 mL, 4.8 mmol) was added, and the reaction mixture was slowly warmed to room temperature overnight. The reaction was quenched with 5 mL of sat. aq. ammonium chloride, and the mixture was partitioned between diethyl ether and water. The aqueous layer was extracted three times with diethyl ether and the combined organic extracts were dried over Na$_2$SO$_4$. Flash chromatography (95:5 hexane:ethyl acetate) provided 210 mg (21% yield) of the title compound, contaminated with small amounts of the other regioisomer. ESI-MS (M+H): 424.3; HPLC A: 5.33 min.

Step C: 2-(R)-(2-Methyl-3-(R)-hydroxymethyl-4-(S)-(3-fluorophenyl)pyrrolidin-1-yl)-3-(cyclopropyl)propionic acid, benzyl ester 2-Methyl-3-(R)-((tert-butyldimethylsilyloxy)methyl)-4-(S)-(3-fluorophenyl)-1-tert-butoxycarbonylpyrrolidine (210 mg, 0.5 mmol, from Step B) was dissolved in 6 mL of a solution of 1% HCl in methanol and heated to 50° C. overnight. The solution was concentrated and converted to the free base by solid phase extraction (column: Varian SCX, loading: methanol, elution: 2M ammonia in methanol). This material (60 mg, 0.29 mmol) was dissolved in 1 mL of CH$_2$Cl$_2$. Diisopropylethylamine (0.061 mL, 0.35 mmol) was added, followed by hydroxy ester 9 (102 mg, 0.29 mmol).

The reaction mixture was stirred under nitrogen for 1.5 h, and was then diluted with $CH_2Cl_2$, washed with 1N NaOH and dried over $Na_2SO_4$. The solution was concentrated and purified by preparative HPLC (column: YMC combiprep ODS-A 20×50 mm, gradient: 10% acetonitrile/water w/0.1% TFA to 100% acetonitrile/water w/0.1% TFA over 8 min, then ramp to 10% acetonitrile/water w/0.1% TFA over 2 min, flow: 20 mL/min) to afford 87 mg (73% yield) of the title compound. $^1$H NMR (400 MHz, $CDCl_3$) δ0.00–0.08 (m, 1H), 0.15–0.21 (m, 1H), 0.36–0.43 (m, 1H), 0.43–0.55 (m, 1H), 0.62–0.75 (m, 1H), 1.55 (d, 3H), 1.74–1.81 (m, 1H), 2.09–2.17 (m, 1H), 2.30–2.40 (m, 1H), 3.39–3.58 (m, 3H), 3.60–3.64 (m, 1H), 3.64–3.73 (m, 1H), 4.18–4.22 (m, 1H), 4.24–4.32 (m, 1H), 5.23–5.38 (m, 2H), 6.94–6.98 (m, 1H), 7.05–7.10 (m, 1H), 7.16–7.20 (m, 1H), 7.26–7.35 (m, 1H), 7.38–7.46 (m, 5H); ESI-MS (M+H): 412.5; HPLC A: 1.79 min.

Step D: 2-(R)-(2-Methyl-3-(R)-formyl-4-(S)-(3-fluorophenyl)pyrrolidin-1-yl)-3-(cyclopropyl)propionic acid, benzyl ester Oxalyl chloride (0.022 mL, 0.25 mmol) was added to 5 mL of $CH_2Cl_2$ in a dry flask under nitrogen. The solution was cooled to −78° C., DMSO (0.040 mL, 0.57 mmol) was added, and the reaction mixture was stirred for 15 minutes. A solution of 2-(R)-(2-Methyl-3-(R)-hydroxymethyl-4-(S)-(3-fluorophenyl)pyrrolidin-1-yl)-3-(cyclopropyl)propionic acid, benzyl ester (88 mg, 0.21 mmol, from Step C) in 0.75 mL of $CH_2Cl_2$ was added, and the reaction mixture was stirred at −78° C. for 30 min. Triethylamine (0.153 mL, 1.1 mmol) was added and the reaction mixture was warmed to room temperature, diluted with $CH_2Cl_2$ and washed twice with 1N NaOH and brine. The solution was dried over $Na_2SO_4$, filtered and concentrated to provide 54 mg (63% yield) of the title compound. $^1$H NMR (400 MHz, $CDCl_3$) δ0.02–0.19 (m, 2H), 0.39–0.55 (m, 2H), 0.78–0.86 (m, 1H), 1.28 (d, 3H), 1.50–1.57 (m, 1H), 1.78–1.85 (m, 1H), 2.60–2.66 (m, 1H), 3.05–3.15 (m, 2H), 3.36–3.47 (m, 2H), 3.69–3.75 (m, 1H), 5.15–5.26 (m, 2H), 6.89–6.96 (m, 1H), 7.00–7.04 (m, 2H), 7.21–7.30 (m, 1H), 7.32–7.43 (m, 5H), 9.57 (d, 1H); ESI-MS (M+H): 410.3; HPLC A: 2.54 min.

Step E: 2-(R)-(2-Methyl-3-(S)-((4-(3-benzyl-1-ethyl-(1H-pyrazol-5-yl))piperidin-1-yl)methyl)-4-(S)-(3-fluorophenyl)pyrrolidin-1-yl)-3-(cyclopropyl)propionic acid 2-(R)-(2-Methyl-3-(R)-formyl-4-(S)-(3-fluorophenyl) pyrrolidin-1-yl)-3-(cyclopropyl)propionic acid, benzyl ester (54 mg, 0.13 mmol, from Step D) and 4-(3-benzyl-1-ethyl-(1H-pyrazol-5-yl))piperidine trifluoroacetate (58 mg, 0.17 mmol, from Example 1, Step C) were reacted via the procedure described in Example 1, Steps D and E to afford 34.3 mg (46% yield) of the title compound. $^1$H NMR (400 MHz, $CDCl_3$) δ0.04–0.11 (m, 1H), 0.14–0.20 (m, 1H), 0.41–0.49 (m, 1H), 0.51–0.57 (m, 1H), 0.68–0.75 (m, 1H), 1.23 (t, 3H), 1.63 (d, 3H), 1.80–2.10 (m, 6H), 2.65–2.78 (m, 1H), 2.84–2.98 (m 2H), 3.00–3.10 (m, 2H), 3.16–3.23 (m, 1H), 3.30–3.40 (m, 1H), 3.50–3.68 (m, 4H), 4.02 (s, 2H), 4.15–4.20 (m, 1H), 4.20–4.30 (m, 3H), 5.24 (d, 1H), 5.39 (d, 1H), 5.93 (s, 1H), 7.02–7.44 (m, 14 H); ESI-MS (M+H): 663.9; HPLC A: 2.04 min.

EXAMPLE 217

Dihydro-3-(R)-(3-(S)-((4-(3-benzyl-1-ethyl-(1H-pyrazol-5-yl))piperidin-1-yl)methyl)-4-(S)-(3-fluorophenyl)-pyrrolidin-1-yl)-4,4-dimethyl-2(3H) furanone Step A: Dihydro-3-(S)-trifluoromethanesulfonoxy-4,4-dimethyl-2(3H)furanone Trifluoromethylsulfonic anhydride (3.2 mL, 27.5 mmol) was added to a solution of (S)-pantolactone (3.0 g, 23.1 mmol) and lutidine (4.5 mL, 27.6 mmol) in 60 mL of $CH_2Cl_2$ at −78° C. under nitrogen. The reaction mixture was warmned to room temperature. After 1.5 h., the reaction was re-cooled to −78° C., and an additional 0.5 mL (6.3 mmol) of trifluoromethylsulfonic anhydride was added. After warming to room temperature and stirring for 2 h., the mixture was diluted with sat. aq. $NaHCO_3$ and extracted with ethyl acetate. The organic layer was dried over $Na_2SO_4$, filtered and concentrated. Flash chromatography (85:15 hexane:ethyl acetate) provided 5.2 g (86% yield) of the title compound. $^1$H NMR (400 MHz, $CDCl_3$). δ1.25 (s, 3H), 1.33 (s, 3H), 4.08 (d, 1H, J=9.2 Hz), 4.16 (d, 1H, J=9.2 Hz), 5.09 (s, 1H).

Step B: Dihydro-3-(R)-(3-(R)-((t-butyldimethylsilyloxy) methyl)4-(S)-(3-fluorophenyl)-pyrrolidin-1-yl)-4,4-dimethyl-2(3H)furanone Pyrrolidine 2 (3.07g, 10 mmol) was added to a solution of dihydro-3-(S)-trifluoromethanesulfonoxy-4,4-dimethyl-2 (3H)furanone (2.0 g, 7.6 mmol, from Step A) in 10 mL of dry DMF. Diisopropylethylamine (2.12 mL, 12.2 mmol) was then added, and the reaction mixture was stirred at 40° C. overnight. The mixture was cooled, diluted with diethyl ether, and washed with water and brine. The solution was dried over $Na_2SO_4$, filtered and concentrated. Flash chromatography (9:1 hexane:ethyl acetate) afforded 450 mg (14% yield) of the title compound. $^1$H NMR (300 MHz, $CDCl_3$). δ0.00 (s, 6H), 0.83 (s, 9H), 1.15 (s, 3H), 1.22 (s, 3H), 2.39–2.48 (m, 1H), 2.95–3.20 (m, 6H), 3.50–3.63 (m, 2H), 3.85–3.96 (m, 2H), 6.82–6.92 (m, 1H), 7.00–7.09 (m, 2H), 7.19–7.25 (m, 1H). ESI-MS. M/z; (M+H)=422.6.

Step C: Dihydro-3-(R)-(3-(R)-(hydroxymethyl)-4-(S)-(3-fluorophenyl)-pyrrolidin-1-yl)-4,4-dimethyl-2(3H) furanone Tetrabutylammonium fluoride (3.6 mL, 1N in THF, 3.6 mmol) was added to a solution of dihydro-3-(R)-(3-(R)-((t-butyldimethylsilyloxy)methyl)-4-(S)-(3-fluorophenyl)-pyrrolidin-1-yl)-4,4-dimethyl-2(3H)furanone (500 mg, 1.2 mmol, from Step A) in 1 mL of THF. After 2 h. at room temperature, the solution was diluted with diethyl ether and washed with 1N NaOH and brine. The solution was dried over $Na_2SO_4$, filtered and concentrated. Flash chromatography (1:1 hexane:ethyl acetate) provided 203 mg (55% yield) of the title compound. $^1$H NMR (300 MHz, $CDCl_3$). δ1.17 (s, 3H), 1.22 (s, 3H), 1.80–1.90 (m, 1H), 2.39–2.52 (m, 1H), 3.03–3.20 (m, 5H), 3.25–3.32 (m, 1H), 3.58–3.67 (m, 1H), 3.69–3.78 (m, 1H), 3.88–3.98 (m, 2H), 6.85–6.95 (m, 1H), 7.00–7.10 (m, 2H), 7.21–7.32 (m, 1H). ESI-MS. M/z; (M+H)=308.2.

Step D: Dihydro-3-(R)-(3-(R)-formyl-4-(S)-(3-fluorophenyl)-pyrrolidin-1-yl)-4,4-dimethyl-2(3H) furanone Dimethylsulfoxide (0.121 mL, 1.7 mmol) was added to a solution of oxalyl chloride (0.07 mL, 0.8 mmol) in 10 mL of $CH_2Cl_2$ at −78° C. under nitrogen. The reaction mixture was stirred at −78° C. for 20 min., then a solution of dihydro-3-(R)-(3-(R)-(hydroxymethyl)-4-(S)-(3-fluorophenyl)-pyrrolidin-1-yl)-4,4-dimethyl-2(3H)furanone (200 mg, 0.65 mmol) in 1 mL of $CH_2Cl_2$ was added. The mixture was stirred at −78° C. for an additional 45 min., then triethylamine (0.46 mL, 3.3 mmol) was added and the cold bath was removed. After the reaction mixture had warmed to room temperature, it was diluted with $CH_2Cl_2$ and washed with 1N NaOH and brine. The solution was dried over $Na_2SO_4$, filtered and concentrated to afford 100 mg (50% yield) of the title compound. $^1$H NMR (400 MHz, $CDCl_3$). δ1.17 (s, 3H), 1.24 (s, 3H), 3.08–3.24 (m, 4H), 3.35 (t, 1H, J=8.4 Hz), 3.55 (dd, 1H, J=5.9, 9.6 Hz), 3.66 (dd, 1H, J=7.9, 16 Hz), 3.91 (d, 1H, J=9.0 Hz), 3.98 (d, 1H, J=9.0 Hz), 6.95–6.97 (m, 1H), 7.04 (dt, 1H, J=2.1, 10 Hz), 7.10 (d, 1H, J=7.8 Hz), 7.27–7.32 (m, 1H), 9.71 (d, 1H, J=2.0 Hz). ESI-MS. M/z; (M+H)=306.2.

Step E: Dihydro-3-(R)-(3-(S)-((4-(3-benzyl-1-ethyl-(1H-pyrazol-5-yl))piperidin-1-yl)methyl)-4-(S)-(3-fluorophenyl)-pyrrolidin-1-yl)-4,4-dimethyl-2(3H)furanone Diisopropylethylamine (0.018 mL, 0.1 mmol) was added to a solution of 4-(3-benzyl-1-ethyl-(1H-pyrazol-5-yl)) piperidine trifluoroacetate (37 mg, 0.1 mmol, from Example 1, Step C) in 0.5 mL of 1,2-dichloroethane (DCE). A solution of dihydro-3-(R)-(3-(R)-formyl-4-(S)-(3-fluorophenyl)-pyrrolidin-1-yl)-4,4-dimethyl-2(3H)furanone (25 mg, 0.082 mmol, from Step D) in 0.5 mL of DCE was then added, followed by a slurry of sodium triacetoxyborohydride (30 mg, 0.144 mmol) in 0.5 mL of DCE. The reaction mixture was mixed well, then allowed to stand at room temperature for 2 h. The mixture was concentrated and purified by preparative HPLC (column: YMC combiprep ODS-A 20×50 mm, gradient: 10% acetonitrile/water w/0.1% TFA to 100% acetonitrile/water w/0.1% TFA over 8 min, then ramp to 10% acetonitrile/water w/0.1% TFA over 2 min, flow: 20 mL/min), followed by conversion to the free base by solid phase extraction (column: Varian SCX, loading: methanol, elution: 2.0M ammonia in methanol) to afford 17.2 mg (37% yield) of the title compound. ESI-MS. M/z; (M+H)=559.7; HPLC A: 2.34 min.

EXAMPLES 218–219

THERE ARE NO EXAMPLES 218 AND 219

EXAMPLE 220

α-(R)-(3-(S)-((4-(4-Benzyl-2-difluoromethyl-(imidazo-1-yl))piperidin-1-yl)methyl)-4-(S)-(3-fluorophenyl)pyrrolidin-1-yl)-isopropylacetic Acid Step A: 1-N-Benzyl-4-N-(2-hydroxy-3-phenylprop-1-yl)-4-aminopiperidine A mixture of 1-N-benzyl-4-aminopiperidine and 2,3-epoxypropyl benzene in methanol was refluxed for 3 hours. After removal of methanol in vacuo, the crude reaction mixture was purified by flash chromatography on silica. ESI-MS 311 (M+H); HPLC A: 1.96 min.

Step B: 1-N-Benzyl-4-N-difluoroaceto-4-N-(2-hydroxy-3-phenylprop-1-yl)-4-aminopiperidine A mixture of difluoroacetic acid, DIC and N-hydroxysuccinamide in dichloromethane was stirred for 25 min. before it was filtered and added to a dichloromethane solution of 1-N-benzyl-4-N-(2-hydroxy-3-phenylprop-1-yl)-4-aminopiperidine. The mixture was stirred for 16 hours before filtered. After removal of solvent in vacuo, the crude product was purified by flash chromatography on silica. ESI-MS 403 (M+H); HPLC A: 2.96 min. FTIR:1671 cm$^{-1}$ Step C: 1-N-Benzyl-4-N-difluoroaceto-4-N-(2-oxo-3-phenylprop-1-yl)-4-aminopiperidine To a solution of DMSO in dichloromethane was added oxalyl chloride at −78° C. under inert atmosphere. The mixture was stirred for 10 min. before a solution of 1-N-benzyl-4-N-difluoroaceto-4-N-(2-hydroxy-3-phenylprop-1-yl)-4-aminopiperidine was added at −78° C. The mixture was stirred for additional 15 min. at −78° C. before triethylamine was added. This mixture was stirred for additional 40 min. while being allowed to warm up to ambient temperature. The reaction was quenched with methanol and solvent removed in vacuo. The crude product was purified by flash chromatography. ESI-MS 401 (M+H); HPLC A: 2.24 min.

Step D: 1-N-Benzyl-4-(4-benzyl-2-difluoromethyl-(imidazo-1-yl))piperidine

A mixture of 1-N-benzyl-4-N-difluoroaceto-4-N-(2-oxo-3-phenylprop-1-yl)-4-aminopiperidine and ammonium chloride was dissolved in acetic acid. The mixture was heated at 80° C. for 16 hours before heated at 100° C. for additional 2 hours. After extractive work up, the crude product was purified by flash chromatography. ESI-MS 382 (M+H); HPLC A: 2.10 min Step E: 4-(4-Benzyl-2-difluoromethyl-(imidazo-1-yl))piperidine Into a solution of 1-N-benzyl-4-(4-benzyl-2-difluoromethyl-(imidazo-1-yl))piperidine in ethyl acetate was added 50% weight of 10% Pd/C. The mixture was vigorously stirred under 1 atm of H$_2$ for 24 hours. The reaction was worked up by filtration and evaporation. The product was used without any further purification. ESI-MS 292 (M+H); HPLC A: 1.40 min.

Step F: α-(R)-(3-(S)-((4-(4-Benzyl-2-difluoromethyl-(imidazo-1-yl))piperidin-1-yl)methyl)-4-(S)-(3-fluorophenyl)pyrrolidin-1-yl)-isopropylacetic acid, 4-methoxybenzyl ester To a solution of 4-(4-benzyl-2-difluoromethyl-(imidazo-1-yl))piperidine and Aldehyde 11 in CH$_2$Cl$_2$ was added NaHB(OAc)$_3$ and HOAc. The reaction mixture was stirred at r.t. for 16 hours. After extractive work up, the crude product was purified by flash chromatography on silica. ESI-MS 689 (M+H); HPLC A: 2.90 min.

Step G: α-(R)-(3-(S)-((4-(4-Benzyl-2-difluoromethyl-(imidazo-1-yl))piperidin-1-yl)methyl)-4-(S)-(3-fluorophenyl)pyrrolidin-1-yl)-isopropylacetic acid The title compound was prepared by dissolving α-(R)-(3-(S)-((4-(4-benzyl-2-difluoromethyl-(imidazo-1-yl))piperidin-1-yl)methyl)-4-(S)-(3-fluorophenyl)pyrrolidin-1-yl)-isopropylacetic acid, 4-methoxybenzyl ester in neat formic acid, the solution was allowed to stand for 16 hours before the formic acid was removed in vacuo. The crude product was purified by reverse phase HPLC. ESI-MS 569 (M+H); HPLC A: 2.06 min.

EXAMPLE 221

α-(R)-(3-(S)-((4-(4-Benzyl-2-difluoromethyl-(imidazo-1-yl))piperidin-1-yl)methyl)-4-(S)-(3-fluorophenyl)pyrrolidin-1-yl)-cyclobutylpropionic Acid The title compound was prepared using a procedure analogous to that described in Example 1, except that in Step G, the 4-methoxybenzyl ester of Aldehyde 2 was used instead of Aldehyde 2. ESI-MS 595 (M+H); HPLC A: 2.34 min.

EXAMPLE 222

α-(R)-(3-(S)-((4-(4-Benzylimidazo-1-yl))piperidin-1-yl)methyl)4-(S)-(3-fluorophenyl)pyrrolidin-1-yl)-isopropylacetic Acid, Trifluoroacetic Acid Salt Step A: 4-N-Formyl-4-N-(2-hydroxy-3-phenylprop-1-yl)-1-N-benzylaminopiperidine A solution of 1-N-benzyl-4-N-(2-hydroxy-3-phenylprop-1-yl)-4-aminopiperidine in ethyl formate was refluxed for 30 hours before the solvent was removed in vacuo. The crude product was purified by flash chromatography. ESI-MS 353; HPLC: 1.08 min.; FTIR:1658 cm$^{-1}$ Step B: 4-N-Formyl-4-N-(2-oxo-3-phenylprop-1-yl)-1-N-benzylaminopiperidine The title compound was prepared using a procedure analogous to that described in Example 1, Step C, except that 4-N-formyl-4-N-(2-hydroxy-3-phenylprop-1-yl)-1-N-benzylaminopiperidine was used instead of 1-N-benzyl-4-N-difluoroaceto-4-N-(2-hydroxy-3-phenylprop-1-yl)-4-aminopiperidine. ESI-MS 351 (M+H); IHPLC A: 1.93 min.

Step C: 1-N-Benzyl-4-(4-benzylimidazo-1-yl))piperidine

The title compound was prepared using a procedure analogous to that described in Example 1, Step D, except that 4-N-formyl-4-N-(2-oxo-3-phenylprop-1-yl)-1-N-benzylaminopiperidine was used instead of 1-N-benzyl-4-N-difluoroaceto-4-N-(2-oxo-3-phenylprop-1-yl)-4-aminopiperidine. ESI-MS 332 (M+H); HPLC A: 1.54 min.

Step D: 4-(4-Benzylimidazo-1-yl))piperidine

The title compound was prepared using a procedure analogous to that described in Example 1, Step E, except that 1-N-benzyl-4-(4-benzylimidazo-1-yl))piperidine was used instead of 1-N-benzyl-4-(4-benzyl-2-difluoromethyl-(imidazo-1-yl))piperidine. ESI-MS 242 (M+H); HPLC A: 0.95 min.

Step E: α-(R)-(3-(S)-((4-(4-Benzyl-2-difluoromethyl-(imidazo-1-yl))piperidin-1-yl)methyl)-4-(S)-(3-fluorophenyl)pyrrolidin-1-yl)-isopropylacetic acid, trifluoroacetic acid salt The title compound was prepared using a procedure analogous to that described in Example 1, Step F to G, except that 4-(4-benzylimidazo-1-yl))piperidine was used instead of 4-(4-benzyl-2-difluoromethyl-(imidazo-1-yl)) piperidine; and the final purification was performed by semi-prep HPLC. ESI-MS 519 (M+H); HPLC A: 1.64 min.

EXAMPLE 223

α-(R)-(3-(S)-((4-(4-Benzylimidazo-1-yl))piperidin-1-yl)methyl)-4-(S)-(3-fluorophenyl)pyrrolidin-1-yl)-cyclobutylpropionic Acid The title compound was prepared using a procedure analogous to that described in Example 3, except that in Step E, 2-(R)-(3-(R)-formyl-4-(S)-(3-fluorophenyl)pyrrolidin-1-yl)-3-(cyclobutyl)propionic acid, 4-methoxybenzyl ester was used instead of 2-(R)-(3-(R)-fornyl-4-(S)-(3-fluorophenyl)pyrrolidin-1-yl)-3-methyl butanonic acid. ESI-MS 545 (M+H); HPLC A: 1.86 min.

EXAMPLES 224–230

Examples 224–230 were made using procedures analogous to those described in EXAMPLE 121 substituting the appropriate benzyl bromide in Step C and employing Aldehyde 12 in Step E:

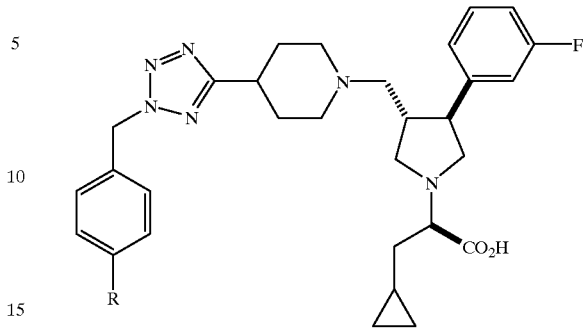

| EXAMPLE | R | ESI-MS (M + H) | HPLC A |
|---|---|---|---|
| 224 | —Cl | 567 | 2.32 |
| 225 | —CF₃ | 601 | 2.45 |
| 226 | —CN | | |
| 227 | —F | 551 | 2.15 |
| 228 | —OCF₃ | 617 | 2.51 |
| 229 | —H | 533 | 2.11 |
| 230 | —SO₂CH₃ | 611 | |

EXAMPLE 231

2-(R)-((3-(S)-(4-((3-Benzyl)phenyl)piperidin-1-yl)methyl)-4-(S)-(3-fluorophenyl)pyrrolidin-1-yl)-3-(cyclopropyl)propanoic Acid Step A: (3-Hydroxyphenyl), phenylmethane To a solution of 1.01 g (5.0 mmol) of 3-hydroxybenzophenone in 10 mL of CH₂Cl₂ at 0° C. was added 1.8 mL (20.3 mmol) of triflic acid in 10 mL of CH₂Cl₂ dropwise over 10 minutes. A solution of 2.4 mL (15.0 mmol) of triethylsilane in 10 mL of CH₂Cl₂ was added dropwise over 10 minutes. The reaction was warmed to room temperature and stirred for 1.5 hours. The reaction was poured into 100 mL of 1N NaHCO₃ and phases were separated. The aqueous layer was extracted with 3 ×25 mL of CH₂Cl₂. The combined organic phases were dried over MgSO₄ and concentrated under reduced pressure. The residue was purified by flash chromatography eluting with a gradient of hexane, 9:1 v/v hexanes/EtOAc and 4:1 v/v hexane/EtOAc to yield 561 mg (59%) of the title compound: R$_f$: 0.50 (4:1 v/v hexanes/EtOAc); ¹H NMR (300 MHz, CDCl₃) δ3.92 (s, 2H), 6.61–6.67 (m, 2H), 6.77 (d, J=6.8 Hz, 1H), 7.12–7.31 (m, 6H).

Step B: ((3-Benzyl)phenyl) trifluoromethanesulfonate

To a solution of 545 mg (2.9 mmol) of (3-hydroxyphenyl), phenylmethane (from Step A) and 0.62 mL (3.5 mmol) of DIEA in 6 mL of CH₂Cl₂ at −78° C. was added 0.5 mL (2.9 mmol) of triflic anhydride. After warming to 0° C. and stirring for 10 minutes, the reaction was poured into 100 mL of Et₂O and washed with 100 mL of brine and 100 mL of NaHCO₃. After separating phases, the organic layer was dried over MgSO₄ and concentrated under reduced pressure. The residue was purified by flash chromatography eluting with 19:1 v/v hexane/Et₂O to yield 779 mg (83%) of the title compound: R$_f$: 0.62 (9:1 v/v hexanes/Et₂O); ¹H NMR (300 MHz, CDCl₃) δ4.01 (s, 2H), 7.08–7.37 (m, 9H).

Step C: 1-Tert-butoxycarbonyl-4-trifluoromethanesulfonoxy-1,2,3,6-tetrahydropyridine To a solution of 14 mL (14 mmol) 1.0M LiHMDS in 6 mL of TBF at −78° C. was added a solution of 2.0 g (10 mmol)

of 1-tert-butoxycarbonyl-4-piperidone in 10 mL of THF (Temperature maintained ←−70° C.). After stirring at −78° C. for 30 minutes and 0° C. for 15 minutes, the reaction was cooled to −78° C. and a solution of 5.51 g (14 mmol) of 2-[N, N-bis(trifluoromethanesulfonyl)amino]-5-chloropyridine in 10 mL THF was added. After stirring for 30 minutes at −78° C. and for 6 hours at −30° C., the reaction was quenched with 1N NaHCO$_3$ and volatiles removed under reduced pressure. The residue was partitioned between 100 mL EtOAc and 100 mL of 1N NaHCO$_3$. After separating phases, the aqueous layer was extracted with 2×100 mL of EtOAc. The combined organic phases were dried over Na$_2$SO$_4$ and concentrated under reduced pressure. The residue was purified by flash chromatography eluting with CH$_2$Cl$_2$ to yield 1.74 g (52%) of the title compound: R$_f$: 0.27 (CH$_2$Cl$_2$); $^1$H NMR (300 MHz, CDCl$_3$) δ1.4 (s, 9H), 2.4 (m, 2H), 3.6 (m, 2H), 4.0 (m, 2H), 5.8 (m, 1H).

Step D: 1-Tert-butoxycarbonyl-4-((3-benzyl)phenyl)-1,2,3,6-tetrahydropyridine

A solution of 513 mg (1.6 mmol) of ((3-benzyl)phenyl) trifluoromethanasulfonate (from Step B), 444 mg (1.7 mmol) bis(pinacolato) diboron and 476 mg (4.8 mmol) KOAc in 10 mL of DMF was degassed 3× under vacuum using argon. After the addition of 41 mg (0.050 mmol) of PdCl$_2$ dppf, the reaction was degassed 3× under vacuum using argon. The reaction was stirred at 80° C. for 2 hours. After the addition of 1.026 g (3.0 mmol) of 1-tert-butoxycarbonyl-4-trifluoromethanesulfonoxy-1,2,3,6-tetrahydropyridine (from Step C) and 3.8 mL of 2M Na$_2$CO$_3$, the reaction was degassed 3× under vacuum using argon. After the addition of 41 mg (0.050 mmol) of PdCl$_2$ dppf, the reaction was degassed 3× under vacuum using argon. After stirring for 20 hours at 80° C., the reaction was cooled to room temperature and partitioned between 50 mL Et$_2$O and 50 mL of H$_2$O. The phases were separated and the organic layer was washed with 50 mL of brine, dried over MgSO$_4$ and concentrated under reduced pressure. The residue was purified by flash chromatography eluting with 9:1 v/v hexanes/EtOAc to yield 74 mg (13%) of the title compound: R$_f$: 0.45 (4:1 v/v hexanes/EtOAc); $^1$H NMR (300 MHz, CDCl$_3$) δ1.48 (s, 9H), 2.47–2.49 (m, 2H), 3.61 (t, J=5.8 Hz), 3.98 (s, 2H), 4.04–4.05 (m, 2H), 5.97 (m, 1H), 7.07–7.31 (m, 9H).

Step E: 1-Tert-butoxycarbonyl-4-((3-benzyl)phenyl)-piperidine

A mixture of 74 mg (0.21 mmol) of 1-tert-butoxycarbonyl-4-((3-benzyl)phenyl)-1,2,3,6-tetrahydropyridine (from Step D) and 6 mg of 10% palladium on carbon in 1 mL of EtOAc and 3 mL of MeOH was hydrogenated at 40 psi of hydrogen on a Parr shaker for 3 hours. The reaction was filtered and concentrated under reduced pressure to yield 71 mg (95%) of the title compound, which was used without further purification. $^1$H NMR (500 MHz, CDCl$_3$) δ1.43–1.83 (m, 13H), 2.62 (m, 1H), 2.80 (m, 2H), 3.99 (s, 2H), 4.25 (m, 2H), 7.06–7.33 (m, 9H).

Step F: 4-((3-Benzyl)phenyl)-piperidine, hydrochloride salt

To 2 mL of MeOH at 0° C. was added 0.17 mL of acetyl chloride. After warming to room temperature and stirring for 15 minutes, a solution of 71 mg (0.20 mmol) of 1-tert-butoxycarbonyl-4-((3-benzyl)phenyl)-piperidine (from Step E) was added. The reaction was stirred for 1 hour at room temperature. Volatiles were removed under reduced pressure to yield the title compound, which was used without further purification.

Step G: 2-(R)-((3-(S)-(4-((3-Benzyl)phenyl)piperidin-1-yl) methyl)-4-(S)-3-fluorophenyl)pyrrolidin-1-yl)-3-(cyclopropyl)propanoic acid The title compound was prepared from 4-((3-benzyl) phenyl)-piperidine, hydrochloride salt (from Step F) and 2-(R)-(3-(R)-formyl-4-(S)-(3-fluorophenyl)pyrrolidin-1-yl)-3-(cyclopropyl)propionic acid, (4-methoxy)benzyl ester (prepared as Aldehyde 12 above) using procedures analogous to those described in Example 112, Step A, and Example 121, Step F. R$_f$: 0.29 (90:10:1 v/v/v CH$_2$Cl$_2$/MeOH/NH$_4$OH); $^1$H NMR (500 MHz, CDCl$_3$) δ0.06–0.07 (m, 2H), 0.43–0.46 (m, 2H), 0.77 (m, 1H), 1.48–3.62 (m, 20H), 3.85 (s, 2H), 6.84–7.27 (m, 13H). ESI-MS 541 (M+H); HPLC A: 2.87.

EXAMPLE 232

2-(R)-((3-(S)-(4-((4-Benzyl)phenyl)piperidin-1-yl) methyl)-4-(S)-3-fluorophenyl)pyrrolidin-1-yl)-3-(cyclopropyl)propanoic Acid The title compound was prepared using procedures analogous to those described in Example 231, except 3-hydroxybenzophenone was replaced with 4-bromobenzophenone in Step A. R$_f$: 0.19 (90:10:1 v/v/v CH$_2$Cl$_2$/MeOH/NH$_4$OH); $^1$H NMR (300 MHz, CD$_3$OD) δ0.05–0.08 (m, 2H), 0.40–0.42 (m, 2H), 0.73 (m, 1H), 1.43–1.65 (m, 5H), 1.77–2.03 (m, 3H), 2.24–2.46 (m, 3H), 2.61–3.32 (m, 6H), 3.46–3.56 (m, 3H), 3.77 (s, 2H), 6.87–7.30 (m, 13H). ESI-MS 541 (M+H); HPLC A: 2.83.

EXAMPLE 233

2-(R)-((3-(S)-(4-((4-Phenylsulfonyl)phenyl) piperidin-1-yl)methyl)-4-(S)-3-fluorophenyl) pyrrolidin-1-yl)-3-(cyclopropyl)propanoic Acid The title compound was prepared using procedures analogous to those described in Example 231, Steps D through G, except ((3-benzyl)phenyl) trifluoromethanasulfonate was replaced with 4-bromophenyl, phenyl sulfone in Step D. R$_f$: 0.34 (90: 10:1 v/v/v CH$_2$Cl$_2$/MeOH/NH$_4$OH); $^1$H NMR (500 MHz, CD$_3$OD) δ0.17–0.20 (m, 2H), 0.51–0.54 (m, 2H), 0.84 (m, 1H), 1.50–1.73 (m, 5H), 1.89–2.10 (m, 3H), 2.37 (m, 1H), 2.49–2.54 (m, 2H), 2.77–2.82 (m, 2H), 2.98 (m, 1H), 3.22–3.48 (m, 3H), 3.64–3.72 (m, 3H), 7.01 (m, 1H), 7.16–7.19 (m, 2H), 7.34–7.39 (m, 3H), 7.52–7.61 (m, 3H), 7.84 (d, J=8.4 Hz, 2H), 7.91 (d, J=8.4 Hz, 2H). ESI-MS 591 (M+H); HPLC A: 2.43.

EXAMPLE 234

2-(R)-((3-(S)-(4-((4-(4-Fluorobenzyl)phenyl) pipeiidin-1-yl)methyl)-4-(S)-3-fluorophenyl) pyrrolidin-1-yl)-3-(cyclopropyl)propanoic Acid Step A: 4-Bromo-4'-fluoro-diphenylmethanol To a solution of 5.01 g (27.0 mmol) of 4-bromobenzaldehyde in 100 mL of Et$_2$O at 0° C. was added 26 mL (52.0 mmol) of 2.0M 4-fluorophenylmagnesium bromide in Et$_2$O. After stirring for 30 minutes at 0° C., the reaction was quenched with saturated NH$_4$Cl and partitioned between 200 mL of Et$_2$O and 200 mL of brine. After separating phases, the organic layer was washed with 200 mL saturated NH$_4$Cl, dried over MgSO$_4$ and concentrated under reduced pressure. The residue was purified by flash chromatography eluting with CH$_2$Cl$_2$ to yield 6.32 g (83%) of the title compound: R$_f$: 0.43 (CH$_2$Cl$_2$); $^1$H NMR (500 MHz, CDCl$_3$) δ2.18 (br m, 1H), 5.79 (s, 1H), 7.04 (t, J=8.7

Hz, 2H), 7.24 (d, J=8.3 Hz, 2H), 7.27–7.33 (m, 2H), 7.48 (d, J=8.3 Hz, 2H).

Step B: 4-Bromo-4'-fluoro-diphenylmethane

To TFA at 0° C. was added 0.69 g (18.2 mmol) of NaBH4 in four portions over 10 minutes. After warming to room temperature, a solution of 1.01 g (3.5 mmol) of 4-bromo-4'-fluoro-diphenylmethanol (from Step A) in 2 mL of $CH_2Cl_2$ was added. The reaction was stirred for 1.5 hours and concentrated under reduced pressure. The crude product was partitioned between 100 mL of $CH_2Cl_2$ and 100 mL of 1N $NaHCO_3$. After separating phases, the aqueous layer was extracted with 2×100 mL of $CH_2Cl_2$. The combined organic phases were dried over $MgSO_4$ and concentrated under reduced pressure. The residue was purified by flash chromatography eluting with hexane to yield 911 mg (95%) of the title compound: $R_f$: 0.33 (hexane); $^1$H NMR (500 MHz, $CDCl_3$) δ3.92 (s, 2H), 6.98–7.14 (m, 6H), 7.43 (d, J=8.3 Hz, 2H).

Step C: 2-(R)-((3-(S)-(4-((4-(4-Fluorobenzyl)phenyl) piperidin-1-yl)methyl)-4-(S)-3-fluorophenyl)pyrrolidin-1-yl)-3-(cyclopropyl)propanoic acid The title compound was prepared using procedures analogous to those described in Example 231, Steps D through G, except ((3-benzyl)phenyl) trifluoromethanasulfonate was replaced with 4-bromo-4'-fluoro-diphenylmethane (from Example 234, Step B) in Step D. $R_f$: 0.35 (90: 10:1 v/v/v $CH_2Cl_2$/MeOH/$NH_4OH$); $^1$H NMR (500 MHz, $CD_3OD$) δ0.2 (m, 2H), 0.5 (m, 2H), 0.9 (m, 1H), 1.5–4.0 (m, 22H), 6.8–7.4 (m, 12H). ESI-MS 559 (M+H); HPLC A: 3.01.

EXAMPLE 235

α-(R)-(3-(S)-((4-(Imidazo[1,2-a]pyridin-3-yl)-piperidine-1-yl)methyl)-4-(S)-(3-fluorophenyl) pyrrolidin-1-yl)-cyclobutylpropanoic Acid Step A: 1-(t-Butoxycarbonyl)-4-(imidazo[1,2-a]pyridin-3-yl)-piperidine To a solution of 1.15 g of 1-(t-butoxycarbonyl)-4-(1-bromo-2-oxoethyl)-piperidine (from Example 292, Step C) in 15 mL ethanol was added 388 mg of 2-aminopyridine. After refluxing for 18 hours, the solvent was evaporated. The mixture was partitioned between EtOAc and saturated sodium bicarbonate solution. Aqueous layer was extracted with EtOAc (3×). The combined organic phase was washed with brine, dried over $MgSO_4$ and concentrated. The residue was purified by flash chromatography with 50% EtOAc in hexanes, followed by 100% EtOAc to give 401 mg of the title compound as a solid. $^1$H NMR (500 MHz, $CDCl_3$) δ1.48 (s, 9H), 1.70 (m, 2H), 2.06 (d, J=13 Hz, 2H), 2.93–3.02 (m, 3H), 4.26 (br, 2H), 6.87 (t, J=6.8 Hz, 1H). 7.21(m, 1H), 7.44(s, 1H), 7. 69(d, J=9.2 Hz,1H), 7.99 (d, J=6.9 Hz, 1H).

Step B: 4-Imidazo[1,2-a]pyridin-3-yl)piperidine, trifluoroacetic acid salt

To 100 mg of 1-(t-butoxycarbonyl)-4-(imidazo[1,2-a]pyridin-3-yl)-piperidine was added 2 mL TFA (from Step A). The reaction was stirred at r.t. for 1 hour. The mixture was concentrated under reduced pressure to afford 180 mg of a viscous oil.

Step C: α-(R)-(3-(S)-((4-Imidazo[1,2-a]pyridin-3-yl)-piperidine-1-yl)methyl)-4-(S)-(3-fluorophenyl) pyrrolidin-1-yl)-cyclobutylpropanoic acid, 4-methoxy-benzyl ester To a solution of 30 mg of 2-(R)-(3-(R)-formyl-4-(S)-(3-fluorophenyl)pyrrolidin-1-yl)-3-(cyclobutyl)propanoic acid, 4-methoxy-benzyl ester (prepared by analogy to Aldehyde 2) in 4 mL $CH_2Cl_2$ was added 0.3 mL N,N-diisopropylethylamine, 40 mg of 4-(imidazo [1,2a]pyridin-3-yl)piperidine, trifluoroacetic acid salt (from Step B), and 40 mg of sodium triacetoxyborohydride. The reaction was stirred at r.t. for 4 hours. The mixture was partitioned between $CH_2Cl_2$ and saturated sodium bicarbonate solution. Aqueous layer was extracted with $CH_2Cl_2$ (3×). The combined organic phase was washed with brine and dried over $MgSO_4$. After concentration, the residue was purified by flash chromatography with 100% EtOAc followed by 10% MeOH in EtOAc to give 26 mg of a viscous oil.

Step D: α-(R)-(3-(S)-((4-(imidazo[1,2-a]pyridin-3-yl)-piperidine-1-yl)methyl)-4-(S)-(3-fluorophenyl) pyrrolidin-1-yl)-cyclobutylpropanoic acid To 26 mg of α-(R)-(3-(S)-((4-(imidazo[1,2-a]pyridin-3-yl)-piperidine-1-yl)methyl)-4-(S)-(3-fluorophenyl) pyrrolidin-1-yl)-cyclobutylpropanoic acid, 4-methoxy-benzyl ester (from Step C) was added 2 mL of TFA and 0.3 mL of anisole. The reaction was stirred at r.t. for 1 hour. The reaction mixture was concentrated and the residue was purified by flash chromatography with 10% MeOH in $CH_2Cl_2$, followed by 15% MeOH and 1% $NH_4OH$ in $CHCl_3$ to provide 23 mg of a foamy solid. $^1$H NMR (500 MHz, $CD_3OD$): δ1.63–1.81 (m, 4H), 1.93–2.15 (m, 5H), 2.33(t, J=15.6 Hz, 2H), 2.44(m, 1H), 2.86(m, 1H), 3.00(d, J=13.8 Hz, 1H), 3.15–3.89(m, 13H), 7.11 (m, 1H), 7.28 (m, 2H), 7.39–7.48 (m, 2H), 7.75 (s, 1H), 7.85 (m, 2H) 8.32 (d, J=6.9 Hz, 1H). ESI-MS 505 (M+H); BLC A 1.64 min.

EXAMPLES 236–266

Examples 236–266 in Table 12 were prepared according to the general procedure given in Example 235, employing the appropriate commercially available 2-amino-substituted heterocycles in place of 2-aminopyridine in Step A, and the appropriate aldehydes in place of 2-(R)-(3-(R)-formyl-4-(S)-3-(fluorophenyl)pyrrolidin-1-yl)-3-(cyclobutyl) propanoic acid, (4-methoxy)benzyl ester in Step C.

TABLE 12

| EXAMPLE # | Ra | Rb | MS m/Z (M + 1) |
|---|---|---|---|
| 236 | imidazo[1,2-a]pyridin-3-yl | cyclopropylmethyl | 491 |
| 237 | imidazo[1,2-a]pyrazin-3-yl | cyclobutyl | 506 |
| 238 | imidazo[1,2-a]pyrimidin-3-yl | isopropyl | 506 |
| 239 | imidazo[1,2-a]pyrimidin-3-yl | cyclobutylmethyl | 479 |
| 240 | 6-chloroimidazo[1,2-b]pyridazin-3-yl | cyclobutylmethyl | 540 |
| 241 | 7-methylimidazo[1,2-a]pyridin-3-yl | cyclobutylmethyl | 519 |

TABLE 12-continued
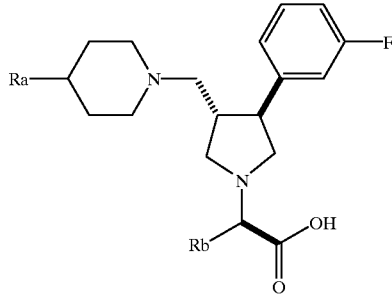
| EXAMPLE # | Ra | Rb | MS m/Z (M + 1) |
|---|---|---|---|
| 242 | 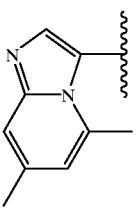 | 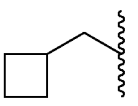 | 533 |
| 243 | 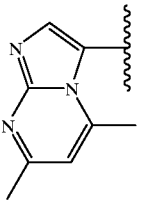 | 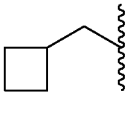 | 534 |
| 244 | 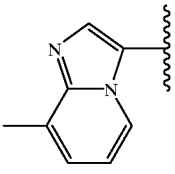 | 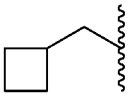 | 519 |
| 245 | 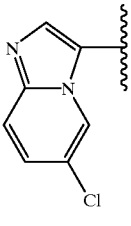 | 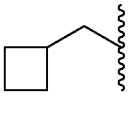 | 540 |
| 246 | 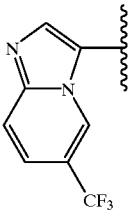 | 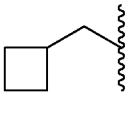 | 573 |

TABLE 12-continued

| EXAMPLE # | Ra | Rb | MS m/Z (M + 1) |
|---|---|---|---|
| 247 | 7-ethyl-imidazo[1,2-a]pyridin-3-yl | cyclobutylmethyl | 533 |
| 248 | 6-bromo-imidazo[1,2-a]pyridin-3-yl | cyclobutylmethyl | 584 |
| 249 | 6-nitro-imidazo[1,2-a]pyridin-3-yl | cyclobutylmethyl | 550 |
| 250 | 6-nitro-imidazo[1,2-a]pyridin-3-yl | isopropyl | 524 |
| 251 | 6,8-dichloro-imidazo[1,2-a]pyridin-3-yl | cyclobutylmethyl | 573 |

TABLE 12-continued

| EXAMPLE # | Ra | Rb | MS m/Z (M + 1) |
|---|---|---|---|
| 252 | imidazo[1,2-a]pyridine with Cl, Cl | isopropyl | 547 |
| 253 | imidazo[1,2-a]pyridine with C(O)NH₂ | cyclobutylmethyl | 548 |
| 254 | imidazo[1,2-a]pyridine with Cl, CF₃ | cyclobutylmethyl | 608 |
| 255 | imidazo[1,2-a]pyridine with Cl, CF₃ | tert-butyl | 595 |
| 256 | imidazo[1,2-a]pyridine with OBn | cyclobutylmethyl | 611 |

TABLE 12-continued
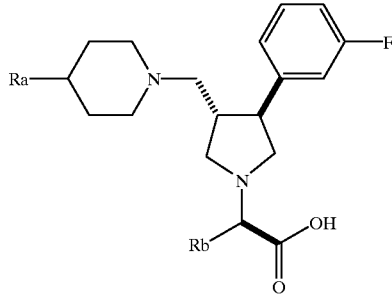
| EXAMPLE # | Ra | Rb | MS m/Z (M + 1) |
|---|---|---|---|
| 257 | 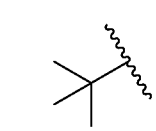 | 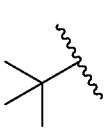 | 599 |
| 258 | 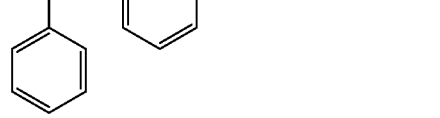 | 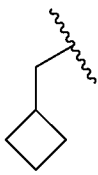 | 564 |
| 259 | 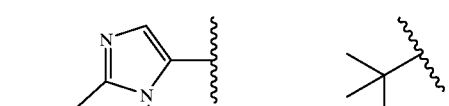 | 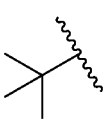 | 552 |
| 260 | 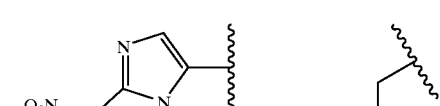 | 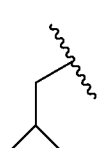 | 564 |
| 261 |  | 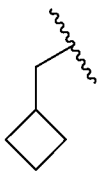 | 511 |

TABLE 12-continued
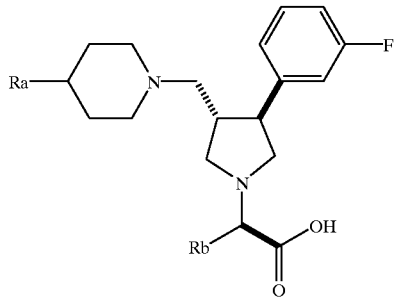
| EXAMPLE # | Ra | Rb | MS m/Z (M + 1) |
|---|---|---|---|
| 262 | 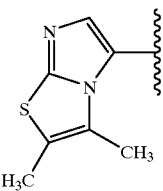 | 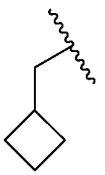 | 539 |
| 263 | 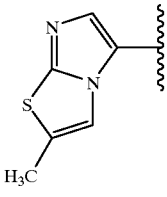 | 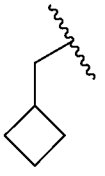 | 525 |
| 264 | 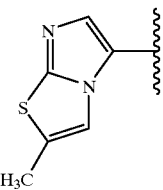 | 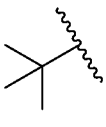 | 513 |
| 265 | 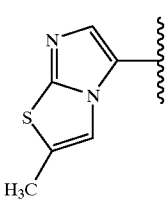 | 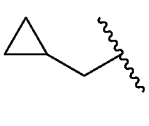 | 511 |
| 266 | 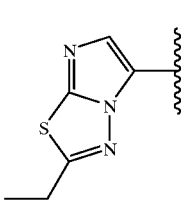 | 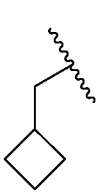 | 540 |

EXAMPLE 267

α-(R)-(3-(S)-((4-(Imidazo[1,2-a]pyridin-2-yl)-
piperidine-1-yl)methyl)-4-(S)- (3-fluorophenyl)
pyrrolidin-1-yl)-cyclobutyl Propanoic Acid Step A: 1-Benzoyl-4-(imidazo[1,2-a]pyridin-2-yl)-
piperidine To a solution of 160 mg of 2-bromo-1-(1-benzoyl-4-piperidyl)-1-ethanone (prepared in analogy with Example 523, Step A) in 6 mL ethanol was added 59 mg of 2-aminopyridine. After refluxing for 18 hours, the solvent was evaporated. The mixture was partitioned between EtOAc and saturated sodium bicarbonate solution. Aqueous layer was extracted with EtOAc (3×). The combined organic phase was washed with brine, dried over MgSO$_4$ and concentrated. The residue was purified by flash chromatography with 100% EtOAc followed by 10% MeOH in EtOAc to give 78 mg of a solid: $^1$H NMR (500 MHz, CDCl$_3$) δ1.80 (d, 2H), 2.16 (d, 2H), 3.17 (m, 3H), 3.87 (br, 1H), 4.85 (br, 1H), 6.76 (t, J=6.8 Hz,1H). 7.15 (m,1H), 7.37(s, 1H), 7.42(m, 5H), 7. 55(d, J=9.1 Hz, 1H), 8.08 (d, J=6.9 Hz,1H).

Step B: 4-(Imidazo[1,2-a]pyridin-2-yl)piperidine

To a solution of 70 mg of 1-benzoyl-4-(imidazo[1,2-a]pyridin-2-yl)-piperidine (from Step A) in 4 mL of ethanol was added 1 mL of 45% KOH solution. The reaction was refluxed for 14 hours. After concentration, the mixture was partitioned between EtOAc and water. Aqueous layer was extracted with EtOAc (3×). The combined organic phase was washed with brine, dried over MgSO$_4$ and concentrated to give 22 mg of the title compound as a viscous oil.

Step C: α-(R)-(3-(S)-((4-(Imidazo[1,2-a]pyridin-2-yl)-
piperidine-1-yl)methyl)-4-(S)-(3-fluorophenyl)
pyrrolidin-1-yl)-cyclobutylpropanoic acid, 4-methoxy-benzyl ester The title compound was prepared from 30 mg of 2-(R)-(3-(R)-formyl-4-(S)-(3-fluorophenyl)pyrrolidin-1-yl)-3-(cyclobutyl)propanoic acid, 4-methoxy-benzyl ester, 20 mg of 4-(imidazo[1,2a]pyridin-2-yl)piperidine (from Step B), 0.3 mL of N,N-diisopropylethaylamine and 40 mg of sodium triacetoxyborohydride in 4 mL of CH$_2$Cl$_2$, using a procedure analogous to that described in Example 235, Step C to provide 19 mg of the title compound as an oil.

Step D: α-(R)-(3-(S)-((4-(Imidazo[1,2-a]pyridin-2-yl)-
piperidine-1-yl)methyl)-4-(S)-(3-fluorophenyl)
pyrrolidin-1-yl)-cyclobutylpropanoic acid The title compound was prepared from 19 mg of α-(R)-(3-(S)-((4-(imidazo[1,2-a]pyridin-2-yl)-piperidine-1-yl) methyl)-4-(S)-(3-fluorophenyl)pyrrolidin-1-yl)-cyclobutylpropanoic acid, 4-methoxy-benzyl ester (from Step C), 2 mL of TFA and 0.2 mL of anisole, using a procedure analogous to that described in Example 235, Step D to provide 16 mg of the title compound as a foamy solid. $^1$H NMR (500 MHz, CD$_3$OD): δ1.45–1.64 (m, 6H), 1.83–2.04 (m, 6H), 2.30(t, J=14.2 Hz, 3H), 2.68–3.85(m, 12H), 6.93 (t, J=6.3 Hz, 1H), 7.27 (d, J=6.7 Hz, 2H), 7.35 (t, J=6.7 Hz, 1H), 7.45 (dd, J=13.6, 6.3Hz, 1H), 7.49 (d, J=13.5 Hz, 1H), 7.67 (s, 1H), 8.38 (d, J=6.9 Hz, 1H). ESI-MS 505 (M+H); HPLC A 2.21 min.

EXAMPLES 268–269

Examples 268–269 in Table 13 were prepared according to the procedure described in Example 267, employing the appropriate commercially available 2-aminopyrazine or 2-aminopyrimidine in place of 2-aminopyridine in Step A.

TABLE 13

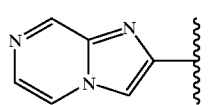

| EXAMPLE # | Ra | MS m/Z (M + 1) |
|---|---|---|
| 268 | 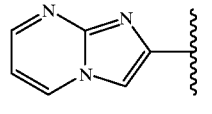 | 506 |
| 269 | | 506 |

EXAMPLE 270

α-(R)-(3-(S)-((4-(7-t-Butyl-imidazo[1,2-a]pyridin-3-yl)-piperidin-1-yl)methyl)-4-(S)-(3-fluorophenyl)
pyrrolidin-1-yl)-cyclobutylpropanoic Acid Step A: 2-Amino-4-t-butyl-pyridine To 790 mg of sodium amide were added 20 mL of N,N-dimethylanaline and 2.74 g of 4-t-butyl pyridine at r.t. The mixture was stirred at 150° C. for 6 hours. During this period, 3 more portions of sodium amide (790 mg each) were added. The reaction was cooled down to r.t. The mixture was partitioned between EtOAc and water. Aqueous layer was extracted with EtOAc (3×). The combined organic phase was washed with brine, dried over MgSO$_4$ and concentrated. The residue was purified by flash chromatography with 50% EtOAc in hexanes followed by 100% EtOAc to give 1.68 g of the title compound as a solid: $^1$H NMR (500 MHz, CDCl$_3$) δ1.21 (s, 9H), 4.55 (br, 2H) 6.44 (t, J=1.1 Hz, 1H), 6.62 (dd, J=5.5, 1.8 Hz, 1H), 7.94 (d, J=5.5Hz, 1H).

Step B: 1-(t-Butoxycarbonyl)-4-(7-t-butyl-imidazo[1,2-a]pyridin-3-yl)-piperidine The title compound was prepared from 470 mg of 1-(t-butoxycarbonyl)-4-(1-bromo-2-oxoethyl)-piperidine (from Example 199, Step C) and 277 mg of 2-amino-4-t-butyl pyridine (from Step A) in 12 mL ethanol using a procedure analogous to that described in Example 235, Step A to provide 130 mg of the title compound as a solid.

Step C: 4-(7-t-Butyl-imidazo[1,2-a]pyridin-3-yl)-piperidine, TFA Salt

The title compound was prepared from 35 mg of 1-(t-butoxycarbonyl)-4-((7-t-butyl)-imidazo[1,2-a]pyridin-3-yl)-piperidine (from Step B) in 2 mL of TFA, using a procedure analogous to that described in Example 235, Step B to provide 60 mg of the title compound as a viscous oil.

Step D: α-(R)-(3-(S)-((4-(7-t-Butyl-imidazo[1,2-a]
pyridin-3-yl)-piperidine-1-yl)methyl)-4-(S)-(3-fluorophenyl)pyrrolidin-1-yl)-cyclobutylpropanoic acid, 4-methoxy-benzyl Ester The title compound was prepared from 48 mg of 2-(R)-(3-(R)-formyl-4-(S)-(3-fluorophenyl)pyrrolidin-1-yl)-3-(cyclobutyl)propanoic acid, 4-methoxybenzyl ester, 60 mg of 4-(7-t-butyl-imidazo[1,2-a]pyridin-3-yl)-piperidine, trifluoroacetic acid salt (from Step C), 0.3 mL of N,N-diisopropylethaylamine and 40 mg of sodium triacetoxyborohydride in 4 mL CH$_2$Cl$_2$, using a procedure analogous to that described in Example 235, Step C to provide 42 mg of the title compound as an oil.

Step E: α-(R)-(3-(S)-((4-(7-t-Butyl-imidazo[1,2-a]pyridin-3-yl)-piperidine-1-yl)methyl)-4-(S)-(3-fluorophenyl)pyrrolidin-1-yl)-cyclobutylpropanoic Acid The title compound was prepared from 40 mg of α-(R)-(3-(S)-((4-(7-t-butyl-imidazo[1,2-a]pyridin-3-yl)-piperidine-1-yl)methyl)-4-(S)-(3-fluorophenyl) pyrrolidin-1-yl)-cyclobutylpropanoic acid, 4-methoxy-benzyl ester (from Step D), 2 mL of TFA and 0.4 mL of anisole, using a procedure analogous to that described in Example 235, Step D to provide 30 mg of the title compound as a foamy solid. ESI-MS 561 (M+H); HPLC A 1.92 min.

EXAMPLES 271–273

Example 271 in Table 14 was prepared according to the general procedure described in Example 270, except that Aldehyde 18 was employed in place of 2-(R)-(3-(R)-formyl-4-(S)-(3-fluorophenyl)pyrrolidin-1-yl)-3-(cyclobutyl)propanoic acid, 4-methoxy-benzyl ester (prepared by analogy to Aldehyde 2) in Step D. Examples 272 and 273 were prepared according to the general procedure described in Example 270, except the commercially available 4-n-propyl pyridine was employed in place of 4-t-butyl pyridine in Step A.

TABLE 14

| EXAMPLE # | Ra | Rb | MS m/Z (M + 1) |
|---|---|---|---|
| 271 | (imidazo[1,2-a]pyridine with t-butyl at 7-position) | (t-butyl) | 550 |
| 272 | (imidazo[1,2-a]pyridine with n-propyl at 6-position) | (t-butyl) | 535 |
| 273 | (imidazo[1,2-a]pyridine with n-propyl at 6-position) | (cyclobutylmethyl) | 549 |

EXAMPLE 274

α-(R)-(3-(S)-((4-(6-Phenyl-imidazo[1,2-a]pyridin-3-yl)-piperidine-1-yl)methyl)-4-(S)-(3-fluorophenyl) pyrrolidin-1-yl)-cyclobutylpropanoic Acid Step A: 1-(t-Butoxycarbonyl)-4-(6-bromo-imidazo[1,2-a]pyridin-3-yl)-piperidine The title compound was prepared from 2-amino-5-bromopyridine and 1-(t-butoxycarbonyl)-4-(1-bromo-2-oxoethyl)-piperidine (from Example 292, Step C) according to the general procedure described in Example 235, Step A.

Step B: 1-(t-Butoxycarbonyl)-4-(6-phenyl-imidazo[1,2-a]pyridin-3-yl)-piperidine

To a solution of 120 mg of 1-(t-butoxycarbonyl)-4-(6-bromo-imidazo[1,2-a]pyridin-3-yl)-piperidine and 78 mg of phenylboronic acid in 5 mL of toluene and 2.5 mL of ethanol was added 8 mg of tetrakis(triphenylphosphine)-palladium (0), followed by 0.85 mL of 1.25N sodium hydroxide solution. The reaction was stirred at 100° C. for 8 hours. The mixture was concentrated under reduced pressure and the mixture was partitioned between EtOAc and water. Aqueous layer was extracted with EtOAc (3×). The combined organic phase was washed with brine and dried over MgSO$_4$. The residue was purified by flash chromatography with 50%

EtOAc in hexanes followed by 100% EtOAc to give 141 mg of the title compound as a viscous oil, which was used in next step without further purification.

Step C: α-(R)-(3-(S)-((4-(6-Phenyl-imidazo[1,2-a]pyridin-3-yl)-piperidine-1-yl)methyl)-4-(S)-(3-fluorophenyl)pyrrolidin-1-yl)-cyclobutylpropanoic Acid The title compound was prepared from 1-(t-butoxycarbonyl)-4-(6-phenyl-imidazo[1,2-a]pyridin-3-yl)-piperidine and 2-(R)-(3-(R)-formyl-4-(S)-(3-fluorophenyl)pyrrolidin-1-yl)-3-(cyclobutyl)propanoic acid, 4-methoxy-benzyl ester according to the procedure described in Example 235, Steps B, C and D to provide 33 mg of the title compound as a solid. ESI-MS 561 (M+H); HPLC A 1.92 min.

EXAMPLE 275

α-(R)-(3-(S)-((4-(6-Vinyl-imidazo[1,2-a]pyridin-3-yl)-piperidine-1-yl)methyl)-4-(S)-(3-fluorophenyl)pyrrolidin-1-yl)-cyclobutylpropanoic Acid Step A: 1-(t-Butoxycarbonyl)-4-(6-vinyl-imidazo[1,2-a]pyridin-3-yl)-piperidine To a solution of 95 mg of 1-(t-butoxycarbonyl)-4-(6-bromo-imidazo[1,2-a]pyridin-3-yl)-piperidine (from Example 274, Step A), and 158 mg of tributyl(vinyl)tin in 6 mL toluene was added 5.3 mg of dichlorobis (triphenyl phosphine)-palladium(II). The mixture was refluxed for 2 hours. The reaction was cooled down to r.t. and partitioned between $CH_2Cl_2$ and water. Aqueous layer was extracted with $CH_2Cl_2$ (3×). The combined organic phase was washed with brine and dried over $MgSO_4$. After concentration, the residue was purified by prep TLC (100% EtOAc) to give 90 mg of the title compound as a viscous oil, which was used in next step without further purification.

Step B: 4-(6-Vinyl-imidazo[1,2-a]pyridin-3-yl)-piperidine, TFA salt The title compound was prepared from 89 mg of 1-(t-butoxycarbonyl)-4-(6-vinyl-imidazo[1,2-a]pyridin-3-yl)-piperidine (from Step A), in 2 mL of TFA, using a procedure analogous to that described in Example 235, Step B to provide 158 mg of the title compound as a viscous oil.

Step C: α-(R)-(3-(S)-((4-(6-Vinyl-imidazo[1,2-a]pyridin-3-yl)-piperidine-1-yl)methyl)-4-(S)-(3-fluorophenyl)pyrrolidin-1-yl)-cyclobutylpropanoic Acid The title compound was prepared from 4-(6-vinyl-imidazo[1,2-a]pyridin-3-yl)-piperidine, TFA salt (from Step B) and 2-(R)-(3-(R)-formyl-4-(S)-(3-fluorophenyl)pyrrolidin-1-yl)-3-(cyclobutyl)propanoic acid, 4-methoxy-benzyl ester (prepared by analogy to Aldehyde 2) according to the procedure described in Example 235, Steps C and D to provide 42 mg of the title compound as a solid. ESI-MS 531 (M+H); HPLC A 1.63 min.

EXAMPLE 276

α-(R)-(3-(S)-((4-(6-Ethyl-imidazo[1,2-a]pyridin-3-yl)-piperidine-1-yl)methyl)-4-(S)-(3-fluorophenyl)pyrrolidin-1-yl)-cyclobutylpropanoic acid Step A: 4-(6-Ethyl-imidazo[1,2-a]pyridin-3-yl)-piperidine, TFA Salt 60 mg of 4-(6-vinyl-imidazo[1,2-a]pyridin-3-yl)-piperidine, TFA salt (from Example 275, Step B) in MeOH was hydrogenated using 6 mg of 10% Pd/C under atmospheric $H_2$ gas at r.t. for 1.5 hours. The mixture was filtered through celite, washed with methanol and concentrated to give 41 mg of a viscous oil, which was used in the next step without further purification.

Step B: α-(R)-(3-(S)-((4-(6-Ethyl-imidazo[1,2-a]pyridin-3-yl)-piperidine-1-yl)methyl)-4-(S)-(3-fluorophenyl)pyrrolidin-1-yl)-cyclobutylpropanoic Acid The title compound was prepared from 4-(6-ethyl-imidazo[1,2-a]pyridin-3-yl)-piperidine, TFA salt (from Step A) and 2-(R)-(3-(R)-formyl-4-(S)-(3-fluorophenyl)pyrrolidin-1-yl)-3-(cyclobutyl)propanoic acid, 4-methoxy-benzyl ester according to the procedure described in Example 235, Steps C and D to provide 21 mg of the title compound as a solid. ESI-MS 533 (M+H); HPLC A 1.73 min.

EXAMPLE 277

α-(R)-(3-(S)-((4-(6-Allyl-imidazo[1,2-a]pyridin-3-yl)-piperidine-1-yl)methyl)-4-(S)-(3-fluorophenyl)pyrrolidin-1-yl)-cyclobutylpropanoic Acid Step A: 1-(t-Butoxycarbonyl)-4-(6-allyl-imidazo[1,2-a]pyridin-3-yl)-piperidine To a solution of 89 mg of 1-(t-butoxycarbonyl)-4-(6-bromo-imidazo [1,2-a]pyridin-3-yl)-piperidine (from Example 274, Step A) and 158 mg tributyl(allyl)tin in 6 mL of toluene was added 5.0 mg of dichlorobis (triphenyl phosphine)-palladium(II). The mixture was refluxed for 8 hours. The reaction was cooled down to r.t. and partitioned between $CH_2Cl_2$ and water. Aqueous layer was extracted with $CH_2Cl_2$ (3×). The combined organic phase was washed with brine and dried over $MgSO_4$. After concentration, the residue was purified by prep TLC (100% EtOAc) to afford 51 mg of a viscous oil.

Step B: α-(R)-(3-(S)-((4-(6-Allyl-imidazo[1,2-a]pyridin-3-yl)-piperidine-1-yl)methyl)-4-(S)-3-fluorophenyl)pyrrolidin-1-yl)-cyclobutylpropanoic Acid The title compound was prepared from 1-(t-butoxycarbonyl)-4-(6-allyl-imidazo[1,2-a]pyridin-3-yl)-piperidine (from Step A) and 2-(R)-(3-(R)-formyl-4-(S)-(3-fluorophenyl)pyrrolidin-1-yl)-3-(cyclobutyl)propanoic acid, 4-methoxy-benzyl ester according to the procedure described in Example 235, Step B, C and D to provide 25 mg of the title compound as a solid. ESI-MS 545 (M+H); HPLC A 1.24 min.

EXAMPLE 278

α-(R)-(3-(S)-((4-(7-Chloro-imidazo[1,2-a]pyridin-3-yl)-piperidine-1-yl)methyl)-4-(S)-(3-fluorophenyl)pyrrolidin-1-yl)-cyclobutylpropanoic Acid Step A: 1-(t-Butoxycarbonyl)-4-(7-chloro-imidazo[1,2-a]pyridin-3-yl)-piperidine The title compound was prepared from 350 mg of 1-(t-butoxycarbonyl)-4-(1-bromo-2-oxoethyl)-piperidine (from Example 292, Step C) and 162 mg of 2-amino-4-chloropyridine (prepared using procedures analogous to those described by R. J. Sundberg et al, *Org. Preparations & Procedures Int.* 1997, 29, (1), 117–122) in 10 mL ethanol using a procedure analogous to that described in Example 235, Step A to provide 240 mg of the title compound as a solid.

Step B: α-(R)-(3-(S)-((4-(7-chloro-imidazo[1,2-a]pyridin-3-yl)-piperidine-1-yl)methyl)-4-(S)-(3-fluorophenyl)pyrrolidin-1-yl)-cyclobutylpropanoic Acid The title compound was prepared from 1-(t-butoxycarbonyl)-4-(7-chloro-imidazo[1,2-a]pyridin-3-yl)- piperidine (from Step A) and 2-(R)-(3-(R)-formyl-4-(S)-(3-fluorophenyl)pyrrolidin-1-yl)-3-(cyclobutyl)propanoic acid, 4-methoxy-benzyl ester according to the procedure described in Example 235, Steps B, C and D to provide 39 mg of the title compound as a solid. ESI-MS 540 (M+H); HPLC A 1.46 min.

EXAMPLE 279

α-(R)-(3-(S)-((4-(Imidazo[1,5-a]pyridin-3-yl)piperidin-1-yl)methyl)-4-(S)-phenylpyrrolidin-1-yl)-cyclohexaneacetic Acid Step A: 1-(4-(Imidazo[1,5-a]pyridin-3-yl)piperidin-1-yl)ethanone To a solution of 2-(aminomethyl)pyridine (3.17 g, 29.3 mmol), 1-acetylpiperidine-4-carboxylic acid (5.02 g, 29.3 mmol) and HOBT (4.78 g, 35.2 mmol) in 30 mL of $CH_2Cl_2$ was added EDC (8.43 g, 44.0 mmol) at rt. After stirring at rt overnight, the reaction mixture was diluted with methylene chloride and washed with aqueous sodium bicarbonate followed by brine. The organic phase was dried over anhydrous $MgSO_4$. Concentration under reduced pressure afforded a viscous oil, which was dissolved in polyphosphoric acid (5 mL). The mixture was heated at ~120° C. for 18 h. After cooling to rt, the syrup was poured onto ice and water was added to keep the solution temperature below 10° C. The resulting dark brown solution was basified with ammonium hydroxide. Aqueous layer was extracted with EtOAC (3×). The combined organic phase was washed with brine and dried over anhydrous $MgSO_4$. Concentration under reduced pressure afforded 761 mg of the title compound as a viscous oil. $^1$H NMR (400 MHz, $CDCl_3$): δ 1.80~2.20 (m, 6H), 2.88~2.95 (m, 1H), 3.30~3.34 (m, 2H), 4.00~4.04 (br d, 1H), 4.62~4.65 (br d, 1H), 6.58 (dt, J=6.8, 1.1 Hz, 1H), 6.68 (dt, J=6.4, 0.7 Hz, 1H), 7.38 (s, 1H), 7.44 (d, J=9.2 Hz, 1H), 7.79 (dd, J=7.3, 0.8 Hz, 1H).

Step B: 3-(Piperidin-4-yl)imidazo[1,5-a]pyridine

The title compound was prepared from 1-(4-(imidazo[1,5-a]pyridin-3-yl)piperidin-1-yl)ethanone (from Step A) using a procedure analogous to that described in Example 89, Step B. $^1$H NMR (400 MHz, $CDCl_3$): δ 1.94~2.06 (m, 4H), 2.85 (dt, J=12.5, 3.1 Hz, 2H), 3.12~3.17 (m, 1H), 3.27 (t, J=3.4 Hz, 1H), 3.31 (t, J=3.5 Hz, 1H) 6.55 (dt, J=7.2, 1.0 Hz, 1H), 6.65 (m, 1H), 7.28 (s, 1H), 7.44 (d, J=9.2 Hz, 1H), 7.80 (d, J=7.2 Hz, 1H).

Step C: α-(R)-(3-(S)-((4-(Imidazo[1,5-a]pyridin-3-yl)piperidin-1-yl)methyl)-4-(S)-phenylpyrrolidin-1-yl)-cyclohexaneacetic Acid The title compound was prepared from 3-(piperidin-4-yl)imidazo[1,5-a]pyridine (from Step B) and 2-(R)-(3-(R)-formyl-4-(S)-phenylpyrrolidin-1-yl)-cyclohexaneacetic acid, (4-methoxy)benzyl ester (Aldehyde 5) using procedures analogous to those described in Example 95 (Steps C and D). ESI-MS 501 (M+1); HPLC A: 1.20 min.

EXAMPLES 280–281

Examples 280–281, in Table 15 were prepared according to the general procedure given in Example 95 (Steps D and E), employing 3-(piperidin-4-yl)imidazo[1,5-a]pyridine (from Example 279 Step B) and the appropriate aldehyde in place of 2-(R)-(3-(R)-formyl-4-(S)-phenylpyrrolidin-1-yl)-cyclohexaneacetic acid, (4-methoxy)benzyl ester (Aldehyde 5) in Step D.

TABLE 15

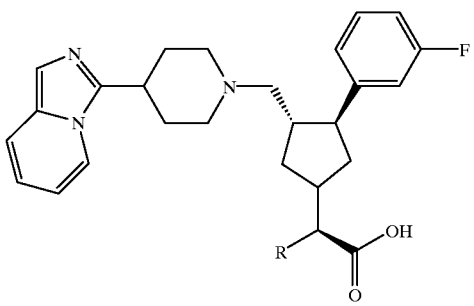

| EXAMPLE # | R | MS m/Z (M + 1) |
|---|---|---|
| 280 | ![cyclobutylmethyl] | 505 |
| 281 | ![isopropyl] | 479 |

EXAMPLE 282

α-(R)-(3-(S)-((4-([1,2,4]triazolo[4,3-a]pyridin-3-yl)piperidin-1-yl)methyl)-4-(S)-(3-fluorophenyl)pyrrolidin-1-yl)-3-(cyclobutyl)propanoic Acid Step A: 1-(t-Butoxycarbonyl)-4-(2-(2-pyridinyl)hydrazino)carbonyl-piperidine To a mixture of 2-hydrazinopyridine dihydrochloride (2.49 g, 13.7 mmol) and 1-Boc-piperidine-4-carboxylic acid (3.14 g, 13.7 mmol) in 30 mL of $CH_2Cl_2$ was added DIPEA (5.96 mL) followed by HOBT (2.22 g, 16.4 mmol) and EDC (3.93 g, 20.5 mmol) at rt. After stirring at rt for 18 h, the reaction mixture was partitioned between $CH_2Cl_2$ and water. The aqueous layer was extracted with $CH_2Cl_2$ (3×). Combined organic phase was washed with brine and dried over anhydrous $MgSO_4$. Concentration under reduced pressure afforded the title compound (3.3 g) as a white solid. $^1$H NMR (500 MHz, $CDCl_3$): δ 1.47 (s, 9H), 1.68–1.76 (m, 2H), 1.86–1.88 (m, 2H), 2.44 (m, 1H), 2.70–2.90 (br, 2H), 4.15–4.22 (br, 2H), 6.71 (d, J=8.5 Hz, 1H), 6.81 (t, J=6.4 Hz, 1H), 7.56 (m, 1H), 8.11 (d, J=5.0 Hz, 1H), 8.20~8.55 (br s, 1H).

Step B: 1-(t-Butoxycarbonyl)-4-([1,2,4]triazolo[4,3-a]pyridin-3-yl)piperidine

To a solution of 1-(t-butoxycarbonyl)-4-(2-(2-pyridinyl)hydrazino)carbonyl-piperidine (320 mg, 1.0 mmol) and dichlorotriphenylphosphorane (666 mg, 2.1 mmol) in $CH_3CN$ (10 mL) was added $Et_3N$ (0.42 mL, 3.0 mmol). After refluxing for 2h, the solution was diluted with EtOAc. The aqueous layer was extracted with EtOAc (3×). Combined organic phase was washed with brine and dried over anhydrous $MgSO_4$. Concentration followed by flash chromatography eluting with 100% EtOAc, then 10% MeOH/$CH_2Cl_2$ afforded the title compound (180 mg) as a foamy solid. $^1$H NMR (500 MHz, $CDCl_3$): δ 1.50 (s, 9H), 2.05~2.11 (m, 4H), 3.03 (br s, 2H), 3.24 (m, 1H), 4.25 (br d, J=11.7 Hz, 1H), 6.86 (dt, J=6.9, 0.9 Hz, 1H), 7.25 (m, 1H), 7.78 (dt, J=9.4, 1.2 Hz, 1H), 7.95 (dt, J=6.8, 1.1 Hz, 1H), 7.79 (dd, J=7.3, 0.8 Hz, 1H).

Step C: α-(R)-(3-(S)-((4-([1,2,4]triazolo[4,3-a]pyridin-3-yl)piperidin-1-yl)methyl)-4-(S)-(3-fluorophenyl)pyrrolidin-1-yl)-3-(cyclobutyl)propanoic Acid The title compound was prepared from 1-(t-butoxycarbonyl)-4-([1,2,4]triazolo[4,3-a]pyridin-3-yl)piperidine (from Step B) and 2-(R)-(3-(R)-formyl-4-(S)-3-(fluorophenyl)pyrrolidin-1-yl)-3-(cyclobutyl)propanoic acid, (4-methoxy)benzyl ester using procedures analogous to those described in Example 235 (Steps B, C and D). ESI-MS 506 (M+1); HPLC A: 1.76 min.

EXAMPLE 283

α-(R)-(3-(S)-((4-(5,7-Dimethylpyrazolo[1,5-a]pyrimidin-3-yl)piperidin-1-yl)methyl)-4-(S)-(3-fluorophenyl)pyrrolidin-1-yl)-3-(cyclobutyl)propanoic Acid Step A: 3-Bromo-5,7-dimethylpyrazolo[1,5-a]pyrimidine The title compound was prepared according to the procedure described by D. E. O'Brien et al, J. Med. Chem. 1974, 17, 645. $^1$H NMR (500 MHz, CDCl$_3$): δ 2.63 (s, 3H), 2.74 (s, 3H), 6.63 (d, J=0.9 Hz, 1H), 8.08 (s, 1H).

Step B: 1-(t-Butoxycarbonyl)-4-trifluoromethanesulfonyl-[1,2,3,6]tetrahydropyridine To a solution of tert-butyl 4-oxo-1-piperidinecarboxylate (2.61 g, 13.1 mmol) in THF (20 mL) was added 2 M-LDA (7.85 mL, 15.7 mmol) at −78° C. After stirring at −78° C. for 30 min, was added 2-[N,N-bis(trifluoromethylsulfonyl)amino]-5-chloropyridine (4.23 g, 10.8 mmol) in THF (5 mL) at −78° C. After stirring at −78° C. for 30 min, the solution was warmed to rt and stirred overnight. The reaction mixture was partitioned between EtOAc and H$_2$O. Aqueous layer was extracted with EtOAc (3×). Combined organic phase was washed with brine and dried over anhydrous MgSO$_4$. Concentration afforded the title compound (4.70 g) as a viscous oil. $^1$H NMR (500 MHz, CDCl$_3$): δ 1.49 (s, 9H), 2.45 (br s, 2H), 3.64 (br s, 2H), 4.05 (br s, 2H), 5.77 (br s, 1H).

Step C: 1-(t-Butoxycarbonyl)-4-trimethylstannyl-[1,2,3,6]tetrahydropyridine

To a solution of 1-(t-butoxycarbonyl)-4-trifluoromethanesulfonyl-[1,2,3,6]tetrahydropyridine (from Step B, 2.07 g, 6.25 mmol), hexamethylditin (2.46 g, 7.50 mmol) and Pd(Ph$_3$P)$_4$ (361 mg, 0.31 mmol) in THF (15 mL) was added LiCl (2.65 g, 62.5 mmol). After refluxing for 18 h, the mixture was partitioned between EtOAc and H$_2$O. Organic phase was washed with brine and dried over anhydrous MgSO$_4$. Concentration followed by flash chromatography eluting with 10/1 hexanes/EtOAc, then 50% EtOAc in hexanes afforded the title compound (1.03 g) as a viscous oil. $^1$H NMR (500 MHz, CDCl$_3$): δ 0.13 (t, J=27 Hz, 9H), 1.48 (s, 9H), 2.28 (br s, 2H), 3.48 (t, J=5.5 Hz, 2H), 3.92 (d, J=2.1 Hz), 5.77 (br t, 1H).

Step D: 1-(t-Butoxycarbonyl)-4-(5,7-dimethylpyrazolo[1,5-a]pyrimidin-3-yl)-[1,2,3,6]tetrahydropyridine To a solution of 1-(t-butoxycarbonyl)-4-trimethylstannyl-[1,2,3,6]tetrahydropyridine (from Step C, 734 mg, 2.13 mmol) and 3-bromo-5,7-dimethylpyrazolo[1,5-a]pyrimidine (from Step A, 399 mg, 1.77 mmol) in 1,4-dioxane (5 mL) was added Pd (II) (Ph$_3$P)$_2$Cl$_2$ (62 mg, 0.09 mmol) at rt. After refluxing for 6 h, the mixture was partitioned between EtOAc and H$_2$O. The aqueous layer was extracted with EtOAc (3×). Combined organic phase was washed with brine and dried over anhydrous MgSO$_4$. Concentration followed by flash chromatography eluting with 10% EtOAc in hexanes, then 50% EtOAc in hexanes afforded the title compound (90 mg) as a viscous oil. $^1$H NMR (500 MHz, CDCl$_3$): δ 1.50 (s, 9H), 2.60 (s, 3H), 2.69 (br s, 2H), 2.74 (s, 3H), 3.70 (br m, 2H), 4.16 (d, J=2.7 Hz, 2H), 6.59 (s, 1H), 6.73 (m, 1H), 8.06 (s, 1H).

Step E: 1-(t-Butoxycarbonyl)-4-(5,7-dimethylpyrazolo[1,5-a]pyrimidin-3-yl)piperidine A solution of 1-(t-butoxycarbonyl)-4-(5,7-dimethylpyrazolo[1,5-a]pyrimidin-3-yl)-[1,2,3,6]tetrahydropyridine (from Step D, 90 mg, 0.27 mmol) in EtOH (2 mL) and EtOAc (2 mL) was hydrogenated using 10% Pd/C (10 mg) under one atmosphere of H$_2$ gas at rt. After checking TLC, EtOH (5 mL), EtOAc (5 mL), and 10% Pd/C (75 mg) were added and hydrogenation was continued for additional 2 h. The mixture was filtered through celite and concentrated to give the title compound (52 mg) as a viscous oil. $^1$H NMR (500 MHz, CDCl$_3$): δ 1.50 (s, 9H), 1.60~1.80 (m, 4H), 2.02 (br d, 2H), 2.56 (s, 3H), 2.72 (s, 3H), 2.80~3.00 (br, 2H), 3.15 (m, 1H), 4.05~4.35 (br, 2H), 6.54 (s, 1H). 7.93 (s, 1H).

Step F: α-(R)-(3-(S)-((4-(5,7-Dimethylpyrazolo[1,5-a]pyrimidin-3-yl)piperidin-1-yl)methyl)-4-(S)-(3-fluorophenyl)pyrrolidin-1-yl)-3-(cyclobutyl)propanoic Acid The title compound was prepared from 1-(t-butoxycarbonyl)-4-(5,7-dimethylpyrazolo[1,5-a]pyrimidin-3-yl)piperidine (from Step E) and and 2-(R)-(3-(R)-formyl-4-(S)-3-(fluorophenyl)pyrrolidin-1-yl)-3-(cyclobutyl)propanoic acid, (4-methoxy)benzyl ester using procedures analogous to those described in Example 235, Steps B, C and D: ESI-MS 534 (M+1); HPLC A: 2.29 min.

EXAMPLE 284

α-(R)-(3-(S)-((4-(6-Fluoro-imidazo[1,2-a]pyridin-3-yl)piperidin-1-yl)methyl)-4-(S)-(3-fluorophenyl)pyrrolidin-1-yl)-(3,3-dimethyl)butanoic Acid Step A: 1-(t-Butoxycarbonyl)-4-(6-fluoro-imidazo[1,2-a]pyridn-3-yl)piperidine The title compound was prepared from 1-(t-butoxycarbonyl)-4-(1-bromo-2-oxoethyl)-piperidine (from Example 292, Step C) and 2-amino-5-fluoropyridine (prepared using procedures analogous to those described by D.C. Baker et al, Synthesis. 1989, 905) using a procedure similar to that described in Example 235, Step A. $^1$H NMR (500 MHz, CDCl$_3$): δ 1.51 (s, 9H), 1.60~1.80 (m, 2H), 2.07 (br d, 2H), 2.85~3.00 (m, 3H), 4.20~4.40 (br, 2H), 7.11 (m, 1H), 7.47 (s, 3H), 7.60(m, 1H), 7.89 (m, 1H).

Step B: α-(R)-(3-(S)-((4-(6-Fluoro-imidazo[1,2-a]pyridin-3-yl)piperidin-1-yl)methyl)-4-(S)-(3-fluorophenyl)pyrrolidin-1-yl)-(3,3-dimethyl)butanoic Acid The title compound was prepared from 1-(t-butoxycarbonyl)-4-(6-fluoro-imidazo[1,2-a]pyridin-3-yl)piperidine (from Step A) and 2-(R)-(3-(R)-formyl-4-(S)-3-(fluorophenyl)pyrrolidin-1-yl)-(3,3-dimethyl)butanoic acid, (4-methoxy)benzyl ester (Aldehyde 18) using procedures analogous to those described in Example 235 Steps B, C and D ESI-MS 511 (M+1); HPLC A: 1.47 min.

EXAMPLES 284A AND 285

Example 284A in Table 16 was prepared using procedures analogous to those described in Example 235 Steps B, C and D, employing 1-(t-butoxycarbonyl)- 4-(6-fluoro-imidazo[1,2-a]pyridin-3-yl)piperidine (from Example 284 Step A) and 2-(R)-(3-(R)-formyl-4-(S)-3-(fluorophenyl)pyrrolidin-1-yl)-3-(cyclobutyl)propanoic acid, (4-methoxy)benzyl ester in place of 2-(R)-(3-(R)-formyl-4-(S)-3-(fluorophenyl)pyrrolidin-1-yl)-(3,3-dimethyl)butanoic acid, (4-methoxy)benzyl ester (Aldehyde 18) in Step C. Example 285 in Table 16 was prepared using procedures analogous to those described in Example 235, except 2-amino-5-fluoro-4-methylpyridine (prepared using procedures analogous to those described by D.C. Baker et al, *Synthesis*. 1989, 905) was employed in place of 2-amino-5-fluoropyridine in Step A.

TABLE 16

| EXAMPLE # | R | MS m/Z (M + 1) |
|---|---|---|
| 284A | (6-fluoro-imidazo[1,2-a]pyridin-3-yl) | 523 |
| 285 | (6-fluoro-7-methyl-imidazo[1,2-a]pyridin-3-yl) | 537 |

EXAMPLE 286

α-(R)-(3-(S)-((4-(7-Methoxy-imidazo[1,2-a]pyridin-3-yl)piperidin-1-yl)methyl)-4-(S)-(3-fluorophenyl)pyrrolidin-1-yl)-(3,3-dimethyl)butanoic Acid Step A: 1-(t-Butoxycarbonyl)4-(7-methoxy-imidazo[1,2-a]pyridin-3-yl)piperidine The title compound was prepared from 1-(t-butoxycarbonyl)-4-(1-bromo-2-oxoethyl)-piperidine (from Example 292, Step C) and 2-amino-4-methoxypyridine (prepared using procedures analogous to those described by R. J. Sundberg et al, *Org. Preparations & Procedures Int.* 1997, 29, (1), 117–122) using a procedure similar to that described in Example 235 Step A. $^1$H NMR (500 MHz, CDCl$_3$): δ 1.50 (s, 9H), 1.63~1.75 (m, 2H), 2.05 (br d, J=13 Hz, 2H), 2.85~3.00 (br, 3H), 3.88 (s, 3H), 4.15~4.35 (br, 2H), 6.58 (d, J=7.4 Hz, 1H), 6.93 (br s, 1H), 7.25 (br s, 1H), 7.79 (d, J=7.5 Hz, 1H).

Step B: α-(R)-(3-(S)-((4-(7-Methoxy-imidazo[1,2-a]pyridin-3-yl)piperidin-1-yl)methyl)-4-(S)-(3-fluorophenyl)pyrrolidin-1-yl)- )-3,3 dimethyl)butanoic Acid The title compound was prepared from 1-(t-butoxycarbonyl)-4-(7-methoxy-imidazo[1,2-a]pyridin-3-yl)piperidine and 2-(R)-(3-(R)-formyl-4-(S)-3-(fluorophenyl)pyrrolidin-1-yl)-(3,3-dimethyl)butanoic acid, (4-methoxy)benzyl ester (Aldehyde 18) using procedures analogous to those described in Example 235 Steps B, C and D ESI-MS 523 (M+1); HPLC A: 1.07 min.

EXAMPLES 287–289

Example 287 in Table 17 was prepared using procedures analogous to those described in Example 235, employing 1-(t-butoxycarbonyl)-4-(7-methoxy-imidazo[1,2-a]pyridin-3-yl)piperidine (from Example 286, Step A) and 2-(R)-(3-(R)-formyl-4-(S)-3-(fluorophenyl)pyrrolidin-1-yl)-3-(cyclobutyl)propanoic acid, (4-methoxy)benzyl ester in place of 2-(R)-(3-(R)-formyl-4-(S)-3-(fluorophenyl)pyrrolidin-1-yl)-(3,3-dimethyl)butanoic acid, (4-methoxy)benzyl ester (Aldehyde 18). Examples 288 and 289 in Table 17 were prepared using procedures analogous to those described in Example 235, except 2-amino-4-ethoxypyridine (prepared using procedures analogous to those described by R. J. Sundberg et al, *Org. Preparations & Procedures Int.* 1997, 29, (1), 117–122) was employed in place of 2-ethoxypyridine.

TABLE 17

| EXAMPLE # | Ra | Rb | MS m/Z (M + 1) |
|---|---|---|---|
| 287 | (7-MeO-imidazo[1,2-a]pyridin-3-yl) | cyclobutylmethyl | 535 |
| 288 | (7-EtO-imidazo[1,2-a]pyridin-3-yl) | t-butyl | 537 |

TABLE 17-continued

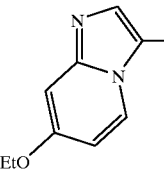

| EXAMPLE # | Ra | Rb | MS m/Z (M + 1) |
|---|---|---|---|
| 289 | 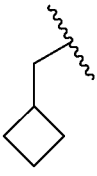 (EtO-imidazo[1,2-a]pyridinyl) | (cyclobutylmethyl) | 549 |

EXAMPLE 290

α(R)-(3-(S)-((4-(2-Ethyl-5,6,7,8-tetrahydroimidazo[1,2-a]pyridin-3-yl)piperidin-1-yl)methyl)-4-(S)-(3-fluorophenyl)pyrrolidin-1-yl)-(3,3-dimethyl)butanoic Acid Step A: 2-Ethyl-imidazo[1,2-a]pyridine The title compound was prepared from 2-aminopyridine and 1-bromo-2-butanone, employng procedures analogous to those described in Example 235, Step A. $^1$H NMR (500 MHz, CDCl$_3$): δ 1.34 (t, J=7.3 Hz, 3H), 2.82 (q, J=7.6Hz, 2H), 6.70 (t, J=6.6 Hz, 1H), 7.10 (m, 1H), 7.32 (s, 3H), 7.51 (d, J=8.9 Hz, 1H), 8.03 (dd, J=6.6, 0.9 Hz, 1H).

Step B: 3-Bromo-2-ethyl-imidazo[1,2-a]pyridine

To a solution of 2-ethyl-imidazo[1,2-a]pyridine (2.17 g, 14.9 mmol) in EtOH (25 mL) was added Br$_2$ (2.0 g, 12.5 mmol) in H$_2$O (5 mL) dropwise at rt. After stirring at rt for 4 h, EtOH was evaporated under reduced pressure. The residue was basified with aqueous NaHCO$_3$ and extracted with CH$_2$Cl$_2$ (3×). The organic phase was washed with brine and dried over anhydrous MgSO$_4$. Concentration followed by flash chromatography chromatography eluting with 20% EtOAc in hexanes, followed by 50% EtOAc in hexanes afforded the title compound (1.88 g) as a viscous oil. $^1$H NMR (500 MHz, CDCl$_3$): δ 1.36 (t, J=7.5 Hz, 3H), 2.83 (q, J=7.6 Hz, 2H), 6.88 (t, J=6.8 Hz, 1H), 7.20 (m, 1H), 7.55 (dd, J=8.9, 0.9 Hz, 1H), 8.05 (dd, J=6.9, 1.2 Hz, 1H).

Step C: 2-Ethyl-3-(4-pyridyl)-imidazo[1,2-a]pyridine

To a solution of 3-bromo-2-ethyl-imidazo[1,2-a]pyridine (1.4 g, 6.28 mmol), 4-tributylstannylpyridine (2.31 g, 6.28 mmol) and Pd (II) (Ph$_3$P)$_2$Cl$_2$ (442 mg, 0.63 mmol) in toluene (5 mL) was added LiCl (26.7 mg, 0.63). After refluxing for 18 h, the mixture was partitioned between EtOAc and aqueous NaHCO$_3$. The aqueous layer was extracted with EtOAc (3×). Combined organic phase was washed with brine and dried over anhydrous MgSO$_4$. Concentration followed by flash chromatography eluting with 100% EtOAc, then 10% MeOH in CH$_2$Cl$_2$ afforded the title compound (543 mg) as a viscous oil. $^1$H NMR (500 MHz, CDCl$_3$): δ 1.36 (t, J=7.5 Hz, 3H), 2.84 (q, J=7.5 Hz, 2H), 6.68 (dt, J=6.8, 1.1 Hz, 1H), 7.21 (m, 1H), 7.39 (dd, J=5.9, 1.6 Hz, 2H), 7.61 (dd, J=8.9, 1.0 Hz, 1H), 8.75 (d, J=5.9 Hz, 2H).

Step D: 4-(2-Ethyl-5,6,7,8-tetrahydroimidazo[1,2-a]pyridin-3-yl)piperidine, Acetic Acid Salt A solution of 2-ethyl-3-(4-pyridyl)-imidazo[1,2-a]pyridine (700 mg, 3.13 mmol) in EtOH (12 mL) and HOAc (4 mL) was hydrogenated using Platinum (IV) oxide (40 mg) under 40 psi of H$_2$ gas in a Parr shaker at rt for 18 h. The mixture was filtered through celite and concentrated to give the title compound (1.47 g) as a viscous oil.

Step E: α-(R)-(3-(S)-((4-(2-Ethyl-5,6,7,8-tetrahydroimidazo[1,2-a]pyridin-3-yl)piperidin-1-yl)methyl)-4-(S)-(3-fluorophenyl)pyrrolidin-1-yl)-(3,3-dimethyl)butanoic Acid The title compound was prepared from 4-(2-ethyl-5,6,7,8-tetrahydroimidazo[1,2-a]pyridin-3-yl)piperidine, acetic acid salt and 2-(R)-(3-(R)-formyl-4-(S)-3-(fluorophenyl)pyrrolidin-1-yl)-(3,3-dimethyl)butanoic acid, (4-methoxy)benzyl ester (Aldehyde 18) using procedures analogous to those described in Example 235, Steps B, C and D ESI-MS 525 (M+1); HPLC A: 1.49 min.

EXAMPLE 291

2-(R)-(3-(S)-(4-(2-Benzyl-thiazol-5-yl)-piperidin-1-yl)methyl)-4-(S)-3-fluorophenyl pyrrolidin-1-yl)-3-methylbutyric Acid Step A: 1-t-Butyloxycarbonyl-4-(nitromethylcarbonyl)piperidine To a solution of 1-t-butyloxycarbonyl-piperidine-4-carboxylic acid (22.9 g, 100 mmol) in 200 mL of anhydrous THF was added carbonyl diimidazole (20.0 g, 125 mmol) under nitrogen. Effervescence was observed and the reaction mixture was stirred 1 hr at ambient temperature. Freshly distilled nitromethane (7.4 mL, 135 mmol) followed by DBU (21.0 mL, 140 mmol) were added. The resulting reaction mixture was stirred for 1 day at room temperature. After dilution with EtOAc, the mixture was washed with 2N HCl and brine. The organic phase was dried over anhydrous MgSO4. Evaporation of the solvent followed by the purification of the residue on silica gel using 1:1 mixture of EtOAc-hexane with 1% HOAc as an eluant gave 25 g of the nitroketone as a semi-solid after removal of last traces of HOAc by azeotroping with toluene. 1H NMR (CDCl3) 1.48(s,9H), 1.65 (m, 2H), 1.90 (m, 2H), 2.6~2.9 (m, 3H), 2.80,4.15 (m, 2H); 5.36(s, 2H).

Step B: 1-t-Butyloxycarbonyl-4-(1-hydroxy-2-nitro)ethyl)-piperidine

Sodium borohydride (1.52 g, 40 mmol) was added portionwise to a suspension of 1-t-butyloxycarbonyl-4-(nitromethylcarbonyl) piperidine (10.5 g, 40 mmol) in methanol (80 ml) at 0° C. After 6.5 hr, the solvent was removed in vacuo. The residue was diluted with EtOAc and stirred with 2N HCl and the layers were separated. The organic phase was washed with brine and dried over MgSO4. Solvent removal gave 9.1 g of the desired product as amorphous solid. 1H NMR(CDCl3) 1.3 (m, 2H), 1.45 (9H, s); 1.6~1.9 (m, 4H), 2.7 (m, 2H), 4.2 (m, 2H) 4.45(2H, m).

Step C: 1-t-Butyloxycarbonyl-4-(1-hydroxy-2-amino)ethyl-piperidine

To a stirred suspension of 1-t-butyloxycarbonyl-4-(1-hydroxy-2-nitro)ethyl)-piperidine (9.0 g, 33 mmol) ) in anhydrous methanol (100 mL),10% Pd-C (2.0 g) followed by ammonium formate (12.6 g, 200 mmol) were cautiously added. The reaction mixture was stirred 1.5 days at ambient temperature. The catalyst was filtered through a pad of celite and washed with methanol. The filtrate was concentrated after adding 42 mL of triethylamine to free the product from any formic acid salts. The residue was purified on silica gel using 10:10:1 mixture of EtOAc, hexane and NH4OH as solvent to yield 6.9 g of the desired amino alcohol as white solid after azeotroping with toluene. 1H NMR (CDCl3): 1.2 (m, 2H), 1.5(9H,s), 1.55–4.2 (m, 13H) 3.6(2H,s).

Step D: 1-t-Butyloxycarbonyl-4-(1-hydroxy-2-phenylacetylamino)ethyl-piperidine

Phenylacetyl chloride (0.44 mL, 3.3 mmol) was added dropwise to a mixture of 1-t-Butyloxycarbonyl-4-(1-hydroxy-2-amino)ethyl-piperidine (0.732 g, 3 mmol) and triethylamine (0,465 mL, 3.3 mmol) in CH2Cl2 (15 mL) at ice bath temperature and the bath was removed. After stirring for 3 hr at room temperature, the reaction mixture was diluted with EtOAc and washed with saturated NaHCO3 and brine. The organic phase was dried over anydrous MgSO4. Solvent removal gave a crude product which was used in the next step without further purification. 1H NMR (CDCl3) 1.2 (m, 2H), 1.45(9H,s), 1.6~3.5 (m, 7H), 3.62(s, 2H), 4.12 (m, 2H).

Step E: 1-t-Butyloxycarbonyl-4-(2-phenylacetamido)acetyl-piperidine

To a stirred solution of 1-t-butyloxycarbonyl-4-(1-hydroxy-2-phenylacetylamino)ethyl-piperidine (step D) in 5 mL of acetone at ice bath temperature 8 N Jones reagent was added dropwise until the orange color of the reagent persisted. After stirring for 0.5 hr, 0.2 mL of isopropanol was added and the stirring was continued for 0.5 hr. Solvent was removed in vacuo and the residue was partitioned between water and EtOAc. The organic phase was washed with brine and dried over anhydrous magnesium sulfate. Solvent removal gave an oil which was purified on silica gel using 1:1 EtOAc-hexane as solvent to yield 606 mg of the desired ketone as oil. 1H NMR (CDCl3): 1.46 (s, 9H), 1.8 (m, 2H), 2.44–2.84 (m, 3H), 3.62 (s, 2H), 4.1 (m, 2H), 4.18 (d, 2H),6.18 (s, 1H), 7.2–7.4 (m, 5H).

Step F: 1-t-Butyloxycarbonyl-4-(2-benzyl-thiazol-5-yl)piperidine

A mixture of 1-t-butyloxycarbonyl-4-(2-phenylacetamido)acetyl-piperidine (595 mg, 1.653 mmol) and Lawesson's reagent (607 mg, 1.66 mmol) in 5 mL of toluene was heated at 120° C. for 3.5 hr. After cooling, 3:1 mixture of EtOAc and CH2Cl2 and saturated NaHCO3 solution were added and the mixture was stirred for 0.5 hr. The organic phase was separated and washed with brine. Solvent removal gave a crude product which was purified on silica gel using 2:3 mixture of EtOAc-hexane as solvent to give 330 mg of the desired product. 1H NMR (CDCl3): 1.45(9H,s); 1.58 (m, 2H), 1.95 (m, 2H), 2.74~3.0 (m, 3H),4.2 (m, 2H) 4.4 (s, 2H). 7.46(s, 1H).

Step G: 4-(2-Benzyl-thiazol-5-yl)piperidine Dihydrochloride

Acetyl chloride (0.3 mL) was added dropwise to a solution of 320 mg of 1-t-butyloxycarbonyl-4-(2-benzyl-thiazol-5-yl)piperidine in methanol (2 mL) at ice bath temperature. The reaction mixture was stirred 3.5 hr as it warmed to room temperature. Solvent removal in vacuo gave the desired amine as glassy solid. 1H NMR (CD$_3$OD): 1.94 (m, 2H), 2.24 (m, 2H), 3.1~3.5 (m, 5H), 4.58 (s, 2H), 7.4 (m, 5H) 8.02(s, 1H).

Step H: 2-(R)-(3-(S)-(4-(2-Benzyl-thiazol-5-yl)-piperidin-1-yl)methyl)-4-(S)-(3-fluorophenyl)pyrrolidin-1-yl)-3-methylbutyric Acid, 4-methoxybenzyl Ester To 33 mg (0.1 mmol) of 4-(2-benzyl-thiazol-5-yl) piperidine dihydrochloride in 2 mL of DCE, 0.051 mL (0.3 mmol) of DIEA and 37 mg (0.09 mmol) of 2-(R)-(3-(R)-formyl-4-(S)-(3-fluorophenyl)pyrrolidin-1-yl)-3-methylbutanoic acid, (4-methoxy)benzyl ester were added. After 5 min 42 mg (0.2 mmol) of sodium triacetoxyborohydride was added and the reaction was stirred overnight. The solution was diluted with EtOAc, washed with water and brine. The organic layer was dried and concentrated. The residue was purified on prep TLC using 5% MeOH—CH2Cl2 to isolate 40 mg of the desired product.

Step I: 2-(R)-(3-(S)-(4-(2-Benzyl-thiazol-5-yl)-piperidin-1-yl)methyl)-4-(S)-(3-fluorophenyl)pyrrolidin-1-yl)-3-methylbutyric Acid Formic acid (1 mL) was added to 40 mg of 2-(R)-(3-(S)-(4-(2-benzyl-thiazol-5-yl)-piperidin-1-yl)methyl)-4-(S)-(3-fluorophenyl)pyrrolidin-1-yl)-3-methylbutyric acid, 4-methoxybenzyl ester (step H) and the solution was stirred overnight. The reaction was concentrated and the residue was purified on a Varian SCX (ion exchange) column using 2N NH3 in MeOH to elute the product. Concentration of the solution furnished 32 mg of the title compound. Mass spec 536.3 (M+1), HPLC A 2.59 min.

EXAMPLE 292

2-(R)-(3-(S)-(4-(2-Benzyl-thiazol-5-yl)-piperidin-1-yl)methyl)-4-(S)-(3-fluorophenyl)pyrrolidin-1-yl)-3-(cyclobutyl)propionoic Acid Step A: 1-t-Butyloxycarbonyl-4-(2-hydroxyethyl) piperidine A mixture of 4-(2-hydroxyethyl) piperidine (5.0 g, 40 mmol), di-t-butyl dicarbonate (10.9 g, 50 mmol), and triethylamine (7 mL, 50 mmol) in 100 mL of anhydrous CH2Cl2 was stirred overnight at room temperature. Volatiles were removed in vacuo and the resulting oil was purified on a silica gel column using 20% EtOAc in hexane as eluant to give 7.9 g of the desired product as a colorless oil.

Step B: 1-t-Butyloxycarbonyl-4-formylmethyl-piperidine

Oxalyl chloride (2.2 mL, 25 mmol) was added to 75 mL of anhydrous CH2Cl2 at −78° C. DMSO (3.5 mL, 50 mmol) was then added dropwise over 5 min, and the resulting mixture was stirred for 15 min. 1-t-Butyloxycarbonyl-4-(2-hydroxyethyl)piperidine (2.29 g, 10 mmol, step A) was dissolved in 5 mL of anhydrous CH2Cl2 and added over 10 min to the above mixture. After stirring 30 min, DIEA (17.4 mL, 100 mmol) was added over 10 min. The mixture was then warmed to 0° C. and maintained at that temperature for 1 hr. After quenching with water, the reaction mixture was diluted with 75 mL of CH2Cl2 and the layers were separated. The organic phase was washed with 3×50 mL of water and dried over anhydrous magnesium sulfate. Solvent removal gave an oil, which was purified on silica gel using 20% EtOAc in hexane to give 2.05 g of the desired aldehyde which hardened overnight into an oily solid. NMR: 1.2 (m, 2H),1.5~1.7 (m, 3H), 2.15 (d, 2H, J=3), 2.75 (m, 2H), 4.1 (m, 2H) 9.8(s, 1H).

Step C: 1-t-Butyloxycarbonyl-4-(1-bromo-2-oxo-ethyl)-piperidine

A mixture of 1-t-butyloxycarbonyl-4-formylmethyl-piperidine (0.57 g, 2.25 mmol, step B), and 3,3-dibromo-Meldrum's acid (0.75 g, 2.5 mmol) in 10 mL of anhydrous ether was stirred for 2 days at room temperature under nitrogen. The reaction mixture was diluted with EtOAc and washed with satd. NaHCO3 solution. The organic phase was dried over anhydrous MgSO4. Solvent removal followed by purification on silica gel using 20% ethyl acetate in hexane as solvent gave 59% of the pure bromo aldehyde as a colorless oil. 1H NMR (CDCl$_3$): 1.35 (s, 9H), 1.7–2.1 (m, 3H), 2.75 (m, 2H), 4.04 (dd, 1H, J=1.5;2), 4.2 (m, 2H), 9.46 (d, 1H, J=1.5).

Step D: 1-t-Butyloxycarbonyl-4-(2-Benzyl-thiazol-5-yl)piperidine

A mixture of 1-t-butyloxycarbonyl-4-(1-bromo-2-oxo-ethyl)-piperidine (612 mg, 2 mmol), and benzyl thioamide (500 mg, 2.55 mmol) in 10 mL of anhydrous toluene was heated to reflux for 6 hr. Solvent was then removed and the residue was purified on silica gel using 25% EtOAc in hexane as solvent to give 350 mg of the desired thiazole as an oil. 1H NMR (CDCl3): 1.45 (s, 9H), 1.95 (m, 2H), 2.8–3.0 (m, 3H), 4.2(m, 2H), 4.4 (s, 2H), 7–7.5 (m, 5H), 7.46 (s, 1H).

Step E: 4-(2-Benzyl-thiazol-5-yl)piperidine Dihydrochloride

The title compound was prepared by removal of the t-butyloxy group of 1-t-butyloxycarbonyl-4-(2-benzyl-thiazol-5-yl)piperidine as described in example 291, step G.

Step F: 2-(R)-(3-(S)-(4-(2-Benzyl-thiazol-5-yl)-piperidin-1-yl)methyl)-4-(S)-(3-fluorophenyl)pyrrolidin-1-yl)-3-(cyclobutyl)propionoic acid, 4-methoxybenzyl Ester Reaction of 4-(2-benzyl-thiazol-5-yl)piperidine dihydrochloride with 2-(R)-(3-(R)-formyl-4-(S)-(3-fluorophenyl) pyrrolidin-1-yl)-3-(cyclobutyl)propionic acid, 4-methoxybenzyl ester according to example 291, step H gave the desired product.

Step G: 2-(R)-(3-(S)-(4-(2-Benzyl-thiazol-5-yl)-piperidin-1-yl)methyl)-4-(S)-(3-fluorophenyl)pyrrolidin-1-yl)-3-(cyclobutyl)propionoic Acid Reaction of 2-(R)-(3-(S)-(4-(2-benzyl-thiazol-5-yl)-piperidin-1-yl)methyl)-4-(S)-(3-fluorophenyl)pyrrolidin-1-yl)-3-(cyclobutyl)propionic acid, 4-methoxybenzyl ester with formic acid as described in example 291, step I furnished 20 mg of the title compound. Mass spec. 562.3 (M+1), HPLC A 2.93.

EXAMPLE 293

4-(2-Benzyl-4-methyl-thiazol-5-yl)piperidine

This thiazole was prepared according to the method of example 291 by substituting nitroethane for nitromethane in step A.

EXAMPLE 294

4-(2-Benzyl-4-ethyl-thiazol-5-yl)piperidine

The title compound was obtained by the procedure of example 291 by substituting nitropropane for nitromethane in step A.

EXAMPLE 295

2-(R)-(3-(S)-(4-(2-(2-Pyridylmethyl)-thiazol-5-yl)-piperidin-1-yl)methyl)-4-(S)-3-fluorophenyl pyrrolidin-1-yl)-3-methylpropionic Acid Step A: 1-t-Butyloxycarbonyl-4-((1-hydroxy)-2-(2-pyridylmethyl)carbonylamino)ethyl-piperidine To 0.361 g (2.08 mmol) of 2-pyridylacetic acid hydrochloride in 8 mL of CH2Cl2, 0.337 g (2.5 mmol) of 1-hydroxybenzotriazole, 0.478 g (2.5 mmol) of EDC and 0.57 mL (5.2 mmol) of N-methylmorpholine were added. After 10 min, 0.508 g (2.08 mmol) of 1-t-butyloxycarbonyl-4-(2-amino-1-hydroxy)ethyl-piperidine (example 291, step C) was added the solution was stirred overnight. The reaction was quenched with saturated NaHCO3 and extracted with CH2Cl2. The combined CH2Cl2 layer was washed with brine, dried and concentrated. The residue was chromatographed on a flash column using a gradient of 5–10% MeOH in EtOAC containing 1% triethylamine to isolate 0.68 g of the desired product. 1H NMR (CDCl3) 1.24 (m, 3H), 1.45 (s, 9H), 1.58 (m, 1H), 1.82 (m, 1H), 2.6 (br, 2H), 3.21 (m, 1H), 3.49 (m, 2H), 3.75 (s, 2H), 4.12 (br, 2H), 7.22 (m, 1H), 7.29 (d, 1H), 7.69 (m, 1H), 852 (m, 1H).

Step B: 1-t-Butyloxycarbonyl-4-(2-(2-pyridylmethyl)carbonylamino)acetyl-piperidine To a solution of 0.22 mL (3.2 mmol) of DMSO in 1 mL of CH2Cl2 cooled in a dry ice-acetone bath, 0 14 mL (1.6 mmol) of oxalyl chloride was added. After 0.5 hr, 0.145 g of 1-t-butyloxycarbonyl-4-((1-hydroxy)-2-(2-pyridylmethyl) carbonylamino)ethyl-piperidine (step A) in 1 mL of CH2Cl2 was added. After 1 hr, 0.89 mL (6.38 mmol) of triethylamine was added, the cold bath was removed and the reaction was stirred for 1.5 hr. The solution was partitioned between water and CH2Cl2. The organic layer was washed with brine, dried and concentrated. The residue was purified on a prep TLC plate using 5% MeOH—EtOAc as an eluant to furnish 67 mg of the desired product. 1H NMR (CDCl3) 1.45 (s, 9H), 1.5–2.0 (m, 4H), 2.53 9m, 1H), 2.77 (br, 2H), 3.79 (s, 2H), 4.1 (br, 2H), 4.22 (d, 2H), 7.2–8.0 (m, 3H), 8.61 (d, 1H).

Step C: 1-t-Butyloxycarbonyl-4-(2-(2-pyridylmethyl) thiazol-5-yl)piperidine

The title compound was prepared by reacting 1-t-butyloxycarbonyl-4-(2-(2-pyridylmethyl)carbonylamino) acetyl-piperidine (step B) with Lawesson's reagent as described in example 291, step F. 1H NMR (CDCl3) 1.47 (s, 9H), 1.6 (m, 2H), 1.99 (m, 2H), 2.82 (br, 2H), 2.94 (m, 1H), 4.17 (br, 2H), 4.48 (s, 2H), 7.2–7.8 (m, 4H), 8.6 (br, 1H).

Step D: 4-(2-(2-Pyridylmethyl)thiazol-5-yl)piperidine

Removal of the t-butyloxycarbonyl protecting group as described in example 291, step G furnished the title compound.

Step E: 2-(R)-(3-(S)-(4-(2-(2-Pyridylmethyl)-thiazol-5-yl)-piperidin-1-yl)methyl)-4-(S)-3-fluorophenyl pyrrolidin-1-yl)-3-methylpropionoic Acid, 4-methoxybenzyl Ester The desired product was obtained by reductive amination of 2-(R)-(3-(R)-formyl-4-(S)-(3-fluorophenyl)pyrrolidin-1-yl)-3-methylbutanoic acid, (4-methoxy)benzyl ester with 4-(2-(2-pyridylmethyl)thiazol-5-yl)piperidine by the method of example 291, step H.

Step F: 2-(R)-(3-(S)-(4-(2-(2-Pyridylmethyl)-thiazol-5-yl)-piperidin-1-yl)methyl)-4-(S)-3-fluorophenyl pyrrolidin-1-yl)-3-methylpropionoic Acid The title compound was obtained according to the procedure described in example 291, step I. Mass spec. 537.5 (M+1), HPLC A 1.41 min.

EXAMPLES 296–508

The substituted benzylthiazoles used for the compounds listed in Tables 18 and 19 were prepared by a method analogous to that described in example 291 by employing the requisite acid chloride in step D or by the method of example 295 by employing a carboxylic acid. The final compounds listed in these Tables were synthesized by reacting the appropriate aldehyde with an amine according to the procedure of example 291, step H followed by removal of ester protecting group according to example 291, step I.

TABLE 18

| EXAMPLE # | R¹ | R² | R³ | R⁴ | HPLC RT (min) | MS m/Z (M + 1) |
|---|---|---|---|---|---|---|
| 296 | cyclopropylmethyl | F | H | H | 2.83 | 548.3 |
| 297 | cyclohexylmethyl | H | H | H | 2.96 | 558.3 |
| 298 | cyclobutylmethyl | F | Et | H | 2.53 | 590.2 |
| 299 | isobutyl | F | Et | H | 2.32 | 564.2 |
| 300 | cyclopropylmethyl | F | Et | H | 2.37 | 576.2 |
| 301 | cyclohexylmethyl | H | Et | H | 2.53 | 586.2 |
| 302 | cyclobutylmethyl | F | Me | H | 2.27 | 550.2 |
| 303 | cyclopropylmethyl | F | Me | H | 2.29 | 562.2 |
| 304 | cyclobutylmethyl | F | Me | H | 2.56 | 576.2 |
| 305 | cyclohexylmethyl | H | Me | H | 2.56 | 572.2 |
| 306 | isobutyl | F | Me | H | 2.51 | 564.2 |

TABLE 18-continued

| EXAMPLE # | R¹ | R² | R³ | R⁴ | HPLC RT (min) | MS m/Z (M + 1) |
|---|---|---|---|---|---|---|
| 307 | cyclohexylmethyl | H | H | 4-F | 2.48 | 576.5 |
| 308 | cyclopropylmethyl | F | H | 4-F | 2.35 | 566.5 |
| 309 | cyclobutylmethyl | F | H | 4-F | 2.48 | 580.5 |
| 310 | isobutyl | F | H | 4-F | 2.29 | 554.5 |
| 311 | isobutyl | F | Me | 4-F | 2.21 | 568.5 |
| 312 | cyclopropylmethyl | F | Me | 4-F | 2.27 | 580.2 |
| 313 | cyclobutylmethyl | F | Me | 4-F | 2.43 | 594.2 |
| 314 | cyclohexylmethyl | H | Me | 4-F | 2.35 | 590.3 |
| 315 | isobutyl | F | Et | 4-F | 2.37 | 582.2 |
| 316 | cyclopropylmethyl | F | Et | 4-F | 2.37 | 594.5 |
| 317 | cyclobutylmethyl | F | Et | 4-F | 2.53 | 608.4 |
| 318 | cyclohexylmethyl | H | Et | 4-F | 2.53 | 604.5 |

TABLE 18-continued

| EXAMPLE # | R¹ | R² | R³ | R⁴ | HPLC RT (min) | MS m/Z (M + 1) |
|---|---|---|---|---|---|---|
| 319 | isopropyl | F | H | 4-Cl | 2.43 | 570.4 |
| 320 | cyclopropylmethyl | F | H | 4-Cl | 2.45 | 582.4 |
| 321 | cyclobutylmethyl | F | H | 4-Cl | 2.59 | 596.4 |
| 322 | cyclohexyl | H | H | 4-Cl | 2.59 | 592.4 |
| 323 | isopropyl | F | Me | 4-Cl | 2.37 | 584.5 |
| 324 | cyclopropylmethyl | F | Me | 4-Cl | 2.43 | 596.5 |
| 325 | cyclobutylmethyl | F | Me | 4-Cl | 2.56 | 610.5 |
| 326 | cyclohexyl | H | Me | 4-Cl | 2.61 | 606.5 |
| 327 | isopropyl | F | Et | 4-Cl | 2.56 | 598.5 |
| 328 | cyclopropylmethyl | F | Et | 4-Cl | 2.61 | 610.5 |
| 329 | cyclobutylmethyl | F | Et | 4-Cl | 2.75 | 624.6 |
| 330 | cyclohexyl | H | Et | 4-Cl | 2.75 | 620.6 |
| 331 | isopropyl | F | H | 4-CF3 | 2.61 | 604.4 |
| 332 | cyclopropylmethyl | F | H | 4-CF3 | 2.64 | 616.4 |
| 333 | isopropyl | F | Me | 4-CF3 | 2.59 | 618.5 |
| 334 | cyclopropylmethyl | F | Me | 4-CF3 | 2.61 | 630.5 |
| 335 | isopropyl | F | Et | 4-CF3 | 2.72 | 632.5 |
| 336 | cyclopropylmethyl | F | Et | 4-CF3 | 2.75 | 644.5 |
| 337 | tert-butyl | F | H | 4-F | 2.24 | 568.7 |
| 338 | tert-butyl | F | Me | 4-F | 2.16 | 582.7 |
| 339 | tert-butyl | F | Et | 4-F | 2.53 | 596.4 |
| 340 | tert-butyl | F | H | 4-Cl | 2.37 | 584.5 |
| 341 | tert-butyl | F | Me | 4-Cl | 2.35 | 598.5 |
| 342 | tert-butyl | F | Et | 4-Cl | 2.48 | 612.6 |
| 343 | tert-butyl | F | H | 2,4-F2 | 1.55 | 572.6 |

TABLE 18-continued

| EXAMPLE # | R¹ | R² | R³ | R⁴ | HPLC RT (min) | MS m/Z (M + 1) |
|---|---|---|---|---|---|---|
| 344 | cyclopropylmethyl | F | H | 2,4-F2 | 1.57 | 584.6 |
| 345 | t-Bu | F | H | 2,4-F2 | 1.58 | 586.6 |
| 346 | i-Pr | F | Me | 2,4-F2 | 1.53 | 586.6 |
| 347 | cyclopropylmethyl | F | Me | 2,4-F2 | 1.55 | 598.6 |
| 348 | t-Bu | F | Me | 2,4-F2 | 1.57 | 601.6 |
| 349 | i-Pr | F | Et | 2,4-F2 | 1.60 | 601.6 |
| 350 | cyclopropylmethyl | F | Et | 2,4-F2 | 1.62 | 613.6 |
| 351 | t-Bu | F | Et | 2,2-F2 | 1.64 | 615.6 |
| 352 | i-Pr | F | H | 2,4-Cl2 | 1.73 | 604.2 |
| 353 | cyclopropylmethyl | F | H | 2,4-Cl2 | 1.75 | 615.9 |
| 354 | t-Bu | F | H | 2,4-Cl2 | 1.79 | 618.1 |
| 355 | i-Pr | F | Me | 2,4-Cl2 | 1.77 | 618.3 |
| 356 | cyclopropylmethyl | F | Me | 2,4-Cl2 | 2.75 | 630.3 |
| 357 | t-Bu | F | Me | 2,4-Cl2 | 1.77 | 632.3 |
| 358 | i-Pr | F | Et | 2,4-Cl2 | 1.77 | 632.3 |
| 359 | cyclopropylmethyl | F | Et | 2,4-Cl2 | 1.77 | 644.4 |
| 360 | t-Bu | F | Et | 2,4-Cl2 | 1.83 | 646.3 |
| 361 | i-Pr | F | H | 3-CF3 | 2.48 | 604.3 |
| 362 | cyclopropylmethyl | F | H | 3-CF3 | 2.53 | 616.3 |
| 363 | t-Bu | F | H | 3-CF3 | 2.56 | 618.3 |
| 364 | i-Pr | F | Me | 3-CF3 | 2.45 | 618.3 |
| 365 | cyclopropylmethyl | F | Me | 3-CF3 | 2.48 | 630.3 |
| 366 | t-Bu | F | Me | 3-CF3 | 2.51 | 632.3 |
| 367 | i-Pr | F | Et | 3-CF3 | 2.59 | 632.3 |
| 368 | cyclopropylmethyl | F | Et | 3-CF3 | 2.64 | 644.4 |
| 369 | t-Bu | F | Et | 3-CF3 | 2.67 | 646.4 |

TABLE 18-continued

| EXAMPLE # | R¹ | R² | R³ | R⁴ | HPLC RT (min) | MS m/Z (M + 1) |
|---|---|---|---|---|---|---|
| 370 | t-Bu | F | H | 3,4-F2 | 1.58 | 572.4 |
| 371 | neopentyl | F | H | 3,4-F2 | 1.62 | 586.4 |
| 372 | cyclopropyl-CH | F | H | 3,4-F2 | 1.60 | 584.4 |
| 373 | t-Bu | F | Me | 3,4-F2 | 1.55 | 586.4 |
| 374 | cyclopropyl-CH | F | Me | 3,4-F2 | 1.59 | 598.4 |
| 375 | neopentyl | F | Me | 3,4-F2 | 1.60 | 600.4 |
| 376 | neopentyl | F | Et | 3,4-F2 | 1.64 | 600.4 |
| 377 | cyclopropyl-CH | F | Et | 3,4-F2 | 1.64 | 612.4 |
| 378 | neopentyl | F | Et | 3,4-F2 | 1.68 | 614.4 |
| 379 | neopentyl | F | H | 3,4-Cl2 | 1.74 | 604.2 |
| 390 | cyclopropyl-CH | F | H | 3,4-Cl2 | 1.76 | 616.3 |
| 391 | neopentyl | F | H | 3,4-Cl2 | 1.78 | 618.3 |
| 392 | neopentyl | F | Me | 3,4-Cl2 | 1.73 | 618.3 |
| 393 | cyclopropyl-CH | F | Me | 3,4-Cl2 | 1.75 | 630.3 |
| 394 | neopentyl | F | Me | 3,4-Cl2 | 1.79 | 632.7 |
| 395 | t-Bu | F | Et | 3,4-Cl2 | 1.82 | 633.8 |
| 396 | cyclopropyl-CH | F | Et | 3,4-Cl2 | 1.83 | 645.8 |
| 397 | neopentyl | F | Et | 3,4-Cl2 | 1.86 | 647.8 |
| 398 | t-Bu | F | H | 3,5-F2 | 2.35 | 572.4 |
| 399 | cyclopropyl-CH | F | H | 3,5-F2 | 2.37 | 584.4 |
| 400 | neopentyl | F | H | 3,5-F2 | 2.40 | 586.4 |
| 401 | t-Bu | F | Me | 3,5-F2 | 2.29 | 586.4 |
| 402 | cyclopropyl-CH | F | Me | 3,5-F2 2.29 | 2.35 | 598.4 |
| 403 | neopentyl | F | Me | 3,5-F2 | 2.40 | 600.4 |
| 404 | t-Bu | F | Et | 3,5-F2 | 2.45 | 600.4 |
| 405 | cyclopropyl-CH | F | Et | 3,5-F2 | 2.51 | 612.4 |

TABLE 18-continued

| EXAMPLE # | R¹ | R² | R³ | R⁴ | HPLC RT (min) | MS m/Z (M + 1) |
|---|---|---|---|---|---|---|
| 406 | tBu | F | Et | 3,5-F2 | 2.59 | 614.4 |
| 407 | iPr | F | H | 2-Cl | 1.62 | 570.3 |
| 408 | cyclobutylmethyl | F | H | 2-Cl | 1.71 | 596.2 |
| 409 | tBu | F | H | 2-Cl | 1.66 | 584.3 |
| 410 | iPr | F | Et | 2-Cl | 1.69 | 598.3 |
| 411 | cyclobutylmethyl | F | Et | 2-Cl | 1.80 | 624.6 |
| 412 | tBu | F | Et | 2-Cl | 1.73 | 612.3 |
| 413 | iPr | F | H | 3-Cl | 1.62 | 570.3 |
| 414 | cyclopropylmethyl | F | H | 3-Cl | 1.66 | 582.3 |
| 415 | tBu | F | H | 3-Cl | 1.66 | 584.3 |
| 416 | iPr | F | Et | 3-Cl | 1.70 | 598.3 |
| 417 | cyclopropylmethyl | F | Et | 3-Cl | 1.71 | 610.3 |
| 418 | tBu | F | Et | 3-Cl | 1.73 | 612.3 |
| 419 | cyclopropylmethyl | F | H | 2-Cl | 1.60 | 582.0 |
| 420 | cyclopropylmethyl | F | Et | 2-Cl | 1.71 | 610.3 |
| 421 | iPr | F | H | 3-F | 2.21 | 554.5 |
| 422 | cyclopropylmethyl | F | H | 3-F | 2.27 | 566.5 |
| 423 | tBu | F | H | 3-F | 2.29 | 568.5 |
| 424 | iPr | F | Et | 3-F | 2.29 | 582.5 |
| 425 | cyclopropylmethyl | F | Et | 3-F | 2.35 | 594.5 |
| 426 | tBu | F | Et | 3-F | 2.40 | 596.5 |
| 427 | iPr | F | H | 2-CF3 | 1.68 | 604.3 |
| 428 | cyclopropylmethyl | F | H | 2-CF3 | 1.73 | 616.3 |
| 429 | tBu | F | H | 2-CF3 | 1.73 | 618.2 |
| 430 | iPr | F | Et | 2-CF3 | 1.75 | 632.4 |

TABLE 18-continued

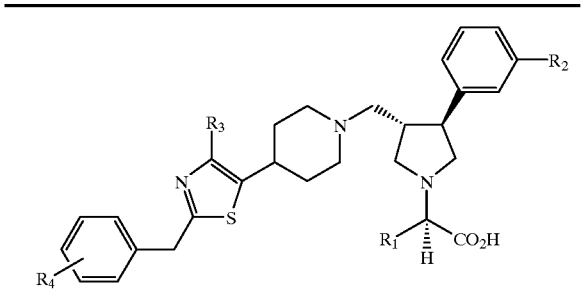 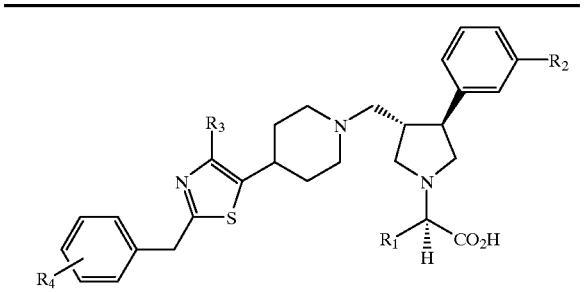

| EXAMPLE # | R¹ | R² | R³ | R⁴ | HPLC RT (min) | MS m/Z (M + 1) |
|---|---|---|---|---|---|---|
| 431 | t-Bu | F | Et | 2-CF3 | 1.82 | 644.4 |
| 432 | t-Bu | F | Et | 2-CF3 | 1.82 | 646.4 |
| 433 | t-Bu | F | H | 4-OCF3 | 1.79 | 620.3 |
| 434 | cyclopropyl-CH2 | F | H | 4-OCF3 | 1.79 | 632.1 |
| 435 | t-Bu | F | H | 4-OCF3 | 1.82 | 634.4 |
| 436 | t-Bu | F | Et | 4-OCF3 | 1.82 | 648.4 |
| 437 | cyclopropyl-CH2 | F | Et | 4-OCF3 | 1.86 | 660.6 |
| 438 | t-Bu | F | Et | 4-OCF3 | 1.90 | 662.6 |
| 439 | t-Bu | F | H | 4-SO2Me |  | 614 |
| 440 | cyclopropyl-CH2 | F | H | 4-SO2Me |  | 626 |
| 441 | t-Bu | F | H | 4-SO2Me |  | 628 |
| 442 | t-Bu | F | Et | 4-SO2Me |  | 642 |
| 443 | cyclopropyl-CH2 | F | Et | 4-SO2Me |  | 654 |
| 444 | t-Bu | F | Et | 4-SO2Me |  | 656 |
| 445 | t-Bu | F | H | 2-F | 1.49 | 554.5 |
| 446 | cyclopropyl-CH2 | F | H | 2-F | 1.53 | 566.6 |
| 447 | t-Bu | F | H | 2-F | 1.53 | 568.6 |
| 448 | t-Bu | F | Et | 2-F | 1.53 | 582.6 |
| 449 | cyclopropyl-CH2 | F | Et | 2-F | 1.58 | 504.6 |
| 450 | t-Bu | F | Et | 2-F | 1.60 | 596.6 |
| 451 | t-Bu | F | H | 4-NO2 | 1.51 | 581.5 |
| 452 | cyclopropyl-CH2 | F | H | 4-NO2 | 1.53 | 593.5 |
| 453 | t-Bu | F | H | 4-NO2 | 1.55 | 595.5 |
| 454 | t-Bu | F | Et | 4-NO2 | 1.58 | 609.5 |
| 455 | cyclopropyl-CH2 | F | Et | 4-NO2 | 1.60 | 621.5 |
| 456 | t-Bu | F | Et | 4-NO2 | 1.64 | 623.6 |

TABLE 18-continued

[Structure with R2, R3, R4, R1, CO2H substituents on piperidine-pyrrolidine-thiazole scaffold]

| EXAMPLE # | R¹ | R² | R³ | R⁴ | HPLC RT (min) | MS m/Z (M + 1) |
|---|---|---|---|---|---|---|
| 457 | t-Bu | F | H | 4-OEt | 1.57 | 580.6 |
| 458 | cyclopropyl | F | H | 4-OEt | 1.58 | 592.6 |
| 459 | t-Bu | F | H | 4-OEt | 1.60 | 594.6 |
| 460 | t-Bu | F | Et | 4-OEt | 1.60 | 608.6 |
| 461 | cyclopropyl | F | Et | 4-OEt | 1.62 | 620.6 |
| 462 | t-Bu | F | Et | 4-OEt | 1.64 | 622.6 |
| 463 | t-Bu | F | H | 4-iPr | 1.77 | 578.5 |
| 464 | cyclopropyl | F | H | 4-iPr | 1.79 | 590.4 |
| 465 | t-Bu | F | H | 4-iPr | 1.80 | 592.5 |
| 466 | t-Bu | F | Et | 4-iPr | 1.80 | 606.4 |
| 467 | cyclopropyl | F | Et | 4-iPr | 1.82 | 618.5 |

TABLE 18-continued

[Structure with R2, R3, R4, R1, CO2H substituents on piperidine-pyrrolidine-thiazole scaffold]

| EXAMPLE # | R¹ | R² | R³ | R⁴ | HPLC RT (min) | MS m/Z (M + 1) |
|---|---|---|---|---|---|---|
| 468 | t-Bu | F | Et | 4-iPr | 1.84 | 620.5 |
| 469 | t-Bu | F | H | 4-OMe | 1.47 | 566.4 |
| 470 | cyclopropyl | F | H | 4-OMe | 1.49 | 578.4 |
| 471 | t-Bu | F | H | 4-OMe | 1.53 | 580.4 |
| 472 | t-Bu | F | Et | 4-OMe | 1.53 | 594.4 |
| 473 | cyclopropyl | F | Et | 4-OMe | 1.55 | 606.4 |
| 474 | t-Bu | F | Et | 4-OMe | 1.55 | 608.4 |
| 475 | t-Bu | F | n-Pr | H | 1.57 | 578.8 |
| 476 | t-Bu | F | n-Pr | H | 1.61 | 592.4 |

Note:
Note: The "  " in R¹ of Table 18 represents a single bond; i.e., it does not denote stereoisomerism.

TABLE 19
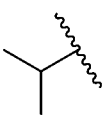
| EXAMPLE # | R₁ | R₂ | R₃ | HPLC RT (min) | MS m/Z (M + 1) |
|---|---|---|---|---|---|
| 477 | 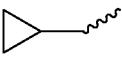 | Me | Ph | 2.16 | 536.5 |
| 478 | 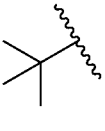 | Me | Ph | 2.21 | 548.6 |
| 479 |  | Me | Ph | 2.24 | 550.6 |
| 480 | 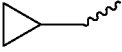 | Et | Ph | 2.35 | 550.6 |
| 481 | 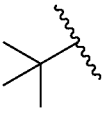 | Et | Ph | 2.40 | 562.6 |
| 482 |  | Et | Ph | 2.43 | 564.6 |
| 483 | 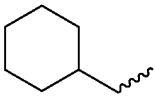 | H | 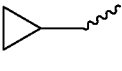 | 1.73 | 542.0 |
| 484 | 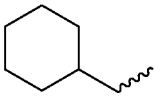 | H | 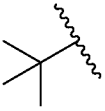 | 1.73 | 554.3 |
| 485 | 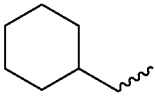 | H | 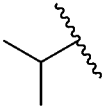 | 1.82 | 556.1 |
| 486 | 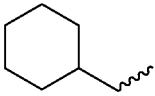 | Et | | 1.62 | 570.4 |

TABLE 19-continued
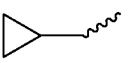
| EXAMPLE # | R₁ | R₂ | R₃ | HPLC RT (min) | MS m/Z (M + 1) |
|---|---|---|---|---|---|
| 487 | 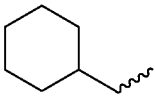 | Et | 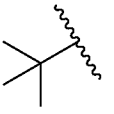 | 1.66 | 582.4 |
| 488 | 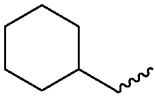 | Et | 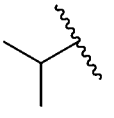 | 1.69 | 584.8 |
| 489 | 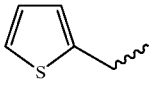 | H | 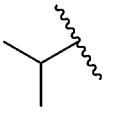 | 2.16 | 542.4 |
| 490 | 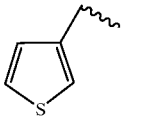 | H | 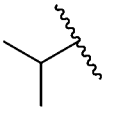 | 2.19 | 542.4 |
| 491 | 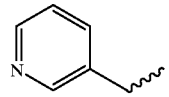 | H | 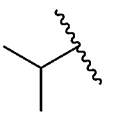 | 1.39 | 537.5 |
| 492 | 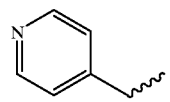 | H | 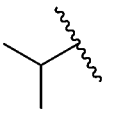 | 1.39 | 537.5 |
| 493 | 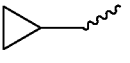 | H | Ph | 2.27 | 522.5 |
| 494 | 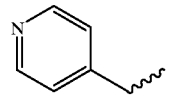 | H | 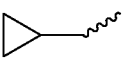 | 1.39 | 549.6 |
| 495 | 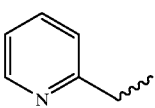 | H |  | 1.44 | 549.5 |

TABLE 19-continued

| EXAMPLE # | R₁ | R₂ | R₃ | HPLC RT (min) | MS m/Z (M + 1) |
|---|---|---|---|---|---|
| 496 | cyclopropylmethyl | H | pyridin-3-yl | 1.41 | 549.6 |
| 497 | isobutyl | Et | pyridin-2-yl | 1.55 | 565.4 |
| 498 | isobutyl | Et | pyridin-3-yl | 1.03 | 565.4 |
| 499 | isobutyl | Et | pyridin-4-yl | 1.00 | 565.2 |
| 500 | cyclopropylmethyl | Et | pyridin-2-yl | 1.09 | 577.6 |
| 501 | cyclopropylmethyl | Et | pyridin-3-yl | 1.02 | 577.7 |
| 502 | cyclopropylmethyl | Et | pyridin-4-yl | 1.05 | 577.4 |
| 503 | isobutyl | Et | thien-2-yl | 1.53 | 570.4 |
| 504 | cyclopropylmethyl | Et | thien-3-yl | 1.49 | 582.5 |

TABLE 19-continued

| EXAMPLE # | R₁ | R₂ | R₃ | HPLC RT (min) | MS m/Z (M + 1) |
|---|---|---|---|---|---|
| 505 | t-Bu-CH₂- | Et | 4-pyridylmethyl | 1.11 | 578.8 |
| 506 | t-Bu-CH₂- | Et | 3-pyridylmethyl | 1.13 | 579.3 |
| 507 | cyclopropylmethyl | Et | 2-thienylmethyl | 1.55 | 582.3 |
| 508 | iso-propylmethyl | Et | 3-thienylmethyl | 1.47 | 570.3 |

Note:
The ∿∿ in R₁ and in R₃ of Table 19 represents a single bond; i.e., it does not denote stereoisomerism.

EXAMPLE 509

2-(R)-(3-(S)-(4-(2-Benzoyl-thiazol-5-yl)-piperidin-1-yl)methyl)-4-(S)-(3-fluorophenyl)pyrrolidin-1-yl)-(3-cyclopropyl)propionoic Acid Step A: 1-t-Butyloxycarbonyl-4-(2-benzoyl-thiazol-5-yl) piperidine To 30 mg of 1-t-butyloxycarbonyl-4-(thiazol-5-yl) piperidine (prepared by method of example 291) in 3 ml THF at −78° C. was added 0.123 mmol of n-BuLi. The reaction was stirred for 20 min, then 18 mg of methyl benzoate was added. The reaction was stirred for 1 hr at −78° C. The solvent was evaporated under reduced pressure. The residue was dissolved in 1:1 MeOH:Et₂O then purified by prep TLC with 1:1 hexane:EtOAc to give 11 mg of the title compound.

Step B: 4-(2-Benzoyl-thiazol-5-yl)piperidine

To 11 mg of 1-t-butyloxycarbonyl-4-(2-benzoyl-thiazol-5-yl)piperidine (step A) was added 1.5 ml of saturated HCl in MeOH. The reaction was stirred at room temperature overnight. The solvent was evaporated under reduced pressure to give 9 mg of the title compound.

Step C: 2-(R)-(3-(S)-(4-(2-Benzoyl-thiazol-5-yl)-piperidin-1-yl)methyl)-4-(S)-(3-fluorophenyl)pyrrolidin-1-yl)-(3-cyclopropyl)propionoic acid, 4-methoxybenzyl Ester To 9 mg of 4-(2-benzoyl-thiazol-5-yl)piperidine (step B) in 2 ml DCE was added 12 mg of 2-(R)-(3-(R)-formyl-4-(S)-3-fluorophenylpyrrolidin-1-yl)-(3-cyclopropyl) propionic acid, 4-methoxybenzyl ester (aldehyde 12) and 3 mg of DIEA followed by 18 mg of sodium triacetoxy borohydride. The reaction was stirred at room temperature overnight. The solvent was evaporated under reduced pressure and the residue was purified by flash chromatography with 1:1 hexane:EtOAc followed by hexane:EtOAc:MeOH, 50:50:10 to give 9 mg of the title compound.

Step D: 2-(R)-(3-(S)-(4-(2-Benzoyl-thiazol-5-yl)-piperidin-1-yl)methyl)-4-(S)-(3-fluorophenyl)pyrrolidin-1-yl)-(3-cyclopropyl)propionoic Acid To 9 mg of 2-(R)-(3-(S)-(4-(2-benzoyl-thiazol-5-yl)-piperidin-1-yl)methyl)-4-(S)-(3-fluorophenyl)pyrrolidin-1-yl)-(3-cyclopropyl)propionoic acid, 4-methoxybenzyl ester (step C) were added 100 mg of anisole and 1.5 ml of triflouroacetic acid. The reaction was stirred at room temperature for 1 hour. The trifluoroacetic acid was evaporated under reduced pressure. The residue was purified by flash chromatography with 20% MeOH in EtOAc followed by 20% MeOH+2% NH₄OH in EtOAc to give 7 mg of the title compound. ESI-MS 562.7 (M+H); HPLC A: 1.73 min.

EXAMPLE 510

2-(R)-(3-(S)-(4-(2-Benzyl-oxazol-5-yl)-piperidin-1-yl)methyl)-4-(S)-3-fluorophenyl pyrrolidin-1-yl)-3-methylbutyric Acid Step A: 1-Benzoyl-isonipecotic Acid To a solution of 10 g of isonipecotic acid in 100 mL of $H_2O$ was added 31 mL of 5 N NaOH at 0° C. The reaction was warmed to room temperature and stirred for 0.5 hr. The reaction was again cooled to 0° C. and 11.97 g of benzoyl chloride was added. The reaction was then warmed to room temperature and stirred for 1.5 hr. Concentrated HCl was then added until a precipitate formed. The mixture was extracted with 3×150 mL of EtOAc and the combined organic layers were dried over $MgSO_4$. The solvent was evaporated under reduced pressure and the residue was dissolved in CH2Cl2. Ether was then slowly added to precipitate the product which was filtered to give 8 g of the title compound. $^1$H NMR (500 MHz) 1.83 (m, 3H), 2.10 (m, 1H), 2.65 (m, 1H), 3.12 (m, 2H), 3.79 (m, 1H), 4.53 (m, 1H), 7.38 (m, 5H).

Step B: 4-Hydroxymethyl-1-benzoyl Piperidine

To a solution of 2 g of 1-benzoyl-isonipecotic acid (step A) in 50 mL THF at 0° C. were added 1.47 g of triethylamine and 1.99 g of isobutyl chloroformate. The reaction was stirred for 1 hr at 0° C. To a solution of 1.10 g of sodium borohydride in 30 ml DMF at 0° C. was slowly added the above THF mixture. The reaction was again stirred for 1 hr at 0° C. Water (80 mL) was slowly added to the reaction and the mixture was extracted with 5×80 mL of EtOAc and the combined organic layers were dried over $MgSO_4$. The solvent was then evaporated under reduced pressure. The residue was purified by flash chromatography with 1:1 hexane EtOAc followed by hexane:EtOAc:MeOH, 50:50:5 to give 1.865 g of the title compound. ESI-MS 219.9 (M+H); HPLC A: 2.34 min.

Step C: 1-Benzoyl-piperidine-4-carboxaldehyde

To 1.99 g of dimethyl sulfoxide in 45 ml $CH_2Cl_2$ at –78° C. was added 2.16 g of oxalyl chloride. After 10 min, 1.865 g of 4-hydroxymethyl-N-benzoyl piperidine (step B) in 15 ml of $CH_2Cl_2$ was added at –78° C. and stirred for 30 min. DIEA (5.49 mL) was added and this mixture was stirred for an additional 30 min. at –78° C. and then warmed to room temperature and stirred another 30 min. The reaction was quenched with 50 mL $H_2O$ and extracted with 3×50 ml $CH_2Cl_2$. The combined organic layers were dried over $MgSO_4$ and evaporated under reduced pressure. The residue was chromatographed with 2:1 hexane:EtOAc, followed by 1:1 hexane: EtOAc to give 1.445 g of the title compound. $^1$H NMR (500 MHz) 1.72 (m, 2H), 1.90 (m, 1H), 2.14 (m, 1H), 2.58 (m, 1H), 3.21 (m, 2H), 3.68 (m, 1H), 4.41 (m, 1H), 7.39 (m, 5H), 9.72 (m, 1H).

Step D: 4-(1-Hydroxy-prop-2-enyl)-1-benzoyl Piperidine

To a solution of 500 mg of 1-benzoyl-piperidine-4-carboxaldehyde (step C) in 10 ml TBF at –78° C., was added 2.99 mmol of vinyl magnesium bromide. The solution was warmed to 0° C. and stirred for 1 hour. The reaction was quenched with 15 mL of aq. $NH_4Cl$ and extracted with 3×20 ml $Et_2O$ and the combined organic layers were dried over MgSO4. The solvent was evaporated under reduced pressure and the residue was purified by flash chromatography with 2:1 hexane:EtOAc followed by 1:1 hexane:EtOAc followed by hexane:EtOAc:MeOH, 50:50:5 to give 411 mg of the title compound. $^1$H NMR (500 MHz) 1.31 (m, 2H), 1.74 (m, 5H), 2.69 (m, 1H), 2.92 (m, 1H), 4.80 (m, 1H), 3.68 (m, 1H), 5.22 (dd, 2H), 5.84 (m, 1H), 7.43 (m, 5H).

Step E: 4-(1-Phenylacetyloxy-prop-2-enyl)-1-benzoylpiperidine

To 264 mg of 4-(1-hydroxy-prop-2-enyl)-1-benzoylpiperidine (step D) in 5 ml DMF was added 220 mg of phenyl acetic acid, 292 mg of 1-hydroxybenzotriazole, 414 mg of EDC, and 419 mg of DIEA. The reaction was stirred at room temperature overnight. The solution was diluted with 50 mL of $Et_2O$ and washed with 2×40 ml water. The aqueous layers were then extracted with 2×50 ml $Et_2O$ and the combined organic layers were dried over MgSO4. The solvent was evaporated under reduced pressure and the residue was purified by flash chromatography with 4:1 hexane:EtOAc followed by 2:1 hexane:EtOAc to give 123 mg of the title compound. ESI-MS 364.1 (M+H).

Step F: 1-Benzoyl-4-(2-benzyl-oxazol-5-yl)piperidine $O_3$ gas was bubbled through a solution of 120 mg of 4-(1-phenylacetyloxy-prop-2-enyl)-1-benzoylpiperidine (step E) in 8 mL $CH_2Cl_2$ at –78° C. until the reaction turned blue. To this solution 205 mg of methyl sulfide was added and the reaction was stirred at room temperature overnight. The solvent was evaporated under reduced pressure to give 121 mg of the residue. This residue was dissolved in 3 ml of acetic acid and 76 mg of $NH_4OAc$ was added. The reaction was stirred at 110° C. for 2.5 hours, 20 ml of $H_2O$ was added and the mixture was extracted with 3×20 mL $CH_2Cl_2$. The combined organic layer was dried over MgSO4. The solvent was evaporated under reduced pressure and the residue was purified by flash chromatography with 2:1 hexane:EtOAc followed by 1:1 hexane:EtOAc followed by hexane:EtOAc:MeOH, 50:50:5 to give 40 mg of the title compound. ESI-MS 347.0 (M+H); HPLC A: 3.68 min.

Step G: 4-(2-Benzyl-oxazol-5-yl)piperidine

To 40 mg of 1-benzoyl-4-(2-benzyl-oxazol-5-yl) piperidine (step F) in 4.5 mL MeOH and 0.5 ml $H_2O$ was added 260 mg of potassium hydroxide. The reaction was stirred at 80° C. overnight, 20 ml of $H_2O$ was added and the mixture was extracted with 3×20 mL EtOAc. The combined organic layer was dried over MgSO4. The solvent was evaporated under reduced pressure to give 22 mg of the title compound. ESI-MS 242.9 (M+H); HPLC A: 2.29 min.

Step H: 2-(R)-(3-(S)-(4-(2-Benzyl-oxazol-5-yl)-piperidin-1-yl)methyl)-4-(S)-3-fluorophenyl pyrrolidin-1-yl)-3-methylbutyric Acid, 4-methoxybenzyl Ester To 22 mg of 4-(2-benzyl-oxazol-5-yl)piperidine (step H) in 3 ml DCE was added 45 mg of 2-(R)-(3-(R)-formyl-4-(S)-3-fluorophenylpyrrolidin-1-yl)-3-methylbutyric acid, 4-methoxybenzyl ester (aldehyde 11) followed by 42 mg of sodium triacetoxy borohydride. The reaction was stirred at room temperature overnight. The solvent was evaporated under reduced pressure and the residue was purified by flash chromatography with 1:1 hexane:EtOAc followed by 1:1 hexane:EtOAc:MeOH, 50:50:10, to give 48 mg of the title compound. $^1$H NMR (500 MHz) 0.89 (d, 3H), 1.02 (2, 3H), 1.72 (m, 2H), 1.87 (m, 2H), 2.02 (m, 4H), 2.43 (m, 2H), 2.58 (m, 2H), 2.81 (m, 4H), 3.10 (d, 1H), 3.19 (m, 2H), 3.51 (s, 3H), 4.14 (s, 2H), 5.09 (m, 2H), 6.60 (s, 1H), 6.87 (m, 5H), 7.32 (m, 7H).

Step I: 2-(R)-(3-(S)-(4-(2-Benzyl-oxazol-5-yl)-piperidin-1-yl)methyl)-4-(S)-3-fluorophenyl pyrrolidin-1-yl)-3-methylbutyric Acid To 48 mg of 2-(R)-(3-(S)-(4-(2-benzyl-oxazol-5-yl)-piperidin-1-yl)methyl)-4-(S)-3-fluorophenyl pyrrolidin-1-yl)-3-methylbutyric acid, 4-methoxybenzyl ester (step H) were added 200 mg of anisole and 3 ml of triflouroacetic acid. The reaction was stirred at room temperature for 1 hour. The trifluoroacetic acid was evaporated under reduced pressure. The residue was purified by flash chromatography with 20% MeOH in EtOAc followed by 20% MeOH+2% NH$_4$OH in EtOAc to give 27 mg of the title compound. ESI-MS 520.3 (M+H); HPLC A: 2.77 min.

EXAMPLES 511–522

Examples 511 to 522 were prepared by procedures analogous to those in Example 510.

TABLE 20

| EXAMPLE # | R$_1$ | R$_2$ | R$_3$ | HPLC RT (min) | MS m/Z (M + 1) |
|---|---|---|---|---|---|
| 511 | isopropyl | H | benzyl | 2.77 | 520.3 |
| 512 | cyclobutylmethyl | H | benzyl | 2.93 | 546.3 |
| 513 | cyclopropylmethyl | H | benzyl | 2.80 | 532.3 |
| 514 | cyclobutylmethyl | Et | benzyl | 2.45 | 574.5 |
| 515 | isopropyl | Et | benzyl | 2.27 | 548.6 |
| 516 | cyclopropylmethyl | Et | 4-fluorobenzyl | 2.32 | 560.6 |
| 517 | cyclopropylmethyl | H | 4-fluorobenzyl | 2.24 | 538.6 |
| 518 | t-butyl | H | benzyl | 2.29 | 550.6 |

TABLE 20-continued

| EXAMPLE # | R₁ | R₂ | R₃ | HPLC RT (min) | MS m/Z (M + 1) |
|---|---|---|---|---|---|
| 519 | t-Bu-CH₂- | Et | benzyl | 2.24 | 562.7 |
| 520 | i-Pr-CH₂- | H | 4-Cl-benzyl | 2.27 | 554.6 |
| 521 | i-Pr-CH₂- | H | 4-CF₃-benzyl | 2.40 | 588.5 |
| 522 | i-Pr-CH₂- | Et | 4-Cl-benzyl | 2.23 | 582.3 |

Note:
The ∿∿∿ in R₁ and in R₃ of Table 20 represents a single bond; i.e., it does not denote stereoisomerism.

EXAMPLE 523

2-(R)-(3-(S)-(4-(2-Benzyl)-1,3-imidazol-5-yl)-piperidin-1-yl)methyl)-4-(S)-(3-fluorophenyl) pyrrolidin-1-yl)-3,3-dimethylbutyric Acid Step A: 4-Bromoacetyl-1-t-butoxycarbonyl-piperidine To a freshly prepared solution of LDA (from diisopropylamine (0.61 g, 6.0 mmol) and n-BuLi (2.2 ml, 2.5 M soln. in hexane) in 10 ml THF at −78° C. was added a solution of 4-acetyl-1-t-butoxycarbonyl-piperidine (1.0 g, 4.7 mmol) in 2.0 ml THF and the resultant mixture was stirred for 20 min. A mixture of TMSCl and triethylamine (1.37 ml, 10.8 mmol and 2.16 ml, 15.5 mmol) was added and the reaction mixture was gradually warmed to RT and stirred for an additional 1 hr. All the volatiles were removed and the crude silyl enolether was dissolved in 10 mL of THF and the mixture was cooled to 0° C. To this mixture was added in succession propylene oxide (1.0 ml) and NBS (1.0 g) and the mixture was stirred for 15 min, quenched with saturated NaHCO3 solution followed by extraction with CH2Cl2. The CH2Cl2 layer was washed with brine, dried, evaporated and purified by silica column chromatography. Elution with methylene chloride and ether (19:1) gave the title compound (1.11 g) as an yellow solid. 1HNMR (500MHz, CDCl₃): δ 4.16 (s, 2H), 4.12 (m, 2H), 2.79–2.84 (m, 3H), 1.5–2. (m, 4H), 1.47 (s, 9H).

Step B: 4-(2-(2,6-Dichloro-benzyl)-1,3-imidazol-5-yl)-1-(t-butoxycarbonyl)piperidine A mixture of the bromo compound (0.4 g, 1.36 mmol) from Step A and 2,6-dichlorophenylacetamidine (0.55 g, 2.7 mmol) in 30 mL of chloroform was refluxed for 4 hr. The reaction mixture was filtered. The filtrate was evaporated and purified by silica column chromatography. Elution with hexane:EtOAc:MeOH 49:49:2 gave (0.28 g) of the title compound. 1HNMR (500MHz, CDCl₃): δ 7.35–7.15 (m, 3H), 6.55 (s, 1H), 4.45 (s, 2H), 4.14 (br, 2H), 2.81–2.69 (m, 3H), 1.46 (s, 9H).

Step C: 4-((2-Benzyl)-1,3-imidazol-5-yl)-1-(t-butoxycarbonyl)piperidine

A mixture of 4-(2-(2,6-dichloro-benzyl)-1,3-imidazol-5-yl)-1-(t-butoxycarbonyl)piperidine (0.51 g, 1.24 mmol) from Step B, Pd/C (0.13 g) and ammonium formate (1.5 g, 24.8 mmol) in 8 mL of MeOH was refluxed for 30 min. The reaction mixture was filtered and the filtrate was evaporated. The residue was partitioned between CH2Cl2 and water (200 ml). The CH2Cl2 layer was washed with brine, dried, evaporated and purified by silica column chromatography. Elution with 3% MeOH—CH2Cl2 gave (0.35 g) of the title compound. 1HNMR (500MHz, CDCl3): δ 7.34–7.22 (m, 5H), 6.58 (s, 1H), 4.18 (br, 2H), 4.08 (s, 2H), 2.71 (br, 2H), 2.68 (m,1H), 1.47 (s, 9H).

Step D: 4-(2-Benzyl-1,3-imidazol-5-yl)piperidine Hydrochloride

To 4-((2-benzyl)-1,3-imidazol-5-yl)-1-(t-butoxycarbonyl) piperidine (0.16 g) from Step C in 2 ml of EtOAc at 0° C. was added a 2 ml saturated solution of HCl in EtOAc. The reaction mixture was stirred for 30 min. Evaporation of EtOAc followed by trituration of the resultant oil gave (0.15 g) of the title compound. 1HNMR (500 MHz, CD$_3$OD): δ 7.40–7.29 (m, 6H), 4.32 (s, 2H), 3.49 (m, 2H), 3.31–3.01 (m, 3H), 2.24 (m, 2H), 1.92 (m, 2H).

Step E: 2-(R)-(3-(S)-(4-(2-Benzyl)-1,3-imidazol-5-yl)-piperidin-1-yl)methyl)-4-(S)-(3-fluorophenyl)pyrrolidin-1-yl)-3,3-dimethylbutyric Acid The title compound was obtained by reaction of 4-(2-benzyl-1,3-imidazol-5-yl)piperidine hydrochloride with 2-(R)-(3-(R)-formyl-4-(S)-(3-fluorophenyl)pyrrolidin-1-yl)-3,3-dimethylbutyric acid, (4-methoxy)benzyl ester as described in example 510, step H followed by removal of the 4-methoxybenzyl group as in example 510, Step I. Mass spec.533.6 (M+1), HPLC A 1.63 min.

EXAMPLE 524

2-(R)-(3-(S)-(4-((2-Benzyl-4-ethyl)-1,3-imidazol-5-yl)-piperidin-1-yl)methyl)-4-(S)-(3-fluorophenyl) pyrrolidin-1-yl)-(3-cyclopropyl)propionic Acid Step A: 4-((2-Benzyl-4-iodo)-1,3-imidazol-5-yl)-1-(t-butoxycarbonyl) piperidine To a mixture of 4-((2-benzyl)-1,3-imidazol-5-yl)-1-(t-butoxycarbonyl)piperidine (0.15 g, 0.43 mmol) example 523, step C, Iodine (0.16 g, 0.65 mmol) and potassium iodide (0.22 g, 1.3 mmol) in 4 ml THF:water (1:1) was added a solution of sodium hydroxide (0.5 ml) and stired at RT for 30 min. After confirming the completion of reaction by TLC, the reaction was quenched with a saturated solution of sodium thiosulfate and the pH was adjusted to 7–8. The resultant mixture was extracted with EtOAc. The EtOAc layer was washed with brine, dried, evaporated and purified by silica column chromatography. Elution with 1% MeOH—CH2Cl2 gave (0.17 g) of the title compound. 1HNMR (500MHz, CDCl$_3$): δ 7.32–7.22 (m, 5H), 4.13 (br, 2H), 4.06 (s, 2H), 2.74 (m, 3H), 1.47 (s, 9H).

Step B: 4-((2-Benzyl-4-ethenyl)-1,3-imidazol-5-yl)-1-(t-butoxycarbonyl)piperidine A mixture of 4-((2-benzyl-4-iodo)-1,3-imidazol-5-yl)-1-(t-butoxycarbonyl)piperidine (0.17 g, 0.36 mmol) from Step A, tri-n-butyl vinyltin 30 (0.17 g, 0.54 mmol) and tetrakistriphenylphosphinyl palladium (0.020 g) in 4 ml toluene was stirred at 100–110° C. until the completion of reaction by TLC. Evaporation of the volatiles followed by purification by silica column and elution with 1% MeOH—CH2Cl2 gave (0.061 g) of the title compound. 1HNMR (500 MHz, CDCl3): δ 7.36–7.26 (m, 5H), 6.61–6.55 (m,1H), 5.10 (m, 2H), 4.33 (br, 2H), 4.13 (s, 2H), 1.47(s, 9H).

Step C: 4-((2-Benzyl-4-ethyl)-1,3-imidazol-2-yl)-1-(t-butoxycarbonyl)piperidine

A mixture of 4-((2-benzyl-4-ethenyl)-1,3-imidazol-5-yl)-1-(t-butoxycarbonyl)piperidine (0.073 g) from step B in 3.0 ml MeOH was hydrogenated over Pd/C (5 mg) at RT. Evaporation of the volatiles followed by purification by preparative silica chromatography and elution with 1% MeOH—CH2Cl2 gave (0.043 g) of the title compound. 1HNMR (500 MHz, CDCl$_3$): δ 7.31–7.20 (m, 5H), 4.19 (br, 2H), 4.01 (s, 2H), 2.74–2.66 9m, 3H), 2.51 (q, 2H), 1.46(s, 3H), 1.15 (t, 9H).

Step D: 4-((2-Benzyl-4-ethyl)-1,3-imidazol-2-yl)-piperidine Hydrochloride

To 4-((2-benzyl-4-ethyl)-1,3-imidazol-2-yl)-1-(t-butoxycarbonyl)-piperidine (0.043 g) from step C in 1.0 ml EtOAc at 0° C. was added a 2.0 ml saturated solution of HCl in EtOAc. The reaction mixture was stirred for 30 min. Evaporation of EtOAc followed by trituration of the resultant oil gave (0.038 g) of the title compound.

Step E: 2-(R)-(3-(S)-(4-((2-Benzyl-4-ethyl)-1,3-imidazol-5-yl)-piperidin-1-yl)methyl)-4-(S)-(3-fluorophenyl)pyrrolidin-1-yl)-(3-cyclopropyl)propionic Acid Reaction of 4-((2-Benzyl4-ethyl)-1,3-imidazol-2-yl)-piperidine hydrochloride with 2-(R)-(3-(R)-formyl-4-(S)-(3-fluorophenyl)pyrrolidin-1-yl)-3,3-dimethylbutyric acid, (4-methoxy)benzyl ester as described in example 510, step H and removal of the ester protecting group as in example 5 10,step I furnished the desired product. Mass spec. 559.6 (M+1), HPLC A 3.73 min.

EXAMPLE 525

2-(R)-(3-(S)-(4-((2-Benzyl-4-chloro)-1,3-imidazol-5-yl)-piperidin-1-yl)methyl)-4-(S)-(3-fluorophenyl) pyrrolidin-1-yl)-(3-cyclopropyl)propionic Acid Step A: 4-((2-Benzyl-4-chloro)-1,3-imidazol-2-yl)-1-(t-butoxycarbonyl)-piperidine To 4-((2-benzyl)-1,3-imidazol-5-yl)-1-(t-butoxycarbonyl) piperidine (0.097 g, 0.28 mmol) from example 523, step C) in 4 ml of chloroform was added NCS (0.120 g, 0.9 mmol) and stirred at RT for 30 min. After confirming the completion of reaction by TLC, the reaction mixture was evaporated and the crude product was purified by silica column chromatography. Elution with hexane/EtOAc:MeOH 49:49:2 gave (0.076 g) of the title compound. 1HNMR (500 MHz, CDCl3): δ 7.31–7.21 (m, 5H), 4.12 (br, 2H), 3.98 (s, 2H), 2.74–2.86 (m, 3H), 1.46 (s, 9H).

Step B: 4-((2-Benzyl-4-chloro)-1,3-imidazol-2-yl) piperidine Hydrochloride

The t-butoxycarbonyl group of 4-((2-benzyl-4-chloro)-1,3-imidazol-2-yl)-1-(t-butoxycarbonyl)piperidine (step A) was removed as described in example 523, step D. 1HNMR (500MHz, D$_2$O): δ 7.41–7.29 (m, 5H), 4.74 (s, 2H), 3.54–3.09 (m, 5H), 2.13–1.95 (m, 4H).

Step C: 2-(R)-(3-(S)-(4-((2-Benzyl-4-chloro)-1,3-imidazol-5-yl)-piperidin-1-yl)methyl)-4-(S)-(3-fluorophenyl)pyrrolidin-1-yl)-(3-cyclopropyl)propionic Acid The title compound was obtained as described in example 524, step E. Mass spec. 565.5 (M+1), HPLC A 1.84 min.

EXAMPLE 526

2-(R)-(3-(S)-(4-((2-Benzyl-1-ethyl)-1,3-imidazol-4-yl)-piperidin-1-yl)methyl)-4-(S)-(3-fluorophenyl) pyrrolidin-1-yl)-(3-cyclobutyl)propionic Acid Step A: 4-((2-Benzyl-1-ethyl)-1,3-imidazol-4-yl)-1-(t-butoxycarbonyl)-piperidine To a suspension of 60% NaH (0.035 g) in 3.0 ml DMF at RT was added 4-((2-benzyl)-1,3-imidazol-5-yl)-1-(t- butoxycarbonyl)piperidine (0.15 g, 0.43 mmol) from example 523 step C in 1.0 ml DMF. After 30 min iodoethane (0.134 g, 0.86 mmol) was added and the stirring continued overnight at RT. Reaction was quenched with saturated solution of NH4Cl and extracted with EtOAc. The EtOAc layer was washed with brine, dried, evaporated and purified by silica column chromatography. Elution with hexane:EtOAc:MeOH, 50:50:5 gave (0.134 g) of the title compound. 1H NMR (500 MHz, CDCl$_3$): δ 7.30–7.15 (m, 5H), 6.54 (s, 1H), 4.14 (br, 2H), 4.11 (s, 2H), 3.71 (q, 2H), 2.85 (br, 2H), 2.73 (m,1H), 1.48 (s, 9H), 1.16 (t, 3H).

Step B: 4-((2-Benzyl-1-ethyl)-1,3-imidazol-4-yl)-piperidine Hydrochloride

The product of step A (0.134 g) in 2.0 ml ethylacetate at 0° C. was treated with 4 mL saturated solution of HCl in EtOAc. The reaction mixture was stirred for 30 min. Evaporation of EtOAc followed by trituration of the resultant oil gave (0.132 g) of the title compound.

Step C: 2-(R)-(3-(S)-(4-((2-Benzyl-1-ethyl)-1,3-imidazol-4-yl)-piperidin-1-yl)methyl)-4-(S)-(3-fluorophenyl)pyrrolidin-1-yl)-(3-cyclobutyl)propionic Acid The title compound was prepared by the method outlined in example 524, step E. Mass spec. 573.6 (M+1), HPLC A 2.56 min.

EXAMPLE 527

2-(R)-(3-(S)-(4-(5-Benzyl-1,2,4-thiadiazol-2-yl)-piperidin-1-yl)methyl)-4-(S)-phenyl pyrrolidin-1-yl)-3-(cyclopropyl)propanoic Acid Step A: N-(1-t-Butyloxycarbonyl-isonipecotic)-N'-phenylacetic hydrazine A solution of 0.459 g (2 mmol) of 1-t-butyloxycarbonyl-isonipecotic acid in 6 mL of CH2Cl2 was cooled in a −20° C. bath and 0.3 mL (2.14 mmol) of triethylamine and 0.28 mL (2.15 mmol) of isobutylchloroformate were added. After stirring for 30 min between −20° C. and −10° C., another 0.3 mL (2.14 mmol) of triethylamine and 0.32 g (2.13 mmol) of phenylacetic hydrazine in 2 mL of CH2Cl2 were added. The solution was allowed to warm to room temperature over the next 1 hr. After stirring for another 1.5 hr at room temperature, the reaction mixture was diluted with CH2Cl2 and washed with water and brine. The CH2Cl2 layer was dried and concentrated and the residue was purified on a flash column using a gradient of 50–100% EtOAc in hexane to isolate 0.568 g of the title compound. 1H NMR (CDCl3) 1.46 (s, 9H),1.64 (m, 2H), 1.76 (m, 2H), 2.37 (m, 1H), 2.72 (m, 2H), 3.63 (s, 2H), 4.1 (br, 2H), 7.4 (m, 5H), 8.76 (br, 1H), 8.88 (br, 1H).

Step B: 4-(5-Benzyl-1,2,4-thiadiazol-2-yl)-1-t-butyoxycarbonyl-pieridine

To a solution of 116 mg (0.32 mmol) of N-(1-t-butyloxycarbonyl-isonipecotic)-N'-phenylacetic hydrazine (from Step A) in 3 mL of dry toluene, 89 mg (0.2 mmol) of phosphorus pentasulfide and 275 mg (33 mg) of NaHCO3 were added. After heating the reaction in a 80° C. bath for 45 min the bath was removed and the solution was diluted with EtOAc and quenched with water. The mixture was stirred for 0.5 hr, then the layers were separated. The organic layer was washed with brine, dried and concentrated. The residue was purified by prep TLC using EtOAc as an eluant to isolate 46 mg of the title compound. 1H NMR (CDCl$_3$) 1.46 (s, 9H), 1.70 (m, 2H), 2.05 (m, 2H), 2.88 (m, 2H), 3.25 (m, 1H), 4.16 (br, 2H), 4.39 (s, 2H), 7.35 (m, 5H).

Step C: 4-(5-Benzyl-1,2,4-thiadiazol-2-yl)-pieridine Hydrochloride

Acetyl chloride (0.2 mL, 2.8 mmol) was added to 2 mL of methanol and stirred for 10 min. This solution of HCl in methanol was added to 46 mg of 4-(5-benzyl-1,2,4-thiadiazol-2-yl)-1-t-butyoxycarbonyl-pieridine (step B) and stirred for 1 hr. The reaction mixture was concentrated and the residue was diluted with EtOAc and concentrated again to isolate 46 mg of the title compound which was sufficiently pure for use in the next step.

Step D: 2-(R)-(3-(S)-(4-(5-Benzyl-1,2,4-thiadiazol-2-yl)-piperidin-1-yl)methyl)-4-(S)-3-fluorophenyl pyrrolidin-1-yl)-3-(cyclopropyl)propionoic Acid, 4-methoxybenzyl Ester To 15 mg (0.051 mmol) of 4-(5-benzyl-1,2,4-thiadiazol-2-yl)-piperidine hydrochloride (step C), 21 mg (0.049 mmol) of 2-(R)-(3-(R)-formyl-4-(S)-(3-fluorophenyl)pyrrolidin-1-yl)-3-(cyclopropyl)propionic acid, 4-methoxybenzyl ester (aldehyde 12) in 1 ml of CH2Cl2 was added. To this reaction 0.01 mL of DIEA and 12 mg of sodium triacetoxyborohydride were added. After 1 hr, the reaction was quenched with 1 mL of water and organic layer was removed with a pipet. This solution was purified on prep TLC using 5% MeOH—CH2Cl2 to isolate 19 mg of the desired product. 1H NMR (CDCl$_3$) 0.06 (m, 2H), 0.4 (m, 2H), 0.72 (m, 1H), 1.6–3.4 (m, 19 H), 3.81 (s, 3H), 4.39 (s, 2H), 5.13 (ABq, 2H), 6.8–7.4 (m, 13H).

Step E: 2-(R)-(3-(S)-(4-(5-Benzyl-1,2,4-thiadiazol-2-yl)-piperidin-1-yl)methyl)-4-(S)-3-fluorophenyl-pyrrolidin-1-yl)-3-(cyclopropyl)propionoic Acid Formic acid (1 mL) was added to 19 mg of 2-(R)-(3-(S)-(4-(5-benzyl-1,2,4-thiadiazol-2-yl)-piperidin-1-yl)methyl)-4-(S)-3-fluorophenyl-pyrrolidin-1-yl)-3-(cyclopropyl)propionoic acid, 4-methoxybenzyl ester (step D) and the solution was stirred overnight. The reaction was concentrated and the residue was purified on a Varian SCX column using 2N NH3 in MeOH to elute the desired product. Mass spec. 549.5 (M+1), HPLC A 2.12 min.

EXAMPLE 528

2-(R)-(3-(S)-(4-(5-Benzyl-1,2,4-oxadiazol-2-yl)-piperidin-1-yl)methyl)-4-(S)-phenyl pyrrolidin-1-yl)-3-methylpropionoic Acid)

Step A: 4-(5-Benzyl-1,2,4-oxadiazol-2-yl)-piperidine

To a solution of 219 mg (0.61 mmol) of N-(1-t-butyloxycarbonyl-isonipecotic)-N'-phenylacetic hydrazine (example 527, step A) in 3 mL of toluene, 0.3 mL (3.22 mmol) of POCl3 was added and the solution was heated in a 110° C. bath. After 1 hr the reaction was cooled, diluted with Et2O and washed with dilute NaOH solution followed by brine. The organic layer was dried and concentrated and the residue was purified on a flash column using a gradient of 5–20% MeOH in CH2Cl2 containing 1% NH4OH to isolate 30 mg of the title compound. 1H NMR (CDCl$_3$) 2.06 (m, 2H), 2.22 (m, 2H), 2.98 (m, 2H), 3.13 (m, 1H), 3.34 (m, 2H), 4.19 (s, 2H), 7.35 (m, 5H).

Step B: 2-(R)-(3-(S)-(4-(5-Benzyl-1,2,4-thiadiazol-2-yl)-piperidin-1-yl)methyl)-4-(S)-3-fluorophenyl-pyrrolidin-1-yl)-3-methylbutanoic Acid, 4-methoxybenzyl Ester A solution of 15 mg (0.062 mmol) of 4-(5-benzyl-1,2,4-oxadiazol-2-yl)-pieridine and 25 mg (0.060 mmol) of 2-(R)-(3-(R)-formyl-4-(S)-(3-fluorophenyl)pyrrolidin-1-yl)-3-methylbutanoic acid, (4-methoxy)benzyl ester (aldehyde 11) in 1 mL of CH2Cl2 was treated with 13 mg (0.061 mmol) of sodium triacetoxyborohydride. After 1 hr the reaction was quenched with water and CH2Cl2 layer was removed with a pipet. This solution was purified by prep TLC using 5% MeOH—CH2Cl2 to isolate 27 mg of the title compound. 1H NMR (CDCl3) 0.9 (d, 3H), 1.02 (d, 3H), 1.6–3.2 (m, 19H), 3.82 (s, 3H), 4.18 (s, 2H), 5.13 (s, 2H), 6.8–7.4 (m, 13H).

Step C: 2-(R)-(3-(S)-(4-(5-Benzyl-1,2,4-thiadiazol-2-yl)-piperidin-1-yl)methyl)-4-(S)-3-fluorophenyl-pyrrolidin-1-yl)-3-methylbutanoic Acid Formic acid (1 mL) was added to 27 mg of 2-(R)-(3-(S)-(4-(5-benzyl-1,2,4-thiadiazol-2-yl)-piperidin-1-yl)methyl)-4-(S)-phenyl pyrrolidin-1-yl)-3-methylbutanoic acid, 4-methoxybenzyl ester (step B) and stirred over night. The solution was concentrated and the residue was purified on a Varian SCX (ion exchange) column using 2N NH3 in MeOH to elute the product. After concentration and acidification with 1 N HCl in Et2O, 25 mg of the title compound was isolated as a dihydrochloride salt. Mass Spec. 521.4 (M+1), HPLC A 2.01 min.

EXAMPLES 529–541

Examples 529–541 were prepared in analogy with the procedures described in Example 528.

TABLE 21

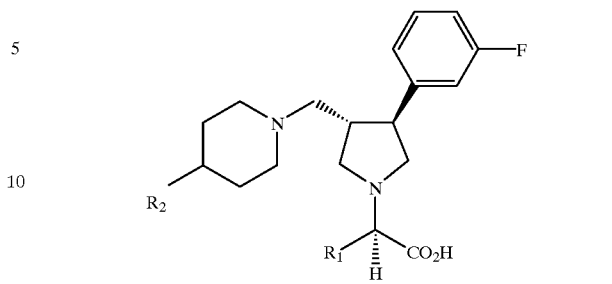

| Example # | R₁ | R₂ | HPLC RT (min) | MS m/Z (M+1) |
|---|---|---|---|---|
| 529 | isopropyl | 2-Cl-benzyl-imidazolyl | 2.37 | 587.5 |
| 530 | cyclobutylmethyl | benzyl-methyl-imidazolyl | 2.72 | 573.5 |
| 531 | isopropyl | benzyl-methyl-imidazolyl | 1.89 | 547.5 |
| 532 | isopropyl | benzyl-N-ethyl-imidazolyl | 1.79 | 547.6 |
| 533 | cyclobutylmethyl | benzyl-Cl-imidazolyl | 2.03 | 579.4 |
| 534 | isopropyl | benzyl-Cl-imidazolyl | 1.81 | 553.5 |
| 535 | cyclopropylmethyl | benzyl-oxadiazolyl | 2.16 | 533.6 |
| 536 | isopropyl | benzyl-oxadiazolyl | 2.13 | 521.6 |
| 537 | tert-butyl | benzyl-oxadiazolyl | 2.19 | 535.6 |
| 538 | isopropyl | benzyl-thiadiazolyl | 2.02 | 537.4 |
| 539 | isopropyl | benzyl-oxadiazolyl | 2.13 | 535.5 |
| 540 | isopropyl | benzyl-thiadiazolyl | 2.22 | 551.5 |
| 541 | cyclopropylmethyl | benzyl-oxadiazolyl | 2.05 | 533.5 |

TABLE 21-continued

| Example # | R₁ | R₂ | HPLC RT (min) | MS m/Z (M + 1) |
|---|---|---|---|---|

Note:
Note: The " ∿∿∿ " in R₁ and in R₂ of Table 21 represents a single bond; i.e., it does not denote stereoisomerism

EXAMPLE 542

2-(S)-(3-(S)-((4-(2-Benzyl-4-ethyl-thiazol-5-yl)-piperidine -1-yl)methyl)-4-(S)-3-fluorophenylpyrrolidin-1-yl)-3-ethylvaleric acid Step A: 3-Ethyl-2-hydroxyvaleric Acid To a solution of 2.5 mL (20.3 mmol) of 2-ethylbutyraldehyde in 50 mL of MeOH, 1.32 g of KCN were added. After all the KCN dissolved, 1.2 mL (21 mmol) of acetic acid was slowly added. The solution was stirred for 4 hr then concentrated. The residue was partitioned between saturated NaHCO3 and Et2O. The aqueous layer was extracted with Et2O. The combined organic layer was washed with water and brine, dried and concentrated in vacuo to obtain 2.85 g of a clear oil. To this cyanohydrin, 50 mL of concentrated HCl was added and stirred for 5 hr at room temperature. The solution was heated to 60° C. for 3 hr, then the bath temperature was raised to 100° C. and stirred overnight at this temperature. The reaction was cooled and partitioned between water and Et2O. The aqueous layer was extracted with Et2O. The combined organic layer was washed with brine, dried and concentrated. The residue was crystallized from hexane (~15 mL) to isolate 2.35 g of the desired acid as a white solid. 1H NMR (CDCl₃) 0.94 (t, 3H), 1.0 (t, 3H), 1.3–1.8 (m, 5H), 4.36 (d, 1H).

Step B: 3-Ethyl-2-hydroxyvaleric Acid, 4-methoxybenzyl Ester

To 1.2 g (8.2 mmol) of 3-ethyl-2-hydroxyvaleric acid (step A) in 15 mL of dry DMF, 1.4 mL (9.6 mmol) of 4-methoxybenzyl chloride and 1.3 g (9.4 mmol) of K2CO3 were added. After stirring the reaction overnight, it was partitioned between Et2O and water. The aqueous layer was extracted with Et2O. The combined organic layer was washed with water, brine, dried and concentrated. The residue was purified on a flash column using a gradient of 10–30% EtOAc in hexane to obtain 2.1 g of the desired product. 1H NMR (CDCl₃) 0.84 (t, 3H), 0.96 (t, 3H), 1.2–1.6 (m, 5H), 2.67 (d, 1H), 3.83 (s, 3H), 4.27 (dd, 1H), 5.17 (ABq, 2H), 6.91(m, 2H), 7.31 (m, 2H).

Step C: 2-(3-(R)-t-Butydimethylsilyloxymethyl-4-(S)-(3-fluorophenyl)pyrrolidin-¹-yl)-3-ethylvaleric Acid, 4-methoxybenzyl Ester A solution of 0.82 g (2.93 mmol) of 3-Ethyl-2-hydroxyvaleric acid, 4-methoxybenzyl ester (step B) in 5 mL of dry CH2Cl2 was cooled in a −78° C. bath and 0.6 mL (3.57 mmol) of trifluoromethanesulfonic anhydride was added. After 5 min, 0.46 mL (4 mmol) of 2,6-lutidine was added and stirred for 15 min. To this solution, 1.3 mL (7.47 mmol) of DIEA was added and after 10 min a solution of 0.907 g (2.93 mmol) of 3-(R)-t-butyldimethylsilyloxymethyl-4-(S)-(3-fluorophenyl)pyrrolidine in 5 mL of CH2Cl2 was added. The cold bath was removed and the reaction was stirred overnight. The reaction was quenched with saturated NaHCO3 and extracted with Et2O. The combined Et2O layer was washed with brine, dried and concentrated. The residue was purified on a flash column using 10% EtOAc-hexane to isolate 1.1 g of the desired product as a mixture of two diastereomers. 1H NMR (CDCl₃) 0.06 and 0.16 (6H), 0.87 (m, 15H), 1.2–3.6 (m, 13H), 3.82 (2s, 3H), 5.11 (s, 2H), 6.8–7.4 (m, 8H), Step D: 2(R)-(3-(R)-Hydroxymethyl-4-(S)-(3-fluorophenyl)pyrrolidin-1-yl)-3-ethylvaleric acid, 4-methoxybenzyl ester and 2(S)-(3-(R)-hydroxymethyl-4-S)-(3-fluorophenyl)pyrrolidin-1-yl)-3-ethylvaleric acid, 4-methoxybenzyl Ester To 5 mL of methanol, 0.5 mL (7 mmol) of acetyl chloride was added and stirred for 5 min. This solution of HCl in methanol was added to 1.1 g (1.97 mmol) of 2-(3-(R)-t-butyldimethylsilyloxymethyl-4-(S)-(3-fluorophenyl)pyrrolidin-1-yl)-3-ethylvaleric acid, 4-methoxybenzyl ester (step C). After 1 hr, the reaction mixture was concentrated and the residue was partitioned between 10% Na2CO3 and EtOAc. The organic layer was washed with brine, dried and concentrated. The residue was purified on a flash column using a gradient of 20–40% EtOAc in hexane to isolate 0.64 g of alcohols as a mixture of diastereomers. This mixture was separated into individual isomers by prep HPLC using a Chiralpak AD column and 7% iPrOH/hexane as an eluant at a flow rate of 9 mL/min in several portions. The faster isomer (RT=7.9 min, analytical Chiralpak AD, 10% iPrOH-hexane, 1 mL/min) was 2(S)-(3-(R)-hydroxymethyl-4-(S)-(3-fluorophenyl)pyrrolidin-1-yl)-3-ethylvaleric acid, 4-methoxybenzyl ester (0.26 g) 1H NMR (CDCl₃) 0.87 (m, 6H), 1.2–1.8 (m, 6H), 2.23 (m,1H), 2.77 (m, 2H), 2.97 (m, 2H), 3.15 (t, 1H), 3,6 (m, 1H), 3.68 (m, 1H), 3.83 (s, 1H), 5.12 (s, 2H), 6.85–7.4 (m, 8H). The slower isomer was 2(R)-(3-(R)-hydroxymethyl-4-(S)-(3-fluorophenyl)pyrrolidin-1-yl)-3-ethylvaleric acid, 4-methoxybenzyl ester (0.26 g, RT=10.6 min, analytical Chiralpak AD, 10% iPrOH-hexane, 1 mL/min). 1H NMR (CDCl₃) 0.88 (m, 6H), 1.2–2.0 (m, 6H), 2.3 (m, 1H), 2.6 (m, 1H), 2.73 (m, 1H), 3.11 (m, 2H), 3.24 (t, 1H), 3.30 (d, 1H), 3.58 (m, 1H), 3.67 (m, 1H), 3.82 (s, 3H), 5.12 (ABq, 2H), 6.85–7.4 (m, 8H).

Step E: 2(S)-(3-(R)-Formyl-4-(S)-(3-fluorophenyl)pyrrolidin-1-yl)-3-ethylvaleric Acid, 4-methoxybenzyl Ester To a solution of 0.1 mL (1.15 mmol) of oxalyl chloride in 2 mL of CH2Cl2 cooled in a −78° C. bath, 0.1 mL (1.41 mmol) of dry DMSO was added. After 0.5 hr, a solution of 0.26 g (0.59 mmol) of 2(S)-(3-(R)-hydroxymethyl-4-(S)-(3-fluorophenyl)pyrrolidin-1-yl)-3-ethylvaleric acid, 4-methoxybenzyl ester (step D) in 2.5 mL of CH2Cl2 was added. After 0.5 hr, 0.5 mL (3.57 mmol) of triethylamine was added to the reaction and the cold bath was removed.

After stirring for 2 hr, the reaction was partitioned between water and CH2Cl2. The organic layer was washed with brine, dried and concentrated. The residue was purified on a flash column using a gradient of 20–30% EtOAc in hexane to isolate 0.23 g of the title compound. 1H NMR (CDCl$_3$) 0.86 (m, 6H), 1.2–1.8 (m, 5H), 2.82 (m, 2H), 3.05 (t, 1H), 3.18 (m, 2H), 3.32 (d, 1H), 3.52 (m, 1H), 3.83 (s, 3H), 5.13 (s, 2H), 6.9–7.4 (m, 8H), 9.64 (d, 1H).

Step F: 2-(S)-(3-(S)-((4-(2-Benzyl-4-ethyl-thiazol-5-yl)-piperidine -1-yl)methyl)-4-(S)-3-fluorophenylpyrrolidin-1-yl)-3-ethylvaleric Acid Reductive amination of 20 mg (0.045 mmol) of 2(S)-(3-(R)-formyl-4-(S)-(3-fluorophenyl)pyrrolidin-1-yl)-3-ethylvaleric acid, 4-methoxybenzyl ester with 15 mg (0.42 mmol) of 4-(2-benzyl-4-ethyl-thiazol-5-yl)piperidine as described in example 527 step D, and removal of 4-methoxybenzyl ester according to example 527 step E furnished 7 mg of the title compound. Mass spec. 592.4 (M+1), HPLC A 2.36 min.

EXAMPLE 543

2-(R)-(3-(S)-((4-(2-Benzyl-thiazol-5-yl)-piperidine -1-yl)methyl)-4-(S)-3-fluorophenylpyrrolidin-1-yl)-3-ethylvaleric Acid Step A: 2(S)-(3-(R)-Formyl-4-(S)-(3-fluorophenyl) pyrrolidin-1-yl)-3-ethylvaleric Acid, 4-methoxybenzyl Ester Oxidation of 0.26 g (0.59 mmol)(2(S)-(3-(R)-hydroxymethyl-4-(S)-(3-fluorophenyl)pyrrolidin-1-yl)-3-ethylvaleric acid, 4-methoxybenzyl ester according to the procedure of Example 542, step E gave 0.23 g of the desired product. 1H NMR (CDCl$_3$) 0.86 (m, 6H), 1.2–1.6 (m, 5H), 2.68 (t, 1H), 2.9 (m, 1H), 3.2 (m, 3H), 3.33 (d, 1H), 3.54 (q, 1H), 3.82 (s, 3H), 5.13 (s, 2H), 6.85–7.4 (m, 8H), 9.63 (d, 1H).

Step B: 2-(S)-(3-(S)-((4-(2-Benzyl-thiazol-5-yl)-piperidine -1-yl)methyl)-4-(S)-3-fluorophenylpyrrolidin-1-yl)-3-ethylvaleric Acid The title compound was prepared from 2(S)-(3-(R)-formyl-4-(S)-(3-fluorophenyl)pyrrolidin-1-yl)-3-ethylvaleric acid, 4-methoxybenzyl ester (step A) according to the method described in example 527, step D and step E. Mass spec. 592.4 (M+1), HPLC A 2.43 min.

EXAMPLE 544

(3-(S)-((4-(2-Benzyl-4-ethyl-thiazol-5-yl)-piperidine-1-yl)methyl)-4-(S)-3-fluorophenylpyrrolidin-1-yl)-acetic Acid Step A: (3-(R)-t-Butyldimethylsilyloxymethyl-4-(S)-(3-fluorophenyl)pyrrolidin-1-yl)-acetic Acid, Methyl Ester A solution of 1.0 g (3.23 mmol) of (3-(R)-t-Butyldimethylsilyloxymethyl-4-(S)-(3-fluorophenyl) pyrrolidine in 8 mL of acetonitrile was treated with 0.47 mL (4.95 mmol) of methyl bromoacetate and 0.86 g (4.95 mmol) of DIEA and the reaction was heated in 80° C. bath. After 2 hr, the solution was cooled, and partitioned between water-EtOAc. The organic layer was washed with brine, dried and concentrated. The residue was purified on a flash column using a gradient of 10–20% EtOAc in hexanes to isolate 0.45 g of the title compound. 1H NMR (CDCl3) 0.027 (2s, 6H), 0.87 (s, 9H), 2.4 (m, 1H), 2.7–3.1 (m, 5H), 3.33 and 3.47 (ABq, 2H), 3.63 (m, 2H), 3.76 (s, 3H), 6.8–7.3 (m 4H).

Step B: (3-(R)-Formyl-4-(S)-(3-fluorophenyl)pyrrolidin-1-yl)-acetic Acid, Methyl Ester A solution of HCl in methanol was prepared by adding 0.5 mL (7 mmol) of acetyl chloride in 5 mL of metahnol and stirring for 10 min. This solution was added to 0.45 g (1.18 mmol) (3-(R)-t-butyldimethylsilyloxymethyl-4-(S)-(3-fluorophenyl)pyrrolidin-1-yl)-acetic acid, methyl ester (step A) and stirred for 1 hr. The reaction was concentrated and the residue was partitioned between 10% Na2CO3 solution and EtOAc. The organic layer was washed with brine, dried and concentrated to furnish the alcohol. Swern oxidation of this crude alcohol according to the procedure described in example 542, step E provided 0.24 g of the title compound after purification on a flash column using a gradient of 50–75% EtOAc in hexanes. 1H NMR (CDCl$_3$) 2.87 (t, 1H), 3.1 (m, 2H), 3.28 (m, 2H), 3.45 (ABq, 2H), 3.71 (q, 1H), 3.76 (s, 3H), 6.9–7.4 (m, 4H), 9.76 (d, 1H).

Step C: (3-(S)-((4-(2-Benzyl-4-ethyl-thiazol-5-yl)-piperidine-1-yl)methyl)-4-(S)-3-fluorophenylpyrrolidin-1-yl)-acetic Acid, Methyl Ester Reductive amination of 14 mg (0.053 mmol) of (3-(R)-formyl-4-(S)-(3-fluorophenyl)pyrrolidin-1-yl)-acetic acid, methyl ester (step B) with 4-(2-benzyl-4-ethyl-thiazol-5-yl) piperidine according to the method of example 527, step D furnished 23 mg of the desired product after purification by prep TLC using 5% MeOH—CH2Cl2. Mass spec. 536.4 (M+1), HPLC A 2.21 min.

Step D (3-(S)-((4-(2-Benzyl-4-ethyl-thiazol-5-yl)-piperidine-1-yl)methyl)-4-(S)-3-fluorophenylpyrrolidin-1-yl)-acetic Acid A solution of 23 mg (0.043 mmol) of (3-(S)-((4-(2-benzyl-4-ethyl-thiazol-5-yl)-piperidine-1-yl)methyl)-4-(S)-3-fluorophenylpyrrolidin-1-yl)-acetic acid, methyl ester in 1 mL of MeOH was treated with 0.1 mL of 1N NaOH. After stirring for 1 hr, another 0.1 mL of 1N NaOH was added and the reaction was heated in a 50° C. bath. After 1.5 hr at 50° C., the solution was cooled and neutralized to pH 7 with 1.2 N HCl. The solution was extracted with EtOAc and the EtOAc layer was washed with brine and dried. After concentration of the filtrate, the residue was purified on a Varian SCX ion exchange column using 2N NH3 in MeOH to elute the product. The isolated free base after concentration of the solution was treated with 1N HCl in Et2O and removal of solvent in vacuo furnished 21 mg of the title compound as a triHCl salt. Mass spec. 522.2 (M+1), HPLC A 1.99 min.

EXAMPLES 545–554

The compounds of Examples 545 to 554 were prepared using procedures analogous to those set forth in Examples 542 and 543.

TABLE 22

[Structure: pyrrolidine core with (3-fluorophenyl) group, CH2-piperidine (with R2 substituent), and N-CH(R1)-CO2H]

| Example # | Stereo chemistry At R1 | R₁ | R₂ | HPLC RT (min) | MS m/Z (M + 1) |
|---|---|---|---|---|---|
| 545 | R | Me | 4-ethyl-2-(benzyl)thiazol-5-yl | 1.98 | 536.2 |
| 546 | S | Me | 4-ethyl-2-(benzyl)thiazol-5-yl | 1.34 | 536.5 |
| 547 | R | Et | 4-ethyl-2-(benzyl)thiazol-5-yl | 2.04 | 550.6 |
| 548 | S | Et | 4-ethyl-2-(benzyl)thiazol-5-yl | 2.04 | 550.6 |
| 549 | R | Et | 4-ethyl-2-(benzyl)thiazol-5-yl | 1.94 | 533.6 |
| 550 | R | n-Pr | 4-ethyl-2-(benzyl)thiazol-5-yl | 2.25 | 564.6 |
| 551 | S | n-Pr | 4-ethyl-2-(benzyl)thiazol-5-yl | 2.26 | 564.6 |
| 552 | R | n-Pr | 1-ethyl-3-(benzyl)pyrazol-5-yl | 2.04 | 547.7 |

TABLE 22-continued

| Example # | Stereo chemistry At R1 | $R_1$ | $R_2$ | HPLC RT (min) | MS m/Z (M + 1) |
|---|---|---|---|---|---|
| 553 | S | i-Pr | Ph–CH₂–thiazole (4-ethyl) | 2.06 | 565.2 |
| 554 | S | i-Pr | Ph–CH₂–pyrazole (1-ethyl) | 1.92 | 548.3 |

Note:
The ∿∿∿ in $R_2$ of Table 22 represents a single bond; i.e., it does not denote stereoisomerism.

EXAMPLE 555

α-(R)-(3-(S)-((4-(3-Benzyl-1-ethyl-(1H-pyrazol-5-yl))piperidin-1-yl)methyl)-4-(S)-(3-fluorophenyl) pyrrolidin-1-yl)-3-(S)-methylpentanoic Acid, Trifluoroacetic Acid Salt Step A: 3-(R)-((4-(3-Benzyl-1-ethyl-(1H-pyrazol-5-yl))piperidin-1-yl)methyl)-4-(S)-(3-fluorophenyl)pyrrolidine Pd/C catalyst (10%, 160 mg) was added slowly in small portions to 5 mL cold methanol. This slurry was added to 0.851 g benzyl ester of the final product in Example 78 (TFA salt) in 17 mL methanol. This mixture was treated with hydrogen for 1.5 hours using a balloon to remove the benzyl group. The flask was purged with nitrogen to remove hydrogen. The resulting slurry was stirred in air over night to remove the cyclohexylacetic acid group. The reaction mixture was filtered to remove catalyst, concentrated to give crude product. The latter was purified by flash chromatography (2:1 v/v EtOAc and MeOH with 2% Et₃N) and preparative RP-HPLC (22.5–80% MeCN in water with 0.5% TFA) to give TFA salt of the title compound. Treating this salt with dilute NaOH and extracting with ether provided 0.235 g title compound as a yellow gel.

Step B: α-(R)-(3-(S)-((4-(3-Benzyl-1-ethyl-(1H-pyrazol-5-yl))piperidin-1-yl)methyl)-4-(S)-(3-fluorophenyl) pyrrolidin-1-yl)-3-(S)-methyl-pentanoic Acid, Benzyl Ester, Trifluoroacetic Acid Salt 3-(S)-((4-(3-Benzyl-1-ethyl-(1H-pyrazol-5-yl))piperidin-1-yl)methyl)-4-(S)-(3-fluorophenyl)pyrrolidine (22.3 mg, 0.050 mmole) obtained above was treated with 19.5 mg 2-(S)-trifluoromethanesulfonyl-3-(S)-methylpentanoic acid, benzyl ester obtained in Aldehyde 14, Step A, and 7.1 mg DIEA in 0.25 mL MeCN for 16 hours. The reaction mixture was purified on preparative HPLC using 37.5–60% MeCN with 0.5% TFA to give 42.7 mg title compound as a gel. ESI-MS 651.3 (M+H), HPLC A: 4.47 min.

Step C: α-(R)-(3-(S)-((4-(3-Benzyl-1-ethyl-(1H-pyrazol-5-yl))piperidin-1-yl)methyl)-4-(S)-(3-fluorophenyl) pyrrolidin-1-yl)-3-(S)-methyl-pentanoic Acid, Trifluoroacetic Acid Salt The product obtained from the last step was treated with hydrogen in the presence of 4.7 mg 10% Pd/C in 1.5 mL MeOH for one hour and filtered. The product obtained after filtration and evaporation was lyophilized to give 31.7 mg title compound as a white solid. HPLC A: 3.50 min.

EXAMPLE 556

α-(R)-(3-(S)-((4-(3-Benzyl-1-ethyl-(1H-pyrazol-5-yl))piperidin-1-yl)methyl)-4-(S)-(3-fluorophenyl) pyrrolidin-1-yl)-3-(R)-methylpentanoic Acid, Trifluoroacetic Acid Salt The title compound was prepared using the same procedure as for Example 555 except triflate from Aldehyde 16, Step A, was used. HPLC A: 3.50 min.

EXAMPLE 557

α-(R)-(3-(S)-((4-(3-Benzyl-1-ethyl-(1H-pyrazol-5-yl))piperidin-1-yl)methyl)-4-(S)-(3-fluorophenyl) pyrrolidin-1-yl)-2-methylpropionic Acid, Trifluoroacetic Acid Salt Step A: 2-(R)-(3-(R)-(Hydroxymethyl)-4-(S)-(3-fluorophenyl)pyrrolidin-1-yl)-2-methylpropionic Acid, Trifluoroacetic Acid Salt Solutions of 167 mg (1.00 mmole) 2-bromo-2-methylpropionic acid and 270 mg (1.05 mmole) silver trifluoromethanesulfonate in 2.5 mL anhydrous THF were added to 309 mg (1.00 mmole) 3-(R)-(t-butyldimethylsilyloxymethyl)-4-(S)-(3-fluorophenyl)pyrrolidine (Pyrrolidine 1) and 0.517 g (4.00 mmole) DIEA in 5 mL THF simultaneously using syringe pumps with stir over one hour. After stirring for additional 15 minutes, 0.5 mL 4 M KBr solution was added and the mixture stirred for 15 minutes more, and filtered through Celite. The crude product was concentrated and treated with 2 mL 1 N tetrabutylammonium fluoride in THF till deprotection of the TBS group was complete by HPLC. The residual after evaporation was purified on preparative HPLC (20~37.5% MeCN in water with 0.5% TFA) to give 280 mg title compound as a gel. $^1$H NMR (500 MHz, CD$_3$OD) δ 7.37~7.43 (m, 1H), 7.19 (d, 7.6 Hz, 1H), 7.15 (br d, 10.0 HZ, 1H), 7.02~7.06 (m, 1H), 3.85~3.89 (m, 1H), 3.78~3.82 (m, 1H), 3.55~3.62 (m, 3H), 2.43~3.48 (m, 2H), 2.63~2.69 (m, 1H), 1.70 (s, 3H), 1.69 (s, 3H). ESI-MS 282.1 (M+H), HPLC A: 1.39 min. In addition, 77.4 mg bis-alkylation product, 2-({2-[(3R,4S)-3-(hydroxymethyl)-4-(3-fluorophenyl)pyrrolidinyl]-2-methylpropanoyl}oxy)-2-methylpropanoic acid, trifluoroacetic acid, was also obtained. $^1$H NMR (500 MHz, CD$_3$OD) δ 7.38~7.43 (m, 1H), 7.19 (d, 8.0 Hz, 1H), 7.16 (br d, 9.6 Hz, 1H), 7.04~7.08 (m, 1H), 3.85~3.89 (m, 1H), 3.81 (dd, 8.3 & 11.7 Hz, 1H), 3.54~3.62 (m, 3H), 3.46 (dd, 5.3 & 11.5 Hz, 1H), 2.61~2.68 (m, 1H), 1.74 (s, 3H), 1.71 (s, 3H), 1.66 (s, 6H). ESI-MS 368.3 (M+H), HPLC A: 2.97 min. Silver trifluoroacetate gave similar results.

Step B: 2-(R)-(3-(R)-(Hydroxymethyl)-4-(S)-(3-fluorophenyl)pyrrolidin-1-yl)-2-methylpropionic Acid, Benzyl Ester 2-(R)-(3-(R)-(Hydroxymethyl)-4-(S)-(3-fluorophenyl)pyrrolidin-1-yl)-2-methylpropionic acid, trifluoroacetic acid salt (164 mg, 0.415 mmole) obtained in Step A above was treated with 85 mg (0.50 mmole) benzyl bromide, 135 mg Cs$_2$CO$_3$ in 2 mL DMF for two days. The reaction mixture was diluted with 60 mL water and extracted with ethyl acetate (3×40 mL). The combined organic layer was washed with water (3×30 mL) and saturated brine (30 mL), dried over sodium sulfate, and concentrated under vacuum to give 0.15 g crude product. FC on silica gel (10~70% ethyl acetate in hexanes) gave 99 mg title compound as a colorless oil. $^1$H NMR (500 MHz) δ 7.34~7.42 (m, 5H), 7.21~7.25 (m, 1H), 6.96~6.98 (m, 1H), 6.88~6.94 (m, 2H), 5.20 (AB d, 12.3 Hz, 1H), 5.18 (AB d, 12.3 Hz, 1H), 3.67 (dd, 4.4 & 10.6 Hz, 1H), 3.55 (dd, 6.2 & 10.6 Hz, 1H), 3.30~3.33 (m, 1H), 3.16~3.19 (m, 1H), 3.05~3.10 (m, 1H), 2.85~2.94 (m, 2H), 2.42 (v br s, 1H), 2.30~2.37 (m, 1H), 1.44 (s, 3H), 1.43 (s, 3H). ESI-MS 372.4 (M+H), HPLC A: 3.63 min.

Step C: 2-(R)-(3-(R)-(Formyl)-4-(S)-(3-fluorophenyl)pyrrolidin-1-yl)-2-methylpropionic Acid, Benzyl Ester Oxalyl chloride (68 mg, 0.533 mmole) was added to 1 mL DCM in dry ice acetone bath followed by 83 mg (1.07 mmole) DMSO. After stirring for 15 minutes, a solution of 99 mg -(R)-(3-(R)-(hydroxymethyl)-4-(S)-(3-fluorophenyl)pyrrolidin-1-yl)-2-methylpropionic acid, benzyl ester prepared in Step B above in 4 mL DCM was added over two minutes. After 20 minutes, 216 mg triethylamine was added. After five hours, the reaction mixture was diluted with 100 mL ether and washed with 0.25 M NaOH, water, and saturated brine. The organic layer was dried over sodium sulfate and evaporated under vacuum to give 90 mg title compound. $^1$H NMR (500 MHz) δ 9.61 (d, 2.3 Hz, 1H), 7.34~7.41 (m, 5H), 7.23~7.27 (m, 1H), 6.98~7.00 (m, 1H), 6.90~6.96 (m, 2H), 5.20 (AB d, 12.1 Hz, 1H), 5.19 (AB d, 12.1 Hz, 1H), 3.51~3.55 (m, 1H), 3.31~3.35 (m, 1H), 3.29 (dd, 6.2 & 9.4 Hz, 1H), 3.21~3.24 (m, 2H), 2.91~2.97 (m, 2H), 1.45 (s, 3H), 1.44 (s, 3H). ESI-MS 370.4 (M+H), HPLC A: 3.53 min.

Step D: α-(R)-(3-(S)-((4-(3-Benzyl-1-ethyl-(1H-pyrazol-5-yl))piperidin-1-yl)methyl)-4-(S)-(3-fluorophenyl)pyrrolidin-1-yl)-2-methylpropionic Acid, Benzyl Ester, Trifluoroacetic Acid Salt A similar procedure as described in Example 1 Step D was used to prepare the title compound from 45 mg 2-(R)-(3-(R)-(formyl)-4-(S)-(3-fluorophenyl)pyrrolidin-1-yl)-2-methylpropionic acid, benzyl ester prepared in Step C above and 68.5 mg 4-(3-benzyl-1-ethyl-(1H-pyrazol-5-yl))piperidine, trifluoroacetic acid salt from Example 1 Step C, giving 106.8 mg colorless gel. ESI-MS 623.5 (M+H), HPLC A: 4.20 min.

Step E: α-(R)-(3-(S)-((4-(3-Benzyl-1-ethyl-(1H-pyrazol-5-yl))piperidin-1-yl)methyl)-4-(S)-(3-fluorophenyl)pyrrolidin-1-yl)-2-methylpropionic Acid, Trifluoroacetic Acid Salt The product from Step D above was dissolved in 4 mL MeOH and to it was added 5.8 mg 10% Pd/C, and the mixture was stirred under a balloon of hydrogen for 1 hr. After filtering the reaction mixture, the filtrate was concentrated under reduced pressure, and the residue was lyophilized from 7:3 water and acetonitrile mixture to give 75.9 mg of the title compound as a white solid. ESI-MS 533.6 (M+H), HPLC A: 3.27 min.

EXAMPLE 558

2-({2-[(3S,4S)-3-{[4-(3-benzyl-1-ethyl-1H-pyrazol-5-yl)-1-piperidinyl]-methyl}-4-(3-fluorophenyl)pyrrolidinyl]-2-methylpropanoyl}oxy)-2-methylpropanoic Acid, Trifluoroacetic Acid Salt Step A: 2-({2-[(3R,4S)-3-(Hydroxymethyl)-4-(3-fluorophenyl)-pyrrolidinyl]-2-methylpropanoyl}oxy)-2-methylpropanoic Acid, Benzyl Ester The title compound was prepared from 301 mg 2-({2-[(3R,4S)-3-(hydroxymethyl)-4-(3-fluorophenyl)pyrrolidinyl]-2-methylpropanoyl}oxy)-2-methylpropanoic acid, trifluoroacetic acid obtained as the side-product in Example 557 Step A, 159 mg benzyl bromide, and 204 mg Cs$_2$CO$_3$ as described in Example 557 Step B. Similar purification gave 0.186 g title compound as a colorless gel. $^1$H NMR (500 MHz) δ 7.29~7.34 (m, 5H), 7.24~7.28 (m, 1H), 7.05 (d, 7.6 Hz, 1H), 7.00~7.03 (m, 1H), 6.90~6.94 (m, 1H), 5.18 (AB d, 12.2 Hz, 1H), 5.17 (AB d, 12.4 Hz, 1H), 3.69 (dd, 4.1 & 10.5 Hz, 1H), 3.56~3.59 (m, 1H), 3.29~3.33 (m, 1H), 3.14~3.18 (m, 2H), 2.86~2.94 (m, 2H), 2.35 (v br s, ~2H, OH+H$_4$), 1.63 (s, 6H), 1.38 (s, 3H), 1.35 (s, 3H). ESI-MS 458.6 (M+H), HPLC A: 4.03 min.

Step B: 2-({2-[(3R,4S)-3-(Formyl)-4-(3-fluorophenyl)pyrrolidinyl]-2-methylpropanoyl}oxy)-2-methylpropanoic Acid, Benzyl Ester The title compound was prepared in nearly quantitative yield from 2-({2-[(3R,4S)-3-(hydroxymethyl)-4-(3-fluorophenyl)pyrrolidinyl]-2-methylpropanoyl}oxy)-2-methylpropanoic acid, benzyl ester prepared in the last Step using a procedure similar to that in Example 557, Step C. $^1$H NMR (500 MHz) δ 9.62 (d, 2.3 Hz, 1H), 7.25~7.34 (m, 6H), 7.02~7.06 (m, 2H), 6.91~6.95 (m, 1H), 5.18 (AB d, 12.4 Hz, 1H), 5.17 (AB d, 12.2 Hz, 1H), 3.51~3.56 (m, 1H), 3.26~3.29 (m, 1H), 3.18~3.25 (m, 2H), 2.93~2.99 (m, 2H), 1.62 (s, 6H), 1.36 (s, 3H), 1.35 (s, 3H).

Step C: 2-({2-[(3S,4S)-3-{[4-(3-benzyl-1-ethyl-1H-pyrazol-5-yl)-1-piperidinyl]methyl}-4-(3-fluorophenyl)pyrrolidinyl]-2-methylpropanoyl}oxy)-2-methylpropanoic Acid, Benzyl Ester, Trifluoroacetic Acid Salt A similar procedure as described in Example 1 Step D was used to prepare the title compound from 61 mg 2-({2-[(3R,4S)-3-(formyl)-4-(3-fluorophenyl)pyrrolidinyl]-2-methylpropanoyl}oxy)-2-methylpropanoic acid, benzyl ester prepared in Step B above and 79.9 mg 4-(3-benzyl-1-ethyl-(1H-pyrazol-5-yl))piperidine, trifluoroacetic acid salt from Example 1 Step C, giving 95 mg colorless gel. ESI-MS 709.5 (M+H), HPLC A: 4.60 min.

Step D: 2-({2-[(3S,4S)-3-{[4-(3-benzyl-1-ethyl-1H-pyrazol-5-yl)-1-piperidinyl]methyl}-4-(3-fluorophenyl)pyrrolidinyl]-2-methylpropanoyl}oxy)-2-methylpropanoic Acid, Trifluoroacetic Acid Salt The product from Step C above was dissolved in 5 mL MeOH and to it was added 8.8 mg 10% Pd/C, and the mixture was stirred under a balloon of hydrogen for 1 hr. After filtering the reaction mixture, the filtrate was concentrated under reduced pressure, and the residue was lyophilized from 7:3 water and acetonitrile mixture to give 75.2 mg of the title compound as a white solid. ESI-MS 619.4 (M+H), HPLC A: 3.63 min.

EXAMPLE 559

α-(R)-(3-(S)-((4-(3-Benzyl-1-ethyl-(1H-pyrazol-5-yl))piperidin-1-yl)methyl)-4-(S)-(3-fluorophenyl)pyrrolidin-1-yl)-2-(R),3-dimethylbutanoic Acid, Ammonium Salt Step A: 2-Bromo-2,3-dimethylbutanoic Acid A solution of 38 mL 48% HBr in 140 mL water was added to a mixture of 20.0 g (152 mmole) DL-α-methyl valine and 62.5 g (525 mmole) KBr with stir. The mixture was cooled with ice acetone bath to −12° C. under nitrogen. A solution of 12 g sodium nitrite in 20 mL water was added with stirring in one hour. The reaction mixture was stirred for 2 hour, during which time the temperature was allowed to rise to 0° C. The reaction mixture was partitioned between 200 mL ether and some water. The aqueous layer was extracted with 2×100 mL ether. The combined ether solution was washed with saturated brine, dried over sodium sulfate, and evaporated under vacuum to give 15.462 g yellowish oil. FC on 200 g silica gel (20~60% ethyl acetate in hexanes and repeat again with 5~20% ethyl acetate in hexanes) provided 2.258 g mixture of solid and liquid. It is about 50% pure and used as is in the next step. It appeared the title compound was not stable on silica gel. It decomposes to give trimethylacrylic acid, which was a solid. $^1$H NMR (500 MHz) δ 2.50 (septet, 6.8 Hz, 1H), 1.83 (s, 3H), 1.17 (d, 6.9 Hz, 3H), 1.02 (d, 6.9 Hz, 3H). HPLC A: 3.03 min. Starting with D-α-methyl valine resulted in a similar product mixture without optical rotation.

Step B: 2-(R)-(3-(R)-(Hydroxymethyl)-4-(S)-(3-fluorophenyl)pyrrolidin-1-yl)-2,3-dimethylbutanoic Acid, Trifluoroacetic Acid Salt A solution of semi-crude 2-bromo-2,3-dimethylbutanoic acid prepared above in Step 1 in 15 mL THF was added via a syringe pump over 2.2 hours into a stirred solution of 3.584 (11.58 mmole) 3-(R)-(t-butyldimethylsilyloxymethyl)-4-(S)-(3-fluorophenyl)pyrrolidine (Pyrrolidine 1), 2.65 g (12 mmole) silver trifluoroacetate, and 6.20 g (48 mmole) DIEA in 130 mL THF. After stirring for additional 0.5 hour, 1.25 mL 4 M KBr solution was added to the reaction mixture. The reaction mixture was worked up after 10 minute as described in Example 557 Step A to give 8.101 g yellow oil as crude product. Repeated FC on 200 g silica gel (20~100% ethyl acetate in hexanes and 2~75% methanol in ethyl acetate) gave one fraction of product containing the fast-eluting diastereomer (HPLC A: 4.87 min., later identified as 2-(R),3-dimethylbutanoic acid isomer) and other fractions of mixtures of two diastereomers (HPLC A: 4.87 and 4.97 min.). All were contaminated by starting pyrrolidine. They were further purified on preparative HPLC (20~45% MeCN in water with 0.5% TFA) with concurrent loss of TBS group to give title compounds. HPLC A: 2.43 min. (both diastereomers); $^1$H NMR (500 MHz, CD$_3$OD) corresponding to 4.87 minute (TBS ether isomer) δ 7.38~7.42 (m, 1H), 7.18~7.19 (m, 1H), 7.13~7.16 (m, 1H), 7.03~7.07 (m, 1H), 3.68~3.93 (m, 4H), 3.61 (dd, 3.1 & 11.5 Hz, 1H), 3.43~3.49 (m, 2H), 2.61~2.68 (m, 1H), 2.35~2.41 (m, 1H), 1.64 (s, 3H), 1.13 (d, 6.8 Hz, 3H), 1.09 (d, 6.9 Hz, 3H).

Step C: 2-(R)-(3-(R)-(Hydroxymethyl)-4-(S)-(3-fluorophenyl) pyrrolidin-1-yl)-2-(R),3-dimethylbutanoic acid, p-methoxybenzyl Ester The pure diastereomer, 2-(R)-(3-(R)-(hydroxymethyl)-4-(S)-(3-fluorophenyl)pyrrolidin-1-yl)-2-(R),3-dimethylbutanoic acid, trifluoroacetic acid salt (0.235 g, 0.555 mmole) from Step B above was treated with 139 mg p-methoxybenzyl chloride and 181 mg Cs$_2$CO$_3$ in 2.5 mL DMF for 4 days. Similar work-up as described in Example 557 Step B gave 0.469 g crude product. FC on silica gel (10~70% ethyl acetate in hexanes) gave 0.182 g title compound as a colorless oil. R$_f$ 0.22 (1:3 v/v EtOAc and MeOH with 1% Et$_3$N). $^1$H NMR (500 MHz) δ 7.34~7.37 (m, 2H), 7.20~7.25 (m, 1H), 6.87~6.93 (m, 5H), 5.19 (d, 11.9 Hz, 1H), 5.08 (d, 11.9 Hz, 1H), 3.83 (s, 3H), 3.64 (dd, 4.6 & 10.3 Hz, 1H), 3.53 (dd, 6.0 & 10.6 Hz, 1H), 3.08~3.15 (m, 1H), 2.87~2.96 (m, 4H), 2.29~2.37 (m, 1H), 2.16~2.22 (m, 1H), 1.23 (s, 3H), 0.94 (d, 6.8 Hz, 3H), 0.82 (d, 6.8 Hz, 3H). ESI-MS 430.4 (M+H), HPLC A: 3.93 min.

Step D: 2-(R)-(3-(R)-(Formyl)-4-(S)-(3-fluorophenyl)pyrrolidin-1-yl)-2-(R),3-dimethylbutanoic Acid, p-methoxybenzyl Ester The title compound was prepared from 0.182 g 2-(R)-(3-(R)-(hydroxymethyl)-4-(S)-(3-fluorophenyl)pyrrolidin-1-yl)-2-(R),3-dimethylbutanoic acid, p-methoxybenzyl ester from Step C above using a procedure described in Example 557 Step C in 88% yield. $^1$H NMR (500 MHz) δ 9.59 (d, 2.3 Hz, 1H), 7.34~7.37 (m, 2H), 7.22~7.27 (m, 1H), 6.88~6.94 (m, 5H), 5.20 (d, 11.9 Hz, 1H), 5.08 (d, 11.9Hz, 1H), 3.83 (s, 3H), 3.37~3.41 (m, 1H), 3.31 (dd, 5.8 & 9.5 Hz, 1H), 3.10~3.14 (m, 1H), 2.92~2.97 (m, 2H), 2.77~2.82 (m, 1H), 2.29~2.37 (m, 1H), 1.22 (s, 3H), 0.93 (d, 6.9 Hz, 3H), 0.83 (d, 6.9 Hz, 3H). The stereochemistry at 2-methyl center was assigned tentatively based on NMR of the title compound and product from Example 560 Step B with both isomers of corresponding 2-(R)-methylpropionic acid derivatives.

Step E: α-(R)-(3-(S)-((4-(3-Benzyl-1-ethyl-(1H-pyrazol-5-yl))piperidin-1-yl)methyl)-4-(S)-(3-fluorophenyl)pyrrolidin-1-yl)-2-(R),3-dimethylbutanoic Acid, p-methoxybenzyl Ester The title compound was prepared from 32 mg 2-(R)-(3-(R)-(formyl)-4-(S)-(3-fluorophenyl)pyrrolidin-1-yl)-2-(R),3-dimethylbutanoic acid, p-methoxybenzyl ester from Step D above and 51.2 mg 4-(3-benzyl-1-ethyl-(1H-pyrazol-5-yl))piperidine, trifluoroacetic acid salt from Example 1 Step C using procedure described in Example 1 Step D, giving 76.6 mg colorless gel. ESI-MS 681.5 (M+H), HPLC A: 4.40 min.

Step F: α-(R)-(3-(S)-((4-(3-Benzyl-1-ethyl-(1H-pyrazol-5-yl))piperidin-1-yl)methyl)-4-(S)-(3-fluorophenyl)pyrrolidin-1-yl)-2-(R),3-dimethylbutanoic Acid, Ammonium Salt The product of the last step was treated with 3 mL 96% formic acid at RT over night. The residue from concentration under reduced pressure was dissolved in methanol and loaded onto Varian SCX Bond-Elut cartridge. After washing with methanol, the product was eluted with 2 N ammonia in methanol. After removal of solvent under reduced pressure, the residue was dissolved in 3:7 acetonitrile and water, filtered through a 0.2 µm PTFE disc, and lyophilized to give 33.1 mg white solid. ESI-MS 561.6 (M+H), HPLC A: 3.40 min.

EXAMPLE 560

α-(R)-(3-(S)-((4-(3-Benzyl-1-ethyl-(1H-pyrazol-5-yl))piperidin-1-yl)methyl)-4-(S)-(3-fluorophenyl)pyrrolidin-1-yl)-2-(S),3-dimethylbutanoic Acid, Ammonium Salt Step A: 2-(R)-(3-(R)-(Hydroxymethyl)-4-(S)-(3-fluorophenyl)pyrrolidin-1-yl)-2-(S),3-dimethylbutanoic Acid, p-methoxybenzyl Ester The mixture of diasteromers of 2-(R)-(3-(R)-(hydroxymethyl)-4-(S)-(3-fluorophenyl)pyrrolidin-1-yl)-2,3-dimethylbutanoic acid, trifluoroacetic acid obtained in Example 559 Step B was esterified with p-methoxybenzyl chloride as described in Example 559 Step C. Repeated FC on silica gel (10~70% ethyl acetate in hexanes) gave the slightly-faster eluting title compound as a white solid. $^1$H NMR (500 MHz) δ 7.34~7.37 (m, 2H), 7.20~7.24 (m, 1H), 6.87~6.92 (m, 5H), 5.16 (AB d, 11.9 Hz, 1H), 5.09 (AB d, 11.7 Hz, 1H), 3.82 (s, 3H), 3.62 (dd, 4.6 & 10.6 Hz, 1H), 3.51 (dd, 6.1 & 10.3 Hz, 1H), 3.35~3.39 (m, 1H), 3.26 (dd, 7.8 & 9.2 Hz, 1H), 2.94~2.99 (m, 1H), 2.67 (dd, 5.4 & 9.3 Hz, 1H), 2.52 (dd, 7.8 & 9.2 Hz, 1H), 2.27~2.35 (m, 1H), 2.19~2.25 (m, 1H), 2.08 (v br, 1H, OH?), 1.23 (s, 3H), 0.94 (6.7 Hz, 3H), 0.83 (d, 6.7 Hz, 3H).

Step B: 2-(R)-(3-(R)-(Formyl)-4-(S)-(3-fluorophenyl)pyrrolidin-1-yl)-2-(S),3-dimethylbutanoic Acid, p-methoxybenzyl Ester The title compound was prepared from product in the last step using a procedure similar to that in Example 559 Step D in quantitative yield. $^1$H NMR (500 MHz) δ 9.59 (d, 2.1 Hz, 1H), 7.33~7.36 (m, 2H), 7.22~7.26 (m, 1H), 6.87~6.94 (m, 5H), 6.16 (AB d, 11.7 Hz, 1H), 5.11 (AB d, 11.9 Hz, 1H), 3.83 (s, 3H), 3.43~3.47 (m, 1H), 3.38~3.41 (m, 1H), 3.28 (dd, 8.7 & 9.9 Hz, 1H), 3.12 (dd, 5.0 & 9.6 Hz, 1H), 2.79~2.84 (m, 1H), 2.55 (dd, 7.3 & 8.7 Hz, 1H), 2.30~2.38 (m, 1H), 1.23 (s, 3H), 0.92(d, 6.9 Hz, 1H), 0.83 (d, 6.7 Hz, 3H).

Step C: α-(R)-(3-(S)-((4-(3-Benzyl-1-ethyl-(1H-pyrazol-5-yl))piperidin-1-yl)methyl)-4-(S)-(3-fluorophenyl)pyrrolidin-1-yl)-2-(S),3-dimethylbutanoic Acid, p-methoxybenzyl Ester, Trifluoroacetic Salt The title compound was prepared from 24.6 mg 2-(R)-(3-(R)-(formyl)-4-(S)-(3-fluorophenyl)pyrrolidin-1-yl)-2-(S),3-dimethylbutanoic acid, p-methoxybenzyl ester from Step B above and 30.6 mg 4-(3-benzyl-1-ethyl-(1H-pyrazol-5-yl))piperidine, trifluoroacetic acid salt from Example 1 Step C using procedure described in Example 1 Step D, giving 54.9 mg colorless gel. ESI-MS 681.7 (M+H), HPLC A: 4.33 min.

Step D: α-(R)-(3-(S)-((4-(3-Benzyl-1-ethyl-(1H-pyrazol-5-yl))piperidin-1-yl)methyl)-4-(S)-(3-fluorophenyl)pyrrolidin-1-yl)-2-(S),3-dimethylbutanoic Acid, Ammonium Salt The title compound was prepared from the product in Step C above using procedure described in Example 559 Step F as 23.7 mg white solid. ESI-MS 561.6 (M+H), HPLC A: 3.43 min.

EXAMPLE 561

α-(R)-(3-(S)-((4-(3-(4-Trifluoromethoxybenzyl)-1-ethyl-(1H-pyrazol-5-yl))piperidin-1-yl)methyl)-4-(S)-(3-fluorophenyl)pyrrolidin-1-yl)-2-(S),3-dimethylbutanoic Acid, Ammonium Salt The title compound was prepared from the aldehyde in Example 560 Step B and piperidine from Example 613 using procedure described in Example 560 Steps C and D. ESI-MS 645.6 (M+H), HPLC A: 3.93 min.

EXAMPLE 562

α-(R)-(3-(S)-((4-(3-(4-Ethoxybenzyl)-1-ethyl-(1H-pyrazol-5-yl))piperidin-1-yl)methyl)-4-(S)-(3-fluorophenyl)pyrrolidin-1-yl)-2-(S),3-dimethylbutanoic Acid, Ammonium Salt The title compound was prepared from the aldehyde in Example 560 Step B and piperidine from Example 617 using procedure described in Example 560 Steps C and D. ESI-MS 605.6 (M+H), HPLC A: 3.60 min.

EXAMPLE 563

α-(R)-(3-(S)-((4-(3-(4-Ethoxybenzyl)-1-ethyl-(1H-pyrazol-5-yl))piperidin-1-yl)methyl)-4-(S)-(3-fluorophenyl)pyrrolidin-1-yl)-3-ethylpentanoic Acid, Ammonium Salt The title compound was prepared from the aldehyde in Example 542 ( and piperidine from 4-(3-benzyl-1-ethyl-(1H-pyrazol-5-yl))piperidine, trifluoroacetic acid salt from Example 1 Step C using procedure described in Example 560 Steps C and D. ESI-MS 619.6 (M+H), HPLC A: 3.87 min.

EXAMPLE 564

α-(R)-(3-(S)-((4-(3-(4-Ethoxybenzyl)-(1H-pyrazol-5-yl))piperidin-1-yl)methyl)-4-(S)-(3-fluorophenyl)pyrrolidin-1-yl)-3-(R)-methylpentanoic Acid, Trifluoroacetic Salt Step A: 1-(t-Butoxycarbonyl)-4-(3-(4-ethoxybenzyl)-(1H-pyrazol-5-yl))piperidine The title compound was prepared using procedure described in Example 2 Step A. $^1$H NMR (500 MHz) δ 7.12~7.15 (m, 2H), 6.83~6.86 (m, 2H), 5.85 (s, 1H), 4.10~4.20 (m, 2H), 4.03 (q, 6.9 Hz, 2H), 3.91 (s, 2H), 2.78~2.86 (m, 2H), 2.77 (tt, 3.7 & 11.7 Hz, 1H), 1.89~1.93 (m, 2H), 1.54~1.63 (m, 2H), 1.48 (s, 9H), 1.42 (t, 7.0 Hz, 3H). ESI-MS 386.4 (M+H), HPLC A: 4.33 min.

Step B: 4-(3-(4-Ethoxybenzyl)-(1H-pyrazol-5-yl))piperidine, Hydrochloride or Trifluoroacetic Acid Salt The title compound was prepared by deprotection of product from the last step with HCl in methanol or trifluoroacetic acid. HPLC A: 2.70 min.

Step C: α-(R)-(3-(S)-((4-(3-(4-Ethoxybenzyl)-(1H-pyrazol-5-yl))piperidin-1-yl)methyl)-4-(S)-(3-fluorophenyl)pyrrolidin-1-yl)-3-(R)-methylpentanoic Acid, Benzyl Ester, Trifluoroacetic Acid Salt The title compound was prepared from 17.9 mg 4-(3-(4-ethoxybenzyl)-(1H-pyrazol-5-yl))piperidine, hydrochloride salt from the above and 21.9 mg 2-(R)-(3-(R)-formyl-4-(S)-(3-fluorophenyl)pyrrolidin-1-yl)-3-(S)-methylpentanoic acid, benzyl ester from Aldehyde 15 using procedure described in Example 1 Step D. ESI-MS 667.4 (M+H), HPLC A: 4.33 min.

Step D: α-(R)-(3-(S)-((4-(3-(4-Ethoxybenzyl)-(1H-pyrazol-5-yl))piperidin-1-yl)methyl)-4-(S)-(3-fluorophenyl) pyrrolidin-1-yl)-3-(R)-methylpentanoic Acid, Trifluoroacetic Acid Salt The title compound was prepared from the product of the last step using procedure described in Example 1 Step E to give 38.2 mg white solid. ESI-MS 577.5 (M+H), HPLC A: 3.57 min.

EXAMPLE 565

α-(R)-(3-(S)-((4-(3-(4-Ethoxybenzyl)-(1H-pyrazol-5-yl))piperidin-1-yl)methyl)-4-(S)-(3-fluorophenyl) pyrrolidin-1-yl)-3-(S)-methylpentanoic Acid, Trifluoroacetic Salt The title compound was prepared using procedures described Example 564 Steps C and D using Aldehyde 14. ESI-MS 577.4 (M+H), HPLC A: 3.53 min.

EXAMPLE 566

α-(R)-(3-(S)-((4-(3-(4-Ethoxybenzyl)-(1H-pyrazol-5-yl))piperidin-1-yl)methyl)-4-(S)-(3-fluorophenyl) pyrrolidin-1-yl)-3,3-dimethylbutanoic Acid, Ammonium Salt The title compound was prepared using procedures described in Example 559 Steps E and F using 4-(3-(4-ethoxybenzyl)-(1H-pyrazol-5-yl))piperidine, trifluoroacetic acid salt and Aldehyde 18. ESI-MS 577.4 (M+H), HPLC A: 3.50 min.

EXAMPLE 567

α-(R)-(3-(S)-((4-(3-(4-Ethoxybenzyl)-1-(2-fluoroethyl)-(1H-pyrazol-5-yl))piperidin-1-yl) methyl)-4-(S)-(3-fluorophenyl)pyrrolidin-1-yl)-3-(R)-methylpentanoic Acid, Trifluoroacetic Salt Step A: 1-(t-Butoxycarbonyl)-4-(3-(4-ethoxybenzyl)-1-(2-fluoroethyl)(1H-pyrazol-5-yl))piperidine, Trifluoroacetic Acid Salt To a solution of 0.318 g 1-(t-butoxycarbonyl)-4-(3-(4-ethoxybenzyl)-(1H-pyrazol-5-yl))piperidine from Example 564 Step A in 2 mL dry DMF was added 0.050 g 60% NaH oil dispersion. After stirring over night, the reaction mixture was purified on preparative HPLC to give about 1:1.8 ratio of title compound and undesired 1-(t-butoxycarbonyl)-4-(5-(4-ethoxybenzyl)-1-(2-fluoroethyl)-(1H-pyrazol-3-yl)) piperidine. $^1$H NMR (500 MHz, CD$_3$OD) of TFA salt the title compound δ 7.10~7.13 (m, 2H), 6.79~6.83 (m, 2H), 5.96 (s, 1H), 4.72 (dt, $J_{H-F}$=47.3, $J_{H-H}$=4.8 Hz, 2H), ), 4.42 (dt, $J_{H-F}$=26.1, $J_{H-H}$=4.7 Hz, 2H), 4.14 (br d, 13.3 Hz, 2H), 3.98 (q, 6.9 Hz, 2H), 3.85 (s, 2H), 2.90 (tt, 11.9 & 3.6 Hz, 1H), 2.80~2.90 (m, 2H), 1.84 (br d, 12.8 Hz, 2H), 1.43~1.52 (m, 2H), 1.45 (s, 9H), 1.35 (t, 7.0 Hz, 3H). ESI-MS 432.5 (M+H), HPLC A: 5.07 min. $^1$H NMR (500 MHz, CD$_3$OD) of TFA salt the major isomer δ 7.10~7.13 (m, 2H), 6.79~6.83 (m, 2H), 5.92 (s, 1H), 4.71 (dt, $J_{H-F}$=47.2, $J_{H-H}$=4.8 Hz, 2H), ), 4.40 (dt, $J_{H-F}$=26.6, $J_{H-H}$=4.8 Hz, 2H), 3.98 (q, 6.9 Hz, 2H), 3.83 (s, 2H), 3.42~3.46 (m, 2H), 3.07~3.13 (m, 2H), 3.08 (tt, 11.9 & 3.6 Hz, 1H), 2.09 (br d, 14.6 Hz, 2H), 1.72~1.82 (m, 2H), 1.35 (t, 7.0 Hz, 3H). ESI-MS 432.5 (M+H), HPLC A: 5.20 min. The isomers were assigned based on NOE difference spectra.

Step B: 4-(3-(4-Ethoxybenzyl)-1-(2-fluoroethyl)-(1H-pyrazol-5-yl))piperidine, Trifluoroacetic Acid Salt The title compound was obtained from the minor product of the last step using a procedure similar to that in Example 1 Step C. HPLC A: 3.10 min.

Step C: α-(R)-(3-(S)-((4-(3-(4-Ethoxybenzyl)-1-(2-fluoroethyl)-(1H-pyrazol-5-yl))piperidin-1-yl)methyl)-4-(S)-(3-fluorophenyl)pyrrolidin-1-yl)-3-(R)-methylpentanoic Acid, Benzyl Ester, Trifluoroacetic Salt The title compound was prepared from 22.0 mg 4-(3-(4-ethoxybenzyl)-1-(2-fluoroethyl)-(1H-pyrazol-5-yl)) piperidine, trifluoroacetic salt from the above and 15.3 mg 2-(R)-(3-(R)-formyl-4-(S)-(3-fluorophenyl)pyrrolidin-1-yl)-3-(S)-methylpentanoic acid, benzyl ester from Aldehyde 15 using procedure described in Example 1 Step D, giving 40.8 mg product as a gel. ESI-MS 713.4 (M+H), HPLC A: 4.60 min.

Step D: α-(R)-(3-(S)-((4-(3-(4-Ethoxybenzyl)-1-(2-fluoroethyl)-(1H-pyrazol-5-yl))piperidin-1-yl)methyl)-4-(S)-(3-fluorophenyl) pyrrolidin-1-yl)-3-(R)-methylpentanoic Acid, Trifluoroacetic Salt The title compound was prepared from product of the last step using procedure described in Example 1 Step E as 29.6 white solid. ESI-MS 623.5 (M+H), HPLC A: 3.77 min.

EXAMPLE 568

α-(R)-(3-(S)-((4-(3-(4-Ethoxybenzyl)-1-(2-fluoroethyl)-(1 H-pyrazol-5-yl))piperidin-1-yl) methyl)-4-(S)-(3-fluorophenyl)pyrrolidin-1-yl)-3-(S)-methylpentanoic Acid, Trifluoroacetic Salt The title compound was prepared with procedures described in Example 567 Steps C and D using 4-(3-(4-ethoxybenzyl)-1-(2-fluoroethyl)-(1H-pyrazol-5-yl)) piperidine, trifluoroacetic acid salt from Example 567 Step B and Aldehyde 14. ESI-MS 623.4 (M+H), HPLC A: 3.73 min.

EXAMPLE 569

α-(R)-(3-(S)-((4-(3-(4-Ethoxybenzyl)-1-(2-fluoroethyl)-(1H-pyrazol-5-yl))piperidin-1-yl) methyl)-4-(S)-(3-fluorophenyl)pyrrolidin-1-yl)-3,3-dimethylbutanoic Acid, Ammonium Salt The title compound was prepared using procedures described in Example 559 Steps E and F using 4-(3-(4-ethoxybenzyl)-1-(2-fluoroethyl)-(1H-pyrazol-5-yl)) piperidine, trifluoroacetic acid salt from Example 567 Step B and Aldehyde 18. ESI-MS 623.4 (M+H), HPLC A: 3.70 min.

EXAMPLE 570

α-(R)-(3-(S)-((4-(3-(4-t-Butoxybenzyl)-1-ethyl-(1H-pyrazol-5-yl))piperidin-1-yl)methyl)-4-(S)-(3-fluorophenyl)pyrrolidin-1-yl)-3,3-dimethylbutanoic Acid, Ammonium Salt Step A: 1-(1-Benzylpiperidin-4-yl)-4-(4-t-butoxyphenyl) butane-1,3-dione The title compound was prepared using a procedure similar to that described in Example 13 Step C from 1-benzyl-4-acetylpiperidine and methyl 4-t-butoxyphenylacetate in 87% yield. 1H NMR (500 MHz) δ 7.30~7.35 (m, 4H), 7.24~7.29 (m, 1H), 7.12~7.15 (m, 2H), 6.95~6.97 (m, 2H), 3.57 (s, 2H), 3.50 (s, 2H), 2.91~2.95 (m, 2H), 2.15 (tt, 3.9 & 11.8 Hz, 1H), 1.95~2.01 (m, 2H), 1.75~1.80 (m, 2H), 1.63~1.72 (m, 2H), 1.36 (s, 9H).

Step B: 1-(t-Butoxycarbonyl)-4-(3-(4-t-butoxybenzyl)-1-ethyl-(1H-pyrazol-5-yl))piperidine The title compound was prepared from the diketone in last step using procedure similar to that used in Example 1 Step B in 54% yield. 1H NMR (500 MHz) δ 7.31~7.35 (m, 4H), 7.25~7.30 (m, 1H), 7.13~7.16 (m, 2H), 6.89~6.92 (m, 2H), 5.75 (s, 1H), 4.06 (q, 7.2 Hz, 2H), 3.90 (s, 2H), 3.54 (s, 2H), 2.96~3.00 (m, 2H), 2.51 (tt, 3.9 & 11.9 Hz, 1H), 2.04~2.10 (m, 2H), 1.80~1.85 (m, 2H), 1.67~1.75 (m, 2H), 1.43 (t, 7.2 Hz, 3H), 1.34 (s, 9H).

Step C: 4-(3-(4-t-butoxybenzyl)-1-ethyl-(1H-pyrazol-5-yl))piperidine

The title compound was prepared from the product in last step using procedure similar to that used in Example 8 Step F in quantitative yield. $^1$H NMR (500 MHz) δ 7.13~7.16 (m, 2H), 6.90–6.93 (m, 2H), 5.74 (s, 1H), 4.07 (q, 7.2 Hz, 2H), 3.91 (s, 2H), 3.14~3.18 (m, 2H), 2.69~2.75 (m, 2H), 2.64 (tt, 3.7 & 11.9 Hz, 1H), 1.82~1.86 (m, 2H), 1.51~1.59 (m, 2H), 1.45 (t, 7.2 Hz, 3H), 1.34 (s, 9H).

Step D: α-(R)-(3-(S)-((4-(3-(4-t-Butoxybenzyl)-1-ethyl-(1H-pyrazol-5yl))piperidin-1-yl)methyl)-4-(S)-(3-fluorophenyl)pyrrolidin-1-yl)-3,3-dimethylbutanoic Acid, Benzyl Ester The title compound was prepared from the product in last step and Aldehyde 17 using procedure similar to that used in Example 1 Step D omitting DIEA. The reaction mixture was purified directly on silica gel (5% methanol in DCM). ESI-MS 723.5 (M+H), HPLC A: 4.93 min.

Step E: α-(R)-(3-(S)-((4-(3-(4-t-Butoxybenzyl)-1-ethyl-(1H-pyrazol-5-yl))piperidin-1-yl)methyl)-4-(S)-(3-fluorophenyl)pyrrolidin-1-yl)-3,3-dimethylbutanoic Acid, Ammonium Salt The title compound was prepared from the product in last step using procedure similar to that used in Example 1 Step E. The crude product after removal of solvent was purified on silica gel (5% methanol in DCM, 5–10% methanol in DCM with 1% ammonia). Lyophilization from 3:7 acetonitrile and water mixture gave title compound as a white solid.). ESI-MS 633.4 (M+H), HPLC A: 3.90 min.

EXAMPLE 571

α-(R)-(3-(S)-((4-(3-(4-t-Butoxybenzyl)-1-ethyl-(1H-pyrazol-5-yl))piperidin-1 -yl)methyl)-4-(S)-(3-fluorophenyl)pyrrolidin-1-yl)-3-(S)-methylpentanoic Acid, Ammonium Salt The title compound was prepared using procedures described in Example 570 Steps D and E using 4-(3-(4-t-butoxybenzyl)-1-ethyl-(1H-pyrazol-5-yl))piperidine, from Example 570 Step C and Aldehyde 16. ESI-MS 633.4 (M+H), HPLC A: 3.93 min.

EXAMPLE 572

α-(R)-(3-(S)-((4-(3-(4-t-Butoxybenzyl)-1-ethyl-(1H-pyrazol-5-yl))piperidin-1-yl)methyl)-4-(S)-(3-fluorophenyl)pyrrolidin-1-yl)-3-(R)-methylpentanoic Acid, Ammonium Salt The title compound was prepared using procedures described in Example 570 Steps D and E using 4-(3-(4-t-butoxybenzyl)-1-ethyl-(1H-pyrazol-5-yl))piperidine, from Example 570 Step C and Aldehyde 15. ESI-MS 633.4 (M+H), HPLC A: 3.93 min.

EXAMPLE 573

α-(R)-(3-(S)-((4-(3-(4-t-Butoxybenzyl)-1-ethyl-(1H-pyrazol-5-yl))piperidin-1-yl)methyl)-4-(S)-(3-fluorophenyl)pyrrolidin-1-yl)-3-methylbutanoic Acid, Ammonium Salt The title compound was prepared using procedures described in Example 570 Steps D and E using 4-(3-(4-t-butoxybenzyl)-1-ethyl-(1H-pyrazol-5-yl))piperidine, from Example 570 Step C and Aldehyde 9. ESI-MS 619.3 (M+H), HPLC A: 3.77 min.

EXAMPLE 574

α-(R)-(3-(S)-((4-(3-(4-t-Butoxybenzyl)-1-ethyl-(1H-pyrazol-5-yl))piperidin-1-yl)methyl)-4-(S)-(3-fluorophenyl)pyrrolidin-1-yl)-2-cyclohexylacetic Acid, Ammonium Salt The title compound was prepared using procedures described in Example 570 Steps D and E using 4-(3-(4-t-butoxybenzyl)-1-ethyl-(1H-pyrazol-5-yl))piperidine, from Example 570 Step C and Aldehyde 6. ESI-MS 659.4 (M+H), HPLC A: 4.10 min.

EXAMPLES 575 and 576

Example 575 and 576 in Table 23 were prepared from Aldehyde 9 and corresponding piperidines using procedures similar to that used in Example 6 Steps E and F. The piperidines were synthesized from a) condensation of 4-acetyl-1-(t-butoxycarbonyl)-piperidine and dimethyl carbonate using sodium hydride, b) cyclization of the resulting β-ketoester with benzylhydrazine, c) alkylation of pyrazolone with ethyl iodide and sodium hydride in DMF and separation of isomers by HPLC, and d) removal of Boc protecting group with TFA in DCM in the presence of anisole.

TABLE 23

| EXAMPLE # | R | ESI-MS (M + H) | HPLC A (min.) |
|---|---|---|---|
| 575 | | 591.4 m/Z | 3.53 |

TABLE 23-continued

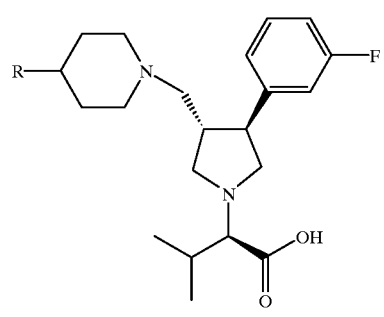

| EXAMPLE # | R | ESI-MS (M + H) | HPLC A (min.) |
|---|---|---|---|
| 576 | (structure: Ph-CH2-N-N(Et)-pyrazolone) | 591.4 m/Z | 4.00 |

EXAMPLES 577–580

Examples 577~580 in Table 24 were prepared from Aldehyde 14 or 15 and piperidines from Examples 291–294 above using procedures described in Example 1 Steps D and E.

TABLE 24

| EXAMPLE # | $R^a$ | $R^b$ | ESI-MS (M + H); HPLC A (min.) |
|---|---|---|---|
| 577 | Et | (sec-butyl, wedge) | 578.4 m/Z; 3.63 |
| 578 | Et | (sec-butyl, dash) | 578.7 m/Z; 3.63 |
| 579 | H | (sec-butyl, wedge) | 550.5 m/Z; 2.21 |
| 580 | H | (sec-butyl, dash) | 550.5 m/Z; 2.24 |

EXAMPLE 581

(2R)-2-[(3S,4S)-3-{[4-(2-ethyl-4,5,6,7-tetrahydro-2H-indazol-3-yl)-1-piperidinyl]methyl}-4-(3-fluorophenyl)pyrrolidinyl]-3,3-dimethylbutanoic Acid, Trifluoroacetic Acid Salt Step A: (1-Benzylpiperidin-4-yl)-(cyclohexanon-2-yl) ketone To a suspension of 1.60 g 60% NaH in 10 mL dry THF was added a solution of 1.963 g (20 mmole) cyclohexanone and 9.893 g (40 mmole) of 1-benzyl-piperidine-4-carboxylic acid ethyl ester in 30 mL THF. This mixture was heated to reflux overnight. Similar work-up as in Example 13 Step C followed by silica gel FC (15~50% ethyl acetate in hexanes with 1% triethylamine) provided 4.409 g product containing about 5.7:1 molar ratio of starting 1-benzyl-piperidine-4-carboxylic acid ethyl ester and title compound. ESI-MS 300.3 (M+H), HPLC A: 2.90 and 3.57 min. (for tautomeric forms).

Step B: 4-(2-Ethyl-4,5,6,7-tetrahydro-2H-indazol-3-yl)-1-benzyl Piperidine

The title compound was best prepared from the semi-crude β-diketone from the last step and 34% aqueous ethylhydrazine in 4:1 acetonitrile and water at room temperature. This provided 8:1 ratio of isomeric ethyl pyrazoles in favor of the title compound. Use of ethyl hydrazine oxalate in the presence of DIEA gave about 2:1 ratio of the same isomers. The 1-benzyl-piperidine-4-carboxylic acid ethyl ester present in the starting β-diketone was removed after saponification of the crude product with sodium hydroxide in water ethanol mixture followed by extractive work-up. The desired ethyl isomer has a higher RF than the other isomer. It was isolated on silica gel (60~100% ethyl acetate in hexanes and 5~20% methanol in ethyl acetate, both with 1% triethylamine). 1H NMR (500 MHz) δ 7.33~7.36 (m, 4H), 7.26~7.30 (m, 1H), 4.07 (q, 7.2 Hz, 2H), 3.57 (s, 2H), 3.00~3.03 (m, 2H), 2.64~2.66 (m, 2H), 2.60~2.63 (m, 2H), 2.57~2.63 (m, 1H), 1.96~2.08 (m, 4H), 1.69~1.81 (m, 6H), 1.39 (t, 7.2 Hz, 3H). The identity of the title compound was confirmed by NOE difference spectroscopy.

Step C: 4-(2-Ethyl-4,5,6,7-tetrahydro-2H-indazol-3-yl)piperidine

A mixture of 0.273 g 4-(2-ethyl-4,5,6,7-tetrahydro-2H-indazol-3-yl)-1-benzylpiperidine from Step B above, 0.789 g ammonium formate, and 35 mg 20% Pd(OH)2 in 6 mL MeOH was heated at 65° C. for 1 hour. Basic aqueous work-up with ether extraction provided 0.192 g title compound as a colorless solid (97%). $^1$H NMR (500 MHz) δ 4.08 (q, 7.2 Hz, 2H), 3.19 (br d, 11.9 Hz, 2H), 2.71~2.77 (m, 1H), 2.68~2.74 (m, 2H), 2.64~2.66 (m, 2H), 2.60~2.62 (m, 2H), 1.82~1.91 (m, 2H), 1.71~1.80 (m, 6H), 1.40 (t, 7.2 Hz, 3H). The identity of the title compound was confirmed again by NOE difference spectroscopy.

Step D: (2R)-2-[(3S,4S)-3-{[4-(2-ethyl-4,5,6,7-tetrahydro-2H-indazol-3-yl)-1-piperidinyl]methyl}-4-(3-fluorophenyl)pyrrolidinyl]-3,3-dimethylbutanoic Acid, Benzyl Ester, Trifluoroacetic Acid Salt The title compound was prepared from 4-(2-ethyl-4,5,6,7-tetrahydro-2H-indazol-3-yl)piperidine from Step C above and Aldehyde 17 using procedure similar to that used in Example 1 Step D omitting DIEA. ESI-MS 615.4 (M+H), HPLC A: 4.07 min.

Step E: (2R)-2-[(3S,4S)-3-{[4-(2-ethyl-4,5,6,7-tetrahydro-2H-indazol-3-yl)-1-piperidinyl]methyl}-4-(3-fluorophenyl)pyrrolidinyl]-3,3-dimethylbutanoic Acid, Trifluoroacetic Acid Salt The title compound was prepared from the product of the last Step using procedure similar to that used in Example 1 Step E. ESI-MS 525.3 (M+H), HPLC A: 2.90 min.

EXAMPLES 582–587

Examples 582–587 in Table 25 were prepared from appropriate aldehydes and the piperidine from Example 581 Step C using procedures described in 581 Steps D and E.

TABLE 25

| EXAMPLE # | From Aldehyde | R | ESI-MS (M + H); HPLC A (min.) |
|---|---|---|---|
| 582 | 16 | (sec-butyl) | 525.4 m/Z; 2.97 |
| 583 | 15 | (sec-butyl, stereo) | 525.2 m/Z; 2.97 |
| 584 | 11 | (isobutyl) | 511.2 m/Z; 2.70 |
| 585 | 6 | (cyclohexylmethyl) | 551.3 m/Z; 3.17 |
| 586 | 12 | (cyclopropylmethyl) | 523.2 m/Z; 2.77 |
| 587 | PMB analogue of Aldehyde 2 | (cyclobutylmethyl) | 537.5 m/Z; 3.07 |

EXAMPLE 588

(2R)-2-[(3S,4S)-3-{[4-(4,5,6,7-tetrahydro-2H-indazol-3-yl)-1-piperidinyl]methyl}-4-(3-fluorophenyl)pyrrolidinyl]-3,3-dimethylbutanoic Acid, Trifluoroacetic Acid Salt Step A: 4-(4,5,6,7-Tetrahydro-2H-indazol-3-yl)-1-benzyl Piperidine, Trifluoroacetic Acid Salt The title compound was prepared using a procedure similar to that in Example 581 Step B with hydrazine instead of ethyl hydrazine. It was further purified on HPLC. $^1$H NMR (500 MHz, CD$_3$OD) δ 7.47~7.55 (m, 5H), 4.35 (s, 2H), 3.61 (br d, 12.3 Hz, 2H), 3.13~3.21 (m, 3H), 2.71~2.73 (m, 2H), 2.56~2.58 (m, 2H), 2.17 (br d, 13.3 Hz, 2H), 2.04~2.12 (m, 2H), 1.79~1.89 (m, 4H). ESI-MS 296.3 (M+H), HPLC A: 2.33 min.

Step B: 4-(4,5,6,7-tetrahydro-2H-indazol-3-yl)piperidine

The title compound was prepared using a procedure similar to that in Example 581 Step C as a white solid. $^1$H NMR (500 MHz) δ 3.20 (br d, 12.4 Hz, 2H), 2.72~2.797 (m, 3H), 2.64~2.66 (m, 2H), 2.49~2.52 (m, 2H), 1.87~1.90 (m, 2H), 1.70~1.84 (m, 6H). ESI-MS 206.2 (M+H), HPLC A: 0.80 min.

Step C: (2R)-2-[(3S,4S)-3-{[4-(4,5,6,7-tetrahydro-2H-indazol-3-yl)-1-piperidinyl]methyl}-4-(3-fluorophenyl)pyrrolidinyl]-3,3-dimethylbutanoic Acid, 4-methoxybenzyl Ester, Trifluoroacetic Acid Salt The title compound was prepared from 4-(4,5,6,7-tetrahydro-2H-indazol-3-yl)piperidine from Step B above and Aldehyde 18 using procedure similar to that used in Example 1 Step D (omitting DIEA). ESI-MS 617.3 (M+H), HPLC A: 3.97 min.

Step D: (2R)-2-[(3S,4S)-3-{[4-(4,5,6,7-tetrahydro-2H-indazol-3-yl)-1-piperidinyl]methyl}-4-(3-fluorophenyl)pyrrolidinyl]-3,3-dimethylbutanoic Acid, Trifluoroacetic Acid Salt The title compound was prepared from the product in Step C above using procedure similar to that used in Example 1 Step E. ESI-MS 497.5 (M+H), HPLC A: 2.80 min.

EXAMPLES 589–592

Examples 589–592 in Table 26 were prepared from appropriate aldehyde and the piperidine from Example 588 Step B using procedures described in Example 588 Steps D and E.

TABLE 26

| EXAMPLE # | From Aldehyde | R | ESI-MS (M + H); HPLC A (min.) |
|---|---|---|---|
| 589 | 16 | (sec-butyl) | 497.5 m/Z; 2.87 |
| 590 | 15 | (sec-butyl) | 497.5 m/Z; 2.90 |
| 591 | 11 | (isopropyl) | 483.5 m/Z; 2.67 |
| 592 | 6 | (cyclohexyl) | 523.5 m/Z; 3.10 |

EXAMPLES 593–594

Examples 593 and 594 in Table 27 were prepared from Aldehyde 11 and the piperidines from Example 26 and Example 5 Step B, respectively using procedures described in Example 6 Steps E and F.

TABLE 27

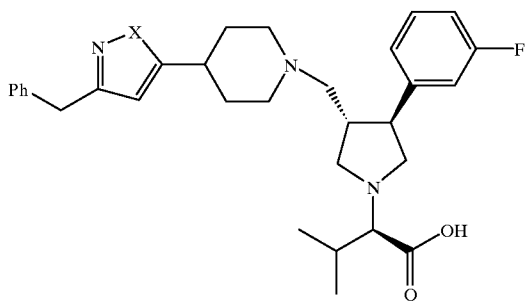

| EXAMPLE # | X | ESI-MS (M + H) | HPLC A (min.) |
|---|---|---|---|
| 593 | NCH$_3$ | 533.5 m/Z | 3.23 |
| 594 | O | 520.4 m/Z | 3.60 |

EXAMPLES 595–623

Examples 595–623 in Table 28 were prepared from Aldehyde 11 and appropriate piperidines using procedures described in Example 6 Steps E and F or Example 1 Steps D and E. The piperidines were prepared using Method A or Method B of Example 1.

TABLE 28

| EXAMPLE # | R | ESI-MS (M + H) | HPLC A (min.) |
|---|---|---|---|
| 595 | 4-Cyanobenzyl | 572.6 m/Z | 3.33 |
| 596 | 4-Phenoxybenzyl | 639.5 m/Z | 4.03 |
| 597 | 4-Phenylbenzyl | 623.3 m/Z | 3.97 |
| 598 | 4-Cyclobutoxybenzyl | 617.5 m/Z | 3.97 |
| 599 | 4-Ethoxy-3-flourobenzyl | 609.5 m/Z | 3.63 |
| 600 | 4-Hydroxybenzyl | 563.5 m/Z | 3.30 |
| 601 | 4-n-Butoxybenzyl | 619.5 m/Z | 4.03 |
| 602 | 2-Phenylethyl | 561.5 m/Z | 3.33 |
| 603 | 4-Chlorobenzyl | 581.6 m/Z | 3.57 |
| 604 | 3,5-Difluorobenzyl | 583.5 m/Z | 3.53 |
| 605 | 3-Fluorobenzyl | 565.2 m/Z | 3.43 |
| 606 | 4-Trifluoromethylbenzyl | 615.5 m/Z | 3.70 |
| 607 | 4-Methoxybenzyl | 577.3 m/Z | 3.23 |
| 608 | 2-Fluorobenzyl | 565.3 m/Z | 3.40 |
| 609 | (3-Pyridinyl)methyl | 548.3 m/Z | 1.87 |
| 610 | 2,4-Difluorobenzyl | ND | 3.50 |
| 611 | 4-Methylsulfonylbenzyl | 625.3 m/Z | 3.00 |
| 612 | 3,5-Bis(trifluoromethyl)benzyl | 683.6 m/Z | 4.23 |
| 613 | 4-Trifluoromethoxybenzyl | 631.7 m/Z | 3.83 |
| 614 | 3-Cyanobenzyl | 572.5 m/Z | 3.37 |
| 615 | 4-Difluoromethoxybenzyl | 613.6 m/Z | 3.63 |
| 616 | Cyclohexylmethyl | 553.6 m/Z | 3.53 |

TABLE 28-continued

[Structure: pyrazole-piperidine-pyrrolidine scaffold with R group, 3-fluorophenyl, and isopropyl-carboxylic acid substituent]

| EXAMPLE # | R | ESI-MS (M + H) | HPLC A (min.) |
|---|---|---|---|
| 617 | 4-Ethoxybenzyl | 591.5 m/Z | 3.53 |
| 618 | 4-Methoxy-3-cyanobenzyl | 602.6 m/Z | 3.33 |
| 619 | 4-Cylcopropoxybenzyl | 603.5 m/Z | 3.93 |
|  | 4-n-Propoxybenzyl | 605.5 m/Z | 3.77 |
| 621 | 4-n-Butoxybenzyl | 619.5 m/Z | 4.03 |
| 622 | 3,4-Dichlorobenzyl | 615.3 m/Z | 3.93 |
| 623 | 4-Phenylsulfonylbenzyl | 687.4 m/Z | 3.63 |

EXAMPLE 624

α-(R)-(3-(S)-((4-(4-(2-phenylethyl)-1-ethyl-(1H-pyrazol-5-yl))piperidin-1-yl)methyl)-4-(S)-phenylpyrrolidin-1-yl)-3-methylbutanoic Acid, Trifluoroacetic Acid Salt The title compound was prepared from 4-(4-(2-phenylethyl)-1-ethyl-(1H-pyrazol-5-yl))-piperidine, trifluoroacetic acid salt from Example 9 Step G and Aldehyde 11 using procedure in Example 6 Steps E and F. ESI-MS 561.4 (M+H), HPLC A: 3.43 min.

EXAMPLES 625–642

Examples 625–642 in Table 29 were prepared from Aldehydes 7 or 6 and appropriate piperidines using procedures described in Example 6 Steps E and F or Example 1 Steps D and E. The piperidines were prepared using Method A or Method B in Step B of Example 1.

TABLE 29

[Structure: pyrazole-piperidine-pyrrolidine scaffold with R group, 3-fluorophenyl, and cyclohexyl-carboxylic acid substituent]

| EXAMPLE # | R | ESI-MS (M + H) | HPLC A (min.) |
|---|---|---|---|
| 625 | 4-Cyanobenzyl | 612.6 m/Z | 3.67 |
| 626 | 4-Hydroxybenzyl | 603.5 m/Z | 3.30 |
| 627 | 4-Phenylbenzyl | 663.5 m/Z | 4.33 |
| 628 | 4-n-Butoxybenzyl | 659.5 m/Z | 4.30 |
| 629 | 4-Chlorobenzyl | 621.6 m/Z | 3.90 |
| 630 | 3,5-Difluorobenzyl | 623.6 m/Z | 3.87 |
| 631 | 3-Fluorobenzyl | 605.5 m/Z | 3.80 |
| 632 | 4-Trifluoromethylbenzyl | 655.6 m/Z | 4.07 |
| 633 | 4-Methoxybenzyl | 617.3 m/Z | 3.60 |
| 634 | 2-Fluorobenzyl | 605.2 m/Z | 3.73 |
| 635 | (3-Pyridinyl)methyl | 588.3 m/Z | 2.80 |
| 636 | 4-Methylsulfonylbenzyl | 665.4 m/Z | 3.37 |
| 637 | 4-Ethoxybenzyl | 631.6 m/Z | 3.87 |
| 638 | 4-Phenoxybenzyl | 679.5 m/Z | 4.30 |
| 639 | 4-Cyclopropoxybenzyl | 643.6 m/Z | 3.93 |
| 640 | 4-n-Propoxybenzyl | 645.5 m/Z | 4.07 |
| 641 | 4-Phenylsulfonylbenzyl | 727.5 m/Z | 3.93 |
| 642 | 2,4-Difluorobenzyl | 623.5 m/Z | 3.87 |

EXAMPLES 643–674

Examples 643–674 in Table 30 were prepared from Aldehydes 14 or 16 and appropriate piperidines using procedures described in Example 6 Steps E and F or Example 1 Steps D and E. The piperidines were prepared using Method A or Method B in Step B of Example 1. Examples 673 and 674 were obtained as side-products of Examples 645 and 647 respectively, during the final catalytic hydrogenation.

TABLE 30

[Structure: pyrazole-piperidine-pyrrolidine scaffold with R group, 3-fluorophenyl, and sec-butyl-carboxylic acid substituent]

| EXAMPLE # | R | ESI-MS (M + H) | HPLC A (min.) |
|---|---|---|---|
| 643 | 3,5-Bis(trifluoromethyl)benzyl | 697.5 m/Z | 4.30 |
| 644 | 4-Trifluoromethoxybenzyl | 645.4 m/Z | 3.97 |

TABLE 30-continued

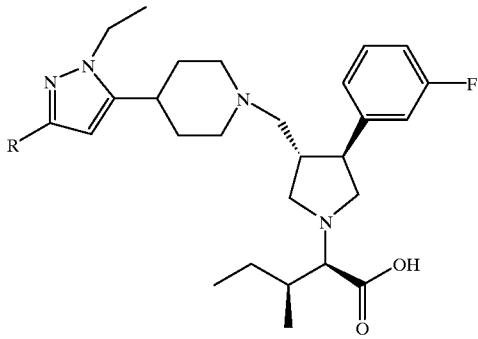

| EXAMPLE # | R | ESI-MS (M + H) | HPLC A (min.) |
|---|---|---|---|
| 645 | 4-Cyanobenzyl | 586.5 m/Z | 3.43 |
| 646 | 4-Trifluoromethylbenzyl | 629.6 m/Z | 4.03 |
| 647 | 3-Cyanobenzyl | 586.5 m/Z | 3.63 |
| 648 | 4-Difluoromethoxybenzyl | 627.4 m/Z | 3.83 |
| 649 | Cyclohexylmethyl | 567.6 m/Z | 3.73 |
| 650 | 4-Ethoxybenzyl | 605.5 m/Z | 3.80 |
| 651 | 4-Methylbenzyl | 575.7 m/Z | 3.63 |
| 652 | 4-i-Propylbenzyl | 603.6 m/Z | 4.00 |
| 653 | 3-Methoxybenzyl | 591.6 m/Z | 3.50 |
| 654 | 3,4-Methylenedioxybenzyl | 605.6 m/Z | 3.40 |
| 655 | 4-i-Propoxybenzyl | 619.7 m/Z | 3.73 |
| 656 | 3,4-Dimethoxybenzyl | 621.6 m/Z | 3.27 |
| 657 | 3-Cyano-4-methoxybenzyl | 616.6 m/Z | 3.47 |
| 658 | 3-Ethoxybenzyl | 605.3 m/Z | 3.67 |
| 659 | 4-t-Butylbenzyl | 617.6 m/Z | 4.13 |
| 660 | (1-Naphthyl)methyl | 611.4 m/Z | 3.83 |
| 661 | (2-Naphthyl)methyl | 611.3 m/Z | 3.83 |
| 662 | 4-Phenylbenzyl | 637.4 m/Z | 4.13 |
| 663 | 4-(2,2,2-Trifluoroethyl)benzyl | 659.5 m/Z | 3.93 |
| 664 | 4-Cyclobutoxybenzyl | 631.4 m/Z | 3.93 |
| 665 | 3-Fluoro-4-Ethoxybenzyl | 623.4 m/Z | 3.73 |
| 666 | 4-Hydroxybenzyl | 577.4 m/Z | 3.03 |
| 667 | 4-Benzoxybenzyl | 667.5 m/Z | 4.13 |
| 668 | 4-Phenoxybenzyl | 653.5 m/Z | 4.13 |
| 669 | 4-n-Butoxybenzyl | 633.6 m/Z | 4.07 |
| 670 | 4-Cyclopropoxybenzyl | 617.5 m/Z | 3.73 |
| 671 | 4-n-Propoxybenzyl | 619.5 m/Z | 3.87 |
| 672 | 4-Phenylsulfonylbenzyl | 701.3 m/Z | 3.77 |
| 673 | 4-Aminomethylbenzyl | 590.5 m/Z | 2.73 |
| 674 | 3-Aminomethylbenzyl | 590.5 m/Z | 2.93 |

$^1$H NMR of Example 644 (400 MHz, CD$_3$OD, HCl salt) δ 7.43~7.48 (m, 1H), 7.32~7.38 (m, 4H), 7.19 (br d, 8.2 Hz, 2H), 7.09~7.13 (m, 1H), 6.15 (s, 1H), 4.35~4.46 (m, 1H), 4.22 (q, 7.2 Hz, 2H), 4.00 (s, 2H), 3.81~3.86 (m, 1H), 3.67 (br d, 7.4 Hz, 1H), 3.46~3.55 (m, 2H), 3.18~3.25 (m, 1H), 3.03~3.14 (m, 2H), 2.92~2.99 (m, 1H), 2.16~2.22 (m, 1H), 2.05~2.09 (m, 3H), 1.78~1.85 (m, 1H), 1.41 (t, 7.2 Hz, 3H), 1.24 (d, 6.9 Hz, 3H), 1.02~1.13 (m, 1H), 0.98~1.03 (m, 3H).

EXAMPLES 675–710

Examples 675–710 in Table 31 were prepared from Aldehydes 18 or 17 and appropriate piperidines using procedures described in Example 6 Steps E and F or Example 1 Steps D and E. The piperidines were prepared using Method A or Method B in Step B of Example 1. Examples 707–710 were obtained as side-products of Examples 687–690 during the final removal of PMB with 96% formic acid, respectively.

TABLE 31

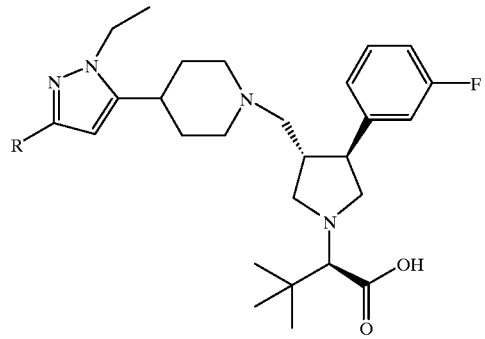

| EXAMPLE # | R | ESI-MS (M + H) | HPLC A (min.) |
|---|---|---|---|
| 675 | 4-Cyanobenzyl | 586.3 m/Z | 3.40 |
| 676 | 4-Methylsulfonylbenzyl | 639.3 m/Z | 3.10 |
| 677 | 4-Methoxybenzyl | 591.3 m/Z | 3.43 |
| 678 | 3,5-Bis(trifluoromethyl)benzyl | 697.6 m/Z | 4.30 |
| 679 | 4-Trifluoromethoxybenzyl | 645.5 m/Z | 3.90 |
| 680 | 4-Ethoxybenzyl | 605.4 m/Z | 3.70 |
| 681 | 4-Trifluoromethylbenzyl | 629.7 m/Z | 3.93 |
| 682 | Cyclohexylmethyl | 567.6 m/Z | 3.63 |
| 683 | 3-Cyanobenzyl | 586.4 m/Z | 3.47 |
| 684 | 4-Difluoromethoxybenzyl | 627.5 m/Z | 3.80 |
| 685 | 4-Methylbenzyl | 575.5 m/Z | 3.70 |
| 686 | 4-i-Propylbenzyl | 603.5 m/Z | 4.03 |
| 687 | 3-Methoxybenzyl | 591.4 m/Z | 3.47 |
| 688 | 3,4-Methylenedioxybenzyl | 605.3 m/Z | 3.40 |
| 689 | 4-i-Propoxybenzyl | 619.4 m/Z | 3.73 |
| 690 | 3,4-Dimethoxybenzyl | 621.4 m/Z | 3.23 |
| 691 | 3-Cyano-4-methoxybenzyl | 616.6 m/Z | 3.43 |
| 692 | 3-Ethoxybenzyl | 605.6 m/Z | 1.25 |
| 693 | 4-t-Butylbenzyl | 617.6 m/Z | 1.41* |
| 694 | (1-Naphthyl)methyl | 611.6 m/Z | 1.30* 3.87 |
| 695 | (2-Naphthyl)methyl | 611.6 m/Z | 1.31* 3.90 |
| 696 | 4-Phenylbenzyl | 637.4 m/Z | 4.07 |
| 697 | 4-(2,2,2-Trifluoroethyl)benzyl | 659.5 m/Z | 3.87 |
| 698 | 4-Cyclobutoxybenzyl | 631.5 m/Z | 3.97 |
| 689 | 3-Fluoro-4-Ethoxybenzyl | 623.5 m/Z | 3.70 |
| 700 | 4-Hydroxybenzyl | 577.5 m/Z | 3.00 |
| 701 | 4-Benzoxybenzyl | 631.4 m/Z | 4.10 |
| 702 | 4-Phenoxybenzyl | 653.4 m/Z | 4.13 |
| 703 | 4-n-Butoxybenzyl | 633.6 m/Z | 4.07 |
| 704 | 4-Cyclopropoxybenzyl | 617.2 m/Z | 3.67 |
| 705 | 4-n-Propoxybenzyl | 619.5 m/Z | 3.87 |
| 706 | 4-Phenylsulfonylbenzyl | 701.5 m/Z | 3.73 |
| 707 | 3-Methoxy-2-(4-methoxybenzyl)benzyl | 711.4 m/Z | 4.10 |
| 708 | 3,4-Methylenedioxy-2-(4-ethoxybenzyl)benzyl | 725.7 m/Z | 4.07 |
| 709 | 4-i-Propoxy-2-(4-ethoxybenzyl)benzyl | ND | 4.53 |
| 710 | 3,4-Dimethoxy-2-(4-ethoxybenzyl)benzyl | 741.7 | 3.87 |

*These samples were analyzed on a different column from the rest in the table.

$^1$H NMR of Example 680: (400 MHz, CD$_3$OD, HCl salt) δ 7.42~7.48 (m, 1H), 7.29~7.33 (m, 2H), 7.06~7.13 (m, 3H), 6.76~6.81 (m, 2H), 5.72 (s, 1H), 4.15~4.21 (m, 1H), 4.07~4.13 (m, 1H), 4.07 (q, 7.2 Hz, 2H), 3.97 (q, 7.0 Hz, 2H), 3.87 (s, 1H), 3.77~3.83 (m, 1H), 3.78 (s, 2H), 3.52~3.66 (m, 4H), 3.39~3.47 (m, 1H), 3.17~3.25 (m, 1H), 3.05~3.13 (m, 1H), 2.91~2.99 (m, 2H), 2.74~2.82 (m, 1H), 1.83~2.04 (m, 4H), 1.35 (t, 7.2 Hz, 3H), 1.34 (t, 7.1 Hz, 3H), 1.15 (s, 9H).

EXAMPLES 711–732

Examples 711–732 in Table 32 were prepared from Aldehyde 15 and appropriate piperidines using procedures described in Example 1 Steps D and E. The piperidines were prepared using Method A or Method B in Step B of Example 1. Example 732 was obtained as side-products of Example 711 during the final catalytic hydrogenation step for removal of benzyl group.

TABLE 32

![structure]

| EXAMPLE # | R | ESI-MS (M + H) | HPLC A (min.) |
|---|---|---|---|
| 711 | 4-Cyanobenzyl | 586.3 m/Z | 3.43 |
| 712 | 3,5-Bis(trifluoromethyl)benzyl | 697.5 m/Z | 4.43 |
| 713 | 4-Trifluoromethoxybenzyl | 645.4 m/Z | 3.97 |
| 714 | 4-Trifluoromethylbenzyl | 629.9 m/Z | 4.00 |
| 715 | 4-Difluoromethoxybenzyl | 627.4 m/Z | 3.80 |
| 716 | 3-Ethoxybenzyl | 605.6 m/Z | 3.67 |
| 717 | 4-t-Butylbenzyl | 617.7 m/Z | 4.17 |
| 718 | (1-Naphthyl)methyl | 612.0 m/Z | 3.87 |
| 719 | (2-Naphthyl)methyl | 611.6 m/Z | 3.87 |
| 720 | 4-Phenylbenzyl | 637.4 m/Z | 4.13 |
| 721 | 4-(2,2,2-Trifluoroethyl)benzyl | 659.4 m/Z | 3.90 |
| 722 | 4-Phenoxybenzyl | 653 m/Z | 4.13 |
| 723 | 4-Cyclobutoxybenzyl | 631.5 m/Z | 3.97 |
| 724 | 3-Fluoro-4-Ethoxybenzyl | 623.5 m/Z | 3.73 |
| 725 | 4-Hydroxybenzyl | 577.3 m/Z | 3.1 |
| 726 | 4-n-Butoxybenzyl | 633.6 m/Z | 4.10 |
| 727 | 4-n-Benzoxybenzyl | 667.5 m/Z | 1.55* |
| 728 | 4-Cyclopropoxybenzyl | 617.5 m/Z | 3.73 |
| 729 | 4-n-Propoxybenzyl | 619.5 m/Z | 3.87 |
| 730 | 4-Phenylsulfonylbenzyl | 701.4 m/Z | 3.77 |
| 731 | 3,4-Dimethoxybenzyl | 621.5 m/Z | 3.47 |
| 732 | 4-Aminomethylbenzyl | 590.3 m/Z | 2.70 |

*This sample was analyzed on a different column from the rest in the table.

EXAMPLES 733–743

Examples 733–743 in Table 33 were prepared from appropriate piperidines and appropriate aldehydes described previously using procedures described in Example 6 Steps E and F or Example 1 Steps D and E. Example 738 was obtained as side-product of Example 737 during the final removal of PMB with 96% formic acid. Piperidines in Examples 733–737 were commercially available. Piperidines used Examples 740 and 741 were the same as in Example 602. The piperidines used in Example 739 and 742 were prepared similarly to that in Example 602 and 645, respectively.

TABLE 33

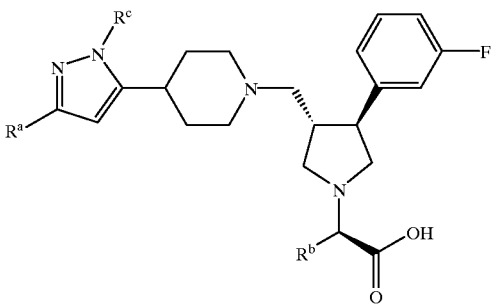

| EXAMPLE # | $R^a$ | $R^b$ | $R^c$ | ESI-MS (M + H); HPLC A (min) |
|---|---|---|---|---|
| 733 | 2,4-Dichlorophenyl | Cyclohexyl | H | 613.2 m/Z |
| 734 | 4-Chlorophenyl | Cyclohexyl | H | 579.3 m/Z |
| 735 | 4-Methoxyphenyl | Cyclohexyl | H | 575.3 m/Z |
| 736 | 2,4-Dichlorophenyl | i-Propyl | H | 573.2 m/Z |
| 737 | 2-Furyl | Cyclohexyl | H | 535.3 m/Z |
| 738 | 4-(4-ethoxybenzyl)-2-furyl | Cyclohexyl | H | 655.3 m/Z |
| 739 | 2-Phenylethyl | Cyclohexyl | H | 573.3 m/Z |
| 740 | 2-Phenylethyl | Cyclopropylmethyl | Et | 573.4 m/Z |
| 741 | 2-Phenylethyl | Cyclobutylmethyl | Et | 587.6 m/Z |
| 742 | 4-Cyanobenzyl | t-Butyl | n-Pr | 600.4 m/Z |
| 743 | Benzyl | Cyclohexyl | H | 559.4 m/Z; 3.50 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

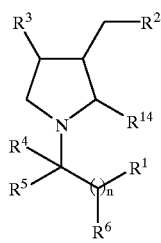

wherein:
$R^1$ is selected from:
(1) —$CO_2H$,
(2) —$NO_2$, (3) -tetrazolyl,
(4) -hydroxyisoxazole,
(5) —$SO_2NH$—($CO_{0-3}$ alkyl)—$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
(6) —$SO_2NHCO$—($CO_{0-3}$ alkyl)-$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
(7) —$P(O)(OH)_2$;

$R^2$ is selected from the group consisting of:

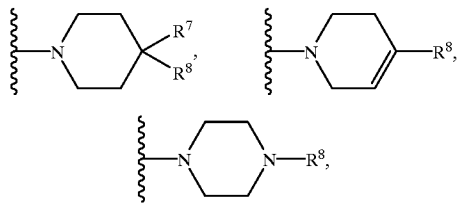

wherein $R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) cyano,
(4) hydroxy, and
(5) halo,
and wherein $R^8$ is selected from:
phenyl, naphthyl, biphenyl, and heterocycle, which is unsubstituted or substituted with 1–7 of $R^{11}$ where $R^{11}$ is independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_2(C_{1-6}$ alkyl), trifluoromethyl, —$NR^9R^1O$ (where $R^9$ is defined above and $R^{10}$ is independently selected from the definitions of $R^9$), phenyl, naphthyl, biphenyl, and heterocycle, wherein phenyl, naphthyl, biphenyl, or heterocycle is unsubstituted or substituted with 1–7 of $R^{13}$ where $R^{13}$ is independently selected from: halo, cyano, hydroxy, $C_{1-6}$ alkyl, $C_{1-6}$ alkoxy, —$CO_2H$, —$CO_2(C_{1-6}$ alkyl), trifluoromethyl, —$NR^9R^{10}$, —($C_{1-6}$ alkyl)—$NR^9R^{10}$, —$SO_2R^9$, $C_{1-6}$ fluoroalkoxy, —($C_{1-6}$ alkyl)hydroxy, $C_{3-6}$ cycloalkyloxy, benzyloxy, phenoxy, and —$NO_2$,
(e) —O—$C_{1-6}$ alkyl, which is unsubstituted or substituted with 1–5 of $R^{12}$,
(f) —O-phenyl, which is unsubstituted or substituted with 1–5 of $R^{13}$,
(g) —O-heterocycle, which is unsubstituted or substituted with 1–5 of $R^{13}$,
(h) —$CF_3$,
(i) —$CHF_2$,
(j) —$CH_2F$,
(k) —$NO_2$,
(j) phenyl,
(m) —$CO_2R^9$,
(n) tetrazolyl,
(o) —$NR^9R^{10}$,
(p) —$NR^9$—$COR^{10}$,
(q) —$NR^9$—$CO_2R^{10}$,
(r) —CO—$NR^9R^{10}$,
(s) —OCO—$NR^9R^{10}$,
(t) —$NR^9CO$—$NR^9R^{10}$,
(u) —$S(O)_m$—$R^9$, wherein m is an integer selected from 0, 1 and 2,
(v) —$S(O)_2$—$NR^9R^{10}$,
(w) —$NR^9S(O)_2$—$R^{10}$,
(x) —$NR^9S(O)_2$—$NR^9R^{10}$,
(y) $C_{2-6}$ alkenyl,
(z) furanyl, which is unsubstituted or substituted with benzyl which is unsubstituted or substituted with 1–7 of $R^{13}$ wherein $R^{13}$ is independently as defined above, and
(aa) $R^9$, and
(bb) —O—$C_{3-6}$ cycloalkyl;

$R^3$ is selected from the group consisting of:
phenyl, naphthyl, and heterocycle, which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^4$ is selected from:
$C_{1-10}$ alkyl, $C_{3-8}$ cycloalkyl, —($C_{1-3}$ alkyl)-$C_{3-8}$ cycloalkyl, —($C_{0-2}$ alkyl)-($C_{3-8}$ cycloalkylidenyl)-($C_{1-2}$ alkyl), $C_{2-10}$ alkenyl, $C_{2-10}$ alkynyl, phenyl, —($C_{1-6}$ alkyl)-phenyl, naphthyl, biphenyl, heterocycle, hydrogen, cyclohexenyl, dihydronaphthyl, tetrahydronaphthyl, and octahydronaphthyl, which is unsubstituted or substituted with 1–7 of $R^{11}$ where $R^{11}$ is independently as defined above;

$R^5$ is selected from:
hydrogen or $C_{1-6}$ alkyl, wherein the alkyl is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$,
or where $R^4$ and $R^5$ may be joined together to form a $C_{3-8}$ cycloalkyl ring which may be unsubstituted or substituted with 1–7 of $R^{11}$;

$R^6$ is independently selected from:
hydrogen or $C_{1-6}$ alkyl, wherein the alkyl is unsubstituted or substituted with 1–7 substituents where the substituents are independently selected from:
(a) halo,
(b) trifluoromethyl, (c) hydroxy,
(d) $C_{1-3}$ alkyl,
(e) —O—$C_{1-3}$ alkyl,
(f) —$CO_2R^9$,
(g) —$NR^9R^{10}$, and
(h) —$CONR^9R^{10}$;

$R^{14}$ is hydrogen or $C_{1-6}$ alkyl;

n is an integer selected from 0, 1, 2 and 3;

or a pharmaceutically acceptable salt thereof or an individual diastereomer thereof.

2. The compound of claim 1, which is a compound of formula I':

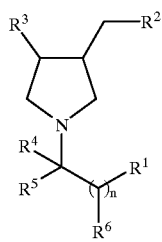

wherein:

$R^1$ is selected from:
(1) —$CO_2H$,
(2) —$NO_2$,
(3) -tetrazolyl,
(4) -hydroxyisoxazole,
(5) —$SO_2NH$—($C_{0-3}$ alkyl)—$R^9$, wherein $R^9$ is independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl, and
(6) —$P(O)(OH)_2$;

$R^8$ is selected from:
phenyl, naphthyl, biphenyl, and heterocycle, which is unsubstituted or substituted with 1–7 of $R^{11}$ where $R^{11}$ is independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_2(C_{1-6}$ alkyl), trifluoromethyl, —$NR^9R^{10}$ (where $R^9$ is defined above and $R^{10}$ is independently selected from the definitions of $R^9$),
phenyl, naphthyl, biphenyl, and heterocycle, which is unsubstituted or substituted with 1–7 of $R^{13}$ where $R^{13}$ is independently selected from: halo, cyano, hydroxy, $C_{1-6}$ alkyl, $C_{1-6}$ alkoxy, —$CO_2H$, —$CO_2(C_{1-6}$ alkyl), trifluoromethyl, and —$NR^9R^{10}$,
(e) —O—$C_{1-6}$ alkyl, which is unsubstituted or substituted with 1–5 of $R^{12}$,
(f) —O-phenyl, which is unsubstituted or substituted with 1–5 of $R^{13}$,
(g) —O-heterocycle, which is unsubstituted or substituted with 1–5 of $R^{13}$,
(h) —$CF_3$,
(i) —$CHF_2$,
(j) —$CH_2F$,
(k) —$NO_2$,
(j) phenyl,
(m) —$CO_2R^9$,
(n) tetrazolyl,
(o) —$NR^9R^{10}$,
(p) —$NR^9$—$COR^{10}$,
(q) —$NR^9$—$CO_2R^{10}$,
(r) —CO—$NR^9R^{10}$,
(s) —OCO—$NR^9R^{10}$,
(t) —$NR^9CO$—$NR^9R^{10}$,
(u) —$S(O)_m$—$R^9$, wherein m is an integer selected from 0, 1 and 2,
(v) —$S(O)_2$—$NR^9R^{10}$,
(w) —$NR^9S(O)_2$—$R^{10}$, and
(x) —$NR^9S(O)_2$—$NR^9R^{10}$;

$R^4$ is selected from:
$C_{1-10}$ alkyl, $C_{3-8}$ cycloalkyl, —($C_{1-3}$ alkyl)-C3-8 cycloalkyl, $C_{2-10}$ alkenyl, $C_{2-10}$ alkynyl, phenyl, —($C_{1-6}$ alkyl)-phenyl, naphthyl, biphenyl, heterocycle, hydrogen, cyclohexenyl, dihydronaphthyl, tetrahydronaphthyl, and octahydronaphthyl, which is unsubstituted or substituted with 1–7 of $R^{11}$ where $R^{11}$ is independently as defined above;

or a pharmaceutically acceptable salt thereof or an individual diastereomer thereof.

3. The compound of claim 1 wherein $R^1$ is selected from:
(1) —$CO_2H$,
(2) —$P(O)(OH)_2$, and
(3) -tetrazolyl.

4. The compound of claim 1 wherein $R^1$ is selected from:
(1) —$CO_2H$, and
(2) -tetrazolyl.

5. The compound of claim 1 wherein $R^1$ is —$CO_2H$.

6. The compound of claim 2 wherein $R^1$ is —$CO_2H$.

7. The compound of claim 1 wherein $R^3$ is selected from the group consisting of:
phenyl and thienyl,
which may be unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl.

8. The compound of claim 1 wherein $R^3$ is selected from the group consisting of:
phenyl and thienyl, which may be unsubstituted or substituted with 1–5 substituents where the substituents are independently selected from:
(a) halo,
(b) trifluoromethyl,
(c) hydroxy, and
(d) $C_{1-3}$ alkyl.

9. The compound of claim 1 wherein $R^3$ is selected from the group consisting of:
phenyl, which may be unsubstituted or substituted with 1–5 substituents where the substituents are independently selected from:
(a) fluoro, and
(b) chloro; and
unsubstituted thienyl.

10. The compound of claim 1 wherein $R^3$ is unsubstituted phenyl, (3-fluoro)phenyl or 3-thienyl.

11. The compound of claim 2 wherein $R^3$ is unsubstituted phenyl, (3-fluoro)phenyl or 3-thienyl.

12. The compound of claim 1 wherein $R^4$ is $C_{1-10}$ alkyl, $C_{3-8}$ cycloalkyl, or —($C_{1-3}$ alkyl)-$C_{3-8}$ cycloalkyl,
which is unsubstituted or substituted with 1–5 substituents where the substituents are independently selected from:
(a) halo,
(b) hydroxy,
(c) —$C_{1-6}$ alkyl, which is unsubstituted or substituted with halo, cyano, —$CO_2H$, hydroxy or trifluoromethyl,
(d) —O—$C_{1-6}$ alkyl, which is unsubstituted or substituted halo, cyano, —$CO_2H$, hydroxy or trifluoromethyl,
(e) —$CF_3$,
(f) —$CHF_2$,
(g) —$CH_2F$, and
(h) —$CO_2H$.

13. The compound of claim 1 wherein $R^4$ is selected from: isopropyl, isobutyl, sec-butyl, t-butyl, cyclohexyl, cyclopentyl, cyclobutyl, cyclopropyl, —$CH_2$-cyclohexyl, —$CH_2$-cyclopentyl, —$CH_2$-cyclobutyl, and —$CH_2$-cyclopropyl.

14. The compound of claim 1 wherein $R^4$ is selected from: isopropyl, sec-butyl, t-butyl, cyclohexyl, cyclopentyl, cyclobutyl, cyclopropyl, —$CH_2$-cyclobutyl, and —$CH_2$-cyclopropyl.

15. The compound of claim 1 wherein $R^4$ is selected from: cyclohexyl, isopropyl, sec-butyl, t-butyl, —$CH_2$-cyclobutyl and —$CH_2$-cyclopropyl.

16. The compound of claim 1 wherein $R^5$ is hydrogen.

17. The compound of claim 1 wherein $R^6$ is hydrogen or unsubstituted $C_{1-6}$ alkyl.

18. The compound of claim I wherein $R^6$ is hydrogen.

19. The compound of claim 1 wherein $R^7$ is hydrogen, fluoro, hydroxy or $C_{1-6}$ alkyl.

20. The compound of claim 1 wherein $R^7$ is hydrogen or fluoro.

21. The compound of claim 1 wherein $R^7$ is hydrogen.

22. The compound of claim 1 wherein $R^8$ is selected from unsubstituted or substituted: pyrazolyl, thiazolyl, oxazolyl, pyridyl, imidazolyl, isoxazolyl, imidazopyridyl, imidazothiophenyl, indazolyl, tetrahydroimidazopyridyl, and tetrahydroindazolyl.

23. The compound of claim 1 wherein $R^8$ is selected from: phenyl, benzoimidazolyl, imidazolyl, imidazopyridyl, isoxazolyl, oxazolyl, pyrazolyl, pyridyl, thiazolyl, imidazothiophenyl, indazolyl, tetrahydroimidazopyridyl, and tetrahydroindazolyl,
which is unsubstituted or substituted with 1–7 substituents where the substituents are independently selected from:
(a) halo,
(b) cyano,
(c) hydroxy,
(d) $C_{1-6}$ alkyl, which is unsubstituted or substituted with 1–5 of $R^{12}$ where $R^{12}$ is independently selected from: halo, cyano, hydroxy, $C_{1-6}$ alkoxy, —$CO_2H$, —$CO_2(C_{1-6}$ alkyl), trifluoromethyl, —$NR^9R^{10}$
where $R^9$ and $R^{10}$ are independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
and phenyl, naphthyl, biphenyl, or heterocycle, which is unsubstituted or substituted with 1–7 of $R^{13}$ where $R^{13}$ is independently selected from:
halo, cyano, hydroxy, $C_{1-6}$ alkoxy, —$CO_2H$, —$CO_2(C_{1-6}$ alkyl), trifluoromethyl, and —$NR^9R^{10}$,
(e) —O—$C_{1-6}$ alkyl, which is unsubstituted or substituted with 1–5 of $R^{12}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$.

24. The compound of claim 1 wherein $R^8$ is selected from unsubstituted or substituted: pyrazolyl, thiazolyl, oxazolyl, imidazolyl, imidazopyridyl, tetrahydroimidazopyridyl, and tetrahydroindazolyl.

25. The compound of claim 1 wherein $R^8$ is selected from: phenyl, pyrazolyl, imidazolyl, benzoimidazolyl, isoxazolyl, oxazolyl, pyridyl, thiazolyl, imidazopyridyl, tetrahydroimidazopyridyl, and tetrahydroindazolyl;
which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) phenyl,
(h) $C_{1-6}$ alkyl, which is unsubstituted or substituted with phenyl, which is unsubstituted or substituted with 14 of $R^{13}$ where $R^{13}$ is independently selected from: halo, cyano, hydroxy, $C_{1-6}$ alkoxy, —$CO_2H$, —$CO_2(C_{1-6}$ alkyl), and trifluoromethyl, and
(i) —O—$C_{1-6}$ alkyl.

26. The compound of claim 1 wherein $R^8$ is selected from substituted or unsubstituted: pyrazolyl, thiazolyl, imidazopyridyl, and tetrahydroindazolyl.

27. The compound of claim 1 wherein $R^8$ is selected from: pyrazolyl, imidazolyl, benzoimidazolyl, isoxazolyl, pyridyl, and thiazolyl, imidazopyridyl, and tetrahydroindazolyl;
which is unsubstituted or substituted with 1–3 substituents where the substituents are independently selected from:
(a) fluoro,
(b) chloro,
(c) $C_{1-6}$ alkyl,
(d) —$CH_2$-phenyl,
(e) —$CH_2CH_2$-phenyl, and
(f) phenyl.

28. The compound of claim 1 wherein $R^8$ is selected from: pyrazolyl, benzoimidazolyl, isoxazolyl, imidazolyl, thiazolyl, imidazopyridyl, and tetrahydroindazolyl;
which is substituted with 1–3 substituents where the substituents are independently selected from:

(a) fluoro,
(b) methyl,
(c) ethyl,
(d) —CH$_2$-phenyl, and
(e) —CH$_2$CH$_2$-phenyl.

29. The compound of claim 1 wherein R$^8$ is selected from:
benzoimidazol-1-yl, (2-methyl)benzoimidazol-1-yl, (2-methyl-5-fluoro)benzoimidazol-1-yl, (2-methyl-5,6-difluoro)benzo-imidazol-1-yl, isoxazolo-5-yl, 5-benzyl-isoxazolo-5-yl, pyrazol-5-yl, 1-ethyl-3-benzyl-pyrazol-5-yl, 3-benzyl-pyrazol-5-yl, and 1-ethyl-4-phenethyl-pyrazol-5-yl.

30. The compound of claim 1 wherein n is an integer selected from 0 and 1.

31. The compound of claim 1 wherein n is an integer which is 0.

32. The compound of claim 1 which is of the stereochemical configuration:

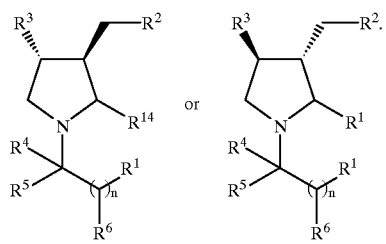

33. The compound of claim 2 which is of the stereochemical configuration:

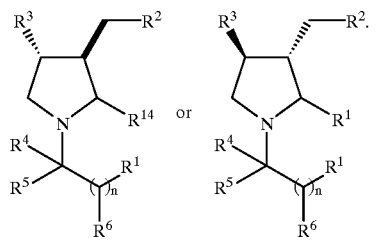

34. The compound of claim 1, which is a compound of formula (II):

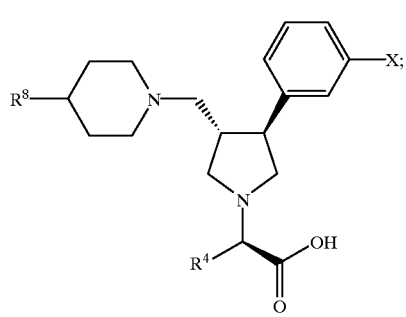

wherein

R$^4$ is selected from the group consisting of

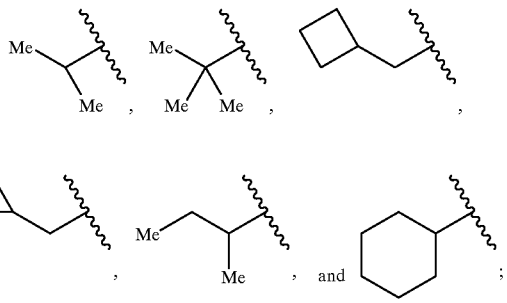

R$^8$ is selected from the group consisting of

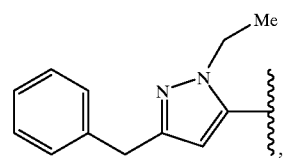

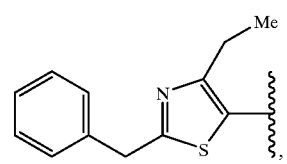

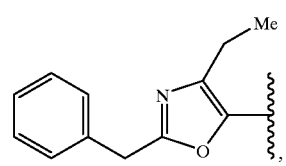

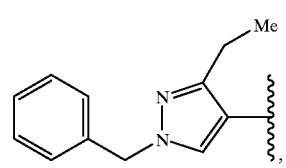

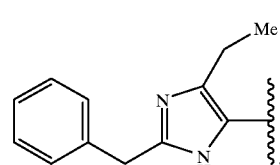

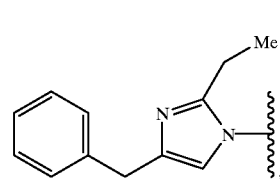

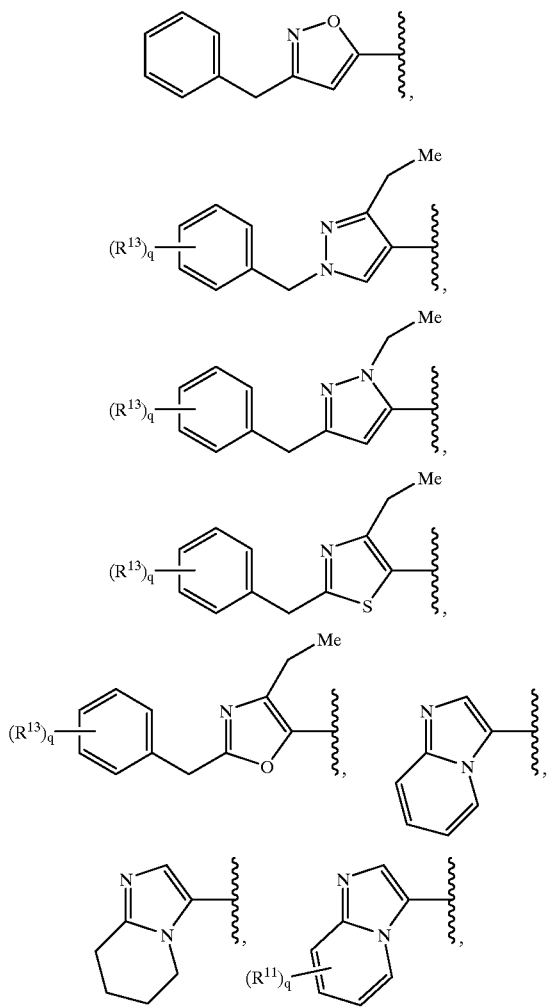

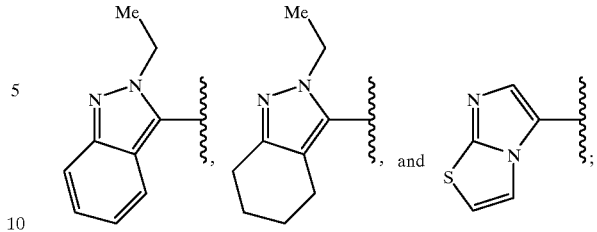

$R^{11}$ and $R^{13}$ are each independently selected from the group consisting of F, Cl, $CF_3$, $OCH_3$, $OCH_2CH_3$, $OCF_3$, O-cyclobutyl, CN, O-cyclopropyl, $CH_3$, $CH_2CH_3$, $CH(CH_3)_2$, $C(CH_3)_3$, and $SO_2CH_3$;

X is hydrogen or fluoro; and q is an integer equal to 1 or 2;

or a pharmaceutically acceptable salt thereof or an individual diastereomer thereof.

35. A pharmaceutical composition which comprises an inert carrier and a compound of claim 1.

36. A method for modulation of chemokine receptor activity in a mammal which comprises the administration of an effective amount of the compound of claim 1.

37. A method for preventing infection by HIV, treating infection by HIV, or delaying of the onset of AIDS, comprising the administration to a patient of an effective amount of the compound of claim 1.

38. A method for the prevention or treatment of an inflammatory and immunoregulatory disorder or disease which comprises the administration to a patient of an effective amount of the compound of claim 1.

39. A method for the prevention or treatment of asthma, allergic rhinitis, dermatitis, conjunctivitis, atherosclerosis or rheumatoid arthritis which comprises the administration to a patient of an effective amount of the compound of claim 1.

* * * * *